US007566711B2

(12) United States Patent
Moon et al.

(10) Patent No.: US 7,566,711 B2
(45) Date of Patent: *Jul. 28, 2009

(54) REVERSE-TURN MIMETICS AND METHOD RELATING THERETO

(75) Inventors: Sung Hwan Moon, Suwon-shi (KR); Jae Uk Chung, Suwon-shi (KR); Sung Chan Lee, Suwon-shi (KR); Masakatsu Eguchi, Bellevue, WA (US); Michael Kahn, Kirkland, WA (US); Kwang Won Jeong, Seoul (KR); Cu Nguyen, Arlington, WA (US); Soo Jin Lee, Suwon-shi (KR)

(73) Assignee: Choongwae Pharma Corporation, Seoul (KR)

( * ) Notice: Subject to any disclaimer, the term of this patent is extended or adjusted under 35 U.S.C. 154(b) by 186 days.

This patent is subject to a terminal disclaimer.

(21) Appl. No.: 11/108,164

(22) Filed: Apr. 15, 2005

(65) Prior Publication Data

US 2007/0043052 A1     Feb. 22, 2007

Related U.S. Application Data

(63) Continuation-in-part of application No. 10/826,972, filed on Apr. 16, 2004, which is a continuation-in-part of application No. 10/803,179, filed on Mar. 17, 2004, which is a continuation-in-part of application No. 10/411,877, filed on Apr. 9, 2003, now abandoned, which is a continuation-in-part of application No. 10/087,443, filed on Mar. 1, 2002, now abandoned, which is a continuation-in-part of application No. 09/976,470, filed on Oct. 12, 2001, now abandoned.

(30) Foreign Application Priority Data

Oct. 11, 2002    (WO) .................... PCT/KR02/01901

(51) Int. Cl.
C07D 487/04 (2006.01)
A61K 31/53 (2006.01)
A61P 35/00 (2006.01)

(52) U.S. Cl. ..................... 514/243; 544/184
(58) Field of Classification Search ................. 544/184; 514/243
See application file for complete search history.

(56) References Cited

U.S. PATENT DOCUMENTS

| | | | |
|---|---|---|---|
| 5,440,013 A | 8/1995 | Kahn | 530/317 |
| 5,475,085 A | 12/1995 | Kahn | 530/317 |
| 5,618,914 A | 4/1997 | Kahn | 530/317 |
| 5,670,155 A | 9/1997 | Kahn | 424/208.1 |
| 5,672,681 A | 9/1997 | Kahn | 530/317 |
| 5,693,325 A | 12/1997 | Kahn | 424/188.1 |
| 5,710,245 A | 1/1998 | Kahn | 530/324 |
| 5,840,833 A | 11/1998 | Kahn | 530/300 |
| 5,859,184 A | 1/1999 | Kahn et al. | 530/300 |
| 5,929,237 A | 7/1999 | Kahn | 544/279 |
| 6,013,458 A | 1/2000 | Kahn et al. | 435/7.1 |
| 6,020,331 A | 2/2000 | Kahn | 514/221 |
| 6,117,896 A | 9/2000 | Qabar et al. | 514/384 |
| 6,184,223 B1 | 2/2001 | Kahn et al. | 514/249 |
| 6,245,764 B1 | 6/2001 | Kahn et al. | 514/248 |
| 6,294,525 B1 | 9/2001 | Stasiak et al. | 514/183 |
| 6,372,744 B1 | 4/2002 | Qabar et al. | 514/248 |
| 6,413,963 B2 | 7/2002 | Kahn et al. | 514/249 |
| 6,440,955 B1 | 8/2002 | Stasiak et al. | 514/183 |
| 6,548,500 B2 | 4/2003 | Kahn et al. | 514/249 |
| 2001/0039274 A1 | 11/2001 | Kahn et al. | 514/221 |
| 2002/0022620 A1 | 2/2002 | Kahn et al. | 514/221 |
| 2002/0065416 A1 | 5/2002 | Stasiak et al. | 544/350 |
| 2002/0068695 A1 | 6/2002 | Scolastico et al. | 514/9 |
| 2003/0021773 A1 | 1/2003 | Moroder et al. | 424/94.1 |
| 2003/0027819 A1 | 2/2003 | Qabar et al. | 514/224.2 |
| 2003/0105103 A1 | 6/2003 | Golebiowski et al. | 514/249 |
| 2004/0072831 A1 | 4/2004 | Moon et al. | 514/243 |

FOREIGN PATENT DOCUMENTS

CA         2 384 126 A1    3/2001

(Continued)

OTHER PUBLICATIONS

Arango, D. et al., "c-myc/p53 Interaction Determines Sensitivity of Human Colon Carcinoma Cells to 5-Fluorouracie in Vitro and in Vivo," *Cancer Research* 61: 4910-4915, Jun. 15, 2001.
Batlle, E. et al., "β-Catenin and TCF Mediate Cell Positioning in the Intestinal Epithelium by Controlling the Expression of EphB/EphrinB," *Cell*, 111:251-263, Oct. 18, 2002.
Behrens, J. et al., "Functional interaction of β-catenin with the transcription factor LEF-1," *Nature* 382: 638-642, Aug. 15, 1996.
Bienz and Clevers, "Linking Colorectal Cancer to Wnt Signaling," *Cell*, 103:311-320, Oct. 13, 2000.
Blanc-Brude, O. P. et al., "Inhibitor of apoptosis protein surviving regulates vascular injury," *Nature Medicine*, 8(9):987-994, Sep. 2002.
Caca, K. et al., "β- and γ-Catenin Mutations, but not E-Cadherin Inactivation, Underlie T-Cell Factor/Lymphoid Enhancer Factor Transcriptional Deregulation in Gastric and Pancreatic Cancer," *Cell Growth & Differentiation* 10: 369-376, 1999.

(Continued)

*Primary Examiner*—Venkataraman Balasubramanian
(74) *Attorney, Agent, or Firm*—Seed IP Law Group PLLC

(57) ABSTRACT

Conformationally constrained compounds that mimic the secondary structure of reverse-turn regions of biologically active peptides and proteins are disclosed. Such reverse-turn mimetic structures have utility over a wide range of fields, including use as diagnostic and therapeutic agents. Libraries containing the reverse-turn mimetic structures of this invention are also disclosed as well as methods for screening the same to identify biologically active members. The invention also relates to the use of such compounds for inhibiting or treating disorders modulated by Wnt-signaling pathway, such as cancer, especially colorectal cancer, restenosis associated with angioplasty, polycystic kidney disease, aberrant angiogenesis disease, rheumatoid arthritis disease, tuberous sclerosis complex, Alzheimer's disease, excess hair growth or loss, or ulcerative colitis.

3 Claims, 23 Drawing Sheets

FOREIGN PATENT DOCUMENTS

| WO | WO 94/03494 A1 | 2/1994 |
| --- | --- | --- |
| WO | WO 97/15577 A1 | 5/1997 |
| WO | 98/05333 A1 | 2/1998 |
| WO | WO 98/49168 A1 | 11/1998 |
| WO | WO 01/00210 A1 | 1/2001 |
| WO | WO 01/16135 A2 | 3/2001 |
| WO | WO 03/006447 A2 | 1/2003 |
| WO | WO 03/031448 A1 | 4/2003 |

OTHER PUBLICATIONS

Cadigan and Nusse, "Wnt signaling: a common theme in animal development," *Genes & Development* 11:3286-3305, 1997.

Cheguillaume, A. et al., "New Potential Monomers for Solid Phase Synthesis of Hydrazinopeptoids: the $N^\alpha$-Substituted-$N^\beta$-Protected Hydrazinoglycines and Hydrazonoglycinals," *Synlett* 2000, No. 3, pp. 331-334, Mar. 2000.

Chen, S. et al., "Wnt-1 Signaling Inhibits Apoptosis by Activating β-Catenin/T Cell Factor-mediated Transcription," *The Journal of Cell Biology* 152(1): 87-96, Jan. 8, 2001.

Chenn and Walsh, "Regulation of Cerebral Cortical Size by Control of Cell Cycle Exit in Neural Precursors," *Science*, 297:365-369, Jul. 19, 2002.

Chrivia, J.C. et al., "Phosphorylated CREB binds specifically to the nuclear protein CBP," *Nature* 365: 855-859, Oct. 28, 1993.

Crawford, H.C. et al., "The metalloproteinase matrilysin is a target of β-catenin transactivation in intestinal tumors," *Oncogene*, 18:2883-2891, 1999.

Daniels, D. L. et al., "β-catenin: molecular plasticity and drug design," *TRENDS in Biochemical Sciences*, 26(11):672-678, Nov. 11, 2001.

DasGupta and Fuchs, "Multiple roles for activated LEF/TCF transcription complexes during hair follicle development and differentiation," *Development*, 126: 4557-4568, 1999.

Davis, P.D. et al., "ZD6126: A Novel Vascular-targeting Agent That Causes Selective Destruction of Tumor Vasculature," *Cancer Research*, 62:7247-7253, Dec. 15, 2002.

De Farrari and Inestrosa, "Wnt signaling function in Alzheimer's disease," *Brain Research Reviews*, 33: 1-12, 2000.

Dolle, R.E. "Comprehensive Survey of Combinatorial Library Synthesis: 1999," *Journal of Combinatorial Chemistry*, 2(5): 383-433, Sep./Oct. 2000.

Dooley and Houghten, "The use of positional scanning synthetic peptide combinatorial libraries for the rapid determination of opioid receptor ligands," *Life Sciences*, 52(18): 1509-1517, 1993.

Dooley, C.T. et al., "Acetalins: Opioid receptor antagonists determined through the use of synthetic peptide combinatorial libraries," *Proc. Natl. Acad. Sci. USA*, 90: 10811-10815, Nov. 1993.

Dooley, C.T. et al., "An All D-Amino Acid Opioid Peptide with Central Analgesic Activity from a Combinatorial Library," *Science* 266: 2019-2022, Dec. 23, 1994.

Eckner, R. et al., "Molecular cloning and functional analysis of the adenovirus E1A-associated 300-kD protein (p300) reveals a protein with properties of a transcriptional adaptor," *Genes & Development*, 8: 869-884, 1994.

Eichler, J. et al., "Cyclic Peptide Template Combinatorial Libraries: Synthesis and Identification of Chymotrypsin Inhibitors," *Peptide Research*, 7(6):300-307, 1994.

Fraser, P.E. et al., "Presenilin function: connections to Alzheimer's disease and signal transduction," *Biochem. Soc. Symp.*, 67:89-100, 2001.

Fleisher, D. et al., "Improved Oral Drug Delivery: Solubility Limitations Overcome by the Use of Prodrugs," *Advanced Drug Delivery Reviews*, 19:115-130, 1996.

Fuchs, E., "Beauty is Skin Deep: The Fascinating Biology of the Epidermis and its Appendages," *The Harvey Lectures, Delivered Under the Auspices of The Harvey Society of New York*, 1998-1999, Wiley-Liss, A John Wiley & Sons, Inc., Publication, Series 94, 47-48, 2000.

Fujimuro, M. et al., "A novel viral mechanism for dysregulation of β-catenin in Kaposi's sarcoma-associated herpesvirus latency," *Nature Medicine*, 9(3):300-306, Mar. 2003.

Gallop, M.A. et al., "Applications of Combinatorial Technologies to Drug Discovery. 1. Background and Peptide Combinatorial Libraries," *Journal of Medicinal Chemistry*, 37(9):1233-1251, Apr. 29, 1994.

Gat, U. et al., "De Novo Hair Follicle Morphogenesis and Hair Tumors in Mice Expressing a Truncated β-Catenin in Skin," *Cell*, 95:605-614, Nov. 25, 1998.

Golik, J. et al., "Synthesis and Antitumor Evaluation of Paclitaxel Phosphonooxymethyl Ethers: A Novel Class of Water Soluble Paclitaxel Pro-Drugs," *Bioorganic & Medicinal Chemistry Letters*, 6(15):1837-1842, 1996.

Gomez, M. R., "History of the tuberous sclerosis complex," *Brain & Development*, 17(suppl):55-7, 1995.

Graminski and Lerner, "A Rapid Bioassay for Platelet-Derived Growth Factor β-Receptor Tyrosine Kinase Function," *Bio/Technology 12*: 1008-1011, Oct. 12, 1994.

Grossman, D. et al., "Inhibition of melanoma tumor growth in vivo by surviving targeting," *PNAS*, 98(2):635-640, Jan. 16, 2001.

Hanai, J., et al., "Endostatin is a potential inhibitor of Wnt signaling," *The Journal of Cell Biology*, 158(3):529-539, Aug. 5, 2002.

Hartmann, D., "From Alzheimer's disease to skin tumors: The catenin connection," *Proc. Natl. Acad. Sci. USA*, 98(19): 10522-10523, Sep. 11, 2001.

Hayashi, S. et al., "A *Drosophila* homolog of the tumor suppressor gene adenomatous *Polyposis coli* down-regulates β-catenin but its zygotic expression is not essential for the regulation of Armadillo," *Proc. Natl. Acad. Sci. USA*, 94:242-247, Jan. 1997.

He, Tong-Chuan et al., "Identification of c-*MYC* as a Target of the APC Pathway," *Science*, 281:1509-1512, Sep. 4, 1998.

He, Tong-Chuan et al., "PPARδ Is an APC-Regulated Target of Nonsteroidal Anti-Inflammatory Drugs," *Cell*, 99:335-345, Oct. 29, 1999.

Hecht, A. et al., "The p300/CBP acetyltransferases function as transcriptional coactivators of β-catenin in vertebrates," *European Molecular Biology Organization Journal*, 19(9):1839-1850, 2000.

Houghten and Dooley, "The use of synthetic peptide combinatorial libraries for the determination of peptide ligands in radio-receptor assays: opioid peptides," *Bioorganic & Medicinal Chemistry Letters*, 3(3):405-412, 1993.

Houghten, R.A. et al., "Generation and use of synthetic peptide combinatorial libraries for basic research and drug discovery," *Nature*, 354:84-86, Nov. 7, 1991.

Houghten, R.A. et al., "The Use of Synthetic Peptide Combinatorial Libraries for the Identification of Bioactive Peptides," *BioTechniques*, 13(3):412-421, 1992.

Hsu, S-C. et al., "Modulation of Transcriptional Regulation by LEF-1 in Response to Wnt-1 Signaling and Association with β-Catenin," *Molecular and Cellular Biology*, 18(8):4807-4818, Aug. 1998.

Janda, K.D., "Tagged versus untagged libraries: Methods for the generation and screening of combinatorial chemical libraries," *Proc. Natl. Acad. Sci. USA*, 91:10779-10785, Nov. 1994.

Janknecht and Hunter, "A growing coactivator network," *Nature*, 383:22-23, Sep. 5, 1996.

Kang, D.E. et al., "Presenilin 1 Facilitates the Constitutive Turnover of β-Catenin: Differential Activity of Alzheimer's Disease-Linked PS1 Mutants in the β-Catenin-Signaling Pathway," *The Journal of Neuroscience*, 19(11):4229-4237, Jun. 1, 1999.

Kim, P.J. et al., "Survivin and molecular pathogenesis of colorectal cancer," *The Lancet*, 362:205-209, Jul. 19, 2003.

Kinzler and Vogelstein, "Lessons from Hereditary Colorectal Cancer," *Cell*, 87:159-170, Oct. 18, 1996.

Kolligs, F.T. et al., "Neoplastic Transformation of RK3E by Mutant β-Catenin Requires Deregulation of Tcf/Lef Transcription but Not Activation of c-*myc* Expression," *Molecular and Cellular Biology*, 19(8):5696-5706, Aug. 1999.

Kosik, K.S., "A partnership the delivers, Alzheimer disease mutations in the presenilins alter the intracellular trafficking of β-catenin, hinting that the presenilins may also determine the fate of other proteins in the endoplasmic reticulum," *Nature Medicine*, 5(2):149-150, Feb. 1999.

Lam, K.S. et al., "A new type of synthetic peptide library for identifying ligand-binding activity," *Nature*, 354:82-84, Nov. 7, 1991.

Levesque, G. et al., "Presenilins Interact with Armadillo Proteins Including Neural-Specific Plakophilin-Related Protein and β-Catenin," *Journal of Neurochemistry*, 72(3):999-1008, 1999.

Mak, B.C. et al., "The Tuberin-Hamartin Complex Negatively Regulates β-Catenin Signaling Activity," *The Journal of Biological Chemistry*, 278(8):5947-5951, Feb. 21, 2003.

Mesri, M. et al., "Cancer gene therapy using a survivin mutant adenovirus," *The Journal of Clinical Investigation*, 108(7):981-990, Oct. 2001.

Miller, J.R. et al., "Mechanism and function of signal transduction by the Wnt/β-catenin and Wnt/Ca$^{2+}$ pathways," *Oncogene 18*: 7860-7872, 1999.

Miloloza, A. et al., "The TSC1 gene product, hamartin, negatively regulates cell proliferation," *Human Molecular Genetics* 9(12):1721-1727, 2000.

Misner, D.L. et al., "Vitamin A deprivation results in reversible loss of hippocampal long-term synaptic plasticity," *PNAS*, 98(20):11714-11719, Sep. 25, 2001.

Molenaar, M. et al., "XTcf-3 Transcription Factors Mediates β-Catenin-Induced Axis Formation in Xenopus Embryos," *Cell*, 86:391-399, Aug. 9, 1996.

Moon, R.T. et al., "WNTs modulate cell fate and behavior during vertebrate development," *Trends in Genetics*, 13(4):157-162, Apr. 1997.

Morin, P.J. et al., "Activation of β-Catenin-Tcf Signaling in Colon Cancer by Mutations in β-Catenin or APC," *Science 275*: 1787-1790, Mar. 21, 1997.

Morin, P.J. et al., "Apoptosis and *APC* in colorectal tumorigenesis," *Proc. Natl. Acad. Sci. USA*, 93:7950-7954, Jul. 1996.

Murai, K.K. et al, "Control of hippocampal dendritic spine morphology through ephrin-A3/EphA4 signaling," *Nature Neuroscience*, 6(2):153-160, Feb. 2003.

Nishimura, M. et al., "Presenilin mutations associated with Alzheimer disease cause defective intracellular trafficking of β-catenin, a component of the presenilin protein complex," *Nature Medicine*, 5(2):164-169, Feb. 1999.

Nusse and Varmus, "*Wnt* Genes," *Cell*, 69:1073-1087, Jun. 26, 1992.

Obrecht, D. et al., "Novel peptide mimetic building blocks and strategies for efficient lead finding," *Advances in Medicinal Chemistry*, 4:1-68, 1999.

Orford, K. et al., "Exogenous Expression of β-Catenin Regulates Contact Inhibition, Anchorage-independent Growth, Anoikis, and Radiation-induced Cell Cycle Arrest," *The Journal of Cell Biology*, 146(4):855-867, Aug. 23, 1999.

Patapoutian and Reichardt, "Roles of Wnt proteins in neural development and maintenance," *Curr. Opin. Neurobiol.*, 10(3):392-399, 2000.

Peifer and Polakis, "Wnt Signaling in Oncogenesis and Embryogenesis—a Look Outside the Nucleus," *Science*, 287:1606-1609, Mar. 3, 2000.

Polakis P., "Wnt signaling and cancer," *Genes & Development*, 14:1837-1851, 2000.

Randolph, J.T. et al., "Major Simplifications in Oligosaccharide Syntheses Arising from a Solid-Phase Based Method: An Application to the Synthesis of the Lewis b Antigen," *Journal of the American Chemical Society 117*: 5712-5719, 1995.

Rebel, V.I. et al., "Distinct roles for CREB-binding protein and p300 in hematopoietic stem cell self-renewal," *PNAS*, 99(23):14789-14798, Nov. 12, 2002.

Reed, J.C., "The Survivin saga goes in vivo," *The Journal of Clinical Investigation*, 108(7):965-969, Oct. 2001.

Reya, T. et al., "A role of Wnt signaling in self-renewal of haematopoietic stem cells," *Nature*, 423:409-414, May 22, 2003.

Rodova, M. et al., "The Polycystic Kidney Disease-1 Promoter Is a Target of the β-Catenin/T-cell Factor Pathway," *The Journal of Biological Chemistry*, 277(33):29577-29583, 2002.

Roose, J. et al., "Synergy Between Tumor Suppressor *APC* and the β-Catenin-Tcf4 Target *Tcf1*," *Science*, 285:1923-1926, Sep. 17, 1999.

Rubinfeld, B. et al., "Binding of GSK3β to the APC-β-Catenin Complex and Regulation of Complex Assembly," *Science*, 272:1023-1026, May 17, 1996.

Rubinfeld, B. et al., "Stabilization of β-Catenin by Genetic Defects in Melanoma Cell Lines," *Science*, 275:1790-1792, Mar. 21, 1997.

Sakanaka and Williams, "Functional Domains of Axin. Importance on the C Terminus as an Oligomerization Domain," *The Journal of Biological Chemistry*, 274(20):14090-14093, May 14, 1999.

Sakanaka, C. et al., "Bridging of β-catenin and glycogen synthase kinase-3β by Axin and inhibition of β-catenin-mediated transcription," *Proc. Natl. Acad. Sci. USA*, 95:3020-3023, Mar. 1998.

Sen, M. et al., "Expression of function of wingless and frizzled homologs in rheumatoid arthritis," *PNAS*, 97(6):2791-2796, Mar. 14, 2000.

Shintani, S. et al., "Infrequent Alternations of RB Pathway (Rb-p16$^{INK4A}$-cyclinD1) in Adenoid Cystic Carcinoma of Salivary Glands," *Anticancer Research*, 20:2169-2176, 2000.

Shikama et al., "The p300/CBP family: integrating signals with transcription factors and chromatin," *Trends in Cell Biology*, 7:230-236, Jun. 1997.

Shtutman, M. et al., "The cyclin D1 gene is a target of the β-catenin/LEF-1 pathway," *Proc. Natl. Acad. Sci.USA*, 96:5522-5527, May 1999.

Soriano, S. et al., "Presenilin 1 Negatively Regulates β-Catenin/T Cell Factor/Lymphoid Enhancer Factor-1 Signaling Independently of β-Amyloid Precursor Protein and Notch Processing," *The Journal of Cell Biology*, 152(4):785-794, Feb. 19, 2001.

Stein, R.W. et al., "Analysis of E1A-Mediated Growth Regulation Functions: Binding of the 300-Kilodalton Cellular Product Correlates with E1A Enhancer Repression Function and DNA Synthesis-Inducing Activity," *Journal of Virology*, 64(9):4421-4427, Sep. 1990.

Stewart and Young, "Solid Phase Peptide Synthesis," *Pierce Chemical Company*, Second Edition, Rockford, Illinois, 1984, Table of Contents (6 pages).

Strovel and Sussman, "Transient Overexpression of Murine *Dishevelled* Genes Results in Apoptotic Cell Death," *Experimental Cell Research*, 253:637-648, 1999.

Su, L-K. et al., "Association of the APC Tumor Suppressor Protein with Catenins," *Science*, 262:1734-1737, Dec. 10, 1993.

Takemaru and Moon, "The Transcriptional Coactivator CBP Interacts with β-Catenin to Activate Gene Expression," *The Journal of Cell Biology*, 149(2):249-254, Apr. 17, 2000.

Tetsu and McCormick, "β-Catenin regulates expression of cyclin D1 in colon carcinoma cells," *Nature*, 398:422-426, Apr. 1, 1999.

Tong, D. et al., "5-Fluorouracil-induced apoptosis in cultured oral cancer cells," *Oral Oncology*, 36:236-241, 2000.

Tumelty, D. et al., "Immobilised, Activated Peptides as Reagents for Cyclic and Derivatised Peptide Libraries," *J. Chem. Soc. Chem. Commun.*, 1067-1068, 1994.

Uthoff, S.M.S. et al., "Identification of candidate genes in ulcerative colitis and Crohn's disease using cDNA array technology," *International Journal of Oncology*, 19:803-810, 2001.

Wilkinson, D.G., "Multiple Roles of EPH Receptor and Ephrins in Neural Development,"*Nature Reviews, Neuroscience*, 2:155-164, Mar. 2001.

Xia, X. et al., "Loss of presenilin 1 is associated with enhanced β-catenin signaling and skin tumorigenesis," *PNAS*, 98(19):10863-10868, Sep. 11, 2001.

Yost, C. et al., "The axis-inducing activity, stability, and subcellular distribution of β-catenin is regulated in *Xenopus* embryos by glycogen synthase kinase 3," *Genes & Development*, 10:1443-1454, 1996.

Yu, G. et al., "The Presenilin 1 Protein Is a Component of a High Molecular Weight Intracellular Complex That Contains β-Catenin," *The Journal of Biological Chemistry*, 273(26):16470-16475, Jun. 26, 1998.

Zaloom and Roberts, "Preparation of Azido Derivatives from Amino Acids and Peptides by Diazo Transfer," *J. Org. Chem.*, 46:5173-5176, 1981.

Zhang, T. et al., "Evidence That APC Regulates Survivin Expression: A Possible Mechanism Contributing to the Stem Cell Origin of Colon Cancer," *Cancer Research*, 62:8664-8667, Dec. 15, 2001.

Zhang, Z. et al., "Destabilization of β-catenin by mutations in presenilin-1 potentiates neuronal apoptosis," *Nature*, 395:698-702, Oct. 15, 1998.

Eguchi, M. et al., "Solid-phase synthesis and solution structure of bicyclic β-turn peptidomimetics: diversity at the i position," *Tetrahedron Letters*, 42:1237-1239, 2001.

REVERSE-TURN MIMETICS AND METHOD RELATING THERETO

CROSS-REFERENCES TO RELATED APPLICATIONS

This application is a continuation-in-part of U.S. patent application Ser. No. 10/826,972, filed Apr. 16, 2004, which is a continuation-in-part of co-pending U.S. patent application Ser. No. 10/803,179 filed Mar. 17, 2004, which is a continuation-in-part of U.S. patent application Ser. No. 10/411,877 filed Apr. 9, 2003 (now abandoned), which is a continuation-in-part of U.S. patent application Ser. No. 10/087,443 filed Mar. 1, 2002 (now abandoned), which is a continuation-in-part of U.S. patent application Ser. No. 09/976,470 filed Oct. 12, 2001 (now abandoned). This application also claims priority to PCT application serial No. PCT/KR02/01901 filed Oct. 11, 2002. The disclosures of these applications are incorporated herein by reference in their entireties.

BACKGROUND OF THE INVENTION

1. Field of the Invention

The present invention relates generally to reverse-turn mimetic structures and to a chemical library relating thereto. The invention also relates to applications in the treatment of medical conditions, e.g., cancer diseases, and pharmaceutical compositions comprising the mimetics.

2. Description of the Related Art

Random screening of molecules for possible activity as therapeutic agents has occurred for many years and resulted in a number of important drug discoveries. While advances in molecular biology and computational chemistry have led to increased interest in what has been termed "rational drug design", such techniques have not proven as fast or reliable as initially predicted. Thus, in recent years there has been a renewed interest and return to random drug screening. To this end, particular strides having been made in new technologies based on the development of combinatorial chemistry libraries, and the screening of such libraries in search for biologically active members.

In general, combinatorial chemistry libraries are simply a collection of molecules. Such libraries vary by the chemical species within the library, as well as the methods employed to both generate the library members and identify which members interact with biological targets of interest. While this field is still young, methods for generating and screening libraries have already become quite diverse and sophisticated. For example, a recent review of various combinatorial chemical libraries has identified a number of such techniques (Dolle, *J. Com. Chem.,* 2(3): 383-433, 2000), including the use of both tagged and untagged library members (Janda, *Proc. Natl. Acad. Sci. USA* 91:10779-10785, 1994).

Initially, combinatorial chemistry libraries were generally limited to members of peptide or nucleotide origin. To this end, the techniques of Houghten et al. illustrate an example of what is termed a "dual-defined iterative" method to assemble soluble combinatorial peptide libraries via split synthesis techniques (*Nature* (London) 354:84-86, 1991; *Biotechniques* 13:412-421, 1992; Bioorg. *Med. Chem. Lett.* 3:405-412, 1993). By this technique, soluble peptide libraries containing tens of millions of members have been obtained. Such libraries have been shown to be effective in the identification of opioid peptides, such as methionine- and leucine-enkephalin (Dooley and Houghten, *Life Sci.* 52, 1509-1517, 1993), and a N-acylated peptide library has been used to identify acetalins, which are potent opioid antagonists (Dooley et al., *Proc. Natl. Acad. Sci. USA* 90:10811-10815, 1993. More recently, an all D-amino acid opioid peptide library has been constructed and screened for analgesic activity against the mu ("µ") opioid receptor (Dooley et al, *Science* 266:2019-2022, 1994).

While combinatorial libraries containing members of peptide and nucleotide origin are of significant value, there is still a need in the art for libraries containing members of different origin. For example, traditional peptide libraries to a large extent merely vary the amino acid sequence to generate library members. While it is well recognized that the secondary structures of peptides are important to biological activity, such peptide libraries do not impart a constrained secondary structure to its library members.

To this end, some researchers have cyclized peptides with disulfide bridges in an attempt to provide a more constrained secondary structure (Tumelty et al., *J. Chem. Soc.* 1067-68, 1994; Eichler et al., *Peptide Res.* 7:300-306, 1994). However, such cyclized peptides are generally still quite flexible and are poorly bioavailable, and thus have met with only limited success.

More recently, non-peptide compounds have been developed which more closely mimic the secondary structure of reverse-turns found in biologically active proteins or peptides. For example, U.S. Pat. No. 5,440,013 to Kahn and published PCT applications nos. WO94/03494, WO01/00210A1, and WO01/16135A2 to Kahn each disclose conformationally constrained, non-peptidic compounds, which mimic the three-dimensional structure of reverse-turns. In addition, U.S. Pat. No. 5,929,237 and its continuation-in-part U.S. Pat. No. 6,013,458, both to Kahn, disclose conformationally constrained compounds which mimic the secondary structure of reverse-turn regions of biologically active peptides and proteins. The synthesis and identification of conformationally constrained, reverse-turn mimetics and their application to diseases were well reviewed by Obrecht (Advances in Med. Chem., 4, 1-68, 1999).

While significant advances have been made in the synthesis and identification of conformationally constrained, reverse-turn mimetics, there remains a need in the art for small molecules which mimic the secondary structure of peptides. There is also a need in the art for libraries containing such members, as well as techniques for synthesizing and screening the library members against targets of interest, particularly biological targets, to identify bioactive library members.

The present invention also fulfills these needs, and provides further related advantages by providing confomationally constrained compounds which mimic the secondary structure of reverse-turn regions of biologically active peptides and proteins.

Wnt signaling pathway regulates a variety of processes including cell growth, oncogenesis, and development (Moon et al., 1997, Trends Genet. 13, 157-162; Miller et al., 1999, Oncogene 18, 7860-7872; Nusse and Varmus, 1992, Cell 69, 1073-1087; Cadigan and Nusse, 1997, Genes Dev. 11, 3286-3305; Peifer and Polakis, 2000 Science 287, 1606-1609; Polakis 2000, Genes Dev. 14, 1837-1851). Wnt signaling pathway has been intensely studied in a variety of organisms. The activation of TCF4/β-catenin mediated transcription by Wnt signal transduction has been found to play a key role in its biological functions (Molenaar et al., 1996, Cell 86:391-399; Gat et al., 1998 Cell 95:605-614; Orford et al., 1999 J. Cell. Biol. 146:855-868; Bienz and Clevers, 2000, Cell 103: 311-20).

In the absence of Wnt signals, tumor suppressor gene adenomatous polyposis coli (APC) simultaneously interacts with the serine kinase glycogen synthase kinase (GSK)-3β and β-catenin (Su et al., 1993, Science 262, 1734-1737: Yost et al., 1996 Genes Dev. 10, 1443-1454: Hayashi et al., 1997, Proc. Natl. Acad. Sci. USA, 94, 242-247: Sakanaka et al., 1998, Proc. Natl. Acad. Sci. USA, 95, 3020-3023: Sakanaka and William, 1999, J. Biol. Chem 274, 14090-14093). Phosphorylation of APC by GSK-3β regulates the interaction of APC with β-catenin, which in turn may regulate the signaling function of β-catenin (B. Rubinfeld et al., Science 272, 1023, 1996). Wnt signaling stabilizes β-catenin allowing its translocation to the nucleus where it interacts with members of the lymphoid enhancer factor (LEF1)/T-cell factor (TCF4) family of transcription factors (Behrens et al., 1996 Nature 382, 638-642: Hsu et al., 1998, Mol. Cell. Biol. 18, 4807-4818: Roose et all., 1999 Science 285, 1923-1926).

Recently c-myc, a known oncogene, was shown to be a target gene for β-catenin/TCF4-mediated transcription (He et al., 1998 Science 281 1509-1512: Kolligs et al., 1999 Mol. Cell. Biol. 19, 5696-5706). Many other important genes, including cyclin D1, and metalloproteinase, which are also involved in oncogenesis, have been identified to be regulated by TCF4/bata-catenin transcriptional pathway (Crawford et al., 1999, Oncogene 18, 2883-2891: Shtutman et al., 1999, Proc. Natl. Acad. Sci. USA., 11, 5522-5527: Tetsu and McCormick, 1999 Nature, 398, 422-426).

Moreover, overexpression of several downstream mediators of Wnt signaling has been found to regulate apoptosis (Moris et al., 1996, Proc. Natl. Acad. Sci. USA, 93, 7950-7954: He-et al., 1999, Cell 99, 335-345: Orford et al, 1999 J. Cell. Biol., 146, 855-868: Strovel and Sussman, 1999, Exp. Cell. Res., 253, 637-648). Overexpression of APC in human colorectal cancer cells induced apoptosis (Moris et al., 1996, Proc. Natl. Acad. Sci. USA., 93, 7950-7954), ectopic expression of β-catenin inhibited apoptosis associated with loss of attachment to extracellular matrix (Orford et al, 1999, J. Cell Biol. 146, 855-868). Inhibition of TCF4/β-catenin transcription by expression of dominant-negative mutant of TCF4 blocked Wnt-1-mediated cell survival and rendered cells sensitive to apoptotic stimuli such as anti-cancer agent (Shaoqiong Chen et al., 2001, J. Cell. Biol., 152, 1, 87-96) and APC mutation inhibits apoptosis by allowing constitutive survivin expression, a well-known anti-apoptotic protein (Tao Zhang et al., 2001, Cancer Research, 62, 8664-8667).

Although mutations in the Wnt gene have not been found in human cancer, a mutation in APC or β-catenin, as is the case in the majority of colorectal tumors, results in inappropriate activation of TCF4, overexpression of c-myc and production of neoplastic growth (Bubinfeld et al, 1997, Science, 275, 1790-1792 Morin et al, 1997, Science, 275, 1787-1790: Casa et al, 1999, Cell. Growth. Differ. 10, 369-376). The tumor suppressor gene (APC) is lost or inactivated in 85% of colorectal cancers and in a variety of other cancers as well (Kinzler and Vogelstein, 1996, Cell 87, 159-170). APC's principal role is that of a negative regulator of the Wnt signal transduction cascade. A center feature of this pathway involves the modulation of the stability and localization of a cytosolic pool of β-catenin by interaction with a large Axin-based complex that includes APC. This interaction results in phosphorylation of β-catenin thereby targeting it for degradation.

CREB binding proteins (CBP)/p300 were identified initially in protein interaction assays, first through its association with the transcription factor CREB (Chrivia et al, 1993, Nature, 365, 855-859) and later through its interaction with the adenoviral-transforming protein E1A (Stein et al., 1990, J. Viol., 64, 4421-4427: Eckner et al., 1994, Genes. Dev., 8, 869-884). CBP had a potential to participate in variety of cellular functions including transcriptional coactivator function (Shikama et al., 1997, Trends. Cell. Biol., 7, 230-236: Janknecht and Hunter, 1996, Nature, 383, 22-23). CBP/p300 potentiates β-catenin-mediated activation of the siamois promoter, a known Wnt target (Hecht et al, 2000, EMBO J. 19, 8, 1839-1850). β-catenin interacts directly with the CREB-binding domain of CBP and β-catenin synergizes with CBP to stimulate the transcriptional activation of TCF4/β-catenin (Ken-Ichi Takemaru and Randall T. Moon, 2000 J. Cell. Biol., 149, 2, 249-254).

BRIEF SUMMARY OF THE INVENTION

From this background, it is seen that TCF4/β-catenin and CBP complex of Wnt pathway can be taken as target molecules for the regulation of cell growth, oncogenesis and apoptosis of cells, etc. Accordingly, the present invention addresses a need for compounds that block TCF4/β-catenin transcriptional pathway by inhibiting CBP, and therefore can be used for treatment of cancer, especially colorectal cancer.

In brief, the present invention is directed to a new type of conformationally constrained compounds, which mimic the secondary structure of reverse-turn regions of biologically active peptides and proteins. This invention also discloses libraries containing such compounds, as well as the synthesis and screening thereof.

The compounds of the present invention have the following general formula (I):

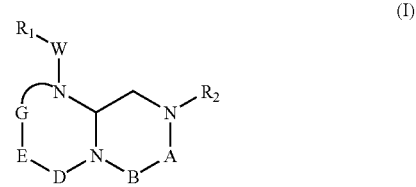

wherein A is —(CHR$_3$)— or —(C=O)—, B is —(CHR$_4$)— or —(C=O)—, D is —(CHR$_5$)— or —(C=O)—, E is -(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or is absent, Y is oxygen, sulfur, or —NH—, X and Z is independently nitrogen or CH, n=0 or 1; and R$_1$, R$_2$, R$_3$, R$_4$, R$_5$, R$_6$, R$_7$, R$_8$ and R$_9$ are the same or different and independently selected from an amino acid side chain moiety or derivative thereof, the remainder of the molecule, a linker and a solid support, and stereoisomers thereof.

In an embodiment wherein A is —CHR$_3$)—, B is —(C=O)—, D is —(CHR$_5$)—, E is —(C=O)—, and G is —XR$_7$)$_n$—, the compounds of this invention have the following formula (II):

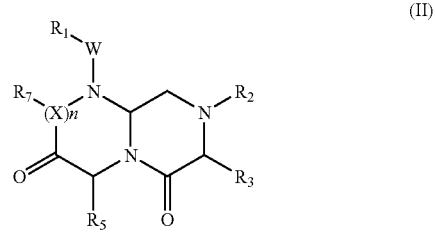

wherein W, X, Y and n are as defined above, and $R_1$, $R_2$, $R_3$, $R_5$ and $R_7$ are as defined in the following detailed description.

In an embodiment wherein A is —(C═O)—, B is —(CHR$_4$)—, D is —(C═O)—, E is -(ZR$_6$)—, and G is —(C═O)—(XR$_9$)—, the compounds of this invention have the following formula (III):

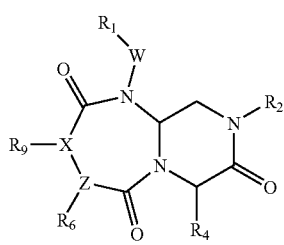

(III)

wherein W, X and Y are as defined above, Z is nitrogen or CH (with the proviso that when Z is CH, then X is nitrogen), and $R_1$, $R_2$, $R_4$, $R_6$ and $R_9$ are as defined in the following detailed description.

In an embodiment wherein A is —(C═O)—, B is —(CHR$_4$)—, D is —(C═O)—, E is -(ZR$_6$)—, and G is (XR$_7$)$_n$—, the compounds of this invention have the following general formula (IV):

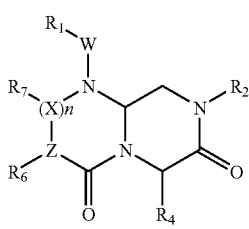

(IV)

wherein W, Y and n are as defined above, Z is nitrogen or CH (when Z is nitrogen, then n is zero, and when Z is CH, then X is nitrogen and n is not zero), and $R_1$, $R_2$, $R_4$, $R_6$ and $R_7$, are as defined in the following detailed description.

In certain embodiments, the compounds of this invention have the following general formula (VI):

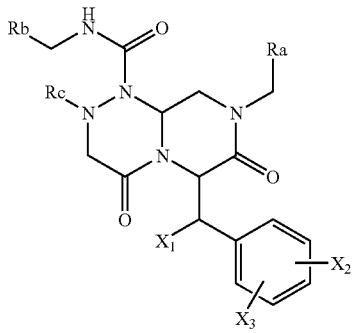

(VI)

wherein $R_a$ is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group having 8 to 11 ring members, which may have 1 to 3 heteroatoms selected from nitrogen, oxygen or sulfur; $R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy groups; $R_c$ is a saturated or unsaturated $C_{1-6}$alkyl, $C_{1-6}$alkoxy, perfluoro $C_{1-6}$alkyl group; and $X_1$, $X_2$, and $X_3$ may be the same or different and independently selected from hydrogen, hydroxyl, and halide.

The present invention is also related to prodrugs using the libraries containing one or more compounds of formula (I). A prodrug is typically designed to release the active drug in the body during or after absorption by enzymatic and/or chemical hydrolysis. The prodrug approach is an effective means of improving the oral bioavailability or i.v. administration of poorly water-soluble drugs by chemical derivatization to more water-soluble compounds. The most commonly used prodrug approach for increasing aqueous solubility of drugs containing a hydroxyl group is to produce esters containing an ionizable group; e.g., phosphate group, carboxylate group, alkylamino group (Fleisher et al., *Advanced Drug Delivery Reviews*, 115-130, 1996; Davis et al., *Cancer Res.*, 7247-7253, 2002, Golik et al., *Bioorg. Med. Chem. Lett.*, 1837-1842, 1996).

In certain embodiments, the prodrugs of the present invention have the following general formula (VII):

(VI)—Y—$R_{10}$ wherein (VI) is general formula (VI) as described above; Y is oxygen, sulfur, or nitrogen of a group selected from $R_a$, $R_b$, $R_c$, $X_1$, $X_2$ and $X_3$;

$R_{10}$ is phosphate, hemisuccinate, hemimalate, phosphoryloxymethyloxycarbonyl, dimethylaminoacetate, dimethylaminoalkylcarbamates, hydroxyalkyls, amino acid, glycosyl, substituted or unsubstituted piperidine oxycarbonyl, or a salt thereof; and wherein the prodrugs are capable of serving as a substrate for a phosphatase or a carboxylase and are thereby converted to compounds having general formula (VI).

In some embodiments, $R_{10}$ of the general formula (VII) is not an amino acid group or a phospho-amino acid group.

The present invention is also directed to libraries containing one or more compounds of formula (I) above, as well as methods for synthesizing such libraries and methods for screening the same to identify biologically active compounds. Compositions containing a compound of this invention in combination with a pharmaceutically acceptable carrier or diluent are also disclosed.

The present invention is also related to methods for identifying a biologically active compound using the libraries containing one or more compound of formula (I). In a related aspect, the present invention provides a method for performing a binding assay, comprising (a) providing a composition comprising a first co-activator and an interacting protein, said first co-activator comprising a binding motif of LXXLL, LXXLI or FXXFF wherein X is any amino acid; (b) combining the first co-activator and the interacting protein with a test compound; and (c) detecting alteration in binding between the first co-activator and the interacting protein in the presence of the compound having general formula (I).

The present invention also provides methods for preventing or treating disorders associated with Wnt signaling pathway. Disorders that may be treated or prevented using a compound or composition of the present invention include tumor or cancer (e.g., KSHV-associated tumor), restenosis associated with angioplasty, polycystic kidney disease, aberrant angiogenesis disease, rheumatoid arthritis disease, ulcerative colitis, tuberous sclerosis complex, hair loss, and Alzheimer's disease. Such methods comprise administering to a subject in need thereof a compound or composition of the present invention in an amount effective to achieve the desired outcome.

In a related aspect, the present invention further provides methods for promoting neurite outgrowth, differentiation of a neural stem cell, and apoptosis in cancer cells. Such methods comprise administering to appropriate cells a compound or composition of the present invention in an amount effective to achieve the desired outcome.

These and other aspects of this invention will be apparent upon reference to the attached figure and following detailed description. To this end, various references are set forth herein, which describe in more detail certain procedures, compounds and/or compositions, and are incorporated by reference in their entirety.

DETAILED DESCRIPTION OF THE INVENTION

Figure 1:
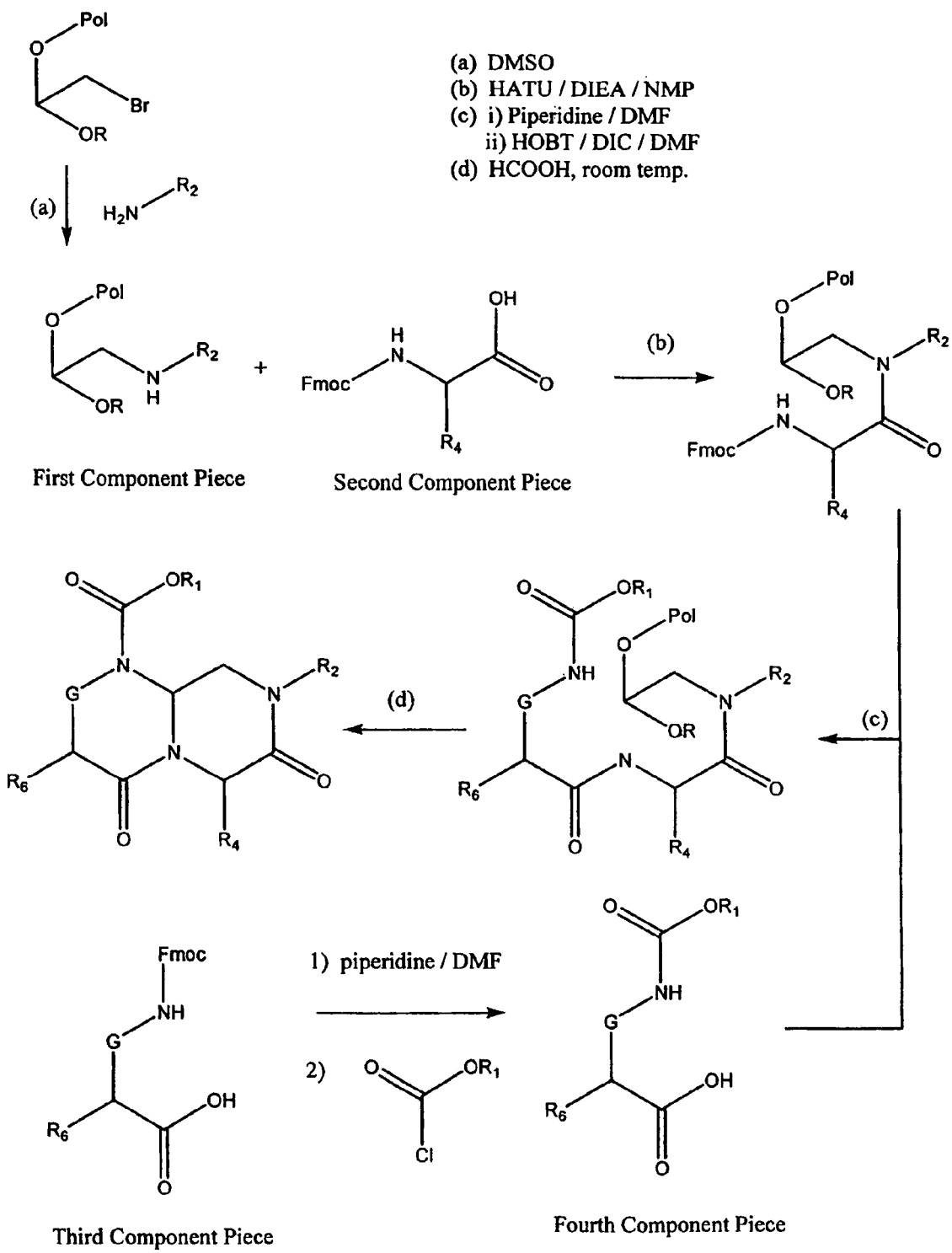
FIG. 1 provides a general synthetic scheme for preparing reverse-turn mimetics of the present invention.

The present invention is directed to conformationally constrained compounds that mimic the secondary structure of reverse-turn regions of biological peptide and proteins (also referred to herein as "reverse-turn mimetics", and is also directed to chemical libraries relating thereto.

The reverse-turn mimetic structures of the present invention are useful as bioactive agents, including (but not limited to) use as diagnostic, prophylactic and/or therapeutic agents. The reverse-turn mimetic structure libraries of this invention are useful in the identification of bioactive agents having such uses. In the practice of the present invention, the libraries may contain from tens to hundreds to thousands (or greater) of individual reverse-turn structures (also referred to herein as "members").

In one aspect of the present invention, a reverse-turn mimetic structure is disclosed having the following formula (I):

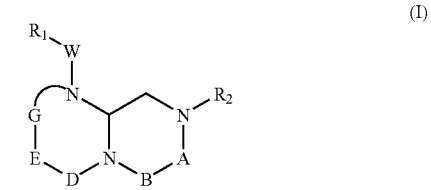

wherein A is —(CHR$_3$)— or —(C=O)—, B is —(CHR$_4$)— or —(C=O)—, D is —(CHR$_5$)— or —(C=O)—, E is -(ZR$_6$)— or —(C=O)—, G is —(XR$_7$)$_n$—, —(CHR$_7$)— (NR$_8$)—, —(C=O)—(XR$_9$)—, or —(C=O)—, W is —Y(C=O)—, —(C=O)NH—, —(SO$_2$)— or nothing, Y is oxygen, sulfur, or —NH—, X and Z is independently nitrogen or CH, n=0 or 1; and R$_1$, R$_2$, R$_3$, R$_4$, R$_5$, R$_6$, R$_7$, R$_8$ and R$_9$ are the same or different and independently selected from an amino acid side chain moiety or derivative thereof, the remainder of the molecule, a linker and a solid support, and stereoisomers thereof.

In one embodiment, R$_1$, R$_2$, R$_3$, R$_4$, R$_5$, R$_6$, R$_7$, R$_8$ and R$_9$ are independently selected from the group consisting of aminoC$_{2-5}$alkyl, guanidineC$_{2-5}$alkyl, C$_{1-4}$alkylguanidinoC$_{2-5}$alkyl, diC$_{1-4}$alkylguanidinoC$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, phenyl, substituted phenyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl, (where the substituents are independently selected from one or more of amino amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, amidazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), triazin-2-yl-C$_{1-4}$alkyl, substituted triazin-2-yl-C$_{1-4}$alkyl (where the triazine substituents are independently selected from one or more of amino, amidino, guanidino, hydrazino, amidazonyl, C$_{1-4}$alkylamino, C$_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazo$C_{1-4}$alkyl, substituted imidazol $C_{1-4}$alkl (where the imidazole sustituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazolinyl$C_{1-4}$alkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl.

In one embodiment, $R_1$, $R_2$, $R_6$ of E, and $R_7$, $R_8$ and $R_9$ of G are the same or different and represent the remainder of the compound, and $R_3$ of A, $R_4$ of B or $R_5$ of D is selected from an amino acid side chain moiety or derivative thereof. As used herein, the term "remainder of the compound" means any moiety, agent, compound, support, molecule, linker, amino acid, peptide or protein covalently attached to the reverse-turn mimetic structure at $R_1$, $R_2$, $R_5$, $R_6$, $R_7$, $R_8$ and/or $R_9$ positions. This term also includes amino acid side chain moieties and derivatives thereof.

In another embodiment $R_3$ of A, $R_5$ of D, $R_6$ of E, and $R_7$, $R_8$, and $R_9$ of G are the same or different and represent the remainder of the compound, while one or more of, and in one aspect all of, $R_1$, $R_2$ and $R_4$ of B represent an amino acid sidechain. In this case, the term "remainder of the compound" means any moiety, agent, compound, support, molecule, linker, amino acid, peptide or protein covalently attached to the reverse-turn mimetic structure at $R_3$, $R_5$, $R_6$, $R_7$, $R_8$ and/or $R_9$ positions. This term also includes amino acid side chain moieties and derivatives thereof.

As used herein, the term "remainder of the compound" means any moiety, agent, compound, support, molecule, atom, linker, amino acid, peptide or protein covalently attached to the reverse-turn mimetic structure. This term also includes amino acid side chain moieties and derivatives thereof. In one aspect of the invention, any one or more of the $R_1$, $R_2$, $R_3$, $R_4$, $R_5$, $R_6$, $R_7$, $R_8$ and/or $R_9$ positions may represent the remainder of the compound. In one aspect of the invention, one or more of $R_1$, $R_2$ and $R_4$ represents an amino acid side chain moiety or a derivative thereof.

As used herein, the term "amino acid side chain moiety" represents any amino acid side chain moiety present in naturally occurring proteins including (but not limited to) the naturally occurring amino acid side chain moieties identified in Table 1. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 1

| Amino Acid Side Chain Moiety | Amino Acid |
| --- | --- |
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3^+$ | Lysine |
| —(CH$_2$)$_3$NHC(NH$_2$)NH$_2^+$ | Arginine |

TABLE 1-continued

| Amino Acid Side Chain Moiety | Amino Acid |
| --- | --- |
|  | Histidine |
| —CH$_2$COO$^-$ | Aspartic acid |
| —CH$_2$CH$_2$COO | Glutamic acid |
| —CH$_2$CONH$_2$ | Asparagine |
| —CH$_2$CH$_2$CONH$_2$ | Glutamine |
| 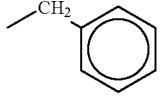 | Phenylalanine |
| 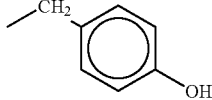 | Tyrosine |
| 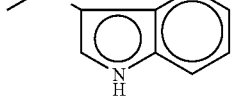 | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| 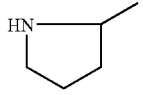 | Proline |
| 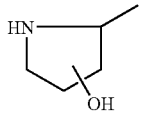 | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and phenylalanine may generally be classified as lower chain alkyl, aryl, or arylalkyl moieties. Derivatives of amino acid side chain moieties include other straight chain or branched, cyclic or noncyclic, substituted or unsubstituted, saturated or unsaturated lower chain alkyl, aryl or arylalkyl moieties.

As used herein, "lower chain alkyl moieties" contain from 1-12 carbon atoms, "lower chain aryl moieties" contain from 6-12 carbon atoms and "lower chain aralkyl moieties" contain from 7-12 carbon atoms. Thus, in one embodiment, the amino acid side chain derivative is selected from a $C_{1-12}$ alkyl, a $C_{6-12}$ aryl and a $C_{7-12}$ arylalkyl, and in a more preferred embodiment, from a $C_{1-7}$ alkyl, a $C_{6-10}$ aryl and a $C_{7-11}$ arylalkyl.

Amino side chain derivatives of this invention further include substituted derivatives of lower chain alkyl, aryl, and arylalkyl moieties, wherein the substituent is selected from (but is not limited to) one or more of the following chemical moieties: —OH, —OR, —COOH, —COOR, —CONH$_2$, —NH$_2$, —NHR, —NRR, —SH, —SR, —SO$_2$R, —SO$_2$H, —SOR and halogen (including F, Cl, Br and I), wherein each occurrence of R is independently selected from straight chain or branched, cyclic or noncyclic, substituted or unsubstituted, saturated or unsaturated lower chain alkyl, aryl and aralkyl moieties. Moreover, cyclic lower chain alkyl, aryl and aralkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

Representative R$_1$, R$_2$, R$_3$, R$_4$, R$_5$, R$_6$, R$_7$, R$_8$ and R$_9$ moieties specifically include (but are not limited to) —OH, —OR, —COR, —COOR, —CONH$_2$, —CONR, —CONRR, —NH$_2$, —NHR, —NRR, —SO$_2$R and —COSR, wherein each occurrence of R is as defined above.

In a further embodiment, and in addition to being an amino acid side chain moiety or derivative thereof (or the remainder of the compound in the case of R$_1$, R$_2$, R$_3$, R$_5$, R$_6$, R$_7$, R$_8$ and R$_9$), R$_1$, R$_2$, R$_3$, R$_4$, R$_5$, R$_6$, R$_7$, R$_8$ or R$_9$ may be a linker facilitating the linkage of the compound to another moiety or compound. For example, the compounds of this invention may be linked to one or more known compounds, such as biotin, for use in diagnostic or screening assay. Furthermore, R$_1$, R$_2$, R$_3$, R$_4$, R$_5$, R$_6$, R$_7$, R$_8$ or R$_9$ may be a linker joining the compound to a solid support (such as a support used in solid phase peptide synthesis) or alternatively, may be the support itself. In this embodiment, linkage to another moiety or compound, or to a solid support, is preferable at the R$_1$, R$_2$, R$_7$ or R$_8$, or R$_9$ position, and more preferably at the R$_1$ or R$_2$ position.

In the embodiment wherein A is —CHR$_3$—, B is —(C=O)—, D is —(CHR$_5$)—, E is —(C=O)—, and G is —XR$_7)_n$—, the reverse turn mimetic compound of this invention has the following formula (II):

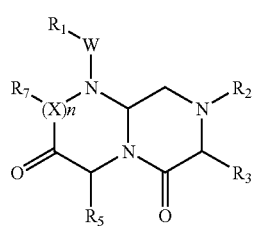

(II)

wherein R$_1$, R$_2$, R$_3$, R$_5$, R$_7$, W, X and n are as defined above. In a preferred embodiment, R$_1$, R$_2$ and R$_7$ represent the remainder of the compound, and R$_3$ or R$_5$ is selected from an amino acid side chain moiety.

In the embodiment wherein A is —(C=O)—, B is —(CHR$_4$)—, D is —(C=O)—, E is -(ZR$_6$)—, G is —(C=O)—(XR$_9$)—, the reverse turn mimetic compound of this invention has the following general formula (III):

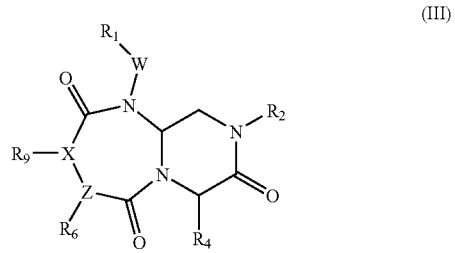

(III)

wherein R$_1$, R$_2$, R$_4$, R$_6$, R$_9$, W and X are as defined above, Z is nitrogen or CH (when Z is CH, then X is nitrogen). In a preferred embodiment, R$_1$, R$_2$, R$_6$ and R$_9$ represent the remainder of the compound, and R$_4$ is selected from an amino acid side chain moiety.

In a more specific embodiment wherein A is —(C=O)—, B is —(CHR$_4$)—, D is —(C=O)—, E is -(ZR$_6$)—, and G is (XR$_7)_n$—, the reverse turn mimetic compound of this invention has the following formula (IV):

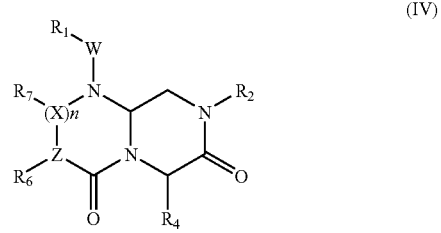

(IV)

wherein R$_1$, R$_2$, R$_4$, R$_6$, R$_7$, W, X and n are as defined above, and Z is nitrogen or CH (when Z is nitrogen, then n is zero, and when Z is CH, then X is nitrogen and n is not zero). In a preferred embodiment, R$_1$, R$_2$, R$_6$ and R$_7$ represent the remainder of the compound, and R$_4$ is selected from an amino acid side chain moiety. In one aspect, R$_6$ or R$_7$ is selected from an amino acid side chain moiety when Z and X are both CH.

These compounds may be prepared by utilizing appropriate starting component molecules (hereinafter referred to as "component pieces"). Briefly, in the synthesis of reverse-turn mimetic structures having formula (I), first and second component pieces are coupled to form a combined first-second intermediate, if necessary, third and/or fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the reverse-turn mimetic structures of this invention. Alternatively, the reverse-turn mimetic structures of formula (I) may be prepared by sequential coupling of the individual component pieces either stepwise in solution or by solid phase synthesis as commonly practiced in solid phase peptide synthesis.

Specific component pieces and the assembly thereof to prepare compounds of the present invention are illustrated in FIG. 1. For example, a "first component piece" may have the following formula S1:

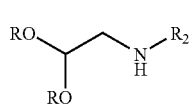
(S1)

wherein $R_2$ is as defined above, and R is a protective group suitable for use in peptide synthesis, where this protection group may be joined to a polymeric support to enable solid-phase synthesis. Suitable R groups include alkyl groups and, in a preferred embodiment, R is a methyl group. In FIG. 1, one of the R groups is a polymeric (solid) support, indicated by "Pol" in the Figure. Such first component pieces may be readily synthesized by reductive amination of $H_2N—R_2$ with $CH(OR)_2$—CHO, or by a displacement reaction between $H_2N—R_2$ and $CH(OR)_2—CH_2$-LG (wherein LG refers to a leaving group, e.g., a halogen (Hal) group).

A "second component piece" may have the following formula S2:

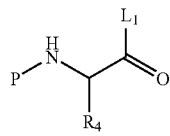
(S2)

where P is an amino protection group suitable for use in peptide synthesis, $L_1$ is hydroxyl or a carboxyl-activation group, and $R_4$ is as defined above. Preferred protection groups include t-butyl dimethylsilyl (TBDMS), t-butyloxycarbonyl (BOC), methyloxycarbonyl (MOC), 9H-fluorenylmethyloxycarbonyl (FMOC), and allyloxycarbonyl (Alloc). N-Protected amino acids are commercially available; for example, FMOC amino acids are available from a variety of sources. In order for the second component piece to be reactive with the first component piece, $L_1$ is a carboxyl-activation group, and the conversion of carboxyl groups to activated carboxyl groups may be readily achieved by methods known in the art for the activation of carboxyl groups. Suitable activated carboxylic acid groups include acid halides where $L_1$ is a halide such as chloride or bromide, acid anhydrides where $L_1$ is an acyl group such as acetyl, reactive esters such as an N-hydroxysuccinimide esters and pentafluorophenyl esters, and other activated intermediates such as the active intermediate formed in a coupling reaction using a carbodiimide such as dicyclohexylcarbodiimide (DCC). Accordingly, commercially available N-protected amino acids may be converted to carboxylic activated forms by means-known to one of skill in the art.

In the case of the azido derivative of an amino acid serving as the second component piece, such compounds may be prepared from the corresponding amino acid by the reaction disclosed by Zaloom et al. (*J. Org. Chem.* 46:5173-76, 1981).

Alternatively, the first component piece of the invention may have the following formula S1':

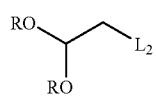
(S1')

wherein R is as defined above and $L_2$ is a leaving group such as halogen atom or tosyl group, and the second component piece of the invention may have the following formula S2':

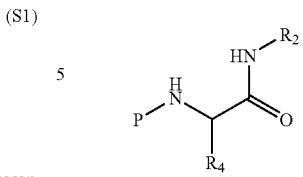
(S2')

wherein $R_2$, $R_4$ and P are as defined above,

A "third component piece" of this invention may have the following formula S3:

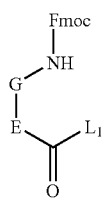
(S3)

where G, E, $L_1$ and $L_2$ are as defined above. Suitable third component pieces are commercially available from a variety of sources or can be prepared by methods well known in organic chemistry.

Figure 2:
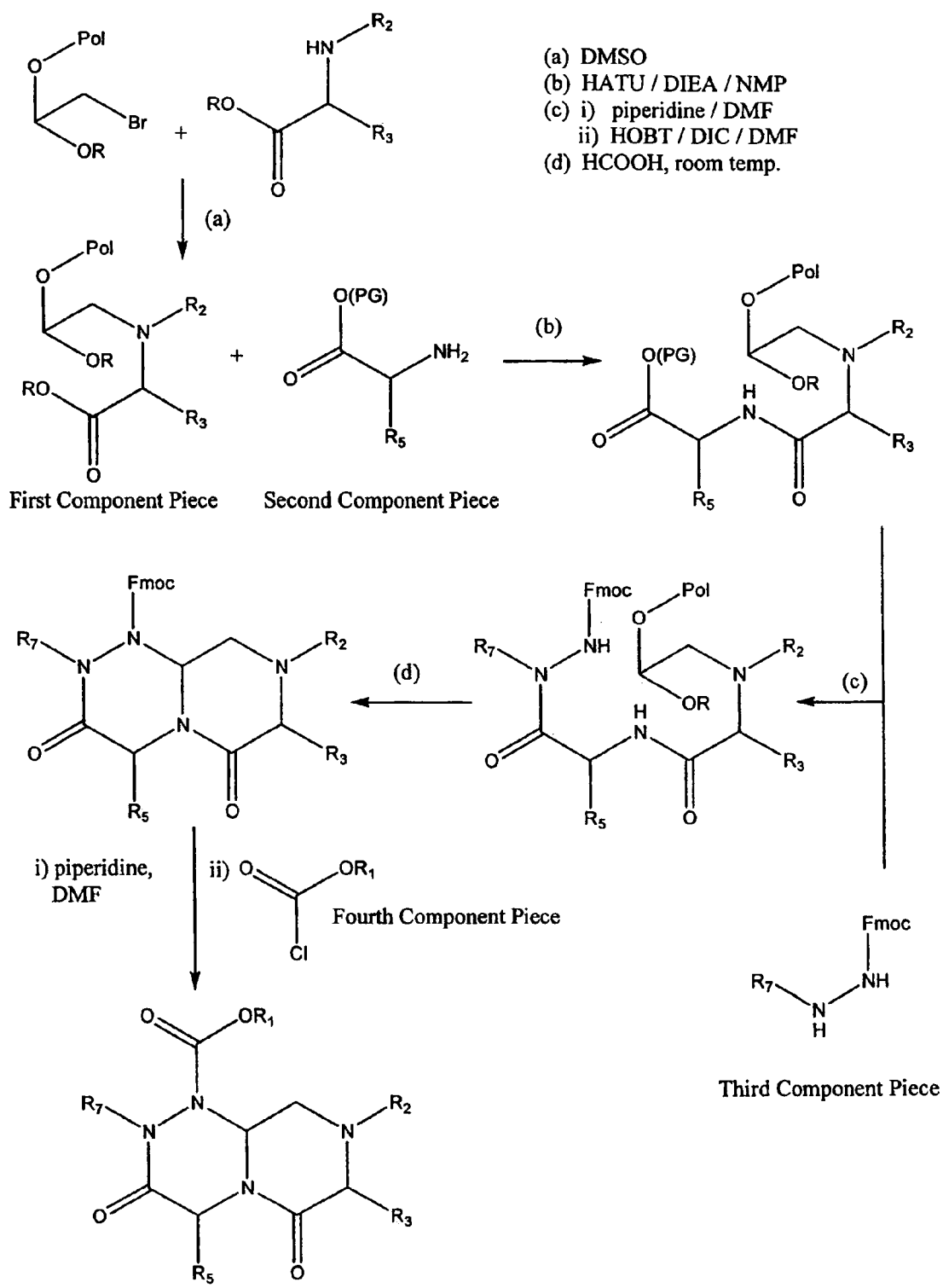
FIG. 2 provides a general synthetic scheme for preparing reverse-turn mimetics of the present invention.

In FIG. 1, the compound of formula (1) has —(C=O)— for A, —(CHR$_4$)— for B, —(C=O)— for D, and —(CR$_6$)— for E. Compounds of formula (1) wherein a carbonyl group is at position B and an R group is at position B, i.e., compounds wherein A is —(CHR$_3$)— and B is —(C=O)—, may be prepared in a manner analogous to that shown in FIG. 1, as illustrated in FIG. 2. FIG. 2 also illustrates adding a fourth component piece to the first-second-third component intermediate, rather than attaching the fourth component piece to the third component piece prior to reaction with the first-second intermediate piece. In addition, FIG. 2 illustrates the prepartion of compounds of the present invention wherein D is —(CHR$_5$)— (rather than —(C=O)— as in FIG. 1), and E is —(C=O)— (rather than —(CHR$_6$)— as in FIG. 1). Finally, FIG. 2 illustrates the preparation of compounds wherein G is NR$_7$.

Thus, as illustrated above, the reverse-turn mimetic compounds of formula (I) may be synthesized by reacting a first component piece with a second component piece to yield a combined first-second intermediate, followed by reacting the combined first-second intermediate with third component pieces sequentially to provide a combined first-second-third-fourth intermediate, and then cyclizing this intermediate to yield the reverse-turn mimetic structure.

The syntheses of representative component pieces of this invention are described in Preparation Examples and working Examples.

The reverse-turn mimetic structures of formula (III) and (IV) may be made by techniques analogous to the modular component synthesis disclosed above, but with appropriate modifications to the component pieces.

The reverse-turn mimetic structures of the present invention are useful as bioactive agents, such as diagnostic, prophylactic, and therapeutic agents. For example, the reverse-turn mimetic structures of the present invention may be used for modulating a cell signaling transcription factor related peptides in a warm-blooded animal, by a method comprising administering to the animal an effective amount of the compound of formula (I).

Further, the reverse-turn mimetic structures of the present invention may also be effective for inhibiting peptide binding to PTB domains in a warm-blooded animal; for modulating G protein coupled receptor (GPCR) and ion channel in a warm-blooded animal; for modulating cytokines in a warm-blooded animal.

Meanwhile, it has been found that the compounds of the formula (I), especially compounds of formula (VI) are effective for inhibiting or treating disorders modulated by Wnt-signaling pathway, such as cancer, especially colorectal cancer.

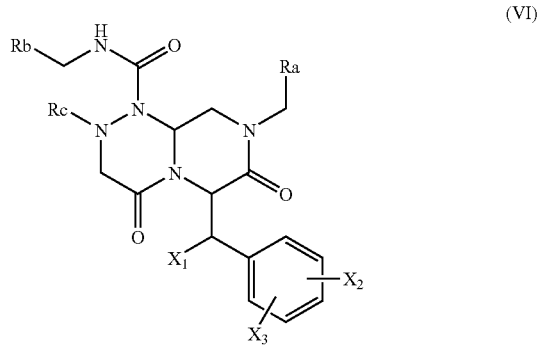

(VI)

wherein $R_a$ is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group having 8 to 11 ring members, which may have 1 to 3 heteroatoms selected from nitrogen, oxygen or sulfur; $R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy groups; Rc is a saturated or unsaturated $C_{1-6}$alkyl, $C_{1-6}$alkoxy, perfluoro $C_{1-6}$alkyl group; and $X_1$, $X_2$, and $X_3$ may be the same or different and independently selected from hydrogen, hydroxyl, and halide.

In another aspect, it is an object of the present invention to provide a pharmaceutical composition comprising a safe and effective amount of the compound having general formula (VI) and pharmaceutically acceptable carrier, which can be used for treatment of disorders modulated by Wnt signaling pathway, especially by TCF4-β-catenin-CBP complex.

Further, the present invention is to provide a method for inhibiting the growth of tumor cells by using the above-described composition of the present invention; a method for inducing apoptosis of tumor cells by using the above-described composition of the present invention; a method for treating a disorder modulated by TCF4-β catenin-CBP complex by using the above-described composition of the present invention; and a method of treating cancer such as colorectal cancer by administering the composition of the present invention together with other anti-cancer agent such as 5-fluorouracil (5-FU), taxol, cisplatin, mitomycin C, tegafur, raltitrexed, capecitabine, and irinotecan, etc.

In a preferred embodiment of the present invention, the compound of the present invention has a (6S,10R)-configuration as follows:

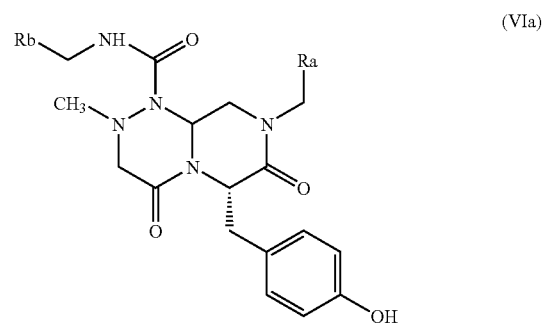

(VIa)

wherein $R_a$ and $R_b$ have the same meanings as defined above.

In another aspect of this invention, prodrugs derived from compounds having general formula (I) are disclosed. The prodrugs generally increase aqueous solubility and thus bioavailability of compounds having general formula (I). In certain embodiments, the prodrugs of the present invention have the following general formula (VII):

(VI)—Y—$R_{10}$ wherein (VI) is general formula (VI) as described above; Y is oxygen, sulfur, or nitrogen of a group selected from $R_a$, $R_b$, $R_c$, $X_1$, $X_2$ and $X_3$; $R_{10}$ is phosphate, hemisuccinate, hemimalate, phosphoryloxymethyloxycarbonyl, dimethylaminoacetate, dimethylaminoalkylcarbamate, hydroxyalkyl, amino acid, glycosyl, substituted or unsubstituted piperidine oxycarbonyl, or a salt thereof; and wherein the prodrugs are capable of serving as a substrate for a phosphatase or a carboxylase and are thereby converted to compounds having general formula (VI). In some embodiments, $R_{10}$ of the general formula (VII) is not an amino acid group or a phosphoamino acid group.

In another aspect of this invention, libraries containing reverse-turn mimetic structures of the present invention are disclosed. Once assembled, the libraries of the present invention may be screened to identify individual members having bioactivity. Such screening of the libraries for bioactive members may involve; for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with the target of interest, are referred to herein as "bioactive library members" or "bioactive mimetics". For example, a bioactive mimetic may be a library member which is capable of binding to an antibody or receptor, or which is capable of inhibiting an enzyme, or which is capable of eliciting or antagonizing a functional response associated, for example, with a cell line. In other words, the screening of the libraries of the present invention determines which library members are capable of interacting with one or more biological targets of interest.

Furthermore, when interaction does occur, the bioactive mimetic (or mimetics) may then be identified from the library members. The identification of a single (or limited number) of bioactive mimetic(s) from the library yields reverse-turn mimetic structures which are themselves biologically active, and thus are useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the first, second and third component pieces of this invention. More specifically, any amino acid sequence may be added to the N-terminal and/or C-terminal of the conformationally constrained reverse-turn mimetic. To this end, the mimetics may be synthesized on a solid support (such as PAM resin) by known techniques (see, e.g., John M. Stewart and Janis D. Young, Solid Phase Peptide Synthesis, 1984, Pierce Chemical Comp., Rockford, Ill.) or on a silyl-linked resin by alcohol attachment (see Randolph et al., *J. Am Chem. Soc.* 117:5712-14, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained reverse-turn is added to the sequence. A suitable conformationally constrained reverse-turn mimetic structure which has been previously synthesized by solution synthesis techniques may then be added as the next "amino acid" to the solid phase synthesis (i.e., the conformationally constrained reverse-turn mimetic, which has both an N-terminus and a C-terminus, may be utilized as the next amino acid to be added to the linear peptide). Upon incorporation of the conformationally constrained reverse-turn mimetic structures into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained reverse-turn mimetic structures in solution using known solution coupling techniques.

In another aspect of this invention, methods for constructing the libraries are disclosed. Traditional combinatorial chemistry techniques (see, e.g., Gallop et al., *J. Med. Chem.* 37:1233-1251, 1994) permit a vast number of compounds to be rapidly prepared by the sequential combination of reagents to a basic molecular scaffold. Combinatorial techniques have been used to construct peptide libraries derived from the naturally occurring amino acids. For example, by taking 20 mixtures of 20 suitably protected and different amino acids and coupling each with one of the 20 amino acids, a library of 400 (i.e., $20^2$) dipeptides is created. Repeating the procedure seven times results in the preparation of a peptide library comprised of about 26 billion (i.e., $20^8$) octapeptides.

Specifically, synthesis of the peptide mimetics of the library of the present invention may be accomplished using known peptide synthesis techniques, for example, the General Scheme of [4,4,0] Reverse-Turn Mimetic Library as follows:

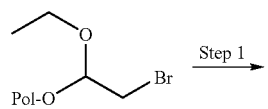

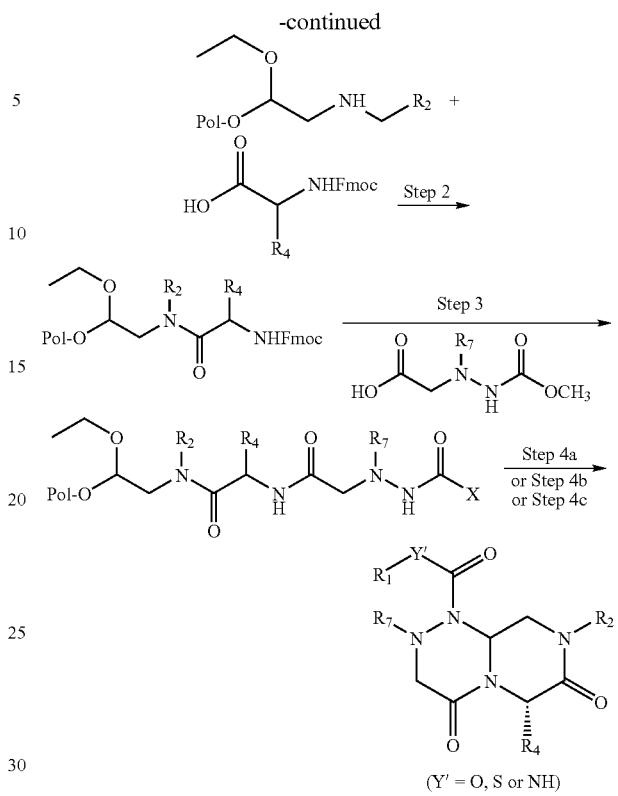

Synthesis of the peptide mimetics of the libraries of the present invention was accomplished using a FlexChem Reactor Block which has 96 well plates by known techniques. In the above scheme 'Pol' represents a bromoacetal resin (Advanced ChemTech) and detailed procedure is illustrated below.

Step 1

A bromoacetal resin (37 mg, 0.98 mmol/g) and a solution of $R_2$-amine in DMSO (1.4 mL) were placed in a Robbins block (FlexChem) having 96 well plates. The reaction mixture was shaken at 60° C. using a rotating oven [Robbins Scientific] for 12 hours. The resin was washed with DMF, MeOH, and then DCM Step 2

A solution of commercial available FmocAmino Acids (4 equiv.), PyBob (4 equiv:), HOAt (4 equiv.), and DIEA (12 equiv.) in DMF was added to the resin. After the reaction mixture was shaken for 12 hours at room temperature, the resin was washed with DMF, MeOH, and then DCM.

Step 3

To the resin swollen by DMF before reaction was added 25% piperidine in DMF and the reaction mixture was shaken for 30 min at room temperature. This deprotection step was repeated again and the resin was washed with DMF, Methanol, and then DCM. A solution of hydrazine acid (4 equiv.), HOBt (4 equiv.), and DIC (4 equiv.) in DMF was added to the resin and the reaction mixture was shaken for 12 hours at room temperature. The resin was washed with DMF, MeOH, and then DCM.

Step 4a (where hydrazine Acid is MOC Carbamate)

The resin obtained in Step 3 was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing.

Step 4b (where Fmoc Hydrazine Acid is Used to Make Urea Through Isocynate)

To the resin swollen by DMF before reaction was added 25% piperidine in DMF and the reaction mixture was shaken for 30 min at room temperature. This deprotection step was repeated again and the resin was washed with DMF, Methanol, then DCM. To the resin swollen by DCM before reaction was added isocynate (5 equiv.) in DCM. After the reaction mixture was shaken for 12 hours at room temperature the resin was washed with DMF, MeOH, then DCM. The resin was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing.

Step 4c (where Fmoc-Hydrazine Acid is Used to Make Urea Through Active Carbamate)

To the resin swollen by DMF before reaction was added 25% piperidine in DMF and the reaction mixture was shaken for 30 min at room temperature. This deprotection step was repeated again and the resin was washed with DMF, MeOH, and then DCM. To the resin swollen by DCM before reaction was added p-nitrophenyl chloroformate (5 equiv.) and diisopropyl ethylamine (5 equiv.) in DCM. After the reaction mixture was shaken for 12 hours at room temperature, the resin was washed with DMF, MeOH, and then DCM. To the resin was added primary amines in DCM for 12 hours at room temperature and the resin was washed with DMF, MeOH, and then DCM. After reaction the resin was treated with formic acid (1.2 mL each well) for 18 hours at room temperature. After the resin was removed by filtration, the filtrate was condensed under a reduced pressure using SpeedVac [SAVANT] to give the product as oil. The pro duct was diluted with 50% water/acetonitrile and then lyophilized after freezing.

To generate these block libraries the key intermediate hydrazine acids were synthesized according to the procedure illustrated in Preparation Examples.

Tables 2A and 2B show a [4,4,0] Reverse turn mimetics library which can be prepared according to the present invention, of which representative preparation is given in Example 4.

TABLE 2A

THE [4,4,0]REVERSE TURN MIMETICS LIBRARY

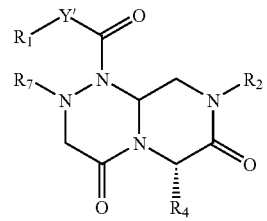

| No | $R_2$ | $R_4$ | $R_7$ | $R_1$-Y' | Mol. Weight | M + H |
|---|---|---|---|---|---|---|
| 1 | 2,4-$Cl_{2\text{-}benzyl}$ | 4-HO-benzyl | Allyl | $OCH_3$ | 533 | 534 |
| 2 | 2,4-$Cl_{2\text{-}benzyl}$ | 4-$NO_2$-benzyl | Allyl | $OCH_3$ | 562 | 563 |
| 3 | 2,4-$Cl_2$-benzyl | 2,4-$F_2$-benzyl | Allyl | $OCH_3$ | 553 | 554 |
| 4 | 2,4-$Cl_2$-benzyl | 4-Cl-benzyl | Allyl | $OCH_3$ | 552 | 553 |
| 5 | 2,4-$Cl_2$-benzyl | 2,2-bisphenylethyl | Allyl | $OCH_3$ | 594 | 595 |
| 6 | 2,4-$Cl_2$-benzyl | 3-t-Bu-4-HO-benzy | Allyl | $OCH_3$ | 590 | 591 |
| 7 | 2,4-$Cl_2$-benzyl | 4-Me-benzyl | Allyl | $OCH_3$ | 531 | 532 |
| 8 | 2,4-$Cl_2$-benzyl | Cyclohexylmethyl | Allyl | $OCH_3$ | 523 | 524 |
| 9 | 2,4-$Cl_2$-benzyl | 4-F-benzyl | Allyl | $OCH_3$ | 535 | 536 |
| 10 | 2,4-$Cl_2$-benzyl | 2-Cl-benzyl | Allyl | $OCH_3$ | 552 | 553 |
| 11 | 2,4-$Cl_2$-benzyl | 2,4-$Cl_2$-benzyl | Allyl | $OCH_3$ | 586 | 587 |
| 12 | 2,4-$Cl_2$-benzyl | Naphth-2-ylmethyl | Allyl | $OCH_3$ | 567 | 568 |
| 13 | 2,4-$Cl_2$-benzyl | 4-HO-benzyl | Benzyl | $OCH_3$ | 583 | 584 |
| 14 | 2,4-$Cl_2$-benzyl | 4-$NO_2$-benzyl | Benzyl | $OCH_3$ | 612 | 613 |
| 15 | 2,4-$Cl_2$-benzyl | 2,4-$F_2$-benzyl | Benzyl | $OCH_3$ | 603 | 604 |
| 16 | 2,4-$Cl_2$-benzyl | 4-Cl-benzyl | Benzyl | $OCH_3$ | 602 | 603 |
| 17 | 2,4-$Cl_2$-benzyl | 2,2-bisphenylethyl | Benzyl | $OCH_3$ | 644 | 645 |
| 18 | 2,4-$Cl_2$-benzyl | 3-t-Bu-4-HO-benzy | Benzyl | $OCH_3$ | 640 | 641 |
| 19 | 2,4-$Cl_2$-benzyl | 4-Me-benzyl | Benzyl | $OCH_3$ | 582 | 583 |
| 20 | 2,4-$Cl_2$-benzyl | Cyclohexylmethyl | Benzyl | $OCH_3$ | 574 | 575 |
| 21 | 2,4-$Cl_2$-benzyl | 4-F-benzyl | Benzyl | $OCH_3$ | 585 | 586 |
| 22 | 2,4-$Cl_2$-benzyl | 2-Cl-benzyl | Benzyl | $OCH_3$ | 602 | 603 |
| 23 | 2,4-$Cl_2$-benzyl | 2,4-$Cl_2$-benzyl | Benzyl | $OCH_3$ | 636 | 637 |
| 24 | 2,4-$Cl_2$-benzyl | Naphth-2-ylmethyl | Benzyl | $OCH_3$ | 618 | 619 |
| 25 | 2,4-$Cl_2$-benzyl | 4-HO-benzyl | Allyl | $OCH_3$ | 479 | 480 |
| 26 | 2,4-$Cl_2$-benzyl | 4-$NO_2$-benzyl | Allyl | $OCH_3$ | 508 | 509 |
| 27 | 2,4-$Cl_2$-benzyl | 2,4-$F_2$-benzyl | Allyl | $OCH_3$ | 499 | 500 |
| 28 | 2,4-$Cl_2$-benzyl | 4-Cl-benzyl | Allyl | $OCH_3$ | 497 | 498 |
| 29 | Phenethyl | 2,2-bisphenylethyl | Allyl | $OCH_3$ | 539 | 540 |
| 30 | Phenethyl | 3-t-Bu-4-HO-benzy | Allyl | $OCH_3$ | 535 | 536 |
| 31 | Phenethyl | 4-Me-benzyl | Allyl | $OCH_3$ | 477 | 478 |

TABLE 2A-continued

THE [4,4,0]REVERSE TURN MIMETICS LIBRARY

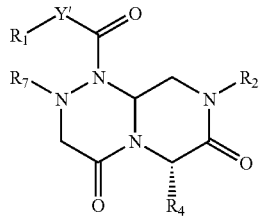

| No | R₂ | R₄ | R₇ | R₁-Y' | Mol. Weight | M + H |
|----|----|----|----|-------|-------------|-------|
| 32 | Phenethyl | Cyclohexylmethyl | Allyl | OCH₃ | 469 | 470 |
| 33 | Phenethyl | 4-F-benzyl | Allyl | OCH₃ | 481 | 482 |
| 34 | Phenethyl | 2-Cl-benzyl | Allyl | OCH₃ | 497 | 498 |
| 35 | Phenethyl | 2,4-Cl₂-benzyl | Allyl | OCH₃ | 531 | 532 |
| 36 | Phenethyl | Naphth-2-ylmethyl | Allyl | OCH₃ | 513 | 514 |
| 37 | Phenethyl | 4-HO-benzyl | Benzyl | OCH₃ | 529 | 530 |
| 38 | Phenethyl | 4-NO₂-benzyl | Benzyl | OCH₃ | 558 | 559 |
| 39 | Phenethyl | 2,4-F₂-benzyl | Benzyl | OCH₃ | 549 | 550 |
| 40 | Phenethyl | 4-Cl-benzyl | Benzyl | OCH₃ | 547 | 548 |
| 41 | Phenethyl | 2,2-bisphenylethyl | Benzyl | OCH₃ | 589 | 590 |
| 42 | Phenethyl | 3-t-Bu-4-HO-benzy | Benzyl | OCH₃ | 585 | 586 |
| 43 | Phenethyl | 4-Me-benzyl | Benzyl | OCH₃ | 527 | 528 |
| 44 | Phenethyl | Cyclohexyl-methyl | Benzyl | OCH₃ | 519 | 520 |
| 45 | Phenethyl | 4-F-benzyl | Benzyl | OCH₃ | 531 | 532 |
| 46 | Phenethyl | 2-Cl-benzyl | Benzyl | OCH₃ | 547 | 548 |
| 47 | Phenethyl | 2,4-Cl₂-benzyl | Benzyl | OCH₃ | 582 | 583 |
| 48 | Phenethyl | Naphth-2-ylmethyl | Benzyl | OCH₃ | 563 | 564 |
| 49 | Phenethyl | 4-HO-benzyl | Allyl | OCH₃ | 497 | 498 |
| 50 | Phenethyl | 4-NO₂-benzyl | Allyl | OCH₃ | 526 | 527 |
| 51 | Phenethyl | 2,4-F₂-benzyl | Allyl | OCH₃ | 517 | 518 |
| 52 | Phenethyl | 4-Cl-benzyl | Allyl | OCH₃ | 515 | 516 |
| 53 | 4-F-phenylethyl | 2,2-bisphenylethyl | Allyl | OCH₃ | 557 | 558 |
| 54 | 4-F-phenylethyl | 3-t-Bu-4-HO-benzyl | Allyl | OCH₃ | 553 | 554 |
| 55 | 4-F-phenylethyl | 4-Me-benzyl | Allyl | OCH₃ | 495 | 496 |
| 56 | 4-F-phenylethyl | Cyclohexyl-methyl | Allyl | OCH₃ | 487 | 488 |
| 57 | 4-F-phenylethyl | 4-F-benzyl | Allyl | OCH₃ | 499 | 500 |
| 58 | 4-F-phenylethyl | 2-Cl-benzyl | Allyl | OCH₃ | 515 | 516 |
| 59 | 4-F-phenylethyl | 2,4-Cl₂-benzyl | Allyl | OCH₃ | 549 | 550 |
| 60 | 4-F-phenylethyl | Naphth-2-ylmethyl | Allyl | OCH₃ | 531 | 532 |
| 61 | 4-F-phenylethyl | 4-HO-benzyl | Benzyl | OCH₃ | 547 | 548 |
| 62 | 4-F-phenylethyl | 4-NO₂-benzyl | Benzyl | OCH₃ | 576 | 577 |
| 63 | 4-F-phenylethyl | 2,4-F₂-benzyl | Benzyl | OCH₃ | 567 | 568 |
| 64 | 4-F-phenylethyl | 4-Cl-benzyl | Benzyl | OCH₃ | 565 | 566 |
| 65 | 4-F-phenylethyl | 2,2-bisphenylethyl | Benzyl | OCH₃ | 607 | 608 |
| 66 | 4-F-phenylethyl | 3-t-Bu-4-HO-benzyl | Benzyl | OCH₃ | 603 | 604 |
| 67 | 4-F-phenylethyl | 4-Me-benzyl | Benzyl | OCH₃ | 545 | 546 |
| 68 | 4-F-phenylethyl | Cyclohexyl-methyl | Benzyl | OCH₃ | 537 | 538 |
| 69 | 4-F-phenylethyl | 4-F-benzyl | Benzyl | OCH₃ | 549 | 550 |
| 70 | 4-F-phenylethyl | 2-Cl-benzyl | Benzyl | OCH₃ | 565 | 566 |
| 71 | 4-F-phenylethyl | 2,4-Cl₂-benzyl | Benzyl | OCH₃ | 599 | 600 |
| 72 | 4-F-phenylethyl | Naphth-2-ylmethyl | Benzyl | OCH₃ | 581 | 582 |
| 73 | 4-F-phenylethyl | 4-HO-benzyl | Allyl | OCH₃ | 509 | 510 |
| 74 | 4-F-phenylethyl | 4-NO₂-benzyl | Allyl | OCH₃ | 538 | 539 |
| 75 | 4-F-phenylethyl | 2,4-F₂-benzyl | Allyl | OCH₃ | 529 | 530 |
| 76 | 4-F-phenylethyl | 4-Cl-benzyl | Allyl | OCH₃ | 527 | 528 |
| 77 | 4-MeO-phenylethyl | 2,2-bisphenylethyl | Allyl | OCH₃ | 569 | 570 |
| 78 | 4-MeO-phenylethyl | 3-t-Bu-4-HO-benzyl | Allyl | OCH₃ | 565 | 566 |
| 79 | 4-MeO-phenylethyl | 4-Me-benzyl | Allyl | OCH₃ | 507 | 508 |
| 80 | 4-MeO-phenylethyl | Cyclohexyl-methyl | Allyl | OCH₃ | 499 | 500 |
| 82 | 4-MeO-phenylethyl | 2-Cl-benzyl | Allyl | OCH₃ | 527 | 528 |
| 83 | 4-MeO-phenylethyl | 2,4-Cl₂-benzyl | Allyl | OCH₃ | 561 | 562 |
| 84 | 4-MeO-phenylethyl | Naphth-2-ylmethyl | Allyl | OCH₃ | 543 | 544 |
| 85 | 4-MeO-phenylethyl | 4-HO-benzyl | Benzyl | OCH₃ | 559 | 560 |
| 86 | 4-MeO-phenylethyl | 4-NO₂-benzyl | Benzyl | OCH₃ | 588 | 589 |
| 87 | 4-MeO-phenylethyl | 2,4-F₂-benzyl | Benzyl | OCH₃ | 579 | 580 |
| 88 | 4-MeO-phenylethyl | 4-Cl-benzyl | Benzyl | OCH₃ | 577 | 578 |
| 89 | 4-MeO-phenylethyl | 2,2-bisphenylethyl | Benzyl | OCH₃ | 619 | 620 |
| 90 | 4-MeO-phenylethyl | 3-t-Bu-4-HO-benzyl | Benzyl | OCH₃ | 615 | 616 |
| 91 | 4-MeO-phenylethyl | 4-Me-benzyl | Benzyl | OCH₃ | 557 | 558 |
| 92 | 4-MeO-phenylethyl | Cyclohexylmethyl | Benzyl | OCH₃ | 549 | 550 |
| 93 | 4-MeO-phenylethyl | 4-F-benzyl | Benzyl | OCH₃ | 561 | 562 |
| 94 | 4-MeO-phenylethyl | 2-Cl-benzyl | Benzyl | OCH₃ | 577 | 578 |
| 95 | 4-MeO-phenylethyl | 2,4-Cl₂-benzyl | Benzyl | OCH₃ | 612 | 613 |

TABLE 2A-continued

THE [4,4,0]REVERSE TURN MIMETICS LIBRARY

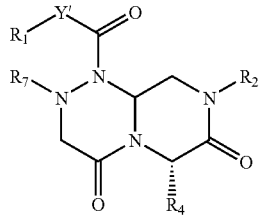

| No | R2 | R4 | R7 | R1-Y' | Mol. Weight | M + H |
|---|---|---|---|---|---|---|
| 96 | 4-MeO-phenylethyl | Naphth-2-ylmethyl | Benzyl | OCH3 | 593 | 594 |
| 97 | Isoamyl | 4-HO-benzyl | Styrylmethyl | OCH3 | 521 | 522 |
| 98 | Isoamyl | 4-NO2-benzyl | Styrylmethyl | OCH3 | 550 | 551 |
| 99 | Isoamyl | 2,4-F2-benzyl | Styrylmethyl | OCH3 | 541 | 542 |
| 100 | Isoamyl | 4-Cl-benzyl | Styrylmethyl | OCH3 | 539 | 540 |
| 101 | Isoamyl | 2,2-bisphenylethyl | Styrylmethyl | OCH3 | 581 | 582 |
| 102 | Isoamyl | 3-t-Bu-4-HO-benzyl | Styrylmethyl | OCH3 | 497 | 498 |
| 103 | Isoamyl | 4-Me-benzyl | Styrylmethyl | OCH3 | 519 | 520 |
| 104 | Isoamyl | Cyclohexylmethyl | Styrylmethyl | OCH3 | 511 | 512 |
| 105 | Isoamyl | 4-F-benzyl | Styrylmethyl | OCH3 | 523 | 524 |
| 106 | Isoamyl | 2-Cl-benzyl | Styrylmethyl | OCH3 | 539 | 540 |
| 107 | Isoamyl | 2,4-Cl2-benzyl | Styrylmethyl | OCH3 | 574 | 575 |
| 108 | Isoamyl | Naphth-2-ylmethyl | Styrylmethyl | OCH3 | 555 | 556 |
| 109 | Isoamyl | 4-HO-benzyl | 2,6-Cl2-benzyl | OCH3 | 563 | 564 |
| 110 | Isoamyl | 4-NO2-benzyl | 2,6-Cl2-benzyl | OCH3 | 592 | 593 |
| 111 | Isoamyl | 2,4-F2-benzyl | 2,6-Cl2-benzyl | OCH3 | 583 | 584 |
| 112 | Isoamyl | 4-Cl-benzyl | 2,6-Cl2-benzyl | OCH3 | 582 | 583 |
| 113 | Isoamyl | 2,2-bisphenylethyl | 2,6-Cl2-benzyl | OCH3 | 624 | 625 |
| 114 | isoamyl | 3-t-Bu-4-HO-benzyl | 2,6-Cl2-benzyl | OCH3 | 540 | 541 |
| 115 | Isoamyl | 4-Me-benzyl | 2,6-Cl2-benzyl | OCH3 | 562 | 563 |
| 116 | Isoamyl | Cyclohexylmethyl | 2,6-Cl2-benzyl | OCH3 | 554 | 555 |
| 117 | Isoamyl | 4-F-benzyl | 2,6-Cl2-benzyl | OCH3 | 565 | 566 |
| 118 | Isoamyl | 2-Cl-benzyl | 2,6-Cl2-benzyl | OCH3 | 582 | 583 |
| 119 | Isoamyl | 2,4-Cl2-benzyl | 2,6-Cl2-benzyl | OCH3 | 616 | 617 |
| 120 | Isoamyl | Naphth-2-ylmethyl | 2,6-Cl2-benzyl | OCH3 | 598 | 599 |
| 121 | 3-MeO-propyl | 4-HO-benzyl | Styrylmethyl | OCH3 | 523 | 524 |
| 122 | 3-MeO-propyl | 4-NO2-benzyl | Styrylmethyl | OCH3 | 552 | 553 |
| 123 | 3-MeO-propyl | 2,4-F2-benzyl | Styrylmethyl | OCH3 | 543 | 544 |
| 124 | 3-MeO-propyl | 4-Cl-benzyl | Styrylmethyl | OCH3 | 541 | 542 |
| 125 | 3-MeO-propyl | 2,2-bisphenylethyl | Styrylmethyl | OCH3 | 583 | 584 |
| 126 | 3-MeO-propyl | 3-t-Bu-4-HO-benzyl | Styrylmethyl | OCH3 | 499 | 500 |
| 127 | 3-MeO-propyl | 4-Me-benzyl | Styrylmethyl | OCH3 | 521 | 522 |
| 128 | 3-MeO-propyl | Cyclohexyl-methyl | Styrylmethyl | OCH3 | 513 | 514 |
| 129 | 3-MeO-propyl | 4-F-benzyl | Styrylmethyl | OCH3 | 525 | 526 |
| 130 | 3-MeO-propyl | 2-Cl-benzyl | Styrylmethyl | OCH3 | 541 | 542 |
| 131 | 3-MeO-propyl | 2,4-Cl2-benzyl | Styrylmethyl | OCH3 | 575 | 576 |
| 132 | 3-MeO-propyl | Naphth-2-ylmethyl | Styrylmethyl | OCH3 | 557 | 558 |
| 133 | 3-MeO-propyl | 4-HO-benzyl | 2,6-Cl2-benzyl | OCH3 | 565 | 566 |
| 134 | 3-MeO-propyl | 4-NO2-benzyl | 2,6-Cl2-benzyl | OCH3 | 594 | 595 |
| 135 | 3-MeO-propyl | 2,4-F2-benzyl | 2,6-Cl2-benzyl | OCH3 | 585 | 86 |
| 136 | 3-MeO-propyl | 4-Cl-benzyl | 2,6-Cl2-benzyl | OCH3 | 584 | 585 |
| 137 | 3-MeO-propyl | 2,2-bisphenylethyl | 2,6-Cl2-benzyl | OCH3 | 626 | 627 |
| 138 | 3-MeO-propyl | 3-t-Bu-4-HO-benzyl | 2,6-Cl2-benzyl | OCH3 | 541 | 542 |
| 139 | 3-MeO-propyl | 4-Me-benzyl | 2,6-Cl2-benzyl | OCH3 | 563 | 564 |
| 140 | 3-MeO-propyl | Cyclohexyl-methyl | 2,6-Cl2-benzyl | OCH3 | 556 | 557 |
| 141 | 3-MeO-propyl | 4-F-benzyl | 2,6-Cl2-benzyl | OCH3 | 567 | 568 |
| 142 | 3-MeO-propyl | 2-Cl-benzyl | 2,6-Cl2-benzyl | OCH3 | 584 | 585 |
| 143 | 3-MeO-propyl | 2,4-Cl2-benzyl | 2,6-Cl2-benzyl | OCH3 | 618 | 619 |
| 144 | 3-MeO-propyl | Naphth-2-ylmethyl | 2,6-Cl2-benzyl | OCH3 | 600 | 601 |
| 145 | 4-MeO-phenylethyl | 4-HO-benzyl | Styrylmethyl | OCH3 | 585 | 586 |
| 146 | 4-MeO-phenylethyl | 4-NO2-benzyl | Styrylmethyl | OCH3 | 614 | 615 |
| 147 | 4-MeO-phenylethyl | 2,4-F2-benzyl | Styrylmethyl | OCH3 | 605 | 606 |
| 148 | 4-MeO-phenylethyl | 4-Cl-benzyl | Styrylmethyl | OCH3 | 603 | 604 |
| 149 | 4-MeO-phenylethyl | 2,2-bisphenylethyl | Styrylmethyl | OCH3 | 645 | 646 |
| 150 | 4-MeO-phenylethyl | 3-t-Bu-4-HO-benzyl | Styrylmethyl | OCH3 | 561 | 562 |
| 151 | 4-MeO-phenylethyl | 4-Me-benzyl | Styrylmethyl | OCH3 | 583 | 584 |
| 152 | 4-MeO-phenylethyl | Cyclohexyl-methyl | Styrylmethyl | OCH3 | 575 | 576 |
| 153 | 4-MeO-phenylethyl | 4-F-benzyl | Styrylmethyl | OCH3 | 587 | 588 |
| 154 | 4-MeO-phenylethyl | 2-Cl-benzyl | Styrylmethyl | OCH3 | 603 | 604 |
| 155 | 4-MeO-phenylethyl | 2,4-Cl2-benzyl | Styrylmethyl | OCH3 | 638 | 639 |
| 156 | 4-MeO-phenylethyl | Naphth-2-ylmethyl | Styrylmethyl | OCH3 | 619 | 620 |
| 157 | 4-MeO-phenylethyl | 4-HO-benzyl | 2,6-Cl2-benzyl | OCH3 | 628 | 629 |
| 158 | 4-MeO-phenylethyl | 4-NO2-benzyl | 2,6-Cl2-benzyl | OCH3 | 657 | 658 |

TABLE 2A-continued

THE [4,4,0]REVERSE TURN MIMETICS LIBRARY

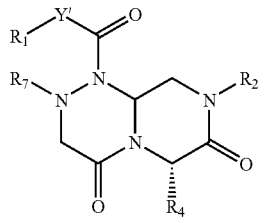

| No | R2 | R4 | R7 | R1-Y' | Mol. Weight | M + H |
|---|---|---|---|---|---|---|
| 159 | 4-MeO-phenylethyl | 2,4-F2-benzyl | 2,6-Cl2-benzyl | OCH3 | 648 | 649 |
| 160 | 4-MeO-phenylethyl | 4-Cl-benzyl | 2,6-Cl2-benzyl | OCH3 | 646 | 647 |
| 161 | 4-MeO-phenylethyl | 2,2-bisphenylethyl | 2,6-Cl2-benzyl | OCH3 | 688 | 689 |
| 162 | 4-MeO-phenylethyl | 3-t-Bu-4-HO-benzyl | 2,6-Cl2-benzyl | OCH3 | 604 | 605 |
| 163 | 4-MeO-phenylethyl | 4-Me-benzyl | 2,6-Cl2-benzyl | OCH3 | 626 | 627 |
| 164 | 4-MeO-phenylethyl | Cyclohexylmethyl | 2,6-Cl2-benzyl | OCH3 | 618 | 619 |
| 165 | 4-MeO-phenylethyl | 4-F-benzyl | 2,6-Cl2-benzyl | OCH3 | 630 | 631 |
| 166 | 4-MeO-phenylethyl | 2-Cl-benzyl | 2,6-Cl2-benzyl | OCH3 | 646 | 647 |
| 167 | 4-MeO-phenylethyl | 2,4-Cl2-benzyl | 2,6-Cl2-benzyl | OCH3 | 680 | 681 |
| 168 | 4-MeO-phenylethyl | Naphth-2-ylmethyl | 2,6-Cl2-benzyl | OCH3 | 662 | 663 |
| 169 | Tetrahydrofuran-2-ylmethyl | 4-HO-benzyl | Styrylmethyl | OCH3 | 535 | 536 |
| 170 | Tetrahydrofuran-2-ylmethyl | 4-NO2-benzyl | Styrylmethy | OCH3 | 564 | 565 |
| 171 | Tetrahydrofuran-2-ylmethyl | 2,4-F2-benzyl | Styrylmethyl | OCH3 | 555 | 556 |
| 172 | Tetrahydrofuran-2-ylmethyl | 4-Cl-benzyl | Styrylmethyl | OCH3 | 553 | 554 |
| 173 | Tetrahydrofuran-2-ylmethyl | 2,2-bisphenylethyl | Styrylmethyl | OCH3 | 595 | 596 |
| 174 | Tetrahydrofuran-2-ylmethyl | 3-t-Bu-4-HO-benzyl | Styrylmethyl | OCH3 | 511 | 512 |
| 175 | Tetrahydrofuran-2-ylmethyl | 4-Me-benzyl | Styrylmethyl | OCH3 | 533 | 534 |
| 176 | Tetrahydrofuran-2-ylmethyl | Cyclohexyl-methyl | Styrylmethyl | OCH3 | 525 | 526 |
| 177 | Tetrahydrofuran-2-ylmethyl | 4-F-benzyl | Styrylmethyl | OCH3 | 537 | 538 |
| 178 | Tetrahydrofuran-2-ylmethyl | 2-Cl-benzyl | Styrylmethyl | OCH3 | 553 | 554 |
| 179 | Tetrahydrofuran-2-ylmethyl | 2,4-Cl2-benzyl | Styrylmethyl | OCH3 | 588 | 589 |
| 180 | Tetrahydrofuran-2-ylmethyl | Naphth-2-ylmethyl | Styrylmethyl | OCH3 | 569 | 570 |
| 181 | Tetrahydrofuran-2-ylmethyl | 4-HO-benzyl | 2,6-Cl2-benzyl | OCH3 | 577 | 578 |
| 182 | Tetrahydrofuran-2-ylmethyl | 4-NO2-benzyl | 2,6-Cl2-benzyl | OCH3 | 606 | 607 |
| 183 | Tetrahydrofuran-2-ylmethyl | 2,4-F2-benzyl | 2,6-Cl2-benzyl | OCH3 | 597 | 598 |
| 184 | Tetrahydrofuran-2-ylmethyl | 4-Cl-benzyl | 2,6-Cl2-benzyl | OCH3 | 596 | 597 |
| 185 | Tetrahydrofuran-2-ylmethyl | 2,2-bisphenylethyl | 2,6-Cl2-benzyl | OCH3 | 638 | 639 |
| 186 | Tetrahydrofuran-2-ylmethyl | 3-t-Bu-4-HO-benzyl | 2,6-Cl2-benzyl | OCH3 | 553 | 554 |
| 187 | Tetrahydrofuran-2-ylmethyl | 4-Me-benzyl | 2,6-Cl2-benzyl | OCH3 | 575 | 576 |
| 188 | Tetrahydrofuran-2-ylmethyl | Cyclohexyl-methyl | 2,6-Cl2-benzyl | OCH3 | 568 | 569 |
| 189 | Tetrahydrofuran-2-ylmethyl | 4-F-benzyl | 2,6-Cl2-benzyl | OCH3 | 579 | 580 |
| 190 | Tetrahydrofuran-2-ylmethyl | 2-Cl-benzyl | 2,6-Cl2-benzyl | OCH3 | 596 | 597 |
| 191 | Tetrahydrofuran-2-ylmethyl | 2,4-Cl2-benzyl | 2,6-Cl2-benzyl | OCH3 | 630 | 631 |
| 192 | Tetrahydrofuran-2-ylmethyl | Naphth-2-ylmethyl | 2,6-Cl2-benzyl | OCH3 | 612 | 613 |
| 193 | Phenethyl | 4-HO-benzyl | Methyl | (4-Me-phenyl)amino | 528 | 529 |
| 194 | Phenethyl | 4-HO-benzyl | Methyl | (4-Cl-phenyl)amino | 548 | 549 |
| 195 | Phenethyl | 4-HO-benzyl | Methyl | Phenylamino | 514 | 515 |
| 196 | Phenethyl | 4-HO-benzyl | Methyl | ((R)-α-methylbenzyl)amino | 542 | 543 |

TABLE 2A-continued

THE [4,4,0]REVERSE TURN MIMETICS LIBRARY

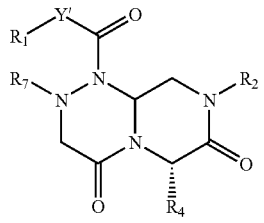

| No | R$_2$ | R$_4$ | R$_7$ | R$_1$-Y' | Mol. Weight | M + H |
|---|---|---|---|---|---|---|
| 197 | Phenethyl | 4-HO-benzyl | Methyl | Benzylamino | 528 | 529 |
| 198 | Phenethyl | 4-HO-benzyl | Methyl | (4-MeO-phenyl)amino | 544 | 545 |
| 199 | Phenethyl | 4-HO-benzyl | Methyl | (4-Br-phenyl)amino | 592 | 593 |
| 200 | Phenethyl | 4-HO-benzyl | Methyl | (4-CF$_3$-phenyl)amino | 582 | 583 |
| 201 | Phenethyl | 4-HO-benzyl | Methyl | Pentylamino | 508 | 509 |
| 202 | Phenethyl | 4-HO-benzyl | Methyl | (2-Phenylethyl)amino | 542 | 543 |
| 203 | Phenethyl | 4-HO-benzyl | Methyl | (4-MeO-benzyl)amino | 558 | 559 |
| 204 | Phenethyl | 4-HO-benzyl | Methyl | Cyclohexylamino | 520 | 521 |
| 205 | 2,2-bisphenylethyl | 4-HO-benzyl | Methyl | (4-Me-phenyl)amino | 604 | 605 |
| 206 | 2,2-bisphenylethyl | 4-HO-benzyl | Methyl | (4-Cl-phenyl)amino | 624 | 625 |
| 207 | 2,2-bisphenylethyl | 4-HO-benzyl | Methyl | Phenylamino | 590 | 591 |
| 208 | 2,2-bisphenylethyl | 4-HO-benzyl | Methyl | ((R)-α-methylbenzyl)amino | 618 | 619 |
| 209 | 2,2-bisphenylethyl | 4-HO-benzyl | Methyl | Benzylamino | 604 | 605 |
| 210 | 2,2-bisphenylethyl | 4-HO-benzyl | Methyl | (4-MeO-phenyl)amino | 620 | 621 |
| 211 | 2,2-bisphenylethyl | 4-HO-benzyl | Methyl | (4-Br-phenyl)amino | 669 | 670 |
| 212 | 2,2-bisphenylethyl | 4-HO-benzyl | Methyl | (4-CF$_3$-phenyl)amino | 658 | 659 |
| 213 | 2,2-bisphenylethyl | 4-HO-benzyl | Methyl | Pentylamino | 584 | 585 |
| 214 | 2,2-bisphenylethyl | 4-HO-benzyl | Methyl | (2-Phenylethyl)amino | 618 | 619 |
| 215 | 2,2-bisphenylethyl | 4-HO-benzyl | Methyl | (4-MeO-benzyl)amino | 634 | 635 |
| 216 | 2,2-bisphenylethyl | 4-HO-benzyl | Methyl | Cyclohexylamino | 596 | 597 |
| 217 | Phenethyl | 3,4-Cl$_2$-benzyl | Methyl | (4-Me-phenyl)amino | 581 | 582 |
| 218 | Phenethyl | 3,4-Cl$_2$-benzyl | Methyl | (4-Cl-phenyl)amino | 601 | 602 |
| 219 | Phenethyl | 3,4-Cl$_2$-benzyl | Methyl | Phenylamino | 566 | 567 |
| 220 | Phenethyl | 3,4-Cl$_2$-benzyl | Methyl | ((R)-α-methylbenzyl)amino | 595 | 596 |
| 221 | Phenethyl | 3,4-Cl$_2$-benzyl | Methyl | Benzylamino | 581 | 582 |
| 222 | Phenethyl | 3,4-Cl$_2$-benzyl | Methyl | (4-MeO-phenyl)amino | 597 | 598 |
| 223 | Phenethyl | 3,4-Cl$_2$-benzyl | Methyl | (4-Br-phenyl)amino | 645 | 646 |
| 224 | Phenethyl | 3,4-Cl$_2$-benzyl | Methyl | (4-CF$_3$-phenyl)amino | 634 | 635 |
| 225 | Phenethyl | 3,4-Cl$_2$-benzyl | Methyl | Pentylamino | 561 | 562 |
| 226 | Phenethyl | 3,4-Cl$_2$-benzyl | Methyl | (2-Phenylethyl)amino | 595 | 596 |
| 227 | Phenethyl | 3,4-Cl$_2$-benzyl | Methyl | (4-MeO-benzyl)amino | 611 | 612 |
| 228 | Phenethyl | 3,4-Cl$_2$-benzyl | Methyl | Cyclohexylamino | 573 | 574 |
| 229 | 2,2-bisphenylethyl | 3,4-Cl$_2$-benzyl | Methyl | (4-Me-phenyl)amino | 657 | 658 |
| 230 | 2,2-bisphenylethyl | 3,4-Cl$_2$-benzyl | Methyl | (4-Cl-phenyl)amino | 677 | 678 |
| 231 | 2,2-bisphenylethyl | 3,4-Cl$_2$-benzyl | Methyl | Phenylamino | 643 | 644 |
| 232 | 2,2-bisphenylethyl | 3,4-Cl$_2$-benzyl | Methyl | ((R)-α-methylbenzyl)amino | 671 | 672 |
| 233 | 2,2-bisphenylethyl | 3,4-Cl$_2$-benzyl | Methyl | Benzylamino | 657 | 658 |
| 234 | 2,2-bisphenylethyl | 3,4-Cl$_2$-benzyl | Methyl | (4-MeO-phenyl)amino | 673 | 674 |
| 235 | 2,2-bisphenylethyl | 3,4-Cl$_2$-benzyl | Methyl | (4-Br-phenyl)amino | 721 | 722 |
| 236 | 2,2-bisphenylethyl | 3,4-Cl$_2$-benzyl | Methyl | (4-CF$_3$-phenyl)amino | 711 | 712 |
| 237 | 2,2-bisphenylethyl | 3,4-Cl$_2$-benzyl | Methyl | Pentylamino | 637 | 638 |
| 238 | 2,2-bisphenylethyl | 3,4-Cl$_2$-benzyl | Methyl | (2-Phenylethyl)amino | 671 | 672 |
| 239 | 2,2-bisphenylethyl | 3,4-Cl$_2$-benzyl | Methyl | (4-MeO-benzyl)amino | 687 | 688 |
| 240 | 2,2-bisphenylethyl | 3,4-Cl$_2$-benzyl | Methyl | Cyclohexylamino | 649 | 650 |
| 241 | Isoamyl | 4-HO-benzyl | Methyl | (4-Me-phenyl)amino | 478 | 479 |
| 242 | Isoamyl | 4-HO-benzyl | Methyl | (4-Cl-phenyl)amino | 498 | 499 |
| 243 | Isoamyl | 4-HO-benzyl | Methyl | Phenylamino | 464 | 465 |
| 244 | Isoamyl | 4-HO-benzyl | Methyl | ((R)-α-methylbenzyl)amino | 492 | 493 |
| 245 | Isoamyl | 4-HO-benzyl | Methyl | Benzylamino | 478 | 479 |
| 246 | Isoamyl | 4-HO-benzyl | Methyl | (4-MeO-phenyl)amino | 494 | 495 |
| 247 | Isoamyl | 4-HO-benzyl | Methyl | (4-Br-phenyl)amino | 542 | 543 |
| 248 | Isoamyl | 4-HO-benzyl | Methyl | (4-CF$_3$-phenyl)amino | 532 | 533 |
| 249 | Isoamyl | 4-HO-benzyl | Methyl | Pentylamino | 458 | 459 |
| 250 | Isoamyl | 4-HO-benzyl | Methyl | (2-Phenylethyl)amino | 492 | 493 |
| 251 | Isoamyl | 4-HO-benzyl | Methyl | (4-MeO-benzyl)amino | 508 | 509 |
| 252 | Isoamyl | 4-HO-benzyl | Methyl | Cyclohexylamino | 470 | 471 |
| 253 | Isoamyl | 4-HO-benzyl | Methyl | (4-Me-phenyl)amino | 554 | 555 |
| 254 | Isoamyl | 4-HO-benzyl | Methyl | (4-Cl-phenyl)amino | 574 | 575 |
| 255 | Isoamyl | 4-HO-benzyl | Methyl | Phenylamino | 540 | 541 |

TABLE 2A-continued

THE [4,4,0]REVERSE TURN MIMETICS LIBRARY

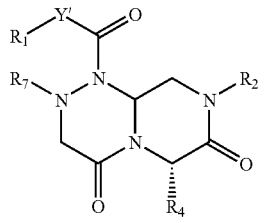

| No | R₂ | R₄ | R₇ | R₁-Y' | Mol. Weight | M + H |
|---|---|---|---|---|---|---|
| 256 | Isoamyl | 4-HO-benzyl | Methyl | ((R)-α-methylbenzyl)amino | 568 | 569 |
| 257 | Isoamyl | 4-HO-benzyl | Methyl | Benzylamino | 554 | 555 |
| 258 | Isoamyl | 4-HO-benzyl | Methyl | (4-MeO-phenyl)amino | 570 | 571 |
| 259 | Isoamyl | 4-HO-benzyl | Methyl | (4-Br-phenyl)amino | 619 | 620 |
| 260 | Isoamyl | 4-HO-benzyl | Methyl | (4-CF₃-phenyl)amino | 608 | 609 |
| 261 | Isoamyl | 4-HO-benzyl | Methyl | Pentylamino | 534 | 535 |
| 262 | Isoamyl | 4-HO-benzyl | Methyl | (2-Phenylethyl)amino | 568 | 569 |
| 263 | Isoamyl | 4-HO-benzyl | Methyl | (4-MeO-benzyl)amino | 584 | 585 |
| 264 | Isoamyl | 4-HO-benzyl | Methyl | Cyclohexylamino | 546 | 547 |
| 265 | 4-methylbenzyl | 3,4-Cl₂-benzyl | Methyl | (4-Me-phenyl)amino | 526 | 527 |
| 266 | 4-methylbenzyl | 3,4-Cl₂-benzyl | Methyl | (4-Cl-phenyl)amino | 546 | 547 |
| 267 | 4-methylbenzyl | 3,4-Cl₂-benzyl | Methyl | Phenylamino | 512 | 513 |
| 268 | 4-methylbenzyl | 3,4-Cl₂-benzyl | Methyl | ((R)-α-methylbenzyl)amino | 540 | 541 |
| 269 | 4-methylbenzyl | 3,4-Cl₂-benzyl | Methyl | Benzylamino | 526 | 527 |
| 270 | 4-methylbenzyl | 3,4-Cl₂-benzyl | Methyl | (4-MeO-phenyl)amino | 542 | 543 |
| 271 | 4-methylbenzyl | 3,4-Cl₂-benzyl | Methyl | (4-Br-phenyl)amino | 591 | 592 |
| 272 | 4-methylbenzyl | 3,4-Cl₂-benzyl | Methyl | (4-CF₃-phenyl)amino | 580 | 581 |
| 273 | 4-methylbenzyl | 3,4-Cl₂-benzyl | Methyl | Pentylamino | 506 | 507 |
| 274 | 4-methylbenzyl | 3,4-Cl₂-benzyl | Methyl | (2-Phenylethyl)amino | 540 | 541 |
| 275 | 4-methylbenzyl | 3,4-Cl₂-benzyl | Methyl | (4-MeO-benzyl)amino | 556 | 557 |
| 276 | 4-methylbenzyl | 3,4-Cl₂-benzyl | Methyl | Cyclohexylamino | 518 | 519 |
| 277 | 4-methylbenzyl | 3,4-Cl₂-benzyl | Methyl | (4-Me-phenyl)amino | 602 | 603 |
| 278 | 4-methylbenzyl | 3,4-Cl₂-benzyl | Methyl | (4-Cl-phenyl)amino | 622 | 623 |
| 279 | 4-methylbenzyl | 3,4-Cl₂-benzyl | Methyl | Phenylamino | 588 | 589 |
| 280 | 4-methylbenzyl | 3,4-Cl₂-benzyl | Methyl | ((R)-60 -methylbenzyl)amino | 616 | 617 |
| 281 | 4-methylbenzyl | 3,4-Cl₂-benzyl | Methyl | Benzylamino | 602 | 603 |
| 282 | 4-methylbenzyl | 3,4-Cl₂-benzyl | Methyl | (4-MeO-phenyl)amino | 618 | 619 |
| 283 | 4-methylbenzyl | 3,4-Cl₂-benzyl | Methyl | (4-Br-phenyl)amino | 667 | 668 |
| 284 | 4-methylbenzyl | 3,4-Cl₂-benzyl | Methyl | (4-CF₃-phenyl)amino | 656 | 657 |
| 285 | 4-methylbenzyl | 3,4-Cl₂-benzyl | Methyl | Pentylamino | 582 | 583 |
| 286 | 4-methylbenzyl | 3,4-Cl₂-benzyl | Methyl | (2-Phenylethyl)amino | 616 | 617 |
| 287 | 4-methylbenzyl | 3,4-Cl₂-benzyl | Methyl | (4-MeO-benzyl)amino | 632 | 633 |
| 288 | 4-methylbenzyl | 3,4-Cl₂-benzyl | Methyl | Cyclohexylamino | 594 | 595 |
| 289 | Naphth-1-ylmethyl | 4-HO-benzyl | Methyl | (N-Cbz-3-Indoleethyl)amino | 751 | 752 |
| 290 | Naphth-1-ylmethyl | 4-HO-benzyl | Methyl | (Naphth-2-ylmethyl)amino | 614 | 615 |
| 291 | Naphth-1-ylmethyl | 4-HO-benzyl | Methyl | (2-Phenylethyl)amino | 578 | 579 |
| 292 | Naphth-1-ylmethyl | 4-HO-benzyl | Methyl | 2-(4-MeO-phenyl)ethyl]amino | 608 | 609 |
| 293 | Naphth-1-ylmethyl | 4-HO-benzyl | Methyl | (3-CF₃-benzyl)amino | 632 | 633 |
| 294 | Naphth-1-ylmethyl | 4-HO-benzyl | Methyl | (4-MeO-benzyl)amino | 594 | 595 |
| 295 | Naphth-1-ylmethyl | 4-HO-benzyl | Methyl | (4-F-phenylethyl)-amino | 596 | 597 |
| 296 | Naphth-1-ylmethyl | 4-HO-benzyl | Methyl | (3,4-Cl₂-benzyl)amino | 633 | 634 |
| 297 | Naphth-1-ylmethyl | 4-HO-benzyl | Methyl | (2-HO-ethyl)amino | 518 | 519 |
| 298 | Naphth-1-ylmethyl | 4-HO-benzyl | Methyl | (3-MeO-propyl)amino | 546 | 547 |
| 299 | Naphth-1-ylmethyl | 4-HO-benzyl | Methyl | (Tetrahydrofuran-2-ylmethyl)amino | 558 | 559 |
| 300 | Naphth-1-ylmethyl | 4-HO-benzyl | Methyl | (cyclohexylmethyl)amio | 570 | 571 |
| 301 | Naphth-1-ylmethyl | 4-HO-benzyl | Propyl | (N-Cbz-3-Indoleethyl)amino | 779 | 780 |
| 302 | Naphth-1-ylmethyl | 4-HO-benzyl | Propyl | (Naphth-2-ylmethyl)amino | 642 | 643 |
| 303 | Naphth-1-ylmethyl | 4-HO-benzyl | Propyl | (2-Phenylethyl)amino | 606 | 607 |
| 304 | Naphth-1-ylmethyl | 4-HO-benzyl | Propyl | [2-(4-MeO-phenyl)ethyl]amino | 636 | 637 |
| 305 | Naphth-1-ylmethyl | 4-HO-benzyl | Propyl | (3-CF₃-benzyl)amino | 660 | 661 |
| 306 | Naphth-1-ylmethyl | 4-HO-benzyl | Propyl | (4-MeO-benzyl)amino | 622 | 623 |
| 307 | Naphth-1-ylmethyl | 4-HO-benzyl | Propyl | (4-F-phenylethyl)amino | 624 | 625 |
| 308 | Naphth-1-ylmethyl | 4-HO-benzyl | Propyl | (3,4-Cl₂-benzyl)amino | 661 | 662 |

TABLE 2A-continued

THE [4,4,0]REVERSE TURN MIMETICS LIBRARY

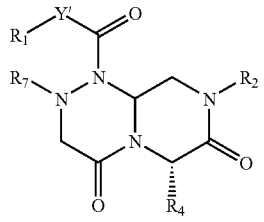

| No | R₂ | R₄ | R₇ | R₁-Y' | Mol. Weight | M + H |
|---|---|---|---|---|---|---|
| 309 | Naphth-1-ylmethyl | 4-HO-benzyl | Propyl | (2-HO-ethyl)amino | 546 | 547 |
| 310 | Naphth-1-ylmethyl | 4-HO-benzyl | Propyl | (3-MeO-propyl)amino | 574 | 575 |
| 311 | Naphth-1-ylmethyl | 4-HO-benzyl | Propyl | (Tetrahydrofuran-2-ylmethyl)amino | 586 | 587 |
| 312 | Naphth-1-ylmethyl | 4-HO-benzyl | Propyl | (cyclohexylmethyl)amino | 598 | 599 |
| 313 | Naphth-1-ylmethyl | 3,4-F₂-benzyl | Methyl | (N-Cbz-3-Indoleethyl)amino | 771 | 772 |
| 314 | Naphth-1-ylmethyl | 3,4-F₂-benzyl | Methyl | (Naphth-2-ylmethyl)amino | 634 | 635 |
| 315 | Naphth-1-ylmethyl | 3,4-F₂-benzyl | Methyl | (2-Phenylethyl)amino | 598 | 599 |
| 316 | Naphth-1-ylmethyl | 3,4-F₂-benzyl | Methyl | (2-(4-MeO-phenyl)ethyl]amino | 628 | 629 |
| 317 | Naphth-1-ylmethyl | 3,4-F₂-benzyl | Methyl | (3-CF₃-benzyl)amino | 652 | 653 |
| 318 | Naphth-1-ylmethyl | 3,4-F₂-benzyl | Methyl | (4-MeO-benzyl)amino | 614 | 615 |
| 319 | Naphth-1-ylmethyl | 3,4-F₂-benzyl | Methyl | (4-F-phenylethyl)amino | 616 | 617 |
| 320 | Naphth-1-ylmethyl | 3,4-F₂-benzyl | Methyl | (3,4-Cl₂-benzyl)amino | 653 | 654 |
| 321 | Naphth-1-ylmethyl | 3,4-F₂-benzyl | Methyl | (2-HO-ethyl)amino | 538 | 539 |
| 322 | Naphth-1-ylmethyl | 3,4-F₂-benzyl | Methyl | (3-MeO-propyl)amino | 566 | 567 |
| 323 | Naphth-1-ylmethyl | 3,4-F₂-benzyl | Methyl | (Tetrahydrofuran-2-ylmethyl)amino | 578 | 579 |
| 324 | Naphth-1-ylmethyl | 3,4-F₂-benzyl | Methyl | cyclohexylmethyl)amino | 590 | 591 |
| 325 | Naphth-1-ylmethyl | 3,4-F₂-benzyl | Propyl | (N-Cbz-3-Indoleethyl)amino | 799 | 800 |
| 326 | Naphth-1-ylmethyl | 3,4-F₂-benzyl | Propyl | (Naphth-2-ylmethyl)amino | 662 | 663 |
| 327 | Naphth-1-ylmethyl | 3,4-F₂-benzyl | Propyl | (2-Phenylethyl)amino | 626 | 627 |
| 328 | Naphth-1-ylmethyl | 3,4-F₂-benzyl | Propyl | [2-(4-MeO-phenyl)ethyl]amino | 656 | 657 |
| 329 | Naphth-1-ylmethyl | 3,4-F₂-benzyl | Propyl | (3-CF₃-benzyl)amino | 680 | 681 |
| 330 | Naphth-1-ylmethyl | 3,4-F₂-benzyl | Propyl | (4-MeO-benzyl)amino | 642 | 643 |
| 331 | Naphth-1-ylmethyl | 3,4-F₂-benzyl | Propyl | (4-F-phenylethyl)amino | 644 | 645 |
| 332 | Naphth-1-ylmethyl | 3,4-F₂-benzyl | Propyl | (3,4-Cl₂-benzyl)amino | 681 | 682 |
| 333 | Naphth-1-ylmethyl | 3,4-F₂-benzyl | Propyl | (2-HO-ethyl)amino | 566 | 567 |
| 334 | Naphth-1-ylmethyl | 3,4-F₂-benzyl | Propyl | (3-MeO-propyl)amino | 594 | 595 |
| 335 | Naphth-1-ylmethyl | 3,4-F₂-benzyl | Propyl | (Tetrahydrofuran-2-ylmethyl)amino | 606 | 607 |
| 336 | Naphth-1-ylmethyl | 3,4-F₂-benzyl | Propyl | (cyclohexylmethyl)amino | 618 | 619 |
| 337 | Naphth-1-ylmethyl | 4-biphenylyl-methyl | Methyl | (N-Cbz-3-Indoleethyl)amino | 811 | 812 |
| 338 | Naphth-1-ylmethyl | 4-biphenylylmethyl | Methyl | (Naphth-2-ylmethyl)amino | 674 | 675 |
| 339 | Naphth-1-ylmethyl | 4-biphenylylmethyl | Methyl | (2-Phenylethyl)amino | 638 | 639 |
| 340 | Naphth-1-ylmethyl | 4-biphenylylmethyl | Methyl | [2-(4-MeO-phenyl)ethyl]amino | 668 | 669 |
| 341 | Naphth-1-ylmethyl | 4-biphenylylmethyl | Methyl | (3-CF₃-benzyl)amino | 692 | 693 |
| 342 | Naphth-1-ylmethyl | 4-biphenylylmethyl | Methyl | (4-MeO-benzyl)amino | 654 | 655 |
| 343 | Naphth-1-ylmethyl | 4-biphenylylmethyl | Methyl | (4-F-phenylethyl)amino | 656 | 657 |
| 344 | Naphth-1-ylmethyl | 4-biphenylylmethyl | Methyl | (3,4-Cl₂-benzyl)amino | 693 | 694 |
| 345 | Naphth-1-ylmethyl | 4-biphenylylmethyl | Methyl | (2-HO-ethyl)amino | 578 | 579 |
| 346 | Naphth-1-ylmethyl | 4-biphenylylmethyl | Methyl | (3-MeO-propyl)amino | 606 | 607 |
| 347 | Naphth-1-ylmethyl | 4-biphenylylmethyl | Methyl | (Tetrahydrofuran-2-ylmethyl)amino | 618 | 619 |
| 348 | Naphth-1-ylmethyl | 4-biphenylylmethyl | Methyl | (cyclohexylmethyl)amino | 630 | 631 |
| 349 | Naphth-1-ylmethyl | 4-biphenylylmethyl | Propyl | (N-Cbz-3-Indoleethyl)amino | 839 | 840 |
| 350 | Naphth-1-ylmethyl | 4-biphenylylmethyl | Propyl | (Naphth-2-ylmethyl)amino | 702 | 703 |
| 351 | Naphth-1-ylmethyl | 4-biphenylylmethyl | Propyl | (2-Phenylethyl)amino | 666 | 667 |
| 352 | Naphth-1-ylmethyl | 4-biphenylylmethyl | Propyl | [2-(4-MeO-phenyl)ethyl]amino | 696 | 697 |
| 353 | Naphth-1-ylmethyl | 4-biphenylylmethyl | Propyl | (3-CF₃-benzyl)amino | 720 | 721 |
| 354 | Naphth-1-ylmethyl | 4-biphenylylmethyl | Propyl | (4-MeO-benzyl)amino | 682 | 683 |
| 355 | Naphth-1-ylmethyl | 4-biphenylylmethyl | Propyl | (4-F-phenylethyl)amino | 684 | 685 |

TABLE 2A-continued

THE [4,4,0]REVERSE TURN MIMETICS LIBRARY

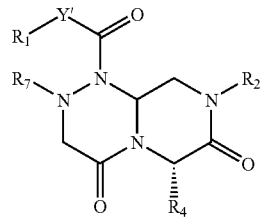

| No | R₂ | R₄ | R₇ | R₁-Y' | Mol. Weight | M + H |
|---|---|---|---|---|---|---|
| 356 | Naphth-1-ylmethyl | 4-biphenylylmethyl | Propyl | (3,4-Cl₂-benzyl)amino | 721 | 722 |
| 357 | Naphth-1-ylmethyl | 4-biphenylylmethyl | Propyl | (2-HO-ethyl)amino | 606 | 607 |
| 358 | Naphth-1-ylmethyl | 4-biphenylylmethyl | Propyl | (3-MeO-propyl)amino | 634 | 635 |
| 359 | Naphth-1-ylmethyl | 4-biphenylylmethyl | Propyl | (Tetrahydrofuran-2-ylmethyl)amino | 646 | 647 |
| 360 | Naphth-1-ylmethyl | 4-biphenylylmethyl | Propyl | (cyclohexylmethyl)amino | 658 | 659 |
| 361 | Naphth-1-ylmethyl | 3-t-Bu-4-HO-benzyl | Methyl | (N-Cbz-3-Indoleethyl)amino | 807 | 808 |
| 362 | Naphth-1-ylmethyl | 3-t-Bu-4-HO-benzyl | Methyl | (Naphth-2-ylmethyl)amino | 670 | 671 |
| 363 | Naphth-1-ylmethyl | 3-t-Bu-4-HO-benzyl | Methyl | (2-Phenylethyl)amino | 634 | 635 |
| 364 | Naphth-1-ylmethyl | 3-t-Bu-4-HO-benzyl | Methyl | [2-(4-MeO-phenyl)ethyl]amino | 664 | 665 |
| 365 | Naphth-1-ylmethyl | 3-t-Bu-4-HO-benzyl | Methyl | (3-CF₃-benzyl)amino | 688 | 689 |
| 366 | Naphth-1-ylmethyl | 3-t-Bu-4-HO-benzyl | Methyl | (4-MeO-benzyl)amino | 650 | 651 |
| 367 | Naphth-1-ylmethyl | 3-t-Bu-4-HO-benzyl | Methyl | (4-F-phenylethyl)amino | 652 | 653 |
| 368 | Naphth-1-ylmethyl | 3-t-Bu-4-HO-benzyl | Methyl | (3,4-Cl₂-benzyl)amino | 689 | 690 |
| 369 | Naphth-1-ylmethyl | 3-t-Bu-4-HO-benzyl | Methyl | (2-HO-ethyl)amino | 574 | 575 |
| 370 | Naphth-1-ylmethyl | 3-t-Bu-4-HO-benzyl | Methyl | (3-MeO-propyl)amino | 602 | 603 |
| 371 | Naphth-1-ylmethyl | 3-t-Bu-4-HO-benzyl | Methyl | (Tetrahydrofuran-2-ylmethyl)amino | 614 | 615 |
| 372 | Naphth-1-ylmethyl | 3-t-Bu-4-HO-benzyl | Methyl | (cyclohexylmethyl)amino | 626 | 627 |
| 373 | Naphth-1-ylmethyl | 3-t-Bu-4-HO-benzyl | Propyl | (N-Cbz-3-Indoleethyl)amino | 835 | 836 |
| 374 | Naphth-1-ylmethyl | 3-t-Bu-4-HO-benzyl | Propyl | (Naphth-2-ylmethyl)amino | 698 | 699 |
| 375 | Naphth-1-ylmethyl | 3-t-Bu-4-HO-benzyl | Propyl | (2-Phenylethyl)amino | 662 | 663 |
| 376 | Naphth-1-ylmethyl | 3-t-Bu-4-HO-benzyl | Propyl | [2-(4-MeO-phenyl)ethyl]amino | 692 | 693 |
| 377 | Naphth-1-ylmethyl | 3-t-Bu-4-HO-benzyl | Propyl | (3-CF₃-benzyl)amino | 716 | 717 |
| 378 | Naphth-1-ylmethyl | 3-t-Bu-4-HO-benzyl | Propyl | (4-MeO-benzyl)amino | 678 | 679 |
| 379 | Naphth-1-ylmethyl | 3-t-Bu-4-HO-benzyl | Propyl | (4-F-phenylethyl)amino | 680 | 681 |
| 380 | Naphth-1-ylmethyl | 3-t-Bu-4-HO-benzyl | Propyl | (3,4-Cl₂-benzyl)amino | 717 | 718 |
| 381 | Naphth-1-ylmethyl | 3-t-Bu-4-HO-benzyl | Propyl | (2-HO-ethyl)amino | 602 | 603 |
| 382 | Naphth-1-ylmethyl | 3-t-Bu-4-HO-benzyl | Propyl | (3-MeO-propyl)amino | 630 | 631 |
| 383 | Naphth-1-ylmethyl | 3-t-Bu-4-HO-benzyl | Propyl | (Tetrahydrofuran-2-ylmethyl)amino | 642 | 643 |
| 384 | Naphth-1-ylmethyl | 3-t-Bu-4-HO-benzyl | Propyl | (cyclohexylmethyl)amino | 654 | 655 |
| 385 | 4-Methoxybenzyl | OCH₃ | 5-F-benzyl | OCH₃ | 470 | 471 |
| 386 | Naphthyl-1-ylmethyl | 4-HO-benzyl | Styrylmethyl | OCH₃ | 591 | 592 |
| 387 | Naphthyl-1-ylmethyl | 4-NO₂-benzyl | Styrylmethyl | OCH₃ | 620 | 621 |
| 388 | Naphthyl-1-ylmethyl | 3,4-F₂-benzyl | Styrylmethyl | OCH₃ | 611 | 612 |
| 389 | Naphthyl-1-ylmethyl | 4-Cl-benzyl | Styrylmethyl | OCH₃ | 609 | 610 |
| 390 | Naphthyl-1-ylmethyl | 4-Phenyl-benzyl | Styrylmethyl | OCH₃ | 651 | 652 |
| 391 | Naphthyl-1-ylmethyl | 3-t-Bu-4-HO-benzyl | Styrylmethyl | OCH₃ | 647 | 648 |
| 392 | Naphthyl-1-ylmethyl | 4-Methyl-benzyl | Styrylmethyl | OCH₃ | 589 | 590 |
| 393 | Naphthyl-1-ylmethyl | Cyclohexylmethyl | Styrylmethyl | OCH₃ | 581 | 582 |
| 394 | Naphthyl-1-ylmethyl | 4-F-benzyl | Styrylmethyl | OCH₃ | 593 | 594 |
| 395 | Naphthyl-1-ylmethyl | 2-Cl-benzyl | Styrylmethyl | OCH₃ | 609 | 610 |
| 396 | Naphthyl-1-ylmethyl | 3,4-Cl₂-benzyl | Styrylmethyl | OCH₃ | 644 | 645 |
| 397 | Naphthyl-1-ylmethyl | Naphthyl-1-ylmethyl | Styrylmethyl | OCH₃ | 625 | 626 |
| 398 | 3,4-Cl₂-benzyl | 4-HO-benzyl | Styrylmethyl | OCH₃ | 610 | 611 |
| 399 | 3,4-Cl₂-benzyl | 4-NO₂-benzyl | Styrylmethyl | OCH₃ | 639 | 640 |
| 400 | 3,4-Cl₂-benzyl | 3,4-F₂-benzyl | Styrylmethyl | OCH₃ | 629 | 630 |
| 401 | 3,4-Cl₂-benzyl | 4-Cl-benzyl | Styrylmethyl | OCH₃ | 628 | 629 |
| 402 | 3,4-Cl₂-benzyl | 4-Phenyl-benzyl | Styrylmethyl | OCH₃ | 670 | 671 |
| 403 | 3,4-Cl₂-benzyl | 3-t-Bu-4-HO-benzyl | Styrylmethyl | OCH₃ | 666 | 667 |
| 404 | 3,4-Cl₂-benzyl | 4-Methyl-benzyl | Styrylmethyl | OCH₃ | 608 | 609 |
| 405 | 3,4-Cl₂-benzyl | Cyclohexylmethyl | Styrylmethyl | OCH₃ | 600 | 601 |
| 406 | 3,4-Cl₂-benzyl | 4-F-benzyl | Styrylmethyl | OCH₃ | 611 | 612 |
| 407 | 3,4-Cl₂-benzyl | 2-Cl-benzyl | Styrylmethyl | OCH₃ | 628 | 629 |
| 408 | 3,4-Cl₂-benzyl | 3,4-Cl₂-benzyl | Styrylmethyl | OCH₃ | 662 | 663 |
| 409 | 3,4-Cl₂-benzyl | Naphthyl-1-ylmethyl | Styrylmethyl | OCH₃ | 644 | 645 |

TABLE 2A-continued

THE [4,4,0]REVERSE TURN MIMETICS LIBRARY

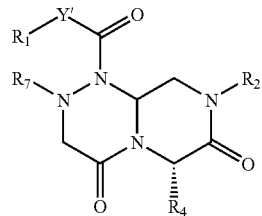

| No | R$_2$ | R$_4$ | R$_7$ | R$_1$-Y' | Mol. Weight | M + H |
|---|---|---|---|---|---|---|
| 410 | Naphthyl-1-ylmethyl | 4-HO-benzyl | 2,6-Cl$_2$-benzyl | OCH$_3$ | 634 | 635 |
| 411 | Naphthyl-1-ylmethyl | 4-NO$_2$-benzyl | 2,6-Cl$_2$-benzyl | OCH$_3$ | 663 | 664 |
| 412 | Naphthyl-1-ylmethyl | 3,4-F$_2$-benzyl | 2,6-Cl$_2$-benzyl | OCH$_3$ | 654 | 655 |
| 413 | Naphthyl-1-ylmethyl | 4-Cl-benzyl | 2,6-Cl$_2$-benzyl | OCH$_3$ | 652 | 653 |
| 414 | Naphthyl-1-ylmethyl | 4-Phenyl-benzyl | 2,6-Cl$_2$-benzyl | OCH$_3$ | 694 | 695 |
| 415 | Naphthyl-1-ylmethyl | 3-t-Bu-4-HO-benzyl | 2,6-Cl$_2$-benzyl | OCH$_3$ | 690 | 691 |
| 416 | Naphthyl-1-ylmethyl | 4-Methyl-benzyl | 2,6-Cl$_2$-benzyl | OCH$_3$ | 632 | 633 |
| 417 | Naphthyl-1-ylmethyl | Cyclohexylmethyl | 2,6-Cl$_2$-benzyl | OCH$_3$ | 624 | 625 |
| 418 | Naphthyl-1-ylmethyl | 4-F-benzyl | 2,6-Cl$_2$-benzyl | OCH$_3$ | 636 | 637 |
| 419 | Naphthyl-1-ylmethyl | 2-Cl-benzyl | 2,6-Cl$_2$-benzyl | OCH$_3$ | 652 | 653 |
| 420 | Naphthyl-1-ylmethyl | 3,4-Cl$_2$-benzyl | 2,6-Cl$_2$-benzyl | OCH$_3$ | 686 | 687 |
| 421 | Naphthyl-1-ylmethyl | Naphthyl-1-ylmethyl | 2,6-Cl$_2$-benzyl | OCH$_3$ | 668 | 669 |
| 422 | 3,4-Cl$_2$-benzyl | 4-HO-benzyl | 2,6-Cl$_2$-benzyl | OCH$_3$ | 652 | 653 |
| 423 | 3,4-Cl$_2$-benzyl | 4-NO$_2$-benzyl | 2,6-Cl$_2$-benzyl | OCH$_3$ | 681 | 682 |
| 424 | 3,4-Cl$_2$-benzyl | 3,4-F$_2$-benzyl | 2,6-Cl$_2$-benzyl | OCH$_3$ | 672 | 673 |
| 425 | 3,4-Cl$_2$-benzyl | 4-Cl-benzyl | 2,6-Cl$_2$-benzyl | OCH$_3$ | 671 | 672 |
| 426 | 3,4-Cl$_2$-benzyl | 4-Phenyl-benzyl | 2,6-Cl$_2$-benzyl | OCH$_3$ | 712 | 713 |
| 427 | 3,4-Cl$_2$-benzyl | 3-t-Bu-4-HO-benzyl | 2,6-Cl$_2$-benzyl | OCH$_3$ | 708 | 709 |
| 428 | 3,4-Cl$_2$-benzyl | 4-Methyl-benzyl | 2,6-Cl$_2$-benzyl | OCH$_3$ | 650 | 651 |
| 429 | 3,4-Cl$_2$-benzyl | Cyclohexylmethyl | 2,6-Cl$_2$-benzyl | OCH$_3$ | 642 | 643 |
| 430 | 3,4-Cl$_2$-benzyl | 4-F-benzyl | 2,6-Cl$_2$-benzyl | OCH$_3$ | 654 | 655 |
| 431 | 3,4-Cl$_2$-benzyl | 2-Cl-benzyl | 2,6-Cl$_2$-benzyl | OCH$_3$ | 671 | 672 |
| 432 | 3,4-Cl$_2$-benzyl | 3,4-Cl$_2$-benzyl | 2,6-Cl$_2$-benzyl | OCH$_3$ | 705 | 706 |
| 433 | 3,4-Cl$_2$-benzyl | Naphthyl-1-ylmethyl | 2,6-Cl$_2$-benzyl | OCH$_3$ | 686 | 687 |
| 434 | 2-Piperidin-1-yl-ethyl | (S)-4-HO-benzyl | Methyl | Benzylamino | 535 | 536 |
| 435 | 2-Pipendin-1-yl-3,4-Cl$_2$-benzyl | (S)-4-HO-benzyl | Methyl | ethylamino | 604 | 605 |
| 436 | 3,4-Cl$_2$-benzyl | (S)-4-HO-benzyl | Methyl | 2-(1-Methyl-pyrrolidin-2-yl)-ethylamino | 604 | 605 |
| 437 | 3-Pyridylmethyl | (S)-4-HO-benzyl | Methyl | 3,4-Cl$_2$-benzylamino | 583 | 584 |
| 438 | 2-Morpholin-4-yl-ethyl | (S)-4-HO-benzyl | Methyl | 3,4-Cl$_2$-benzylamino | 606 | 607 |
| 439 | 3,4-Cl$_2$-benzyl | (S)-4-HO-benzyl | Methyl | 3-Pyridylmethylamino | 583 | 584 |
| 440 | 3,4-Cl$_2$-benzyl | (S)-4-HO-benzyl | Methyl | 2-Morpholin-4-yl-ethylamino | 606 | 607 |
| 441 | Naphthyl-1-ylmethyl | 4-HO-benzyl | Methyl | 3-Imidazol-1-yl-propylamino | 582 | 583 |
| 442 | Naphthyl-1-ylmethyl | 4-HO-benzyl | Methyl | 4-Aminophenethylamino | 593 | 594 |
| 443 | Naphthyl-1-ylmethyl | 4-HO-benzyl | Methyl | 3-Pyridylmethylamino | 565 | 566 |
| 444 | Naphthyl-1-ylmethyl | 4-HO-benzyl | Methyl | 2-(3-Pyridylethyl)amino | 579 | 580 |
| 445 | Naphthyl-1-ylmethyl | 4-HO-benzyl | Methyl | 4-Pyridylmethylamino | 565 | 566 |
| 446 | Naphthyl-1-ylmethyl | 4-HO-benzyl | Methyl | Benzyloxycarbonylamino | 622 | 623 |
| 447 | Naphthyl-1-ylmethyl | 4-HO-benzyl | Methyl | 4-F-benzylamino | 582 | 583 |
| 448 | Naphthyl-1-ylmethyl | 4-HO-benzyl | Methyl | 4-CO2H-benzylamino | 608 | 609 |
| 449 | Naphthyl-1-ylmethyl | 4-HO-benzyl | Methyl | 4-CF$_3$-benzylamino | 632 | 633 |
| 450 | Naphthyl-1-ylmethyl | 4-HO-benzyl | Methyl | (S)-alpha-methylbenzylamino | 578 | 579 |
| 451 | Naphthyl-1-ylmethyl | 4-HO-benzyl | Methyl | (R)-alpha-methylbenzylamino | 578 | 579 |
| 452 | Naphthyl-1-ylmethyl | 4-HO-benzyl | Methyl | 2-F-benzylamino | 582 | 583 |
| 453 | Naphthyl-1-ylmethyl | 4-HO-benzyl | Methyl | Dimethoxybenzylamino | 624 | 625 |
| 454 | Naphthyl-1-ylmethyl | 4-HO-benzyl | Methyl | Cyanomethylamino | 513 | 514 |
| 455 | Naphthyl-1-ylmethyl | 4-HO-benzyl | Methyl | Phenylhydrazino | 565 | 566 |
| 456 | Naphthyl-1-ylmethyl | 4-HO-benzyl | Methyl | 4-Aminobenzylamino | 579 | 580 |
| 457 | Naphthyl-1-ylmethyl | 4-HO-benzyl | Methyl | (S,S){2-[(2-hydroxy-1-methyl-2-phenyl-ethyl)-methyl-carbamoyl]ethyl}-amino | 693 | 694 |
| 458 | Naphthyl-1-ylmethyl | 4-HO-benzyl | Methyl | [4-(1,3-dioxo-1,3-dihydro-isoindol-2-ylmethyl)-cyclohexyl]-methylamino | 715 | 716 |

TABLE 2A-continued

THE [4,4,0]REVERSE TURN MIMETICS LIBRARY

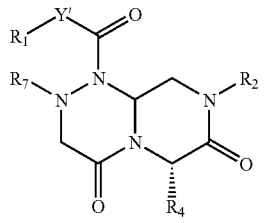

| No | R$_2$ | R$_4$ | R$_7$ | R$_1$-Y' | Mol. Weight | M + H |
|---|---|---|---|---|---|---|
| 459 | Naphthyl-1-ylmethyl | 4-HO-benzyl | Methyl | Indan-1-ylamino | 590 | 591 |
| 460 | Naphthyl-1-ylmethyl | 4-HO-benzyl | Methyl | PhenylGlycine | 622 | 623 |
| 461 | Naphthyl-1-ylmethyl | 4-HO-benzyl | Methyl | 2,6-F$_2$-benzylamino | 600 | 601 |
| 462 | Naphthyl-1-ylmethyl | 4-HO-benzyl | Methyl | 3-F-benzylamino | 582 | 583 |
| 463 | Naphthyl-1-ylmethyl | 4-HO-benzyl | Methyl | Benzimidazol-2-yl-amino | 604 | 605 |
| 464 | Naphthyl-1-ylmethyl | 4-HO-benzyl | Methyl | Diphenylmethylamino | 640 | 641 |
| 465 | Naphthyl-1-ylmethyl | 4-HO-benzyl | Methyl | Furan-2-yl-methylamino | 554 | 555 |
| 466 | Naphthyl-1-ylmethyl | 4-HO-benzyl | Methyl | 4-Dimethylamino-benzylamino | 607 | 608 |
| 467 | Naphthyl-1-ylmethyl | 4-HO-benzyl | Methyl | Thiofuran-2-yl-methylamino | 584 | 585 |
| 468 | Naphthyl-1-ylmethyl | 4-HO-benzyl | Methyl | 4-NO$_2$-benzylamino | 609 | 610 |
| 469 | Naphthyl-1-ylmethyl | 4-HO-benzyl | Methyl | BnO | 565 | 566 |
| 470 | 4-Methoxy-naphthyl-1-ylmethyl | 4-HO-benzyl | Methyl | Benzylamino | 594 | 595 |
| 471 | Naphthyl-1-ylmethyl | 4-HO-benzyl | Methyl | Phenethyl | 563 | 564 |
| 472 | Naphthyl-1-ylmethyl | 4-Methoxy-benzyl | Methyl | Benzylamino | 578 | 579 |
| 473 | Naphthyl-1-ylmethyl | 4-HO-benzyl | Methyl | 4-CF$_3$-phenylamino | 618 | 619 |
| 474 | Naphthyl-1-ylmethyl | 4-NO$_2$-benzyl | Methyl | 4-CF$_3$-phenylamino | 647 | 648 |
| 475 | Naphthyl-1-ylmethyl | 4-NO$_2$-benzyl | Methyl | Benzylamino | 593 | 594 |
| 476 | Benzyl | Naphthyl-1-ylmethyl | 4-CN-benzyl | OCH$_3$ | 574 | 575 |
| 477 | Thiofuran-2-yl-methyl | Naphthyl-1-ylmethyl | 4-CN-benzyl | OCH$_3$ | 594 | 595 |
| 478 | 4-Dimethylamino-benzyl | Naphthyl-1-ylmethyl | 4-CN-benzyl | OCH$_3$ | 617 | 618 |
| 479 | Phenethyl | Naphthyl-1-ylmethyl | 4-CN-benzyl | OCH$_3$ | 588 | 589 |
| 480 | 8-Quinoline-1yl-methyl | 4-HO-benzyl | Methyl | Benzylamino | 565 | 566 |
| 481 | 4-Pyridylmethyl | Naphthyl-1-ylmethyl | Benzyl | OCH$_3$ | 550 | 551 |
| 482 | 3,4-Dimethoxybenzyl | Naphthyl-1-ylmethyl | Benzyl | OCH$_3$ | 609 | 610 |
| 483 | 3,4-Dimethoxy-phenethyl | Naphthyl-1-ylmethyl | Benzyl | OCH$_3$ | 623 | 624 |
| 484 | Thiofuran-2-yl-methyl | Naphthyl-1-ylmethyl | Benzyl | OCH$_3$ | 569 | 570 |
| 485 | Naphthyl-1-ylmethyl | 3-Pyridylmethyl | Methyl | Benzylamino | 549 | 550 |
| 486 | Naphthyl-1-ylmethyl | Pentafluorobenzyl | Methyl | Benzylamino | 638 | 639 |
| 487 | Naphthyl-1-ylmethyl | 3-F-4-HO-benzyl | Methyl | Benzylamino | 582 | 583 |
| 488 | 4-F-phenethyl | 4-Methyl-benzyl | Methyl | 4-CF$_3$-phenylamino | 598 | 599 |
| 489 | 4-Methoxyphenethyl | 4-Methyl-benzyl | Methyl | 4-CF$_3$-phenylamino | 610 | 611 |
| 490 | 3,4-Dimethoxy-phenethyl | 4-Methyl-benzyl | Methyl | 4-CF$_3$-phenylamino | 640 | 641 |
| 491 | Naphthyl-1-ylmethyl | 4-Methyl-benzyl | Methyl | 4-CF$_3$-phenylamino | 616 | 617 |
| 492 | 3,4-Dimethoxybenzyl | Naphthyl-1-ylmethyl | 4-CN-benzyl | OCH$_3$ | 634 | 635 |
| 493 | 3,4-Dimethoxy-phenethyl | Naphthyl-1-ylmethyl | 4-CN-benzyl | OCH$_3$ | 648 | 649 |
| 494 | 4-Quinoline-1yl-methyl | 4-HO-benzyl | Methyl | Benzylamino | 565 | 566 |
| 495 | 2-Pyridylmethyl | 4-Methyl-benzyl | Methyl | 4-CF$_3$-phenylamino | 567 | 568 |
| 496 | 3-Pyridylmethyl | 4-Methyl-benzyl | Methyl | 4-CF$_3$-phenylamino | 567 | 568 |
| 497 | 3,4-Dimethoxybenzyl | 4-Methyl-benzyl | Methyl | 4-CF$_3$-phenylamino | 626 | 627 |
| 498 | 4-Methyl-benzyl | 4-Methyl-benzyl | Methyl | 4-CF$_3$-phenylamino | 580 | 581 |
| 499 | Thiofuran-2-yl-methyl | 4-Methyl-benzyl | Methyl | 4-CF$_3$-phenylamino | 572 | 573 |
| 500 | 4-CF$_3$-benzyl | 4-Methyl-benzyl | Methyl | 4-CF$_3$-phenylamino | 634 | 635 |
| 501 | 2,6-F$_2$-benzyl | 4-Methyl-benzyl | Methyl | 4-CF$_3$-phenylamino | 602 | 603 |
| 502 | 4-F-benzyl | 4-Methyl-benzyl | Methyl | 4-CF$_3$-phenylamino | 584 | 585 |
| 503 | Thiofuran-2-yl-ethyl | 4-Methyl-benzyl | Methyl | 4-CF$_3$-phenylamino | 586 | 587 |
| 504 | 3,4-Cl$_2$-benzyl | 4-Methyl-benzyl | Methyl | 4-CF$_3$-phenylamino | 634 | 635 |
| 505 | 4-CO$_2$H-Benzyl | 4-HO-benzyl | Methyl | Benzylamino | 558 | 559 |
| 506 | Naphthyl-1-ylmethyl | 3-t-Bu-4-HO-benzyl | Methyl | Benzylamino | 620 | 621 |
| 507 | Naphthyl-1-ylmethyl | 3,4-(OH)2-benzyl | Methyl | Benzylamino | 580 | 581 |
| 508 | 2-F-benzyl | 4-HO-benzyl | Methyl | Benzylamino | 532 | 533 |
| 509 | 3-F-benzyl | 4-HO-benzyl | Methyl | Benzylamino | 532 | 533 |
| 510 | 4-F-benzyl | 4-HO-benzyl | Methyl | Benzylamino | 532 | 533 |
| 511 | 2,4-F$_2$-benzyl | 4-HO-benzyl | Methyl | Benzylamino | 550 | 551 |

TABLE 2A-continued

THE [4,4,0]REVERSE TURN MIMETICS LIBRARY

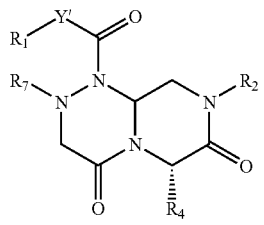

| No | R2 | R4 | R7 | R1-Y' | Mol. Weight | M + H |
|---|---|---|---|---|---|---|
| 512 | 2,6-F2-benzyl | 4-HO-benzyl | Methyl | Benzylamino | 550 | 551 |
| 513 | 2,5-F2-benzyl | 4-HO-benzyl | Methyl | Benzylamino | 550 | 551 |
| 514 | 3-CF3-benyl | 4-HO-benzyl | Methyl | Benzylamino | 582 | 583 |
| 515 | 4-CF3-benyl | 4-HO-benzyl | Methyl | Benzylamino | 582 | 583 |
| 516 | 3,4,5-F3-benyl | 4-HO-benzyl | Methyl | Benzylamino | 568 | 569 |
| 517 | 2-Cl-benzyl | 4-HO-benzyl | Methyl | Benzylamino | 548 | 549 |
| 518 | 3-Cl-benzyl | 4-HO-benzyl | Methyl | Benzylamino | 548 | 549 |
| 519 | 2,4-Cl2-benzyl | 4-HO-benzyl | Methyl | Benzylamino | 582 | 583 |
| 520 | (S)-Methylphenyl | 4-HO-benzyl | Methyl | Benzylamino | 528 | 529 |
| 521 | (R)-Methylphenyl | 4-HO-benzyl | Methyl | Benzylamino | 528 | 529 |
| 522 | 4-Methyl-benzyl | 4-HO-benzyl | Methyl | Benzylamino | 528 | 529 |
| 523 | 4-Methoxybenzyl | 4-HO-benzyl | Methyl | Benzylamino | 544 | 545 |
| 524 | 3,4-Dimethoxybenzyl | 4-HO-benzyl | Methyl | Benzylamino | 574 | 575 |
| 525 | Furan-2-yl-methylamino | 4-HO-benzyl | Methyl | Benzylamino | 504 | 505 |
| 526 | (R)-Methylnaphthyl-1-ylmethyl | 4-HO-benzyl | Methyl | Benzylamino | 578 | 579 |
| 527 | (S)-Methylnaphthyl-1-ylmethyl | 4-HO-benzyl | Methyl | Benzylamino | 578 | 579 |
| 528 | Naphthyl-1-ylmethyl | 3-Oxy-pyridin-1-ylmethyl | Methyl | Benzylamino | 565 | 566 |
| 529 | (R)-alpha methylbenzyl | 4-HO-benzyl | Methyl | Benzylamino | 578 | 579 |
| 530 | Naphthyl-2-ylmethyl | 4-HO-benzyl | Methyl | Benzylamino | 564 | 565 |
| 531 | 4-F-naphthyl-1-ylmethyl | 4-HO-benzyl | Methyl | Benzylamino | 582 | 583 |
| 532 | 2-Methoxybenzyl | 4-HO-benzyl | Methyl | Benzylamino | 544 | 545 |
| 533 | 4-Cl-benzyl | 4-HO-benzyl | Methyl | Benzylamino | 548 | 549 |
| 534 | 3,4-Cl2-benzyl | 4-HO-benzyl | Methyl | Benzylamino | 582 | 583 |
| 535 | 2-CF3Obenzyl | 4-HO-benzyl | Methyl | Benzylamino | 598 | 599 |
| 536 | 2-CF3Sbenzyl | 4-HO-benzyl | Methyl | Benzylamino | 614 | 615 |
| 537 | 2-CF3benzyl | 4-HO-benzyl | Methyl | Benzylamino | 582 | 583 |
| 538 | 5-Quinoline-1yl-methyl | 4-HO-benzyl | Methyl | Benzylamino | 565 | 566 |
| 539 | 8-Quinoline-1yl-methyl | 3-t-Bu-4-HO-benzyl | Methyl | Benzylamino | 621 | 622 |
| 540 | 8-Quinoline-1yl-methyl | 4-NO2-benzyl | Methyl | Benzylamino | 594 | 595 |
| 541 | 8-Quinoline-1yl-methyl | (1H-Pyrrol-2-yl)-methyl | Methyl | Benzylamino | 538 | 539 |
| 542 | Naphthyl-1-ylmethyl | 4-Benzyloxy-carbonylaminobenzyl | Methyl | Benzylamino | 697 | 698 |
| 543 | 2,3-Cl2-benzyl | 4-HO-benzyl | Methyl | Benzylamino | 582 | 583 |
| 544 | Pentafluorobenzyl | 4-HO-benzyl | Methyl | Benzylamino | 604 | 605 |
| 545 | Benzyl | 4-HO-benzyl | Methyl | Benzylamino | 514 | 515 |
| 546 | Quinoxaline-5yl-methyl | 4-HO-benzyl | Methyl | Benzylamino | 566 | 567 |
| 547 | 8-Quinoline-1yl-methyl | 3-Pyridylmethyl | Methyl | Benzylamino | 550 | 551 |
| 548 | 8-Quinoline-1 yl-methyl | Pentafluorobenzyl | Methyl | Benzylamino | 639 | 640 |
| 549 | Naphthyl-1-ylmethyl | 4-HO-benzyl | Methyl | Benzylamino(thiourea) | 580 | 581 |
| 550 | Naphthyl-1-ylmethyl | 4-Amino-benzyl | Methyl | Benzylamino | 563 | 564 |
| 551 | 3,4,5-tri-Methoxybenzyl | 4-Amino-benzyl | Methyl | Benzylamino | 603 | 604 |
| 552 | Naphthyl-1-ylmethyl | 4-Pyndylmethyl | Methyl | Benzylamino | 549 | 550 |
| 553 | Naphthyl-1-ylmethyl | (R) 4-HO-phenyl | Methyl | Benzylamino | 550 | 551 |
| 554 | 2-HO-3-Methoxy-benzyl | 4-HO-benzyl | Methyl | Benzylamino | 560 | 561 |
| 555 | Naphthyl-1-ylmethyl | 3-Nitro-4-HO-benzyl | Methyl | Benzylamino | 609 | 610 |
| 556 | Naphthyl-1-ylmethyl | 4-CO2H-CH2O-benzyl | Methyl | Benzylamino | 622 | 623 |

TABLE 2A-continued

THE [4,4,0]REVERSE TURN MIMETICS LIBRARY

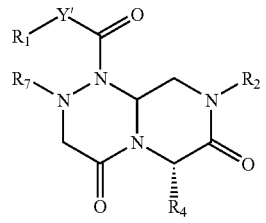

| No | R₂ | R₄ | R₇ | R₁-Y' | Mol. Weight | M + H |
|---|---|---|---|---|---|---|
| 557 | Naphthyl-1-ylmethyl | 1-Naphthylaminomethyl | Methyl | Benzylamino | 641 | 642 |
| 558 | Naphthyl-1-ylmethyl | 4-Oxy-pyridylmethyl | Methyl | Benzylamino | 565 | 566 |
| 559 | 4-F-alpha-methylbenzyl | 4-HO-benzyl | Methyl | Benzylamino | 546 | 547 |
| 560 | Naphthyl-1-ylmethyl | Benzoylaminoethyl | Methyl | Benzylamino | 605 | 606 |
| 561 | 8-Quinoline-1-yl-methyl | 3,4-(OH)2-benzyl | Methyl | Benzylamino | 581 | 582 |
| 562 | 4-N,N-Dimethyl-aminobenzyl | 4-HO-benzyl | Methyl | Benzylamino | 557 | 558 |
| 563 | Naphthyl-1-ylmethyl | (R) 4-F-benzyl | Methyl | Benzylamino | 609 | 610 |
| 564 | Naphthyl-1-ylmethyl | 4-HO-benzyl | Methyl | 2-Chloroethylamino | 536 | 537 |
| 565 | Naphthyl-1-ylmethyl | 4-HO-phenethyl | Methyl | Benzylamino | 578 | 579 |
| 566 | 4-F-benzyl | 3-F,4-HO-benzyl | Methyl | Benzylamino | 550 | 551 |
| 567 | 2,4-F₂-benzyl | 3-F,4-HO-benzyl | Methyl | Benzylamino | 568 | 569 |
| 568 | 3-CF₃benzyl | (R) 4-HO-phenyl | Methyl | Benzylamino | 568 | 569 |
| 569 | (S)-Methylnaphthyl-1-ylmethyl | (R) 4-HO-phenyl | Methyl | Benzylamino | 514 | 515 |
| 570 | (R)-Methylnaphthyl-1-ylmethyl | (R) 4-HO-phenyl | Methyl | Benzylamino | 514 | 515 |
| 571 | 2,3,6-F₃-benzyl | (R) 4-HO-phenyl | Methyl | Benzylamino | 554 | 555 |
| 572 | 3-F-benzyl | (R) 4-HO-phenyl | Methyl | Benzylamino | 518 | 519 |
| 573 | 4-Cl-benzyl | (R) 4-HO-phenyl | Methyl | Benzylamino | 534 | 535 |
| 574 | 3-Cl-benzyl | (R) 4-HO-phenyl | Methyl | Benzylamino | 534 | 535 |
| 575 | 2-Cl-benzyl | (R) 4-HO-phenyl | Methyl | Benzylamino | 534 | 535 |
| 576 | 3,4-Cl₂-benzyl | (R)4-HO-phenyl | Methyl | Benzylamino | 568 | 569 |
| 577 | 3-CF₃O-benzyl | (R) 4-HO-phenyl | Methyl | Benzylamino | 584 | 585 |
| 578 | 4-F-benzyl | (R) 4-HO-phenyl | Methyl | Benzylamino | 518 | 519 |
| 579 | 2,4-F₂-benzyl | (R) 4-HO-phenyl | Methyl | Benzylamino | 536 | 537 |
| 580 | 3-(2-Chloro-ethyl)-ureido]-benzyl | 4-HO-benzyl | Methyl | Benzylamino | 634 | 635 |
| 581 | 3-Aminobenzyl | 4-HO-benzyl | Methyl | Benzylamino | 529 | 530 |
| 582 | 3-N-Methylaminobenzyl | 4-HO-benzyl | Methyl | Benzylamino | 543 | 544 |
| 583 | 3-N,N-Dimethylaminobenzyl | 4-HO-benzyl | Methyl | Benzylamino | 557 | 558 |
| 584 | 1H-Benzoimidazol-4-ylmethyl | 4-HO-benzyl | Methyl | Benzylamino | 554 | 555 |
| 585 | 2-HO-benzyl | 4-HO-benzyl | Methyl | Benzylamino | 530 | 531 |
| 586 | 2-Pyridylmethyl | 4-HO-benzyl | Methyl | Benzylamino | 515 | 516 |
| 587 | 4-Pyridylmethyl | 4-HO-benzyl | Methyl | Benzylamino | 515 | 516 |
| 588 | 8-quinolin-2-ylmethyl | 4-HO-benzyl | Methyl | Benzylamino | 565 | 566 |
| 589 | 8-Benzofuran-4-ylmethyl | 4-HO-benzyl | Methyl | Benzylamino | 554 | 555 |
| 590 | Naphthyl-1-ylmethyl | 4-HO-phenyl | Methyl | Benzylamino | 550 | 551 |
| 591 | 4-F-benzyl | 4-HO-phenyl | Methyl | Benzylamino | 518 | 519 |
| 592 | 2,4-F₂-benzyl | 4-HO-phenyl | Methyl | Benzylamino | 536 | 537 |
| 593 | (R)-Toluylmethyl | 4-HO-benzyl | Methyl | Benzylamino | 542 | 543 |
| 594 | (S)-Toluylmethyl | 4-HO-benzyl | Methyl | Benzylamino | 542 | 543 |
| 595 | 1,2,3,4-tetrahydro-naphthalen-2-yl | 4-HO-benzyl | Methyl | Benzylamino | 554 | 555 |
| 596 | Naphthyl-1-ylmethyl | 3,4-Dimethoxybenzyl | Methyl | Benzylamino | 608 | 609 |
| 597 | 2-Dimethylamino-6-F-benzyl | 4-HO-benzyl | Methyl | Benzylamino | 575 | 576 |
| 598 | 2-Dimethylaminobenzyl | 4-HO-benzyl | Methyl | Benzylamino | 557 | 558 |
| 599 | Naphthyl-1-ylmethyl | 4-CN-benzyl | Methyl | Benzylamino | 573 | 574 |
| 600 | 4-F-2-CF₃-benzyl | 4-HO-benzyl | Methyl | Benzylamino | 599 | 600 |
| 601 | 4-Cl-2-Dimethylaminobenzyl | 4-HO-benzyl | Methyl | Benzylamino | 591 | 592 |

TABLE 2A-continued

THE [4,4,0]REVERSE TURN MIMETICS LIBRARY

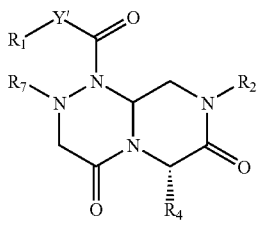

| No | R$_2$ | R$_4$ | R$_7$ | R$_1$-Y' | Mol. Weight | M + H |
|---|---|---|---|---|---|---|
| 602 | 3-N,N-Ethylmethyllamino-benzyl | 4-HO-benzyl | Methyl | Benzylamino | 571 | 572 |
| 603 | 3-Diethylaminobenzyl | 4-HO-benzyl | Methyl | Benzylamino | 585 | 586 |
| 604 | 4-Cl-3-Dimethylaminobenzyl | 4-HO-benzyl | Methyl | Benzylamino | 591 | 592 |
| 605 | 4-F-2-Dimethylaminobenzyl | 4-HO-benzyl | Methyl | Benzylamino | 575 | 576 |
| 606 | 3,5-(CH$_3$)$_2$)2-Dimethylamino-benzyl | 4-HO-benzyl | Methyl | Benzylamino | 585 | 586 |
| 607 | 3-(CH$_3$)-2-Dimethylaminobenzyl | 4-HO-benzyl | Methyl | Benzylamino | 571 | 572 |
| 608 | 6093,4-F$_2$-2-6-(CH$_3$)-2-Dimethylaminobenzyl | 4-HO-benzyl | Methyl | Benzylamino | 571 | 572 |
| 609 | 3,4-F$_2$-2-Dimethylaminobenzyl | 4-HO-benzyl | Methyl | Benzylamino | 593 | 594 |

TABLE 2B

THE [4,4,0]REVERSE TURN MIMETICS LIBRARY

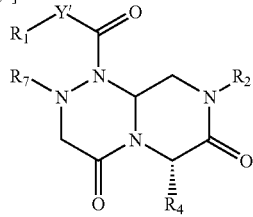

| No | MOLSTRUCTURE | Mol. Weight | M + H (MS) |
|---|---|---|---|
| 802 | | 480 | 481 |

TABLE 2B-continued
THE [4,4,0]REVERSE TURN MIMETICS LIBRARY
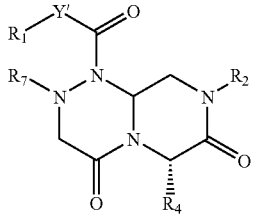
| No | MOLSTRUCTURE | Mol. Weight | M + H (MS) |
|---|---|---|---|
| 803 | | 430 | 431 |
| 804 | | 416 | 417 |
| 805 | | 464 | 465 |

TABLE 2B-continued

THE [4,4,0]REVERSE TURN MIMETICS LIBRARY

| No | MOLSTRUCTURE | Mol. Weight | M + H (MS) |
|---|---|---|---|
| 806 | | 430 | 431 |
| 807 | | 430 | 431 |
| 808 | | 448 | 448 |

TABLE 2B-continued

THE [4,4,0]REVERSE TURN MIMETICS LIBRARY

| No | MOLSTRUCTURE | Mol. Weight | M + H (MS) |
|---|---|---|---|
| 809 | | 416 | 417 |
| 810 | | 431 | 432 |
| 811 | | 446 | 447 |

TABLE 2B-continued
THE [4,4,0]REVERSE TURN MIMETICS LIBRARY
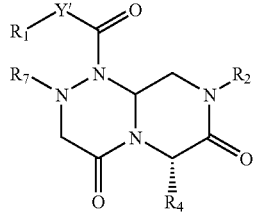
| No | MOLSTRUCTURE | Mol. Weight | M + H (MS) |
|---|---|---|---|
| 812 | | 450 | 451 |
| 813 | | 515 | 516 |

TABLE 2B-continued
THE [4,4,0]REVERSE TURN MIMETICS LIBRARY
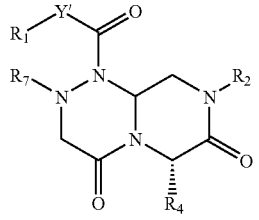
| No | MOLSTRUCTURE | Mol. Weight | M + H (MS) |
|---|---|---|---|
| 814 | | 582 | 583 |
| 815 | | 532 | 533 |
| 816 | | 518 | 519 |

TABLE 2B-continued
THE [4,4,0]REVERSE TURN MIMETICS LIBRARY
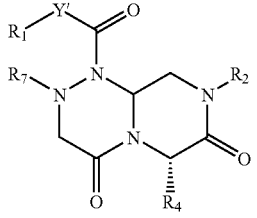
| No | MOLSTRUCTURE | Mol. Weight | M + H (MS) |
|---|---|---|---|
| 817 | | 566 | 567 |
| 818 | | 532 | 533 |
| 819 | | 532 | 533 |

TABLE 2B-continued

THE [4,4,0]REVERSE TURN MIMETICS LIBRARY

| No | MOLSTRUCTURE | Mol. Weight | M + H (MS) |
|---|---|---|---|
| 820 | | 550 | 551 |
| 821 | | 518 | 519 |
| 822 | | 534 | 535 |

TABLE 2B-continued
THE [4,4,0]REVERSE TURN MIMETICS LIBRARY
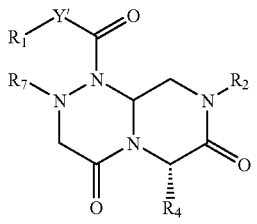
| No | MOLSTRUCTURE | Mol. Weight | M + H (MS) |
|----|--------------|-------------|------------|
| 823 | | 548 | 549 |
| 824 | | 552 | 553 |

TABLE 2B-continued
THE [4,4,0]REVERSE TURN MIMETICS LIBRARY
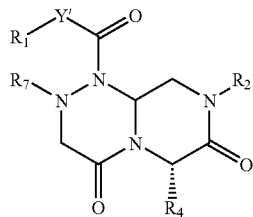
| No | MOLSTRUCTURE | Mol. Weight | M + H (MS) |
|---|---|---|---|
| 825 | 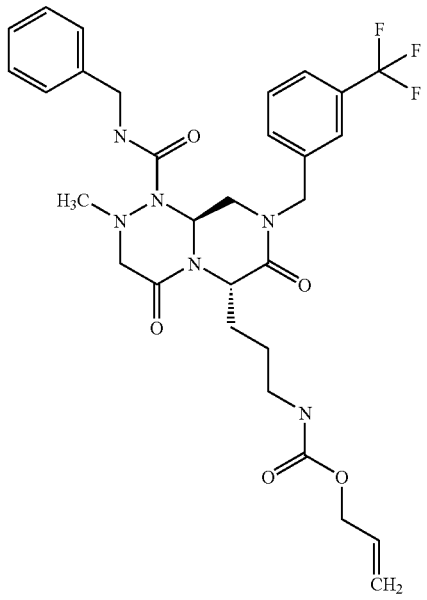 | 617 | 618 |
| 826 | 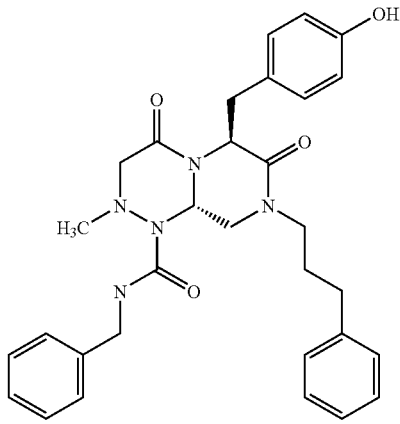 | 542 | 543 |

TABLE 2B-continued
THE [4,4,0]REVERSE TURN MIMETICS LIBRARY
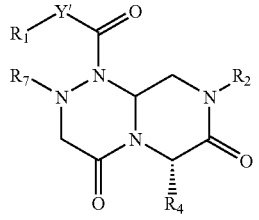
| No | MOLSTRUCTURE | Mol. Weight | M + H (MS) |
|---|---|---|---|
| 827 | | 492 | 493 |
| 828 | | 478 | 479 |
| 829 | | 526 | 527 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 830 | | 492 | 493 |
| 831 | | 492 | 493 |
| 832 | | 510 | 511 |

TABLE 2B-continued

THE [4,4,0]REVERSE TURN MIMETICS LIBRARY

| No | MOLSTRUCTURE | Mol. Weight | M + H (MS) |
|---|---|---|---|
| 833 | | 478 | 479 |
| 834 | | 494 | 495 |
| 835 | | 508 | 509 |

TABLE 2B-continued
THE [4,4,0]REVERSE TURN MIMETICS LIBRARY
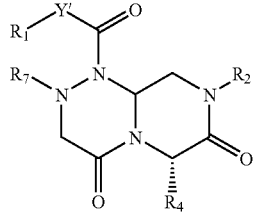
| No | MOLSTRUCTURE | Mol. Weight | M + H (MS) |
|---|---|---|---|
| 836 | | 512 | 513 |
| 837 | | 577 | 578 |

TABLE 2B-continued
THE [4,4,0]REVERSE TURN MIMETICS LIBRARY
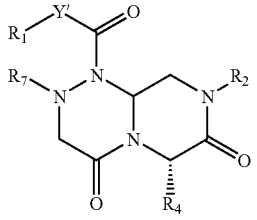
| No | MOLSTRUCTURE | Mol. Weight | M + H (MS) |
|---|---|---|---|
| 838 | | 468 | 469 |
| 839 | | 516 | 517 |
| 840 | | 482 | 483 |

TABLE 2B-continued
THE [4,4,0]REVERSE TURN MIMETICS LIBRARY
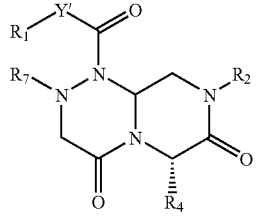
| No | MOLSTRUCTURE | Mol. Weight | M + H (MS) |
|---|---|---|---|
| 841 | | 482 | 483 |
| 842 | | 468 | 469 |
| 843 | | 484 | 485 |

TABLE 2B-continued
THE [4,4,0]REVERSE TURN MIMETICS LIBRARY
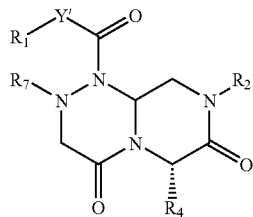
| No | MOLSTRUCTURE | Mol. Weight | M + H (MS) |
|---|---|---|---|
| 844 | 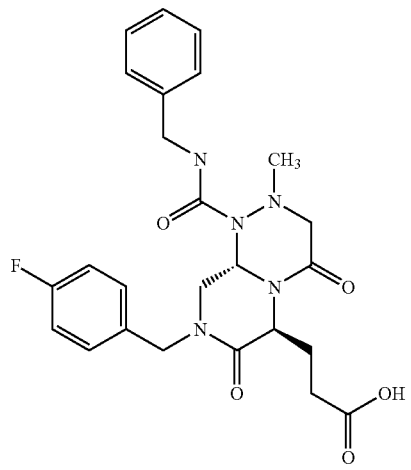 | 498 | 499 |
| 845 | 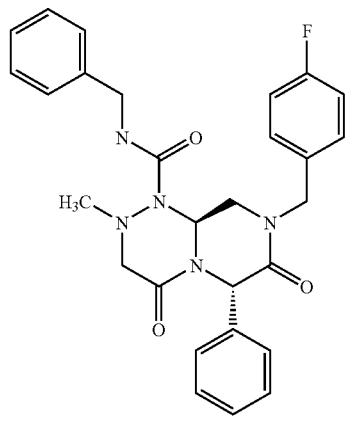 | 502 | 503 |

TABLE 2B-continued
THE [4,4,0]REVERSE TURN MIMETICS LIBRARY
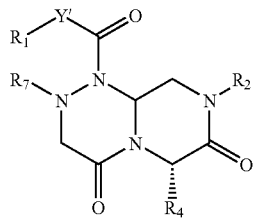
| No | MOLSTRUCTURE | Mol. Weight | M + H (MS) |
|---|---|---|---|
| 846 | 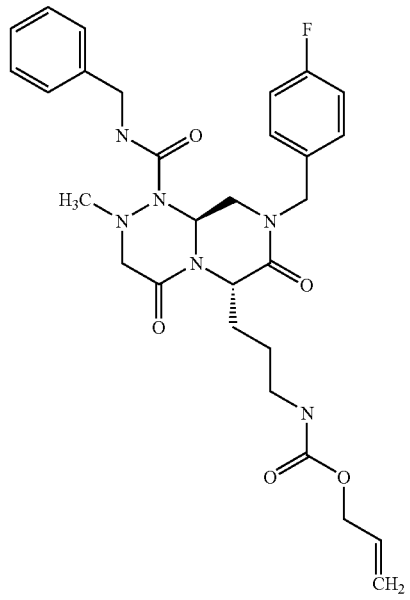 | 567 | 568 |
| 847 | 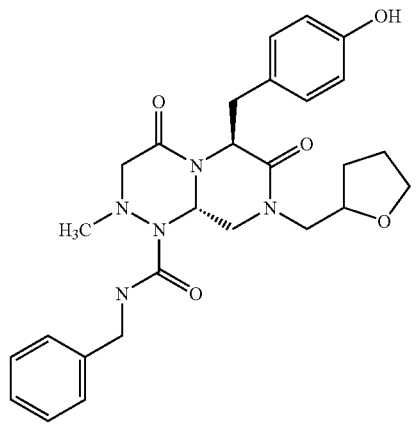 | 508 | 509 |

TABLE 2B-continued
THE [4,4,0]REVERSE TURN MIMETICS LIBRARY
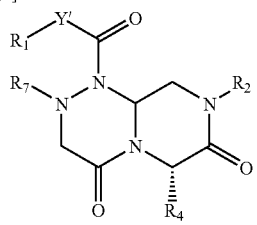
| No | MOLSTRUCTURE | Mol. Weight | M + H (MS) |
|---|---|---|---|
| 848 | | 458 | 459 |
| 849 | | 444 | 445 |
| 850 | | 492 | 493 |

TABLE 2B-continued

THE [4,4,0]REVERSE TURN MIMETICS LIBRARY

| No | MOLSTRUCTURE | Mol. Weight | M + H (MS) |
|---|---|---|---|
| 851 | | 458 | 459 |
| 852 | | 458 | 459 |
| 853 | | 476 | 477 |

TABLE 2B-continued
THE [4,4,0]REVERSE TURN MIMETICS LIBRARY
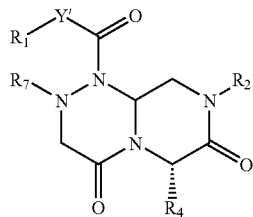
| No | MOLSTRUCTURE | Mol. Weight | M + H (MS) |
|---|---|---|---|
| 854 | 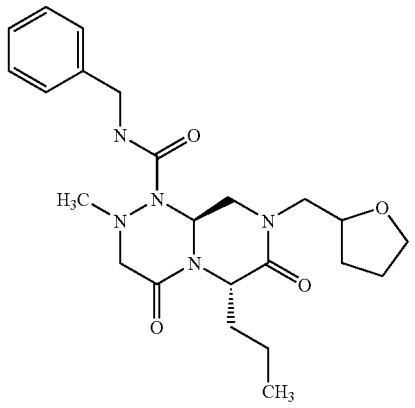 | 444 | 445 |
| 855 | 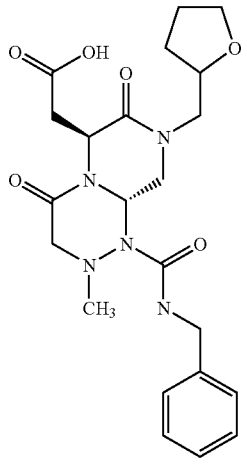 | 460 | 461 |

TABLE 2B-continued
THE [4,4,0]REVERSE TURN MIMETICS LIBRARY
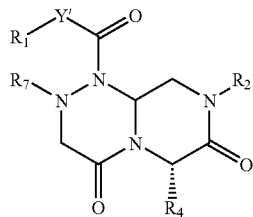
| No | MOLSTRUCTURE | Mol. Weight | M + H (MS) |
|---|---|---|---|
| 856 | 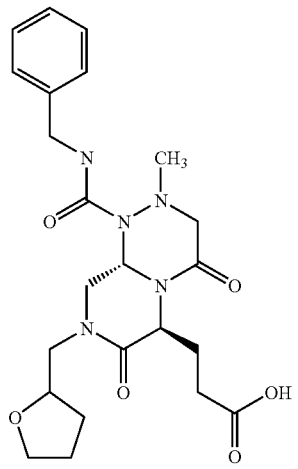 | 474 | 475 |
| 857 | 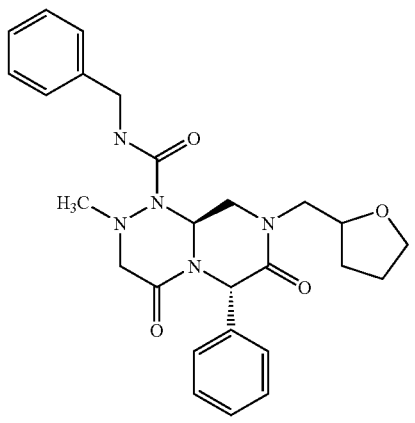 | 478 | 479 |

TABLE 2B-continued
THE [4,4,0]REVERSE TURN MIMETICS LIBRARY
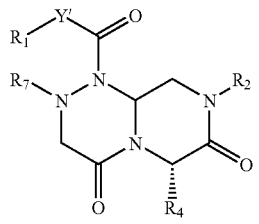
| No | MOLSTRUCTURE | Mol. Weight | M + H (MS) |
|---|---|---|---|
| 858 | 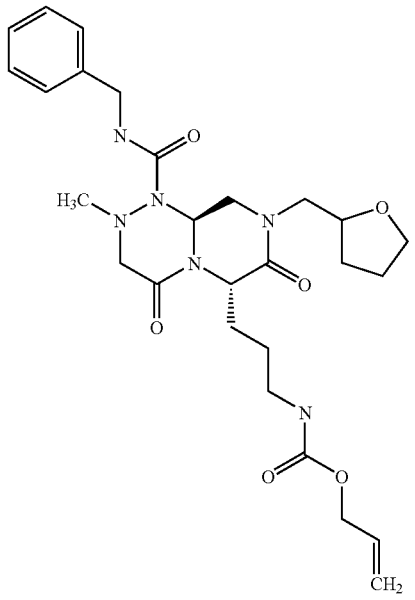 | 543 | 544 |
| 859 | 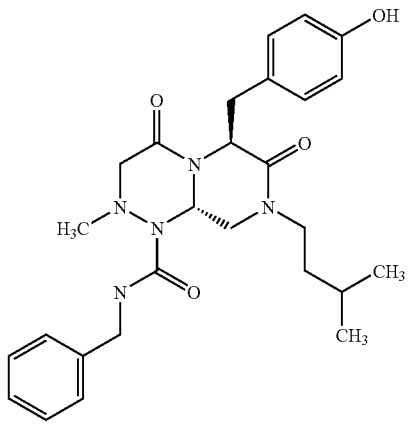 | 494 | 495 |

TABLE 2B-continued
THE [4,4,0]REVERSE TURN MIMETICS LIBRARY
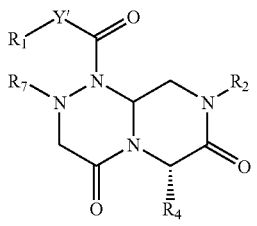
| No | MOLSTRUCTURE | Mol. Weight | M + H (MS) |
|---|---|---|---|
| 860 | | 444 | 445 |
| 861 | | 430 | 431 |
| 862 | | 478 | 479 |

TABLE 2B-continued

THE [4,4,0]REVERSE TURN MIMETICS LIBRARY

| No | MOLSTRUCTURE | Mol. Weight | M + H (MS) |
|---|---|---|---|
| 863 | | 444 | 445 |
| 864 | | 444 | 445 |
| 865 | | 462 | 463 |

TABLE 2B-continued

THE [4,4,0]REVERSE TURN MIMETICS LIBRARY

| No | MOLSTRUCTURE | Mol. Weight | M + H (MS) |
|---|---|---|---|
| 866 | | 430 | 431 |
| 867 | | 446 | 447 |
| 868 | | 460 | 461 |

TABLE 2B-continued
THE [4,4,0]REVERSE TURN MIMETICS LIBRARY
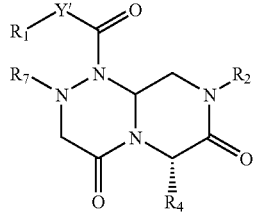
| No | MOLSTRUCTURE | Mol. Weight | M + H (MS) |
|----|---|---|---|
| 869 | | 464 | 465 |
| 870 | | 529 | 530 |

TABLE 2B-continued
THE [4,4,0]REVERSE TURN MIMETICS LIBRARY
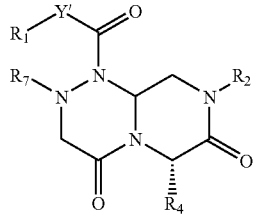
| No | MOLSTRUCTURE | Mol. Weight | M + H (MS) |
|----|--------------|-------------|------------|
| 871 | | 558 | 559 |
| 872 | | 508 | 509 |
| 873 | | 494 | 495 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 874 | | 542 | 543 |
| 875 | | 508 | 509 |
| 876 | | 508 | 509 |

TABLE 2B-continued

THE [4,4,0]REVERSE TURN MIMETICS LIBRARY

| No | MOLSTRUCTURE | Mol. Weight | M + H (MS) |
|---|---|---|---|
| 877 | | 526 | 527 |
| 878 | | 494 | 495 |
| 879 | | 510 | 511 |

TABLE 2B-continued
THE [4,4,0]REVERSE TURN MIMETICS LIBRARY
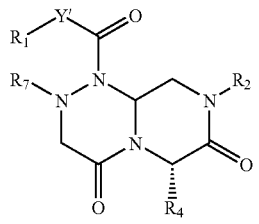
| No | MOLSTRUCTURE | Mol. Weight | M + H (MS) |
|---|---|---|---|
| 880 | 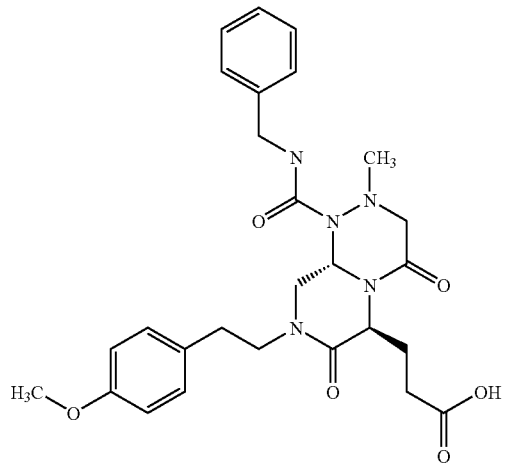 | 524 | 525 |
| 881 | 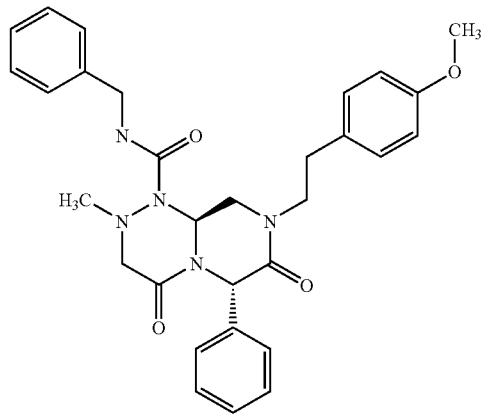 | 528 | 529 |

TABLE 2B-continued
THE [4,4,0]REVERSE TURN MIMETICS LIBRARY
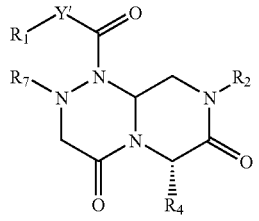
| No | MOLSTRUCTURE | Mol. Weight | M + H (MS) |
|----|--------------|-------------|------------|
| 882 | 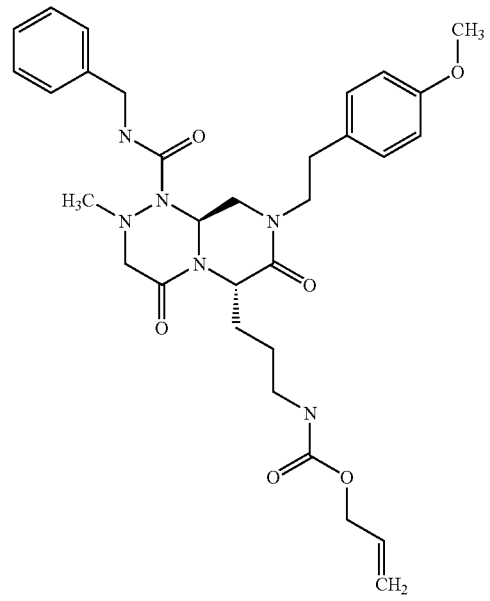 | 593 | 594 |
| 883 | 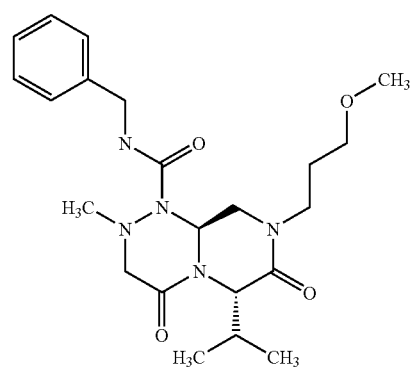 | 432 | 433 |

TABLE 2B-continued

THE [4,4,0]REVERSE TURN MIMETICS LIBRARY

| No | MOLSTRUCTURE | Mol. Weight | M + H (MS) |
|---|---|---|---|
| 884 | | 480 | 481 |
| 885 | | 446 | 447 |
| 886 | | 446 | 447 |

TABLE 2B-continued

THE [4,4,0]REVERSE TURN MIMETICS LIBRARY

| No | MOLSTRUCTURE | Mol. Weight | M + H (MS) |
|---|---|---|---|
| 887 | | 464 | 465 |
| 888 | | 432 | 433 |
| 889 | | 447 | 448 |

TABLE 2B-continued
THE [4,4,0]REVERSE TURN MIMETICS LIBRARY
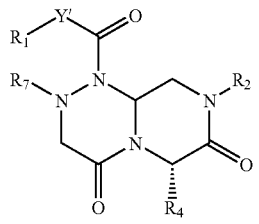
| No | MOLSTRUCTURE | Mol. Weight | M + H (MS) |
|---|---|---|---|
| 890 | 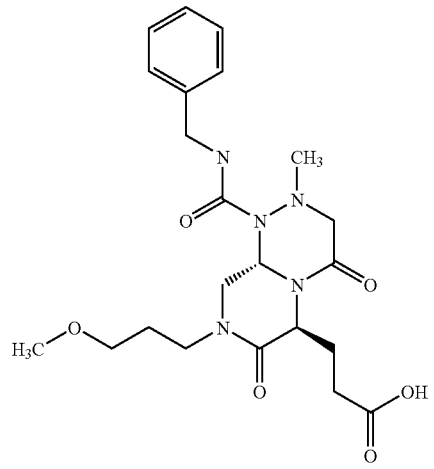 | 462 | 463 |
| 891 | 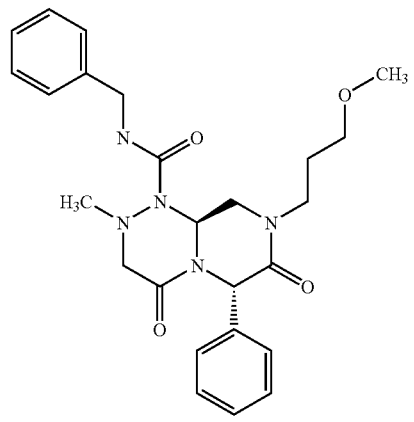 | 466 | 467 |

TABLE 2B-continued
THE [4,4,0]REVERSE TURN MIMETICS LIBRARY
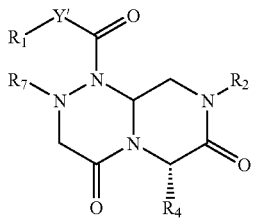
| No | MOLSTRUCTURE | Mol. Weight | M + H (MS) |
|----|--------------|-------------|------------|
| 892 | 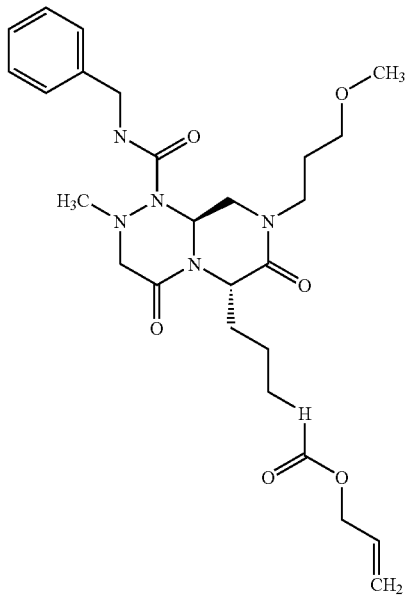 | 531 | 532 |
| 893 | 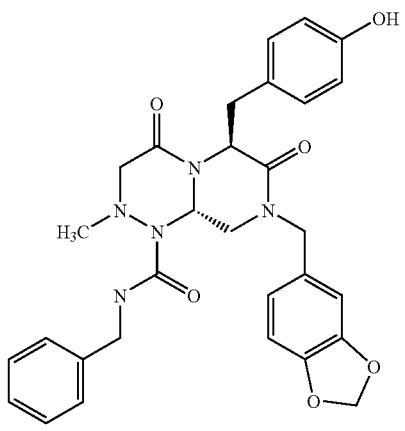 | 558 | 559 |

TABLE 2B-continued
THE [4,4,0]REVERSE TURN MIMETICS LIBRARY
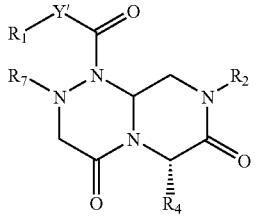
| No | MOLSTRUCTURE | Mol. Weight | M + H (MS) |
|---|---|---|---|
| 894 | | 508 | 509 |
| 895 | | 494 | 495 |
| 896 | | 542 | 543 |

TABLE 2B-continued

THE [4,4,0]REVERSE TURN MIMETICS LIBRARY

| No | MOLSTRUCTURE | Mol. Weight | M + H (MS) |
|---|---|---|---|
| 897 | | 508 | 509 |
| 898 | | 508 | 509 |
| 899 | | 526 | 527 |

TABLE 2B-continued

THE [4,4,0]REVERSE TURN MIMETICS LIBRARY

| No | MOLSTRUCTURE | Mol. Weight | M + H (MS) |
|---|---|---|---|
| 900 | | 494 | 495 |
| 901 | | 510 | 511 |
| 902 | | 524 | 525 |

TABLE 2B-continued
THE [4,4,0]REVERSE TURN MIMETICS LIBRARY
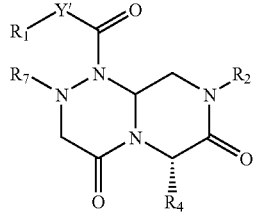
| No | MOLSTRUCTURE | Mol. Weight | M + H (MS) |
|---|---|---|---|
| 903 | | 528 | 529 |
| 904 | | 593 | 594 |

TABLE 2B-continued
THE [4,4,0]REVERSE TURN MIMETICS LIBRARY
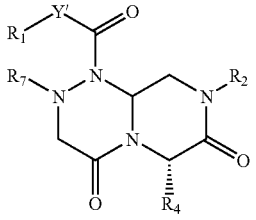
| No | MOLSTRUCTURE | Mol. Weight | M + H (MS) |
|---|---|---|---|
| 905 | | 544 | 545 |
| 906 | | 494 | 495 |
| 907 | | 480 | 481 |

TABLE 2B-continued
THE [4,4,0]REVERSE TURN MIMETICS LIBRARY
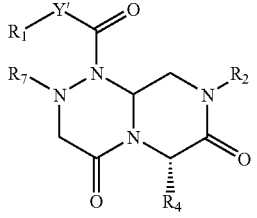
| No | MOLSTRUCTURE | Mol. Weight | M + H (MS) |
|---|---|---|---|
| 908 | | 528 | 529 |
| 909 | | 494 | 495 |
| 910 | | 494 | 495 |

TABLE 2B-continued

THE [4,4,0]REVERSE TURN MIMETICS LIBRARY

| No | MOLSTRUCTURE | Mol. Weight | M + H (MS) |
|---|---|---|---|
| 911 | | 512 | 513 |
| 912 | | 480 | 481 |
| 913 | | 496 | 497 |

TABLE 2B-continued
THE [4,4,0]REVERSE TURN MIMETICS LIBRARY
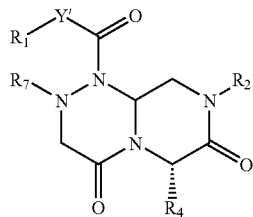
| No | MOLSTRUCTURE | Mol. Weight | M + H (MS) |
|---|---|---|---|
| 914 | 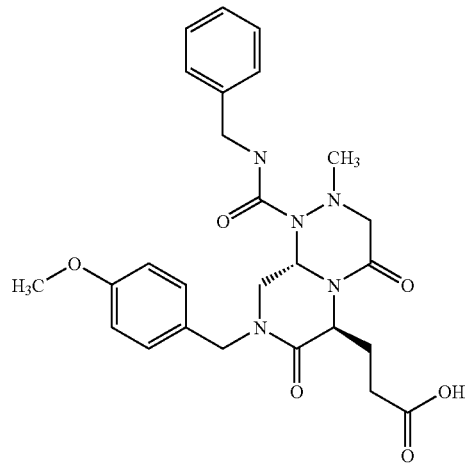 | 510 | 511 |
| 915 | 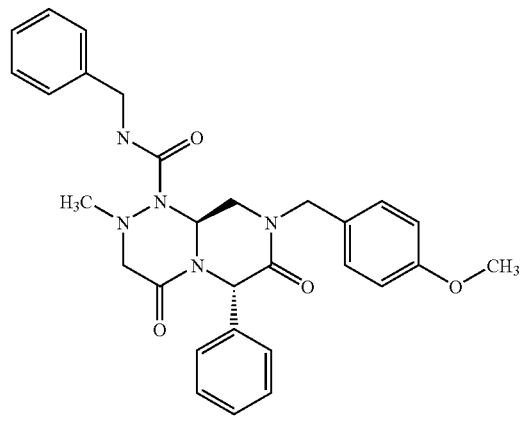 | 514 | 515 |

TABLE 2B-continued
THE [4,4,0]REVERSE TURN MIMETICS LIBRARY
| No | MOLSTRUCTURE | Mol. Weight | M + H (MS) |
|---|---|---|---|
| 916 | | 579 | 580 |
| 917 | | 464 | 465 |

TABLE 2B-continued
THE [4,4,0]REVERSE TURN MIMETICS LIBRARY
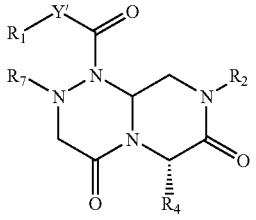
| No | MOLSTRUCTURE | Mol. Weight | M + H (MS) |
|---|---|---|---|
| 918 | | 450 | 451 |
| 919 | | 498 | 499 |
| 920 | | 464 | 465 |

TABLE 2B-continued
THE [4,4,0]REVERSE TURN MIMETICS LIBRARY
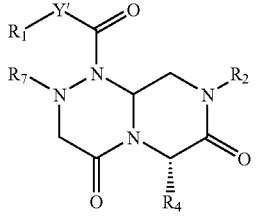
| No | MOLSTRUCTURE | Mol. Weight | M + H (MS) |
|---|---|---|---|
| 921 | | 464 | 465 |
| 922 | | 482 | 483 |
| 923 | | 450 | 451 |

TABLE 2B-continued
THE [4,4,0]REVERSE TURN MIMETICS LIBRARY
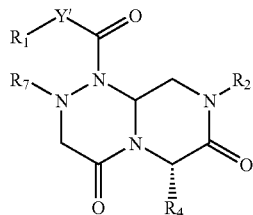
| No | MOLSTRUCTURE | Mol. Weight | M + H (MS) |
|---|---|---|---|
| 924 | | 466 | 467 |
| 925 | | 480 | 481 |
| 926 | | 484 | 485 |

TABLE 2B-continued
THE [4,4,0]REVERSE TURN MIMETICS LIBRARY
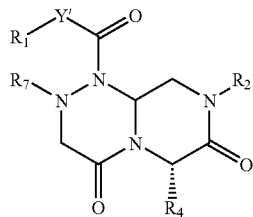
| No | MOLSTRUCTURE | Mol. Weight | M + H (MS) |
|---|---|---|---|
| 927 | | 549 | 550 |
| 928 | | 480 | 481 |
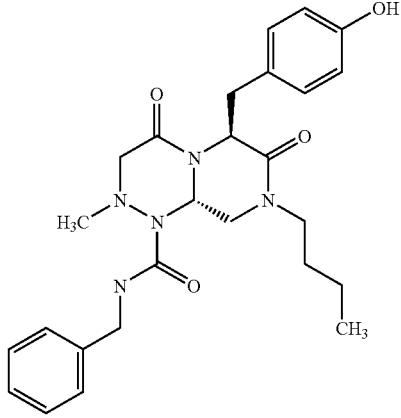

TABLE 2B-continued
THE [4,4,0]REVERSE TURN MIMETICS LIBRARY
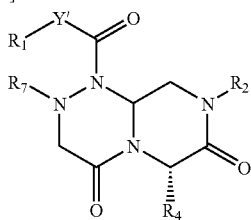
| No | MOLSTRUCTURE | Mol. Weight | M + H (MS) |
|---|---|---|---|
| 929 | | 430 | 431 |
| 930 | | 416 | 417 |
| 931 | | 464 | 465 |

TABLE 2B-continued

THE [4,4,0]REVERSE TURN MIMETICS LIBRARY

| No | MOLSTRUCTURE | Mol. Weight | M + H (MS) |
|---|---|---|---|
| 932 | | 430 | 431 |
| 933 | | 430 | 431 |
| 934 | | 448 | 449 |

TABLE 2B-continued

THE [4,4,0]REVERSE TURN MIMETICS LIBRARY

| No | MOLSTRUCTURE | Mol. Weight | M + H (MS) |
|---|---|---|---|
| 935 | | 416 | 417 |
| 936 | | 431 | 432 |
| 937 | | 446 | 447 |

TABLE 2B-continued
THE [4,4,0]REVERSE TURN MIMETICS LIBRARY
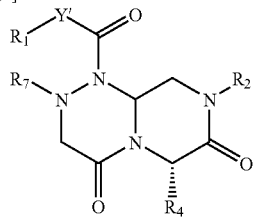
| No | MOLSTRUCTURE | Mol. Weight | M + H (MS) |
|---|---|---|---|
| 938 | | 450 | 451 |
| 939 | | 515 | 516 |

TABLE 2B-continued
THE [4,4,0]REVERSE TURN MIMETICS LIBRARY
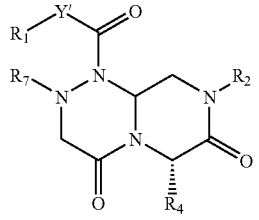
| No | MOLSTRUCTURE | Mol. Weight | M + H (MS) |
|---|---|---|---|
| 940 | | 504 | 505 |
| 941 | | 454 | 455 |
| 942 | | 440 | 441 |

TABLE 2B-continued
THE [4,4,0]REVERSE TURN MIMETICS LIBRARY
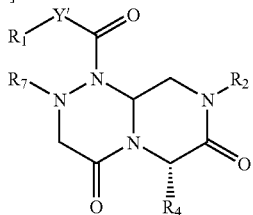
| No | MOLSTRUCTURE | Mol. Weight | M + H (MS) |
|---|---|---|---|
| 943 | | 488 | 489 |
| 944 | | 454 | 455 |
| 945 | | 454 | 455 |

TABLE 2B-continued
THE [4,4,0]REVERSE TURN MIMETICS LIBRARY
| No | MOLSTRUCTURE | Mol. Weight | M + H (MS) |
|---|---|---|---|
| 946 | 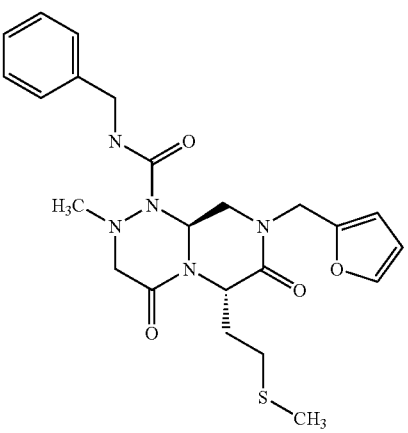 | 472 | 473 |
| 947 | 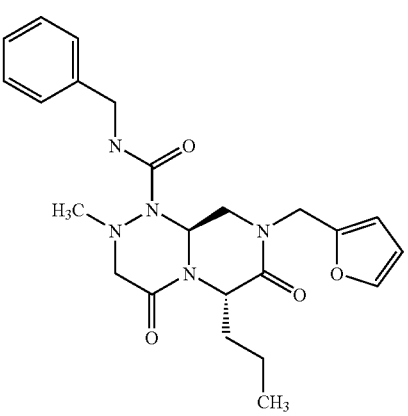 | 440 | 441 |
| 948 | 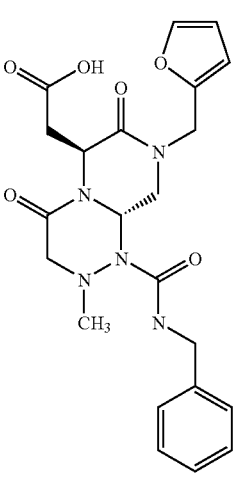 | 455 | 456 |

TABLE 2B-continued
THE [4,4,0]REVERSE TURN MIMETICS LIBRARY
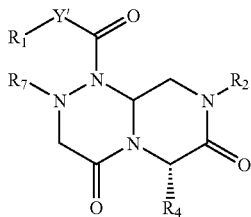
| No | MOLSTRUCTURE | Mol. Weight | M + H (MS) |
|---|---|---|---|
| 949 | 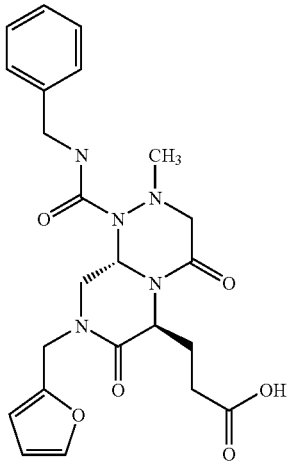 | 470 | 471 |
| 950 | 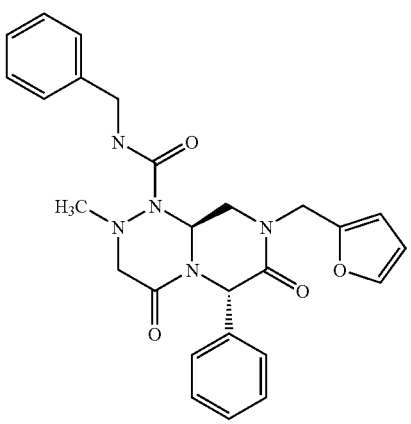 | 474 | 475 |

TABLE 2B-continued
THE [4,4,0]REVERSE TURN MIMETICS LIBRARY
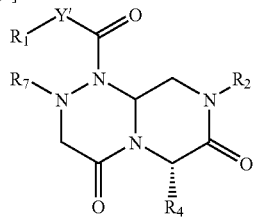
| No | MOLSTRUCTURE | Mol. Weight | M + H (MS) |
|---|---|---|---|
| 951 | 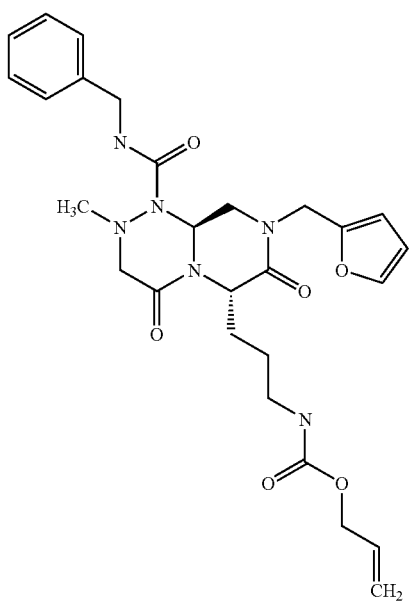 | 539 | 540 |
| 952 | 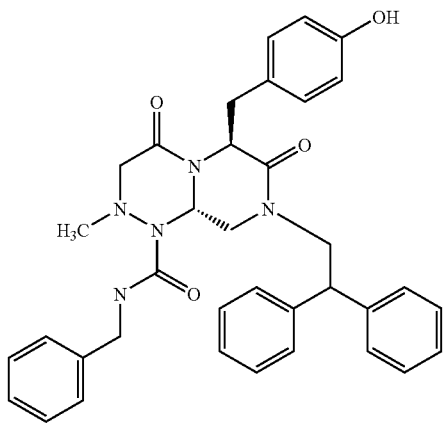 | 604 | 605 |

TABLE 2B-continued
THE [4,4,0]REVERSE TURN MIMETICS LIBRARY
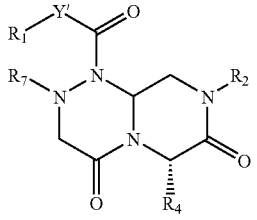
| No | MOLSTRUCTURE | Mol. Weight | M + H (MS) |
|---|---|---|---|
| 953 | | 554 | 555 |
| 954 | | 540 | 541 |
| 955 | | 588 | 589 |

TABLE 2B-continued
THE [4,4,0]REVERSE TURN MIMETICS LIBRARY
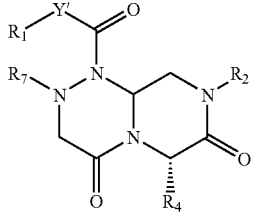
| No | MOLSTRUCTURE | Mol. Weight | M + H (MS) |
|---|---|---|---|
| 956 | | 554 | 555 |
| 957 | | 554 | 555 |
| 958 | | 572 | 573 |

TABLE 2B-continued
THE [4,4,0]REVERSE TURN MIMETICS LIBRARY
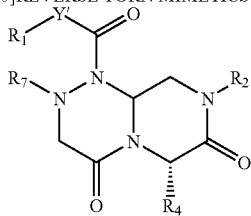
| No | MOLSTRUCTURE | Mol. Weight | M + H (MS) |
|---|---|---|---|
| 959 | | 540 | 541 |
| 960 | | 556 | 557 |
| 961 | | 570 | 571 |

TABLE 2B-continued
THE [4,4,0]REVERSE TURN MIMETICS LIBRARY
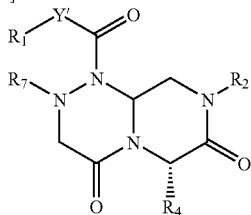
| No | MOLSTRUCTURE | Mol. Weight | M + H (MS) |
|---|---|---|---|
| 962 | | 574 | 575 |
| 963 | | 639 | 640 |

TABLE 2B-continued
THE [4,4,0]REVERSE TURN MIMETICS LIBRARY
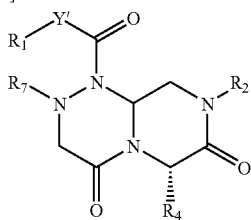
| No | MOLSTRUCTURE | Mol. Weight | M + H (MS) |
|----|--------------|-------------|------------|
| 964 | | 528 | 529 |
| 965 | | 478 | 479 |
| 966 | | 464 | 465 |

TABLE 2B-continued
THE [4,4,0]REVERSE TURN MIMETICS LIBRARY
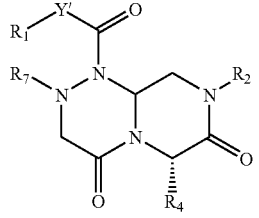
| No | MOLSTRUCTURE | Mol. Weight | M + H (MS) |
|---|---|---|---|
| 967 | | 512 | 513 |
| 968 | | 478 | 479 |
| 969 | | 478 | 479 |

TABLE 2B-continued

THE [4,4,0]REVERSE TURN MIMETICS LIBRARY

| No | MOLSTRUCTURE | Mol. Weight | M + H (MS) |
|---|---|---|---|
| 970 | | 496 | 497 |
| 971 | | 464 | 465 |
| 972 | | 480 | 481 |

TABLE 2B-continued
THE [4,4,0]REVERSE TURN MIMETICS LIBRARY
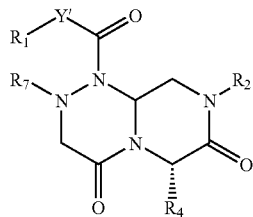
| No | MOLSTRUCTURE | Mol. Weight | M + H (MS) |
|---|---|---|---|
| 973 | 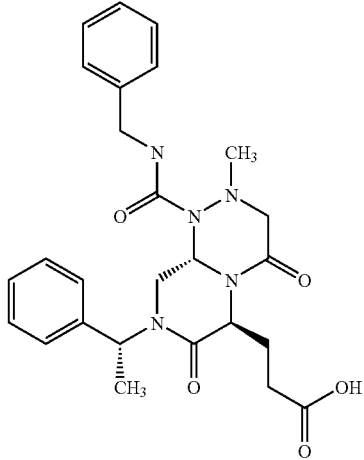 | 494 | 495 |
| 974 | 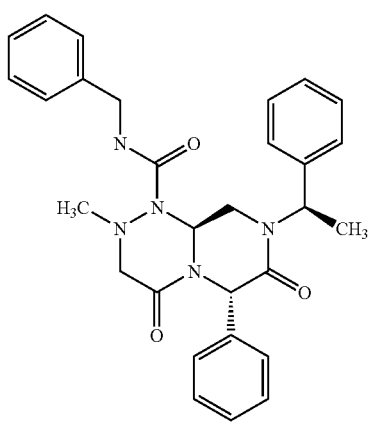 | 498 | 499 |

TABLE 2B-continued
THE [4,4,0]REVERSE TURN MIMETICS LIBRARY
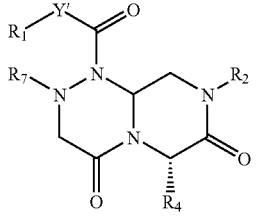
| No | MOLSTRUCTURE | Mol. Weight | M + H (MS) |
|---|---|---|---|
| 975 | | 563 | 564 |
| 976 | | 582 | 583 |

TABLE 2B-continued
THE [4,4,0]REVERSE TURN MIMETICS LIBRARY
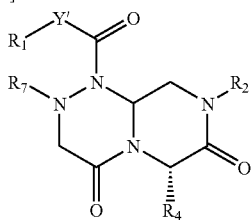
| No | MOLSTRUCTURE | Mol. Weight | M + H (MS) |
|---|---|---|---|
| 977 | | 532 | 533 |
| 978 | | 518 | 519 |
| 979 | | 566 | 567 |

TABLE 2B-continued

THE [4,4,0]REVERSE TURN MIMETICS LIBRARY

| No | MOLSTRUCTURE | Mol. Weight | M + H (MS) |
|---|---|---|---|
| 980 | | 532 | 533 |
| 981 | | 532 | 533 |
| 982 | | 551 | 552 |

TABLE 2B-continued

THE [4,4,0]REVERSE TURN MIMETICS LIBRARY

| No | MOLSTRUCTURE | Mol. Weight | M + H (MS) |
|---|---|---|---|
| 983 | | 518 | 519 |
| 984 | | 534 | 535 |
| 985 | | 548 | 549 |

US 7,566,711 B2
185 186
TABLE 2B-continued
THE [4,4,0]REVERSE TURN MIMETICS LIBRARY
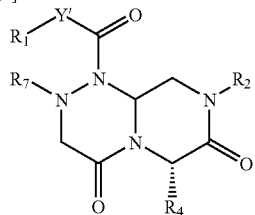
| No | MOLSTRUCTURE | Mol. Weight | M + H (MS) |
|---|---|---|---|
| 986 | | 552 | 553 |
| 987 | | 618 | 619 |

TABLE 2B-continued
THE [4,4,0]REVERSE TURN MIMETICS LIBRARY
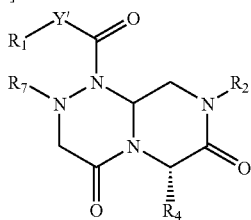
| No | MOLSTRUCTURE | Mol. Weight | M + H (MS) |
|---|---|---|---|
| 988 | | 482 | 483 |
| 989 | | 432 | 433 |
| 990 | | 418 | 419 |

TABLE 2B-continued

THE [4,4,0]REVERSE TURN MIMETICS LIBRARY

| No | MOLSTRUCTURE | Mol. Weight | M + H (MS) |
|---|---|---|---|
| 991 | | 466 | 467 |
| 992 | | 432 | 433 |
| 993 | | 432 | 433 |

TABLE 2B-continued

THE [4,4,0]REVERSE TURN MIMETICS LIBRARY

| No | MOLSTRUCTURE | Mol. Weight | M + H (MS) |
|---|---|---|---|
| 994 | | 450 | 451 |
| 995 | | 418 | 419 |
| 996 | | 433 | 434 |

TABLE 2B-continued
THE [4,4,0]REVERSE TURN MIMETICS LIBRARY
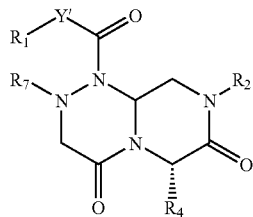
| No | MOLSTRUCTURE | Mol. Weight | M + H (MS) |
|---|---|---|---|
| 997 | 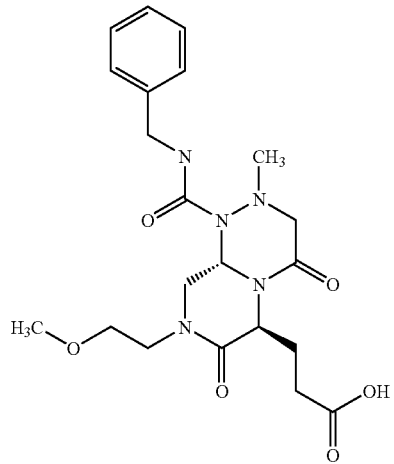 | 447 | 448 |
| 998 | 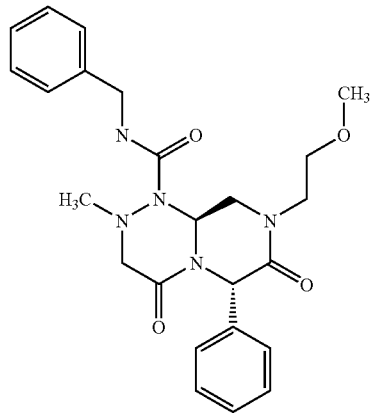 | 452 | 453 |

TABLE 2B-continued
THE [4,4,0]REVERSE TURN MIMETICS LIBRARY
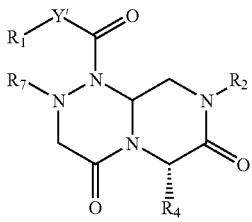
| No | MOLSTRUCTURE | Mol. Weight | M + H (MS) |
|---|---|---|---|
| 999 | | 517 | 518 |
| 1000 | | 548 | 549 |

TABLE 2B-continued
THE [4,4,0]REVERSE TURN MIMETICS LIBRARY
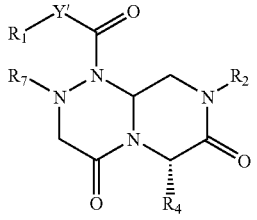
| No | MOLSTRUCTURE | Mol. Weight | M + H (MS) |
|---|---|---|---|
| 1001 | | 498 | 499 |
| 1002 | | 484 | 485 |
| 1003 | | 532 | 535 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 1004 | | 498 | 499 |
| 1005 | | 498 | 499 |
| 1006 | | 516 | 517 |

TABLE 2B-continued

THE [4,4,0]REVERSE TURN MIMETICS LIBRARY

| No | MOLSTRUCTURE | Mol. Weight | M + H (MS) |
|---|---|---|---|
| 1007 | | 484 | 485 |
| 1008 | | 500 | 501 |
| 1009 | | 514 | 515 |

TABLE 2B-continued
THE [4,4,0]REVERSE TURN MIMETICS LIBRARY
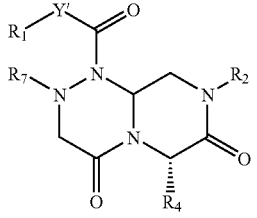
| No | MOLSTRUCTURE | Mol. Weight | M + H (MS) |
|----|--------------|-------------|------------|
| 1010 | | 518 | 519 |
| 1011 | | 583 | 584 |

TABLE 2B-continued
THE [4,4,0]REVERSE TURN MIMETICS LIBRARY
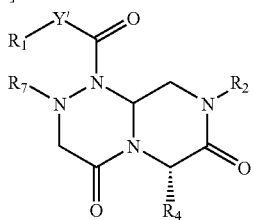
| No | MOLSTRUCTURE | Mol. Weight | M + H (MS) |
|---|---|---|---|
| 1012 | | 532 | 533 |
| 1013 | | 518 | 519 |
| 1014 | | 566 | 567 |

TABLE 2B-continued
THE [4,4,0]REVERSE TURN MIMETICS LIBRARY
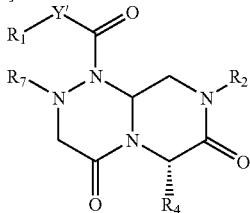
| No | MOLSTRUCTURE | Mol. Weight | M + H (MS) |
|---|---|---|---|
| 1015 | | 532 | 533 |
| 1016 | | 532 | 533 |
| 1017 | | 551 | 552 |

TABLE 2B-continued
THE [4,4,0]REVERSE TURN MIMETICS LIBRARY
| No | MOLSTRUCTURE | Mol. Weight | M + H (MS) |
|---|---|---|---|
| 1018 | 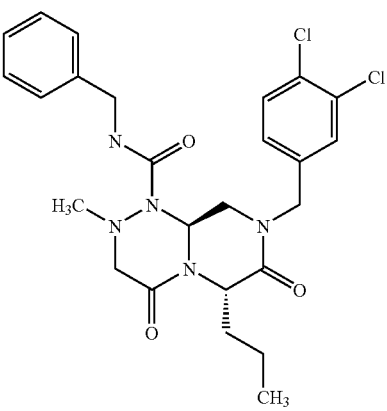 | 518 | 519 |
| 1019 | 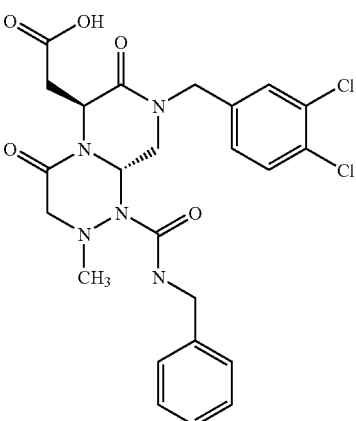 | 534 | 535 |
| 1020 | 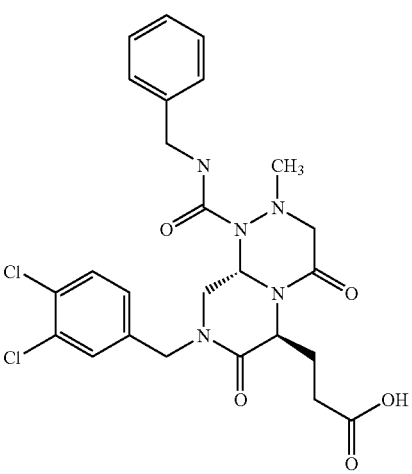 | 548 | 549 |

TABLE 2B-continued
THE [4,4,0]REVERSE TURN MIMETICS LIBRARY
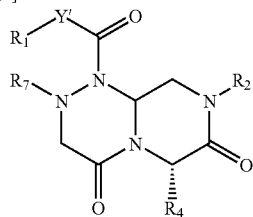
| No | MOLSTRUCTURE | Mol. Weight | M + H (MS) |
|---|---|---|---|
| 1021 | | 552 | 553 |
| 1022 | | 618 | 619 |

TABLE 2B-continued
THE [4,4,0]REVERSE TURN MIMETICS LIBRARY
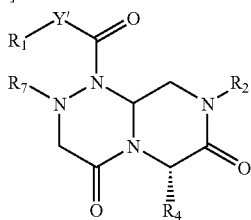
| No | MOLSTRUCTURE | Mol. Weight | M + H (MS) |
|---|---|---|---|
| 1023 | | 528 | 529 |
| 1024 | | 478 | 479 |
| 1025 | | 464 | 465 |

TABLE 2B-continued
THE [4,4,0]REVERSE TURN MIMETICS LIBRARY
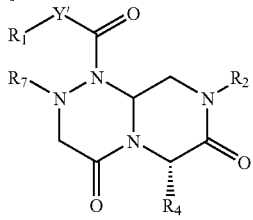
| No | MOLSTRUCTURE | Mol. Weight | M + H (MS) |
|----|--------------|-------------|------------|
| 1026 | | 512 | 513 |
| 1027 | | 478 | 479 |
| 1028 | | 478 | 479 |

TABLE 2B-continued

THE [4,4,0]REVERSE TURN MIMETICS LIBRARY

| No | MOLSTRUCTURE | Mol. Weight | M + H (MS) |
|---|---|---|---|
| 1029 | | 496 | 497 |
| 1030 | | 464 | 465 |
| 1031 | | 480 | 481 |

TABLE 2B-continued
THE [4,4,0]REVERSE TURN MIMETICS LIBRARY
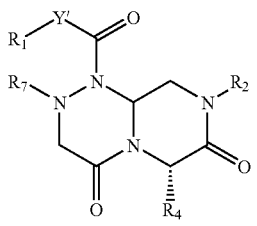
| No | MOLSTRUCTURE | Mol. Weight | M + H (MS) |
|---|---|---|---|
| 1032 | 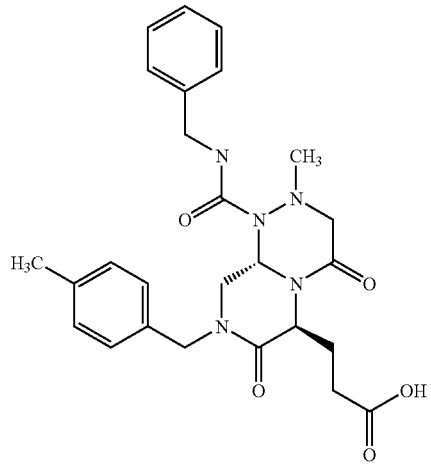 | 494 | 495 |
| 1033 | 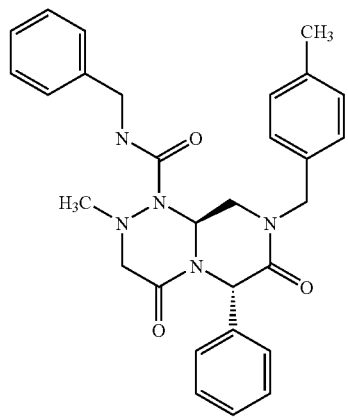 | 498 | 499 |

TABLE 2B-continued
THE [4,4,0]REVERSE TURN MIMETICS LIBRARY
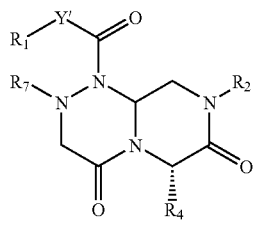
| No | MOLSTRUCTURE | Mol. Weight | M + H (MS) |
|---|---|---|---|
| 1034 | 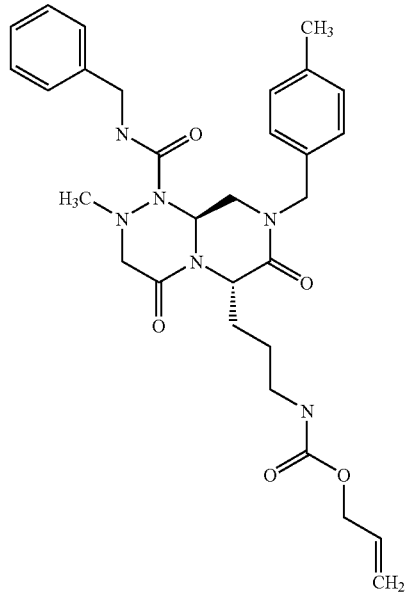 | 563 | 564 |
| 1035 | 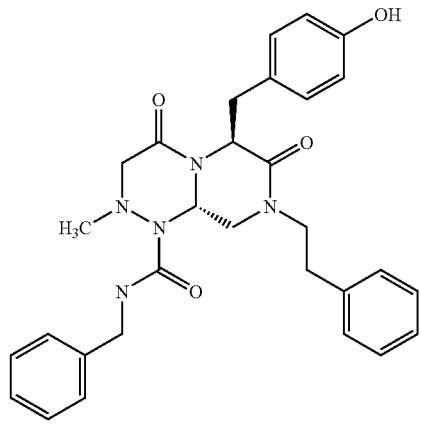 | 528 | 529 |

TABLE 2B-continued
THE [4,4,0]REVERSE TURN MIMETICS LIBRARY
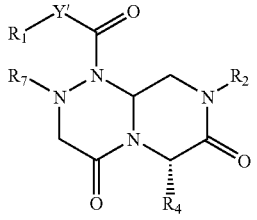
| No | MOLSTRUCTURE | Mol. Weight | M + H (MS) |
|---|---|---|---|
| 1036 | | 478 | 479 |
| 1037 | | 464 | 465 |
| 1038 | | 512 | 513 |

TABLE 2B-continued

THE [4,4,0]REVERSE TURN MIMETICS LIBRARY

| No | MOLSTRUCTURE | Mol. Weight | M + H (MS) |
|---|---|---|---|
| 1039 | | 478 | 479 |
| 1040 | | 478 | 479 |
| 1041 | | 496 | 497 |

TABLE 2B-continued

THE [4,4,0]REVERSE TURN MIMETICS LIBRARY

| No | MOLSTRUCTURE | Mol. Weight | M + H (MS) |
|---|---|---|---|
| 1042 | | 464 | 465 |
| 1043 | | 480 | 481 |
| 1044 | | 494 | 495 |

TABLE 2B-continued
THE [4,4,0]REVERSE TURN MIMETICS LIBRARY
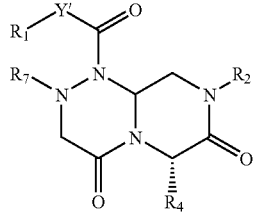
| No | MOLSTRUCTURE | Mol. Weight | M + H (MS) |
|---|---|---|---|
| 1045 | | 498 | 499 |
| 1046 | | 563 | 564 |

TABLE 2B-continued
THE [4,4,0]REVERSE TURN MIMETICS LIBRARY
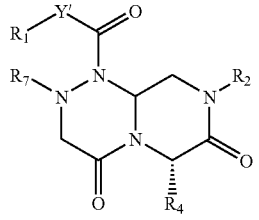
| No | MOLSTRUCTURE | Mol. Weight | M + H (MS) |
|---|---|---|---|
| 1047 | | 556 | 557 |
| 1048 | | 506 | 507 |
| 1049 | | 492 | 493 |

TABLE 2B-continued
THE [4,4,0]REVERSE TURN MIMETICS LIBRARY
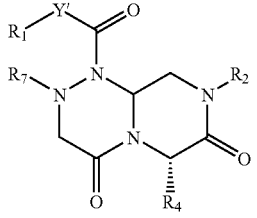
| No | MOLSTRUCTURE | Mol. Weight | M + H (MS) |
|---|---|---|---|
| 1050 | | 540 | 541 |
| 1051 | | 506 | 507 |
| 1052 | | 506 | 507 |

TABLE 2B-continued
THE [4,4,0]REVERSE TURN MIMETICS LIBRARY
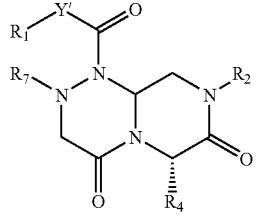
| No | MOLSTRUCTURE | Mol. Weight | M + H (MS) |
|---|---|---|---|
| 1053 | | 524 | 525 |
| 1054 | | 492 | 493 |
| 1055 | | 508 | 509 |

TABLE 2B-continued
THE [4,4,0]REVERSE TURN MIMETICS LIBRARY
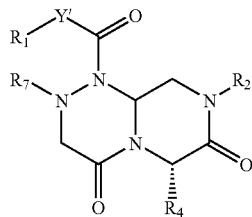
| No | MOLSTRUCTURE | Mol. Weight | M + H (MS) |
|---|---|---|---|
| 1056 | 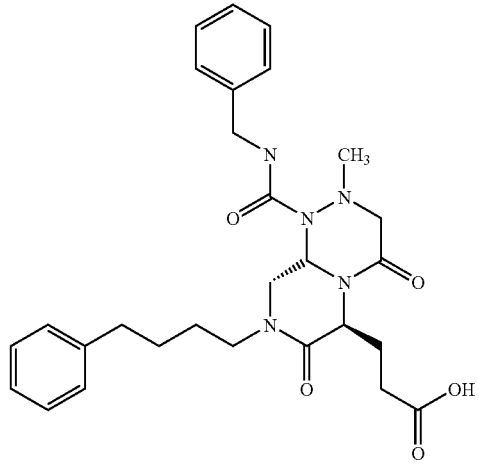 | 522 | 523 |
| 1057 | 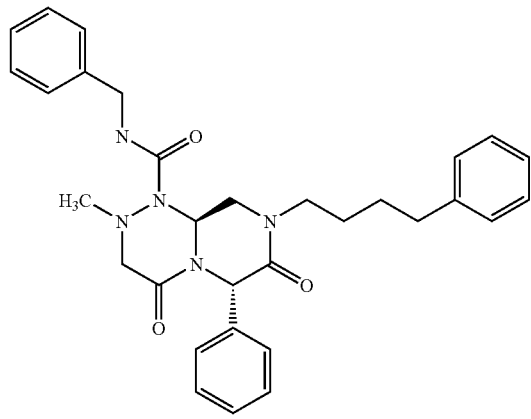 | 526 | 527 |

TABLE 2B-continued
THE [4,4,0]REVERSE TURN MIMETICS LIBRARY
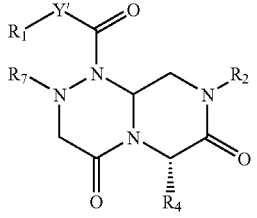
| No | MOLSTRUCTURE | Mol. Weight | M + H (MS) |
|---|---|---|---|
| 1058 | | 591 | 592 |
| 1059 | | 546 | 547 |

TABLE 2B-continued
THE [4,4,0]REVERSE TURN MIMETICS LIBRARY
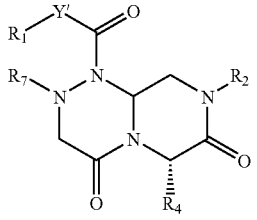
| No | MOLSTRUCTURE | Mol. Weight | M + H (MS) |
|---|---|---|---|
| 1060 | | 496 | 497 |
| 1061 | | 482 | 483 |
| 1062 | | 530 | 531 |

TABLE 2B-continued

THE [4,4,0]REVERSE TURN MIMETICS LIBRARY

| No | MOLSTRUCTURE | Mol. Weight | M + H (MS) |
|---|---|---|---|
| 1063 | | 496 | 497 |
| 1064 | | 496 | 497 |
| 1065 | | 514 | 515 |

TABLE 2B-continued

THE [4,4,0]REVERSE TURN MIMETICS LIBRARY

| No | MOLSTRUCTURE | Mol. Weight | M + H (MS) |
|---|---|---|---|
| 1066 | | 482 | 483 |
| 1067 | | 498 | 499 |
| 1068 | | 512 | 513 |

//247//248
TABLE 2B-continued
THE [4,4,0]REVERSE TURN MIMETICS LIBRARY
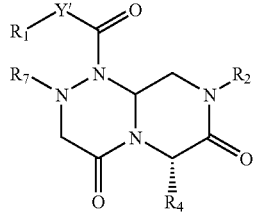
| No | MOLSTRUCTURE | Mol. Weight | M + H (MS) |
|---|---|---|---|
| 1069 | | 516 | 517 |
| 1070 | | 581 | 582 |

TABLE 2B-continued
THE [4,4,0]REVERSE TURN MIMETICS LIBRARY
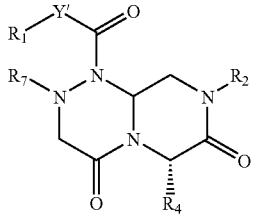
| No | MOLSTRUCTURE | Mol. Weight | M + H (MS) |
|---|---|---|---|
| 1071 | | 528 | 529 |
| 1072 | | 478 | 479 |
| 1073 | | 464 | 465 |

TABLE 2B-continued
THE [4,4,0]REVERSE TURN MIMETICS LIBRARY
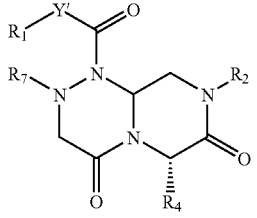
| No | MOLSTRUCTURE | Mol. Weight | M + H (MS) |
|---|---|---|---|
| 1074 | | 512 | 513 |
| 1075 | | 478 | 479 |
| 1076 | | 478 | 479 |

TABLE 2B-continued

THE [4,4,0]REVERSE TURN MIMETICS LIBRARY

| No | MOLSTRUCTURE | Mol. Weight | M + H (MS) |
|---|---|---|---|
| 1077 | | 496 | 497 |
| 1078 | | 464 | 465 |
| 1079 | | 480 | 481 |

TABLE 2B-continued
THE [4,4,0]REVERSE TURN MIMETICS LIBRARY
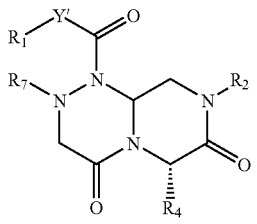
| No | MOLSTRUCTURE | Mol. Weight | M + H (MS) |
|---|---|---|---|
| 1080 | 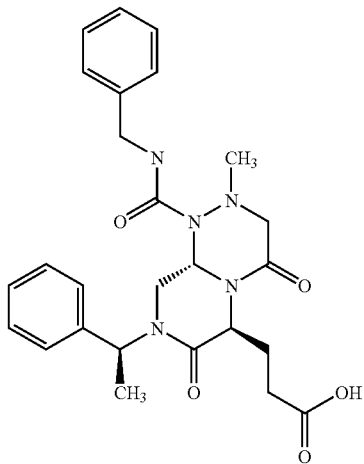 | 494 | 495 |
| 1081 | 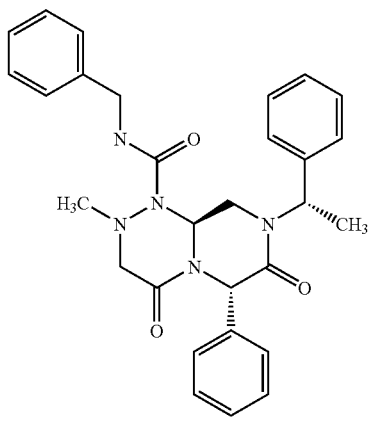 | 498 | 499 |

TABLE 2B-continued
THE [4,4,0]REVERSE TURN MIMETICS LIBRARY
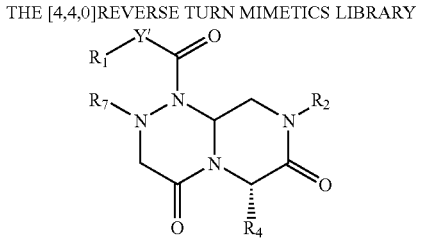
| No | MOLSTRUCTURE | Mol. Weight | M + H (MS) |
|---|---|---|---|
| 1082 | | 563 | 564 |
| 1083 | | 514 | 515 |

TABLE 2B-continued

THE [4,4,0]REVERSE TURN MIMETICS LIBRARY

| No | MOLSTRUCTURE | Mol. Weight | M + H (MS) |
|---|---|---|---|
| 1084 | | 500 | 501 |
| 1085 | | 548 | 549 |
| 1086 | | 514 | 515 |

TABLE 2B-continued
THE [4,4,0]REVERSE TURN MIMETICS LIBRARY
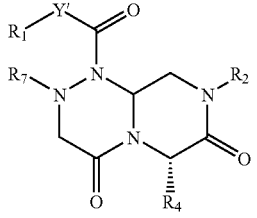
| No | MOLSTRUCTURE | Mol. Weight | M + H (MS) |
|---|---|---|---|
| 1087 | | 514 | 515 |
| 1088 | | 532 | 533 |
| 1089 | | 500 | 501 |

TABLE 2B-continued
THE [4,4,0]REVERSE TURN MIMETICS LIBRARY
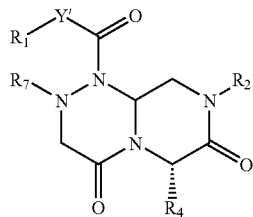
| No | MOLSTRUCTURE | Mol. Weight | M + H (MS) |
|---|---|---|---|
| 1090 | | 516 | 517 |
| 1091 | | 530 | 531 |
| 1092 | | 534 | 535 |

TABLE 2B-continued
THE [4,4,0]REVERSE TURN MIMETICS LIBRARY
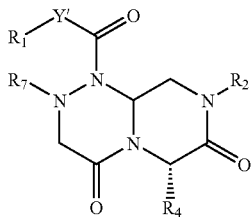
| No | MOLSTRUCTURE | Mol. Weight | M + H (MS) |
|----|--------------|-------------|------------|
| 1093 | | 599 | 600 |
| 1094 | | 520 | 521 |

TABLE 2B-continued
THE [4,4,0]REVERSE TURN MIMETICS LIBRARY
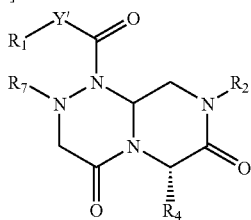
| No | MOLSTRUCTURE | Mol. Weight | M + H (MS) |
|---|---|---|---|
| 1095 | | 470 | 471 |
| 1096 | | 456 | 457 |
| 1097 | | 504 | 505 |

TABLE 2B-continued

THE [4,4,0]REVERSE TURN MIMETICS LIBRARY

| No | MOLSTRUCTURE | Mol. Weight | M + H (MS) |
|---|---|---|---|
| 1098 | | 470 | 471 |
| 1099 | | 470 | 471 |
| 1100 | | 488 | 489 |

TABLE 2B-continued
THE [4,4,0]REVERSE TURN MIMETICS LIBRARY
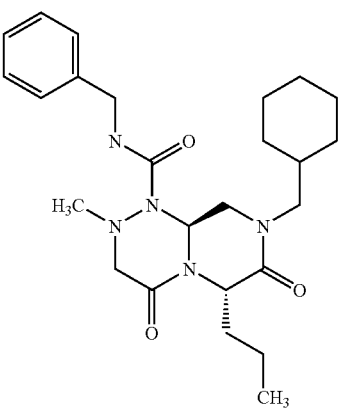
| No | MOLSTRUCTURE | Mol. Weight | M + H (MS) |
|---|---|---|---|
| 1101 | | 456 | 457 |
| 1102 | | 472 | 473 |
| 1103 | | 486 | 487 |

TABLE 2B-continued
THE [4,4,0]REVERSE TURN MIMETICS LIBRARY
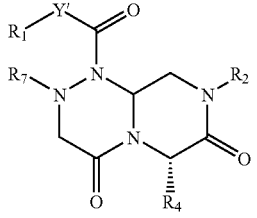
| No | MOLSTRUCTURE | Mol. Weight | M + H (MS) |
|---|---|---|---|
| 1104 | | 490 | 491 |
| 1105 | | 555 | 556 |

TABLE 2B-continued
THE [4,4,0]REVERSE TURN MIMETICS LIBRARY
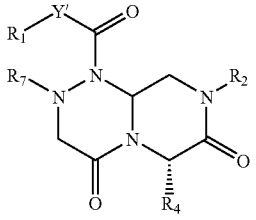
| No | MOLSTRUCTURE | Mol. Weight | M + H (MS) |
|---|---|---|---|
| 1106 | | 496 | 497 |
| 1107 | | 482 | 483 |
| 1108 | | 530 | 531 |

TABLE 2B-continued

THE [4,4,0]REVERSE TURN MIMETICS LIBRARY

| No | MOLSTRUCTURE | Mol. Weight | M + H (MS) |
|---|---|---|---|
| 1109 | | 496 | 497 |
| 1110 | | 496 | 497 |
| 1111 | | 514 | 515 |

TABLE 2B-continued

THE [4,4,0]REVERSE TURN MIMETICS LIBRARY

| No | MOLSTRUCTURE | Mol. Weight | M + H (MS) |
|---|---|---|---|
| 1112 | | 482 | 483 |
| 1113 | | 498 | 499 |
| 1114 | | 512 | 513 |

TABLE 2B-continued
THE [4,4,0]REVERSE TURN MIMETICS LIBRARY
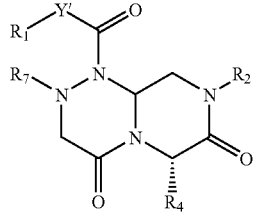
| No | MOLSTRUCTURE | Mol. Weight | M + H (MS) |
|---|---|---|---|
| 1115 | | 516 | 517 |
| 1116 | | 581 | 582 |

TABLE 2B-continued
THE [4,4,0]REVERSE TURN MIMETICS LIBRARY
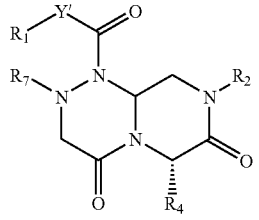
| No | MOLSTRUCTURE | Mol. Weight | M + H (MS) |
|---|---|---|---|
| 1117 | | 542 | 543 |
| 1118 | | 492 | 493 |
| 1119 | | 478 | 479 |

TABLE 2B-continued

THE [4,4,0]REVERSE TURN MIMETICS LIBRARY

| No | MOLSTRUCTURE | Mol. Weight | M + H (MS) |
|---|---|---|---|
| 1120 | | 526 | 527 |
| 1121 | | 492 | 493 |
| 1122 | | 492 | 493 |

TABLE 2B-continued
THE [4,4,0]REVERSE TURN MIMETICS LIBRARY
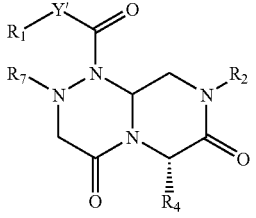
| No | MOLSTRUCTURE | Mol. Weight | M + H (MS) |
|---|---|---|---|
| 1123 | | 510 | 511 |
| 1124 | | 478 | 479 |
| 1125 | | 494 | 495 |

TABLE 2B-continued
THE [4,4,0]REVERSE TURN MIMETICS LIBRARY
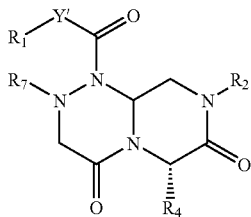
| No | MOLSTRUCTURE | Mol. Weight | M + H (MS) |
|----|--------------|-------------|------------|
| 1126 | 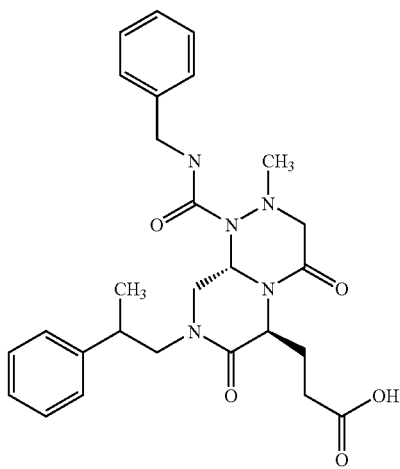 | 508 | 509 |
| 1127 | 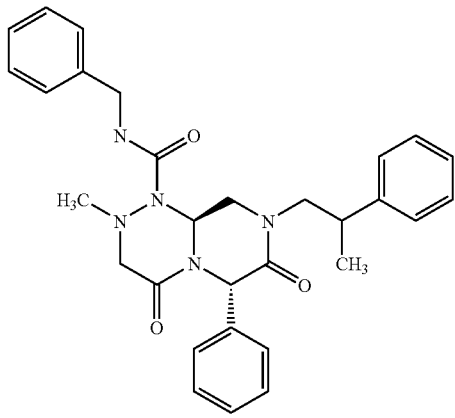 | 512 | 513 |

TABLE 2B-continued
THE [4,4,0]REVERSE TURN MIMETICS LIBRARY
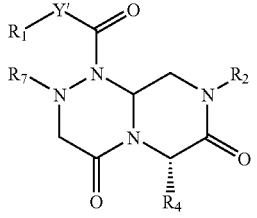
| No | MOLSTRUCTURE | Mol. Weight | M + H (MS) |
|---|---|---|---|
| 1128 | | 577 | 578 |
| 1129 | | 550 | 551 |

TABLE 2B-continued
THE [4,4,0]REVERSE TURN MIMETICS LIBRARY
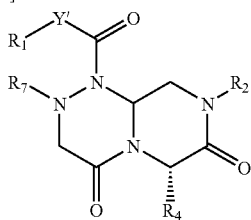
| No | MOLSTRUCTURE | Mol. Weight | M + H (MS) |
|---|---|---|---|
| 1130 | | 500 | 501 |
| 1131 | | 486 | 487 |
| 1132 | | 534 | 535 |

TABLE 2B-continued

THE [4,4,0]REVERSE TURN MIMETICS LIBRARY

| No | MOLSTRUCTURE | Mol. Weight | M + H (MS) |
|---|---|---|---|
| 1133 | | 500 | 501 |
| 1134 | | 500 | 501 |
| 1135 | | 518 | 519 |

TABLE 2B-continued
THE [4,4,0]REVERSE TURN MIMETICS LIBRARY
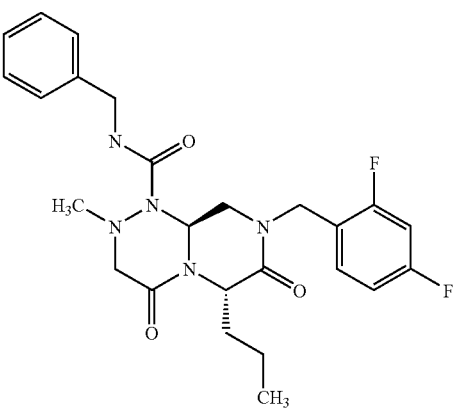
| No | MOLSTRUCTURE | Mol. Weight | M + H (MS) |
|---|---|---|---|
| 1136 | 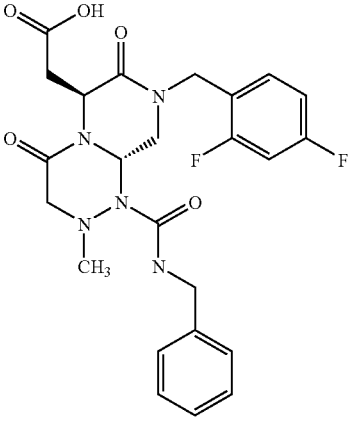 | 486 | 487 |
| 1137 | | 501 | 502 |
| 1138 | 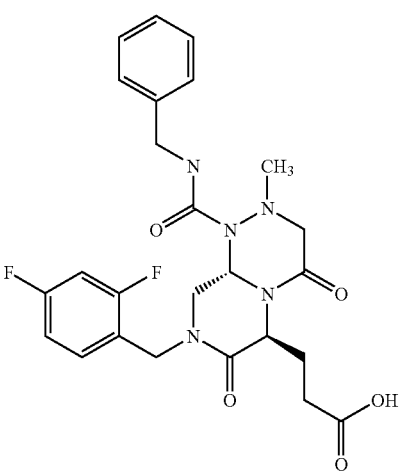 | 516 | 517 |

TABLE 2B-continued
THE [4,4,0]REVERSE TURN MIMETICS LIBRARY
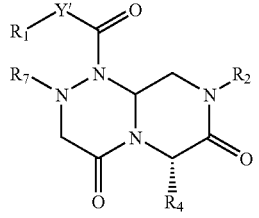
| No | MOLSTRUCTURE | Mol. Weight | M + H (MS) |
|----|--------------|-------------|------------|
| 1139 | | 520 | 521 |
| 1140 | | 585 | 586 |

TABLE 2B-continued
THE [4,4,0]REVERSE TURN MIMETICS LIBRARY
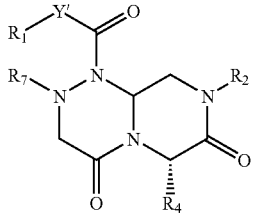
| No | MOLSTRUCTURE | Mol. Weight | M + H (MS) |
|---|---|---|---|
| 1141 | | 588 | 589 |
| 1142 | | 538 | 539 |
| 1143 | | 524 | 525 |

TABLE 2B-continued
THE [4,4,0]REVERSE TURN MIMETICS LIBRARY
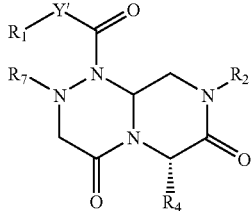
| No | MOLSTRUCTURE | Mol. Weight | M + H (MS) |
|---|---|---|---|
| 1144 | | 572 | 573 |
| 1145 | | 538 | 539 |
| 1146 | | 538 | 539 |

TABLE 2B-continued
THE [4,4,0]REVERSE TURN MIMETICS LIBRARY
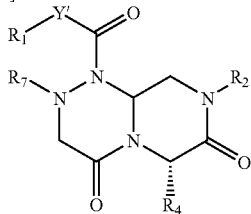
| No | MOLSTRUCTURE | Mol. Weight | M + H (MS) |
|---|---|---|---|
| 1147 | | 556 | 557 |
| 1148 | | 524 | 525 |
| 1149 | | 540 | 541 |

TABLE 2B-continued
THE [4,4,0]REVERSE TURN MIMETICS LIBRARY
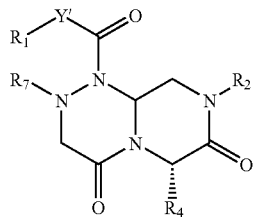
| No | MOLSTRUCTURE | Mol. Weight | M + H (MS) |
|---|---|---|---|
| 1150 | 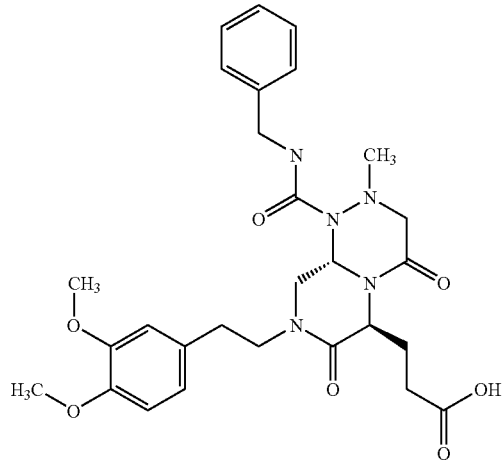 | 554 | 555 |
| 1151 | 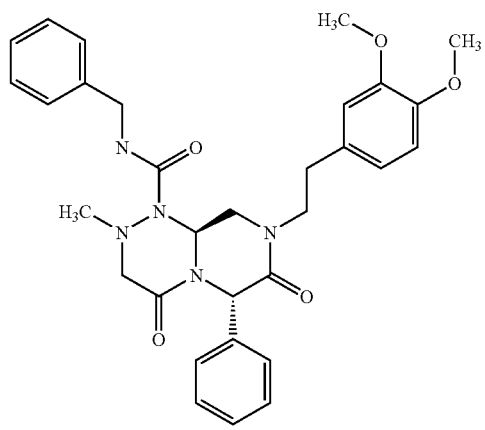 | 558 | 559 |

TABLE 2B-continued
THE [4,4,0]REVERSE TURN MIMETICS LIBRARY
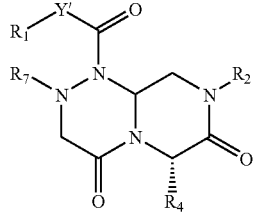
| No | MOLSTRUCTURE | Mol. Weight | M + H (MS) |
|----|--------------|-------------|------------|
| 1152 | | 623 | 624 |
| 1153 | | 508 | 509 |

TABLE 2B-continued
THE [4,4,0]REVERSE TURN MIMETICS LIBRARY
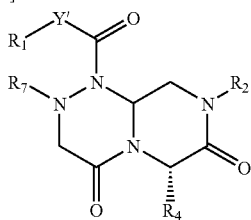
| No | MOLSTRUCTURE | Mol. Weight | M + H (MS) |
|---|---|---|---|
| 1154 | | 458 | 459 |
| 1155 | | 444 | 445 |
| 1156 | | 492 | 493 |

TABLE 2B-continued
THE [4,4,0]REVERSE TURN MIMETICS LIBRARY
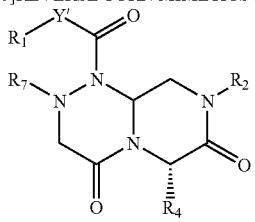
| No | MOLSTRUCTURE | Mol. Weight | M + H (MS) |
|---|---|---|---|
| 1157 | | 458 | 459 |
| 1158 | | 458 | 459 |
| 1159 | | 476 | 477 |

TABLE 2B-continued

THE [4,4,0]REVERSE TURN MIMETICS LIBRARY

| No | MOLSTRUCTURE | Mol. Weight | M + H (MS) |
|---|---|---|---|
| 1160 | | 444 | 445 |
| 1161 | | 460 | 461 |
| 1162 | | 474 | 475 |

TABLE 2B-continued
THE [4,4,0]REVERSE TURN MIMETICS LIBRARY
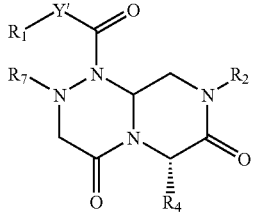
| No | MOLSTRUCTURE | Mol. Weight | M + H (MS) |
|---|---|---|---|
| 1163 | | 478 | 479 |
| 1164 | | 543 | 544 |

TABLE 2B-continued
THE [4,4,0]REVERSE TURN MIMETICS LIBRARY
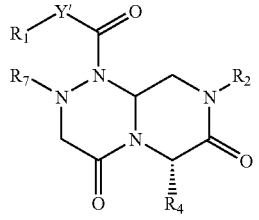
| No | MOLSTRUCTURE | Mol. Weight | M + H (MS) |
|---|---|---|---|
| 1165 | | 618 | 619 |
| 1166 | | 568 | 569 |
| 1167 | | 554 | 555 |

TABLE 2B-continued

THE [4,4,0]REVERSE TURN MIMETICS LIBRARY

| No | MOLSTRUCTURE | Mol. Weight | M + H (MS) |
|---|---|---|---|
| 1168 | | 602 | 603 |
| 1169 | | 568 | 569 |
| 1170 | | 568 | 569 |

TABLE 2B-continued
THE [4,4,0]REVERSE TURN MIMETICS LIBRARY
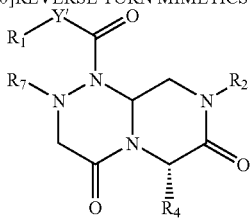
| No | MOLSTRUCTURE | Mol. Weight | M + H (MS) |
|----|--------------|-------------|------------|
| 1171 | | 586 | 587 |
| 1172 | | 554 | 555 |
| 1173 | | 570 | 571 |

TABLE 2B-continued
THE [4,4,0]REVERSE TURN MIMETICS LIBRARY
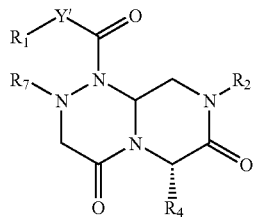
| No | MOLSTRUCTURE | Mol. Weight | M + H (MS) |
|---|---|---|---|
| 1174 | 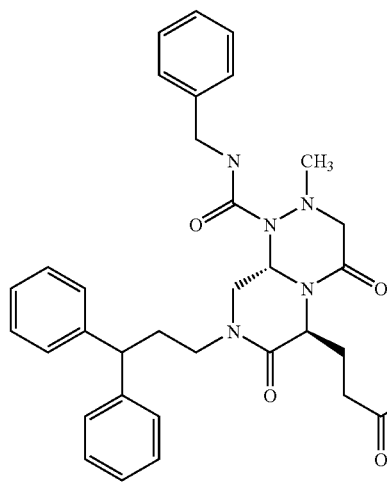 | 584 | 585 |
| 1175 | 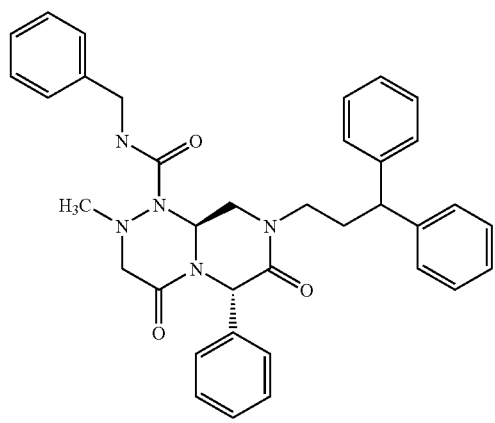 | 588 | 589 |

TABLE 2B-continued
THE [4,4,0]REVERSE TURN MIMETICS LIBRARY
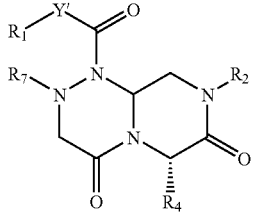
| No | MOLSTRUCTURE | Mol. Weight | M + H (MS) |
|---|---|---|---|
| 1176 | | 653 | 654 |
| 1177 | | 494 | 495 |

TABLE 2B-continued
THE [4,4,0]REVERSE TURN MIMETICS LIBRARY
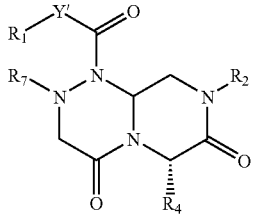
| No | MOLSTRUCTURE | Mol. Weight | M + H (MS) |
|---|---|---|---|
| 1178 | | 444 | 445 |
| 1179 | | 430 | 431 |
| 1180 | | 478 | 479 |

TABLE 2B-continued
THE [4,4,0]REVERSE TURN MIMETICS LIBRARY
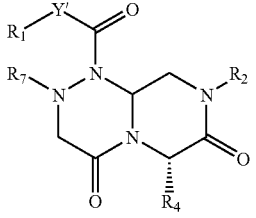
| No | MOLSTRUCTURE | Mol. Weight | M + H (MS) |
|----|--------------|-------------|------------|
| 1181 | | 444 | 445 |
| 1182 | | 444 | 445 |
| 1183 | | 462 | 463 |

TABLE 2B-continued

THE [4,4,0]REVERSE TURN MIMETICS LIBRARY

| No | MOLSTRUCTURE | Mol. Weight | M + H (MS) |
|---|---|---|---|
| 1184 | | 430 | 431 |
| 1185 | | 446 | 447 |
| 1186 | | 460 | 461 |

TABLE 2B-continued
THE [4,4,0]REVERSE TURN MIMETICS LIBRARY
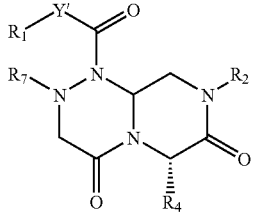
| No | MOLSTRUCTURE | Mol. Weight | M + H (MS) |
|---|---|---|---|
| 1187 | | 464 | 465 |
| 1188 | | 529 | 530 |

TABLE 2B-continued
THE [4,4,0]REVERSE TURN MIMETICS LIBRARY
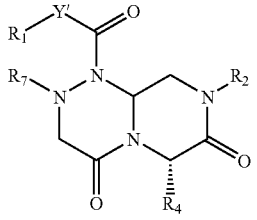
| No | MOLSTRUCTURE | Mol. Weight | M + H (MS) |
|---|---|---|---|
| 1189 | | 506 | 507 |
| 1190 | | 456 | 457 |
| 1191 | | 442 | 443 |

TABLE 2B-continued
THE [4,4,0]REVERSE TURN MIMETICS LIBRARY
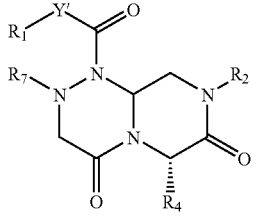
| No | MOLSTRUCTURE | Mol. Weight | M + H (MS) |
|---|---|---|---|
| 1192 | | 490 | 491 |
| 1193 | | 456 | 457 |
| 1194 | | 456 | 457 |

TABLE 2B-continued

THE [4,4,0]REVERSE TURN MIMETICS LIBRARY

| No | MOLSTRUCTURE | Mol. Weight | M + H (MS) |
|---|---|---|---|
| 1195 | | 474 | 475 |
| 1196 | | 442 | 443 |
| 1197 | | 458 | 459 |

TABLE 2B-continued
THE [4,4,0]REVERSE TURN MIMETICS LIBRARY
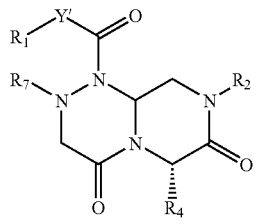
| No | MOLSTRUCTURE | Mol. Weight | M + H (MS) |
|----|--------------|-------------|------------|
| 1198 | 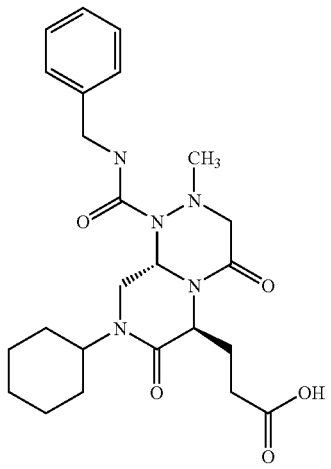 | 472 | 473 |
| 1199 | 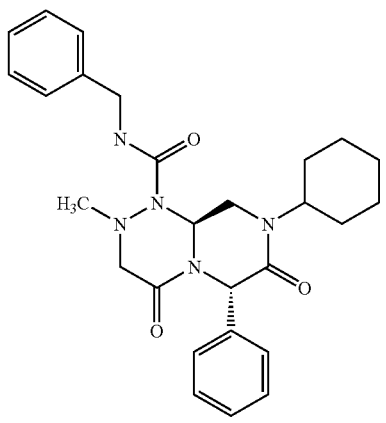 | 476 | 477 |

TABLE 2B-continued
THE [4,4,0]REVERSE TURN MIMETICS LIBRARY
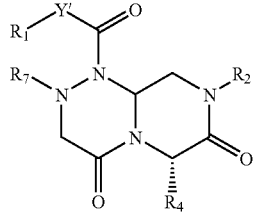
| No | MOLSTRUCTURE | Mol. Weight | M + H (MS) |
|---|---|---|---|
| 1200 | | 541 | 542 |
| 1201 | | 592 | 593 |

TABLE 2B-continued
THE [4,4,0]REVERSE TURN MIMETICS LIBRARY
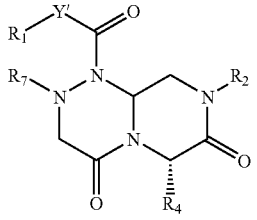
| No | MOLSTRUCTURE | Mol. Weight | M + H (MS) |
|---|---|---|---|
| 1202 | | 542 | 543 |
| 1203 | | 528 | 529 |
| 1204 | | 576 | 577 |

TABLE 2B-continued

THE [4,4,0]REVERSE TURN MIMETICS LIBRARY

| No | MOLSTRUCTURE | Mol. Weight | M + H (MS) |
|---|---|---|---|
| 1205 | | 542 | 543 |
| 1206 | | 542 | 543 |
| 1207 | | 561 | 562 |

TABLE 2B-continued

THE [4,4,0]REVERSE TURN MIMETICS LIBRARY

| No | MOLSTRUCTURE | Mol. Weight | M + H (MS) |
|---|---|---|---|
| 1208 | | 528 | 529 |
| 1209 | | 544 | 545 |
| 1210 | | 558 | 559 |

TABLE 2B-continued
THE [4,4,0]REVERSE TURN MIMETICS LIBRARY
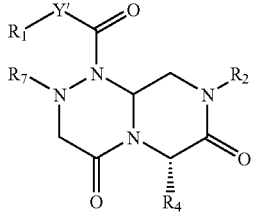
| No | MOLSTRUCTURE | Mol. Weight | M + H (MS) |
|---|---|---|---|
| 1211 | | 562 | 563 |
| 1212 | | 628 | 629 |

TABLE 2B-continued
THE [4,4,0]REVERSE TURN MIMETICS LIBRARY
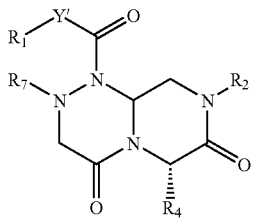
| No | MOLSTRUCTURE | Mol. Weight | M + H (MS) |
|---|---|---|---|
| 1213 | 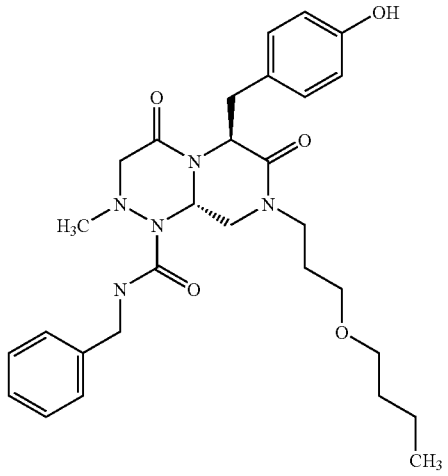 | 538 | 539 |
| 1214 | 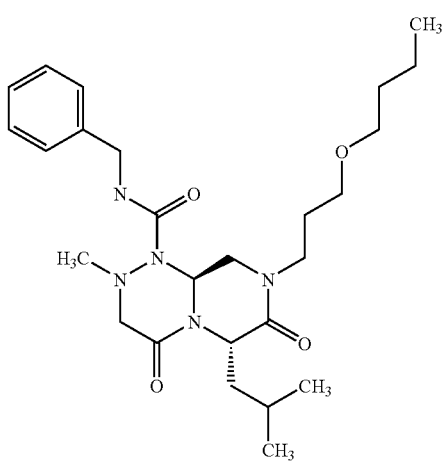 | 488 | 489 |

TABLE 2B-continued
THE [4,4,0]REVERSE TURN MIMETICS LIBRARY
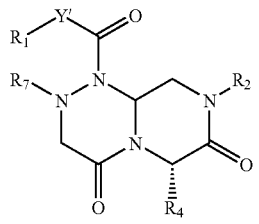
| No | MOLSTRUCTURE | Mol. Weight | M + H (MS) |
|---|---|---|---|
| 1215 | 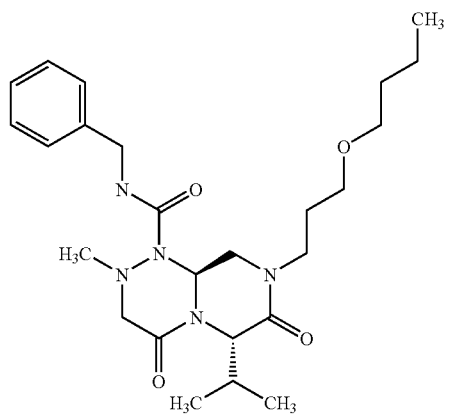 | 474 | 475 |
| 1216 | 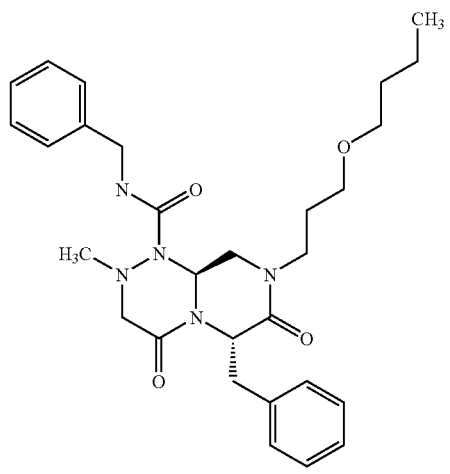 | 522 | 523 |

TABLE 2B-continued
THE [4,4,0]REVERSE TURN MIMETICS LIBRARY
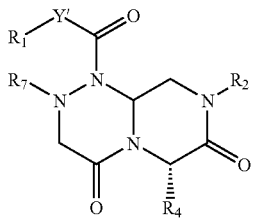
| No | MOLSTRUCTURE | Mol. Weight | M + H (MS) |
|---|---|---|---|
| 1217 | 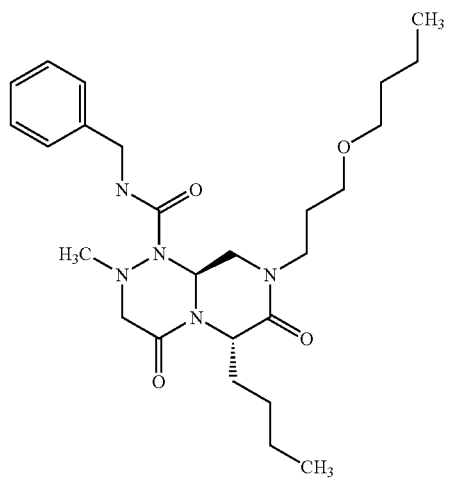 | 488 | 489 |
| 1218 | 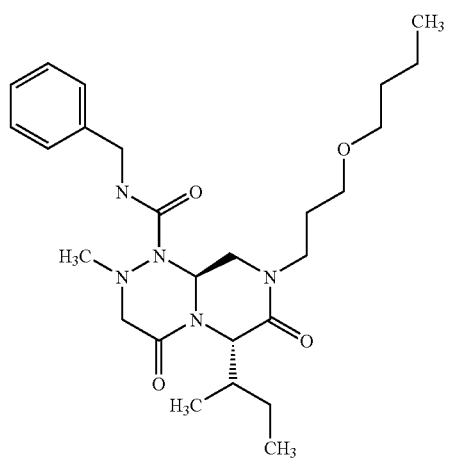 | 488 | 489 |

TABLE 2B-continued
THE [4,4,0]REVERSE TURN MIMETICS LIBRARY
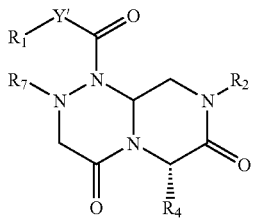
| No | MOLSTRUCTURE | Mol. Weight | M + H (MS) |
|---|---|---|---|
| 1219 | 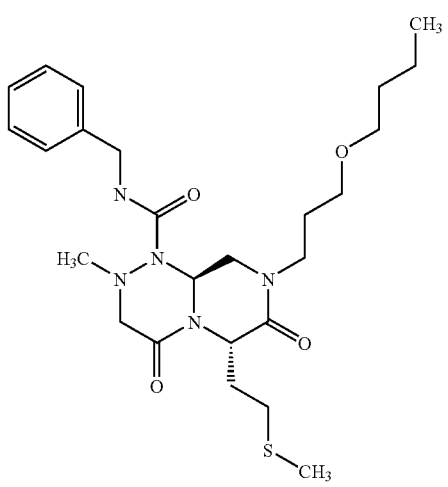 | 506 | 507 |
| 1220 | 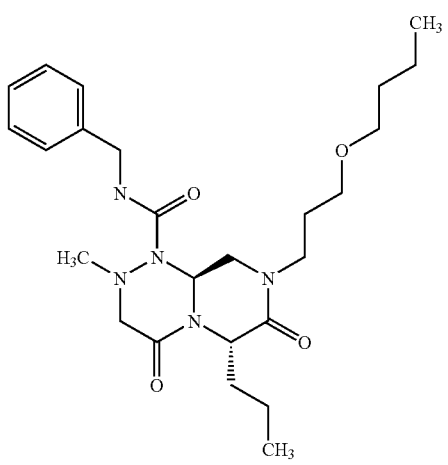 | 474 | 475 |

TABLE 2B-continued
THE [4,4,0]REVERSE TURN MIMETICS LIBRARY
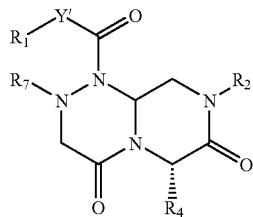
| No | MOLSTRUCTURE | Mol. Weight | M + H (MS) |
|---|---|---|---|
| 1221 | | 490 | 491 |
| 1222 | | 504 | 505 |

TABLE 2B-continued
THE [4,4,0]REVERSE TURN MIMETICS LIBRARY
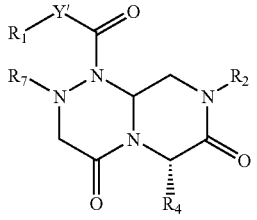
| No | MOLSTRUCTURE | Mol. Weight | M + H (MS) |
|---|---|---|---|
| 1223 | 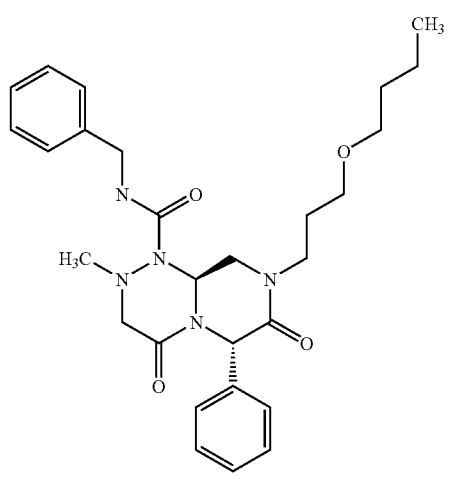 | 508 | 509 |
| 1224 | 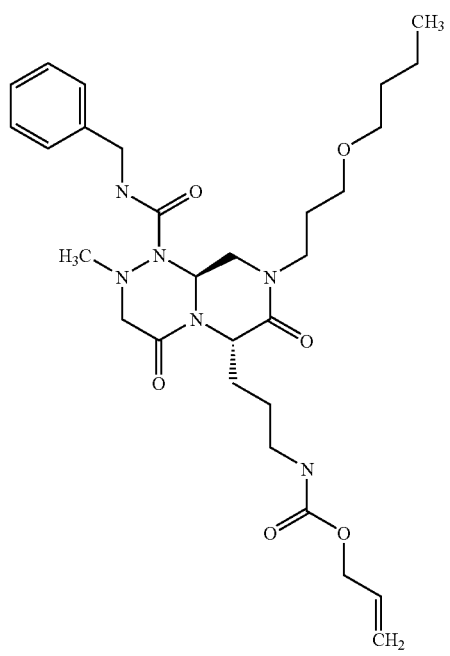 | 573 | 574 |

TABLE 2B-continued
THE [4,4,0]REVERSE TURN MIMETICS LIBRARY
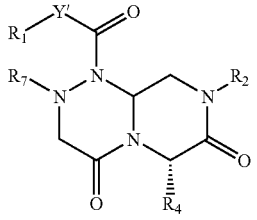
| No | MOLSTRUCTURE | Mol. Weight | M + H (MS) |
|---|---|---|---|
| 1225 | | 510 | 511 |
| 1226 | | 558 | 559 |
| 1227 | | 524 | 525 |

TABLE 2B-continued
THE [4,4,0]REVERSE TURN MIMETICS LIBRARY
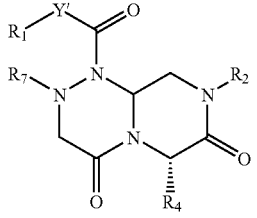
| No | MOLSTRUCTURE | Mol. Weight | M + H (MS) |
|---|---|---|---|
| 1228 | | 524 | 525 |
| 1229 | | 510 | 511 |
| 1230 | | 526 | 527 |

TABLE 2B-continued
THE [4,4,0]REVERSE TURN MIMETICS LIBRARY
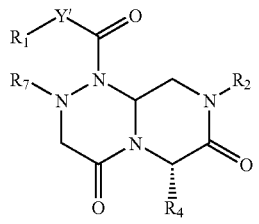
| No | MOLSTRUCTURE | Mol. Weight | M + H (MS) |
|---|---|---|---|
| 1231 | 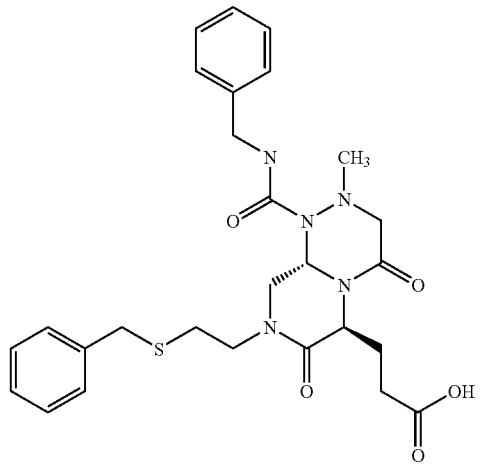 | 540 | 541 |
| 1232 | 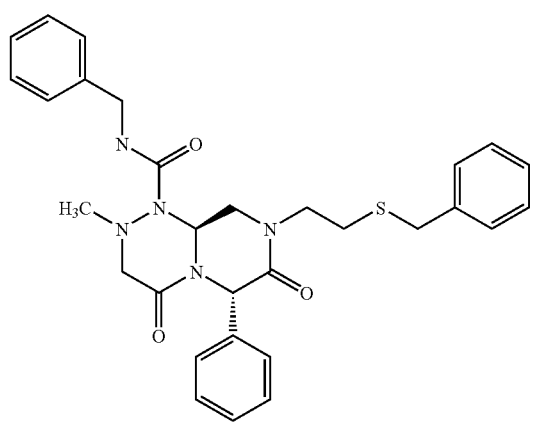 | 544 | 545 |

TABLE 2B-continued
THE [4,4,0]REVERSE TURN MIMETICS LIBRARY
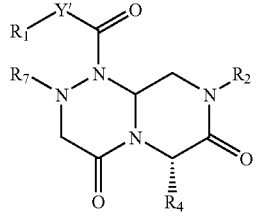
| No | MOLSTRUCTURE | Mol. Weight | M + H (MS) |
|---|---|---|---|
| 1233 | | 609 | 610 |
| 1234 | | 548 | 549 |

TABLE 2B-continued
THE [4,4,0]REVERSE TURN MIMETICS LIBRARY
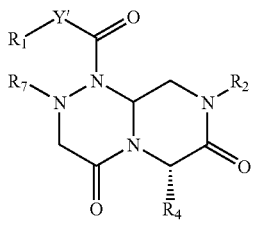
| No | MOLSTRUCTURE | Mol. Weight | M + H (MS) |
|---|---|---|---|
| 1235 | | 498 | 499 |
| 1236 | | 484 | 485 |
| 1237 | | 532 | 533 |

TABLE 2B-continued

THE [4,4,0]REVERSE TURN MIMETICS LIBRARY

| No | MOLSTRUCTURE | Mol. Weight | M + H (MS) |
|---|---|---|---|
| 1238 | | 498 | 499 |
| 1239 | | 498 | 499 |
| 1240 | | 516 | 517 |

TABLE 2B-continued
THE [4,4,0]REVERSE TURN MIMETICS LIBRARY
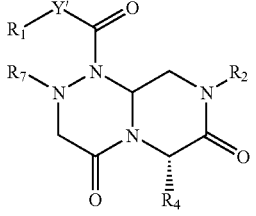
| No | MOLSTRUCTURE | Mol. Weight | M + H (MS) |
|---|---|---|---|
| 1241 | | 484 | 485 |
| 1242 | | 500 | 501 |
| 1243 | | 514 | 515 |

TABLE 2B-continued
THE [4,4,0]REVERSE TURN MIMETICS LIBRARY
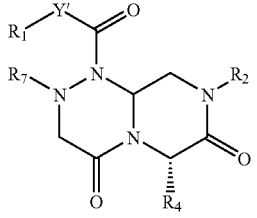
| No | MOLSTRUCTURE | Mol. Weight | M + H (MS) |
|---|---|---|---|
| 1244 | | 518 | 519 |
| 1245 | | 583 | 584 |

TABLE 2B-continued
THE [4,4,0]REVERSE TURN MIMETICS LIBRARY
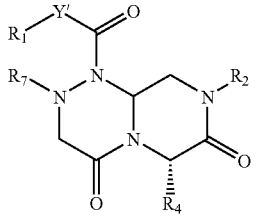
| No | MOLSTRUCTURE | Mol. Weight | M + H (MS) |
|---|---|---|---|
| 1246 | | 534 | 535 |
| 1247 | | 484 | 485 |
| 1248 | | 470 | 471 |

TABLE 2B-continued

THE [4,4,0]REVERSE TURN MIMETICS LIBRARY

| No | MOLSTRUCTURE | Mol. Weight | M + H (MS) |
|---|---|---|---|
| 1249 | | 518 | 519 |
| 1250 | | 484 | 485 |
| 1251 | | 484 | 485 |

TABLE 2B-continued

THE [4,4,0]REVERSE TURN MIMETICS LIBRARY

| No | MOLSTRUCTURE | Mol. Weight | M + H (MS) |
|---|---|---|---|
| 1252 | | 502 | 503 |
| 1253 | | 470 | 471 |
| 1254 | | 486 | 487 |

TABLE 2B-continued
THE [4,4,0]REVERSE TURN MIMETICS LIBRARY
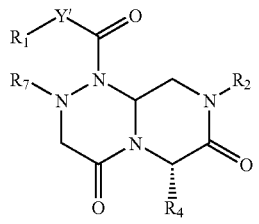
| No | MOLSTRUCTURE | Mol. Weight | M + H (MS) |
|---|---|---|---|
| 1255 | 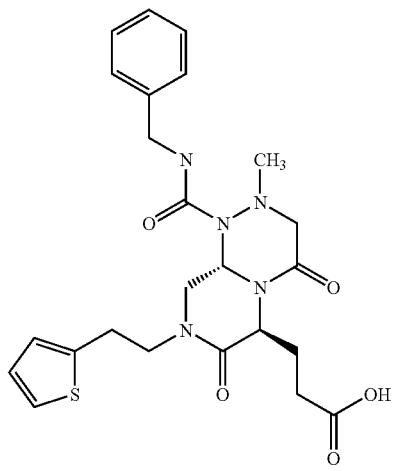 | 500 | 501 |
| 1256 | 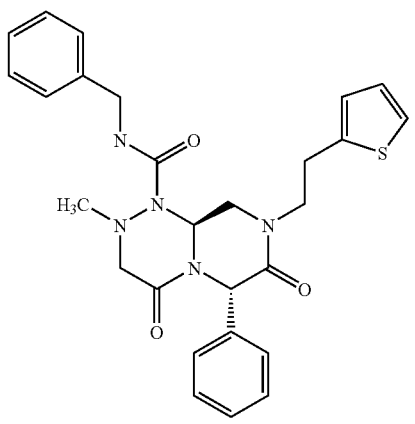 | 504 | 505 |

TABLE 2B-continued
THE [4,4,0]REVERSE TURN MIMETICS LIBRARY
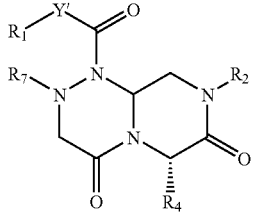
| No | MOLSTRUCTURE | Mol. Weight | M + H (MS) |
|---|---|---|---|
| 1257 | | 569 | 570 |
| 1258 | 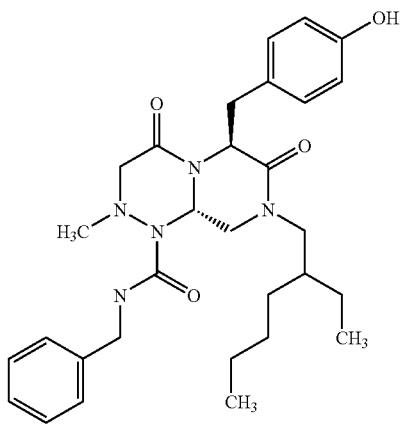 | 536 | 537 |

TABLE 2B-continued
THE [4,4,0]REVERSE TURN MIMETICS LIBRARY
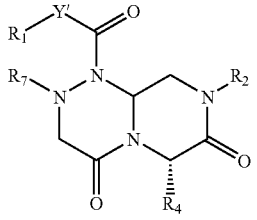
| No | MOLSTRUCTURE | Mol. Weight | M + H (MS) |
|---|---|---|---|
| 1259 | | 486 | 487 |
| 1260 | | 472 | 473 |
| 1261 | | 520 | 521 |

TABLE 2B-continued
THE [4,4,0]REVERSE TURN MIMETICS LIBRARY
| No | MOLSTRUCTURE | Mol. Weight | M + H (MS) |
|---|---|---|---|
| 1262 | 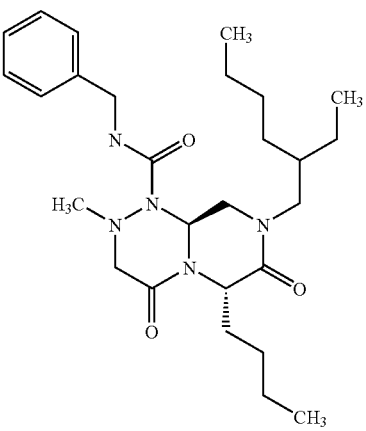 | 486 | 487 |
| 1263 | 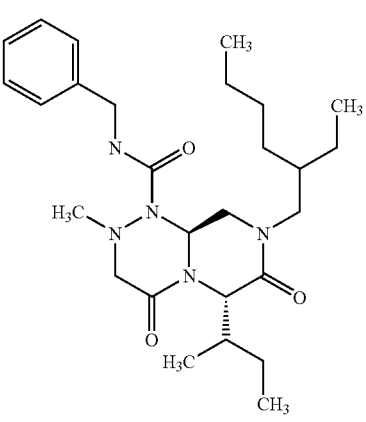 | 486 | 487 |
| 1264 | 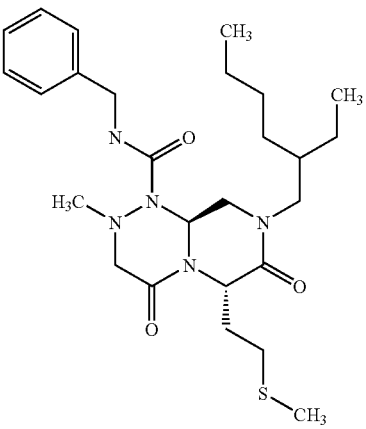 | 504 | 505 |

TABLE 2B-continued

THE [4,4,0]REVERSE TURN MIMETICS LIBRARY

| No | MOLSTRUCTURE | Mol. Weight | M + H (MS) |
|---|---|---|---|
| 1265 | | 472 | 473 |
| 1266 | | 488 | 489 |
| 1267 | | 502 | 503 |

TABLE 2B-continued
THE [4,4,0]REVERSE TURN MIMETICS LIBRARY
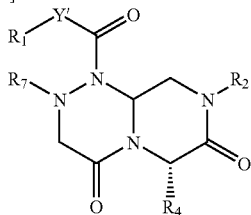
| No | MOLSTRUCTURE | Mol. Weight | M + H (MS) |
|---|---|---|---|
| 1268 | | 506 | 507 |
| 1269 | | 571 | 572 |

TABLE 2B-continued
THE [4,4,0]REVERSE TURN MIMETICS LIBRARY
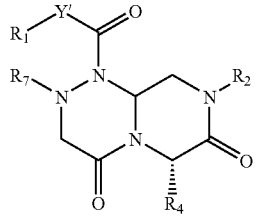
| No | MOLSTRUCTURE | Mol. Weight | M + H (MS) |
|----|---|---|---|
| 1270 | | 558 | 559 |
| 1271 | | 508 | 509 |
| 1272 | | 494 | 495 |

TABLE 2B-continued
THE [4,4,0]REVERSE TURN MIMETICS LIBRARY
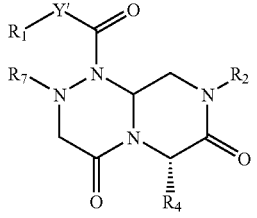
| No | MOLSTRUCTURE | Mol. Weight | M + H (MS) |
|---|---|---|---|
| 1273 | | 542 | 543 |
| 1274 | | 508 | 509 |
| 1275 | | 508 | 509 |

TABLE 2B-continued
THE [4,4,0]REVERSE TURN MIMETICS LIBRARY
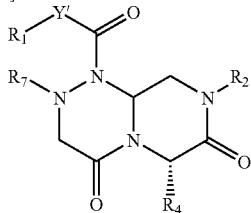
| No | MOLSTRUCTURE | Mol. Weight | M + H (MS) |
|---|---|---|---|
| 1276 | | 526 | 527 |
| 1277 | | 494 | 495 |
| 1278 | | 510 | 511 |

TABLE 2B-continued
THE [4,4,0]REVERSE TURN MIMETICS LIBRARY
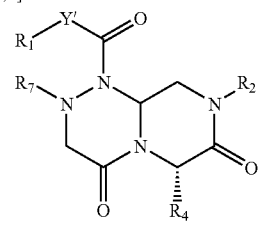
| No | MOLSTRUCTURE | Mol. Weight | M + H (MS) |
|---|---|---|---|
| 1279 | 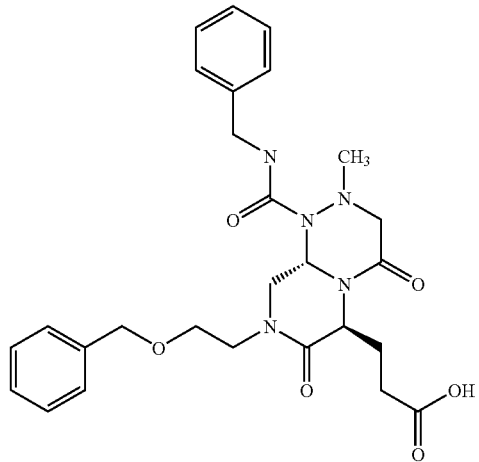 | 524 | 525 |
| 1280 | 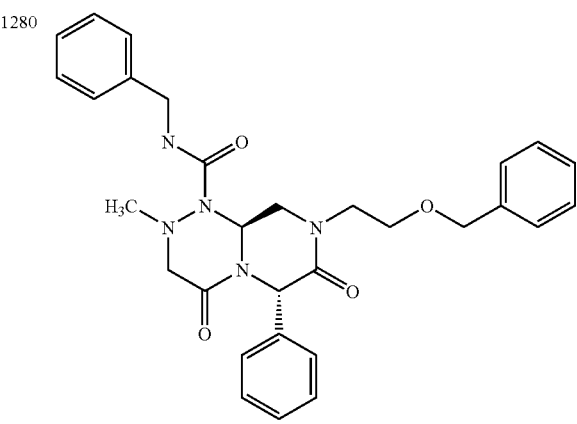 | 528 | 529 |

TABLE 2B-continued
THE [4,4,0]REVERSE TURN MIMETICS LIBRARY
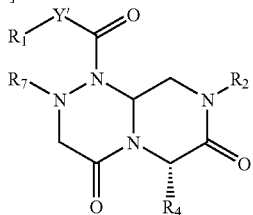
| No | MOLSTRUCTURE | Mol. Weight | M + H (MS) |
|---|---|---|---|
| 1281 | | 593 | 594 |
| 1282 | | 506 | 507 |

TABLE 2B-continued
THE [4,4,0]REVERSE TURN MIMETICS LIBRARY
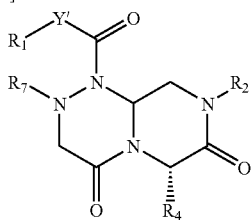
| No | MOLSTRUCTURE | Mol. Weight | M + H (MS) |
|---|---|---|---|
| 1283 | | 456 | 457 |
| 1284 | | 442 | 443 |
| 1285 | | 490 | 491 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 1286 | | 456 | 457 |
| 1287 | | 456 | 457 |
| 1288 | | 474 | 475 |

TABLE 2B-continued

THE [4,4,0]REVERSE TURN MIMETICS LIBRARY

| No | MOLSTRUCTURE | Mol. Weight | M + H (MS) |
|---|---|---|---|
| 1289 | | 442 | 443 |
| 1290 | | 457 | 458 |
| 1291 | | 472 | 473 |

TABLE 2B-continued
THE [4,4,0]REVERSE TURN MIMETICS LIBRARY
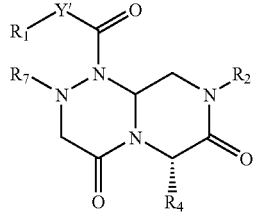
| No | MOLSTRUCTURE | Mol. Weight | M + H (MS) |
|---|---|---|---|
| 1292 | | 476 | 477 |
| 1293 | | 541 | 542 |

TABLE 2B-continued
THE [4,4,0]REVERSE TURN MIMETICS LIBRARY
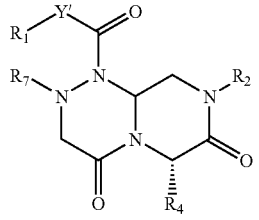
| No | MOLSTRUCTURE | Mol. Weight | M + H (MS) |
|---|---|---|---|
| 1294 | | 572 | 573 |
| 1295 | | 522 | 523 |
| 1296 | | 508 | 509 |

TABLE 2B-continued
THE [4,4,0]REVERSE TURN MIMETICS LIBRARY
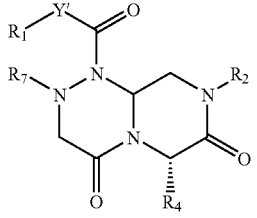
| No | MOLSTRUCTURE | Mol. Weight | M + H (MS) |
|---|---|---|---|
| 1297 | | 556 | 557 |
| 1298 | | 522 | 523 |
| 1299 | | 522 | 523 |

TABLE 2B-continued
THE [4,4,0]REVERSE TURN MIMETICS LIBRARY
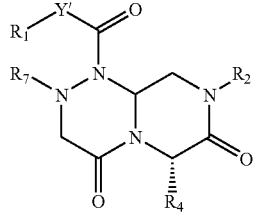
| No | MOLSTRUCTURE | Mol. Weight | M + H (MS) |
|---|---|---|---|
| 1300 | | 540 | 541 |
| 1301 | | 508 | 509 |
| 1302 | | 524 | 525 |

TABLE 2B-continued
THE [4,4,0]REVERSE TURN MIMETICS LIBRARY
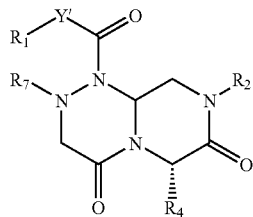
| No | MOLSTRUCTURE | Mol. Weight | M + H (MS) |
|---|---|---|---|
| 1303 | 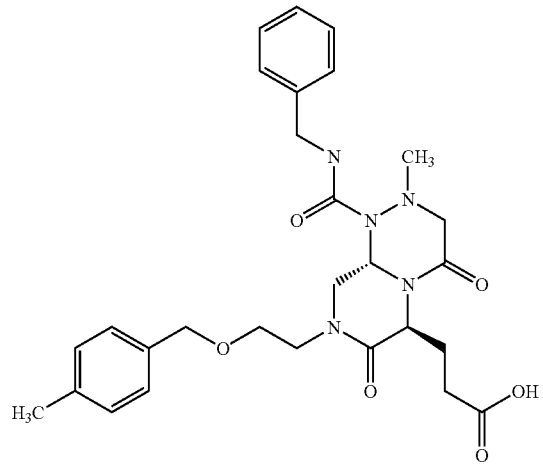 | 538 | 539 |
| 1304 | 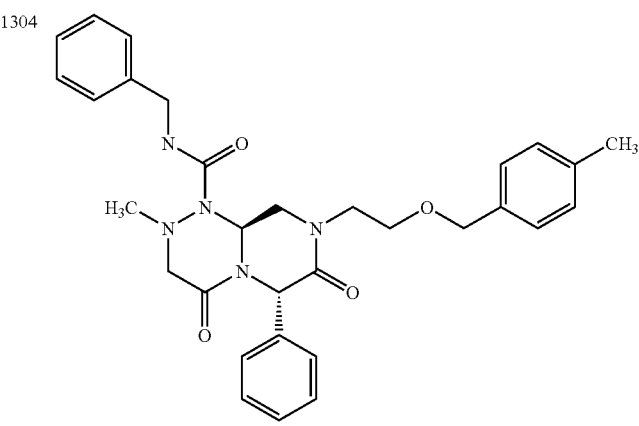 | 542 | 543 |

US 7,566,711 B2
427 428
TABLE 2B-continued
THE [4,4,0]REVERSE TURN MIMETICS LIBRARY
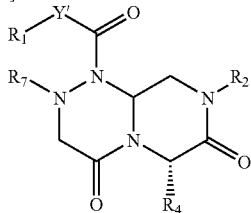
| No | MOLSTRUCTURE | Mol. Weight | M + H (MS) |
|---|---|---|---|
| 1305 | | 607 | 608 |
| 1306 | | 576 | 577 |

TABLE 2B-continued
THE [4,4,0]REVERSE TURN MIMETICS LIBRARY
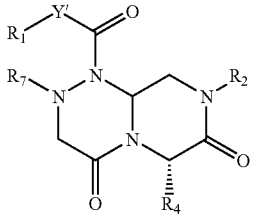
| No | MOLSTRUCTURE | Mol. Weight | M + H (MS) |
|---|---|---|---|
| 1307 | | 526 | 527 |
| 1308 | | 512 | 513 |
| 1309 | | 560 | 561 |

TABLE 2B-continued

THE [4,4,0]REVERSE TURN MIMETICS LIBRARY

| No | MOLSTRUCTURE | Mol. Weight | M + H (MS) |
|---|---|---|---|
| 1310 | | 526 | 527 |
| 1311 | | 526 | 527 |
| 1312 | | 544 | 545 |

TABLE 2B-continued
THE [4,4,0]REVERSE TURN MIMETICS LIBRARY
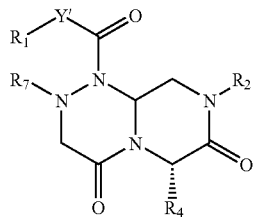
| No | MOLSTRUCTURE | Mol. Weight | M + H (MS) |
|---|---|---|---|
| 1313 | | 512 | 513 |
| 1314 | | 528 | 529 |
| 1315 | | 542 | 543 |

TABLE 2B-continued
THE [4,4,0]REVERSE TURN MIMETICS LIBRARY
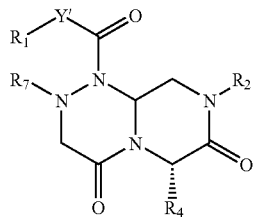
| No | MOLSTRUCTURE | Mol. Weight | M + H (MS) |
|----|--------------|-------------|------------|
| 1316 | | 546 | 547 |
| 1317 | | 611 | 612 |

TABLE 2B-continued
THE [4,4,0]REVERSE TURN MIMETICS LIBRARY
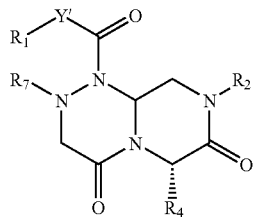
| No | MOLSTRUCTURE | Mol. Weight | M + H (MS) |
|---|---|---|---|
| 1318 | 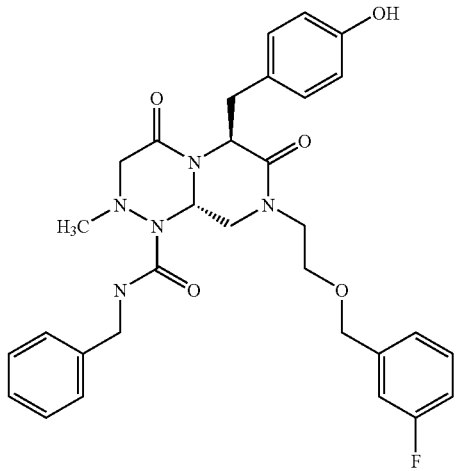 | 576 | 577 |
| 1319 | 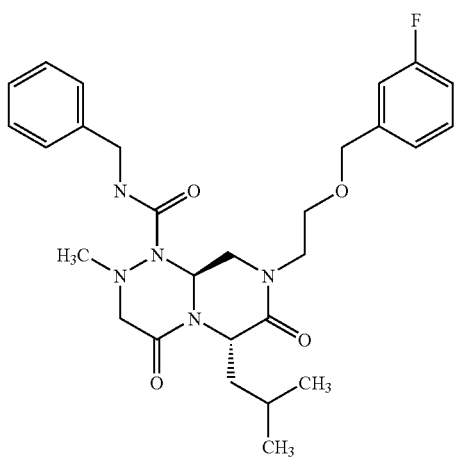 | 526 | 527 |

TABLE 2B-continued
THE [4,4,0]REVERSE TURN MIMETICS LIBRARY
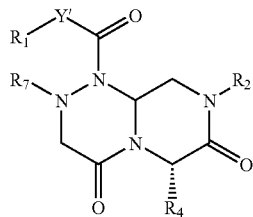
| No | MOLSTRUCTURE | Mol. Weight | M + H (MS) |
|---|---|---|---|
| 1320 | 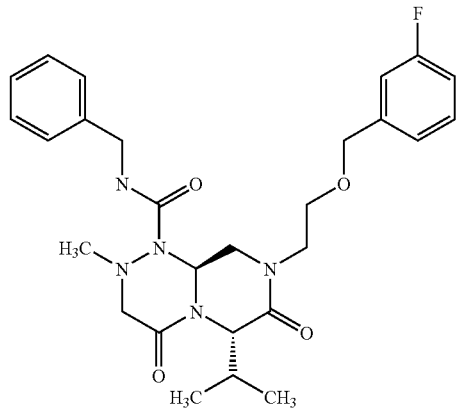 | 512 | 513 |
| 1321 | 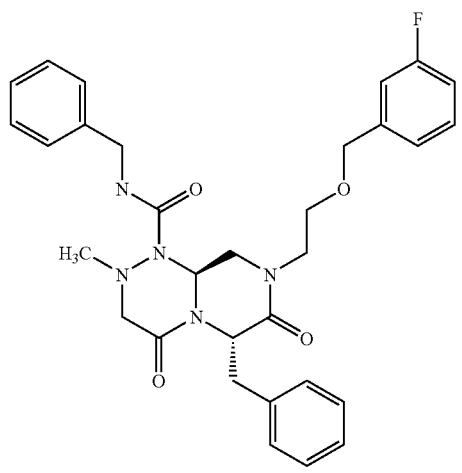 | 560 | 561 |

TABLE 2B-continued
THE [4,4,0]REVERSE TURN MIMETICS LIBRARY
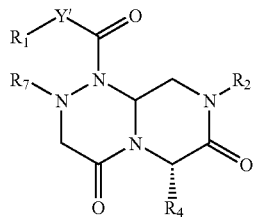
| No | MOLSTRUCTURE | Mol. Weight | M + H (MS) |
|---|---|---|---|
| 1322 | 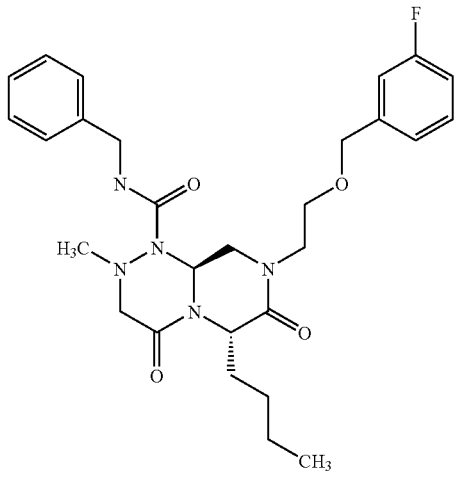 | 526 | 527 |
| 1323 | 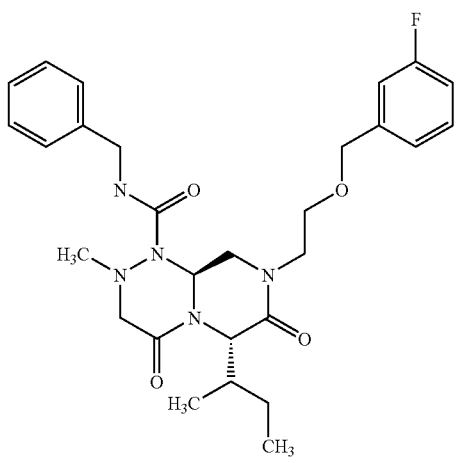 | 526 | 527 |

TABLE 2B-continued
THE [4,4,0]REVERSE TURN MIMETICS LIBRARY
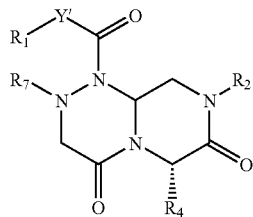
| No | MOLSTRUCTURE | Mol. Weight | M + H (MS) |
|----|--------------|-------------|------------|
| 1324 | 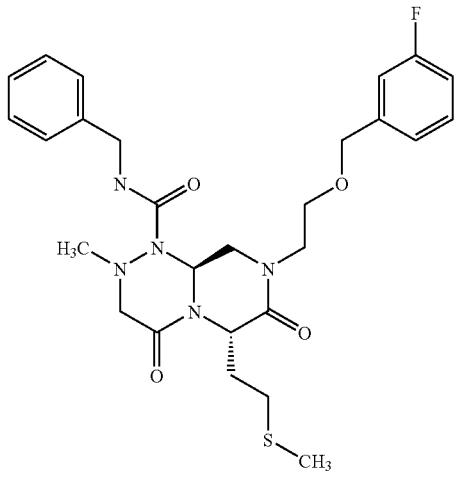 | 544 | 545 |
| 1325 | 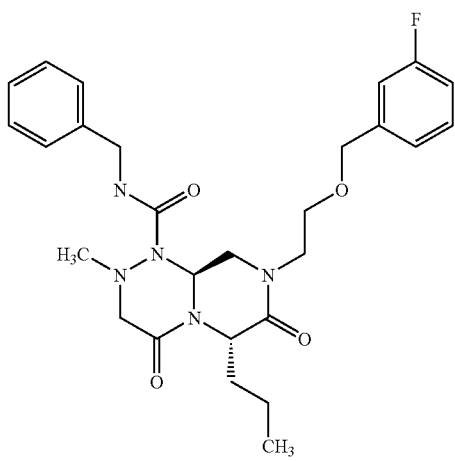 | 512 | 513 |

TABLE 2B-continued
THE [4,4,0]REVERSE TURN MIMETICS LIBRARY
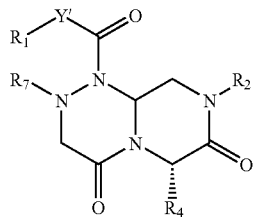
| No | MOLSTRUCTURE | Mol. Weight | M + H (MS) |
|---|---|---|---|
| 1326 | 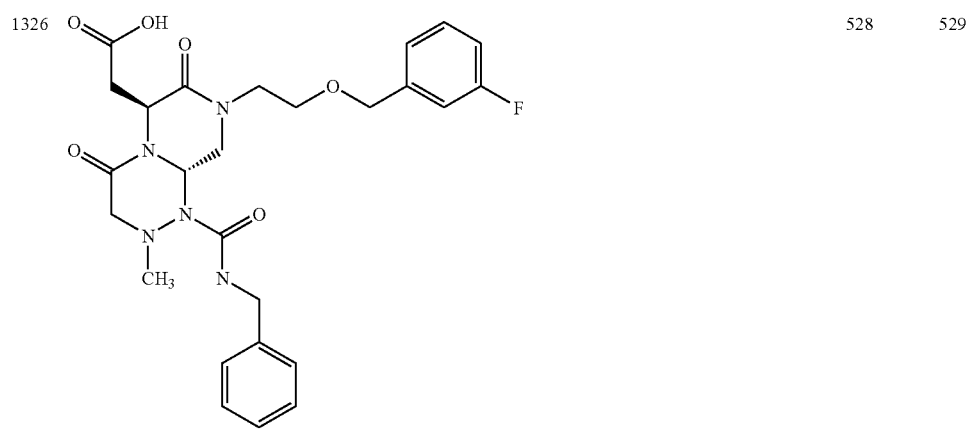 | 528 | 529 |
| 1327 | 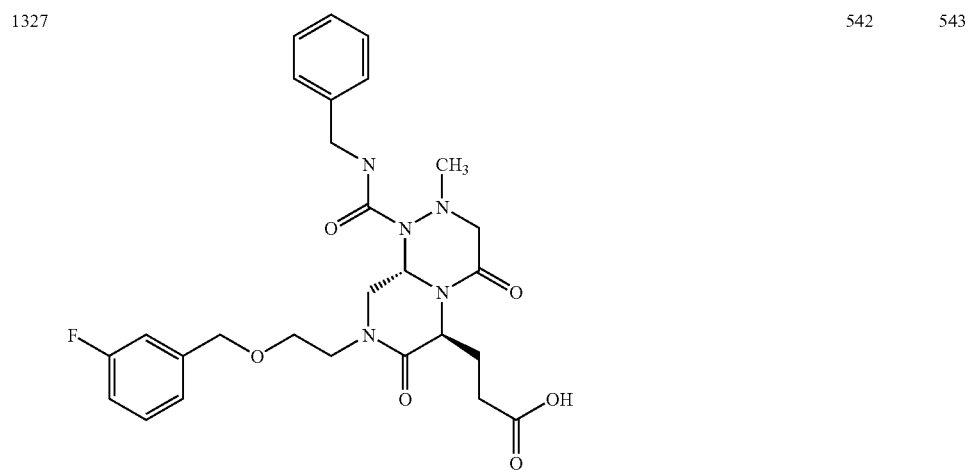 | 542 | 543 |

TABLE 2B-continued
THE [4,4,0]REVERSE TURN MIMETICS LIBRARY
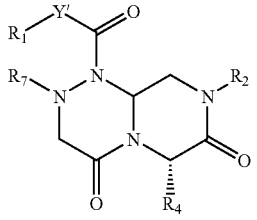
| No | MOLSTRUCTURE | Mol. Weight | M + H (MS) |
|---|---|---|---|
| 1328 | 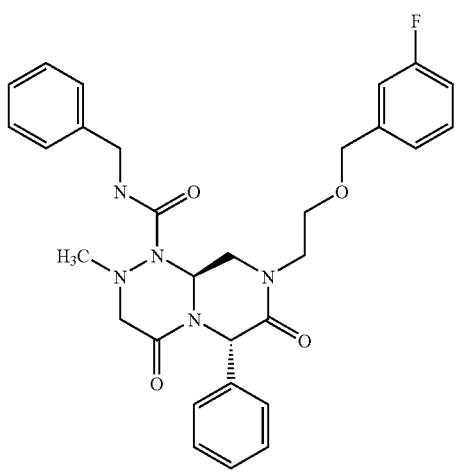 | 546 | 543 |
| 1329 | 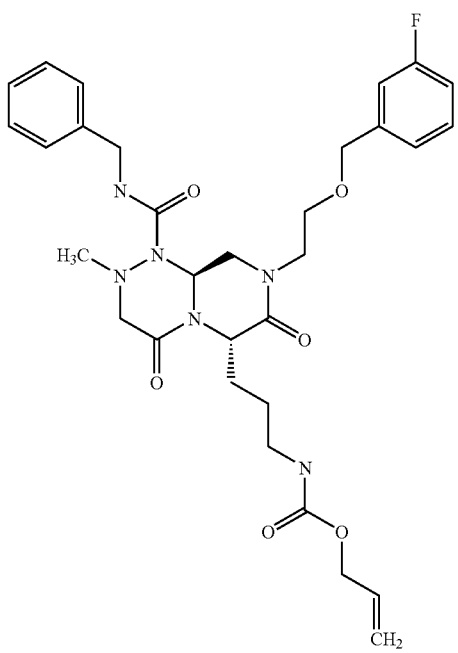 | 611 | 612 |

TABLE 2B-continued
THE [4,4,0]REVERSE TURN MIMETICS LIBRARY
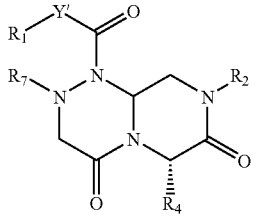
| No | MOLSTRUCTURE | Mol. Weight | M + H (MS) |
|---|---|---|---|
| 1330 | | 576 | 577 |
| 1331 | | 526 | 527 |
| 1332 | | 512 | 513 |

TABLE 2B-continued
THE [4,4,0]REVERSE TURN MIMETICS LIBRARY
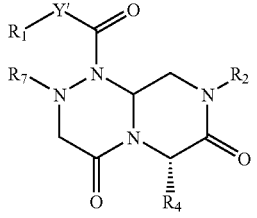
| No | MOLSTRUCTURE | Mol. Weight | M + H (MS) |
|---|---|---|---|
| 1333 | | 560 | 561 |
| 1334 | | 526 | 527 |
| 1335 | | 526 | 527 |

TABLE 2B-continued
THE [4,4,0]REVERSE TURN MIMETICS LIBRARY
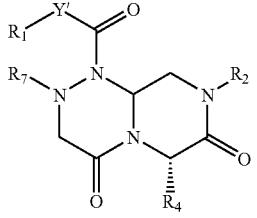
| No | MOLSTRUCTURE | Mol. Weight | M + H (MS) |
|---|---|---|---|
| 1336 | | 544 | 545 |
| 1337 | | 512 | 513 |
| 1338 | | 528 | 529 |

TABLE 2B-continued
THE [4,4,0]REVERSE TURN MIMETICS LIBRARY
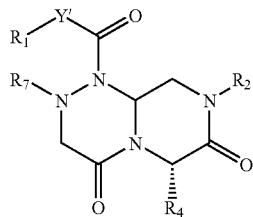
| No | MOLSTRUCTURE | Mol. Weight | M + H (MS) |
|---|---|---|---|
| 1339 | 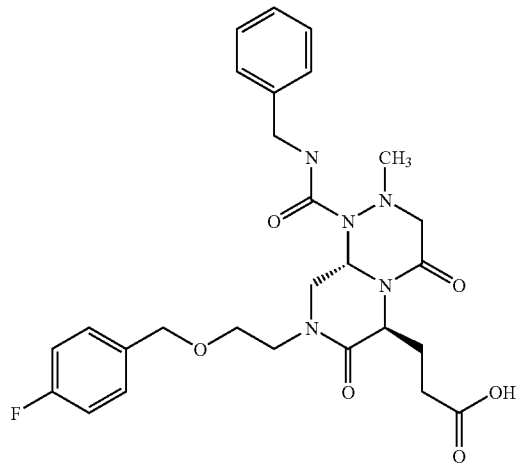 | 542 | 543 |
| 1340 | 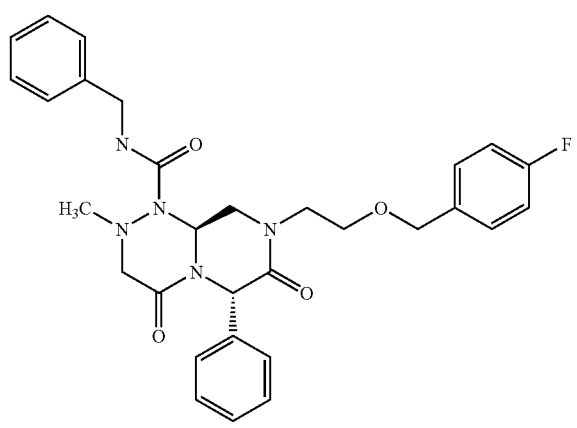 | 546 | 547 |

TABLE 2B-continued
THE [4,4,0]REVERSE TURN MIMETICS LIBRARY
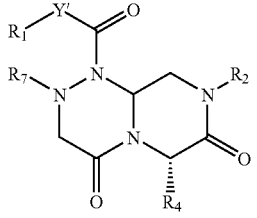
| No | MOLSTRUCTURE | Mol. Weight | M + H (MS) |
|---|---|---|---|
| 1341 | | 611 | 612 |
| 1342 | | 492 | 493 |

TABLE 2B-continued
THE [4,4,0]REVERSE TURN MIMETICS LIBRARY
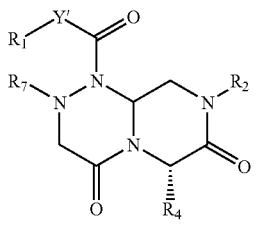
| No | MOLSTRUCTURE | Mol. Weight | M + H (MS) |
|---|---|---|---|
| 1343 | | 442 | 443 |
| 1344 | | 428 | 429 |
| 1345 | | 476 | 477 |

TABLE 2B-continued

THE [4,4,0]REVERSE TURN MIMETICS LIBRARY

| No | MOLSTRUCTURE | Mol. Weight | M + H (MS) |
|---|---|---|---|
| 1346 | | 442 | 443 |
| 1347 | | 442 | 443 |
| 1348 | | 460 | 461 |

TABLE 2B-continued

THE [4,4,0]REVERSE TURN MIMETICS LIBRARY

| No | MOLSTRUCTURE | Mol. Weight | M + H (MS) |
|---|---|---|---|
| 1349 | | 428 | 429 |
| 1350 | | 444 | 445 |
| 1351 | | 458 | 459 |

TABLE 2B-continued
THE [4,4,0]REVERSE TURN MIMETICS LIBRARY
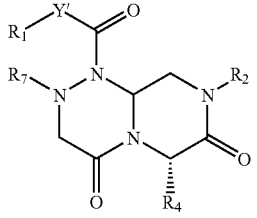
| No | MOLSTRUCTURE | Mol. Weight | M + H (MS) |
|---|---|---|---|
| 1352 | | 462 | 463 |
| 1353 | | 527 | 528 |

TABLE 2B-continued
THE [4,4,0]REVERSE TURN MIMETICS LIBRARY
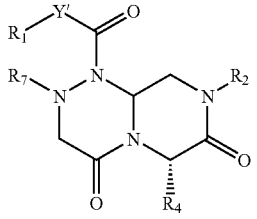
| No | MOLSTRUCTURE | Mol. Weight | M + H (MS) |
|---|---|---|---|
| 1354 | | 522 | 523 |
| 1355 | | 472 | 473 |
| 1356 | | 458 | 459 |

TABLE 2B-continued
THE [4,4,0]REVERSE TURN MIMETICS LIBRARY
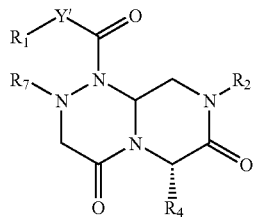
| No | MOLSTRUCTURE | Mol. Weight | M + H (MS) |
|----|--------------|-------------|------------|
| 1357 | | 506 | 507 |
| 1358 | | 472 | 473 |
| 1359 | | 472 | 473 |

TABLE 2B-continued
THE [4,4,0]REVERSE TURN MIMETICS LIBRARY
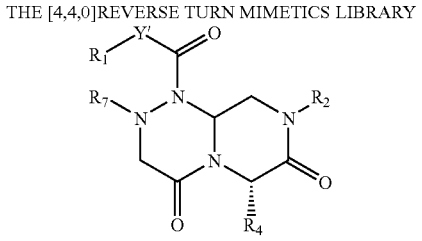
| No | MOLSTRUCTURE | Mol. Weight | M + H (MS) |
|---|---|---|---|
| 1360 | | 490 | 491 |
| 1361 | | 458 | 459 |
| 1362 | | 474 | 475 |

TABLE 2B-continued
THE [4,4,0]REVERSE TURN MIMETICS LIBRARY
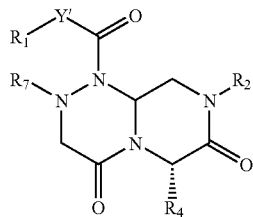
| No | MOLSTRUCTURE | Mol. Weight | M + H (MS) |
|---|---|---|---|
| 1363 | 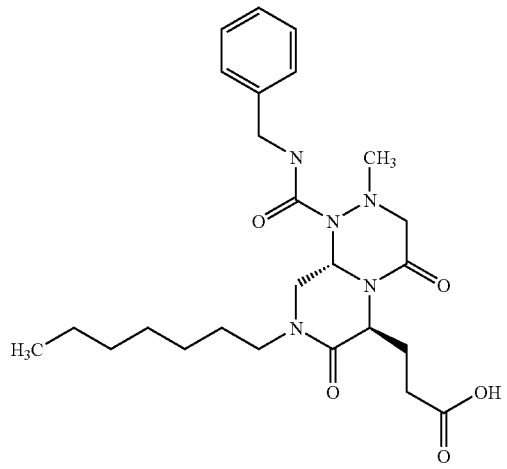 | 488 | 489 |
| 1364 | 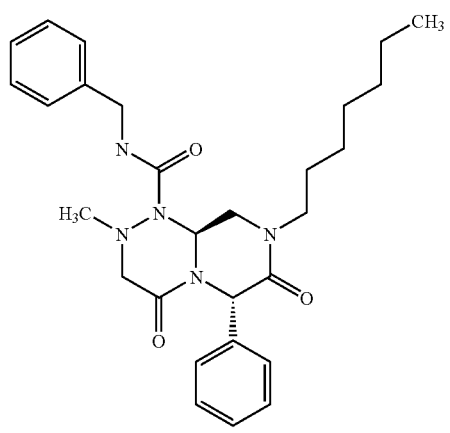 | 492 | 493 |

TABLE 2B-continued
THE [4,4,0]REVERSE TURN MIMETICS LIBRARY
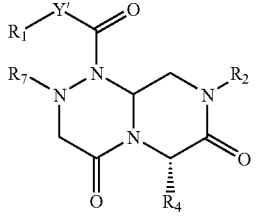
| No | MOLSTRUCTURE | Mol. Weight | M + H (MS) |
|---|---|---|---|
| 1365 | 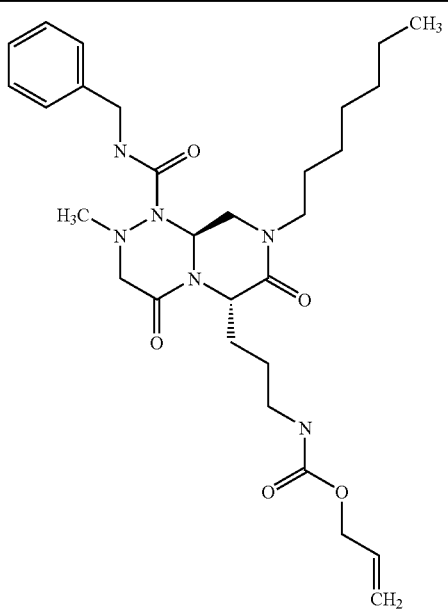 | 557 | 558 |
| 1366 | 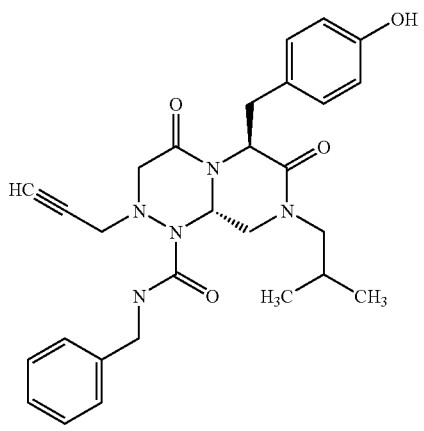 | 504 | 505 |

TABLE 2B-continued
THE [4,4,0]REVERSE TURN MIMETICS LIBRARY
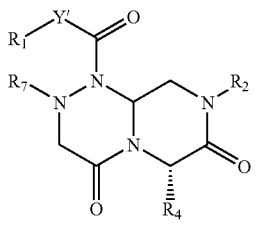
| No | MOLSTRUCTURE | Mol. Weight | M + H (MS) |
|---|---|---|---|
| 1367 | | 454 | 455 |
| 1368 | | 440 | 441 |
| 1369 | | 488 | 489 |

TABLE 2B-continued
THE [4,4,0]REVERSE TURN MIMETICS LIBRARY
| No | MOLSTRUCTURE | Mol. Weight | M + H (MS) |
|---|---|---|---|
| 1370 |  | 454 | 455 |
| 1371 | 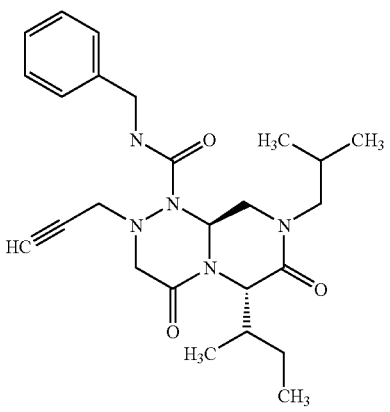 | 454 | 455 |
| 1372 | 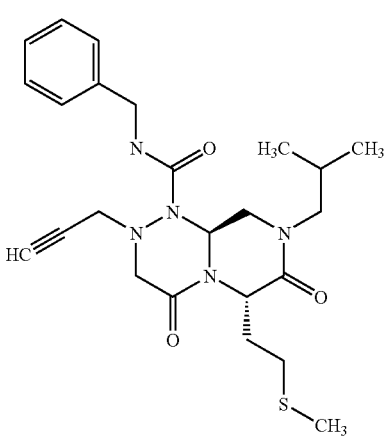 | 472 | 473 |

TABLE 2B-continued

THE [4,4,0]REVERSE TURN MIMETICS LIBRARY

| No | MOLSTRUCTURE | Mol. Weight | M + H (MS) |
|---|---|---|---|
| 1373 | | 440 | 441 |
| 1374 | | 456 | 457 |
| 1375 | | 470 | 471 |

TABLE 2B-continued
THE [4,4,0]REVERSE TURN MIMETICS LIBRARY
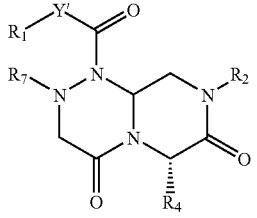
| No | MOLSTRUCTURE | Mol. Weight | M + H (MS) |
|---|---|---|---|
| 1376 | | 474 | 475 |
| 1377 | | 539 | 540 |

TABLE 2B-continued
THE [4,4,0]REVERSE TURN MIMETICS LIBRARY
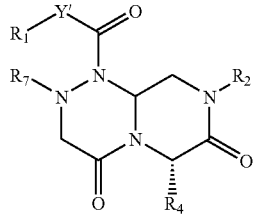
| No | MOLSTRUCTURE | Mol. Weight | M + H (MS) |
|---|---|---|---|
| 1378 | | 606 | 607 |
| 1379 | | 556 | 557 |
| 1380 | | 542 | 543 |

TABLE 2B-continued
THE [4,4,0]REVERSE TURN MIMETICS LIBRARY
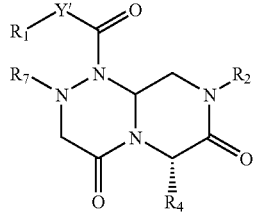
| No | MOLSTRUCTURE | Mol. Weight | M + H (MS) |
|---|---|---|---|
| 1381 | | 590 | 591 |
| 1382 | | 556 | 557 |
| 1383 | | 556 | 557 |

TABLE 2B-continued
THE [4,4,0]REVERSE TURN MIMETICS LIBRARY
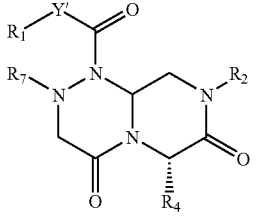
| No | MOLSTRUCTURE | Mol. Weight | M + H (MS) |
|---|---|---|---|
| 1384 | | 574 | 575 |
| 1385 | | 542 | 543 |
| 1386 | | 558 | 559 |

TABLE 2B-continued
THE [4,4,0]REVERSE TURN MIMETICS LIBRARY
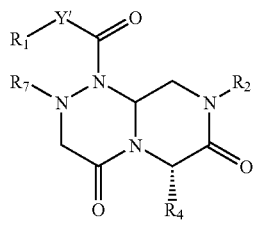
| No | MOLSTRUCTURE | Mol. Weight | M + H (MS) |
|---|---|---|---|
| 1387 | 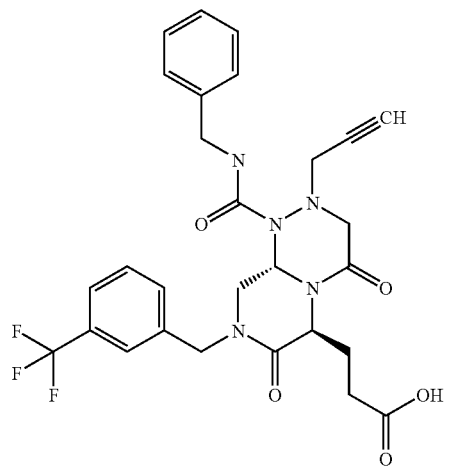 | 572 | 573 |
| 1388 | 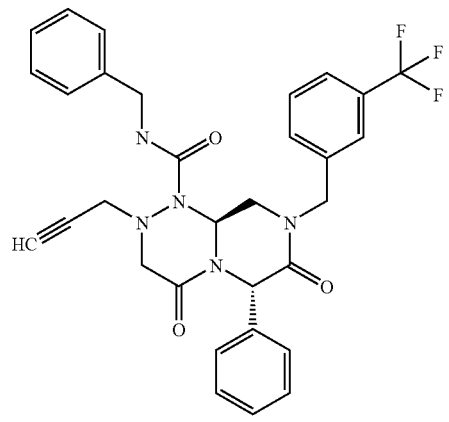 | 576 | 577 |

TABLE 2B-continued
THE [4,4,0]REVERSE TURN MIMETICS LIBRARY
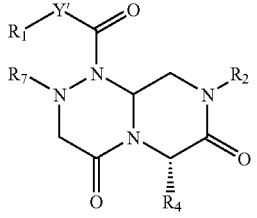
| No | MOLSTRUCTURE | Mol. Weight | M + H (MS) |
|---|---|---|---|
| 1389 | | 641 | 642 |
| 1390 | | 566 | 567 |

TABLE 2B-continued
THE [4,4,0]REVERSE TURN MIMETICS LIBRARY
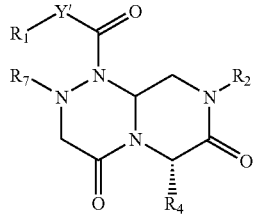
| No | MOLSTRUCTURE | Mol. Weight | M + H (MS) |
|---|---|---|---|
| 1391 | | 516 | 517 |
| 1392 | | 502 | 503 |
| 1393 | | 550 | 551 |

TABLE 2B-continued

THE [4,4,0]REVERSE TURN MIMETICS LIBRARY

| No | MOLSTRUCTURE | Mol. Weight | M + H (MS) |
|---|---|---|---|
| 1394 | | 516 | 517 |
| 1395 | | 516 | 517 |
| 1396 | | 534 | 535 |

TABLE 2B-continued

THE [4,4,0]REVERSE TURN MIMETICS LIBRARY

| No | MOLSTRUCTURE | Mol. Weight | M + H (MS) |
|---|---|---|---|
| 1397 | | 572 | 573 |
| 1398 | | 518 | 518 |
| 1399 | | 532 | 533 |

TABLE 2B-continued
THE [4,4,0]REVERSE TURN MIMETICS LIBRARY
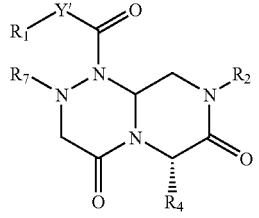
| No | MOLSTRUCTURE | Mol. Weight | M + H (MS) |
|---|---|---|---|
| 1400 | 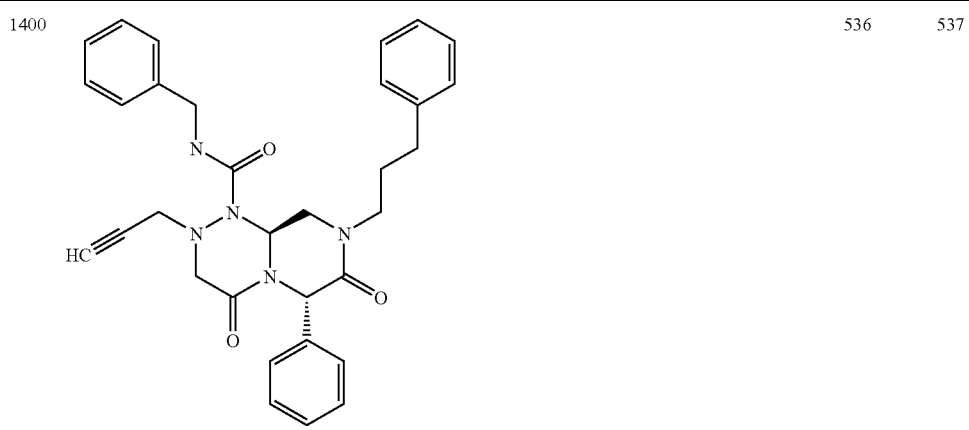 | 536 | 537 |
| 1401 |  | 601 | 602 |

TABLE 2B-continued
THE [4,4,0]REVERSE TURN MIMETICS LIBRARY
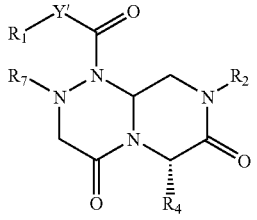
| No | MOLSTRUCTURE | Mol. Weight | M + H (MS) |
|---|---|---|---|
| 1402 | | 556 | 557 |
| 1403 | | 506 | 507 |
| 1404 | | 492 | 493 |

TABLE 2B-continued
THE [4,4,0]REVERSE TURN MIMETICS LIBRARY
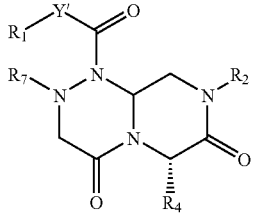
| No | MOLSTRUCTURE | Mol. Weight | M + H (MS) |
|----|--------------|-------------|------------|
| 1405 | | 540 | 541 |
| 1406 | | 506 | 507 |
| 1407 | | 506 | 507 |

TABLE 2B-continued

THE [4,4,0]REVERSE TURN MIMETICS LIBRARY

| No | MOLSTRUCTURE | Mol. Weight | M + H (MS) |
|---|---|---|---|
| 1408 | | 524 | 525 |
| 1409 | | 492 | 493 |
| 1410 | | 508 | 509 |

TABLE 2B-continued
THE [4,4,0]REVERSE TURN MIMETICS LIBRARY
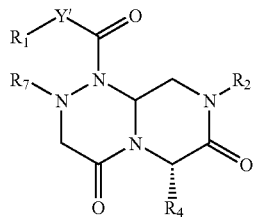
| No | MOLSTRUCTURE | Mol. Weight | M + H (MS) |
|---|---|---|---|
| 1411 | 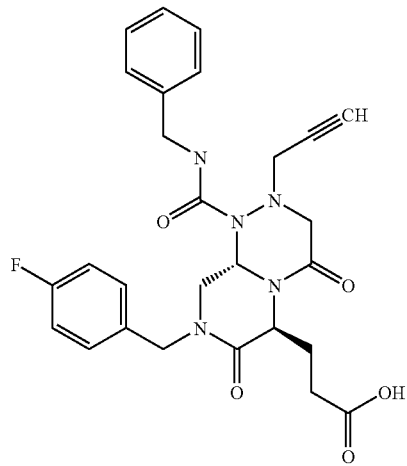 | 522 | 523 |
| 1412 | 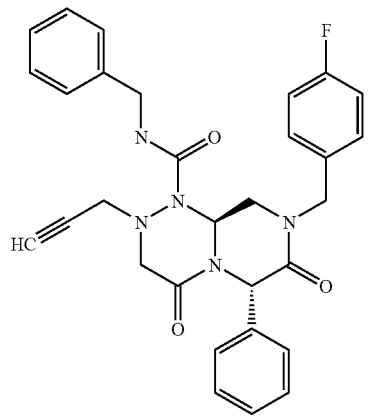 | 526 | 527 |

TABLE 2B-continued
THE [4,4,0]REVERSE TURN MIMETICS LIBRARY
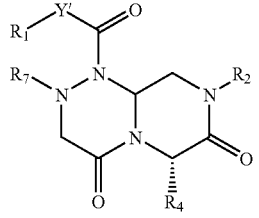
| No | MOLSTRUCTURE | Mol. Weight | M + H (MS) |
|----|--------------|-------------|------------|
| 1413 | | 591 | 592 |
| 1414 | | 532 | 533 |

TABLE 2B-continued
THE [4,4,0]REVERSE TURN MIMETICS LIBRARY
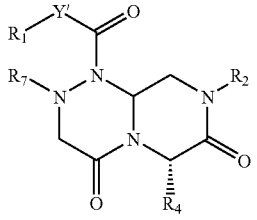
| No | MOLSTRUCTURE | Mol. Weight | M + H (MS) |
|---|---|---|---|
| 1415 | | 582 | 583 |
| 1416 | | 568 | 569 |
| 1417 | | 516 | 517 |

TABLE 2B-continued

THE [4,4,0]REVERSE TURN MIMETICS LIBRARY

| No | MOLSTRUCTURE | Mol. Weight | M + H (MS) |
|---|---|---|---|
| 1418 | | 482 | 483 |
| 1419 | | 582 | 583 |
| 1420 | | 500 | 501 |

TABLE 2B-continued
THE [4,4,0]REVERSE TURN MIMETICS LIBRARY
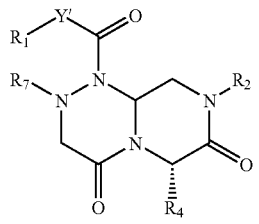
| No | MOLSTRUCTURE | Mol. Weight | M + H (MS) |
|---|---|---|---|
| 1421 | 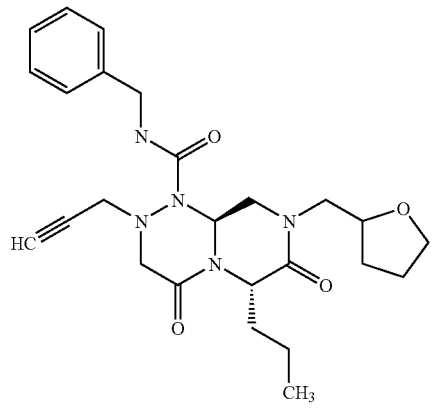 | 468 | 469 |
| 1422 | 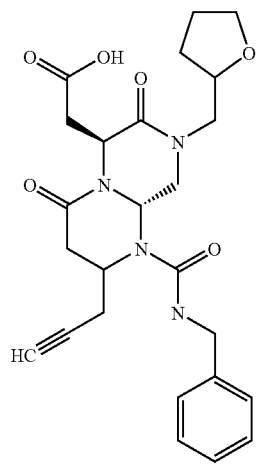 | 484 | 485 |

TABLE 2B-continued
THE [4,4,0]REVERSE TURN MIMETICS LIBRARY
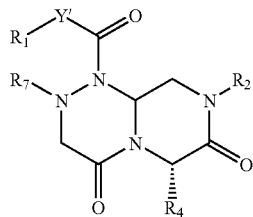
| No | MOLSTRUCTURE | Mol. Weight | M + H (MS) |
|---|---|---|---|
| 1423 | 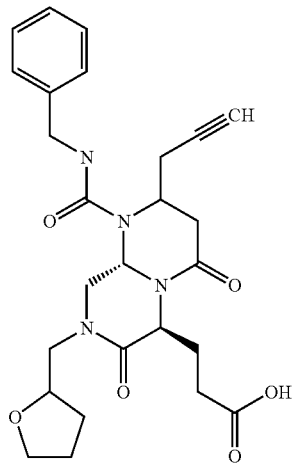 | 498 | 499 |
| 1424 | 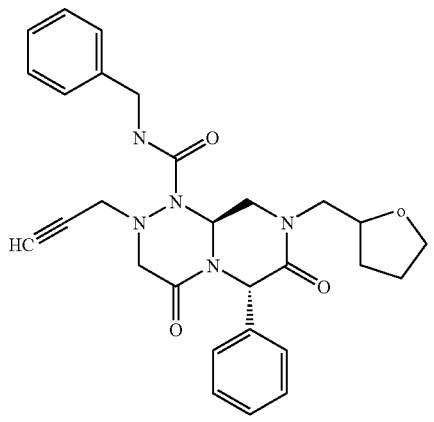 | 502 | 503 |

TABLE 2B-continued
THE [4,4,0]REVERSE TURN MIMETICS LIBRARY
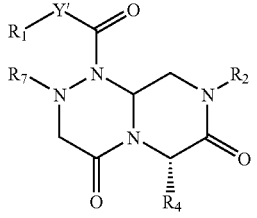
| No | MOLSTRUCTURE | Mol. Weight | M + H (MS) |
|---|---|---|---|
| 1425 | 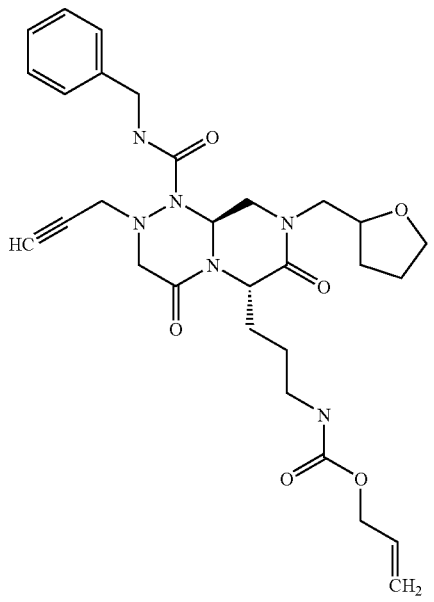 | 567 | 568 |
| 1426 | 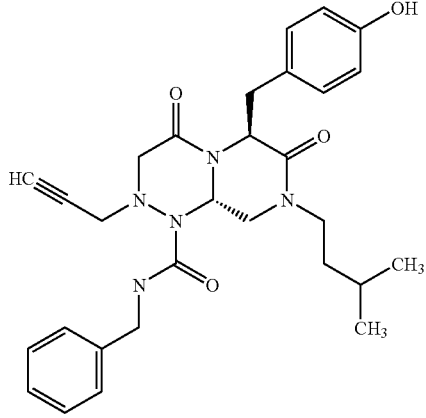 | 518 | 519 |

TABLE 2B-continued
THE [4,4,0]REVERSE TURN MIMETICS LIBRARY
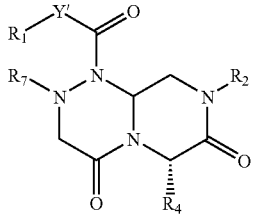
| No | MOLSTRUCTURE | Mol. Weight | M + H (MS) |
|---|---|---|---|
| 1427 | | 568 | 569 |
| 1428 | | 454 | 455 |
| 1429 | | 502 | 503 |

TABLE 2B-continued
THE [4,4,0]REVERSE TURN MIMETICS LIBRARY
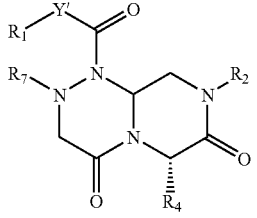
| No | MOLSTRUCTURE | Mol. Weight | M + H (MS) |
|---|---|---|---|
| 1430 | | 568 | 569 |
| 1431 | | 468 | 469 |
| 1432 | | 486 | 487 |

TABLE 2B-continued

THE [4,4,0]REVERSE TURN MIMETICS LIBRARY

| No | MOLSTRUCTURE | Mol. Weight | M + H (MS) |
|---|---|---|---|
| 1433 | | 454 | 455 |
| 1434 | | 470 | 471 |
| 1435 | | 484 | 485 |

TABLE 2B-continued
THE [4,4,0]REVERSE TURN MIMETICS LIBRARY
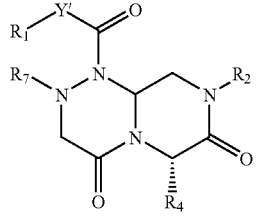
| No | MOLSTRUCTURE | Mol. Weight | M + H (MS) |
|---|---|---|---|
| 1436 | | 488 | 489 |
| 1437 | | 553 | 554 |

TABLE 2B-continued
THE [4,4,0]REVERSE TURN MIMETICS LIBRARY
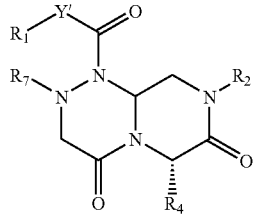
| No | MOLSTRUCTURE | Mol. Weight | M + H (MS) |
|----|--------------|-------------|------------|
| 1438 | | 582 | 583 |
| 1439 | | 532 | 533 |
| 1440 | | 518 | 519 |

TABLE 2B-continued
THE [4,4,0]REVERSE TURN MIMETICS LIBRARY
| No | MOLSTRUCTURE | Mol. Weight | M + H (MS) |
|---|---|---|---|
| 1441 | | 566 | 567 |
| 1442 | | 532 | 533 |
| 1443 | | 532 | 533 |

TABLE 2B-continued
THE [4,4,0]REVERSE TURN MIMETICS LIBRARY
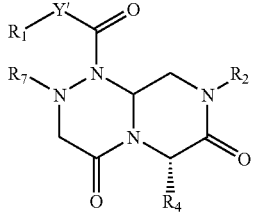
| No | MOLSTRUCTURE | Mol. Weight | M + H (MS) |
|---|---|---|---|
| 1444 | | 550 | 551 |
| 1445 | | 518 | 519 |
| 1446 | | 534 | 535 |

TABLE 2B-continued
THE [4,4,0]REVERSE TURN MIMETICS LIBRARY
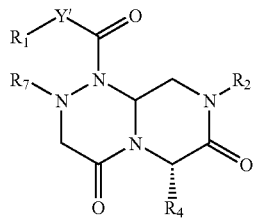
| No | MOLSTRUCTURE | Mol. Weight | M + H (MS) |
|---|---|---|---|
| 1447 | 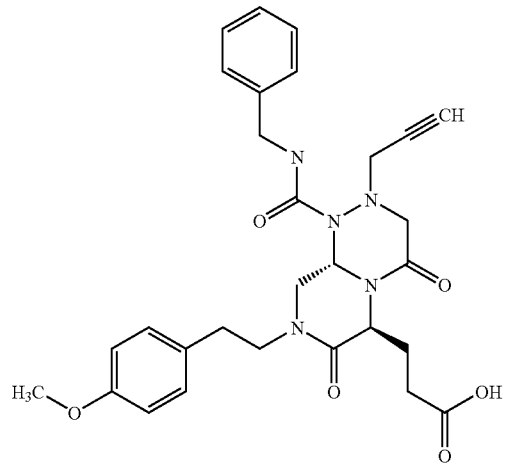 | 548 | 549 |
| 1448 | 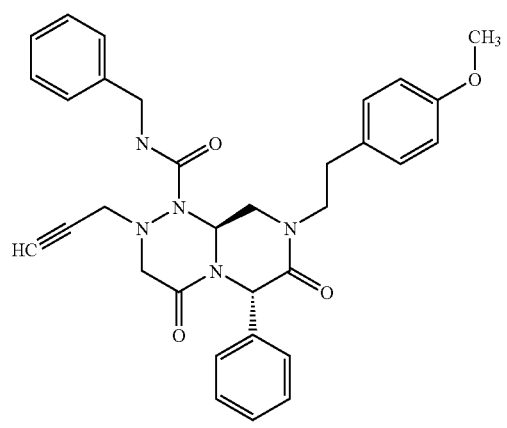 | 552 | 553 |

TABLE 2B-continued
THE [4,4,0]REVERSE TURN MIMETICS LIBRARY
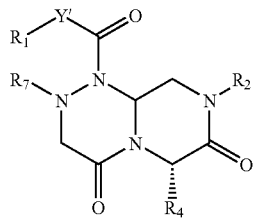
| No | MOLSTRUCTURE | Mol. Weight | M + H (MS) |
|---|---|---|---|
| 1449 | | 617 | 618 |
| 1450 | | 520 | 521 |

TABLE 2B-continued
THE [4,4,0]REVERSE TURN MIMETICS LIBRARY
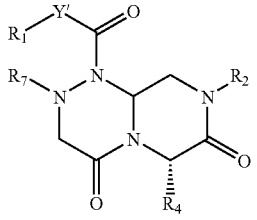
| No | MOLSTRUCTURE | Mol. Weight | M + H (MS) |
|---|---|---|---|
| 1451 | | 470 | 471 |
| 1452 | | 456 | 457 |
| 1453 | | 504 | 505 |

TABLE 2B-continued
THE [4,4,0]REVERSE TURN MIMETICS LIBRARY
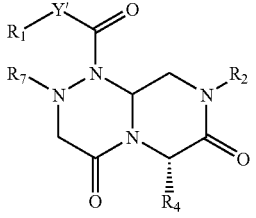
| No | MOLSTRUCTURE | Mol. Weight | M + H (MS) |
|---|---|---|---|
| 1454 | | 470 | 471 |
| 1455 | | 470 | 471 |
| 1456 | | 488 | 489 |

TABLE 2B-continued

THE [4,4,0]REVERSE TURN MIMETICS LIBRARY

| No | MOLSTRUCTURE | Mol. Weight | M + H (MS) |
|---|---|---|---|
| 1457 | | 556 | 557 |
| 1458 | | 472 | 473 |
| 1459 | | 486 | 487 |

TABLE 2B-continued
THE [4,4,0]REVERSE TURN MIMETICS LIBRARY
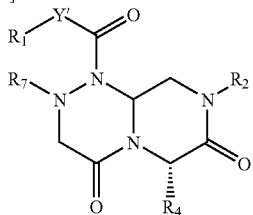
| No | MOLSTRUCTURE | Mol. Weight | M + H (MS) |
|----|--------------|-------------|------------|
| 1460 | | 490 | 491 |
| 1461 | | 555 | 556 |

TABLE 2B-continued
THE [4,4,0]REVERSE TURN MIMETICS LIBRARY
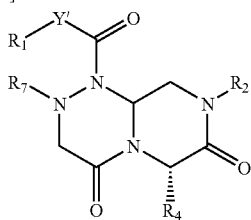
| No | MOLSTRUCTURE | Mol. Weight | M + H (MS) |
|---|---|---|---|
| 1462 | | 582 | 583 |
| 1463 | | 532 | 533 |
| 1464 | | 518 | 519 |

TABLE 2B-continued
THE [4,4,0]REVERSE TURN MIMETICS LIBRARY
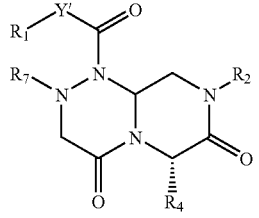
| No | MOLSTRUCTURE | Mol. Weight | M + H (MS) |
|---|---|---|---|
| 1465 | | 566 | 567 |
| 1466 | | 532 | 533 |
| 1467 | | 532 | 533 |

TABLE 2B-continued

THE [4,4,0]REVERSE TURN MIMETICS LIBRARY

| No | MOLSTRUCTURE | Mol. Weight | M + H (MS) |
|---|---|---|---|
| 1468 | | 550 | 551 |
| 1469 | | 518 | 519 |
| 1470 | | 534 | 535 |

TABLE 2B-continued
THE [4,4,0]REVERSE TURN MIMETICS LIBRARY
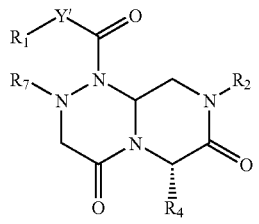
| No | MOLSTRUCTURE | Mol. Weight | M + H (MS) |
|---|---|---|---|
| 1471 | 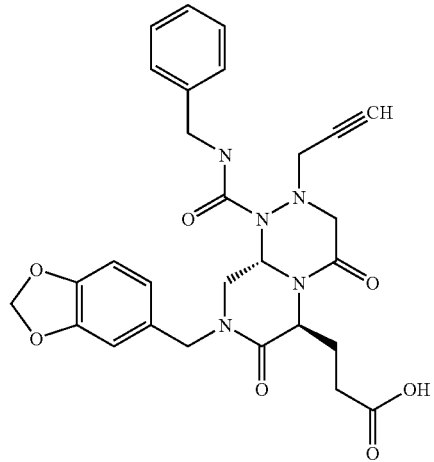 | 548 | 549 |
| 1472 | 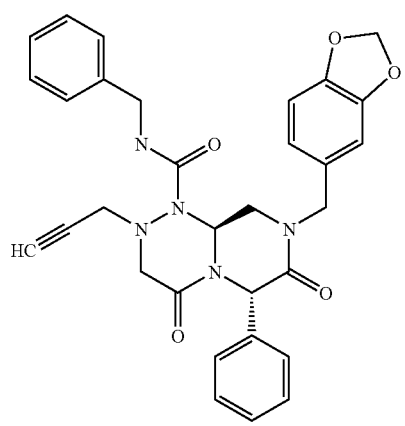 | 552 | 553 |

TABLE 2B-continued
THE [4,4,0]REVERSE TURN MIMETICS LIBRARY
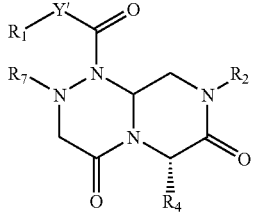
| No | MOLSTRUCTURE | Mol. Weight | M + H (MS) |
|---|---|---|---|
| 1473 | | 517 | 618 |
| 1474 | | 568 | 569 |

TABLE 2B-continued
THE [4,4,0]REVERSE TURN MIMETICS LIBRARY
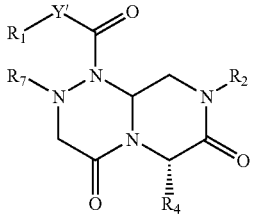
| No | MOLSTRUCTURE | Mol. Weight | M + H (MS) |
|---|---|---|---|
| 1475 | | 518 | 519 |
| 1476 | | 568 | 569 |
| 1477 | | 552 | 553 |

TABLE 2B-continued
THE [4,4,0]REVERSE TURN MIMETICS LIBRARY
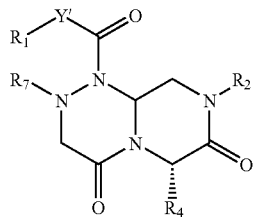
| No | MOLSTRUCTURE | Mol. Weight | M + H (MS) |
|---|---|---|---|
| 1478 | | 518 | 519 |
| 1479 | | 518 | 519 |
| 1480 | | 536 | 537 |

TABLE 2B-continued

THE [4,4,0]REVERSE TURN MIMETICS LIBRARY

| No | MOLSTRUCTURE | Mol. Weight | M + H (MS) |
|---|---|---|---|
| 1481 | | 504 | 505 |
| 1482 | | 520 | 521 |
| 1483 | | 534 | 535 |

TABLE 2B-continued
THE [4,4,0]REVERSE TURN MIMETICS LIBRARY
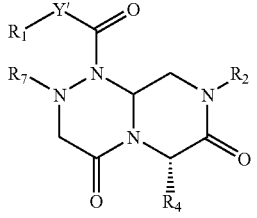
| No | MOLSTRUCTURE | Mol. Weight | M + H (MS) |
|---|---|---|---|
| 1484 | | 538 | 539 |
| 1485 | | 603 | 604 |

TABLE 2B-continued
THE [4,4,0]REVERSE TURN MIMETICS LIBRARY
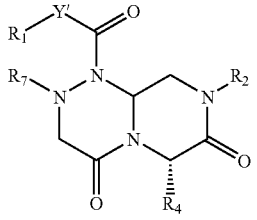
| No | MOLSTRUCTURE | Mol. Weight | M + H (MS) |
|---|---|---|---|
| 1486 | | 538 | 539 |
| 1487 | | 488 | 489 |
| 1488 | | 474 | 475 |

TABLE 2B-continued
THE [4,4,0]REVERSE TURN MIMETICS LIBRARY
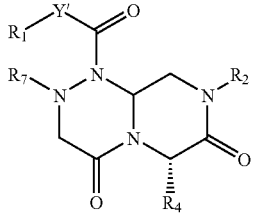
| No | MOLSTRUCTURE | Mol. Weight | M + H (MS) |
|----|--------------|-------------|------------|
| 1489 | | 522 | 523 |
| 1490 | | 488 | 489 |
| 1491 | | 488 | 489 |

TABLE 2B-continued
THE [4,4,0]REVERSE TURN MIMETICS LIBRARY
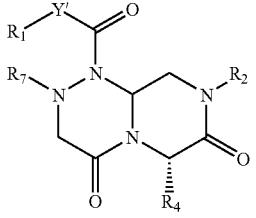
| No | MOLSTRUCTURE | Mol. Weight | M + H (MS) |
|---|---|---|---|
| 1492 | | 506 | 507 |
| 1493 | | 474 | 475 |
| 1494 | | 490 | 491 |

TABLE 2B-continued
THE [4,4,0]REVERSE TURN MIMETICS LIBRARY
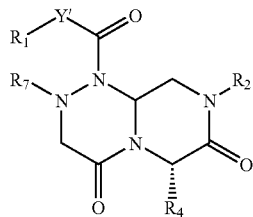
| No | MOLSTRUCTURE | Mol. Weight | M + H (MS) |
|---|---|---|---|
| 1495 | 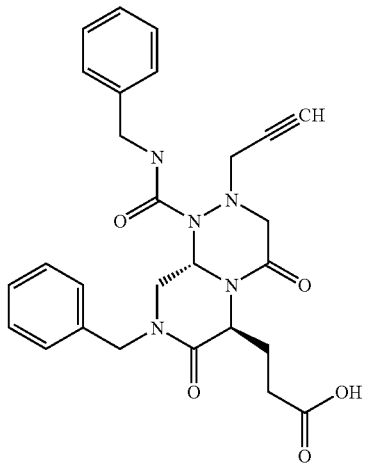 | 504 | 505 |
| 1496 | 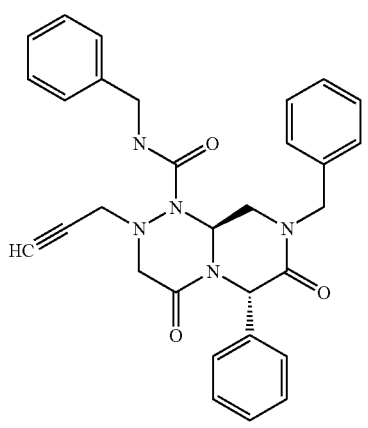 | 508 | 509 |

TABLE 2B-continued
THE [4,4,0]REVERSE TURN MIMETICS LIBRARY
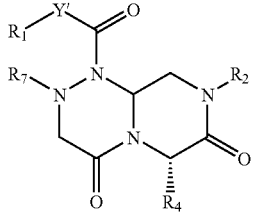
| No | MOLSTRUCTURE | Mol. Weight | M + H (MS) |
|---|---|---|---|
| 1497 | 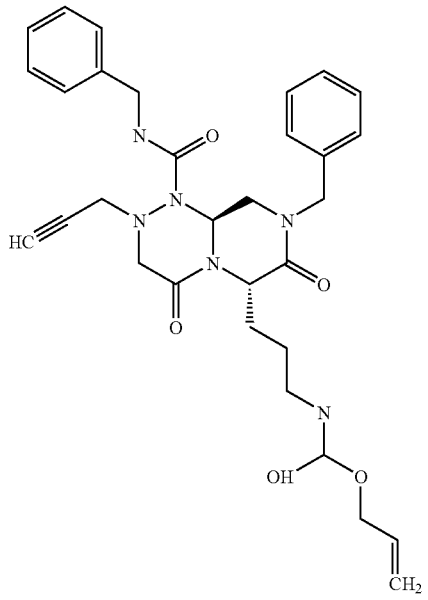 | 573 | 574 |
| 1498 | 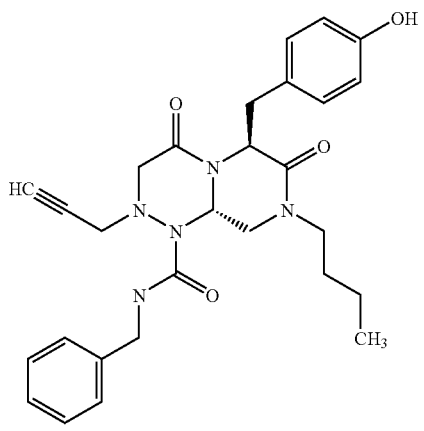 | 504 | 505 |

TABLE 2B-continued
THE [4,4,0]REVERSE TURN MIMETICS LIBRARY
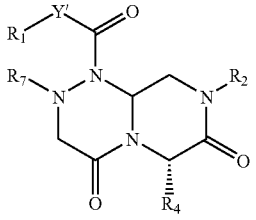
| No | MOLSTRUCTURE | Mol. Weight | M + H (MS) |
|---|---|---|---|
| 1499 | | 454 | 455 |
| 1500 | | 440 | 441 |
| 1501 | | 488 | 489 |

TABLE 2B-continued
THE [4,4,0]REVERSE TURN MIMETICS LIBRARY
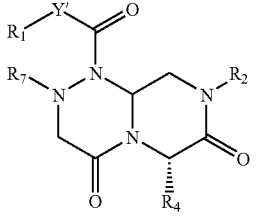
| No | MOLSTRUCTURE | Mol. Weight | M + H (MS) |
|---|---|---|---|
| 1502 | | 454 | 455 |
| 1503 | | 454 | 455 |
| 1504 | | 472 | 473 |

TABLE 2B-continued

THE [4,4,0]REVERSE TURN MIMETICS LIBRARY

| No | MOLSTRUCTURE | Mol. Weight | M + H (MS) |
|---|---|---|---|
| 1505 | | 540 | 441 |
| 1506 | | 456 | 457 |
| 1507 | | 470 | 471 |

TABLE 2B-continued
THE [4,4,0]REVERSE TURN MIMETICS LIBRARY
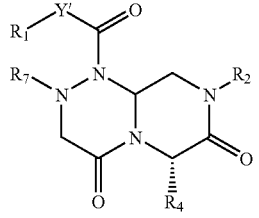
| No | MOLSTRUCTURE | Mol. Weight | M + H (MS) |
|---|---|---|---|
| 1508 | | 474 | 475 |
| 1509 | | 439 | 540 |

TABLE 2B-continued
THE [4,4,0]REVERSE TURN MIMETICS LIBRARY
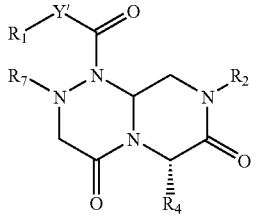
| No | MOLSTRUCTURE | Mol. Weight | M + H (MS) |
|---|---|---|---|
| 1510 | | 428 | 429 |
| 1511 | | 478 | 479 |
| 1512 | | 464 | 465 |

TABLE 2B-continued
THE [4,4,0]REVERSE TURN MIMETICS LIBRARY
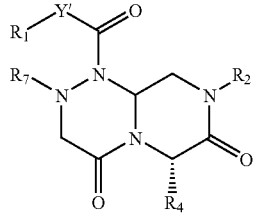
| No | MOLSTRUCTURE | Mol. Weight | M + H (MS) |
|---|---|---|---|
| 1513 | | 512 | 513 |
| 1514 | | 478 | 479 |
| 1515 | | 478 | 479 |

TABLE 2B-continued
THE [4,4,0]REVERSE TURN MIMETICS LIBRARY
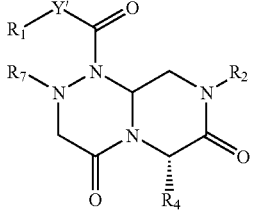
| No | MOLSTRUCTURE | Mol. Weight | M + H (MS) |
|---|---|---|---|
| 1516 | | 496 | 497 |
| 1517 | | 464 | 465 |
| 1518 | | 479 | 580 |

TABLE 2B-continued
THE [4,4,0]REVERSE TURN MIMETICS LIBRARY
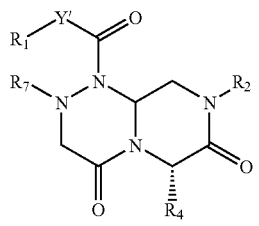
| No | MOLSTRUCTURE | Mol. Weight | M + H (MS) |
|---|---|---|---|
| 1519 | 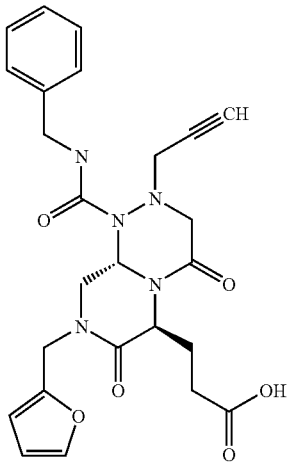 | 494 | 495 |
| 1520 | 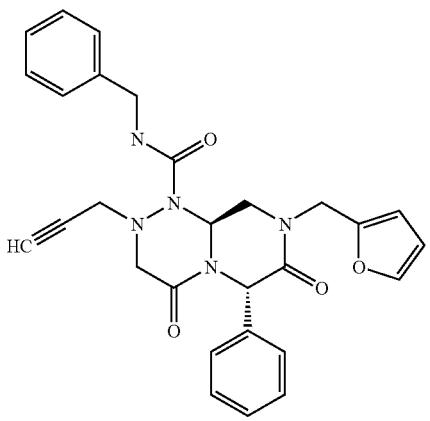 | 498 | 499 |

TABLE 2B-continued
THE [4,4,0]REVERSE TURN MIMETICS LIBRARY
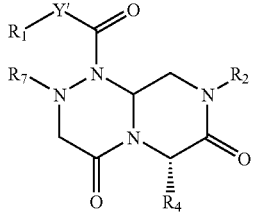
| No | MOLSTRUCTURE | Mol. Weight | M + H (MS) |
|---|---|---|---|
| 1521 | 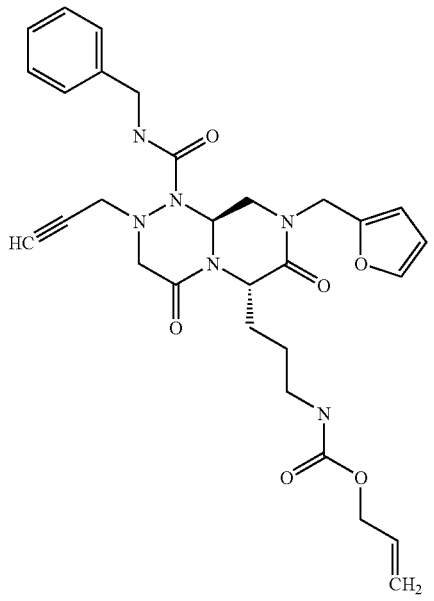 | 463 | 564 |
| 1522 | 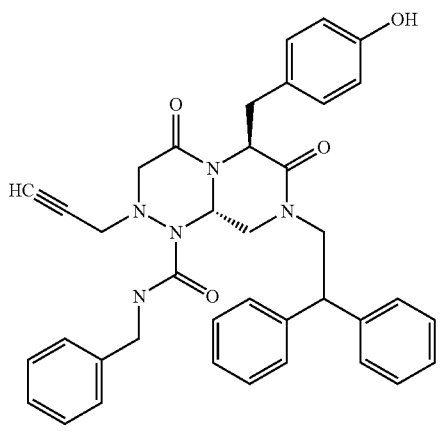 | 628 | 629 |

TABLE 2B-continued
THE [4,4,0]REVERSE TURN MIMETICS LIBRARY
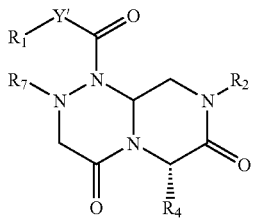
| No | MOLSTRUCTURE | Mol. Weight | M + H (MS) |
|---|---|---|---|
| 1523 | | 578 | 579 |
| 1524 | | 564 | 565 |
| 1525 | | 612 | 613 |

TABLE 2B-continued
THE [4,4,0]REVERSE TURN MIMETICS LIBRARY
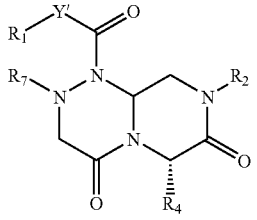
| No | MOLSTRUCTURE | Mol. Weight | M + H (MS) |
|---|---|---|---|
| 1526 | | 578 | 579 |
| 1527 | | 578 | 579 |
| 1528 | | 596 | 597 |

TABLE 2B-continued
THE [4,4,0]REVERSE TURN MIMETICS LIBRARY

| No | MOLSTRUCTURE | Mol. Weight | M + H (MS) |
|---|---|---|---|
| 1529 | | 564 | 565 |
| 1530 | | 580 | 581 |
| 1531 | | 594 | 595 |

TABLE 2B-continued

THE [4,4,0]REVERSE TURN MIMETICS LIBRARY

| No | MOLSTRUCTURE | Mol. Weight | M + H (MS) |
|---|---|---|---|
| 1532 | | 598 | 599 |
| 1533 | | 663 | 664 |
| 1534 | | 607 | 608 |

TABLE 2B-continued
THE [4,4,0]REVERSE TURN MIMETICS LIBRARY
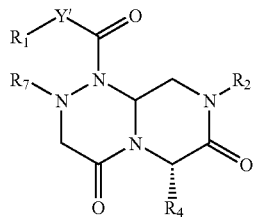
| No | MOLSTRUCTURE | Mol. Weight | M + H (MS) |
|---|---|---|---|
| 1535 | | 556 | 557 |
| 1536 | | 642 | 643 |
| 1537 | | 591 | 592 |

TABLE 2B-continued

THE [4,4,0]REVERSE TURN MIMETICS LIBRARY

| No | MOLSTRUCTURE | Mol. Weight | M + H (MS) |
|---|---|---|---|
| 1538 | | 556 | 557 |
| 1539 | | 556 | 557 |
| 1540 | | 575 | 576 |

TABLE 2B-continued

THE [4,4,0]REVERSE TURN MIMETICS LIBRARY

| No | MOLSTRUCTURE | Mol. Weight | M + H (MS) |
|---|---|---|---|
| 1541 | | 542 | 543 |
| 1542 | | 558 | 559 |
| 1543 | | 572 | 573 |

TABLE 2B-continued
THE [4,4,0]REVERSE TURN MIMETICS LIBRARY
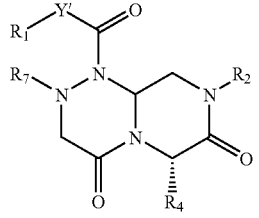
| No | MOLSTRUCTURE | Mol. Weight | M + H (MS) |
|---|---|---|---|
| 1544 | | 576 | 577 |
| 1545 | | 642 | 643 |

TABLE 2B-continued
THE [4,4,0]REVERSE TURN MIMETICS LIBRARY
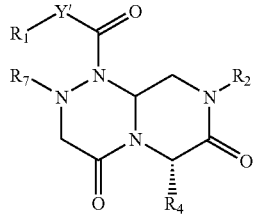
| No | MOLSTRUCTURE | Mol. Weight | M + H (MS) |
|---|---|---|---|
| 1546 | | 506 | 507 |
| 1547 | | 456 | 457 |
| 1548 | | 442 | 443 |

TABLE 2B-continued
THE [4,4,0]REVERSE TURN MIMETICS LIBRARY
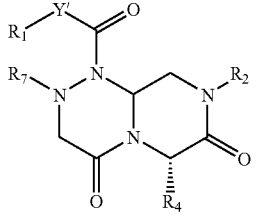
| No | MOLSTRUCTURE | Mol. Weight | M + H (MS) |
|---|---|---|---|
| 1549 | | 490 | 491 |
| 1550 | | 456 | 457 |
| 1551 | | 456 | 457 |

TABLE 2B-continued
THE [4,4,0]REVERSE TURN MIMETICS LIBRARY
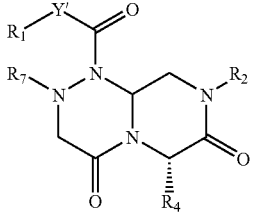
| No | MOLSTRUCTURE | Mol. Weight | M + H (MS) |
|---|---|---|---|
| 1552 | | 474 | 475 |
| 1553 | | 442 | 443 |
| 1554 | | 457 | 458 |

TABLE 2B-continued
THE [4,4,0]REVERSE TURN MIMETICS LIBRARY
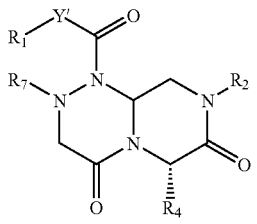
| No | MOLSTRUCTURE | Mol. Weight | M + H (MS) |
|---|---|---|---|
| 1555 | 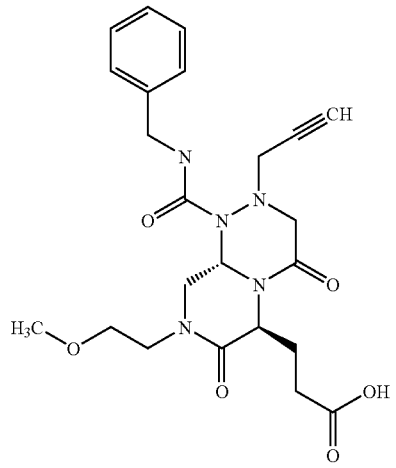 | 472 | 473 |
| 1556 | 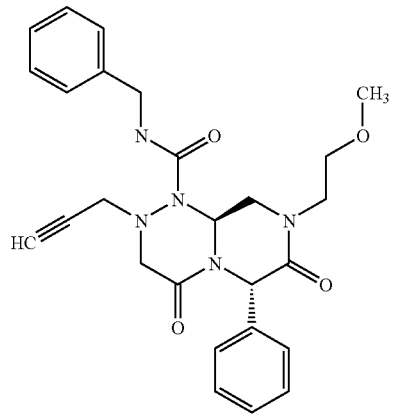 | 476 | 477 |

TABLE 2B-continued
THE [4,4,0]REVERSE TURN MIMETICS LIBRARY
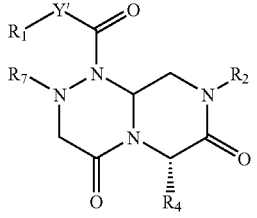
| No | MOLSTRUCTURE | Mol. Weight | M + H (MS) |
|---|---|---|---|
| 1557 | | 541 | 542 |
| 1558 | | 552 | 553 |

TABLE 2B-continued
THE [4,4,0]REVERSE TURN MIMETICS LIBRARY
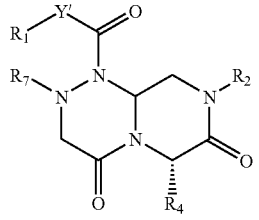
| No | MOLSTRUCTURE | Mol. Weight | M + H (MS) |
|---|---|---|---|
| 1559 | | 502 | 503 |
| 1560 | | 488 | 489 |
| 1561 | | 536 | 437 |

TABLE 2B-continued

THE [4,4,0]REVERSE TURN MIMETICS LIBRARY

| No | MOLSTRUCTURE | Mol. Weight | M + H (MS) |
|---|---|---|---|
| 1562 | | 502 | 503 |
| 1563 | | 502 | 503 |
| 1564 | | 520 | 521 |

TABLE 2B-continued
THE [4,4,0]REVERSE TURN MIMETICS LIBRARY
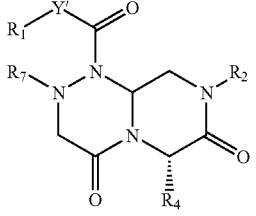
| No | MOLSTRUCTURE | Mol. Weight | M + H (MS) |
|---|---|---|---|
| 1565 | | 488 | 489 |
| 1566 | | 504 | 505 |
| 1567 | | 518 | 419 |

TABLE 2B-continued
THE [4,4,0]REVERSE TURN MIMETICS LIBRARY
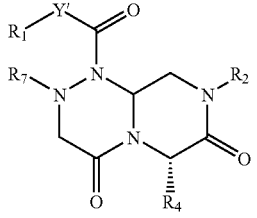
| No | MOLSTRUCTURE | Mol. Weight | M + H (MS) |
|---|---|---|---|
| 1568 | | 522 | 523 |
| 1569 | | 587 | 588 |

TABLE 2B-continued
THE [4,4,0]REVERSE TURN MIMETICS LIBRARY
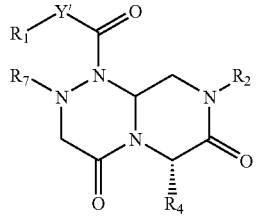
| No | MOLSTRUCTURE | Mol. Weight | M + H (MS) |
|---|---|---|---|
| 1570 | | 572 | 573 |
| 1571 | | 422 | 423 |
| 1572 | | 508 | 509 |

TABLE 2B-continued
THE [4,4,0]REVERSE TURN MIMETICS LIBRARY
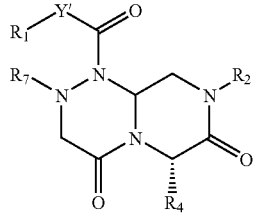
| No | MOLSTRUCTURE | Mol. Weight | M + H (MS) |
|----|--------------|-------------|------------|
| 1573 | | 556 | 557 |
| 1574 | | 522 | 523 |
| 1575 | | 522 | 523 |

TABLE 2B-continued

THE [4,4,0]REVERSE TURN MIMETICS LIBRARY

| No | MOLSTRUCTURE | Mol. Weight | M + H (MS) |
|---|---|---|---|
| 1576 | | 540 | 541 |
| 1577 | | 508 | 509 |
| 1578 | | 524 | 525 |

TABLE 2B-continued
THE [4,4,0]REVERSE TURN MIMETICS LIBRARY
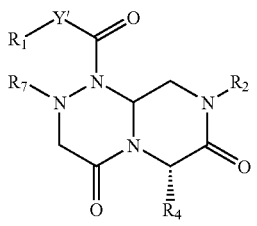
| No | MOLSTRUCTURE | Mol. Weight | M + H (MS) |
|---|---|---|---|
| 1579 | 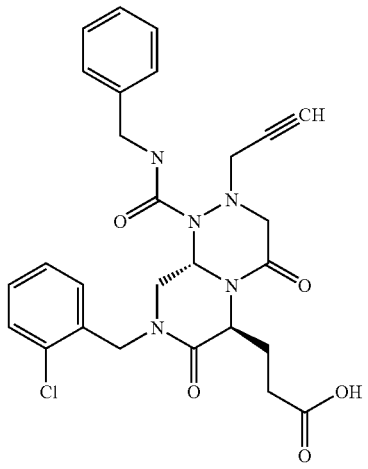 | 438 | 539 |
| 1580 | 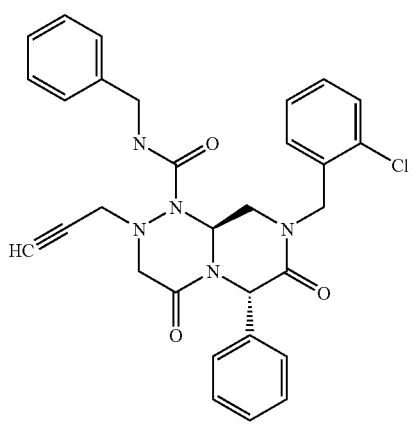 | 542 | 543 |

TABLE 2B-continued
THE [4,4,0]REVERSE TURN MIMETICS LIBRARY
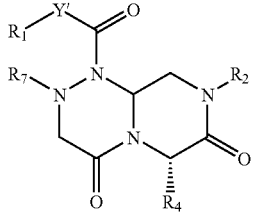
| No | MOLSTRUCTURE | Mol. Weight | M + H (MS) |
|----|--------------|-------------|------------|
| 1581 | | 607 | 608 |
| 1582 | | 607 | 608 |

TABLE 2B-continued
THE [4,4,0]REVERSE TURN MIMETICS LIBRARY
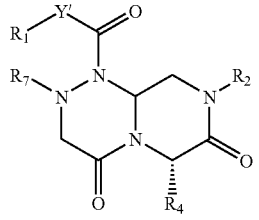
| No | MOLSTRUCTURE | Mol. Weight | M + H (MS) |
|---|---|---|---|
| 1583 | | 556 | 557 |
| 1584 | | 542 | 543 |
| 1585 | | 591 | 592 |

TABLE 2B-continued
THE [4,4,0]REVERSE TURN MIMETICS LIBRARY
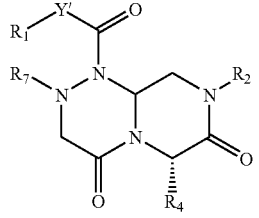
| No | MOLSTRUCTURE | Mol. Weight | M + H (MS) |
|---|---|---|---|
| 1586 | | 556 | 557 |
| 1587 | | 556 | 557 |
| 1588 | | 575 | 576 |

TABLE 2B-continued

THE [4,4,0]REVERSE TURN MIMETICS LIBRARY

| No | MOLSTRUCTURE | Mol. Weight | M + H (MS) |
|---|---|---|---|
| 1589 | | 542 | 543 |
| 1590 | | 558 | 559 |
| 1591 | | 572 | 573 |

TABLE 2B-continued
THE [4,4,0]REVERSE TURN MIMETICS LIBRARY
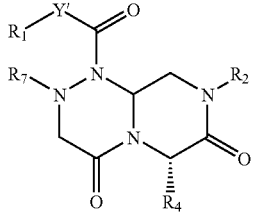
| No | MOLSTRUCTURE | Mol. Weight | M + H (MS) |
|---|---|---|---|
| 1592 | | 576 | 557 |
| 1593 | | 642 | 643 |

TABLE 2B-continued
THE [4,4,0]REVERSE TURN MIMETICS LIBRARY
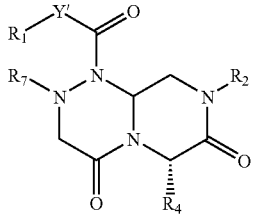
| No | MOLSTRUCTURE | Mol. Weight | M + H (MS) |
|---|---|---|---|
| 1594 | | 552 | 553 |
| 1595 | | 502 | 503 |
| 1596 | | 488 | 589 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 1597 | | 536 | 537 |
| 1598 | | 502 | 503 |
| 1599 | | 502 | 503 |

TABLE 2B-continued

THE [4,4,0]REVERSE TURN MIMETICS LIBRARY

| No | MOLSTRUCTURE | Mol. Weight | M + H (MS) |
|---|---|---|---|
| 1600 | | 520 | 521 |
| 1601 | | 488 | 489 |
| 1602 | | 504 | 505 |

TABLE 2B-continued
THE [4,4,0]REVERSE TURN MIMETICS LIBRARY
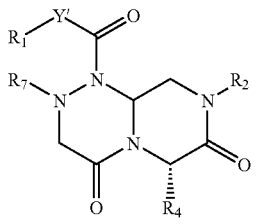
| No | MOLSTRUCTURE | Mol. Weight | M + H (MS) |
|----|--------------|-------------|------------|
| 1603 | 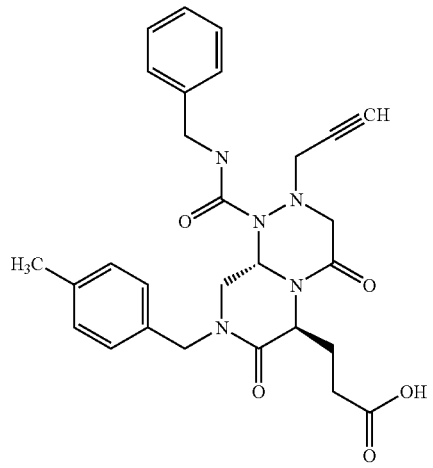 | 518 | 519 |
| 1604 | 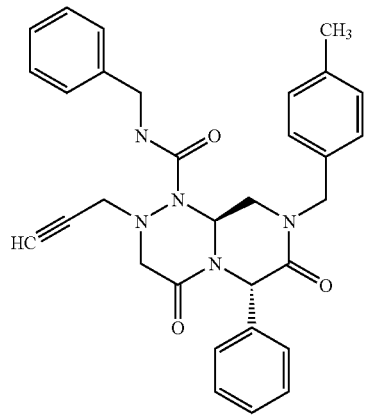 | 422 | 523 |

TABLE 2B-continued
THE [4,4,0]REVERSE TURN MIMETICS LIBRARY
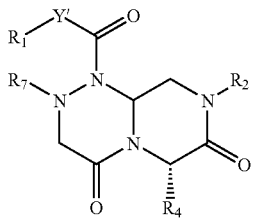
| No | MOLSTRUCTURE | Mol. Weight | M + H (MS) |
|---|---|---|---|
| 1605 | | 587 | 588 |
| 1606 | 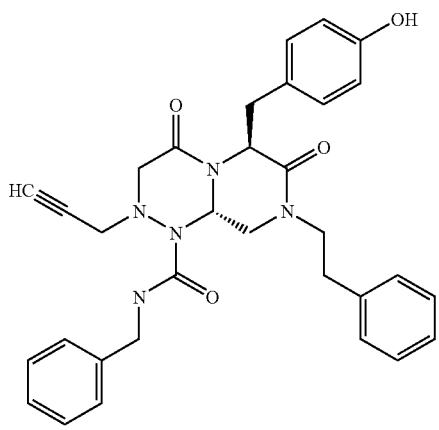 | 552 | 553 |

TABLE 2B-continued
THE [4,4,0]REVERSE TURN MIMETICS LIBRARY
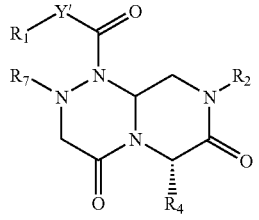
| No | MOLSTRUCTURE | Mol. Weight | M + H (MS) |
|---|---|---|---|
| 1607 | | 502 | 503 |
| 1608 | | 488 | 489 |
| 1609 | | 536 | 537 |

TABLE 2B-continued
THE [4,4,0]REVERSE TURN MIMETICS LIBRARY
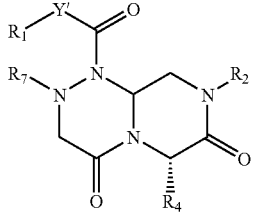
| No | MOLSTRUCTURE | Mol. Weight | M + H (MS) |
|---|---|---|---|
| 1610 | | 502 | 503 |
| 1611 | | 502 | 503 |
| 1612 | | 520 | 521 |

TABLE 2B-continued

THE [4,4,0]REVERSE TURN MIMETICS LIBRARY

| No | MOLSTRUCTURE | Mol. Weight | M + H (MS) |
|---|---|---|---|
| 1613 | | 488 | 489 |
| 1614 | | 504 | 505 |
| 1615 | | 518 | 519 |

TABLE 2B-continued
THE [4,4,0]REVERSE TURN MIMETICS LIBRARY
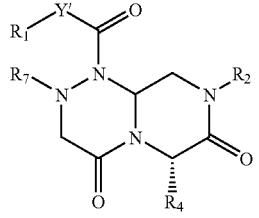
| No | MOLSTRUCTURE | Mol. Weight | M + H (MS) |
|---|---|---|---|
| 1616 | | 522 | 523 |
| 1617 | | 587 | 588 |

TABLE 2B-continued
THE [4,4,0]REVERSE TURN MIMETICS LIBRARY
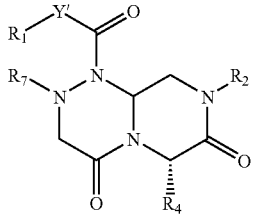
| No | MOLSTRUCTURE | Mol. Weight | M + H (MS) |
|---|---|---|---|
| 1618 | | 480 | 481 |
| 1619 | | 530 | 531 |
| 1620 | | 516 | 517 |

TABLE 2B-continued
THE [4,4,0]REVERSE TURN MIMETICS LIBRARY
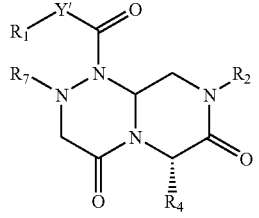
| No | MOLSTRUCTURE | Mol. Weight | M + H (MS) |
|---|---|---|---|
| 1621 | | 564 | 565 |
| 1622 | | 530 | 531 |
| 1623 | | 530 | 531 |

TABLE 2B-continued
THE [4,4,0]REVERSE TURN MIMETICS LIBRARY
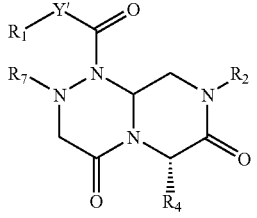
| No | MOLSTRUCTURE | Mol. Weight | M + H (MS) |
|----|--------------|-------------|------------|
| 1624 | | 548 | 549 |
| 1625 | | 516 | 517 |
| 1626 | | 532 | 533 |

TABLE 2B-continued
THE [4,4,0]REVERSE TURN MIMETICS LIBRARY
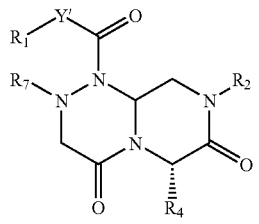
| No | MOLSTRUCTURE | Mol. Weight | M + H (MS) |
|----|--------------|-------------|------------|
| 1627 | 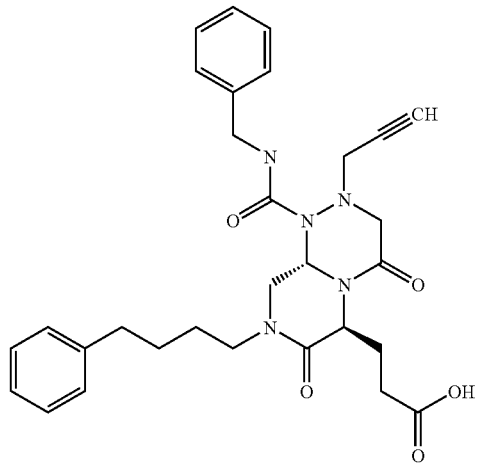 | 546 | 547 |
| 1628 | 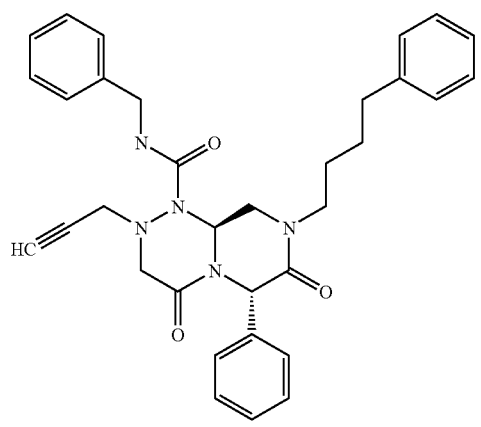 | 550 | 551 |

TABLE 2B-continued
THE [4,4,0]REVERSE TURN MIMETICS LIBRARY
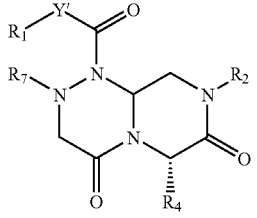
| No | MOLSTRUCTURE | Mol. Weight | M + H (MS) |
|---|---|---|---|
| 1629 | | 615 | 616 |
| 1630 | | 552 | 553 |

TABLE 2B-continued
THE [4,4,0]REVERSE TURN MIMETICS LIBRARY
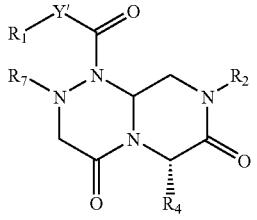
| No | MOLSTRUCTURE | Mol. Weight | M + H (MS) |
|---|---|---|---|
| 1631 | | 502 | 503 |
| 1632 | | 488 | 489 |
| 1633 | | 536 | 537 |

TABLE 2B-continued

THE [4,4,0]REVERSE TURN MIMETICS LIBRARY

| No | MOLSTRUCTURE | Mol. Weight | M + H (MS) |
|---|---|---|---|
| 1634 | | 502 | 503 |
| 1635 | | 502 | 503 |
| 1636 | | 520 | 521 |

TABLE 2B-continued

THE [4,4,0]REVERSE TURN MIMETICS LIBRARY

| No | MOLSTRUCTURE | Mol. Weight | M + H (MS) |
|---|---|---|---|
| 1637 | | 488 | 489 |
| 1638 | | 504 | 505 |
| 1639 | | 518 | 519 |

TABLE 2B-continued
THE [4,4,0]REVERSE TURN MIMETICS LIBRARY
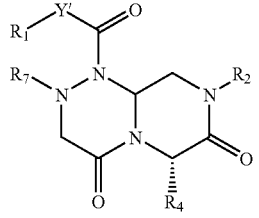
| No | MOLSTRUCTURE | Mol. Weight | M + H (MS) |
|---|---|---|---|
| 1640 | 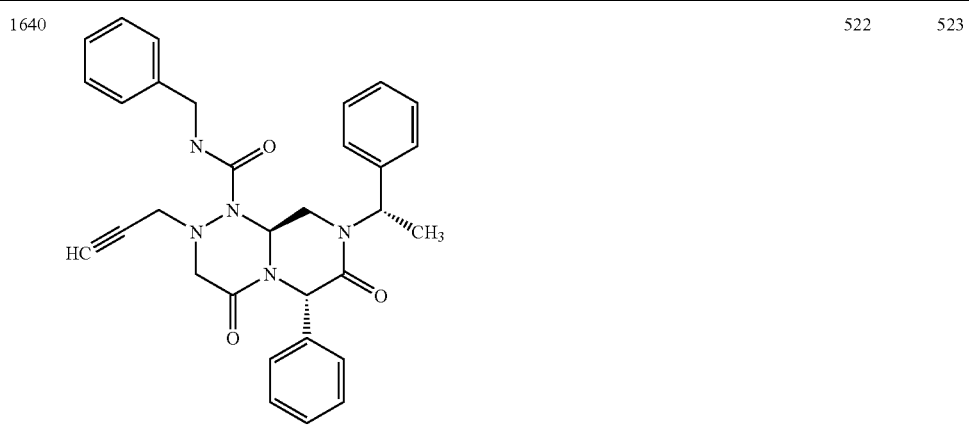 | 522 | 523 |
| 1641 | 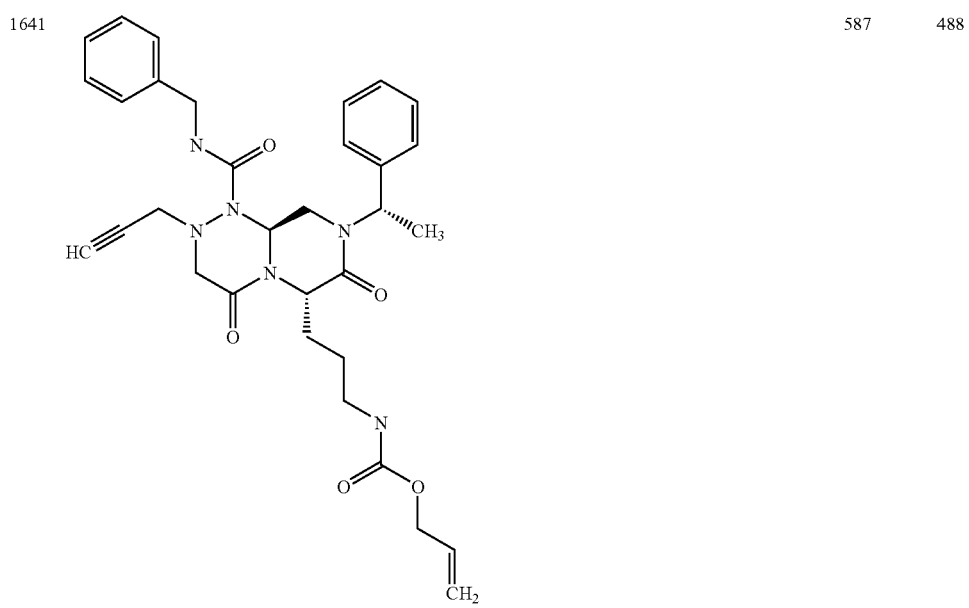 | 587 | 488 |

TABLE 2B-continued
THE [4,4,0]REVERSE TURN MIMETICS LIBRARY
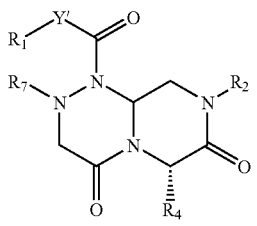
| No | MOLSTRUCTURE | Mol. Weight | M + H (MS) |
|---|---|---|---|
| 1642 | | 570 | 571 |
| 1643 | | 520 | 521 |
| 1644 | | 506 | 507 |

TABLE 2B-continued
THE [4,4,0]REVERSE TURN MIMETICS LIBRARY
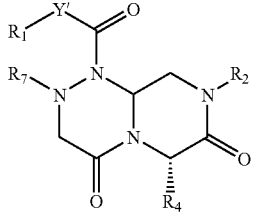
| No | MOLSTRUCTURE | Mol. Weight | M + H (MS) |
|---|---|---|---|
| 1645 | | 554 | 555 |
| 1646 | | 520 | 421 |
| 1647 | | 520 | 521 |

TABLE 2B-continued

THE [4,4,0]REVERSE TURN MIMETICS LIBRARY

| No | MOLSTRUCTURE | Mol. Weight | M + H (MS) |
|---|---|---|---|
| 1648 | | 538 | 539 |
| 1649 | | 506 | 507 |
| 1650 | | 522 | 523 |

TABLE 2B-continued
THE [4,4,0]REVERSE TURN MIMETICS LIBRARY
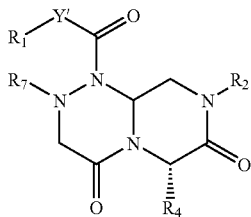
| No | MOLSTRUCTURE | Mol. Weight | M + H (MS) |
|----|--------------|-------------|------------|
| 1651 | 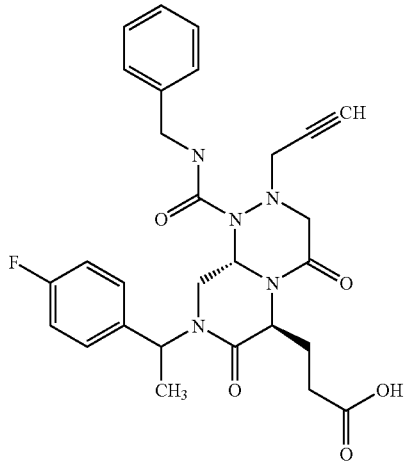 | 536 | 537 |
| 1652 | 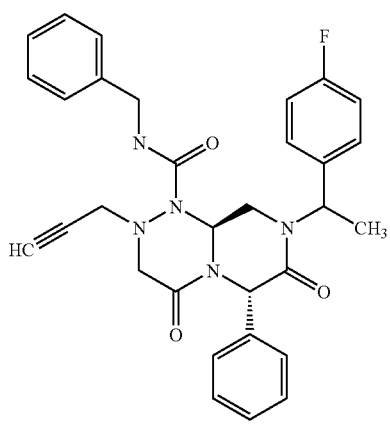 | 540 | 541 |

TABLE 2B-continued
THE [4,4,0]REVERSE TURN MIMETICS LIBRARY
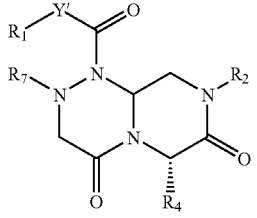
| No | MOLSTRUCTURE | Mol. Weight | M + H (MS) |
|---|---|---|---|
| 1653 | | 605 | 606 |
| 1654 | | 570 | 571 |

TABLE 2B-continued
THE [4,4,0]REVERSE TURN MIMETICS LIBRARY
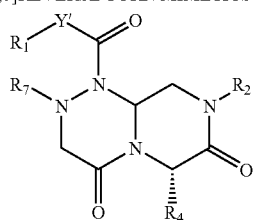
| No | MOLSTRUCTURE | Mol. Weight | M + H (MS) |
|---|---|---|---|
| 1655 | | 520 | 521 |
| 1656 | | 506 | 555 |
| 1657 | | 554 | 555 |

TABLE 2B-continued
THE [4,4,0]REVERSE TURN MIMETICS LIBRARY
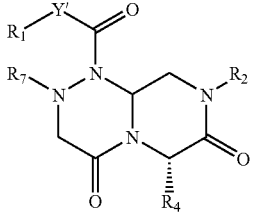
| No | MOLSTRUCTURE | Mol. Weight | M + H (MS) |
|---|---|---|---|
| 1658 | | 520 | 521 |
| 1659 | | 520 | 521 |
| 1660 | | 538 | 539 |

TABLE 2B-continued
THE [4,4,0]REVERSE TURN MIMETICS LIBRARY
| No | MOLSTRUCTURE | Mol. Weight | M + H (MS) |
|---|---|---|---|
| 1661 | 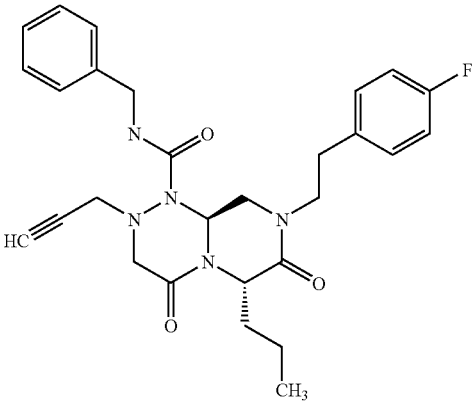 | 506 | 507 |
| 1662 | 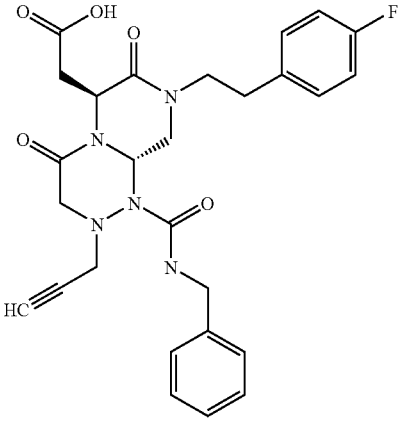 | 522 | 523 |
| 1663 | 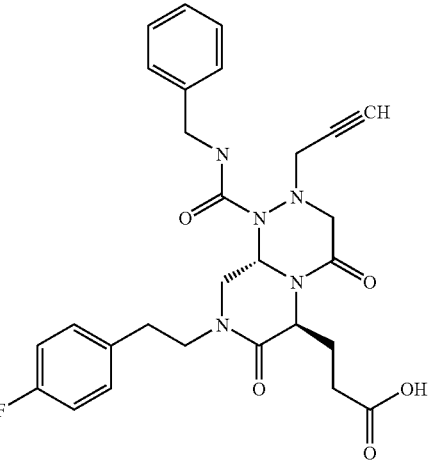 | 536 | 537 |

TABLE 2B-continued
THE [4,4,0]REVERSE TURN MIMETICS LIBRARY
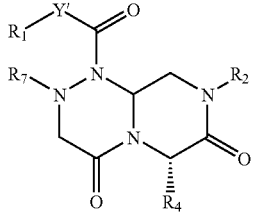
| No | MOLSTRUCTURE | Mol. Weight | M + H (MS) |
|---|---|---|---|
| 1664 | | 640 | 541 |
| 1665 | | 605 | 506 |

TABLE 2B-continued
THE [4,4,0]REVERSE TURN MIMETICS LIBRARY
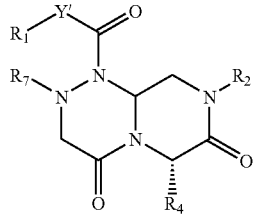
| No | MOLSTRUCTURE | Mol. Weight | M + H (MS) |
|----|--------------|-------------|------------|
| 1666 | | 588 | 589 |
| 1667 | | 538 | 539 |
| 1668 | | 524 | 525 |

TABLE 2B-continued

THE [4,4,0]REVERSE TURN MIMETICS LIBRARY

| No | MOLSTRUCTURE | Mol. Weight | M + H (MS) |
|---|---|---|---|
| 1669 | | 572 | 573 |
| 1670 | | 538 | 539 |
| 1671 | | 536 | 538 |

TABLE 2B-continued

THE [4,4,0]REVERSE TURN MIMETICS LIBRARY

| No | MOLSTRUCTURE | Mol. Weight | M + H (MS) |
|---|---|---|---|
| 1672 | | 556 | 557 |
| 1673 | | 524 | 525 |
| 1674 | | 540 | 541 |

TABLE 2B-continued
THE [4,4,0]REVERSE TURN MIMETICS LIBRARY
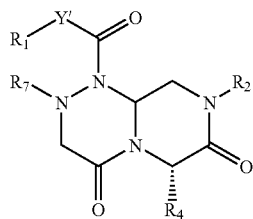
| No | MOLSTRUCTURE | Mol. Weight | M + H (MS) |
|---|---|---|---|
| 1675 | 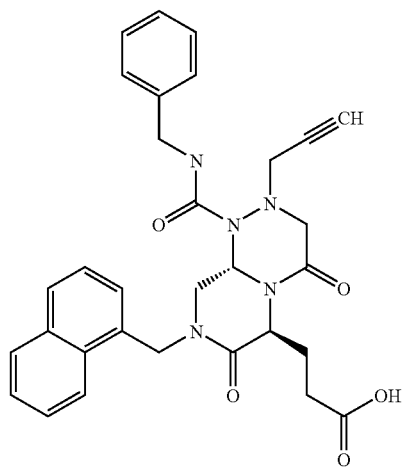 | 554 | 555 |
| 1676 | 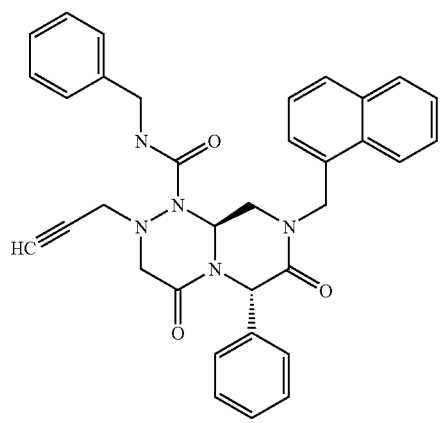 | 558 | 559 |

TABLE 2B-continued
THE [4,4,0]REVERSE TURN MIMETICS LIBRARY
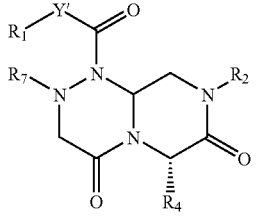
| No | MOLSTRUCTURE | Mol. Weight | M + H (MS) |
|---|---|---|---|
| 1677 | | 623 | 624 |
| 1678 | | 544 | 545 |

TABLE 2B-continued
THE [4,4,0]REVERSE TURN MIMETICS LIBRARY
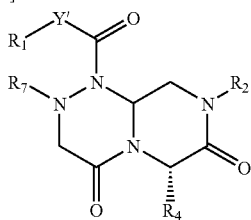
| No | MOLSTRUCTURE | Mol. Weight | M + H (MS) |
|---|---|---|---|
| 1679 | | 594 | 595 |
| 1680 | | 580 | 541 |
| 1681 | | 528 | 529 |

TABLE 2B-continued

THE [4,4,0]REVERSE TURN MIMETICS LIBRARY

| No | MOLSTRUCTURE | Mol. Weight | M + H (MS) |
|---|---|---|---|
| 1682 | | 494 | 495 |
| 1683 | | 494 | 495 |
| 1684 | | 512 | 513 |

TABLE 2B-continued

THE [4,4,0]REVERSE TURN MIMETICS LIBRARY

| No | MOLSTRUCTURE | Mol. Weight | M + H (MS) |
|---|---|---|---|
| 1685 | | 480 | 481 |
| 1686 | | 496 | 497 |
| 1687 | | 510 | 511 |

TABLE 2B-continued
THE [4,4,0]REVERSE TURN MIMETICS LIBRARY
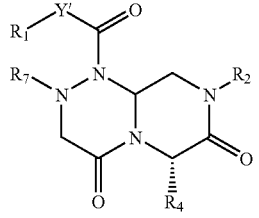
| No | MOLSTRUCTURE | Mol. Weight | M + H (MS) |
|---|---|---|---|
| 1688 | | 514 | 515 |
| 1689 | | 579 | 580 |

TABLE 2B-continued
THE [4,4,0]REVERSE TURN MIMETICS LIBRARY
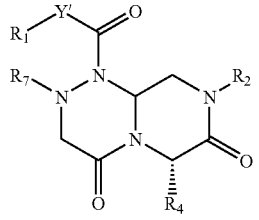
| No | MOLSTRUCTURE | Mol. Weight | M + H (MS) |
|---|---|---|---|
| 1690 | | 566 | 567 |
| 1691 | | 516 | 417 |
| 1692 | | 502 | 503 |

TABLE 2B-continued
THE [4,4,0]REVERSE TURN MIMETICS LIBRARY
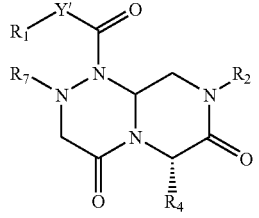
| No | MOLSTRUCTURE | Mol. Weight | M + H (MS) |
|---|---|---|---|
| 1693 | | 550 | 551 |
| 1694 | | 516 | 417 |
| 1695 | | 516 | 417 |

TABLE 2B-continued
THE [4,4,0]REVERSE TURN MIMETICS LIBRARY
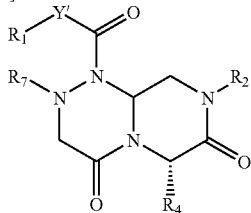
| No | MOLSTRUCTURE | Mol. Weight | M + H (MS) |
|---|---|---|---|
| 1696 | | 534 | 535 |
| 1697 | | 502 | 503 |
| 1698 | | 518 | 519 |

TABLE 2B-continued
THE [4,4,0]REVERSE TURN MIMETICS LIBRARY
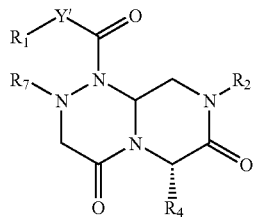
| No | MOLSTRUCTURE | Mol. Weight | M + H (MS) |
|---|---|---|---|
| 1699 | 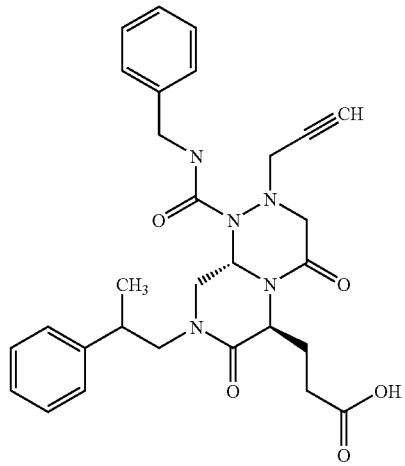 | 532 | 533 |
| 1700 | 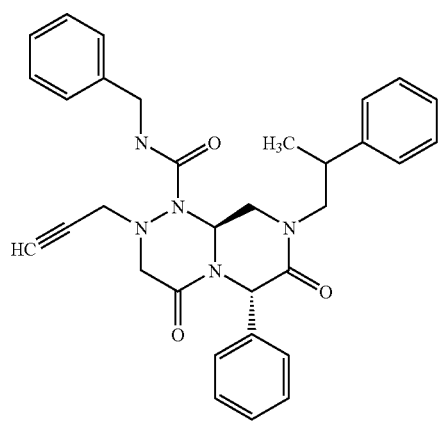 | 536 | 537 |

TABLE 2B-continued
THE [4,4,0]REVERSE TURN MIMETICS LIBRARY
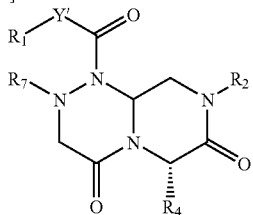
| No | MOLSTRUCTURE | Mol. Weight | M + H (MS) |
|---|---|---|---|
| 1701 | 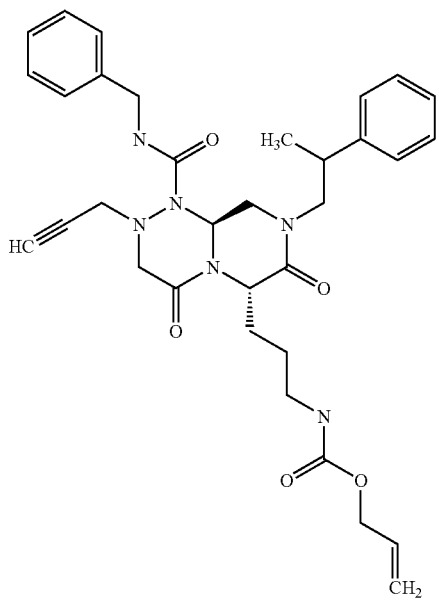 | 301 | 602 |
| 1702 | 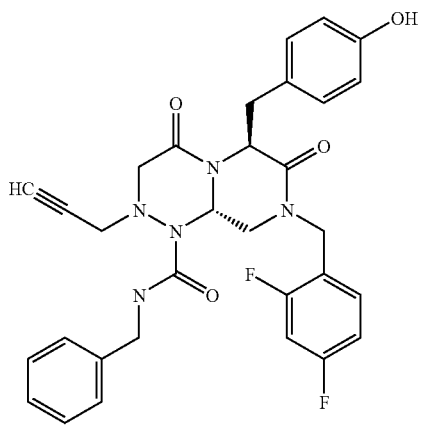 | 574 | 575 |

TABLE 2B-continued
THE [4,4,0]REVERSE TURN MIMETICS LIBRARY
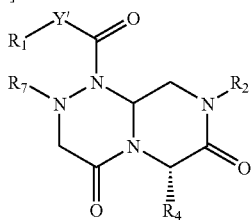
| No | MOLSTRUCTURE | Mol. Weight | M + H (MS) |
|---|---|---|---|
| 1703 | | 524 | 525 |
| 1704 | | 510 | 511 |
| 1705 | | 558 | 559 |

TABLE 2B-continued

THE [4,4,0]REVERSE TURN MIMETICS LIBRARY

| No | MOLSTRUCTURE | Mol. Weight | M + H (MS) |
|---|---|---|---|
| 1706 | | 524 | 525 |
| 1707 | | 524 | 525 |
| 1708 | | 542 | 543 |

TABLE 2B-continued
THE [4,4,0]REVERSE TURN MIMETICS LIBRARY
| No | MOLSTRUCTURE | Mol. Weight | M + H (MS) |
|----|--------------|-------------|------------|
| 1709 | 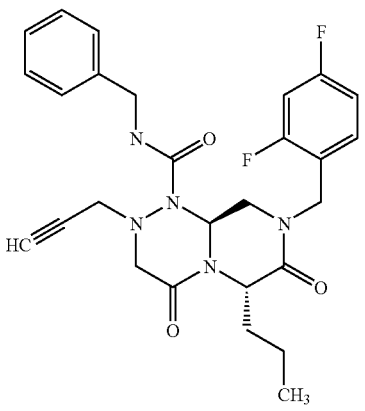 | 510 | 511 |
| 1710 | 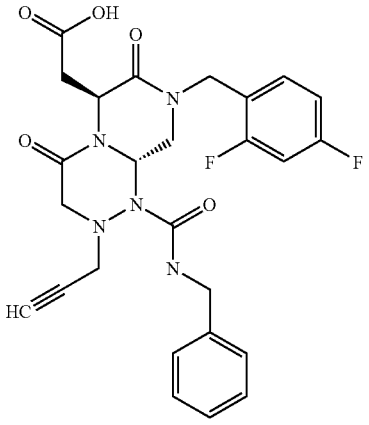 | 526 | 527 |
| 1711 | 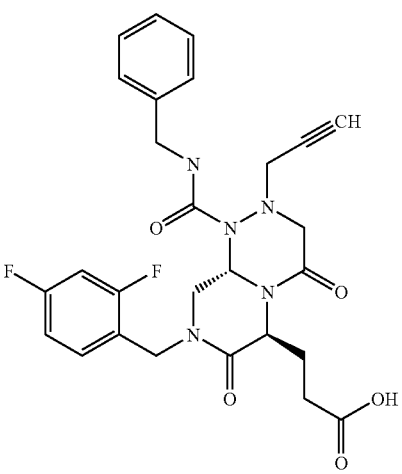 | 540 | 541 |

TABLE 2B-continued
THE [4,4,0]REVERSE TURN MIMETICS LIBRARY
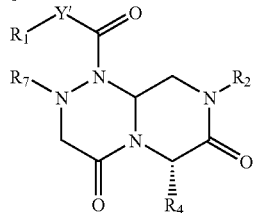
| No | MOLSTRUCTURE | Mol. Weight | M + H (MS) |
|---|---|---|---|
| 1712 | | 544 | 645 |
| 1713 | | 609 | 610 |

TABLE 2B-continued
THE [4,4,0]REVERSE TURN MIMETICS LIBRARY
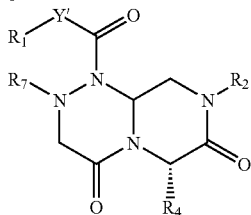
| No | MOLSTRUCTURE | Mol. Weight | M + H (MS) |
|---|---|---|---|
| 1714 | | 612 | 613 |
| 1715 | | 562 | 563 |
| 1716 | | 548 | 579 |

TABLE 2B-continued
THE [4,4,0]REVERSE TURN MIMETICS LIBRARY
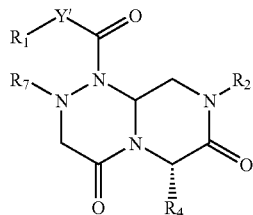
| No | MOLSTRUCTURE | Mol. Weight | M + H (MS) |
|---|---|---|---|
| 1717 | | 596 | 597 |
| 1718 | | 562 | 597 |
| 1719 | | 562 | 563 |

TABLE 2B-continued
THE [4,4,0]REVERSE TURN MIMETICS LIBRARY
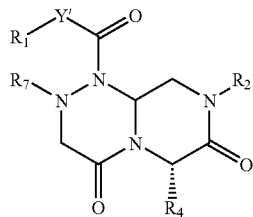
| No | MOLSTRUCTURE | Mol. Weight | M + H (MS) |
|----|--------------|-------------|------------|
| 1720 | | 580 | 581 |
| 1721 | | 548 | 549 |
| 1722 | | 564 | 565 |

TABLE 2B-continued
THE [4,4,0]REVERSE TURN MIMETICS LIBRARY
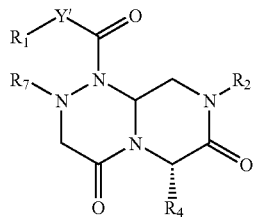
| No | MOLSTRUCTURE | Mol. Weight | M + H (MS) |
|---|---|---|---|
| 1723 | 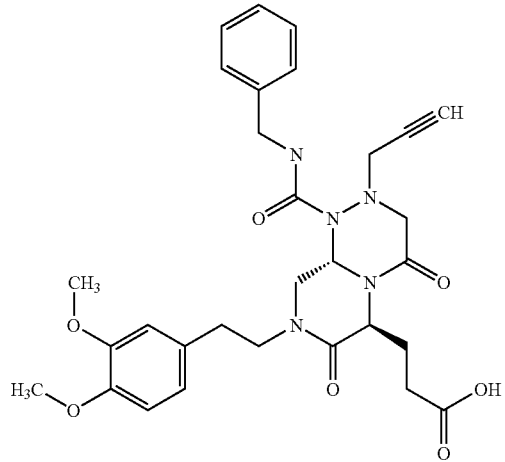 | 578 | 579 |
| 1724 | 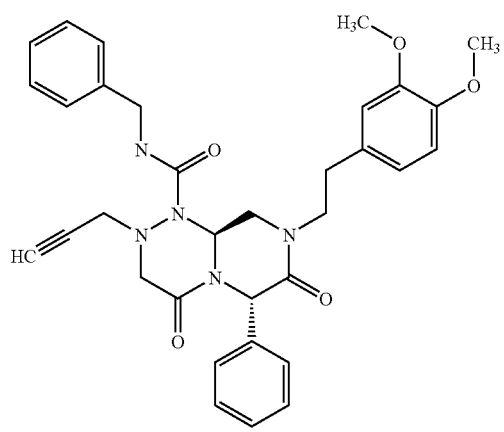 | 582 | 583 |

TABLE 2B-continued
THE [4,4,0]REVERSE TURN MIMETICS LIBRARY
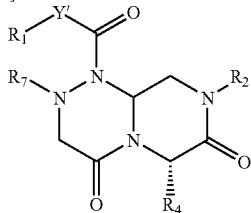
| No | MOLSTRUCTURE | Mol. Weight | M + H (MS) |
|---|---|---|---|
| 1725 | | 647 | 648 |
| 1726 | | 532 | 533 |

TABLE 2B-continued
THE [4,4,0]REVERSE TURN MIMETICS LIBRARY
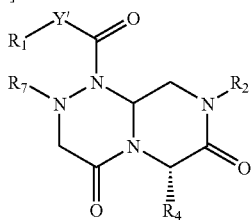
| No | MOLSTRUCTURE | Mol. Weight | M + H (MS) |
|---|---|---|---|
| 1727 | | 482 | 483 |
| 1728 | | 468 | 469 |
| 1729 | | 516 | 517 |

TABLE 2B-continued
THE [4,4,0]REVERSE TURN MIMETICS LIBRARY
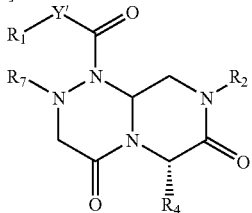
| No | MOLSTRUCTURE | Mol. Weight | M + H (MS) |
|---|---|---|---|
| 1730 | | 482 | 483 |
| 1731 | | 482 | 483 |
| 1732 | | 500 | 501 |

TABLE 2B-continued
THE [4,4,0]REVERSE TURN MIMETICS LIBRARY
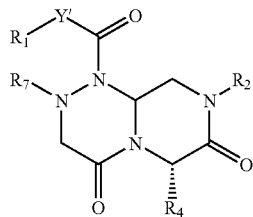
| No | MOLSTRUCTURE | Mol. Weight | M + H (MS) |
|----|--------------|-------------|------------|
| 1723 | 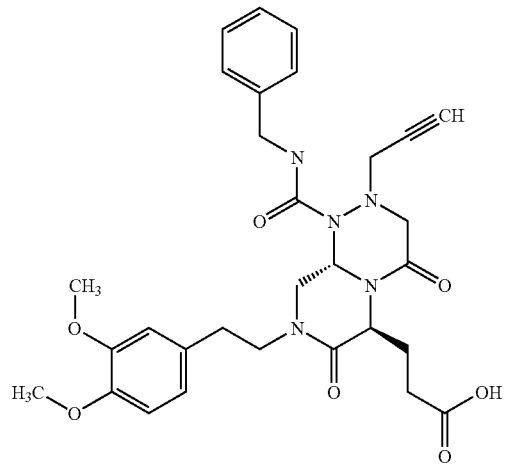 | 578 | 579 |
| 1724 | 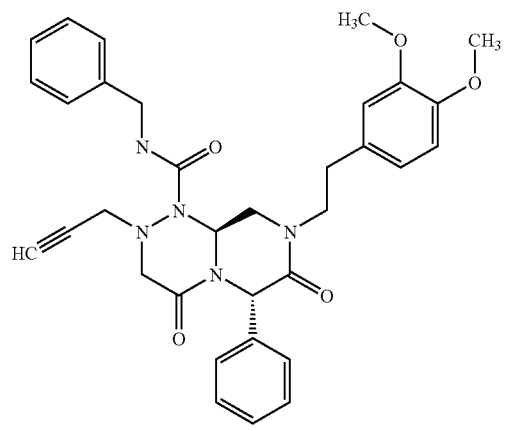 | 582 | 583 |

TABLE 2B-continued
THE [4,4,0]REVERSE TURN MIMETICS LIBRARY
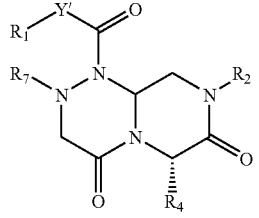
| No | MOLSTRUCTURE | Mol. Weight | M + H (MS) |
|----|--------------|-------------|------------|
| 1725 | | 647 | 648 |
| 1726 | | 532 | 533 |

TABLE 2B-continued
THE [4,4,0]REVERSE TURN MIMETICS LIBRARY
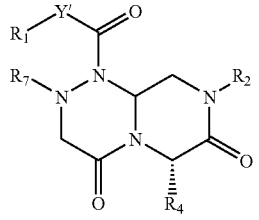
| No | MOLSTRUCTURE | Mol. Weight | M + H (MS) |
|---|---|---|---|
| 1727 | | 482 | 483 |
| 1728 | | 468 | 469 |
| 1729 | | 516 | 517 |

TABLE 2B-continued

THE [4,4,0]REVERSE TURN MIMETICS LIBRARY

| No | MOLSTRUCTURE | Mol. Weight | M + H (MS) |
|---|---|---|---|
| 1730 | | 482 | 483 |
| 1731 | | 482 | 483 |
| 1732 | | 500 | 501 |

TABLE 2B-continued

THE [4,4,0]REVERSE TURN MIMETICS LIBRARY

| No | MOLSTRUCTURE | Mol. Weight | M + H (MS) |
|---|---|---|---|
| 1733 | | 468 | 469 |
| 1734 | | 484 | 485 |
| 1735 | | 498 | 499 |

TABLE 2B-continued
THE [4,4,0]REVERSE TURN MIMETICS LIBRARY
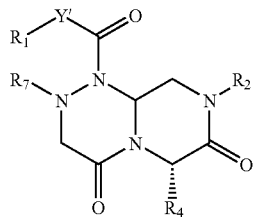
| No | MOLSTRUCTURE | Mol. Weight | M + H (MS) |
|----|--------------|-------------|------------|
| 1736 | | 502 | 503 |
| 1737 | | 567 | 568 |

TABLE 2B-continued
THE [4,4,0]REVERSE TURN MIMETICS LIBRARY
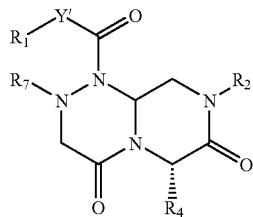
| No | MOLSTRUCTURE | Mol. Weight | M + H (MS) |
|---|---|---|---|
| 1738 | | 642 | 643 |
| 1739 | | 592 | 593 |

TABLE 2B-continued
THE [4,4,0]REVERSE TURN MIMETICS LIBRARY
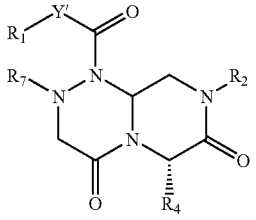
| No | MOLSTRUCTURE | Mol. Weight | M + H (MS) |
|---|---|---|---|
| 1740 | | 578 | 579 |
| 1741 | | 626 | 627 |
| 1742 | | 592 | 593 |

TABLE 2B-continued
THE [4,4,0]REVERSE TURN MIMETICS LIBRARY
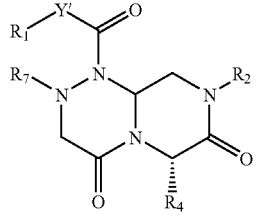
| No | MOLSTRUCTURE | Mol. Weight | M + H (MS) |
|---|---|---|---|
| 1743 | | 592 | 593 |
| 1744 | | 610 | 611 |
| 1745 | | 578 | 579 |

TABLE 2B-continued
THE [4,4,0]REVERSE TURN MIMETICS LIBRARY
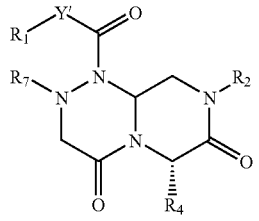
| No | MOLSTRUCTURE | Mol. Weight | M + H (MS) |
|---|---|---|---|
| 1746 | 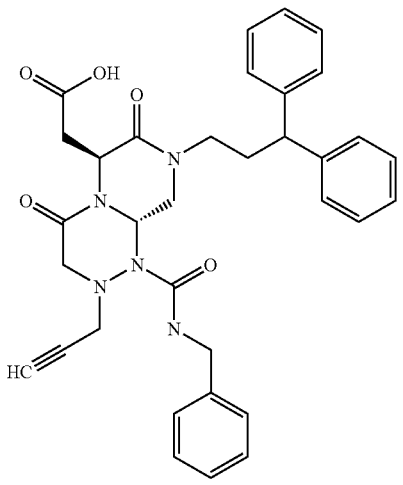 | 594 | 595 |
| 1747 | 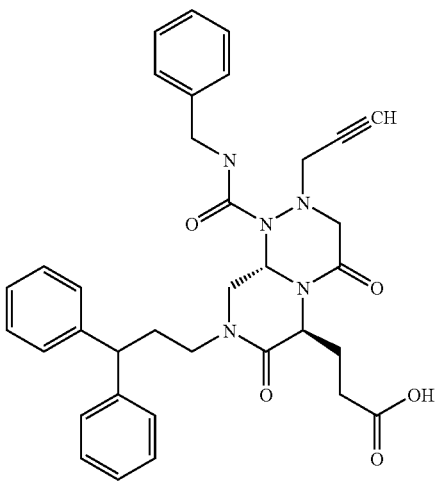 | 608 | 609 |

TABLE 2B-continued
THE [4,4,0]REVERSE TURN MIMETICS LIBRARY
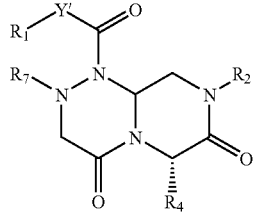
| No | MOLSTRUCTURE | Mol. Weight | M + H (MS) |
|---|---|---|---|
| 1748 | 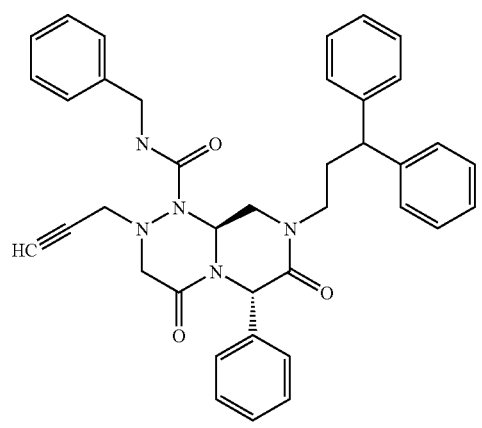 | 612 | 613 |
| 1749 | 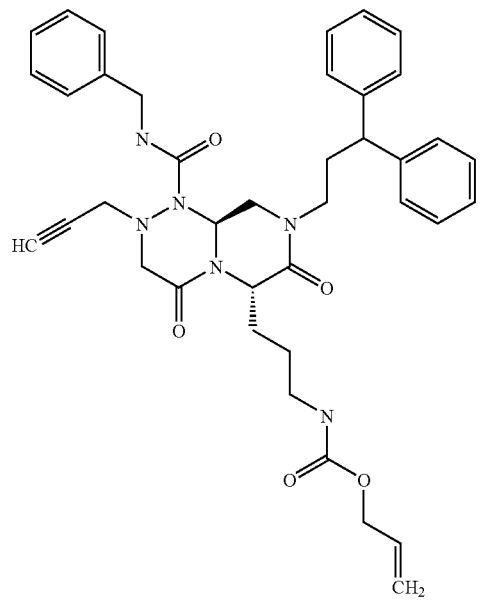 | 677 | 678 |

TABLE 2B-continued
THE [4,4,0]REVERSE TURN MIMETICS LIBRARY
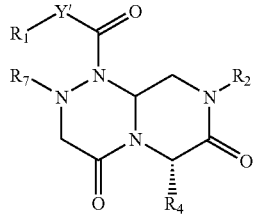
| No | MOLSTRUCTURE | Mol. Weight | M + H (MS) |
|---|---|---|---|
| 1750 | | 518 | 519 |
| 1751 | | 468 | 469 |
| 1752 | | 454 | 455 |

TABLE 2B-continued
THE [4,4,0]REVERSE TURN MIMETICS LIBRARY
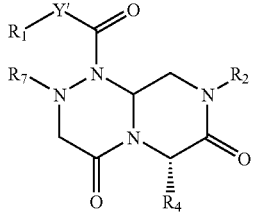
| No | MOLSTRUCTURE | Mol. Weight | M + H (MS) |
|---|---|---|---|
| 1753 | | 502 | 503 |
| 1754 | | 468 | 469 |
| 1755 | | 468 | 579 |

TABLE 2B-continued

THE [4,4,0]REVERSE TURN MIMETICS LIBRARY

| No | MOLSTRUCTURE | Mol. Weight | M + H (MS) |
|---|---|---|---|
| 1756 | | 486 | 487 |
| 1757 | | 454 | 455 |
| 1758 | | 470 | 471 |

TABLE 2B-continued
THE [4,4,0]REVERSE TURN MIMETICS LIBRARY
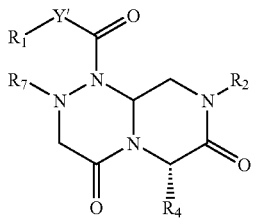
| No | MOLSTRUCTURE | Mol. Weight | M + H (MS) |
|---|---|---|---|
| 1759 | 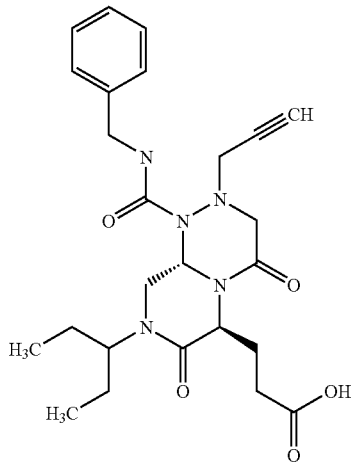 | 484 | 485 |
| 1760 | 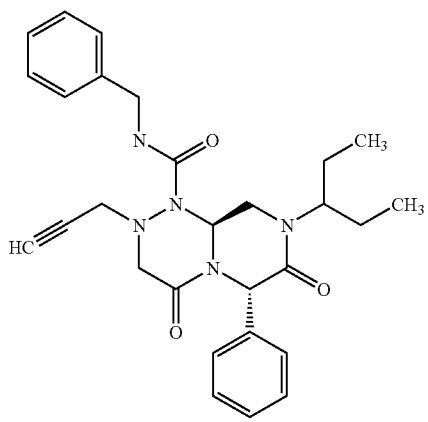 | 488 | 489 |

TABLE 2B-continued
THE [4,4,0]REVERSE TURN MIMETICS LIBRARY
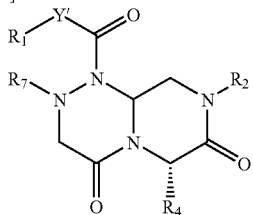
| No | MOLSTRUCTURE | Mol. Weight | M + H (MS) |
|---|---|---|---|
| 1761 | | 455 | 456 |
| 1762 | | 553 | 531 |

TABLE 2B-continued
THE [4,4,0]REVERSE TURN MIMETICS LIBRARY
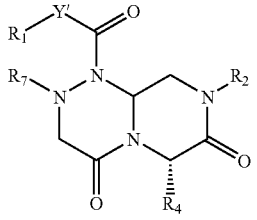
| No | MOLSTRUCTURE | Mol. Weight | M + H (MS) |
|----|--------------|-------------|------------|
| 1763 | | 480 | 481 |
| 1764 | | 466 | 467 |
| 1765 | | 414 | 415 |

TABLE 2B-continued

THE [4,4,0]REVERSE TURN MIMETICS LIBRARY

| No | MOLSTRUCTURE | Mol. Weight | M + H (MS) |
|---|---|---|---|
| 1756 | | 480 | 481 |
| 1767 | | 480 | 481 |
| 1768 | | 498 | 499 |

TABLE 2B-continued

THE [4,4,0]REVERSE TURN MIMETICS LIBRARY

| No | MOLSTRUCTURE | Mol. Weight | M + H (MS) |
|---|---|---|---|
| 1769 | | 466 | 467 |
| 1770 | | 482 | 483 |
| 1771 | | 496 | 497 |

TABLE 2B-continued
THE [4,4,0]REVERSE TURN MIMETICS LIBRARY
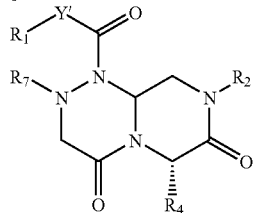
| No | MOLSTRUCTURE | Mol. Weight | M + H (MS) |
|---|---|---|---|
| 1772 | 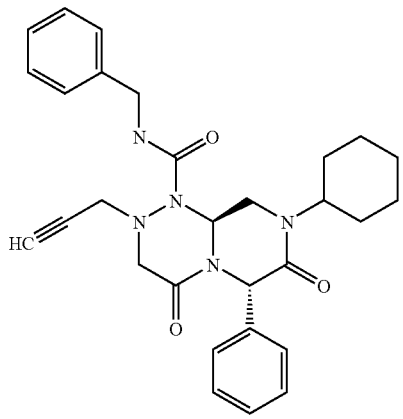 | 500 | 501 |
| 1773 | 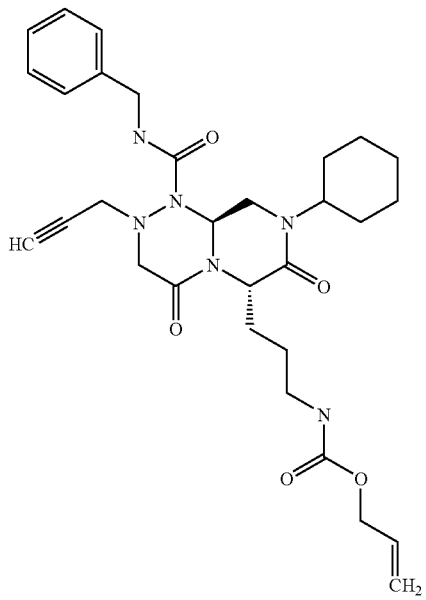 | 565 | 566 |

TABLE 2B-continued
THE [4,4,0]REVERSE TURN MIMETICS LIBRARY
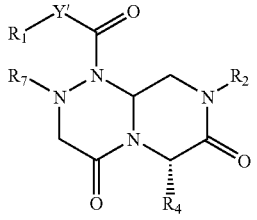
| No | MOLSTRUCTURE | Mol. Weight | M + H (MS) |
|---|---|---|---|
| 1774 | | 617 | 618 |
| 1775 | | 567 | 568 |
| 1776 | | 552 | 553 |

TABLE 2B-continued
THE [4,4,0]REVERSE TURN MIMETICS LIBRARY
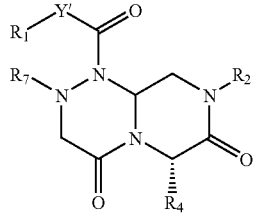
| No | MOLSTRUCTURE | Mol. Weight | M + H (MS) |
|---|---|---|---|
| 1777 | | 601 | 602 |
| 1778 | | 567 | 568 |
| 1779 | | 567 | 568 |

TABLE 2B-continued

THE [4,4,0]REVERSE TURN MIMETICS LIBRARY

| No | MOLSTRUCTURE | Mol. Weight | M + H (MS) |
|---|---|---|---|
| 1780 | | 585 | 586 |
| 1781 | | 552 | 553 |
| 1782 | | 568 | 567 |

TABLE 2B-continued
THE [4,4,0]REVERSE TURN MIMETICS LIBRARY
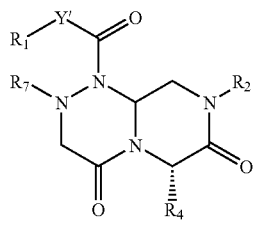
| No | MOLSTRUCTURE | Mol. Weight | M + H (MS) |
|---|---|---|---|
| 1783 | 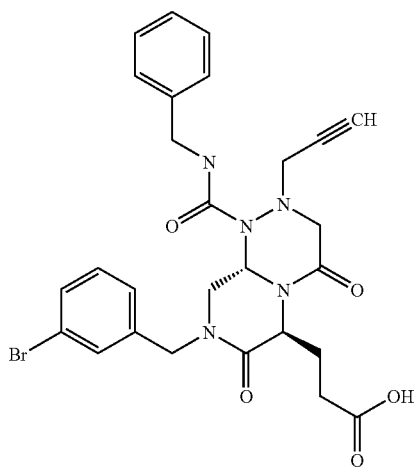 | 582 | 583 |
| 1784 | 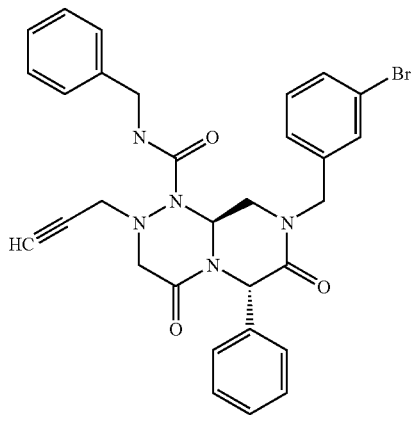 | 586 | 587 |

TABLE 2B-continued
THE [4,4,0]REVERSE TURN MIMETICS LIBRARY
| No | MOLSTRUCTURE | Mol. Weight | M + H (MS) |
|---|---|---|---|
| 1785 | 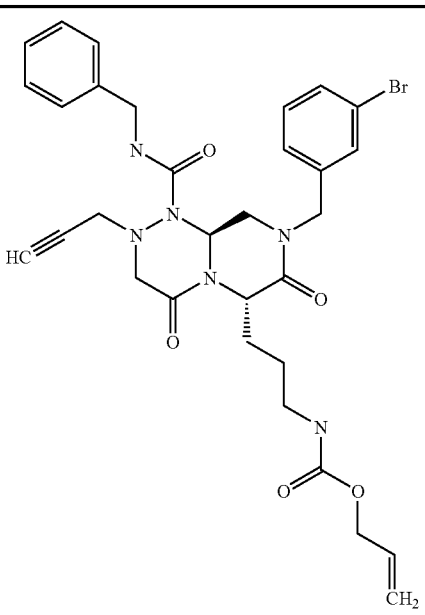 | 652 | 653 |
| 1786 | 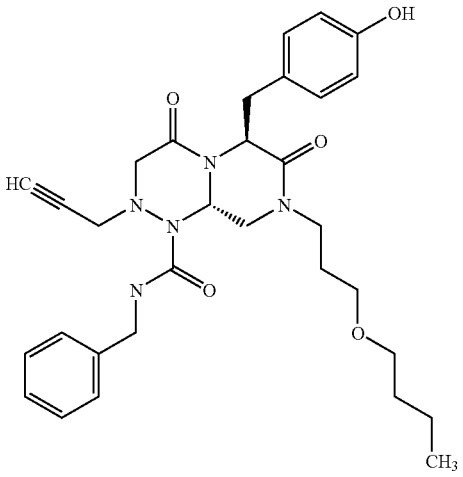 | 562 | 663 |

TABLE 2B-continued
THE [4,4,0]REVERSE TURN MIMETICS LIBRARY
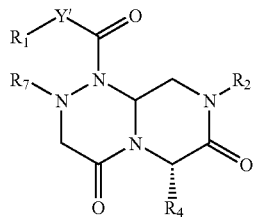
| No | MOLSTRUCTURE | Mol. Weight | M + H (MS) |
|---|---|---|---|
| 1787 | 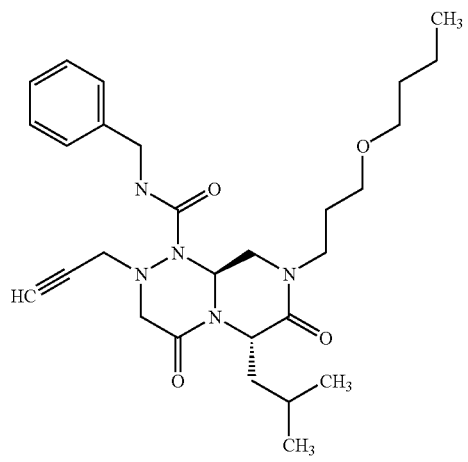 | 512 | 513 |
| 1788 | 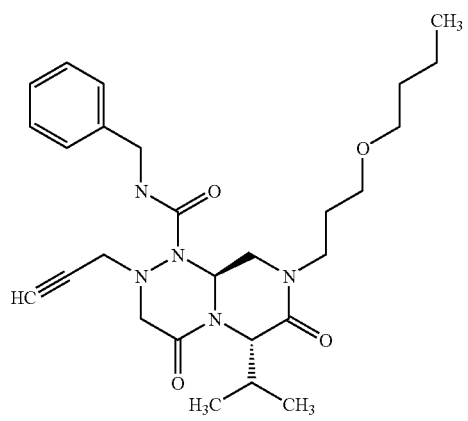 | 498 | 499 |

TABLE 2B-continued
THE [4,4,0]REVERSE TURN MIMETICS LIBRARY
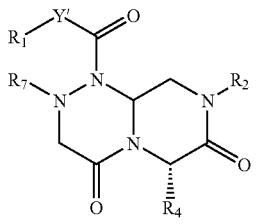
| No | MOLSTRUCTURE | Mol. Weight | M + H (MS) |
|---|---|---|---|
| 1789 | 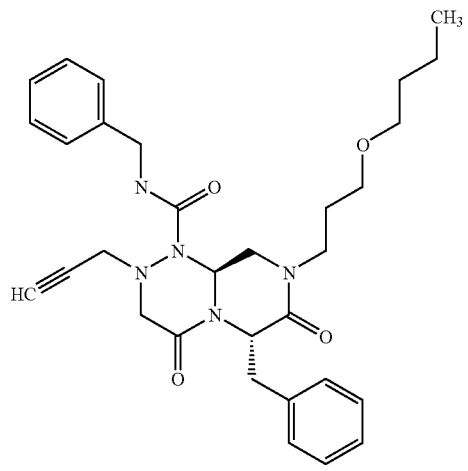 | 546 | 547 |
| 1790 | 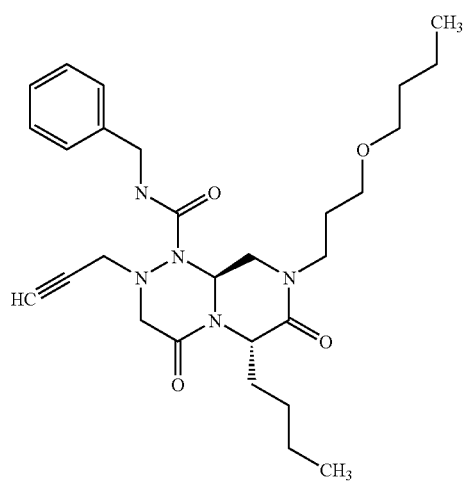 | 512 | 513 |

TABLE 2B-continued
THE [4,4,0]REVERSE TURN MIMETICS LIBRARY

| No | MOLSTRUCTURE | Mol. Weight | M + H (MS) |
|---|---|---|---|
| 1791 | | 512 | 513 |
| 1792 | | 530 | 531 |
| 1793 | | 498 | 499 |

TABLE 2B-continued
THE [4,4,0]REVERSE TURN MIMETICS LIBRARY
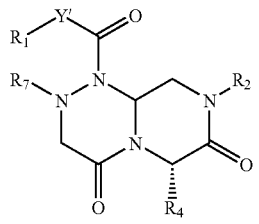
| No | MOLSTRUCTURE | Mol. Weight | M + H (MS) |
|----|--------------|-------------|------------|
| 1794 |  | 514 | 515 |
| 1795 | 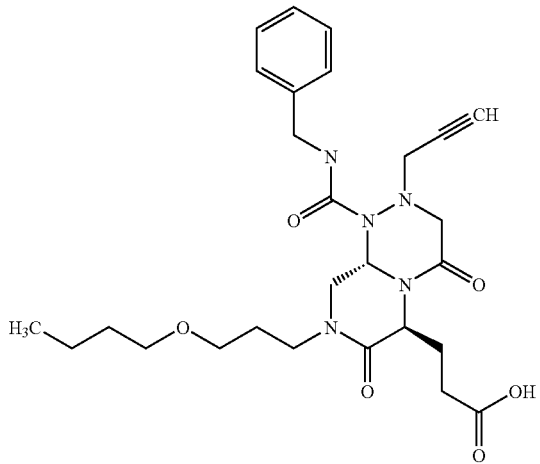 | 528 | 529 |

TABLE 2B-continued
THE [4,4,0]REVERSE TURN MIMETICS LIBRARY
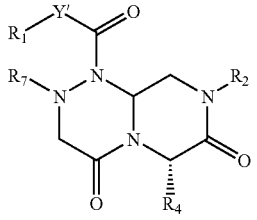
| No | MOLSTRUCTURE | Mol. Weight | M + H (MS) |
|---|---|---|---|
| 1796 | 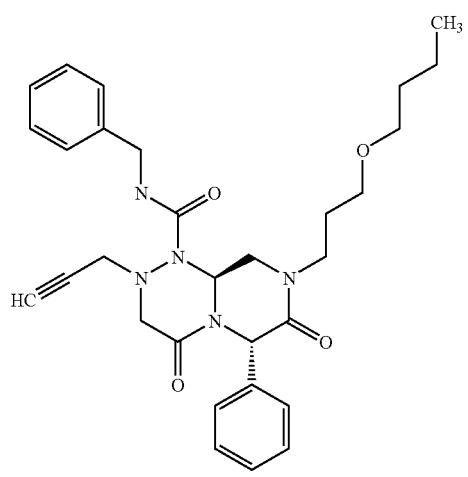 | 532 | 533 |
| 1797 | 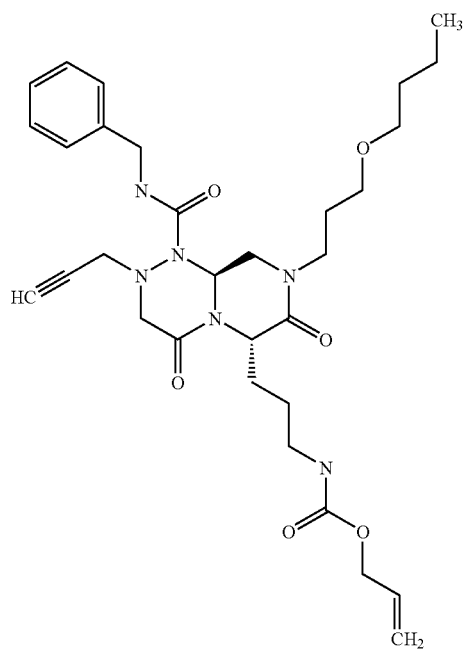 | 597 | 598 |

TABLE 2B-continued
THE [4,4,0]REVERSE TURN MIMETICS LIBRARY
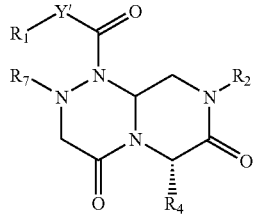
| No | MOLSTRUCTURE | Mol. Weight | M + H (MS) |
|---|---|---|---|
| 1798 | | 598 | 599 |
| 1799 | | 548 | 549 |
| 1800 | | 534 | 535 |

TABLE 2B-continued
THE [4,4,0]REVERSE TURN MIMETICS LIBRARY
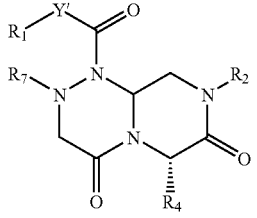
| No | MOLSTRUCTURE | Mol. Weight | M + H (MS) |
|---|---|---|---|
| 1801 | | 512 | 513 |
| 1802 | | 530 | 531 |
| 1803 | | 498 | 499 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 1804 | | 514 | 515 |
| 1805 | | 528 | 529 |
| 1806 | | 532 | 533 |

TABLE 2B-continued
THE [4,4,0]REVERSE TURN MIMETICS LIBRARY
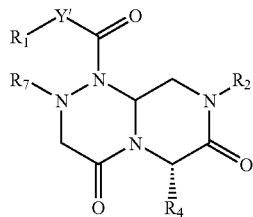
| No | MOLSTRUCTURE | Mol. Weight | M + H (MS) |
|---|---|---|---|
| 1807 |  | 597 | 598 |
| 1808 |  | 598 | 599 |

TABLE 2B-continued
THE [4,4,0]REVERSE TURN MIMETICS LIBRARY
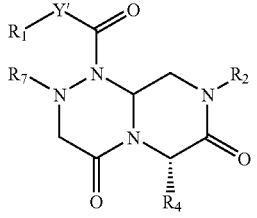
| No | MOLSTRUCTURE | Mol. Weight | M + H (MS) |
|---|---|---|---|
| 1809 | | 548 | 549 |
| 1810 | | 534 | 535 |

TABLE 2B-continued
THE [4,4,0]REVERSE TURN MIMETICS LIBRARY
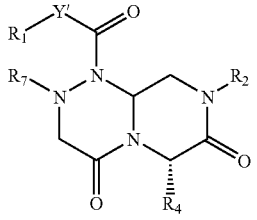
| No | MOLSTRUCTURE | Mol. Weight | M + H (MS) |
|---|---|---|---|
| 1811 | | 508 | 535 |
| 1812 | | 508 | 509 |
| 1813 | | 556 | 557 |

TABLE 2B-continued
THE [4,4,0]REVERSE TURN MIMETICS LIBRARY
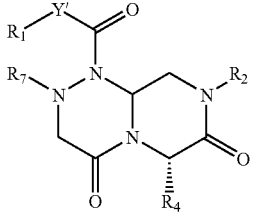
| No | MOLSTRUCTURE | Mol. Weight | M + H (MS) |
|---|---|---|---|
| 1814 | | 522 | 523 |
| 1815 | | 522 | 523 |
| 1816 | | 540 | 541 |

TABLE 2B-continued

THE [4,4,0]REVERSE TURN MIMETICS LIBRARY

| No | MOLSTRUCTURE | Mol. Weight | M + H (MS) |
|---|---|---|---|
| 1817 | | 508 | 509 |
| 1818 | | 524 | 525 |
| 1819 | | 538 | 539 |

TABLE 2B-continued
THE [4,4,0]REVERSE TURN MIMETICS LIBRARY
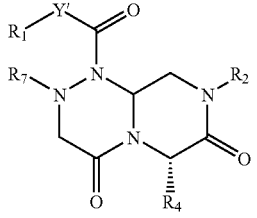
| No | MOLSTRUCTURE | Mol. Weight | M + H (MS) |
|---|---|---|---|
| 1820 | | 542 | 543 |
| 1821 | | 607 | 608 |

TABLE 2B-continued
THE [4,4,0]REVERSE TURN MIMETICS LIBRARY
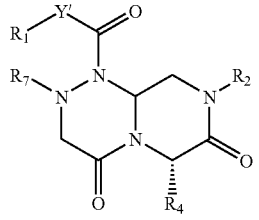
| No | MOLSTRUCTURE | Mol. Weight | M + H (MS) |
|---|---|---|---|
| 1822 | | 558 | 559 |
| 1823 | | 508 | 509 |
| 1824 | | 494 | 495 |

TABLE 2B-continued

THE [4,4,0]REVERSE TURN MIMETICS LIBRARY

| No | MOLSTRUCTURE | Mol. Weight | M + H (MS) |
|---|---|---|---|
| 1825 | | 542 | 543 |
| 1826 | | 508 | 509 |
| 1827 | | 508 | 509 |

TABLE 2B-continued

THE [4,4,0]REVERSE TURN MIMETICS LIBRARY

| No | MOLSTRUCTURE | Mol. Weight | M + H (MS) |
|---|---|---|---|
| 1828 | | 526 | 527 |
| 1829 | | 494 | 495 |
| 1830 | | 510 | 511 |

TABLE 2B-continued
THE [4,4,0]REVERSE TURN MIMETICS LIBRARY
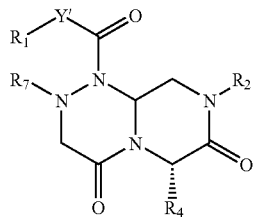
| No | MOLSTRUCTURE | Mol. Weight | M + H (MS) |
|---|---|---|---|
| 1831 | 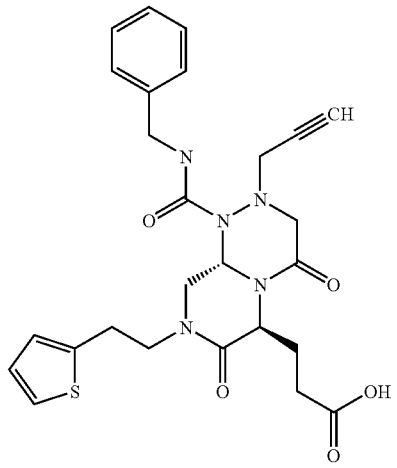 | 524 | 525 |
| 1832 | 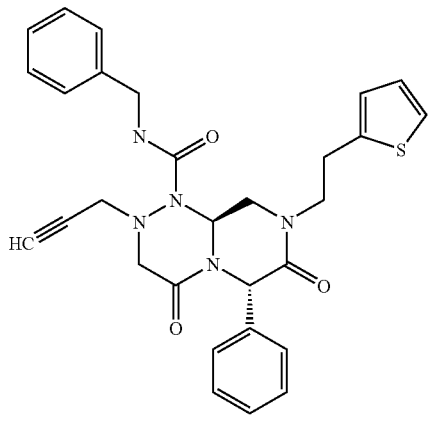 | 528 | 529 |

TABLE 2B-continued
THE [4,4,0]REVERSE TURN MIMETICS LIBRARY
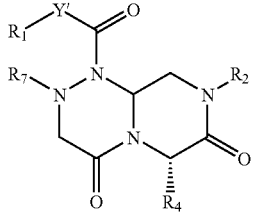
| No | MOLSTRUCTURE | Mol. Weight | M + H (MS) |
|---|---|---|---|
| 1833 | | 593 | 594 |
| 1834 | | 560 | 561 |

TABLE 2B-continued
THE [4,4,0]REVERSE TURN MIMETICS LIBRARY
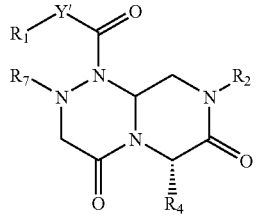
| No | MOLSTRUCTURE | Mol. Weight | M + H (MS) |
|---|---|---|---|
| 1835 | | 510 | 512 |
| 1836 | | 496 | 497 |
| 1837 | | 544 | 545 |

TABLE 2B-continued

THE [4,4,0]REVERSE TURN MIMETICS LIBRARY

| No | MOLSTRUCTURE | Mol. Weight | M + H (MS) |
|---|---|---|---|
| 1838 | | 510 | 511 |
| 1839 | | 510 | 511 |
| 1840 | | 528 | 529 |

TABLE 2B-continued

THE [4,4,0]REVERSE TURN MIMETICS LIBRARY

| No | MOLSTRUCTURE | Mol. Weight | M + H (MS) |
|---|---|---|---|
| 1841 | | 496 | 597 |
| 1842 | | 512 | 513 |
| 1843 | | 526 | 527 |

TABLE 2B-continued
THE [4,4,0]REVERSE TURN MIMETICS LIBRARY
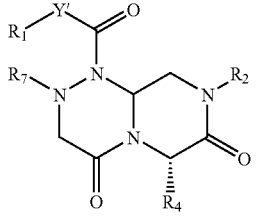
| No | MOLSTRUCTURE | Mol. Weight | M + H (MS) |
|----|--------------|-------------|------------|
| 1844 | | 530 | 531 |
| 1845 | | 595 | 596 |

TABLE 2B-continued
THE [4,4,0]REVERSE TURN MIMETICS LIBRARY
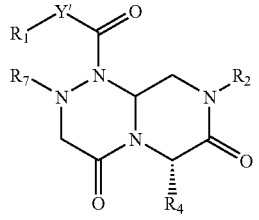
| No | MOLSTRUCTURE | Mol. Weight | M + H (MS) |
|---|---|---|---|
| 1846 | | 582 | 583 |
| 1847 | | 532 | 533 |
| 1848 | | 518 | 519 |

TABLE 2B-continued
THE [4,4,0]REVERSE TURN MIMETICS LIBRARY
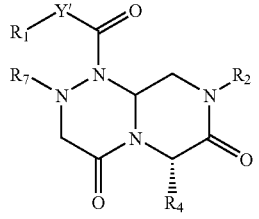
| No | MOLSTRUCTURE | Mol. Weight | M + H (MS) |
|---|---|---|---|
| 1849 | | 566 | 567 |
| 1850 | | 532 | 533 |
| 1851 | | 432 | 533 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 1852 | | 550 | 551 |
| 1853 | | 518 | 519 |
| 1854 | | 534 | 535 |

TABLE 2B-continued
THE [4,4,0]REVERSE TURN MIMETICS LIBRARY
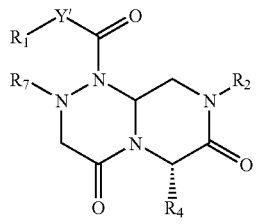
| No | MOLSTRUCTURE | Mol. Weight | M + H (MS) |
|---|---|---|---|
| 1855 | 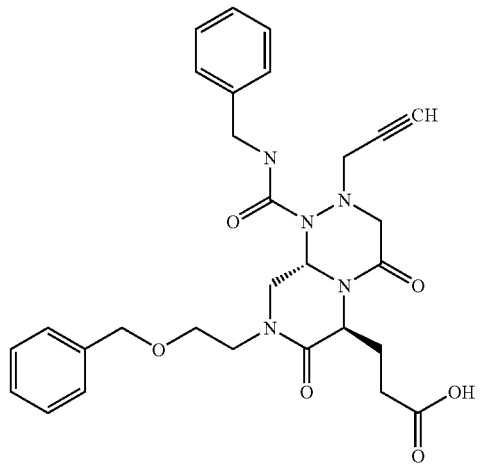 | 548 | 549 |
| 1856 | 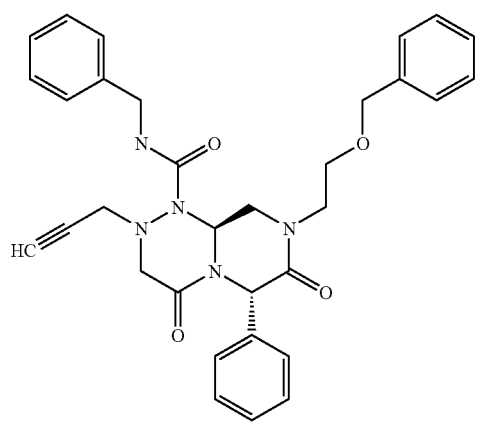 | 552 | 553 |

TABLE 2B-continued
THE [4,4,0]REVERSE TURN MIMETICS LIBRARY
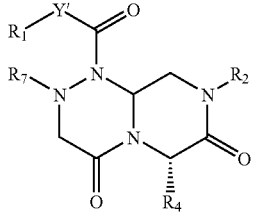
| No | MOLSTRUCTURE | Mol. Weight | M + H (MS) |
|---|---|---|---|
| 1857 | | 617 | 618 |
| 1858 | | 530 | 531 |

TABLE 2B-continued
THE [4,4,0]REVERSE TURN MIMETICS LIBRARY
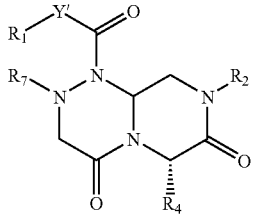
| No | MOLSTRUCTURE | Mol. Weight | M + H (MS) |
|---|---|---|---|
| 1859 | | 480 | 481 |
| 1860 | | 466 | 567 |
| 1861 | | 514 | 515 |

TABLE 2B-continued

THE [4,4,0]REVERSE TURN MIMETICS LIBRARY

| No | MOLSTRUCTURE | Mol. Weight | M + H (MS) |
|---|---|---|---|
| 1862 | | 480 | 481 |
| 1863 | | 480 | 481 |
| 1864 | | 498 | 499 |

TABLE 2B-continued
THE [4,4,0]REVERSE TURN MIMETICS LIBRARY
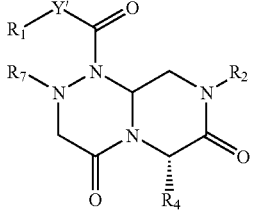
| No | MOLSTRUCTURE | Mol. Weight | M + H (MS) |
|---|---|---|---|
| 1865 | | 466 | 467 |
| 1866 | | 482 | 483 |
| 1867 | | 596 | 597 |

TABLE 2B-continued
THE [4,4,0]REVERSE TURN MIMETICS LIBRARY
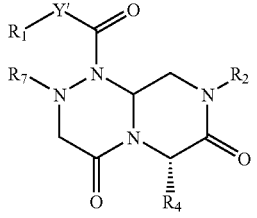
| No | MOLSTRUCTURE | Mol. Weight | M + H (MS) |
|---|---|---|---|
| 1868 | | 500 | 501 |
| 1869 | | 565 | 566 |

TABLE 2B-continued
THE [4,4,0]REVERSE TURN MIMETICS LIBRARY
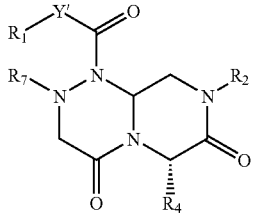
| No | MOLSTRUCTURE | Mol. Weight | M + H (MS) |
|---|---|---|---|
| 1870 | | 596 | 597 |
| 1871 | | 546 | 547 |
| 1872 | | 532 | 533 |

TABLE 2B-continued
THE [4,4,0]REVERSE TURN MIMETICS LIBRARY

| No | MOLSTRUCTURE | Mol. Weight | M + H (MS) |
|----|--------------|-------------|------------|
| 1873 | | 580 | 581 |
| 1874 | | 546 | 547 |
| 1875 | | 546 | 547 |

TABLE 2B-continued
THE [4,4,0]REVERSE TURN MIMETICS LIBRARY
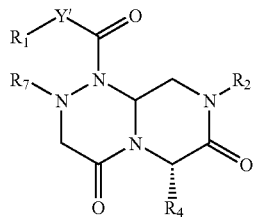
| No | MOLSTRUCTURE | Mol. Weight | M + H (MS) |
|---|---|---|---|
| 1876 | | 564 | 565 |
| 1877 | | 532 | 533 |
| 1878 | | 548 | 549 |

TABLE 2B-continued
THE [4,4,0]REVERSE TURN MIMETICS LIBRARY
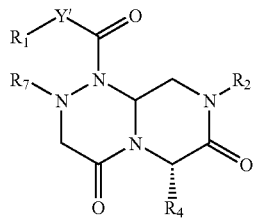
| No | MOLSTRUCTURE | Mol. Weight | M + H (MS) |
|---|---|---|---|
| 1879 | 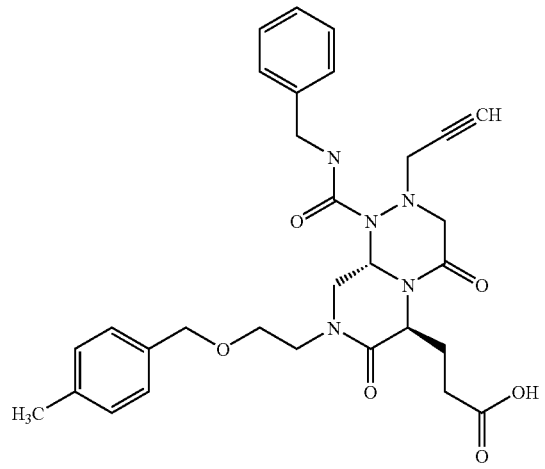 | 562 | 563 |
| 1880 | 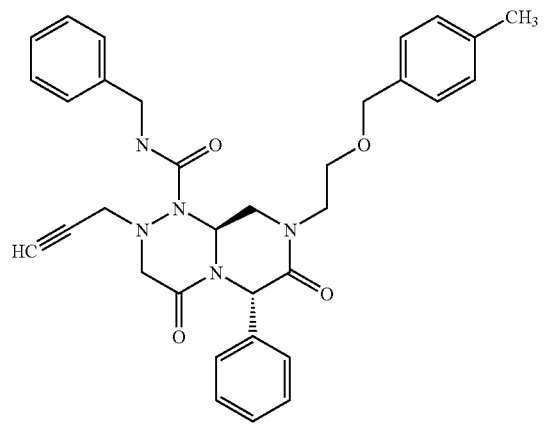 | 566 | 567 |

TABLE 2B-continued
THE [4,4,0]REVERSE TURN MIMETICS LIBRARY
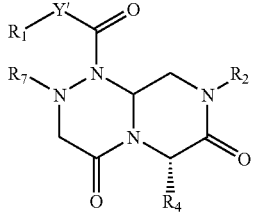
| No | MOLSTRUCTURE | Mol. Weight | M + H (MS) |
|---|---|---|---|
| 1881 | | 631 | 632 |
| 1882 | | 600 | 601 |

TABLE 2B-continued
THE [4,4,0]REVERSE TURN MIMETICS LIBRARY
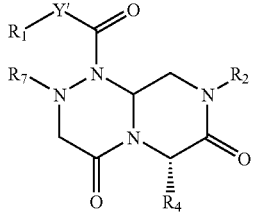
| No | MOLSTRUCTURE | Mol. Weight | M + H (MS) |
|---|---|---|---|
| 1883 | | 550 | 551 |
| 1884 | | 536 | 537 |

TABLE 2B-continued
THE [4,4,0]REVERSE TURN MIMETICS LIBRARY
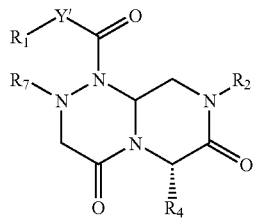
| No | MOLSTRUCTURE | Mol. Weight | M + H (MS) |
|---|---|---|---|
| 1885 | 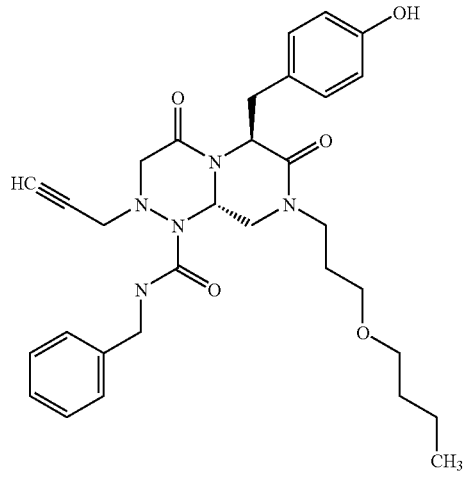 | 584 | 585 |
| 1886 | 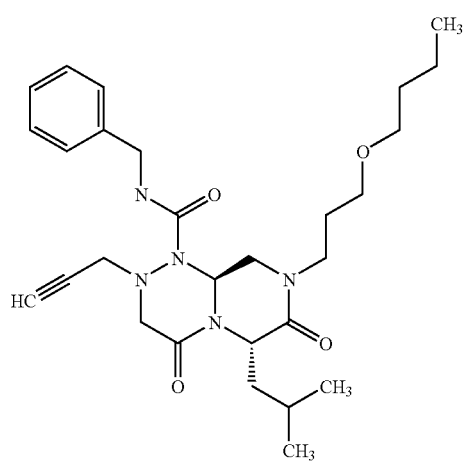 | 550 | 551 |

TABLE 2B-continued
THE [4,4,0]REVERSE TURN MIMETICS LIBRARY
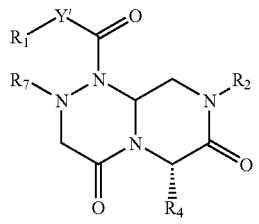
| No | MOLSTRUCTURE | Mol. Weight | M + H (MS) |
|---|---|---|---|
| 1887 | 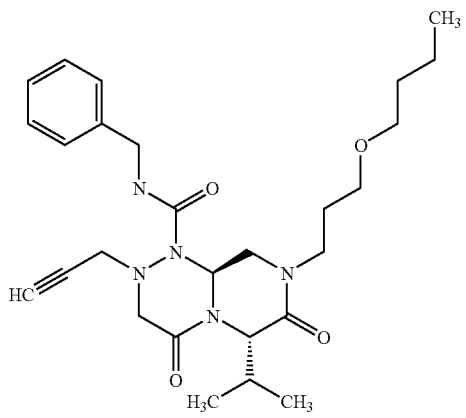 | 550 | 551 |
| 1888 | 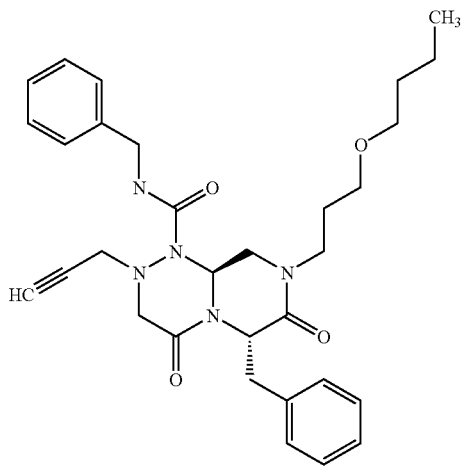 | 568 | 569 |

TABLE 2B-continued
THE [4,4,0]REVERSE TURN MIMETICS LIBRARY
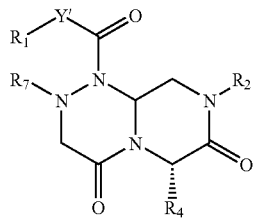
| No | MOLSTRUCTURE | Mol. Weight | M + H (MS) |
|----|--------------|-------------|------------|
| 1889 | 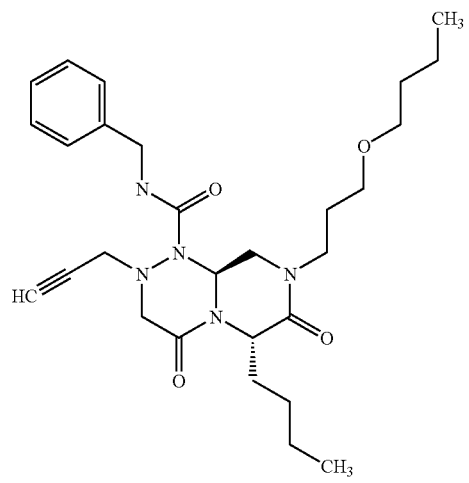 | 536 | 537 |
| 1890 | 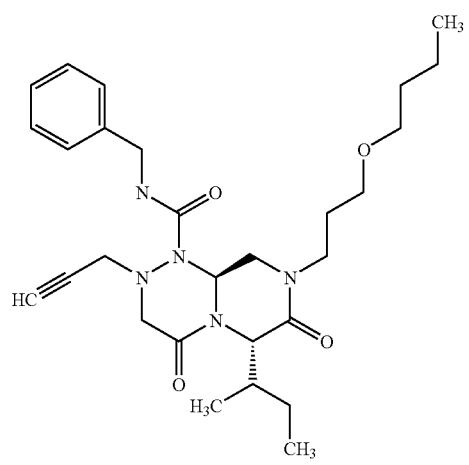 | 552 | 563 |

TABLE 2B-continued
THE [4,4,0]REVERSE TURN MIMETICS LIBRARY
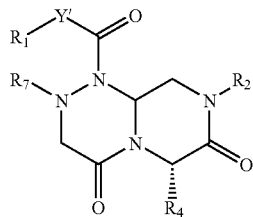
| No | MOLSTRUCTURE | Mol. Weight | M + H (MS) |
|---|---|---|---|
| 1891 | 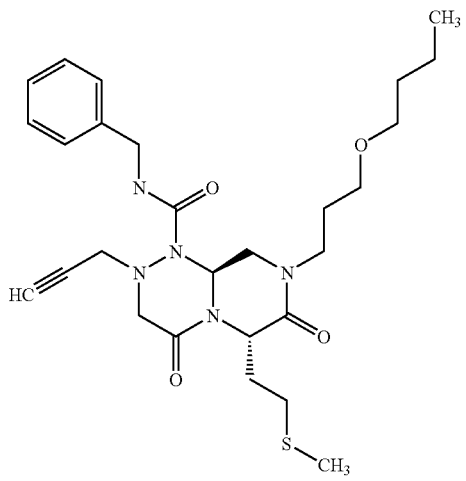 | 566 | 567 |
| 1892 | 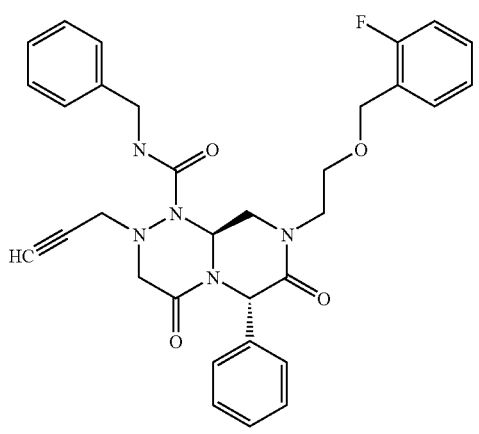 | 570 | 571 |

TABLE 2B-continued
THE [4,4,0]REVERSE TURN MIMETICS LIBRARY
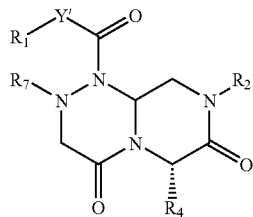
| No | MOLSTRUCTURE | Mol. Weight | M + H (MS) |
|---|---|---|---|
| 1893 | | 635 | 636 |
| 1894 | | 600 | 601 |

TABLE 2B-continued
THE [4,4,0]REVERSE TURN MIMETICS LIBRARY
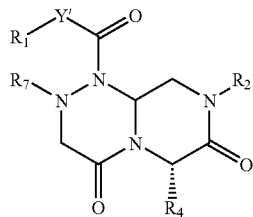
| No | MOLSTRUCTURE | Mol. Weight | M + H (MS) |
|---|---|---|---|
| 1895 | | 550 | 551 |
| 1896 | | 536 | 537 |

TABLE 2B-continued
THE [4,4,0]REVERSE TURN MIMETICS LIBRARY
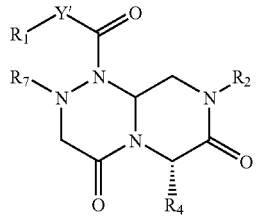
| No | MOLSTRUCTURE | Mol. Weight | M + H (MS) |
|---|---|---|---|
| 1897 | 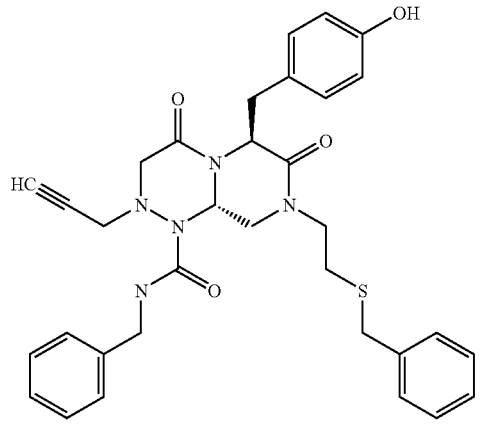 | 584 | 585 |
| 1898 | 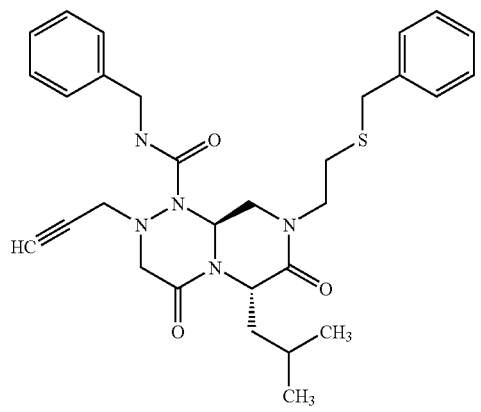 | 550 | 551 |

TABLE 2B-continued
THE [4,4,0]REVERSE TURN MIMETICS LIBRARY
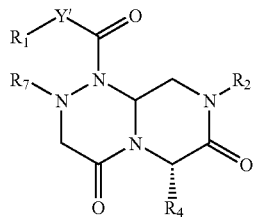
| No | MOLSTRUCTURE | Mol. Weight | M + H (MS) |
|---|---|---|---|
| 1899 | | 550 | 551 |
| 1900 | | 568 | 569 |

TABLE 2B-continued

THE [4,4,0]REVERSE TURN MIMETICS LIBRARY

| No | MOLSTRUCTURE | Mol. Weight | M + H (MS) |
|---|---|---|---|
| 1901 | | 536 | 537 |
| 1902 | | 552 | 553 |
| 1903 | | 566 | 567 |

TABLE 2B-continued
THE [4,4,0]REVERSE TURN MIMETICS LIBRARY
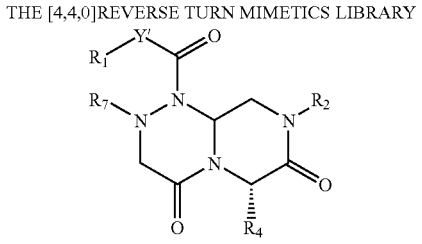
| No | MOLSTRUCTURE | Mol. Weight | M + H (MS) |
|---|---|---|---|
| 1904 | 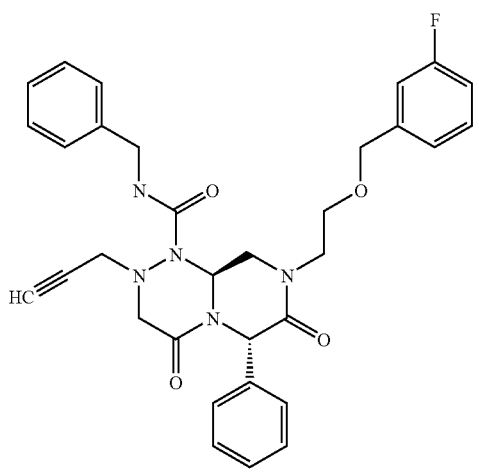 | 570 | 571 |
| 1905 | 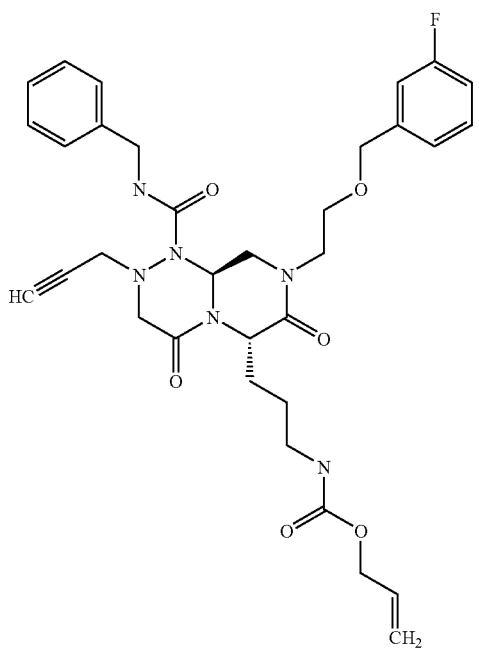 | 635 | 636 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 1906 | | 600 | 601 |
| 1907 | | 550 | 551 |
| 1908 | | 536 | 537 |

TABLE 2B-continued
THE [4,4,0]REVERSE TURN MIMETICS LIBRARY
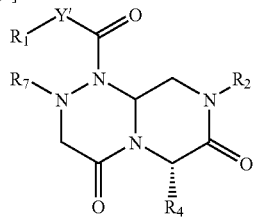
| No | MOLSTRUCTURE | Mol. Weight | M + H (MS) |
|----|--------------|-------------|------------|
| 1909 | | 584 | 585 |
| 1910 | | 550 | 551 |
| 1911 | | 550 | 557 |

TABLE 2B-continued
THE [4,4,0]REVERSE TURN MIMETICS LIBRARY
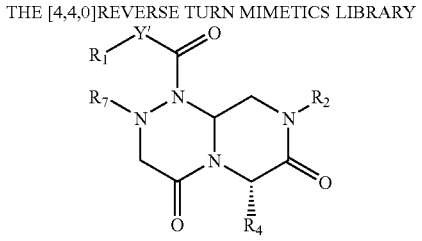
| No | MOLSTRUCTURE | Mol. Weight | M + H (MS) |
|---|---|---|---|
| 1912 | | 568 | 569 |
| 1913 | | 536 | 537 |
| 1914 | | 552 | 553 |

TABLE 2B-continued

THE [4,4,0]REVERSE TURN MIMETICS LIBRARY

| No | MOLSTRUCTURE | Mol. Weight | M + H (MS) |
|---|---|---|---|
| 1915 | | 566 | 567 |
| 1916 | | 570 | 671 |

TABLE 2B-continued
THE [4,4,0]REVERSE TURN MIMETICS LIBRARY
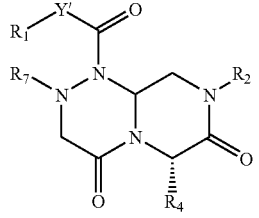
| No | MOLSTRUCTURE | Mol. Weight | M + H (MS) |
|---|---|---|---|
| 1917 | | 635 | 636 |
| 1918 | | 516 | 551 |

TABLE 2B-continued
THE [4,4,0]REVERSE TURN MIMETICS LIBRARY
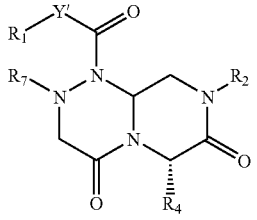
| No | MOLSTRUCTURE | Mol. Weight | M + H (MS) |
|---|---|---|---|
| 1919 | | 466 | 467 |
| 1920 | | 452 | 453 |
| 1921 | | 500 | 501 |

TABLE 2B-continued

THE [4,4,0]REVERSE TURN MIMETICS LIBRARY

| No | MOLSTRUCTURE | Mol. Weight | M + H (MS) |
|---|---|---|---|
| 1922 | | 466 | 467 |
| 1923 | | 466 | 467 |
| 1924 | | 484 | 485 |

TABLE 2B-continued

THE [4,4,0]REVERSE TURN MIMETICS LIBRARY

| No | MOLSTRUCTURE | Mol. Weight | M + H (MS) |
|---|---|---|---|
| 1925 | | 452 | 453 |
| 1926 | | 468 | 469 |
| 1927 | | 482 | 483 |

TABLE 2B-continued
THE [4,4,0]REVERSE TURN MIMETICS LIBRARY
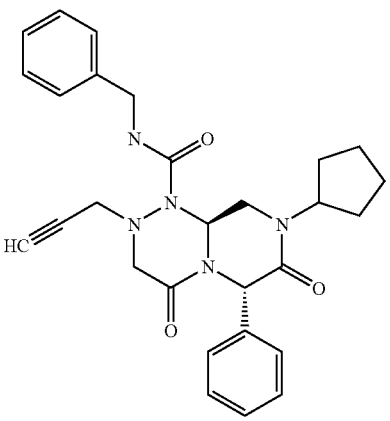
| No | MOLSTRUCTURE | Mol. Weight | M + H (MS) |
|---|---|---|---|
| 1928 | | 486 | 487 |
| 1929 | | 551 | 552 |
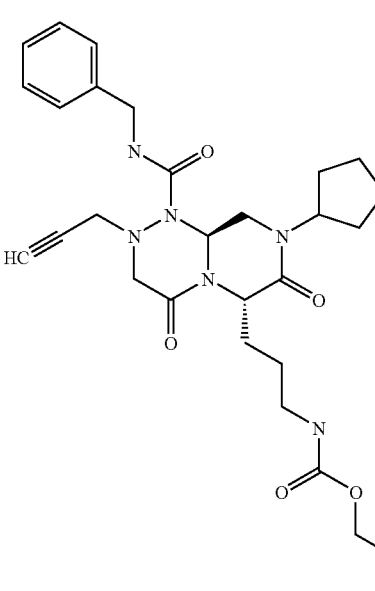

TABLE 2B-continued
THE [4,4,0]REVERSE TURN MIMETICS LIBRARY
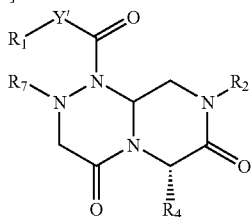
| No | MOLSTRUCTURE | Mol. Weight | M + H (MS) |
|----|--------------|-------------|------------|
| 1930 | | 546 | 547 |
| 1931 | | 496 | 497 |
| 1932 | | 482 | 483 |

TABLE 2B-continued
THE [4,4,0]REVERSE TURN MIMETICS LIBRARY
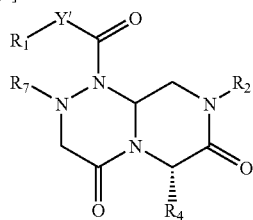
| No | MOLSTRUCTURE | Mol. Weight | M + H (MS) |
|---|---|---|---|
| 1933 | | 530 | 531 |
| 1934 | | 496 | 497 |
| 1935 | | 496 | 497 |

TABLE 2B-continued
THE [4,4,0]REVERSE TURN MIMETICS LIBRARY
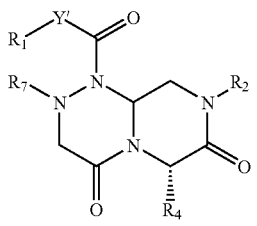
| No | MOLSTRUCTURE | Mol. Weight | M + H (MS) |
|---|---|---|---|
| 1936 | | 514 | 415 |
| 1937 | | 482 | 483 |

TABLE 2B-continued
THE [4,4,0]REVERSE TURN MIMETICS LIBRARY
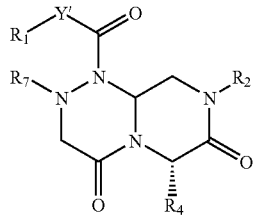
| No | MOLSTRUCTURE | Mol. Weight | M + H (MS) |
|---|---|---|---|
| 1938 | | 498 | 599 |
| 1939 | | 512 | 513 |

TABLE 2B-continued
THE [4,4,0]REVERSE TURN MIMETICS LIBRARY
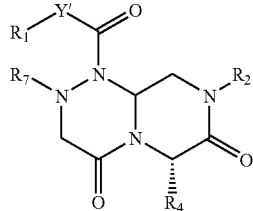
| No | MOLSTRUCTURE | Mol. Weight | M + H (MS) |
|---|---|---|---|
| 1940 | | 516 | 417 |
| 1941 | | 581 | 482 |

TABLE 2B-continued
THE [4,4,0]REVERSE TURN MIMETICS LIBRARY
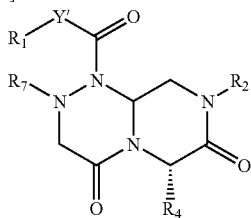
| No | MOLSTRUCTURE | Mol. Weight | M + H (MS) |
|---|---|---|---|
| 1942 | | 498 | 499 |
| 1943 | | 448 | 449 |
| 1944 | | 434 | 435 |

TABLE 2B-continued
THE [4,4,0]REVERSE TURN MIMETICS LIBRARY
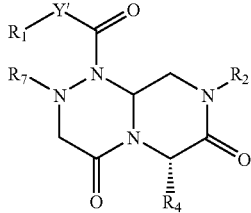
| No | MOLSTRUCTURE | Mol. Weight | M + H (MS) |
|---|---|---|---|
| 1945 | | 482 | 483 |
| 1946 | | 448 | 449 |
| 1947 | | 448 | 449 |

TABLE 2B-continued
THE [4,4,0]REVERSE TURN MIMETICS LIBRARY
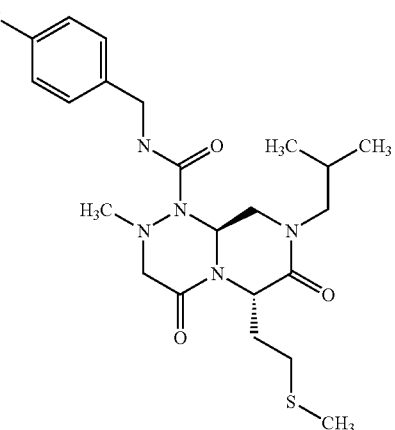
| No | MOLSTRUCTURE | Mol. Weight | M + H (MS) |
|---|---|---|---|
| 1948 | 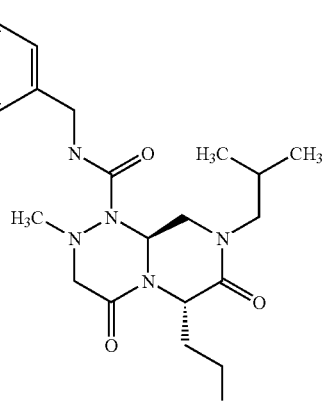 | 466 | 467 |
| 1949 | | 434 | 435 |
| 1950 | 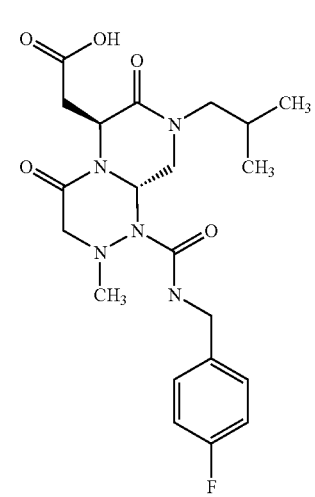 | 449 | 450 |

TABLE 2B-continued
THE [4,4,0]REVERSE TURN MIMETICS LIBRARY
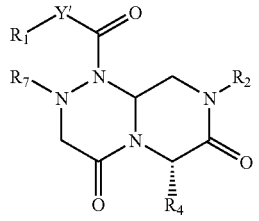
| No | MOLSTRUCTURE | Mol. Weight | M + H (MS) |
|---|---|---|---|
| 1951 | 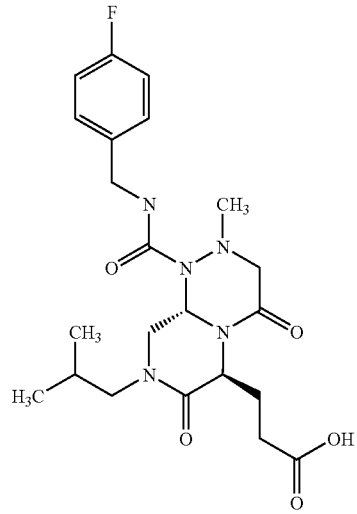 | 464 | 465 |
| 1952 | 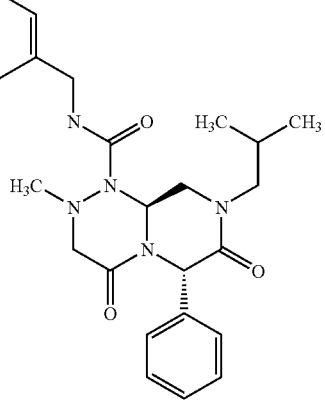 | 468 | 469 |

TABLE 2B-continued
THE [4,4,0]REVERSE TURN MIMETICS LIBRARY
| No | MOLSTRUCTURE | Mol. Weight | M + H (MS) |
|---|---|---|---|
| 1953 | | 533 | 534 |
| 1954 | | 600 | 601 |

TABLE 2B-continued
THE [4,4,0]REVERSE TURN MIMETICS LIBRARY
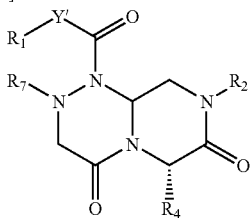
| No | MOLSTRUCTURE | Mol. Weight | M + H (MS) |
|---|---|---|---|
| 1955 | | 550 | 551 |
| 1956 | | 536 | 537 |
| 1957 | | 584 | 585 |

TABLE 2B-continued
THE [4,4,0]REVERSE TURN MIMETICS LIBRARY
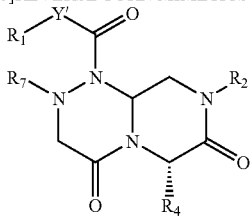
| No | MOLSTRUCTURE | Mol. Weight | M + H (MS) |
|---|---|---|---|
| 1958 | | 550 | 551 |
| 1959 | | 550 | 551 |
| 1960 | | 568 | 569 |

TABLE 2B-continued
THE [4,4,0]REVERSE TURN MIMETICS LIBRARY
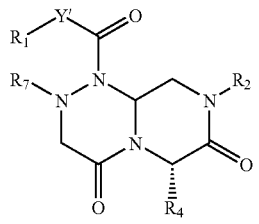
| No | MOLSTRUCTURE | Mol. Weight | M + H (MS) |
|---|---|---|---|
| 1961 | | 536 | 537 |
| 1962 | | 552 | 553 |

TABLE 2B-continued
THE [4,4,0]REVERSE TURN MIMETICS LIBRARY
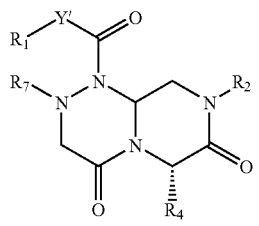
| No | MOLSTRUCTURE | Mol. Weight | M + H (MS) |
|---|---|---|---|
| 1963 | 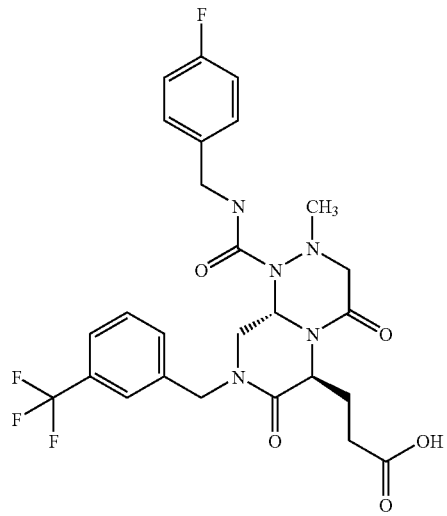 | 566 | 567 |
| 1964 | 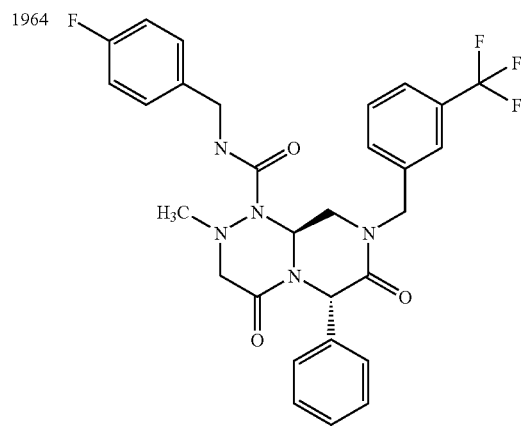 | 570 | 571 |

TABLE 2B-continued
THE [4,4,0]REVERSE TURN MIMETICS LIBRARY
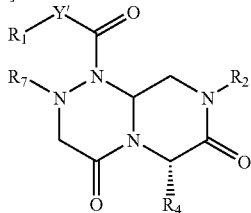
| No | MOLSTRUCTURE | Mol. Weight | M + H (MS) |
|---|---|---|---|
| 1965 | | 635 | 636 |
| 1966 | | 560 | 561 |

TABLE 2B-continued
THE [4,4,0]REVERSE TURN MIMETICS LIBRARY
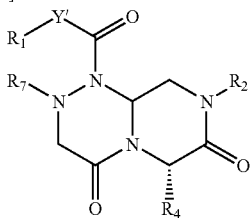
| No | MOLSTRUCTURE | Mol. Weight | M + H (MS) |
|----|--------------|-------------|------------|
| 1967 | | 510 | 511 |
| 1968 | | 496 | 497 |
| 1969 | | 544 | 545 |

TABLE 2B-continued
THE [4,4,0]REVERSE TURN MIMETICS LIBRARY
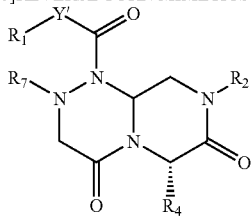
| No | MOLSTRUCTURE | Mol. Weight | M + H (MS) |
|---|---|---|---|
| 1970 | | 510 | 511 |
| 1971 | | 510 | 511 |
| 1972 | | 528 | 529 |

TABLE 2B-continued
THE [4,4,0]REVERSE TURN MIMETICS LIBRARY
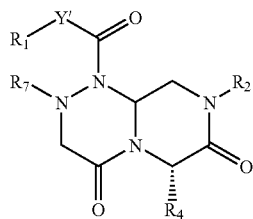
| No | MOLSTRUCTURE | Mol. Weight | M + H (MS) |
|---|---|---|---|
| 1973 | | 496 | 497 |
| 1974 | | 512 | 513 |
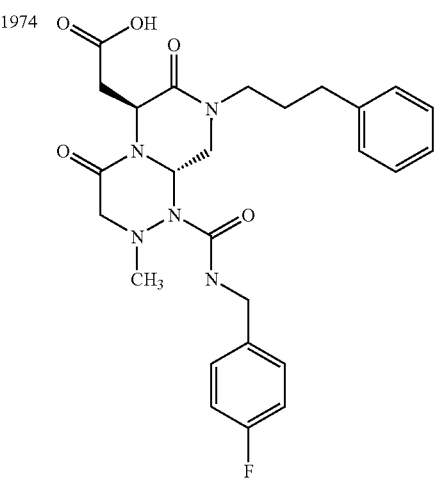

TABLE 2B-continued
THE [4,4,0]REVERSE TURN MIMETICS LIBRARY
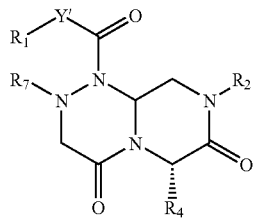
| No | MOLSTRUCTURE | Mol. Weight | M + H (MS) |
|---|---|---|---|
| 1975 | 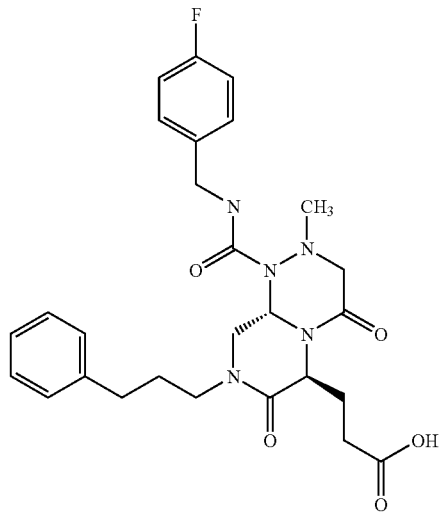 | 526 | 527 |
| 1976 | 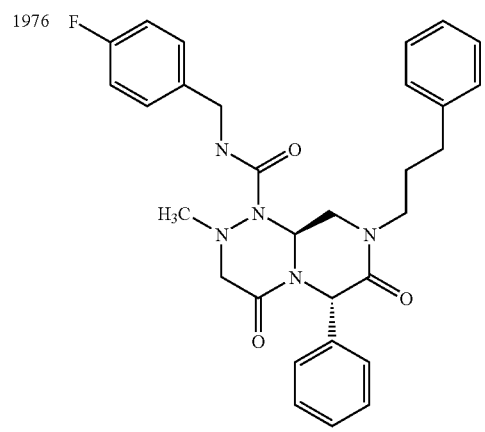 | 530 | 531 |

TABLE 2B-continued
THE [4,4,0]REVERSE TURN MIMETICS LIBRARY
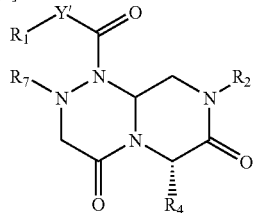
| No | MOLSTRUCTURE | Mol. Weight | M + H (MS) |
|---|---|---|---|
| 1977 | | 595 | 496 |
| 1978 | | 550 | 551 |

TABLE 2B-continued
THE [4,4,0]REVERSE TURN MIMETICS LIBRARY
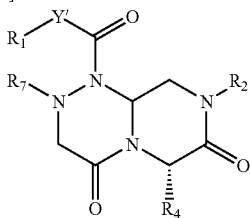
| No | MOLSTRUCTURE | Mol. Weight | M + H (MS) |
|---|---|---|---|
| 1979 | | 500 | 501 |
| 1980 | | 486 | 487 |
| 1981 | | 534 | 535 |

TABLE 2B-continued
THE [4,4,0]REVERSE TURN MIMETICS LIBRARY
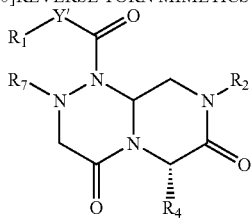
| No | MOLSTRUCTURE | Mol. Weight | M + H (MS) |
|---|---|---|---|
| 1982 | | 528 | 529 |
| 1983 | | 496 | 497 |
| 1984 | | 512 | 513 |

TABLE 2B-continued
THE [4,4,0]REVERSE TURN MIMETICS LIBRARY
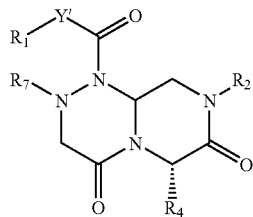
| No | MOLSTRUCTURE | Mol. Weight | M + H (MS) |
|---|---|---|---|
| 1985 | | 526 | 527 |
| 1986 | | 530 | 531 |

TABLE 2B-continued
THE [4,4,0]REVERSE TURN MIMETICS LIBRARY
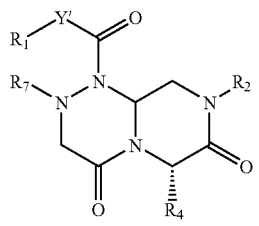
| No | MOLSTRUCTURE | Mol. Weight | M + H (MS) |
|---|---|---|---|
| 1987 | 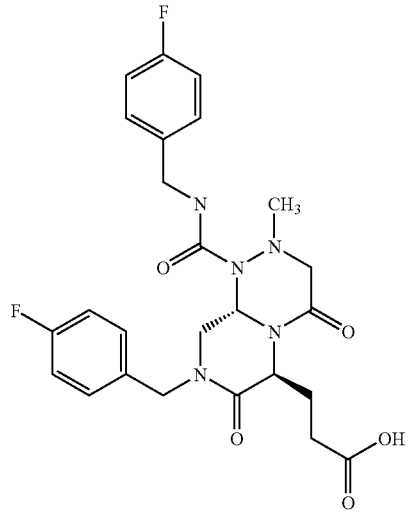 | 595 | 496 |
| 1988 | 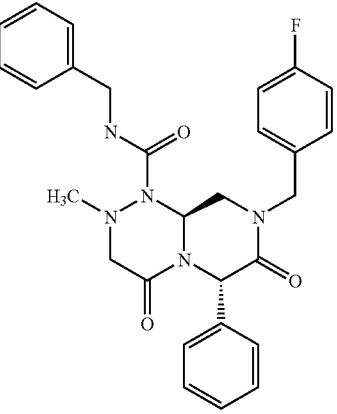 | 550 | 551 |

TABLE 2B-continued
THE [4,4,0]REVERSE TURN MIMETICS LIBRARY
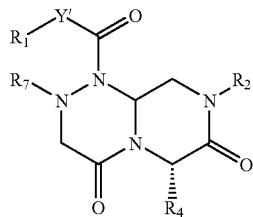
| No | MOLSTRUCTURE | Mol. Weight | M + H (MS) |
|---|---|---|---|
| 1989 | | 500 | 501 |
| 1990 | | 526 | 527 |

TABLE 2B-continued
THE [4,4,0]REVERSE TURN MIMETICS LIBRARY
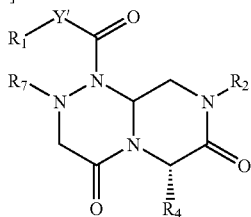
| No | MOLSTRUCTURE | Mol. Weight | M + H (MS) |
|---|---|---|---|
| 1991 | | 476 | 477 |
| 1992 | | 462 | 463 |
| 1993 | | 510 | 511 |

TABLE 2B-continued

THE [4,4,0]REVERSE TURN MIMETICS LIBRARY

| No | MOLSTRUCTURE | Mol. Weight | M + H (MS) |
|---|---|---|---|
| 1994 | | 476 | 477 |
| 1995 | | 476 | 477 |
| 1996 | | 494 | 495 |

TABLE 2B-continued
THE [4,4,0]REVERSE TURN MIMETICS LIBRARY
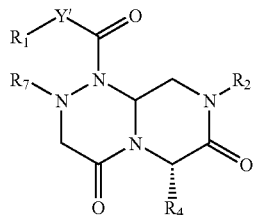
| No | MOLSTRUCTURE | Mol. Weight | M + H (MS) |
|---|---|---|---|
| 1997 | | 462 | 463 |
| 1998 | | 477 | 478 |

TABLE 2B-continued
THE [4,4,0]REVERSE TURN MIMETICS LIBRARY
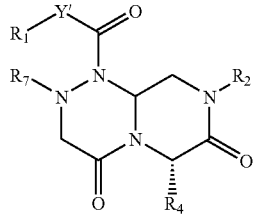
| No | MOLSTRUCTURE | Mol. Weight | M + H (MS) |
|---|---|---|---|
| 1999 | 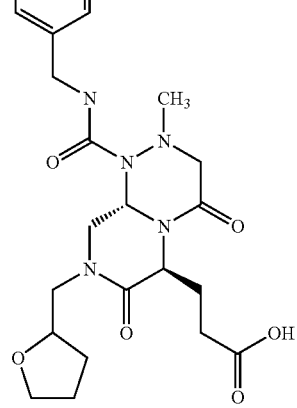 | 492 | 493 |
| 2000 | 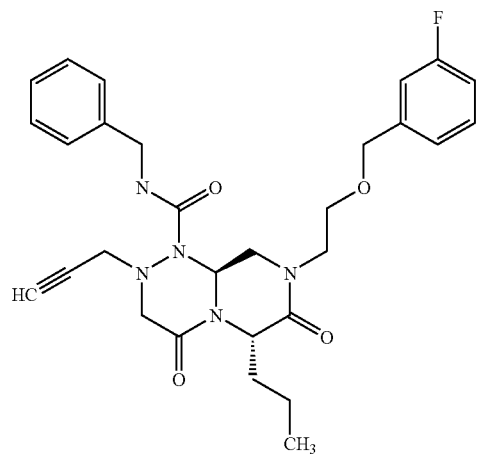 | 496 | 497 |

TABLE 2B-continued
THE [4,4,0]REVERSE TURN MIMETICS LIBRARY
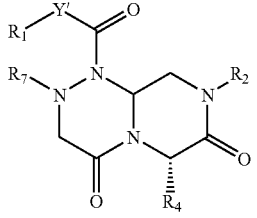
| No | MOLSTRUCTURE | Mol. Weight | M + H (MS) |
|----|--------------|-------------|------------|
| 2001 | | 561 | 562 |
| 2002 | | 512 | 513 |

TABLE 2B-continued

THE [4,4,0]REVERSE TURN MIMETICS LIBRARY

| No | MOLSTRUCTURE | Mol. Weight | M + H (MS) |
|---|---|---|---|
| 2003 | | 462 | 463 |
| 2004 | | 448 | 449 |
| 2005 | | 496 | 497 |

TABLE 2B-continued
THE [4,4,0]REVERSE TURN MIMETICS LIBRARY
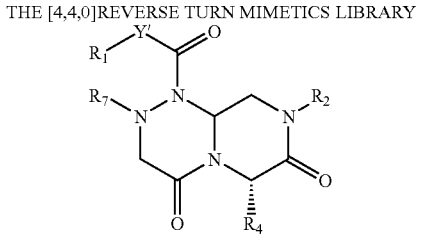
| No | MOLSTRUCTURE | Mol. Weight | M + H (MS) |
|---|---|---|---|
| 2006 | | 462 | 463 |
| 2007 | | 462 | 463 |
| 2008 | | 480 | 481 |

TABLE 2B-continued
THE [4,4,0]REVERSE TURN MIMETICS LIBRARY
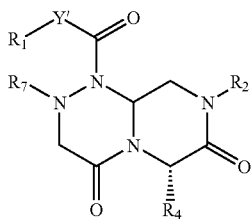
| No | MOLSTRUCTURE | Mol. Weight | M + H (MS) |
|----|--------------|-------------|------------|
| 2009 | | 448 | 449 |
| 2010 | | 464 | 465 |

TABLE 2B-continued
THE [4,4,0]REVERSE TURN MIMETICS LIBRARY
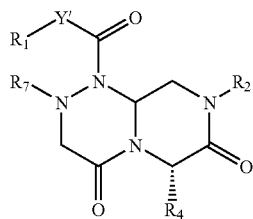
| No | MOLSTRUCTURE | Mol. Weight | M + H (MS) |
|---|---|---|---|
| 2011 | 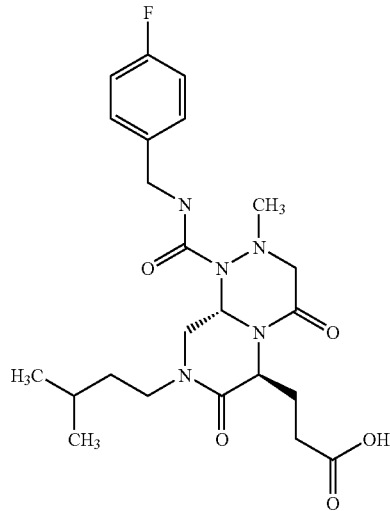 | 478 | 479 |
| 2012 | 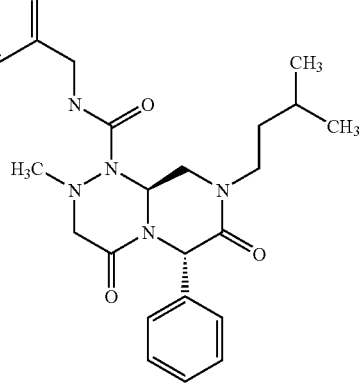 | 482 | 483 |

TABLE 2B-continued
THE [4,4,0]REVERSE TURN MIMETICS LIBRARY
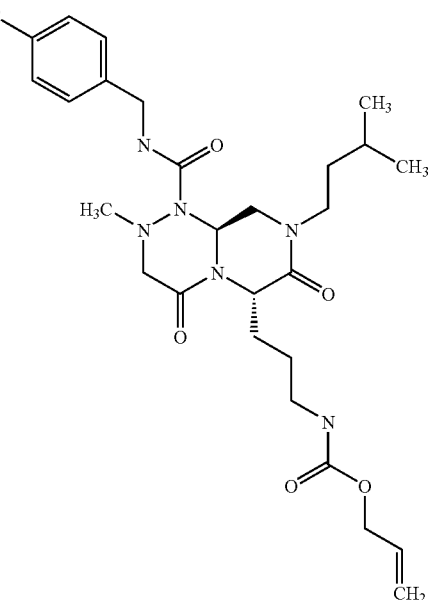
| No | MOLSTRUCTURE | Mol. Weight | M + H (MS) |
|---|---|---|---|
| 2013 | | 547 | 548 |
| 2014 | | 576 | 577 |
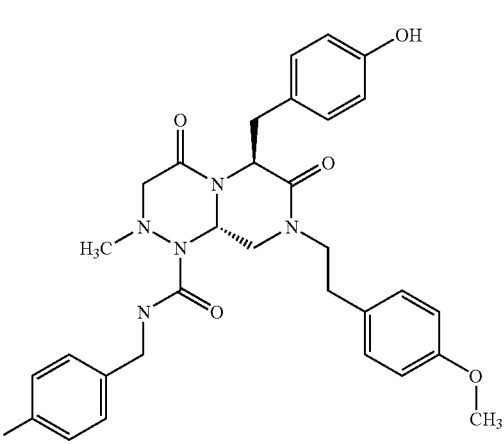

TABLE 2B-continued
THE [4,4,0]REVERSE TURN MIMETICS LIBRARY
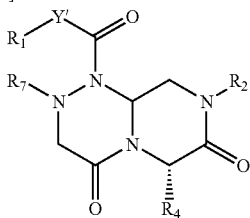
| No | MOLSTRUCTURE | Mol. Weight | M + H (MS) |
|---|---|---|---|
| 2015 | | 526 | 527 |
| 2016 | | 512 | 513 |
| 2017 | | 560 | 561 |

TABLE 2B-continued
THE [4,4,0]REVERSE TURN MIMETICS LIBRARY
| No | MOLSTRUCTURE | Mol. Weight | M + H (MS) |
|---|---|---|---|
| 2018 | 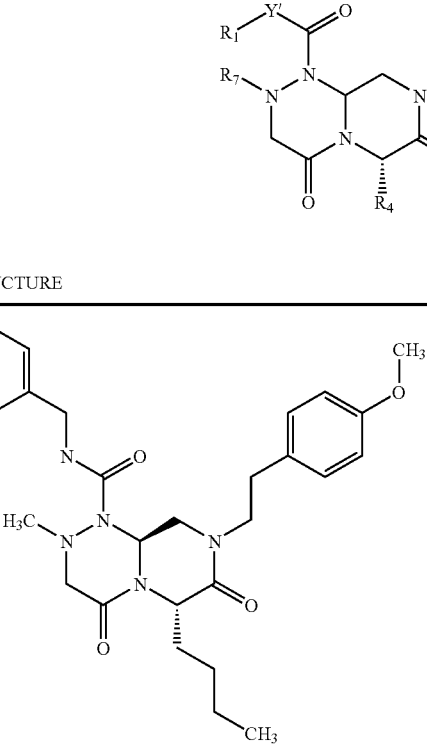 | 526 | 527 |
| 2019 | 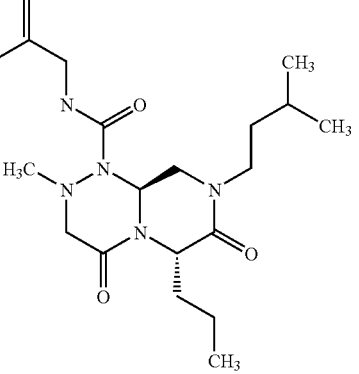 | 526 | 527 |
| 2020 | 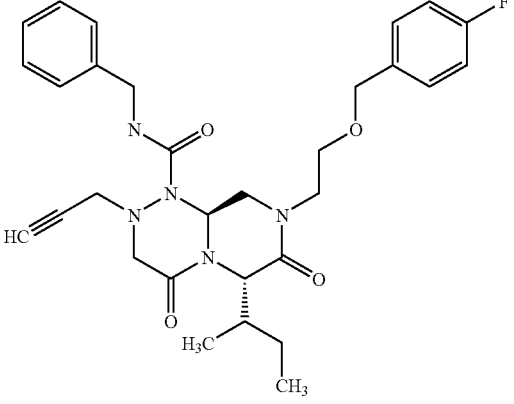 | 544 | 545 |

TABLE 2B-continued
THE [4,4,0]REVERSE TURN MIMETICS LIBRARY
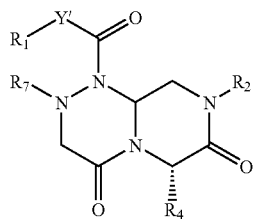
| No | MOLSTRUCTURE | Mol. Weight | M + H (MS) |
|---|---|---|---|
| 2021 | 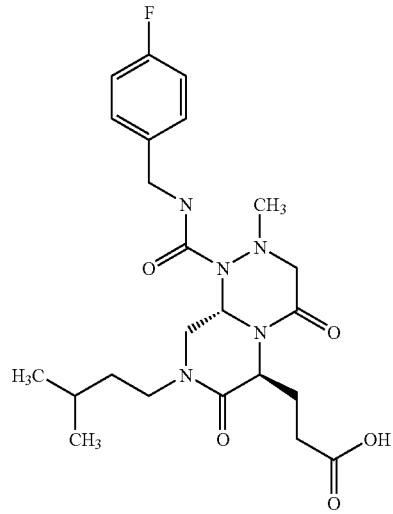 | 512 | 513 |
| 2022 | 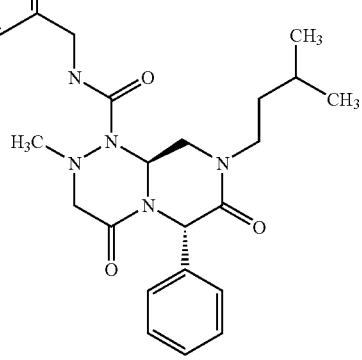 | 528 | 529 |

TABLE 2B-continued
THE [4,4,0]REVERSE TURN MIMETICS LIBRARY
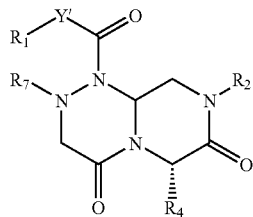
| No | MOLSTRUCTURE | Mol. Weight | M + H (MS) |
|---|---|---|---|
| 2023 | | 542 | 543 |
| 2024 | 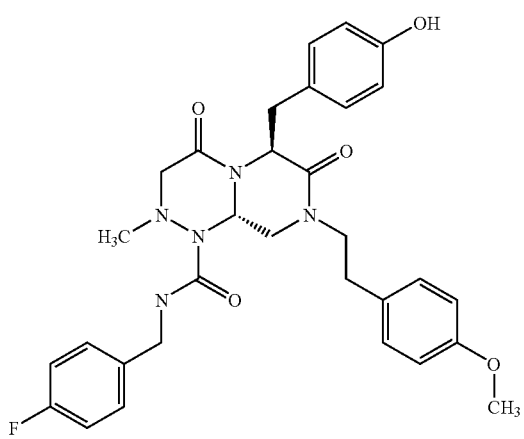 | 546 | 547 |

TABLE 2B-continued
THE [4,4,0]REVERSE TURN MIMETICS LIBRARY
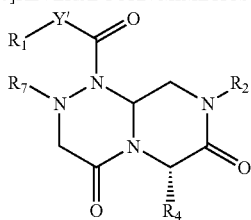
| No | MOLSTRUCTURE | Mol. Weight | M + H (MS) |
|---|---|---|---|
| 2025 | | 611 | 612 |
| 2026 | | 514 | 515 |
| 2027 | | 464 | 465 |

TABLE 2B-continued
THE [4,4,0]REVERSE TURN MIMETICS LIBRARY
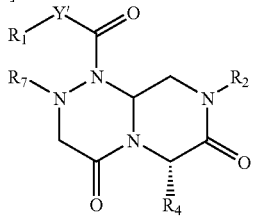
| No | MOLSTRUCTURE | Mol. Weight | M + H (MS) |
|----|--------------|-------------|------------|
| 2028 | | 450 | 451 |
| 2029 | | 498 | 499 |
| 2030 | | 464 | 465 |

TABLE 2B-continued
THE [4,4,0]REVERSE TURN MIMETICS LIBRARY
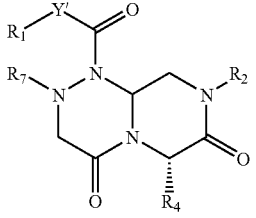
| No | MOLSTRUCTURE | Mol. Weight | M + H (MS) |
|---|---|---|---|
| 2031 | | 464 | 465 |
| 2032 | | 482 | 483 |
| 2033 | | 450 | 451 |

TABLE 2B-continued
THE [4,4,0]REVERSE TURN MIMETICS LIBRARY
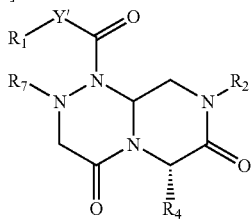
| No | MOLSTRUCTURE | Mol. Weight | M + H (MS) |
|---|---|---|---|
| 2034 | | 465 | 466 |
| 2035 | | 480 | 481 |

TABLE 2B-continued
THE [4,4,0]REVERSE TURN MIMETICS LIBRARY
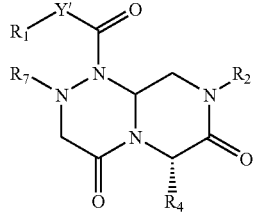
| No | MOLSTRUCTURE | Mol. Weight | M + H (MS) |
|---|---|---|---|
| 2036 | 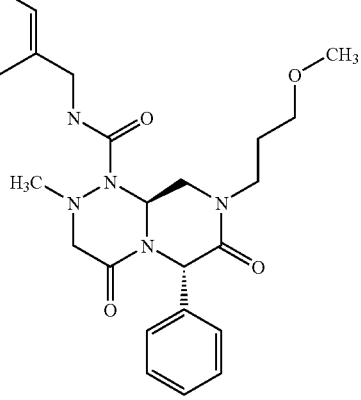 | 484 | 485 |
| 2037 | 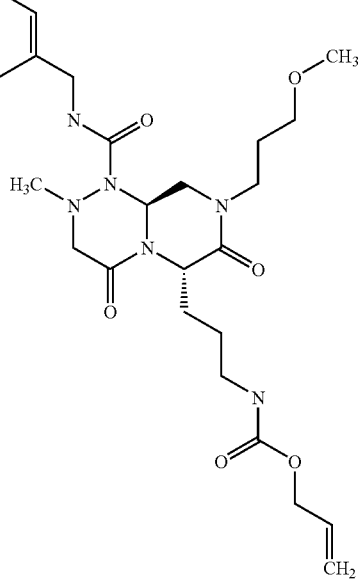 | 549 | 550 |

TABLE 2B-continued
THE [4,4,0]REVERSE TURN MIMETICS LIBRARY
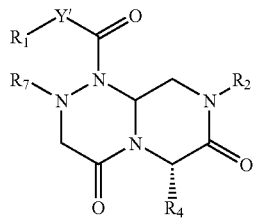
| No | MOLSTRUCTURE | Mol. Weight | M + H (MS) |
|---|---|---|---|
| 2038 | 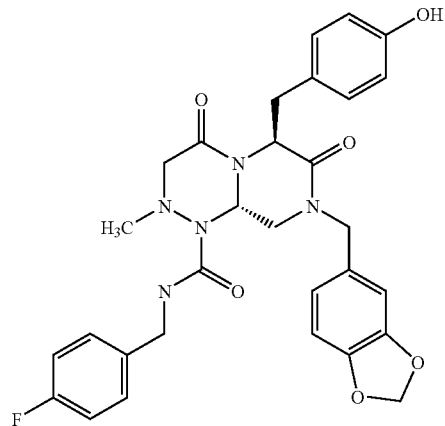 | 576 | 577 |
| 2039 | 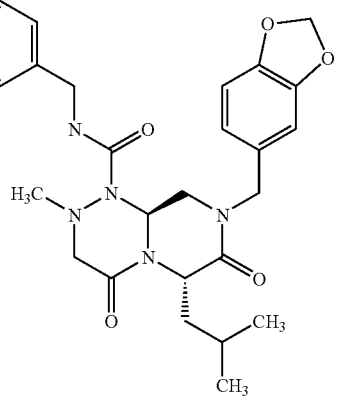 | 526 | 527 |

TABLE 2B-continued
THE [4,4,0]REVERSE TURN MIMETICS LIBRARY
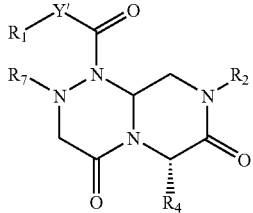
| No | MOLSTRUCTURE | Mol. Weight | M + H (MS) |
|---|---|---|---|
| 2040 | 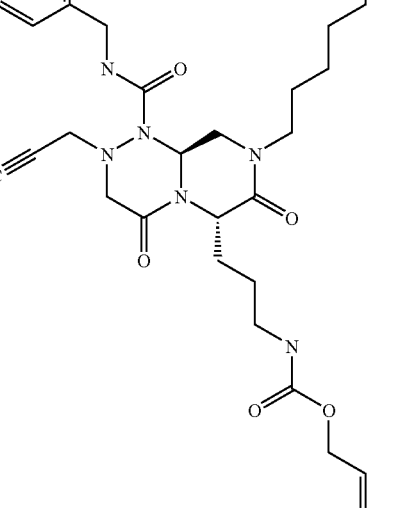 | 512 | 513 |
| 2041 | 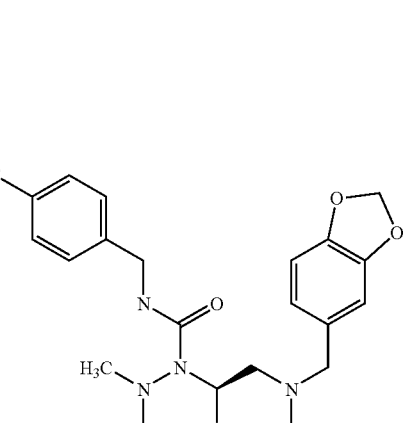 | 546 | 547 |

TABLE 2B-continued
THE [4,4,0]REVERSE TURN MIMETICS LIBRARY
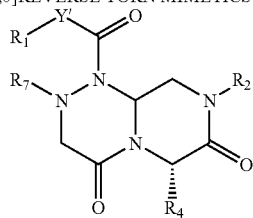
| No | MOLSTRUCTURE | Mol. Weight | M + H (MS) |
|---|---|---|---|
| 2042 | | 526 | 527 |
| 2043 | | 526 | 527 |
| 2044 | | 544 | 545 |

TABLE 2B-continued
THE [4,4,0]REVERSE TURN MIMETICS LIBRARY
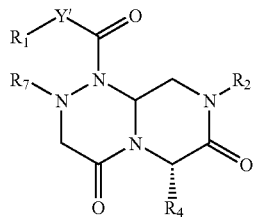
| No | MOLSTRUCTURE | Mol. Weight | M + H (MS) |
|---|---|---|---|
| 2045 | 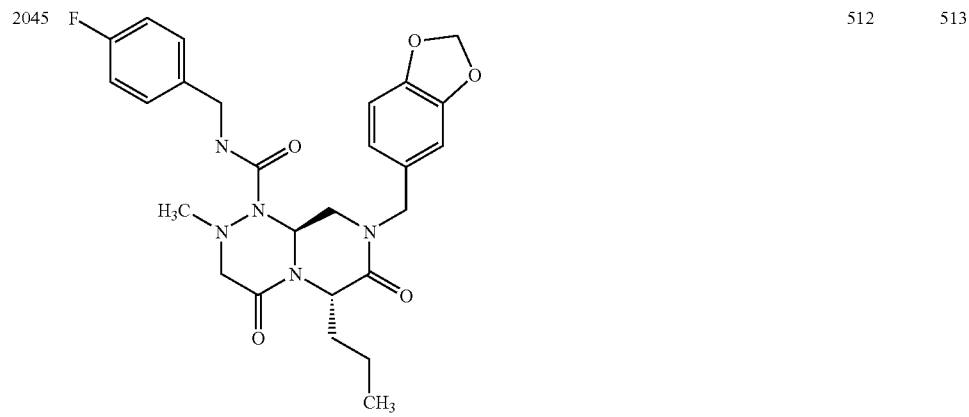 | 512 | 513 |
| 2046 | 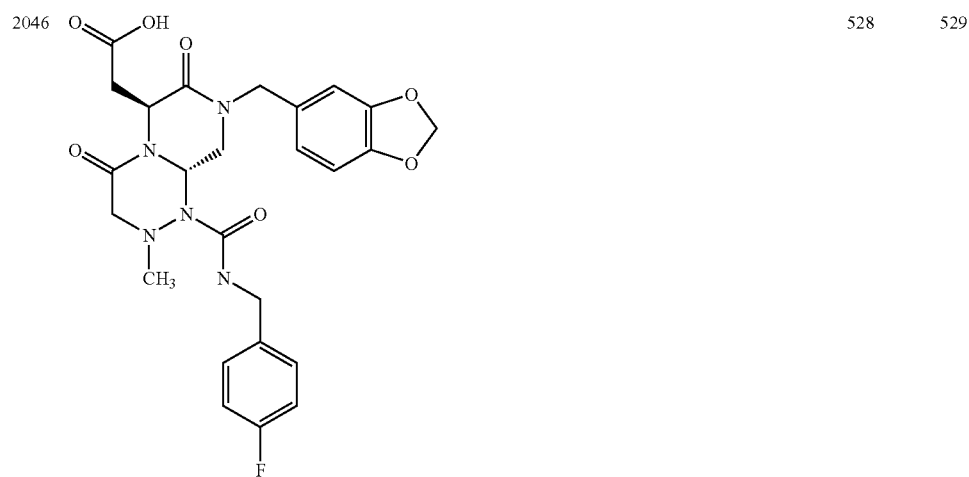 | 528 | 529 |

TABLE 2B-continued
THE [4,4,0]REVERSE TURN MIMETICS LIBRARY
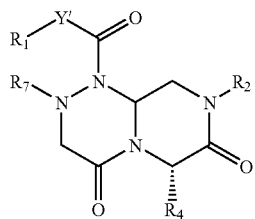
| No | MOLSTRUCTURE | Mol. Weight | M + H (MS) |
|---|---|---|---|
| 2047 | 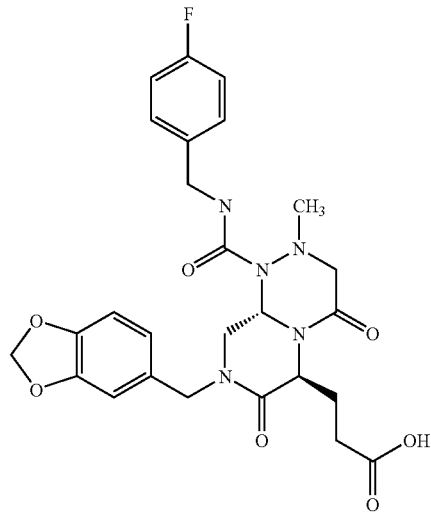 | 542 | 543 |
| 2048 | 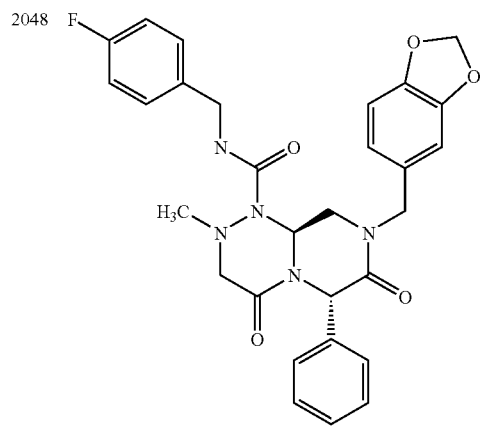 | 546 | 547 |

TABLE 2B-continued
THE [4,4,0]REVERSE TURN MIMETICS LIBRARY
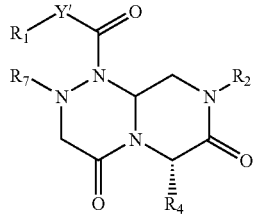
| No | MOLSTRUCTURE | Mol. Weight | M + H (MS) |
|----|--------------|-------------|------------|
| 2049 | | 613 | 612 |
| 2050 | | 562 | 563 |

TABLE 2B-continued
THE [4,4,0]REVERSE TURN MIMETICS LIBRARY
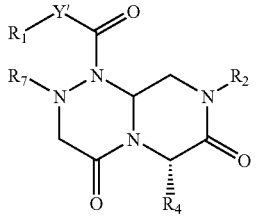
| No | MOLSTRUCTURE | Mol. Weight | M + H (MS) |
|---|---|---|---|
| 2051 | | 512 | 513 |
| 2052 | | 498 | 499 |
| 2053 | | 546 | 547 |

TABLE 2B-continued
THE [4,4,0]REVERSE TURN MIMETICS LIBRARY
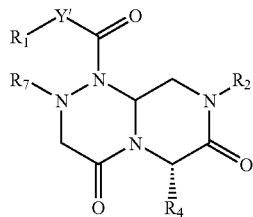
| No | MOLSTRUCTURE | Mol. Weight | M + H (MS) |
|---|---|---|---|
| 2054 | | 512 | 513 |
| 2055 | | 512 | 513 |
| 2056 | | 530 | 531 |

TABLE 2B-continued
THE [4,4,0]REVERSE TURN MIMETICS LIBRARY
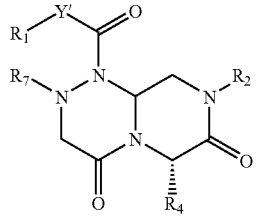
| No | MOLSTRUCTURE | Mol. Weight | M + H (MS) |
|---|---|---|---|
| 2057 | | 498 | 499 |
| 2058 | | 514 | 515 |

TABLE 2B-continued
THE [4,4,0]REVERSE TURN MIMETICS LIBRARY
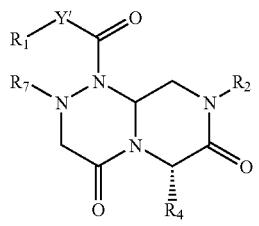
| No | MOLSTRUCTURE | Mol. Weight | M + H (MS) |
|---|---|---|---|
| 2059 | 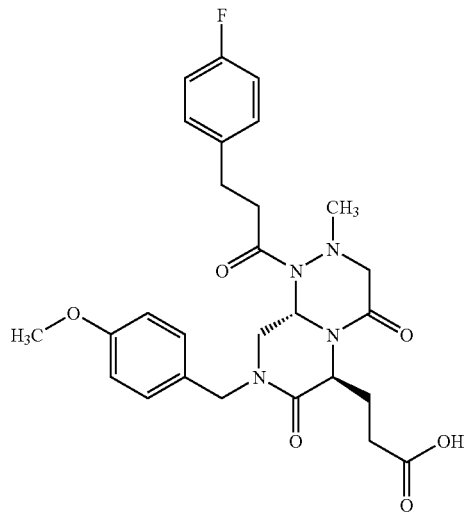 | 528 | 529 |
| 2060 | 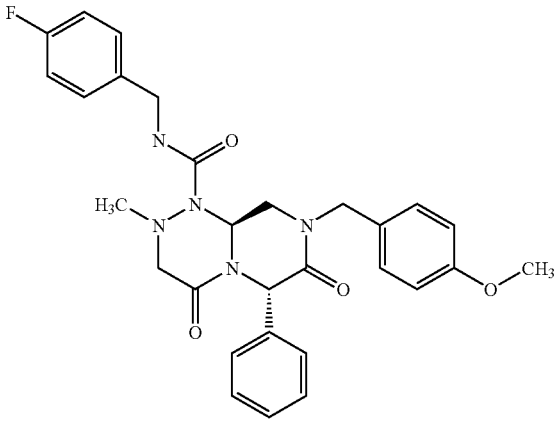 | 532 | 533 |

TABLE 2B-continued
THE [4,4,0]REVERSE TURN MIMETICS LIBRARY
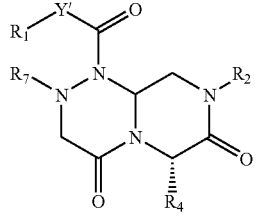
| No | MOLSTRUCTURE | Mol. Weight | M + H (MS) |
|---|---|---|---|
| 2061 | | 597 | 598 |
| 2062 | | 532 | 533 |

TABLE 2B-continued
THE [4,4,0]REVERSE TURN MIMETICS LIBRARY
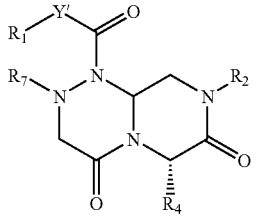
| No | MOLSTRUCTURE | Mol. Weight | M + H (MS) |
|---|---|---|---|
| 2063 | | 482 | 483 |
| 2064 | | 468 | 469 |
| 2065 | | 516 | 517 |

TABLE 2B-continued
THE [4,4,0]REVERSE TURN MIMETICS LIBRARY

| No | MOLSTRUCTURE | Mol. Weight | M + H (MS) |
|---|---|---|---|
| 2066 | | 482 | 483 |
| 2067 | | 482 | 483 |
| 2068 | | 500 | 501 |

TABLE 2B-continued
THE [4,4,0]REVERSE TURN MIMETICS LIBRARY
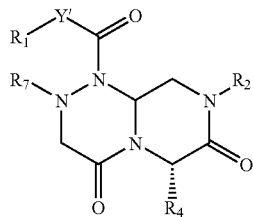
| No | MOLSTRUCTURE | Mol. Weight | M + H (MS) |
|---|---|---|---|
| 2069 | | 468 | 469 |
| 2070 | | 484 | 485 |

TABLE 2B-continued
THE [4,4,0]REVERSE TURN MIMETICS LIBRARY
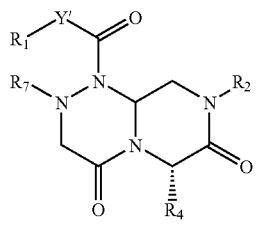
| No | MOLSTRUCTURE | Mol. Weight | M + H (MS) |
|---|---|---|---|
| 2071 | 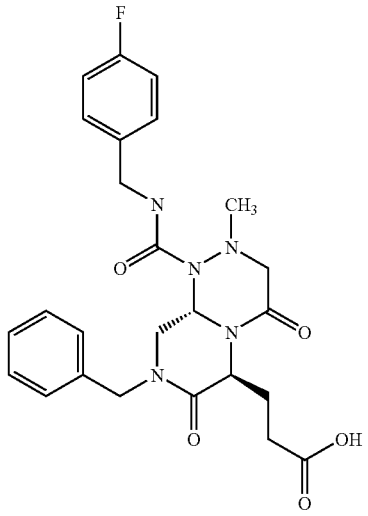 | 498 | 499 |
| 2072 | 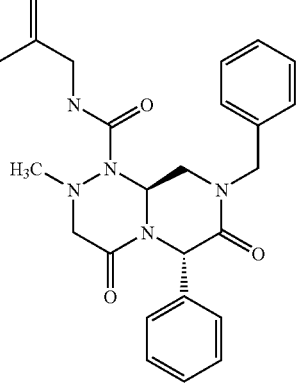 | 502 | 503 |

TABLE 2B-continued
THE [4,4,0]REVERSE TURN MIMETICS LIBRARY
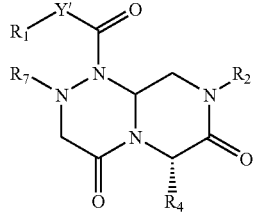
| No | MOLSTRUCTURE | Mol. Weight | M + H (MS) |
|---|---|---|---|
| 2073 | | 567 | 568 |
| 2074 | | 498 | 499 |

TABLE 2B-continued
THE [4,4,0]REVERSE TURN MIMETICS LIBRARY
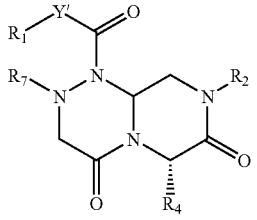
| No | MOLSTRUCTURE | Mol. Weight | M + H (MS) |
|---|---|---|---|
| 2075 | | 448 | 449 |
| 2076 | | 434 | 435 |
| 2077 | | 482 | 483 |

TABLE 2B-continued
THE [4,4,0]REVERSE TURN MIMETICS LIBRARY

| No | MOLSTRUCTURE | Mol. Weight | M + H (MS) |
|---|---|---|---|
| 2078 | | 448 | 449 |
| 2079 | | 448 | 449 |
| 2080 | | 466 | 467 |

TABLE 2B-continued
THE [4,4,0]REVERSE TURN MIMETICS LIBRARY
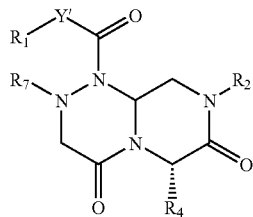
| No | MOLSTRUCTURE | Mol. Weight | M + H (MS) |
|---|---|---|---|
| 2081 | | 434 | 435 |
| 2082 | | 449 | 450 |

TABLE 2B-continued
THE [4,4,0]REVERSE TURN MIMETICS LIBRARY
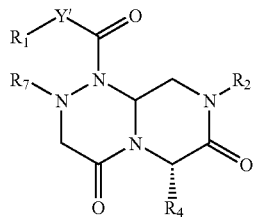
| No | MOLSTRUCTURE | Mol. Weight | M + H (MS) |
|---|---|---|---|
| 2083 | 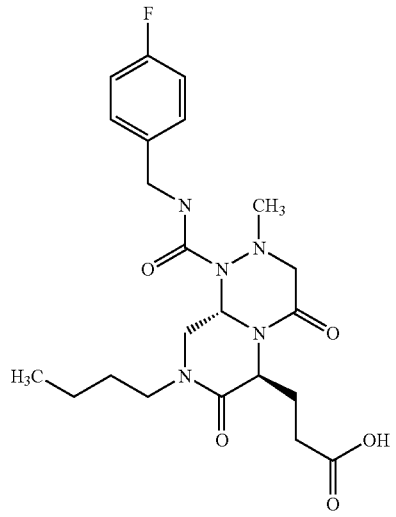 | 464 | 465 |
| 2084 | 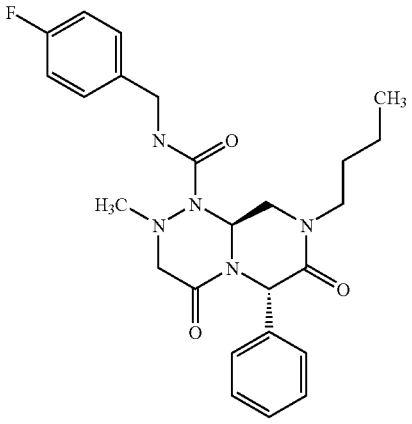 | 468 | 469 |

TABLE 2B-continued
THE [4,4,0]REVERSE TURN MIMETICS LIBRARY
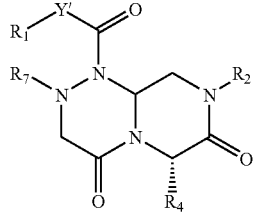
| No | MOLSTRUCTURE | Mol. Weight | M + H (MS) |
|---|---|---|---|
| 2085 | | 533 | 534 |
| 2086 | | 522 | 523 |

TABLE 2B-continued
THE [4,4,0]REVERSE TURN MIMETICS LIBRARY
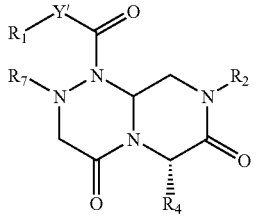
| No | MOLSTRUCTURE | Mol. Weight | M + H (MS) |
|---|---|---|---|
| 2087 | | 472 | 473 |
| 2088 | | 458 | 459 |
| 2089 | | 506 | 507 |

TABLE 2B-continued
THE [4,4,0]REVERSE TURN MIMETICS LIBRARY
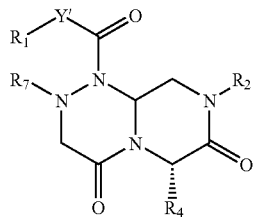
| No | MOLSTRUCTURE | Mol. Weight | M + H (MS) |
|---|---|---|---|
| 2090 | | 472 | 473 |
| 2091 | | 472 | 473 |
| 2092 | | 490 | 491 |

TABLE 2B-continued
THE [4,4,0]REVERSE TURN MIMETICS LIBRARY
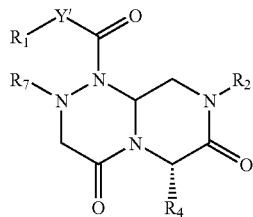
| No | MOLSTRUCTURE | Mol. Weight | M + H (MS) |
|---|---|---|---|
| 2093 | | 458 | 459 |
| 2094 | | 473 | 474 |

TABLE 2B-continued
THE [4,4,0]REVERSE TURN MIMETICS LIBRARY
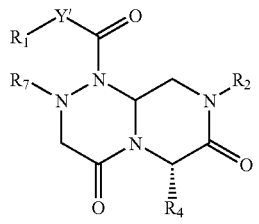
| No | MOLSTRUCTURE | Mol. Weight | M + H (MS) |
|---|---|---|---|
| 2095 | 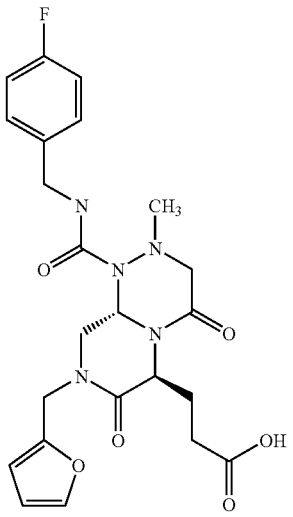 | 487 | 488 |
| 2096 | 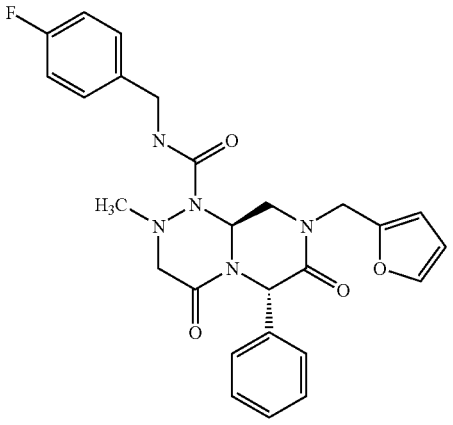 | 492 | 493 |

TABLE 2B-continued
THE [4,4,0]REVERSE TURN MIMETICS LIBRARY
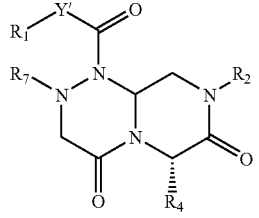
| No | MOLSTRUCTURE | Mol. Weight | M + H (MS) |
|---|---|---|---|
| 2097 | | 557 | 558 |
| 2098 | | 622 | 623 |

TABLE 2B-continued
THE [4,4,0]REVERSE TURN MIMETICS LIBRARY
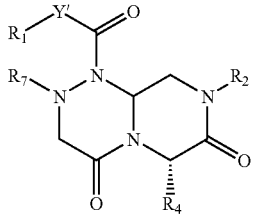
| No | MOLSTRUCTURE | Mol. Weight | M + H (MS) |
|---|---|---|---|
| 2099 | | 572 | 573 |
| 2100 | | 558 | 559 |
| 2101 | | 606 | 607 |

TABLE 2B-continued
THE [4,4,0]REVERSE TURN MIMETICS LIBRARY
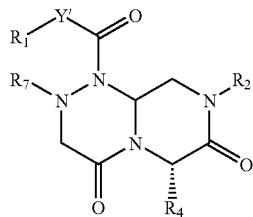
| No | MOLSTRUCTURE | Mol. Weight | M + H (MS) |
|---|---|---|---|
| 2102 | | 572 | 573 |
| 2103 | | 572 | 573 |
| 2104 | | 590 | 591 |

TABLE 2B-continued
THE [4,4,0]REVERSE TURN MIMETICS LIBRARY
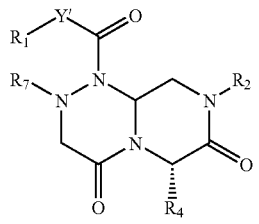
| No | MOLSTRUCTURE | Mol. Weight | M + H (MS) |
|---|---|---|---|
| 2105 | | 558 | 559 |
| 2106 | | 574 | 575 |

TABLE 2B-continued
THE [4,4,0]REVERSE TURN MIMETICS LIBRARY
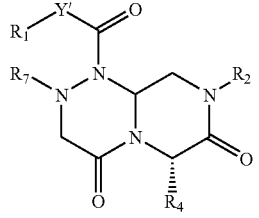
| No | MOLSTRUCTURE | Mol. Weight | M + H (MS) |
|---|---|---|---|
| 2107 | | 588 | 589 |
| 2108 | | 592 | 593 |

TABLE 2B-continued
THE [4,4,0]REVERSE TURN MIMETICS LIBRARY
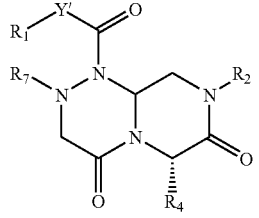
| No | MOLSTRUCTURE | Mol. Weight | M + H (MS) |
|---|---|---|---|
| 2109 | | 657 | 658 |
| 2100 | | 600 | 601 |

TABLE 2B-continued
THE [4,4,0]REVERSE TURN MIMETICS LIBRARY
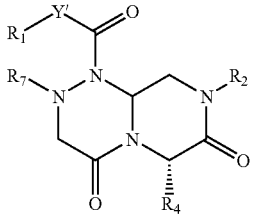
| No | MOLSTRUCTURE | Mol. Weight | M + H (MS) |
|---|---|---|---|
| 2111 | | 550 | 551 |
| 2112 | | 536 | 537 |
| 2113 | | 584 | 585 |

TABLE 2B-continued
THE [4,4,0]REVERSE TURN MIMETICS LIBRARY
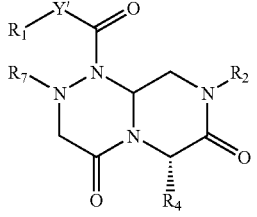
| No | MOLSTRUCTURE | Mol. Weight | M + H (MS) |
|---|---|---|---|
| 2114 | | 550 | 551 |
| 2115 | | 550 | 551 |
| 2116 | | 569 | 570 |

TABLE 2B-continued
THE [4,4,0]REVERSE TURN MIMETICS LIBRARY
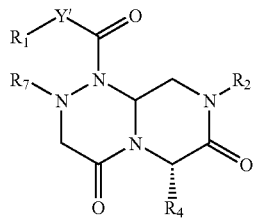
| No | MOLSTRUCTURE | Mol. Weight | M + H (MS) |
|----|--------------|-------------|------------|
| 2117 | | 536 | 537 |
| 2118 | | 552 | 553 |

TABLE 2B-continued
THE [4,4,0]REVERSE TURN MIMETICS LIBRARY
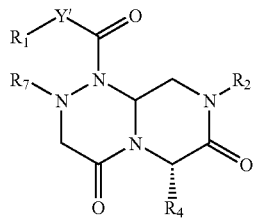
| No | MOLSTRUCTURE | Mol. Weight | M + H (MS) |
|---|---|---|---|
| 2119 | 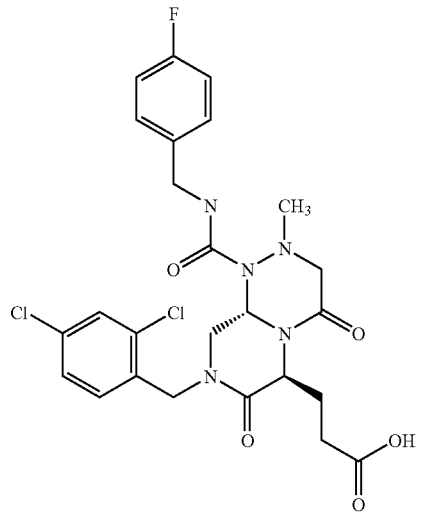 | 566 | 567 |
| 2110 | 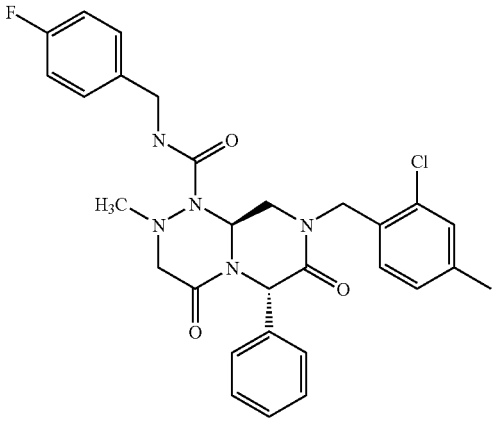 | 570 | 571 |

TABLE 2B-continued
THE [4,4,0]REVERSE TURN MIMETICS LIBRARY
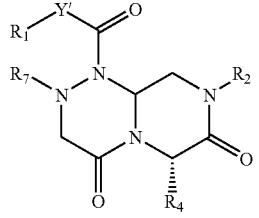
| No | MOLSTRUCTURE | Mol. Weight | M + H (MS) |
|---|---|---|---|
| 2121 | | 636 | 637 |
| 2122 | | 500 | 501 |

TABLE 2B-continued
THE [4,4,0]REVERSE TURN MIMETICS LIBRARY
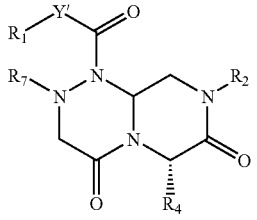
| No | MOLSTRUCTURE | Mol. Weight | M + H (MS) |
|---|---|---|---|
| 2123 | | 450 | 451 |
| 2124 | | 436 | 437 |
| 2125 | | 484 | 485 |

TABLE 2B-continued
THE [4,4,0]REVERSE TURN MIMETICS LIBRARY
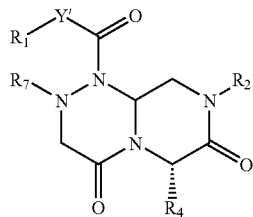
| No | MOLSTRUCTURE | Mol. Weight | M + H (MS) |
|---|---|---|---|
| 2126 | | 450 | 451 |
| 2127 | | 450 | 451 |
| 2128 | | 468 | 469 |

TABLE 2B-continued
THE [4,4,0]REVERSE TURN MIMETICS LIBRARY
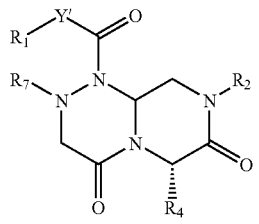
| No | MOLSTRUCTURE | Mol. Weight | M + H (MS) |
|---|---|---|---|
| 2129 | | 436 | 437 |
| 2130 | | 451 | 452 |

TABLE 2B-continued
THE [4,4,0]REVERSE TURN MIMETICS LIBRARY
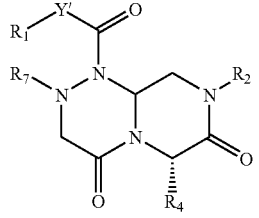
| No | MOLSTRUCTURE | Mol. Weight | M + H (MS) |
|---|---|---|---|
| 2131 | 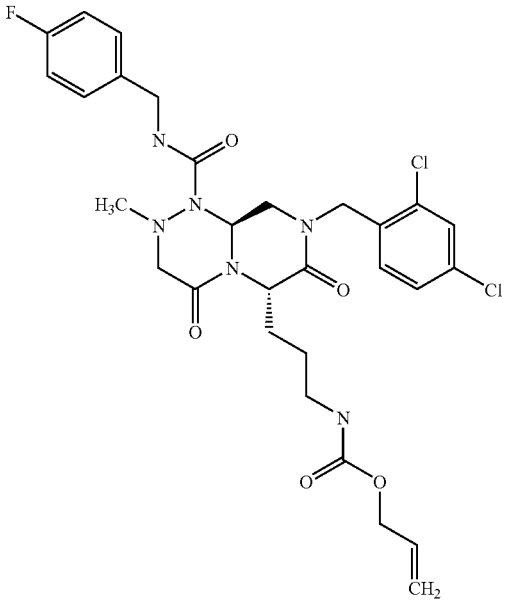 | 465 | 466 |
| 2132 | 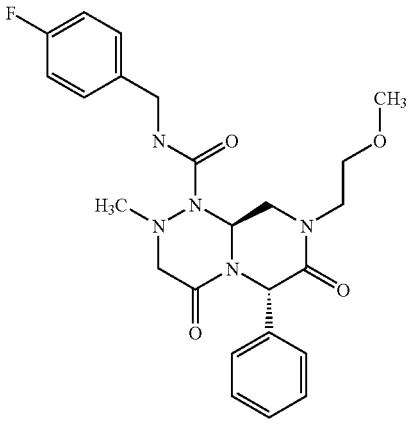 | 470 | 471 |

TABLE 2B-continued
THE [4,4,0]REVERSE TURN MIMETICS LIBRARY
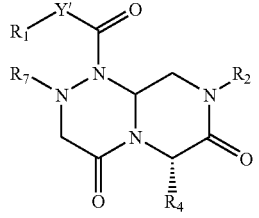
| No | MOLSTRUCTURE | Mol. Weight | M + H (MS) |
|---|---|---|---|
| 2133 | | 535 | 536 |
| 2134 | | 546 | 547 |

TABLE 2B-continued
THE [4,4,0]REVERSE TURN MIMETICS LIBRARY
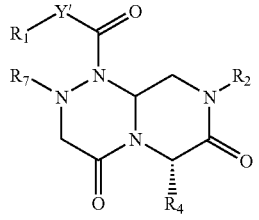
| No | MOLSTRUCTURE | Mol. Weight | M + H (MS) |
|---|---|---|---|
| 2135 | | 496 | 497 |
| 2136 | | 482 | 483 |
| 2137 | | 530 | 531 |

TABLE 2B-continued
THE [4,4,0]REVERSE TURN MIMETICS LIBRARY
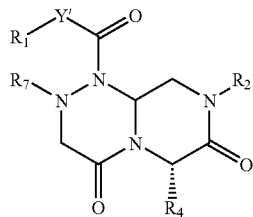
| No | MOLSTRUCTURE | Mol. Weight | M + H (MS) |
|---|---|---|---|
| 2138 | | 496 | 497 |
| 2139 | | 496 | 497 |
| 2140 | | 514 | 515 |

TABLE 2B-continued
THE [4,4,0]REVERSE TURN MIMETICS LIBRARY
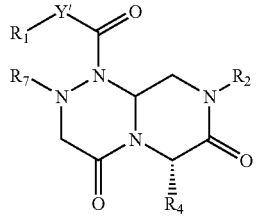
| No | MOLSTRUCTURE | Mol. Weight | M + H (MS) |
|---|---|---|---|
| 2141 | | 482 | 483 |
| 2142 | | 498 | 499 |

TABLE 2B-continued
THE [4,4,0]REVERSE TURN MIMETICS LIBRARY
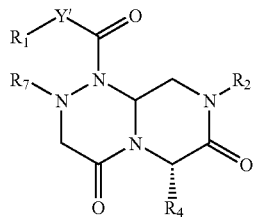
| No | MOLSTRUCTURE | Mol. Weight | M + H (MS) |
|----|--------------|-------------|------------|
| 2143 | 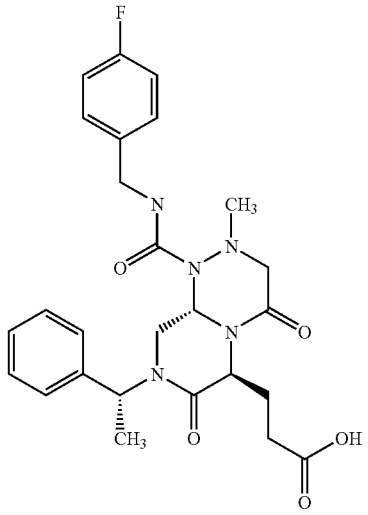 | 512 | 513 |
| 2144 | 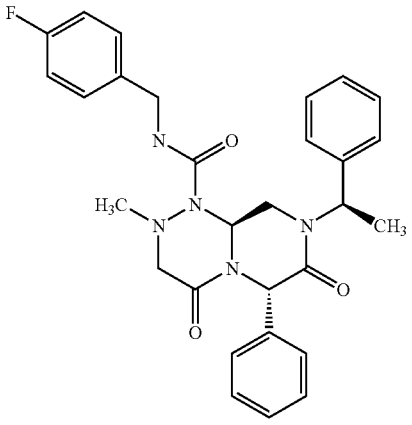 | 516 | 517 |

TABLE 2B-continued
THE [4,4,0]REVERSE TURN MIMETICS LIBRARY
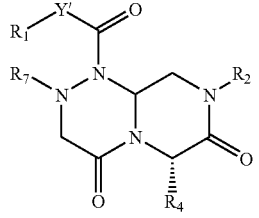
| No | MOLSTRUCTURE | Mol. Weight | M + H (MS) |
|----|--------------|-------------|------------|
| 2145 | | 581 | 582 |
| 2146 | | 566 | 567 |

TABLE 2B-continued
THE [4,4,0]REVERSE TURN MIMETICS LIBRARY
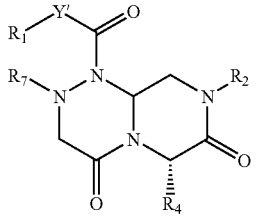
| No | MOLSTRUCTURE | Mol. Weight | M + H (MS) |
|---|---|---|---|
| 2147 | | 516 | 517 |
| 2148 | | 502 | 503 |
| 2149 | | 550 | 551 |

TABLE 2B-continued
THE [4,4,0]REVERSE TURN MIMETICS LIBRARY
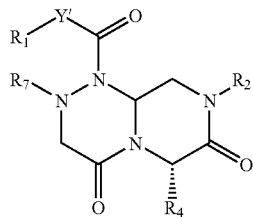
| No | MOLSTRUCTURE | Mol. Weight | M + H (MS) |
|---|---|---|---|
| 2150 | | 516 | 517 |
| 2151 | | 516 | 517 |
| 2152 | | 534 | 535 |

TABLE 2B-continued
THE [4,4,0]REVERSE TURN MIMETICS LIBRARY
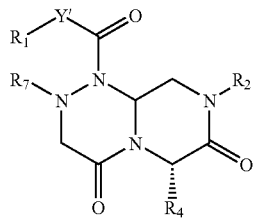
| No | MOLSTRUCTURE | Mol. Weight | M + H (MS) |
|----|--------------|-------------|------------|
| 2153 | | 502 | 503 |
| 2154 | | 518 | 519 |

1101 1102
TABLE 2B-continued
THE [4,4,0]REVERSE TURN MIMETICS LIBRARY
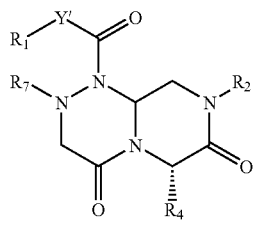
| No | MOLSTRUCTURE | Mol. Weight | M + H (MS) |
|---|---|---|---|
| 2155 | 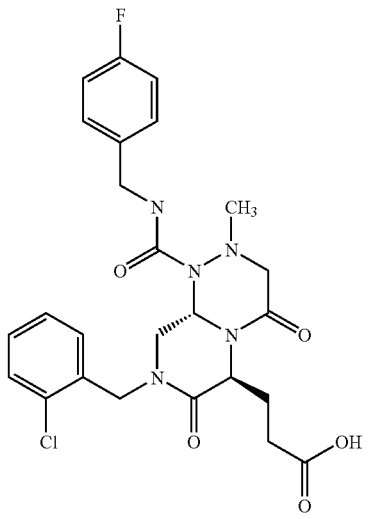 | 532 | 533 |
| 2156 | 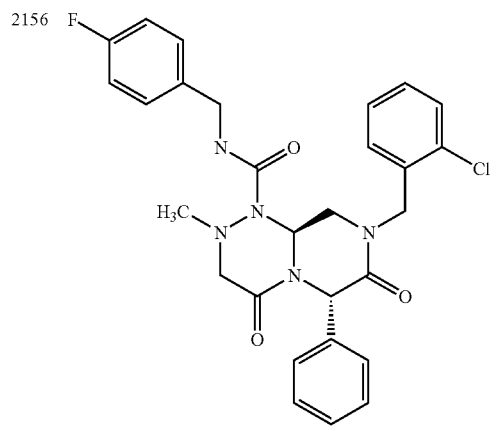 | 536 | 537 |

TABLE 2B-continued
THE [4,4,0]REVERSE TURN MIMETICS LIBRARY
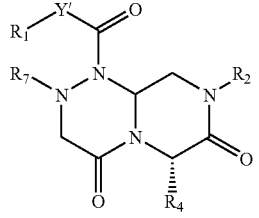
| No | MOLSTRUCTURE | Mol. Weight | M + H (MS) |
|---|---|---|---|
| 2157 | | 601 | 602 |
| 2158 | | 600 | 601 |
| 2159 | | 550 | 551 |

TABLE 2B-continued
THE [4,4,0]REVERSE TURN MIMETICS LIBRARY
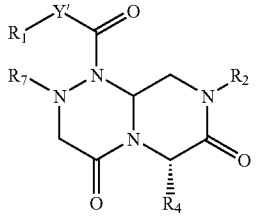
| No | MOLSTRUCTURE | Mol. Weight | M + H (MS) |
|---|---|---|---|
| 2160 | | 536 | 537 |
| 2161 | | 584 | 585 |
| 2162 | | 550 | 551 |

TABLE 2B-continued

THE [4,4,0]REVERSE TURN MIMETICS LIBRARY

| No | MOLSTRUCTURE | Mol. Weight | M + H (MS) |
|---|---|---|---|
| 2163 | | 550 | 570 |
| 2164 | | 569 | 570 |
| 2165 | | 536 | 537 |

TABLE 2B-continued
THE [4,4,0]REVERSE TURN MIMETICS LIBRARY
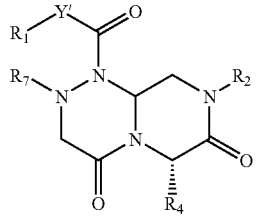
| No | MOLSTRUCTURE | Mol. Weight | M + H (MS) |
|----|--------------|-------------|------------|
| 2166 | | 552 | 553 |
| 2167 | | 566 | 567 |

TABLE 2B-continued
THE [4,4,0]REVERSE TURN MIMETICS LIBRARY
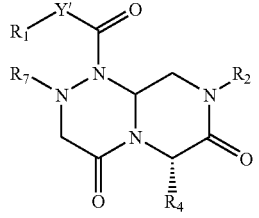
| No | MOLSTRUCTURE | Mol. Weight | M + H (MS) |
|---|---|---|---|
| 2168 | | 570 | 471 |
| 2169 | | 636 | 637 |

TABLE 2B-continued
THE [4,4,0]REVERSE TURN MIMETICS LIBRARY
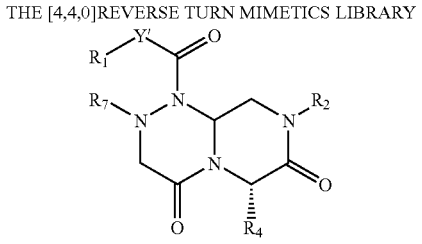
| No | MOLSTRUCTURE | Mol. Weight | M + H (MS) |
|---|---|---|---|
| 2170 | | 546 | 547 |
| 2171 | | 496 | 497 |
| 2172 | | 482 | 483 |

TABLE 2B-continued
THE [4,4,0]REVERSE TURN MIMETICS LIBRARY
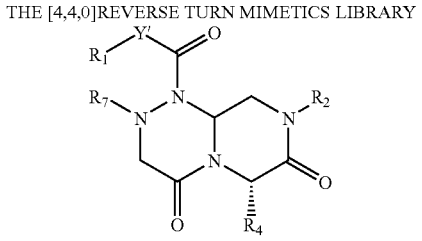
| No | MOLSTRUCTURE | Mol. Weight | M + H (MS) |
|----|--------------|-------------|------------|
| 2173 | | 530 | 531 |
| 2174 | | 496 | 497 |
| 2175 | | 496 | 497 |

TABLE 2B-continued
THE [4,4,0]REVERSE TURN MIMETICS LIBRARY
| No | MOLSTRUCTURE | Mol. Weight | M + H (MS) |
|---|---|---|---|
| 2176 |  | 514 | 515 |
| 2177 |  | 482 | 483 |
| 2178 | 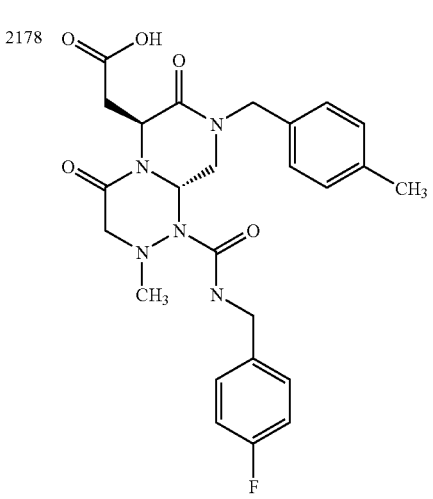 | 498 | 499 |

TABLE 2B-continued
THE [4,4,0]REVERSE TURN MIMETICS LIBRARY
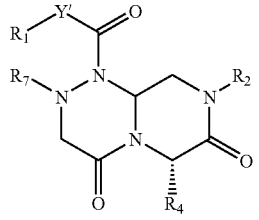
| No | MOLSTRUCTURE | Mol. Weight | M + H (MS) |
|---|---|---|---|
| 2179 | 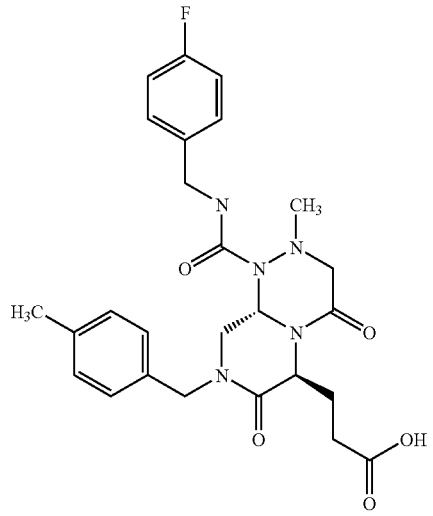 | 612 | 613 |
| 2180 | 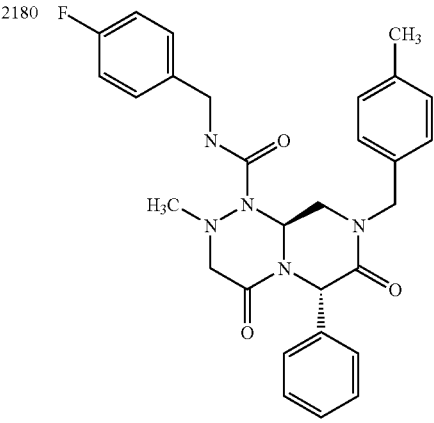 | 516 | 517 |

TABLE 2B-continued
THE [4,4,0]REVERSE TURN MIMETICS LIBRARY
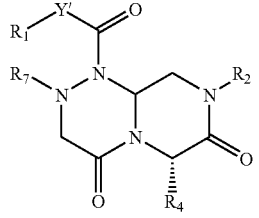
| No | MOLSTRUCTURE | Mol. Weight | M + H (MS) |
|---|---|---|---|
| 2181 | | 581 | 582 |
| 2182 | | 546 | 547 |

TABLE 2B-continued
THE [4,4,0]REVERSE TURN MIMETICS LIBRARY
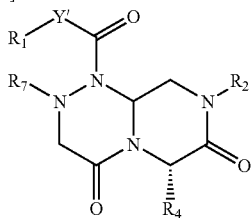
| No | MOLSTRUCTURE | Mol. Weight | M + H (MS) |
|---|---|---|---|
| 2183 | | 496 | 497 |
| 2184 | | 482 | 483 |
| 2185 | | 530 | 531 |

TABLE 2B-continued
THE [4,4,0]REVERSE TURN MIMETICS LIBRARY
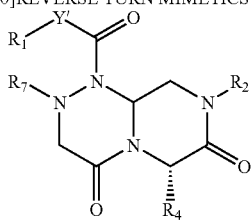
| No | MOLSTRUCTURE | Mol. Weight | M + H (MS) |
|---|---|---|---|
| 2186 | | 496 | 497 |
| 2187 | | 496 | 497 |
| 2188 | | 514 | 515 |

TABLE 2B-continued
THE [4,4,0]REVERSE TURN MIMETICS LIBRARY
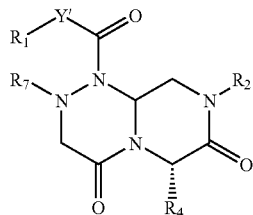
| No | MOLSTRUCTURE | Mol. Weight | M + H (MS) |
|----|--------------|-------------|------------|
| 2189 | | 482 | 483 |
| 2190 | | 498 | 499 |

US 7,566,711 B2
TABLE 2B-continued
THE [4,4,0]REVERSE TURN MIMETICS LIBRARY
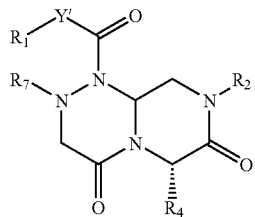
| No | MOLSTRUCTURE | Mol. Weight | M + H (MS) |
|----|---|---|---|
| 2191 | 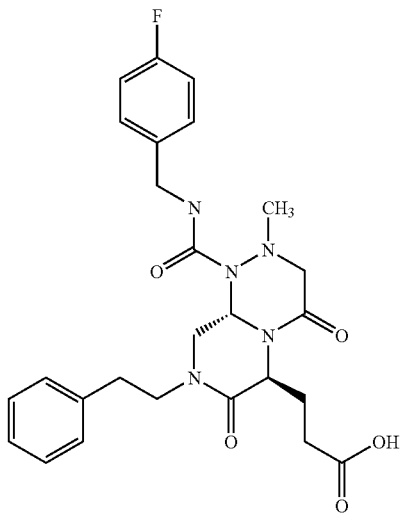 | 512 | 513 |
| 2192 | 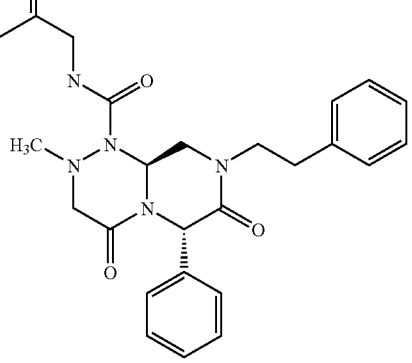 | 516 | 517 |

TABLE 2B-continued
THE [4,4,0]REVERSE TURN MIMETICS LIBRARY
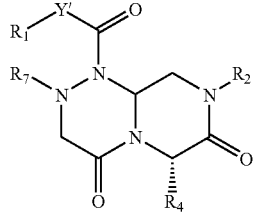
| No | MOLSTRUCTURE | Mol. Weight | M + H (MS) |
|---|---|---|---|
| 2193 | | 581 | 582 |
| 2194 | | 574 | 575 |

TABLE 2B-continued
THE [4,4,0]REVERSE TURN MIMETICS LIBRARY
| No | MOLSTRUCTURE | Mol. Weight | M + H (MS) |
|---|---|---|---|
| 2195 | | 524 | 525 |
| 2196 | | 510 | 511 |
| 2197 | | 558 | 559 |

TABLE 2B-continued
THE [4,4,0]REVERSE TURN MIMETICS LIBRARY
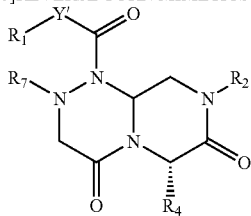
| No | MOLSTRUCTURE | Mol. Weight | M + H (MS) |
|---|---|---|---|
| 2198 | | 524 | 525 |
| 2199 | | 524 | 525 |
| 2190 | | 542 | 543 |

TABLE 2B-continued
THE [4,4,0]REVERSE TURN MIMETICS LIBRARY
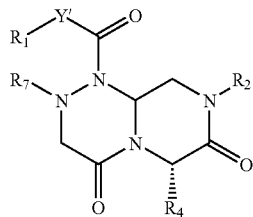
| No | MOLSTRUCTURE | Mol. Weight | M + H (MS) |
|---|---|---|---|
| 2201 | 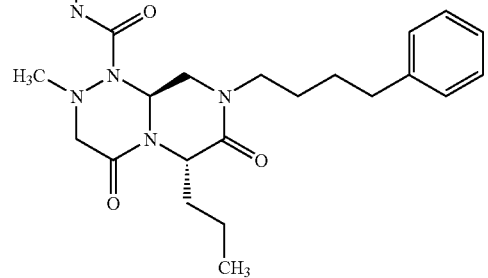 | 510 | 511 |
| 2202 | 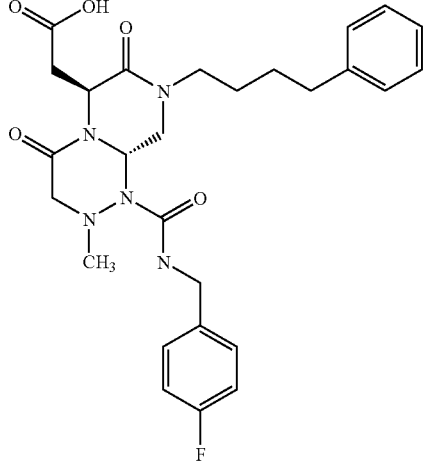 | 526 | 527 |

TABLE 2B-continued
THE [4,4,0]REVERSE TURN MIMETICS LIBRARY
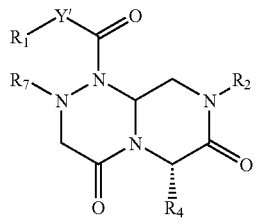
| No | MOLSTRUCTURE | Mol. Weight | M + H (MS) |
|----|--------------|-------------|------------|
| 2203 | 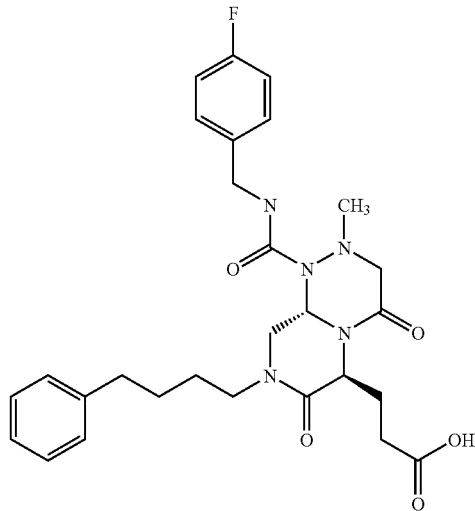 | 540 | 541 |
| 2204 | 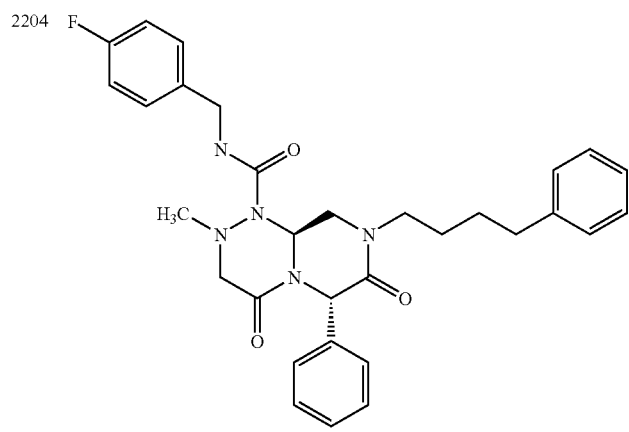 | 544 | 545 |

TABLE 2B-continued
THE [4,4,0]REVERSE TURN MIMETICS LIBRARY
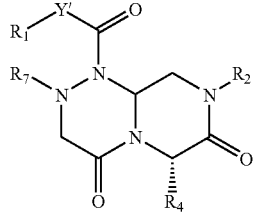
| No | MOLSTRUCTURE | Mol. Weight | M + H (MS) |
|----|--------------|-------------|------------|
| 2205 | | 609 | 610 |
| 2206 | | 546 | 547 |

TABLE 2B-continued
THE [4,4,0]REVERSE TURN MIMETICS LIBRARY
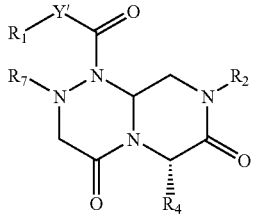
| No | MOLSTRUCTURE | Mol. Weight | M + H (MS) |
|---|---|---|---|
| 2207 | | 496 | 497 |
| 2208 | | 482 | 483 |
| 2209 | | 530 | 531 |

TABLE 2B-continued
THE [4,4,0]REVERSE TURN MIMETICS LIBRARY

| No | MOLSTRUCTURE | Mol. Weight | M + H (MS) |
|---|---|---|---|
| 2210 | | 496 | 497 |
| 2211 | | 496 | 497 |
| 2212 | | 514 | 515 |

TABLE 2B-continued
THE [4,4,0]REVERSE TURN MIMETICS LIBRARY
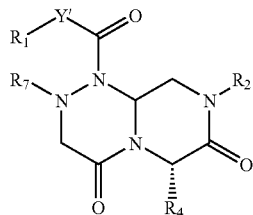
| No | MOLSTRUCTURE | Mol. Weight | M + H (MS) |
|---|---|---|---|
| 2213 | | 482 | 483 |
| 2214 | | 498 | 499 |

TABLE 2B-continued
THE [4,4,0]REVERSE TURN MIMETICS LIBRARY
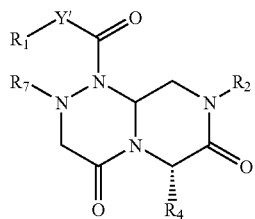
| No | MOLSTRUCTURE | Mol. Weight | M + H (MS) |
|---|---|---|---|
| 2215 | 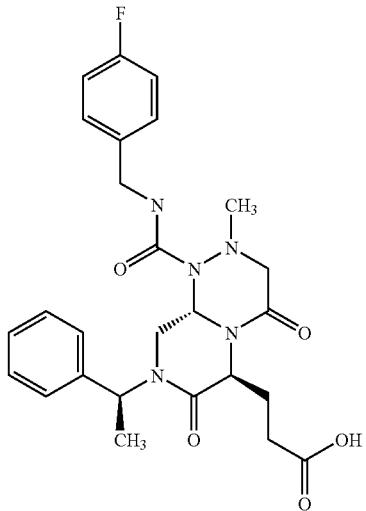 | 412 | 513 |
| 2216 | 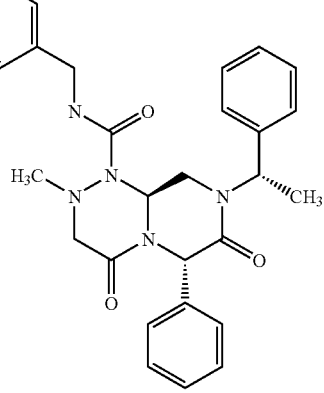 | 516 | 517 |

TABLE 2B-continued
THE [4,4,0]REVERSE TURN MIMETICS LIBRARY
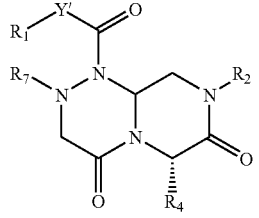
| No | MOLSTRUCTURE | Mol. Weight | M + H (MS) |
|---|---|---|---|
| 2217 | | 581 | 582 |
| 2218 | | 564 | 565 |

TABLE 2B-continued
THE [4,4,0]REVERSE TURN MIMETICS LIBRARY
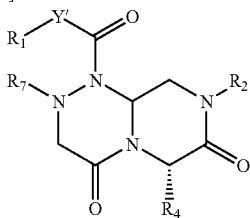
| No | MOLSTRUCTURE | Mol. Weight | M + H (MS) |
|---|---|---|---|
| 2219 | | 514 | 515 |
| 2220 | | 500 | 501 |
| 2221 | | 548 | 549 |

TABLE 2B-continued
THE [4,4,0]REVERSE TURN MIMETICS LIBRARY
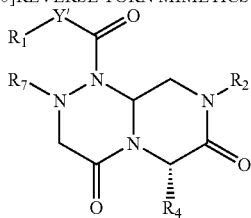
| No | MOLSTRUCTURE | Mol. Weight | M + H (MS) |
|---|---|---|---|
| 2222 | | 514 | 515 |
| 2223 | | 514 | 515 |
| 2224 | | 532 | 533 |

TABLE 2B-continued
THE [4,4,0]REVERSE TURN MIMETICS LIBRARY
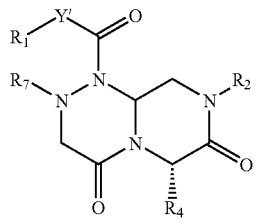
| No | MOLSTRUCTURE | Mol. Weight | M + H (MS) |
|---|---|---|---|
| 2225 | | 500 | 501 |
| 2226 | | 516 | 517 |

TABLE 2B-continued
THE [4,4,0]REVERSE TURN MIMETICS LIBRARY
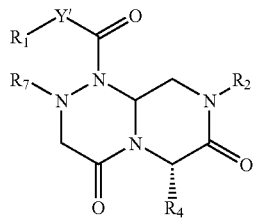
| No | MOLSTRUCTURE | Mol. Weight | M + H (MS) |
|---|---|---|---|
| 2227 | 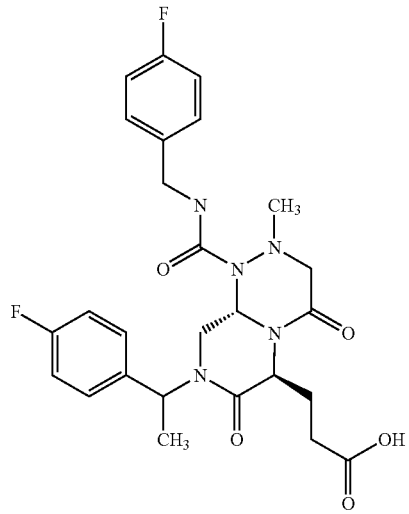 | 530 | 531 |
| 2228 | 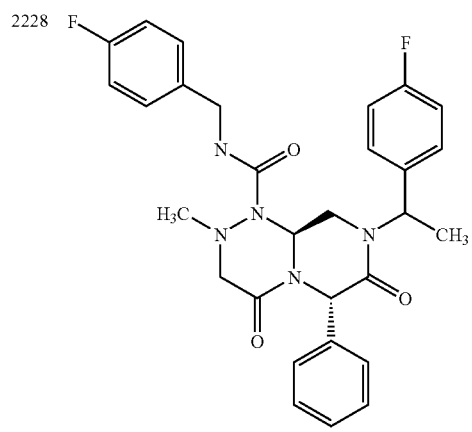 | 534 | 535 |

TABLE 2B-continued
THE [4,4,0]REVERSE TURN MIMETICS LIBRARY
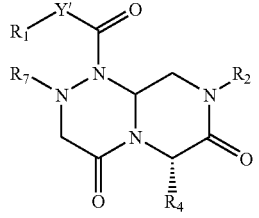
| No | MOLSTRUCTURE | Mol. Weight | M + H (MS) |
|---|---|---|---|
| 2229 | | 599 | 600 |
| 2230 | | 564 | 565 |

TABLE 2B-continued
THE [4,4,0]REVERSE TURN MIMETICS LIBRARY
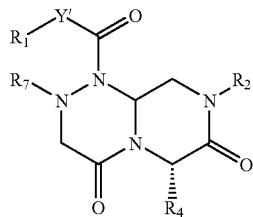
| No | MOLSTRUCTURE | Mol. Weight | M + H (MS) |
|---|---|---|---|
| 2231 | | 514 | 515 |
| 2232 | | 500 | 501 |
| 2233 | | 548 | 549 |

TABLE 2B-continued
THE [4,4,0]REVERSE TURN MIMETICS LIBRARY
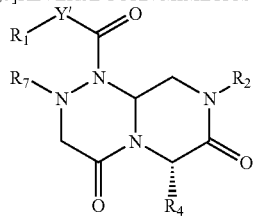
| No | MOLSTRUCTURE | Mol. Weight | M + H (MS) |
|---|---|---|---|
| 2234 | | 514 | 515 |
| 2235 | | 514 | 515 |
| 2236 | | 532 | 533 |

TABLE 2B-continued
THE [4,4,0]REVERSE TURN MIMETICS LIBRARY
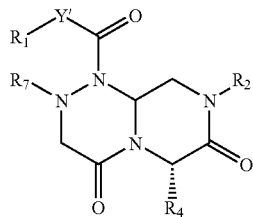
| No | MOLSTRUCTURE | Mol. Weight | M + H (MS) |
|----|--------------|-------------|------------|
| 2237 | 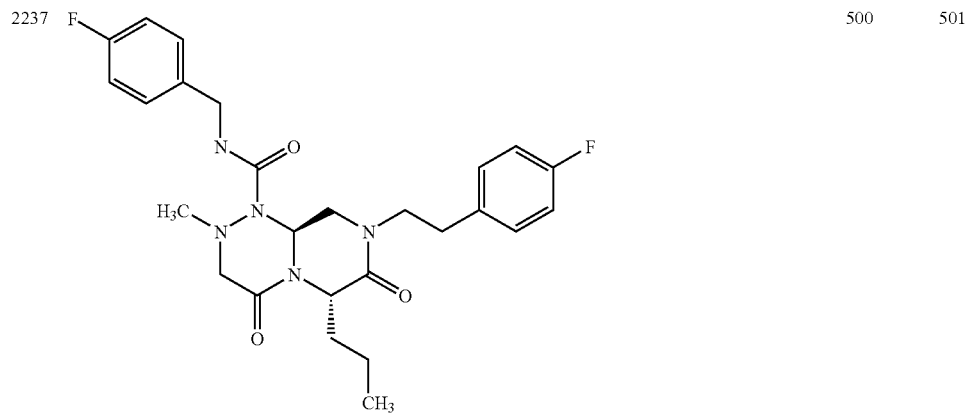 | 500 | 501 |
| 2238 |  | 517 | 517 |

TABLE 2B-continued
THE [4,4,0]REVERSE TURN MIMETICS LIBRARY
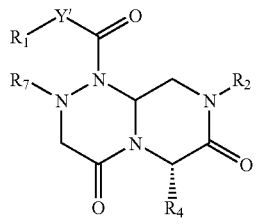
| No | MOLSTRUCTURE | Mol. Weight | M + H (MS) |
|---|---|---|---|
| 2239 | 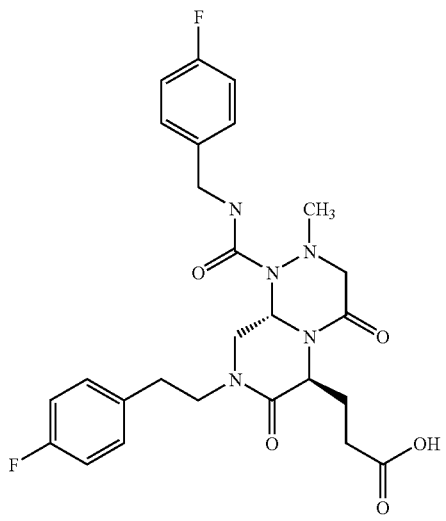 | 530 | 531 |
| 2240 | 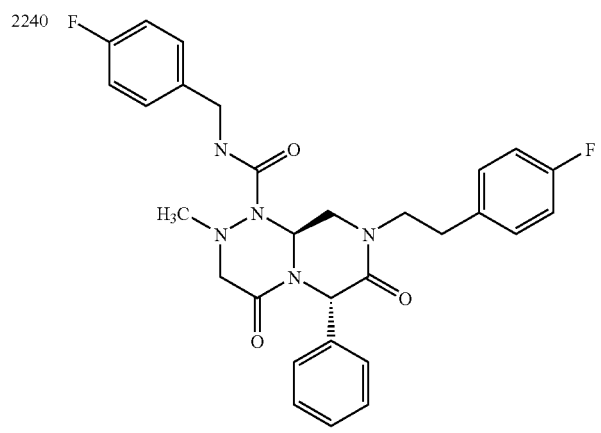 | 534 | 535 |

TABLE 2B-continued
THE [4,4,0]REVERSE TURN MIMETICS LIBRARY
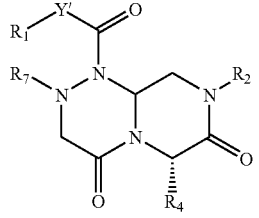
| No | MOLSTRUCTURE | Mol. Weight | M + H (MS) |
|----|--------------|-------------|------------|
| 2241 | | 599 | 600 |
| 2242 | | 582 | 583 |

TABLE 2B-continued
THE [4,4,0]REVERSE TURN MIMETICS LIBRARY
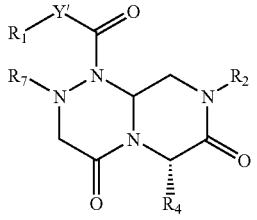
| No | MOLSTRUCTURE | Mol. Weight | M + H (MS) |
|---|---|---|---|
| 2243 | | 532 | 533 |
| 2244 | | 518 | 519 |
| 2245 | | 566 | 567 |

TABLE 2B-continued
THE [4,4,0]REVERSE TURN MIMETICS LIBRARY

| No | MOLSTRUCTURE | Mol. Weight | M + H (MS) |
|---|---|---|---|
| 2246 | | 532 | 533 |
| 2247 | | 532 | 533 |
| 2248 | | 550 | 551 |

TABLE 2B-continued
THE [4,4,0]REVERSE TURN MIMETICS LIBRARY
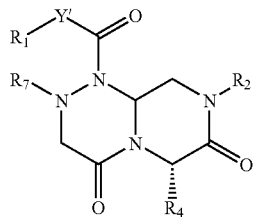
| No | MOLSTRUCTURE | Mol. Weight | M + H (MS) |
|---|---|---|---|
| 2249 | | 518 | 619 |
| 2250 | | 534 | 535 |

TABLE 2B-continued
THE [4,4,0]REVERSE TURN MIMETICS LIBRARY
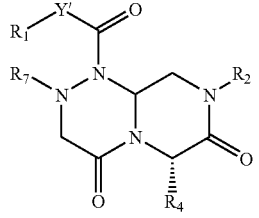
| No | MOLSTRUCTURE | Mol. Weight | M + H (MS) |
|---|---|---|---|
| 2251 | | 548 | 549 |
| 2252 | | 552 | 553 |

TABLE 2B-continued
THE [4,4,0]REVERSE TURN MIMETICS LIBRARY
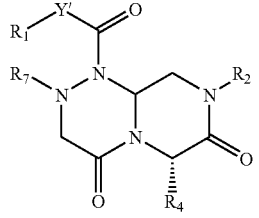
| No | MOLSTRUCTURE | Mol. Weight | M + H (MS) |
|---|---|---|---|
| 2253 | | 617 | 618 |
| 2254 | | 538 | 539 |

TABLE 2B-continued
THE [4,4,0]REVERSE TURN MIMETICS LIBRARY
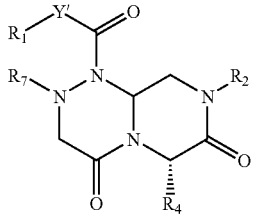
| No | MOLSTRUCTURE | Mol. Weight | M + H (MS) |
|---|---|---|---|
| 2255 | | 488 | 489 |
| 2256 | | 474 | 475 |
| 2257 | | 522 | 523 |

TABLE 2B-continued
THE [4,4,0]REVERSE TURN MIMETICS LIBRARY
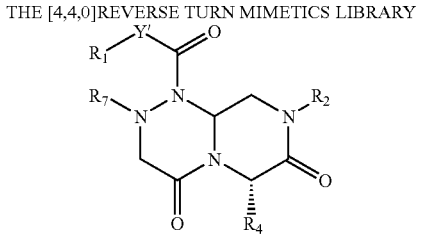
| No | MOLSTRUCTURE | Mol. Weight | M + H (MS) |
|---|---|---|---|
| 2258 | | 448 | 489 |
| 2259 | | 448 | 489 |
| 2260 | | 506 | 507 |

TABLE 2B-continued
THE [4,4,0]REVERSE TURN MIMETICS LIBRARY
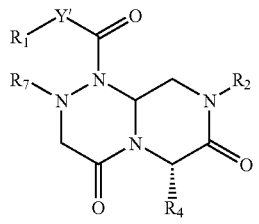
| No | MOLSTRUCTURE | Mol. Weight | M + H (MS) |
|----|--------------|-------------|------------|
| 2261 | | 474 | 475 |
| 2262 | | 490 | 491 |

TABLE 2B-continued
THE [4,4,0]REVERSE TURN MIMETICS LIBRARY
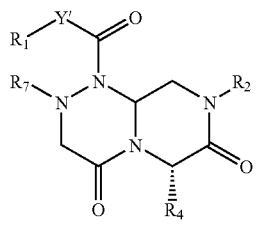
| No | MOLSTRUCTURE | Mol. Weight | M + H (MS) |
|---|---|---|---|
| 2263 | 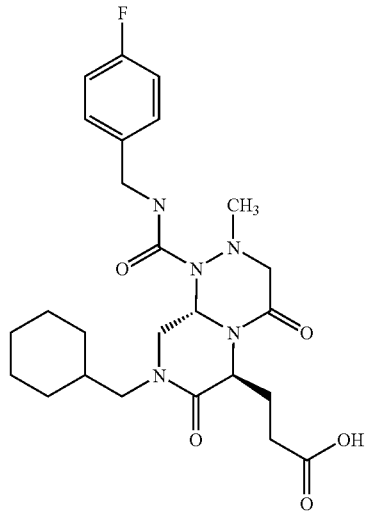 | 504 | 505 |
| 2264 | 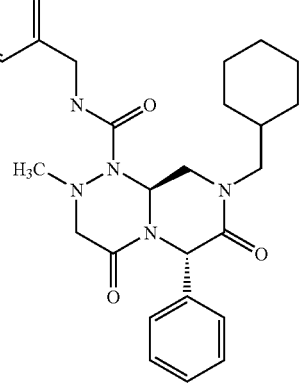 | 508 | 509 |

TABLE 2B-continued
THE [4,4,0]REVERSE TURN MIMETICS LIBRARY
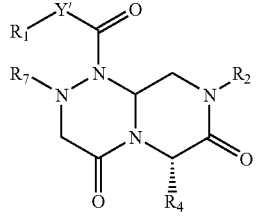
| No | MOLSTRUCTURE | Mol. Weight | M + H (MS) |
|---|---|---|---|
| 2265 | | 573 | 574 |
| 2266 | | 560 | 561 |

TABLE 2B-continued
THE [4,4,0]REVERSE TURN MIMETICS LIBRARY
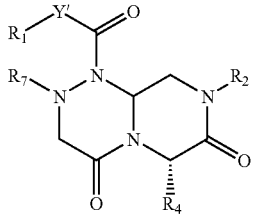
| No | MOLSTRUCTURE | Mol. Weight | M + H (MS) |
|---|---|---|---|
| 2267 | | 510 | 511 |
| 2268 | | 496 | 497 |
| 2269 | | 544 | 545 |

TABLE 2B-continued
THE [4,4,0]REVERSE TURN MIMETICS LIBRARY

| No | MOLSTRUCTURE | Mol. Weight | M + H (MS) |
|---|---|---|---|
| 2270 | | 510 | 511 |
| 2271 | | 510 | 511 |
| 2272 | | 528 | 529 |

TABLE 2B-continued
THE [4,4,0]REVERSE TURN MIMETICS LIBRARY
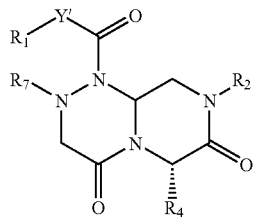
| No | MOLSTRUCTURE | Mol. Weight | M + H (MS) |
|----|--------------|-------------|------------|
| 2273 | | 496 | 497 |
| 2274 | | 512 | 513 |

TABLE 2B-continued
THE [4,4,0]REVERSE TURN MIMETICS LIBRARY
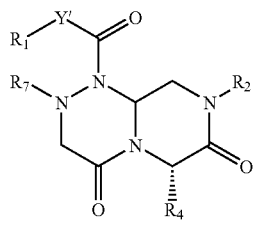
| No | MOLSTRUCTURE | Mol. Weight | M + H (MS) |
|---|---|---|---|
| 2275 | 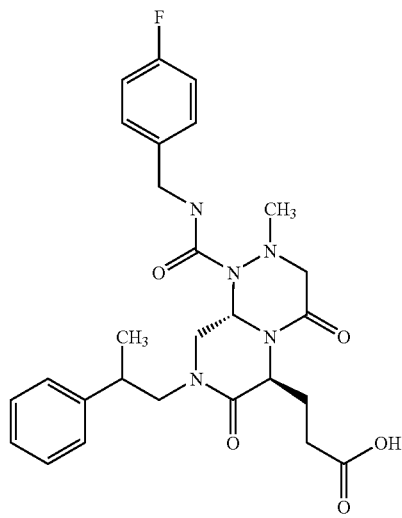 | 526 | 527 |
| 2276 | 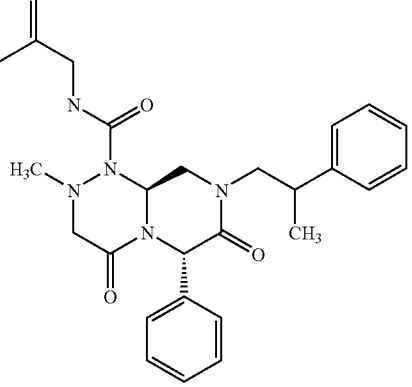 | 530 | 531 |

TABLE 2B-continued
THE [4,4,0]REVERSE TURN MIMETICS LIBRARY
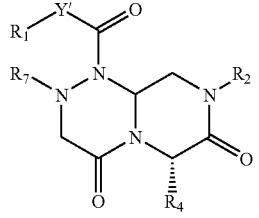
| No | MOLSTRUCTURE | Mol. Weight | M + H (MS) |
|---|---|---|---|
| 2277 | | 595 | 596 |
| 2278 | | 568 | 569 |

TABLE 2B-continued
THE [4,4,0]REVERSE TURN MIMETICS LIBRARY
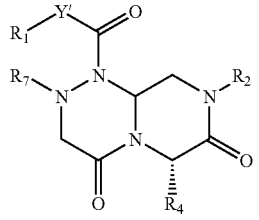
| No | MOLSTRUCTURE | Mol. Weight | M + H (MS) |
|---|---|---|---|
| 2279 | | 518 | 519 |
| 2280 | | 504 | 505 |
| 2281 | | 552 | 553 |

TABLE 2B-continued
THE [4,4,0]REVERSE TURN MIMETICS LIBRARY

| No | MOLSTRUCTURE | Mol. Weight | M + H (MS) |
|----|--------------|-------------|------------|
| 2282 | | 518 | 519 |
| 2283 | | 518 | 519 |
| 2284 | | 536 | 513 |

TABLE 2B-continued
THE [4,4,0]REVERSE TURN MIMETICS LIBRARY
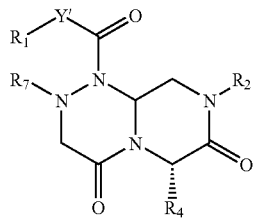
| No | MOLSTRUCTURE | Mol. Weight | M + H (MS) |
|----|--------------|-------------|------------|
| 2285 | | 504 | 527 |
| 2286 | | 519 | 531 |

TABLE 2B-continued
THE [4,4,0]REVERSE TURN MIMETICS LIBRARY
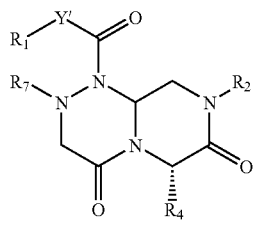
| No | MOLSTRUCTURE | Mol. Weight | M + H (MS) |
|---|---|---|---|
| 2287 | | 534 | 535 |
| 2288 | | 538 | 539 |

TABLE 2B-continued
THE [4,4,0]REVERSE TURN MIMETICS LIBRARY
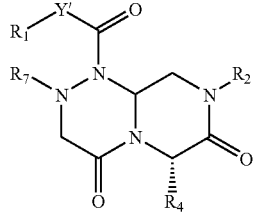
| No | MOLSTRUCTURE | Mol. Weight | M + H (MS) |
|----|--------------|-------------|------------|
| 2289 | | 603 | 604 |
| 2290 | | 606 | 607 |

TABLE 2B-continued
THE [4,4,0]REVERSE TURN MIMETICS LIBRARY
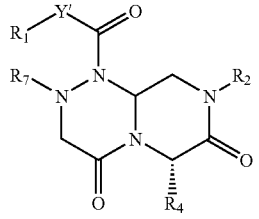
| No | MOLSTRUCTURE | Mol. Weight | M + H (MS) |
|---|---|---|---|
| 2291 | | 556 | 557 |
| 2292 | | 542 | 543 |
| 2293 | | 590 | 591 |

TABLE 2B-continued
THE [4,4,0]REVERSE TURN MIMETICS LIBRARY

| No | MOLSTRUCTURE | Mol. Weight | M + H (MS) |
|---|---|---|---|
| 2294 | | 556 | 557 |
| 2295 | | 556 | 557 |
| 2296 | | 574 | 575 |

1217 1218
TABLE 2B-continued
THE [4,4,0]REVERSE TURN MIMETICS LIBRARY
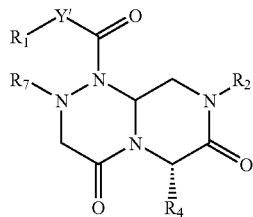
| No | MOLSTRUCTURE | Mol. Weight | M + H (MS) |
|---|---|---|---|
| 2297 | 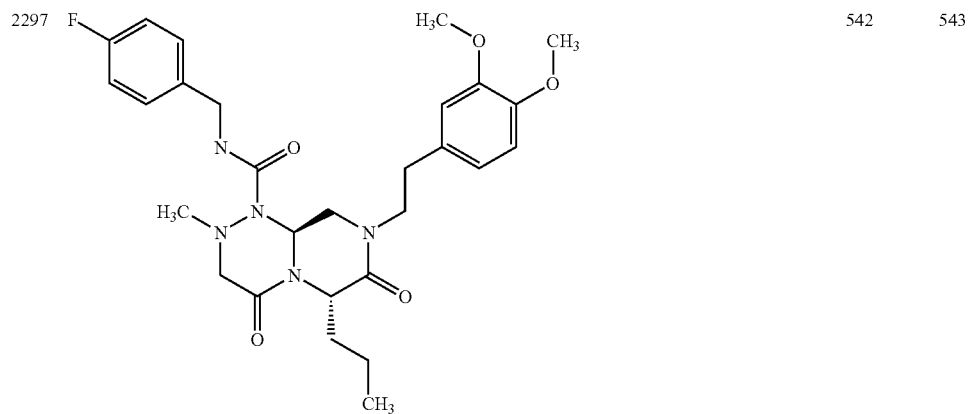 | 542 | 543 |
| 2298 |  | 558 | 559 |

TABLE 2B-continued
THE [4,4,0]REVERSE TURN MIMETICS LIBRARY
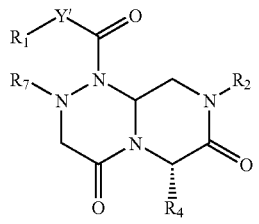
| No | MOLSTRUCTURE | Mol. Weight | M + H (MS) |
|---|---|---|---|
| 2299 | 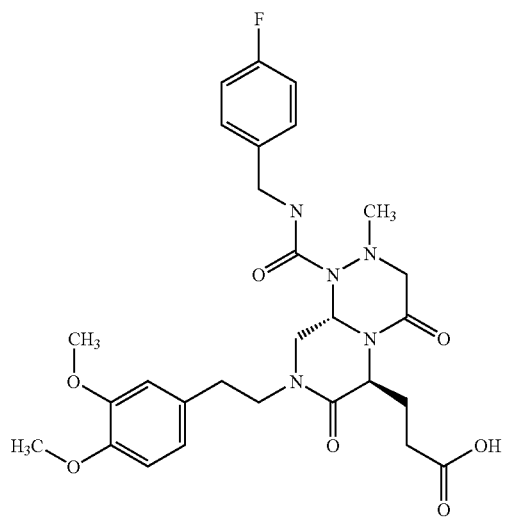 | 572 | 573 |
| 2300 |  | 576 | 577 |

TABLE 2B-continued
THE [4,4,0]REVERSE TURN MIMETICS LIBRARY
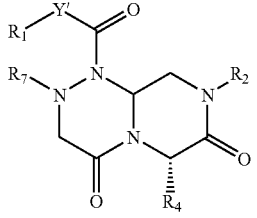
| No | MOLSTRUCTURE | Mol. Weight | M + H (MS) |
|---|---|---|---|
| 2301 | | 641 | 642 |
| 2302 | | 526 | 527 |

TABLE 2B-continued
THE [4,4,0]REVERSE TURN MIMETICS LIBRARY
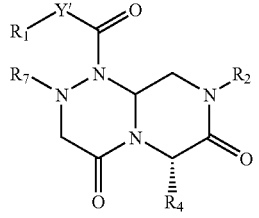
| No | MOLSTRUCTURE | Mol. Weight | M + H (MS) |
|---|---|---|---|
| 2303 | | 476 | 477 |
| 2304 | | 462 | 463 |
| 2305 | | 510 | 511 |

TABLE 2B-continued
THE [4,4,0]REVERSE TURN MIMETICS LIBRARY
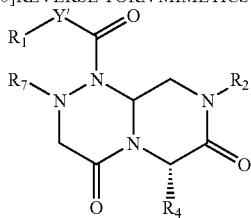
| No | MOLSTRUCTURE | Mol. Weight | M + H (MS) |
|---|---|---|---|
| 2306 | | 476 | 477 |
| 2307 | | 476 | 477 |
| 2308 | | 494 | 495 |

TABLE 2B-continued
THE [4,4,0]REVERSE TURN MIMETICS LIBRARY
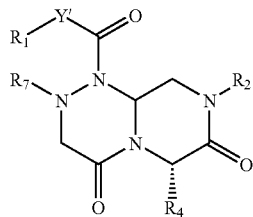
| No | MOLSTRUCTURE | Mol. Weight | M + H (MS) |
|---|---|---|---|
| 2309 | 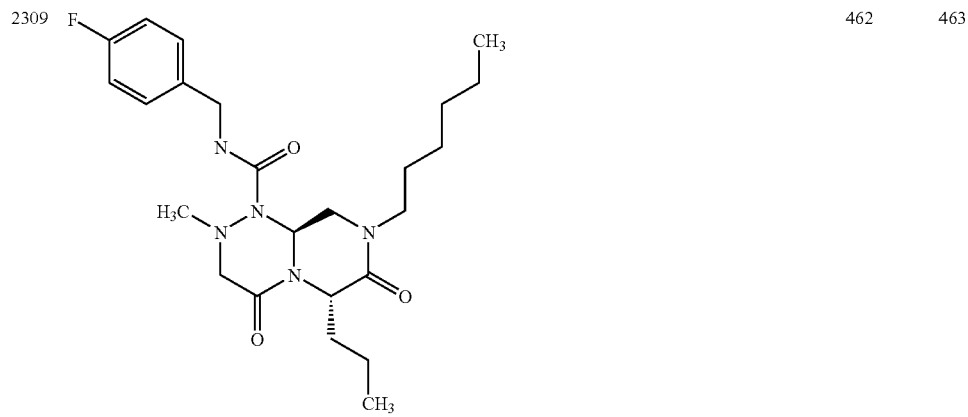 | 462 | 463 |
| 2310 | 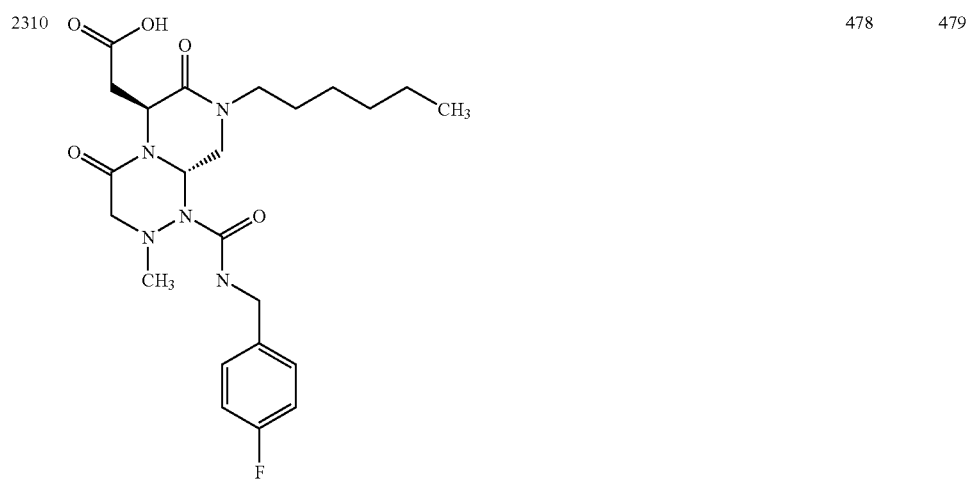 | 478 | 479 |

TABLE 2B-continued
THE [4,4,0]REVERSE TURN MIMETICS LIBRARY
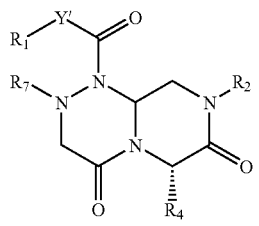
| No | MOLSTRUCTURE | Mol. Weight | M + H (MS) |
|---|---|---|---|
| 2311 | 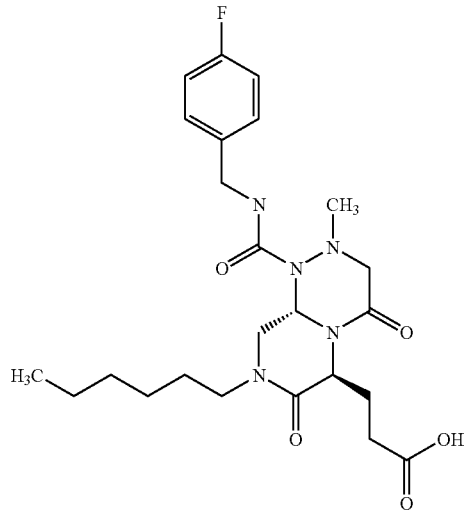 | 492 | 493 |
| 2312 | 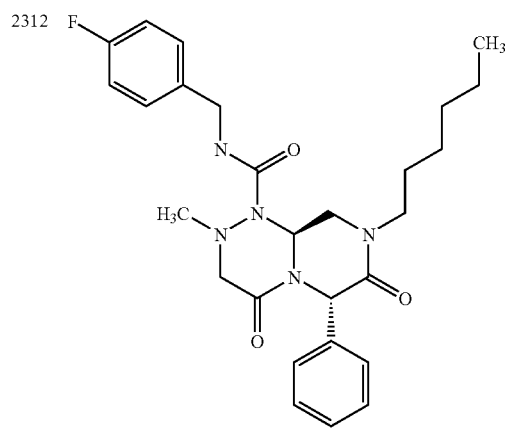 | 496 | 497 |

TABLE 2B-continued
THE [4,4,0]REVERSE TURN MIMETICS LIBRARY
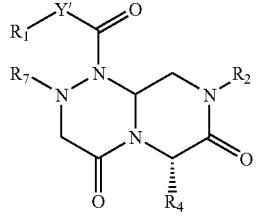
| No | MOLSTRUCTURE | Mol. Weight | M + H (MS) |
|----|--------------|-------------|------------|
| 2313 | | 561 | 562 |
| 2314 | | 632 | 637 |

TABLE 2B-continued
THE [4,4,0]REVERSE TURN MIMETICS LIBRARY
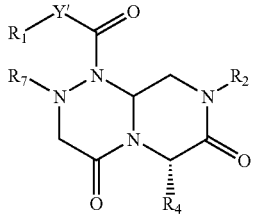
| No | MOLSTRUCTURE | Mol. Weight | M + H (MS) |
|---|---|---|---|
| 2315 | | 586 | 587 |
| 2316 | | 572 | 573 |
| 2317 | | 620 | 621 |

TABLE 2B-continued
THE [4,4,0]REVERSE TURN MIMETICS LIBRARY
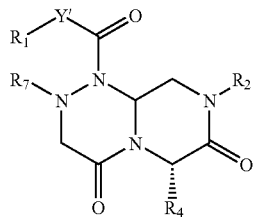
| No | MOLSTRUCTURE | Mol. Weight | M + H (MS) |
|---|---|---|---|
| 2318 | | 586 | 587 |
| 2319 | | 586 | 587 |
| 2320 | | 604 | 605 |

TABLE 2B-continued
THE [4,4,0]REVERSE TURN MIMETICS LIBRARY
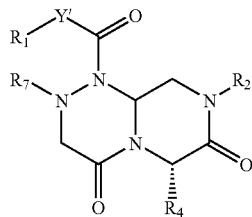
| No | MOLSTRUCTURE | Mol. Weight | M + H (MS) |
|---|---|---|---|
| 2321 | | 572 | 573 |
| 2322 | | 588 | 589 |

TABLE 2B-continued
THE [4,4,0]REVERSE TURN MIMETICS LIBRARY
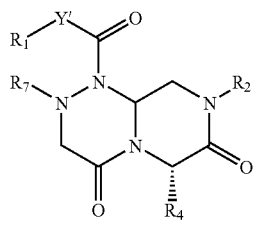
| No | MOLSTRUCTURE | Mol. Weight | M + H (MS) |
|----|--------------|-------------|------------|
| 2323 | 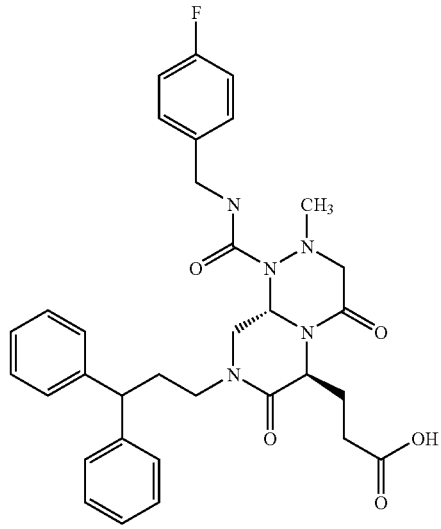 | 602 | 603 |
| 2324 | 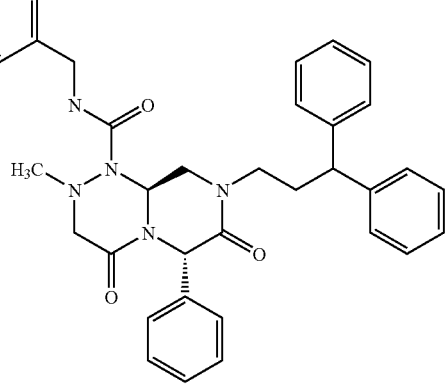 | 606 | 607 |

TABLE 2B-continued
THE [4,4,0]REVERSE TURN MIMETICS LIBRARY
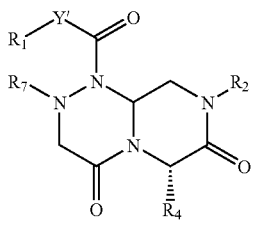
| No | MOLSTRUCTURE | Mol. Weight | M + H (MS) |
|---|---|---|---|
| 2325 | | 606 | 672 |
| 2326 | 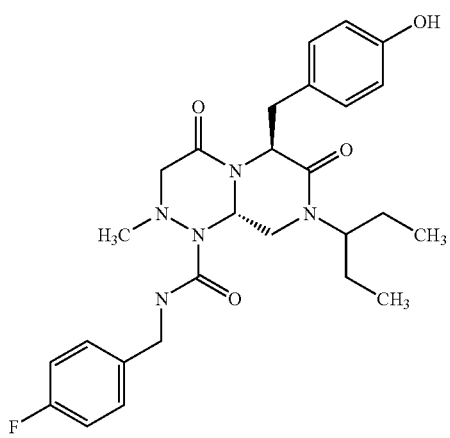 | 512 | 513 |

TABLE 2B-continued
THE [4,4,0]REVERSE TURN MIMETICS LIBRARY
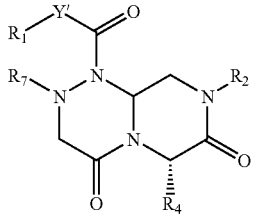
| No | MOLSTRUCTURE | Mol. Weight | M + H (MS) |
|---|---|---|---|
| 2327 | | 462 | 463 |
| 2428 | | 448 | 449 |
| 2329 | | 496 | 497 |

TABLE 2B-continued
THE [4,4,0]REVERSE TURN MIMETICS LIBRARY
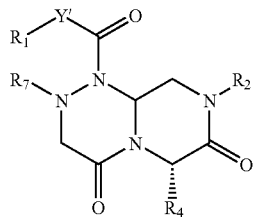
| No | MOLSTRUCTURE | Mol. Weight | M + H (MS) |
|---|---|---|---|
| 2330 | | 462 | 463 |
| 2331 | | 462 | 463 |
| 2332 | | 480 | 481 |

TABLE 2B-continued
THE [4,4,0]REVERSE TURN MIMETICS LIBRARY
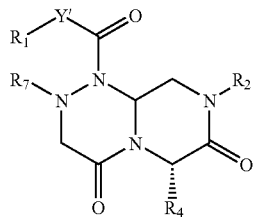
| No | MOLSTRUCTURE | Mol. Weight | M + H (MS) |
|---|---|---|---|
| 2333 | | 448 | 449 |
| 2334 | | 464 | 465 |

TABLE 2B-continued
THE [4,4,0]REVERSE TURN MIMETICS LIBRARY
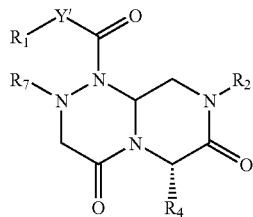
| No | MOLSTRUCTURE | Mol. Weight | M + H (MS) |
|---|---|---|---|
| 2335 | | 478 | 479 |
| 2336 | 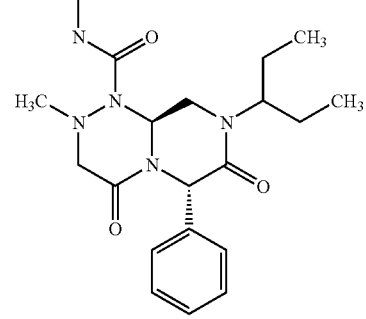 | 482 | 483 |

TABLE 2B-continued
THE [4,4,0]REVERSE TURN MIMETICS LIBRARY

| No | MOLSTRUCTURE | Mol. Weight | M + H (MS) |
|---|---|---|---|
| 2337 | | 547 | 548 |
| 2428 | | 524 | 525 |

TABLE 2B-continued
THE [4,4,0]REVERSE TURN MIMETICS LIBRARY
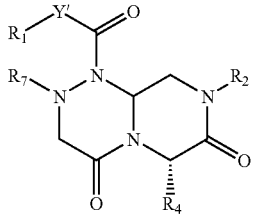
| No | MOLSTRUCTURE | Mol. Weight | M + H (MS) |
|---|---|---|---|
| 2339 | | 474 | 475 |
| 2340 | | 460 | 461 |
| 2341 | | 508 | 509 |

TABLE 2B-continued
THE [4,4,0]REVERSE TURN MIMETICS LIBRARY
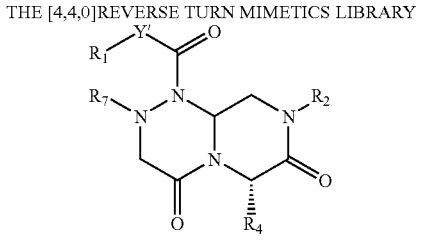
| No | MOLSTRUCTURE | Mol. Weight | M + H (MS) |
|---|---|---|---|
| 2342 | | 474 | 475 |
| 2343 | | 474 | 475 |
| 2344 | | 492 | 493 |

TABLE 2B-continued
THE [4,4,0]REVERSE TURN MIMETICS LIBRARY
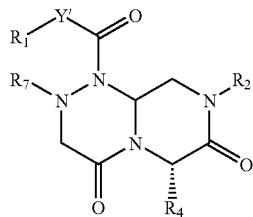
| No | MOLSTRUCTURE | Mol. Weight | M + H (MS) |
|---|---|---|---|
| 2345 | | 460 | 461 |
| 2346 | | 476 | 477 |

TABLE 2B-continued
THE [4,4,0]REVERSE TURN MIMETICS LIBRARY
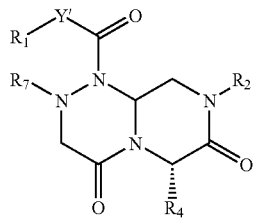
| No | MOLSTRUCTURE | Mol. Weight | M + H (MS) |
|---|---|---|---|
| 2347 | 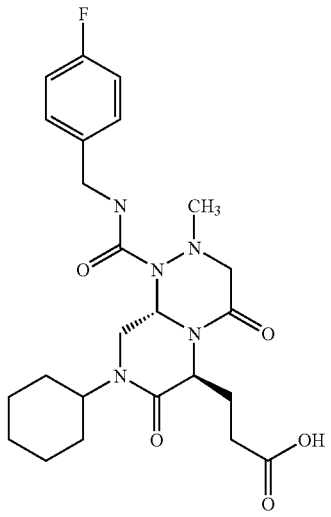 | 490 | 491 |
| 2348 | 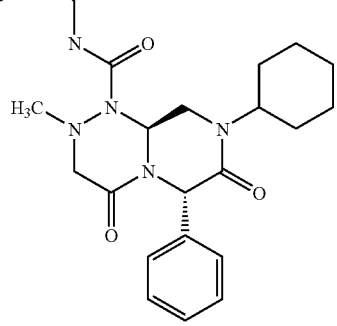 | 494 | 495 |

TABLE 2B-continued
THE [4,4,0]REVERSE TURN MIMETICS LIBRARY
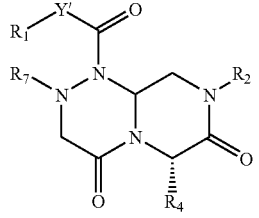
| No | MOLSTRUCTURE | Mol. Weight | M + H (MS) |
|----|--------------|-------------|------------|
| 2349 | | 559 | 560 |
| 2350 | | 610 | 611 |

TABLE 2B-continued
THE [4,4,0]REVERSE TURN MIMETICS LIBRARY
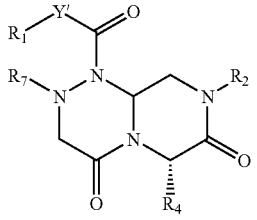
| No | MOLSTRUCTURE | Mol. Weight | M + H (MS) |
|---|---|---|---|
| 2351 | | 560 | 561 |
| 2352 | | 546 | 547 |
| 2353 | | 594 | 595 |

TABLE 2B-continued
THE [4,4,0]REVERSE TURN MIMETICS LIBRARY

| No | MOLSTRUCTURE | Mol. Weight | M + H (MS) |
|---|---|---|---|
| 2354 | | 560 | 561 |
| 2355 | | 560 | 561 |
| 2356 | | 579 | 580 |

TABLE 2B-continued
THE [4,4,0]REVERSE TURN MIMETICS LIBRARY
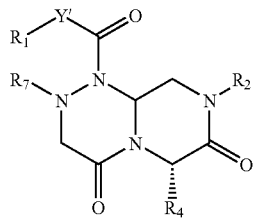
| No | MOLSTRUCTURE | Mol. Weight | M + H (MS) |
|----|--------------|-------------|------------|
| 2357 | | 546 | 547 |
| 2358 | | 562 | 563 |

TABLE 2B-continued
THE [4,4,0]REVERSE TURN MIMETICS LIBRARY
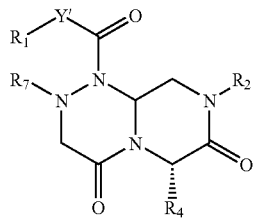
| No | MOLSTRUCTURE | Mol. Weight | M + H (MS) |
|---|---|---|---|
| 2359 | 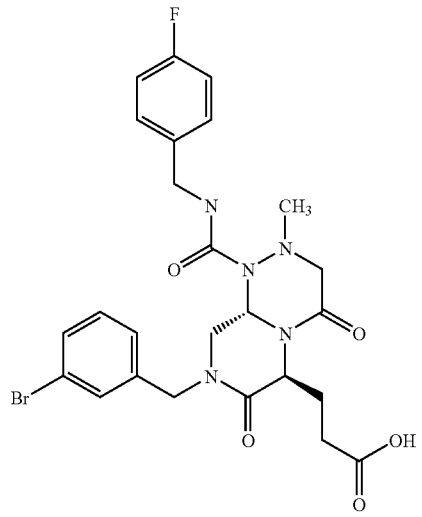 | 576 | 577 |
| 2360 | 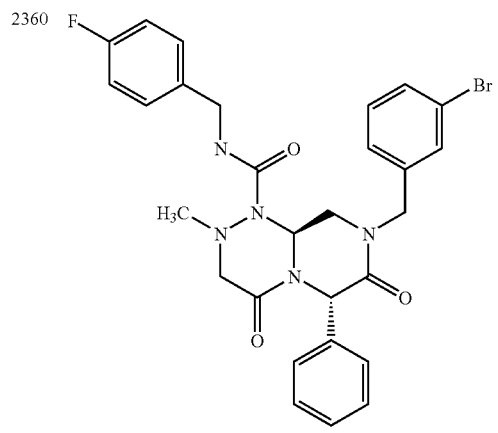 | 580 | 581 |

TABLE 2B-continued
THE [4,4,0]REVERSE TURN MIMETICS LIBRARY
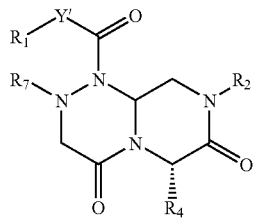
| No | MOLSTRUCTURE | Mol. Weight | M + H (MS) |
|---|---|---|---|
| 2361 | | 646 | 647 |
| 2362 | | 556 | 557 |

TABLE 2B-continued
THE [4,4,0]REVERSE TURN MIMETICS LIBRARY
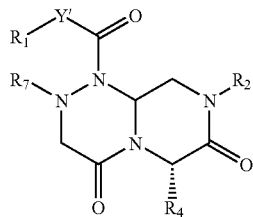
| No | MOLSTRUCTURE | Mol. Weight | M + H (MS) |
|----|--------------|-------------|------------|
| 2363 | 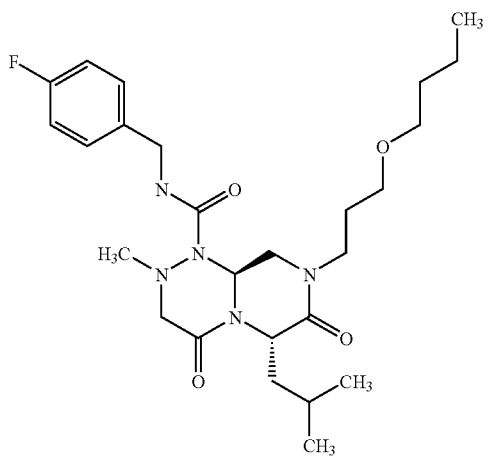 | 506 | 507 |
| 2364 | 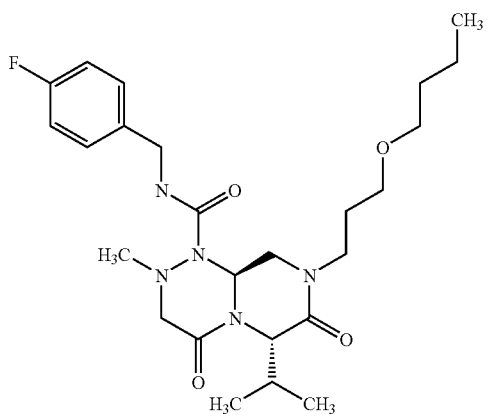 | 492 | 493 |

TABLE 2B-continued
THE [4,4,0]REVERSE TURN MIMETICS LIBRARY
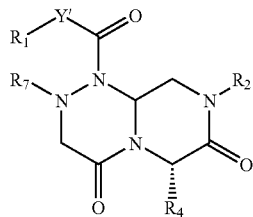
| No | MOLSTRUCTURE | Mol. Weight | M + H (MS) |
|---|---|---|---|
| 2365 | | 540 | 541 |
| 2366 | | 506 | 507 |

TABLE 2B-continued
THE [4,4,0]REVERSE TURN MIMETICS LIBRARY
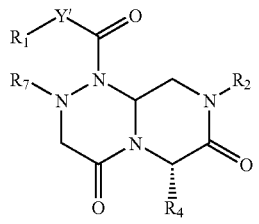
| No | MOLSTRUCTURE | Mol. Weight | M + H (MS) |
|---|---|---|---|
| 2367 | 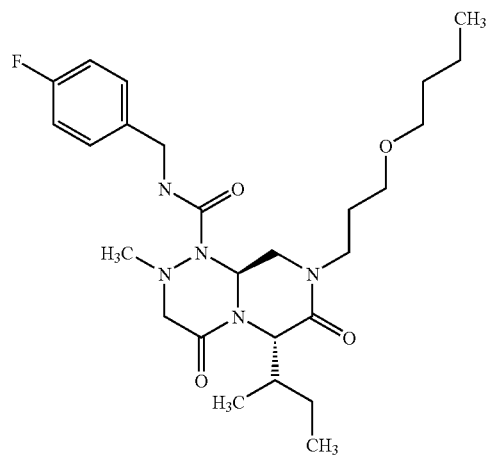 | 506 | 507 |
| 2368 | 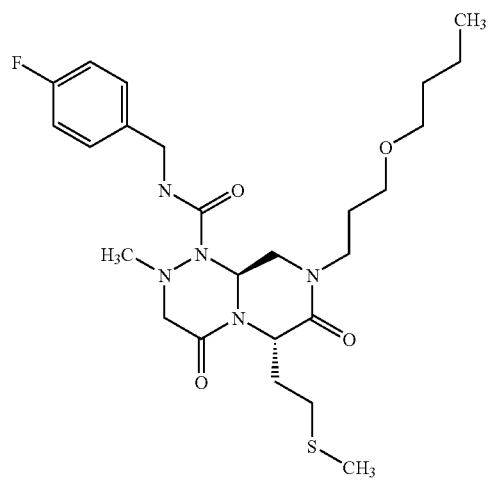 | 524 | 525 |

TABLE 2B-continued
THE [4,4,0]REVERSE TURN MIMETICS LIBRARY
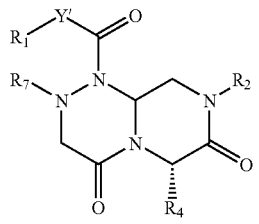
| No | MOLSTRUCTURE | Mol. Weight | M + H (MS) |
|---|---|---|---|
| 2369 | 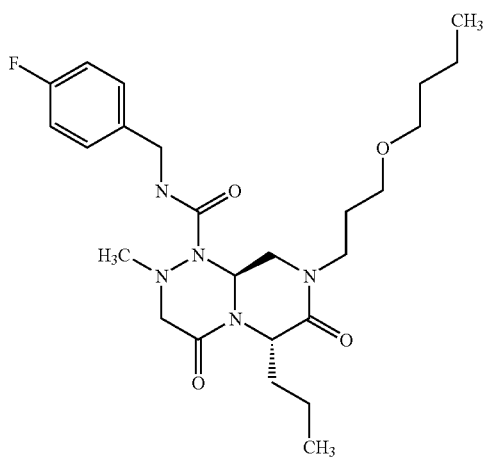 | 492 | 493 |
| 2370 | 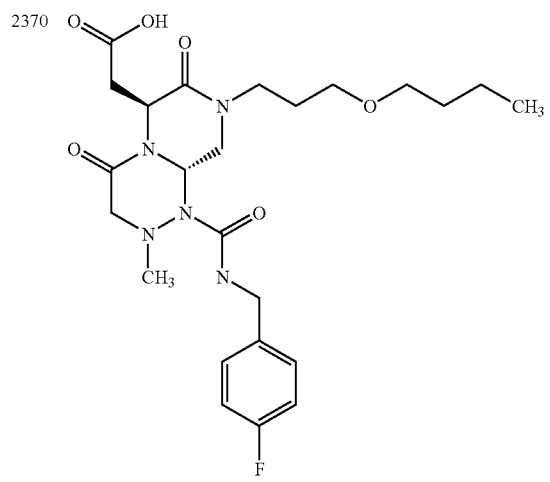 | 508 | 509 |

TABLE 2B-continued
THE [4,4,0]REVERSE TURN MIMETICS LIBRARY
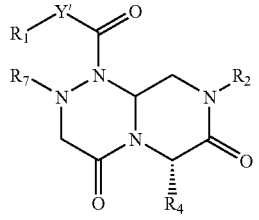
| No | MOLSTRUCTURE | Mol. Weight | M + H (MS) |
|---|---|---|---|
| 2371 | 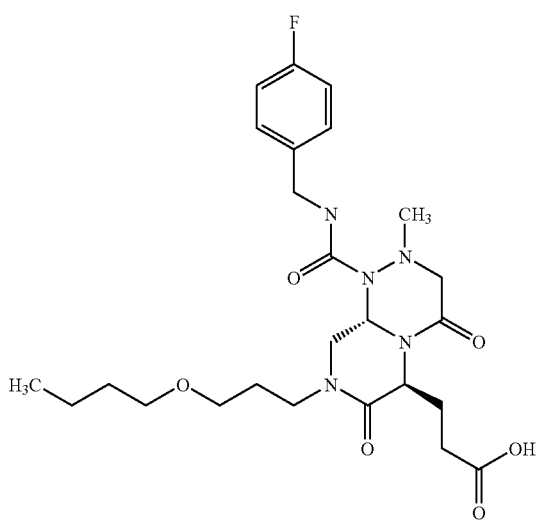 | 522 | 523 |
| 2372 | 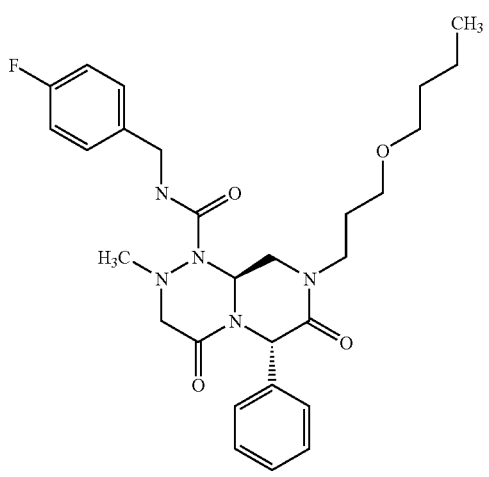 | 526 | 527 |

TABLE 2B-continued
THE [4,4,0]REVERSE TURN MIMETICS LIBRARY
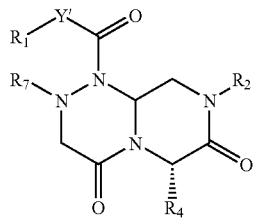
| No | MOLSTRUCTURE | Mol. Weight | M + H (MS) |
|---|---|---|---|
| 2373 | 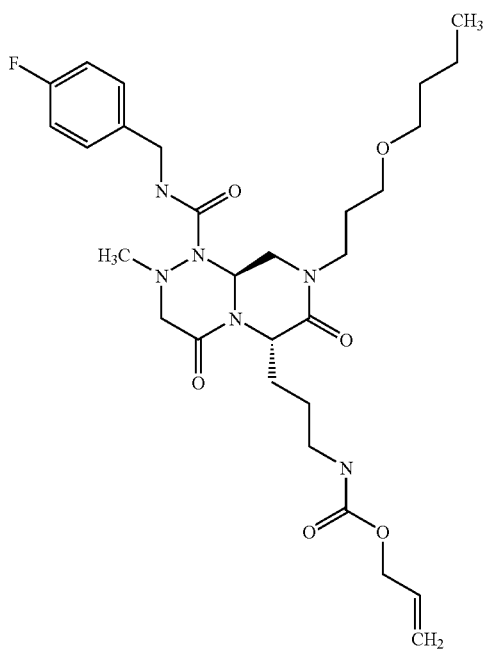 | 591 | 592 |
| 2374 | 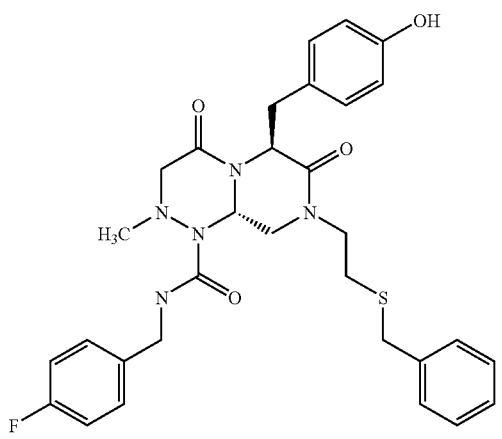 | 592 | 593 |

TABLE 2B-continued
THE [4,4,0]REVERSE TURN MIMETICS LIBRARY
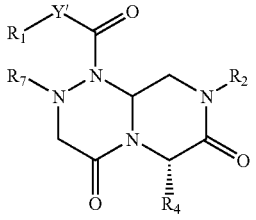
| No | MOLSTRUCTURE | Mol. Weight | M + H (MS) |
|---|---|---|---|
| 2375 | | 542 | 543 |
| 2376 | | 528 | 529 |
| 2377 | | 576 | 577 |

TABLE 2B-continued
THE [4,4,0]REVERSE TURN MIMETICS LIBRARY
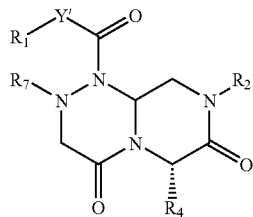
| No | MOLSTRUCTURE | Mol. Weight | M + H (MS) |
|---|---|---|---|
| 2378 | | 542 | 543 |
| 2379 | | 542 | 543 |
| 2380 | | 560 | 561 |

TABLE 2B-continued
THE [4,4,0]REVERSE TURN MIMETICS LIBRARY
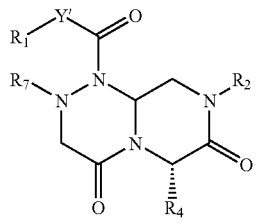
| No | MOLSTRUCTURE | Mol. Weight | M + H (MS) |
|---|---|---|---|
| 2381 | 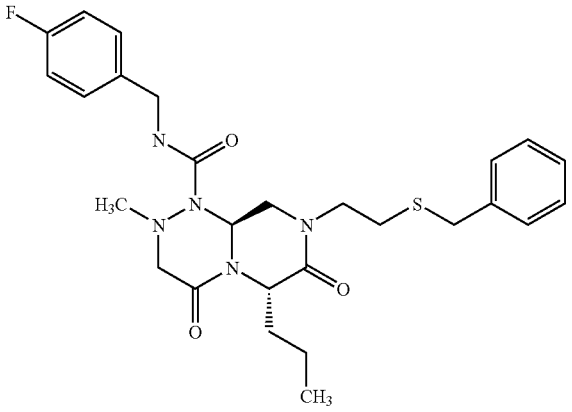 | 528 | 529 |
| 2382 | 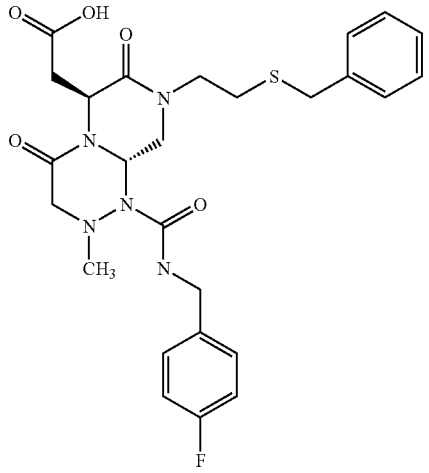 | 544 | 545 |

TABLE 2B-continued
THE [4,4,0]REVERSE TURN MIMETICS LIBRARY
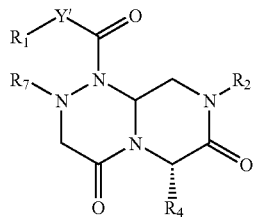
| No | MOLSTRUCTURE | Mol. Weight | M + H (MS) |
|---|---|---|---|
| 2383 | 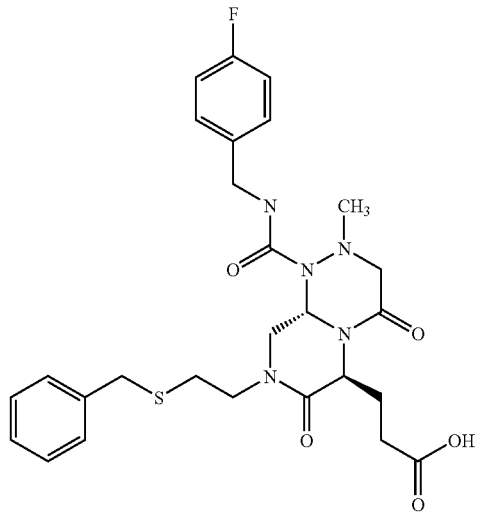 | 558 | 559 |
| 2384 | 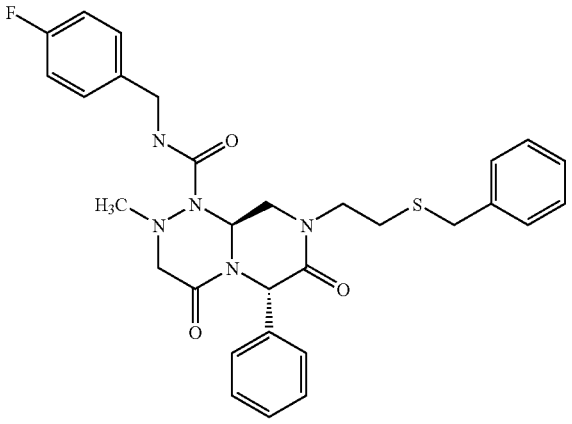 | 562 | 563 |

TABLE 2B-continued
THE [4,4,0]REVERSE TURN MIMETICS LIBRARY
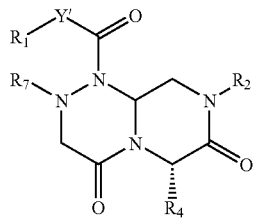
| No | MOLSTRUCTURE | Mol. Weight | M + H (MS) |
|----|--------------|-------------|------------|
| 2385 | 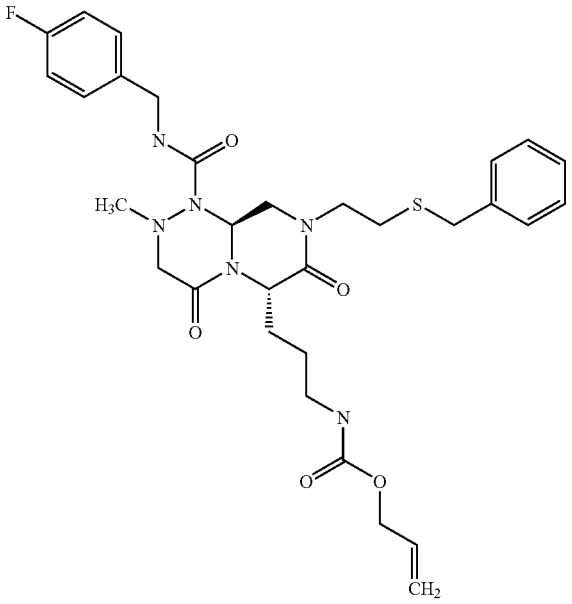 | 627 | 628 |
| 2386 | 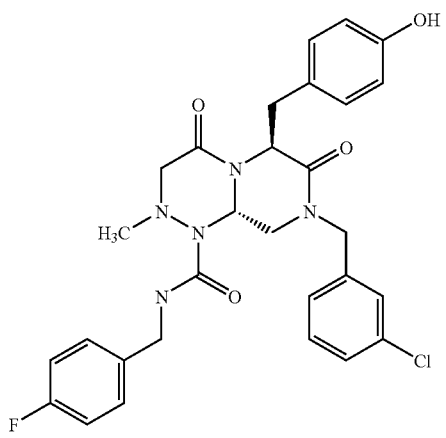 | 566 | 567 |

TABLE 2B-continued
THE [4,4,0]REVERSE TURN MIMETICS LIBRARY
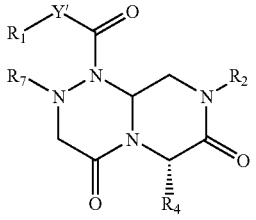
| No | MOLSTRUCTURE | Mol. Weight | M + H (MS) |
|---|---|---|---|
| 2387 | | 516 | 517 |
| 2388 | | 502 | 503 |
| 2389 | | 550 | 551 |

TABLE 2B-continued
THE [4,4,0]REVERSE TURN MIMETICS LIBRARY
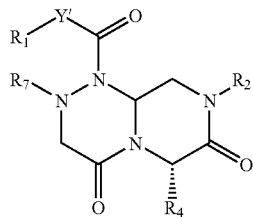
| No | MOLSTRUCTURE | Mol. Weight | M + H (MS) |
|---|---|---|---|
| 2390 | | 516 | 517 |
| 2391 | | 516 | 517 |
| 2392 | | 534 | 535 |

TABLE 2B-continued
THE [4,4,0]REVERSE TURN MIMETICS LIBRARY
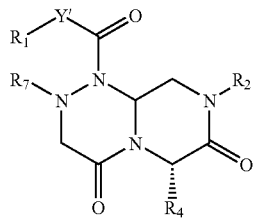
| No | MOLSTRUCTURE | Mol. Weight | M + H (MS) |
|---|---|---|---|
| 2393 | | 502 | 503 |
| 2394 | | 518 | 519 |

TABLE 2B-continued
THE [4,4,0]REVERSE TURN MIMETICS LIBRARY
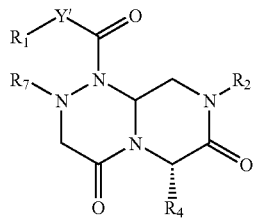
| No | MOLSTRUCTURE | Mol. Weight | M + H (MS) |
|----|--------------|-------------|------------|
| 2395 | 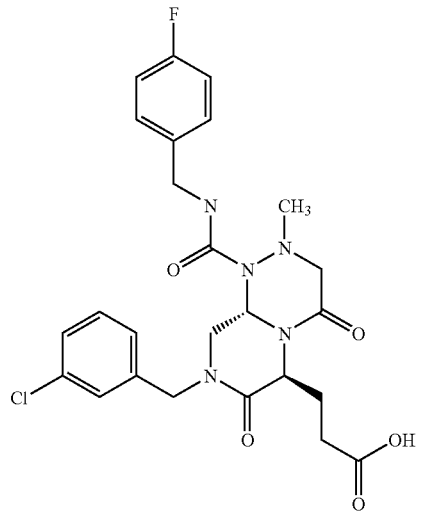 | 532 | 533 |
| 2396 | 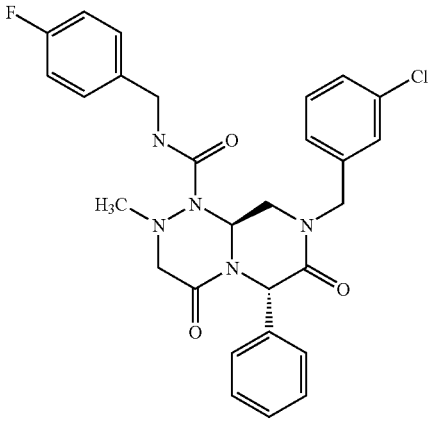 | 536 | 537 |

TABLE 2B-continued
THE [4,4,0]REVERSE TURN MIMETICS LIBRARY
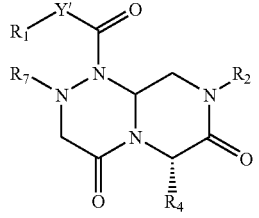
| No | MOLSTRUCTURE | Mol. Weight | M + H (MS) |
|---|---|---|---|
| 2397 | | 601 | 602 |
| 2398 | | 552 | 553 |

TABLE 2B-continued
THE [4,4,0]REVERSE TURN MIMETICS LIBRARY
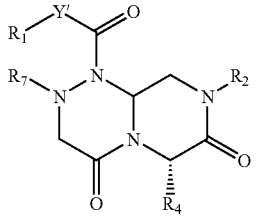
| No | MOLSTRUCTURE | Mol. Weight | M + H (MS) |
|---|---|---|---|
| 2399 | | 502 | 503 |
| 2400 | | 488 | 489 |
| 2401 | | 536 | 537 |

TABLE 2B-continued
THE [4,4,0]REVERSE TURN MIMETICS LIBRARY

| No | MOLSTRUCTURE | Mol. Weight | M + H (MS) |
|---|---|---|---|
| 2402 | | 502 | 503 |
| 2403 | | 502 | 503 |
| 2404 | | 520 | 521 |

TABLE 2B-continued
THE [4,4,0]REVERSE TURN MIMETICS LIBRARY
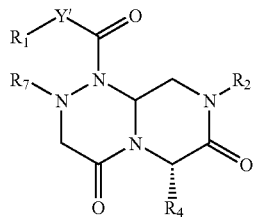
| No | MOLSTRUCTURE | Mol. Weight | M + H (MS) |
|---|---|---|---|
| 2405 | | 488 | 489 |
| 2406 | | 504 | 505 |

TABLE 2B-continued
THE [4,4,0]REVERSE TURN MIMETICS LIBRARY
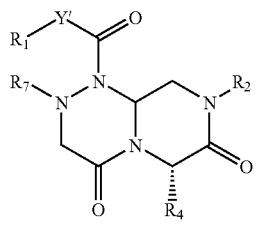
| No | MOLSTRUCTURE | Mol. Weight | M + H (MS) |
|---|---|---|---|
| 2407 | 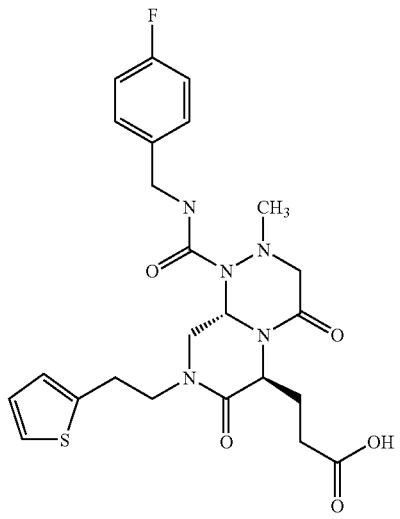 | 518 | 519 |
| 2408 | 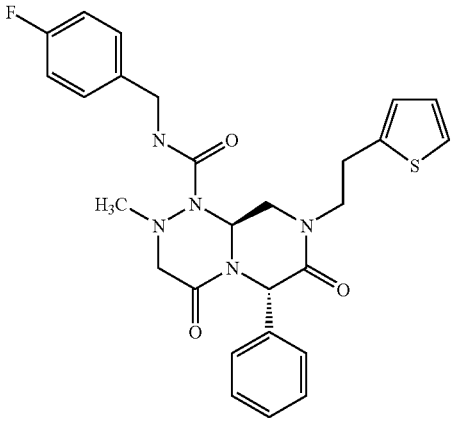 | 522 | 523 |

TABLE 2B-continued
THE [4,4,0]REVERSE TURN MIMETICS LIBRARY
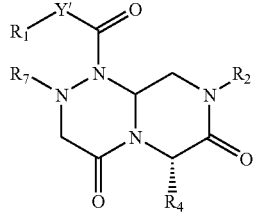
| No | MOLSTRUCTURE | Mol. Weight | M + H (MS) |
|---|---|---|---|
| 2409 | 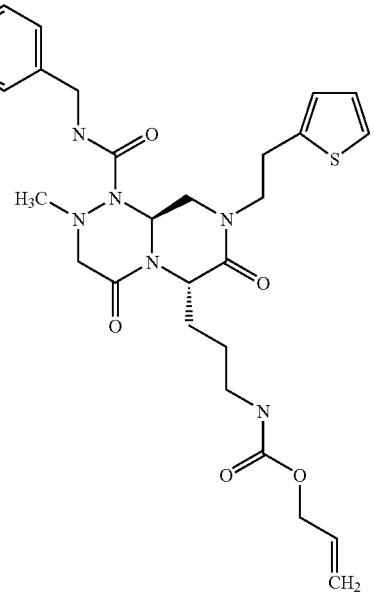 | 587 | 588 |
| 2410 | 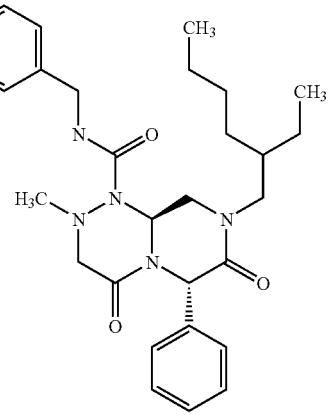 | 554 | 555 |

TABLE 2B-continued
THE [4,4,0]REVERSE TURN MIMETICS LIBRARY
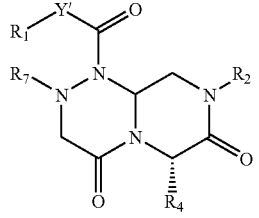
| No | MOLSTRUCTURE | Mol. Weight | M + H (MS) |
|---|---|---|---|
| 2411 | | 504 | 505 |
| 2412 | | 490 | 491 |

TABLE 2B-continued
THE [4,4,0]REVERSE TURN MIMETICS LIBRARY
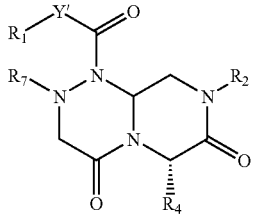
| No | MOLSTRUCTURE | Mol. Weight | M + H (MS) |
|---|---|---|---|
| 2413 | | 538 | 539 |
| 2414 | | 504 | 505 |
| 2415 | | 504 | 505 |

TABLE 2B-continued

THE [4,4,0]REVERSE TURN MIMETICS LIBRARY

| No | MOLSTRUCTURE | Mol. Weight | M + H (MS) |
|---|---|---|---|
| 2416 | | 522 | 523 |
| 2417 | | 490 | 491 |
| 2418 | | 506 | 507 |

TABLE 2B-continued
THE [4,4,0]REVERSE TURN MIMETICS LIBRARY
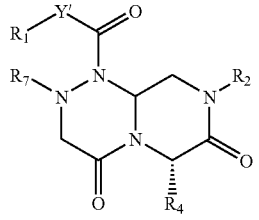
| No | MOLSTRUCTURE | Mol. Weight | M + H (MS) |
|---|---|---|---|
| 2419 | 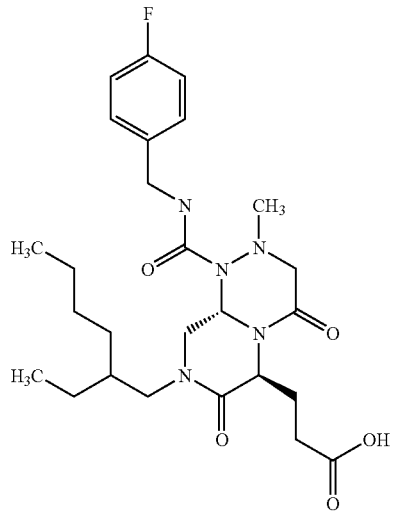 | 520 | 521 |
| 2420 | 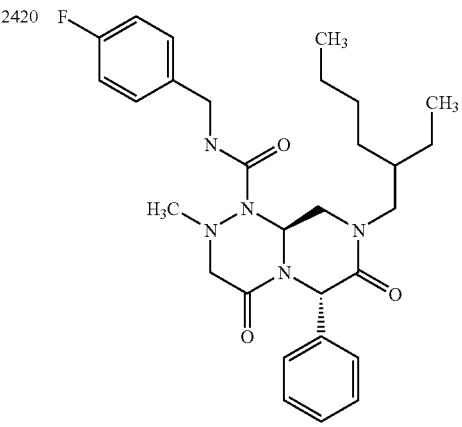 | 524 | 525 |

TABLE 2B-continued
THE [4,4,0]REVERSE TURN MIMETICS LIBRARY
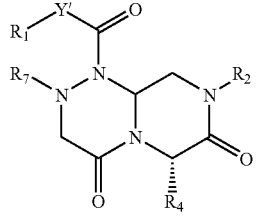
| No | MOLSTRUCTURE | Mol. Weight | M + H (MS) |
|---|---|---|---|
| 2421 | | 589 | 590 |
| 2422 | | 550 | 551 |

TABLE 2B-continued
THE [4,4,0]REVERSE TURN MIMETICS LIBRARY
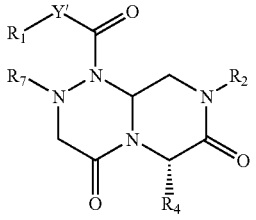
| No | MOLSTRUCTURE | Mol. Weight | M + H (MS) |
|----|--------------|-------------|------------|
| 2423 | | 500 | 501 |
| 2424 | | 486 | 487 |
| 2425 | | 534 | 535 |

TABLE 2B-continued
THE [4,4,0]REVERSE TURN MIMETICS LIBRARY

| No | MOLSTRUCTURE | Mol. Weight | M + H (MS) |
|---|---|---|---|
| 2426 | | 522 | 523 |
| 2427 | | 500 | 501 |
| 2428 | | 500 | 501 |

TABLE 2B-continued
THE [4,4,0]REVERSE TURN MIMETICS LIBRARY
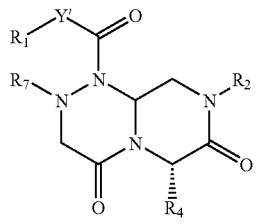
| No | MOLSTRUCTURE | Mol. Weight | M + H (MS) |
|---|---|---|---|
| 2429 | | 518 | 519 |
| 2430 | | 486 | 487 |

TABLE 2B-continued
THE [4,4,0]REVERSE TURN MIMETICS LIBRARY
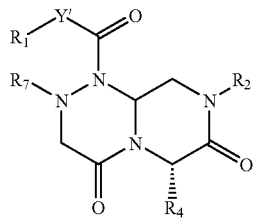
| No | MOLSTRUCTURE | Mol. Weight | M + H (MS) |
|---|---|---|---|
| 2431 | 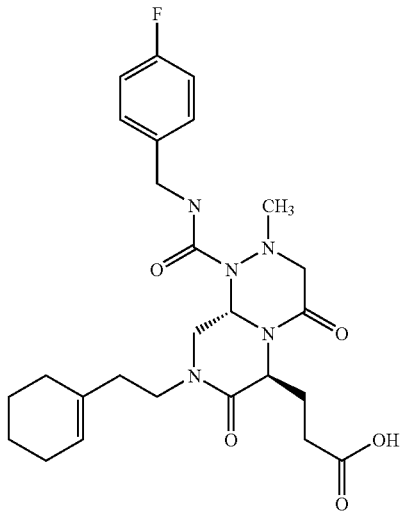 | 502 | 503 |
| 2432 | 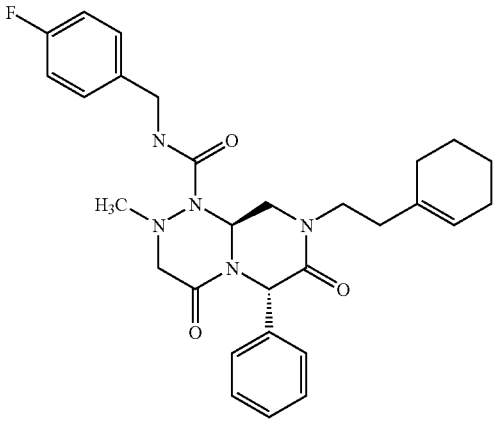 | 516 | 517 |

TABLE 2B-continued
THE [4,4,0]REVERSE TURN MIMETICS LIBRARY
| No | MOLSTRUCTURE | Mol. Weight | M + H (MS) |
|---|---|---|---|
| 2433 | | 585 | 586 |
| 2434 | | 524 | 525 |

TABLE 2B-continued
THE [4,4,0]REVERSE TURN MIMETICS LIBRARY
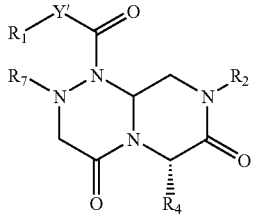
| No | MOLSTRUCTURE | Mol. Weight | M + H (MS) |
|---|---|---|---|
| 2435 | | 474 | 475 |
| 2436 | | 460 | 461 |
| 2437 | | 508 | 509 |

TABLE 2B-continued
THE [4,4,0]REVERSE TURN MIMETICS LIBRARY

| No | MOLSTRUCTURE | Mol. Weight | M + H (MS) |
|---|---|---|---|
| 2438 | | 474 | 475 |
| 2439 | | 474 | 475 |
| 2440 | | 492 | 493 |

TABLE 2B-continued
THE [4,4,0]REVERSE TURN MIMETICS LIBRARY
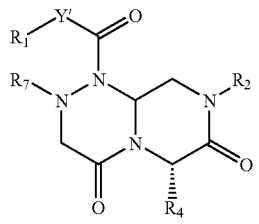
| No | MOLSTRUCTURE | Mol. Weight | M + H (MS) |
|---|---|---|---|
| 2441 | | 460 | 461 |
| 2442 | | 475 | 476 |

TABLE 2B-continued
THE [4,4,0]REVERSE TURN MIMETICS LIBRARY
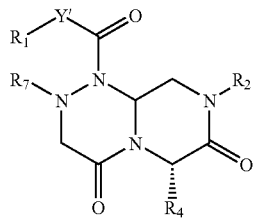
| No | MOLSTRUCTURE | Mol. Weight | M + H (MS) |
|---|---|---|---|
| 2443 | 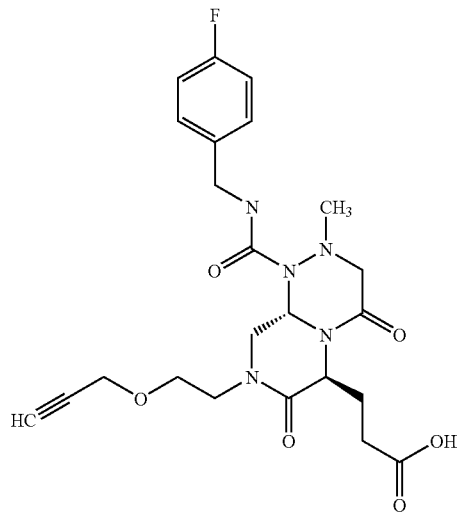 | 490 | 491 |
| 2444 | 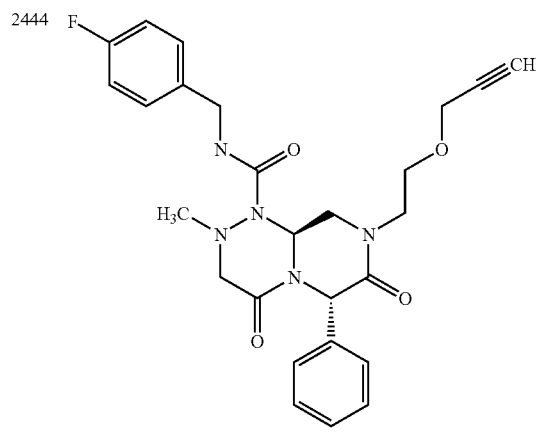 | 494 | 495 |

TABLE 2B-continued
THE [4,4,0]REVERSE TURN MIMETICS LIBRARY
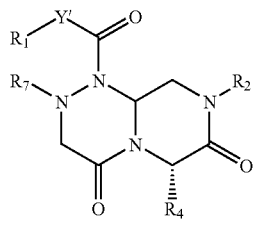
| No | MOLSTRUCTURE | Mol. Weight | M + H (MS) |
|---|---|---|---|
| 2445 | 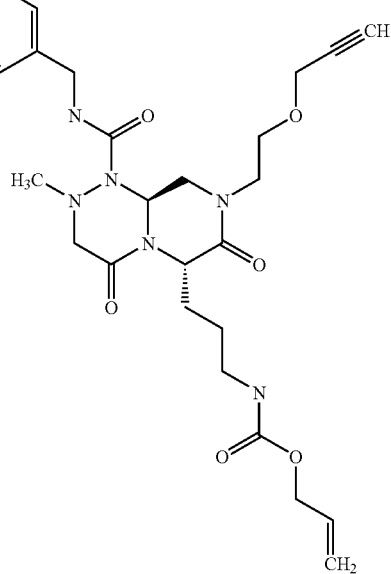 | 559 | 560 |
| 2446 | 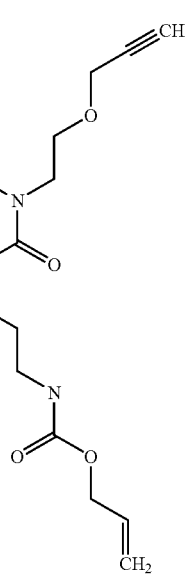 | 590 | 591 |

TABLE 2B-continued
THE [4,4,0]REVERSE TURN MIMETICS LIBRARY
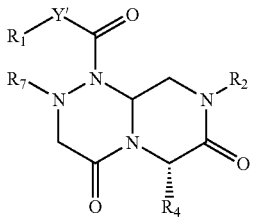
| No | MOLSTRUCTURE | Mol. Weight | M + H (MS) |
|---|---|---|---|
| 2447 | | 540 | 541 |
| 2448 | | 526 | 527 |
| 2449 | | 574 | 575 |

TABLE 2B-continued
THE [4,4,0]REVERSE TURN MIMETICS LIBRARY

| No | MOLSTRUCTURE | Mol. Weight | M + H (MS) |
|---|---|---|---|
| 2450 | | 540 | 541 |
| 2451 | | 540 | 541 |
| 2452 | | 558 | 559 |

TABLE 2B-continued
THE [4,4,0]REVERSE TURN MIMETICS LIBRARY
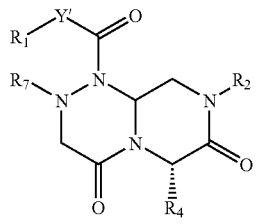
| No | MOLSTRUCTURE | Mol. Weight | M + H (MS) |
|---|---|---|---|
| 2453 | | 526 | 527 |
| 2454 | | 542 | 543 |

TABLE 2B-continued
THE [4,4,0]REVERSE TURN MIMETICS LIBRARY
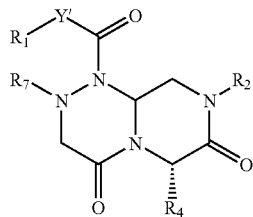
| No | MOLSTRUCTURE | Mol. Weight | M + H (MS) |
|---|---|---|---|
| 2455 | 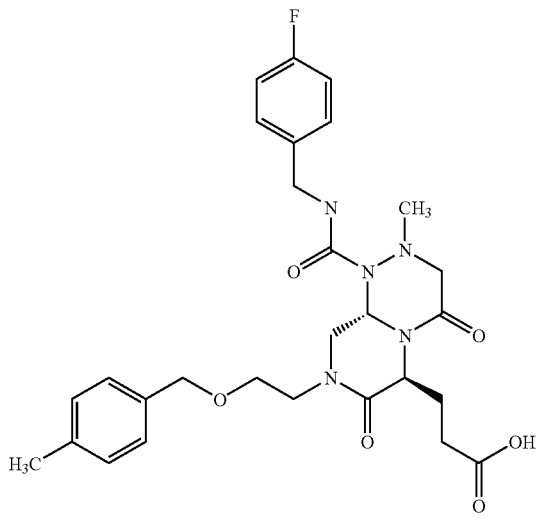 | 556 | 557 |
| 2456 | 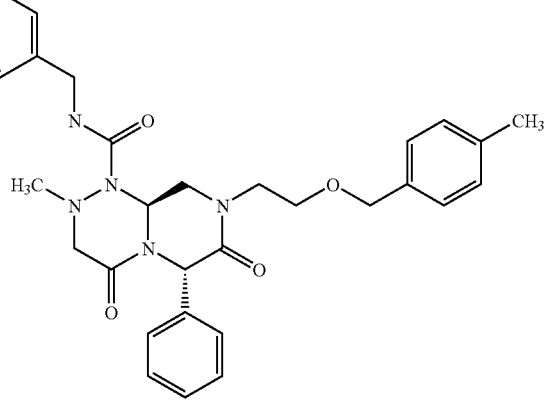 | 560 | 561 |

TABLE 2B-continued
THE [4,4,0]REVERSE TURN MIMETICS LIBRARY
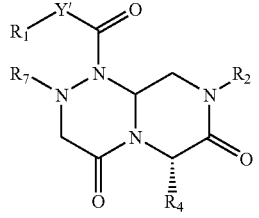
| No | MOLSTRUCTURE | Mol. Weight | M + H (MS) |
|----|--------------|-------------|------------|
| 2457 | | 625 | 626 |
| 2458 | | 594 | 595 |

TABLE 2B-continued
THE [4,4,0]REVERSE TURN MIMETICS LIBRARY
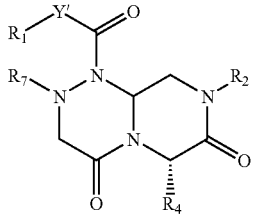
| No | MOLSTRUCTURE | Mol. Weight | M + H (MS) |
|---|---|---|---|
| 2459 | | 544 | 545 |
| 2460 | | 530 | 531 |
| 2461 | | 578 | 579 |

TABLE 2B-continued
THE [4,4,0]REVERSE TURN MIMETICS LIBRARY

| No | MOLSTRUCTURE | Mol. Weight | M + H (MS) |
|---|---|---|---|
| 2462 | | 544 | 545 |
| 2463 | | 544 | 545 |
| 2464 | | 562 | 563 |

TABLE 2B-continued
THE [4,4,0]REVERSE TURN MIMETICS LIBRARY
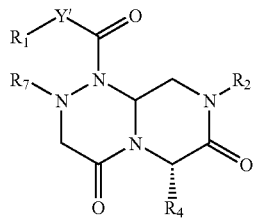
| No | MOLSTRUCTURE | Mol. Weight | M + H (MS) |
|---|---|---|---|
| 2465 |  | 530 | 531 |
| 2466 |  | 546 | 547 |

TABLE 2B-continued
THE [4,4,0]REVERSE TURN MIMETICS LIBRARY
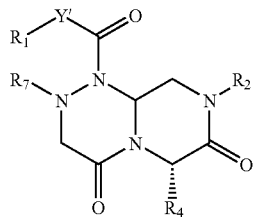
| No | MOLSTRUCTURE | Mol. Weight | M + H (MS) |
|---|---|---|---|
| 2467 | 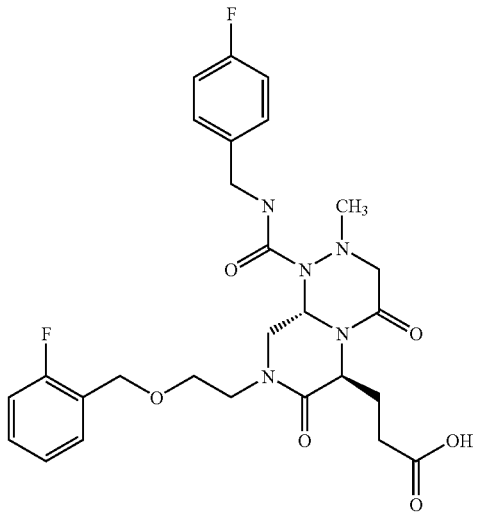 | 560 | 561 |
| 2468 | 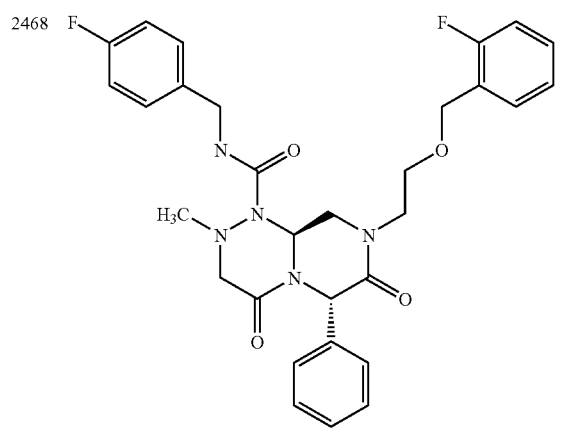 | 564 | 565 |

TABLE 2B-continued
THE [4,4,0]REVERSE TURN MIMETICS LIBRARY
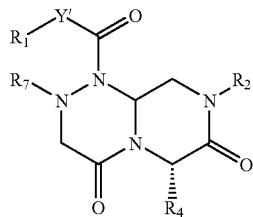
| No | MOLSTRUCTURE | Mol. Weight | M + H (MS) |
|---|---|---|---|
| 2469 | | 629 | 630 |
| 2470 | | 594 | 595 |

TABLE 2B-continued
THE [4,4,0]REVERSE TURN MIMETICS LIBRARY
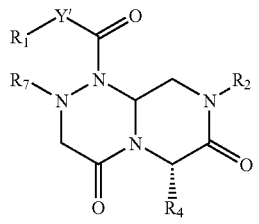
| No | MOLSTRUCTURE | Mol. Weight | M + H (MS) |
|---|---|---|---|
| 2471 | | 544 | 545 |
| 2472 | | 530 | 531 |

TABLE 2B-continued
THE [4,4,0]REVERSE TURN MIMETICS LIBRARY
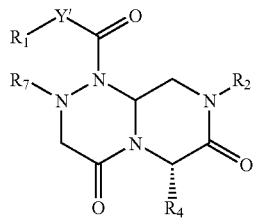
| No | MOLSTRUCTURE | Mol. Weight | M + H (MS) |
|---|---|---|---|
| 2473 | 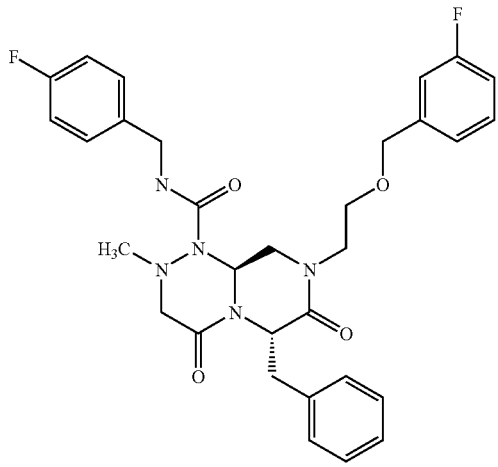 | 578 | 579 |
| 2474 | 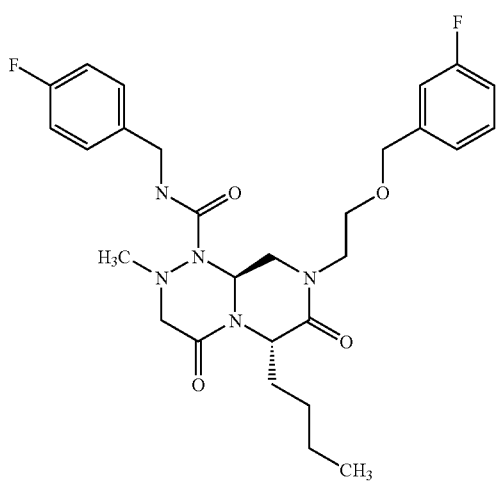 | 544 | 545 |

TABLE 2B-continued
THE [4,4,0]REVERSE TURN MIMETICS LIBRARY
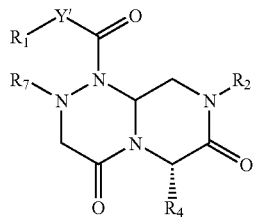
| No | MOLSTRUCTURE | Mol. Weight | M + H (MS) |
|----|--------------|-------------|------------|
| 2475 | 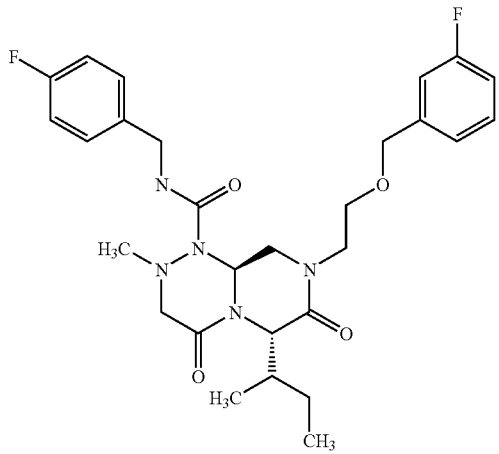 | 544 | 545 |
| 2476 | 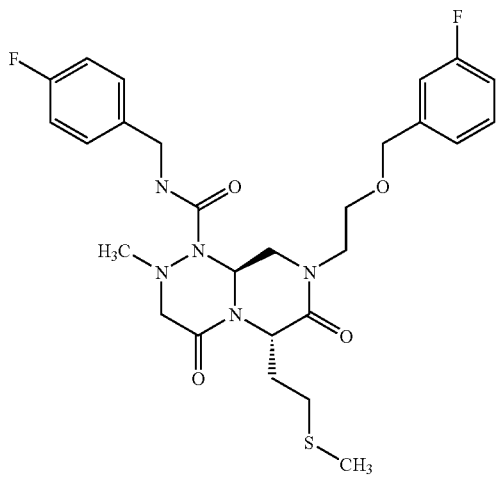 | 562 | 563 |

TABLE 2B-continued
THE [4,4,0]REVERSE TURN MIMETICS LIBRARY
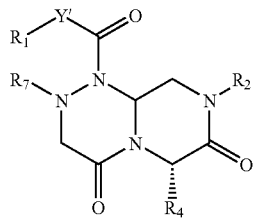
| No | MOLSTRUCTURE | Mol. Weight | M + H (MS) |
|----|---|---|---|
| 2477 | 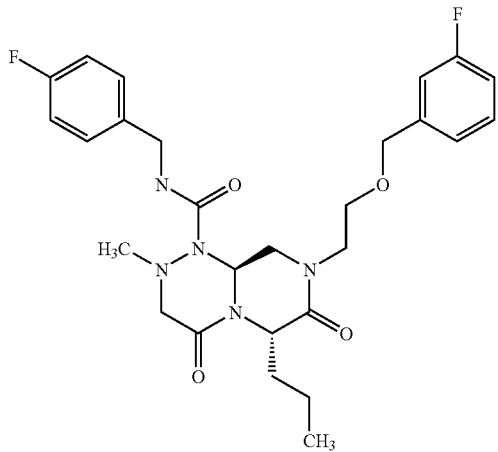 | 530 | 531 |
| 2478 | 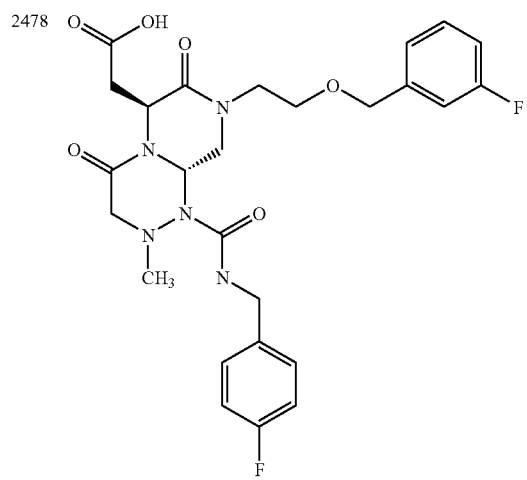 | 546 | 547 |

TABLE 2B-continued
THE [4,4,0]REVERSE TURN MIMETICS LIBRARY
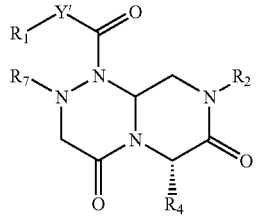
| No | MOLSTRUCTURE | Mol. Weight | M + H (MS) |
|---|---|---|---|
| 2479 | 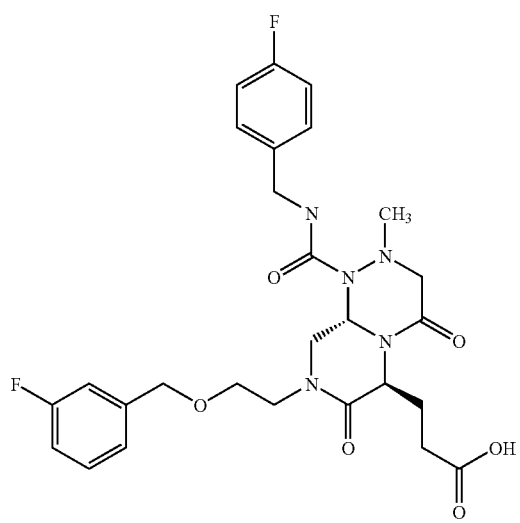 | 560 | 561 |
| 2480 | 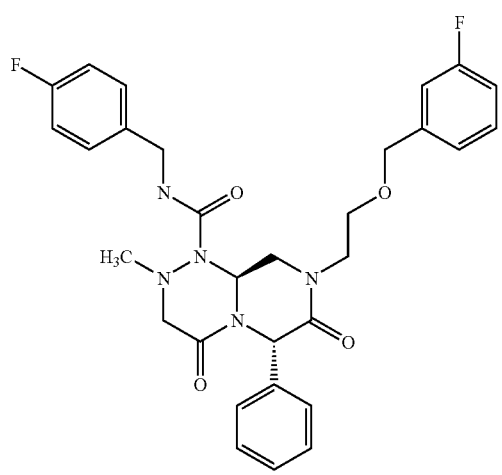 | 564 | 565 |

TABLE 2B-continued
THE [4,4,0]REVERSE TURN MIMETICS LIBRARY
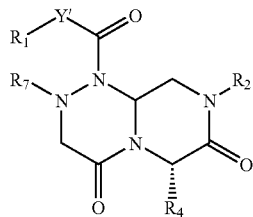
| No | MOLSTRUCTURE | Mol. Weight | M + H (MS) |
|---|---|---|---|
| 2481 | 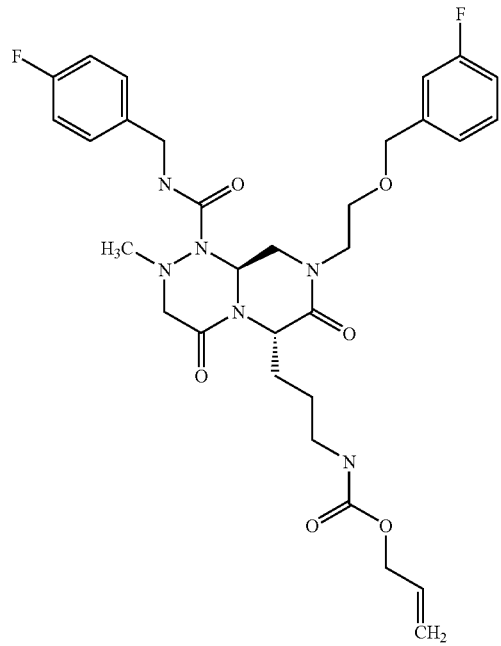 | 629 | 630 |
| 2482 | 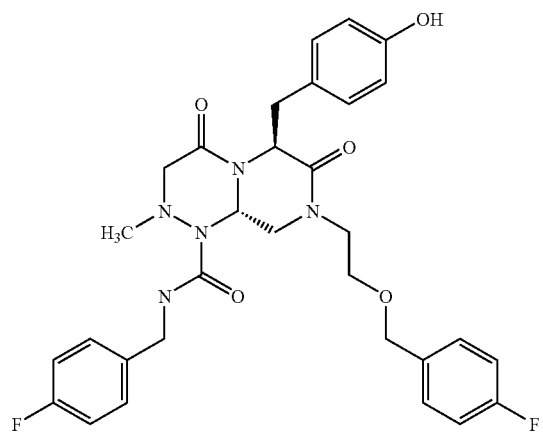 | 594 | 595 |

TABLE 2B-continued
THE [4,4,0]REVERSE TURN MIMETICS LIBRARY
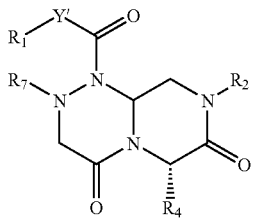
| No | MOLSTRUCTURE | Mol. Weight | M + H (MS) |
|---|---|---|---|
| 2483 | | 544 | 545 |
| 2484 | | 530 | 531 |
| 2485 | | 578 | 579 |

TABLE 2B-continued
THE [4,4,0]REVERSE TURN MIMETICS LIBRARY
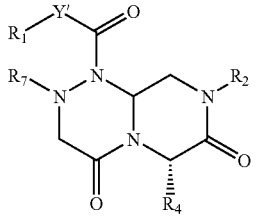
| No | MOLSTRUCTURE | Mol. Weight | M + H (MS) |
|---|---|---|---|
| 2486 | | 544 | 545 |
| 2487 | | 544 | 545 |
| 2488 | | 562 | 563 |

TABLE 2B-continued
THE [4,4,0]REVERSE TURN MIMETICS LIBRARY
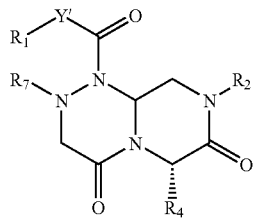
| No | MOLSTRUCTURE | Mol. Weight | M + H (MS) |
|---|---|---|---|
| 2489 | | 530 | 531 |
| 2490 | | 546 | 547 |

TABLE 2B-continued
THE [4,4,0]REVERSE TURN MIMETICS LIBRARY
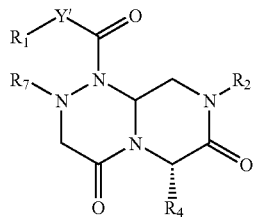
| No | MOLSTRUCTURE | Mol. Weight | M + H (MS) |
|---|---|---|---|
| 2491 | 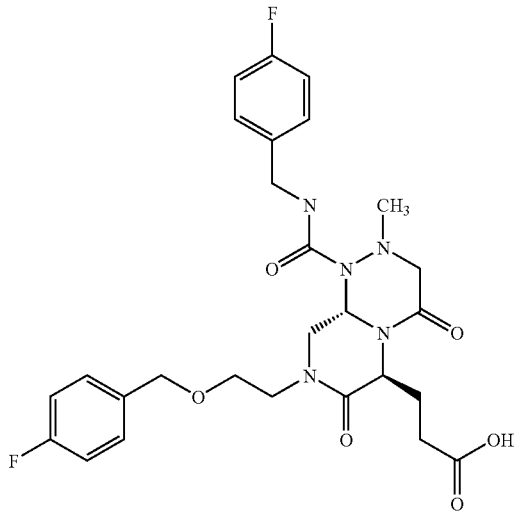 | 560 | 561 |
| 2492 | 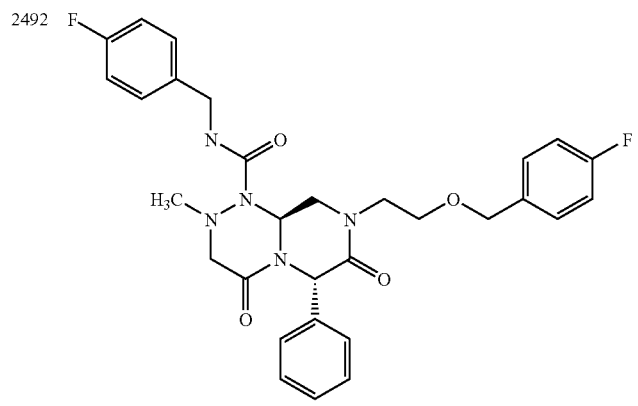 | 564 | 565 |

US 7,566,711 B2
1385 1386
TABLE 2B-continued
THE [4,4,0]REVERSE TURN MIMETICS LIBRARY

| No | MOLSTRUCTURE | Mol. Weight | M + H (MS) |
|---|---|---|---|
| 2493 | 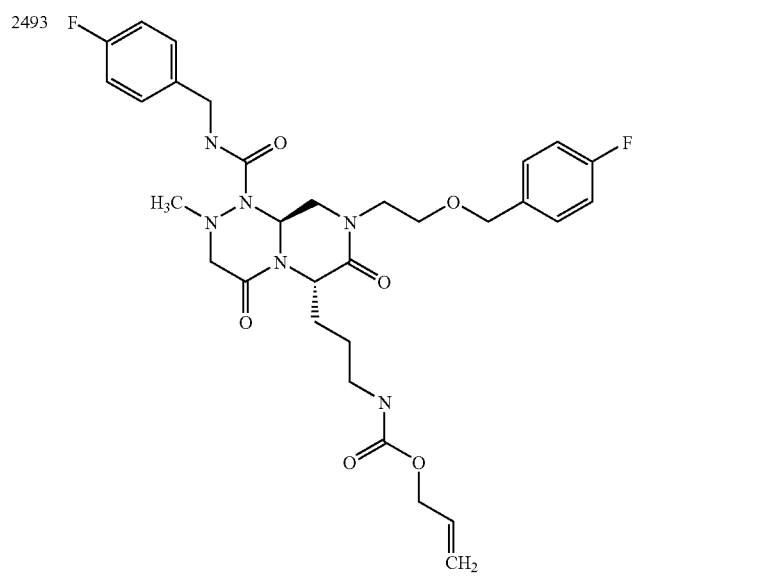 | 629 | 630 |
| 2494 | 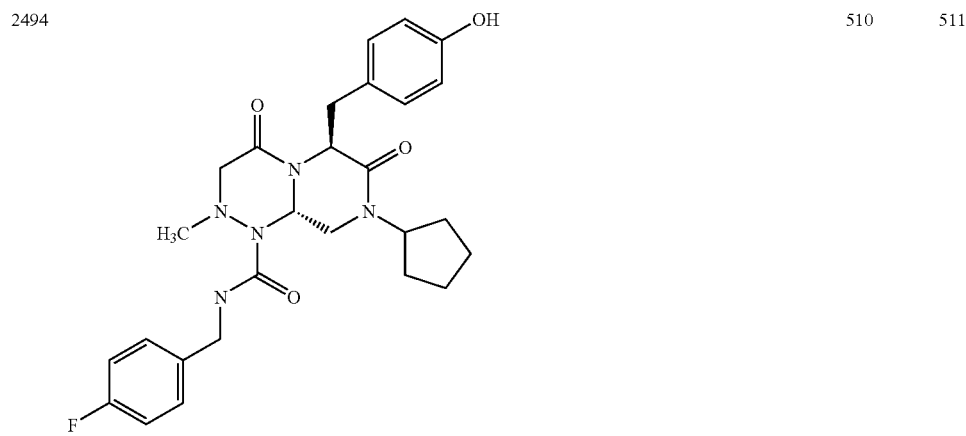 | 510 | 511 |

TABLE 2B-continued
THE [4,4,0]REVERSE TURN MIMETICS LIBRARY
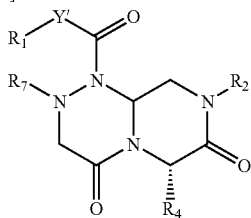
| No | MOLSTRUCTURE | Mol. Weight | M + H (MS) |
|---|---|---|---|
| 2495 | | 460 | 461 |
| 2496 | | 446 | 447 |
| 2497 | | 494 | 495 |

TABLE 2B-continued
THE [4,4,0]REVERSE TURN MIMETICS LIBRARY
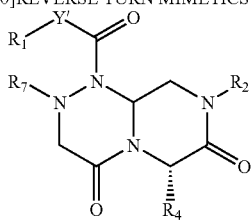
| No | MOLSTRUCTURE | Mol. Weight | M + H (MS) |
|---|---|---|---|
| 2498 | | 460 | 461 |
| 2499 | | 460 | 461 |
| 2500 | | 478 | 479 |

TABLE 2B-continued
THE [4,4,0]REVERSE TURN MIMETICS LIBRARY
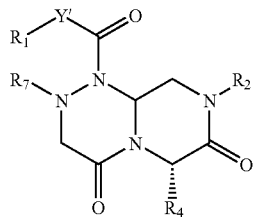
| No | MOLSTRUCTURE | Mol. Weight | M + H (MS) |
|---|---|---|---|
| 2501 | | 446 | 447 |
| 2502 | | 461 | 462 |

TABLE 2B-continued
THE [4,4,0]REVERSE TURN MIMETICS LIBRARY
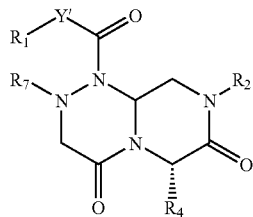
| No | MOLSTRUCTURE | Mol. Weight | M + H (MS) |
|---|---|---|---|
| 2503 | 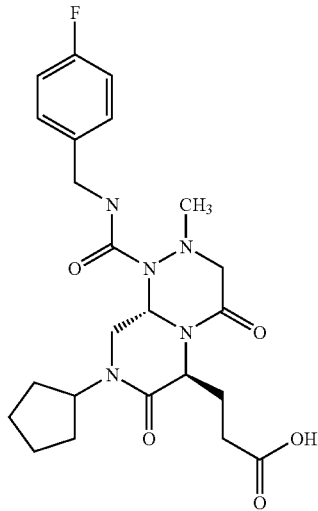 | 476 | 477 |
| 2504 | 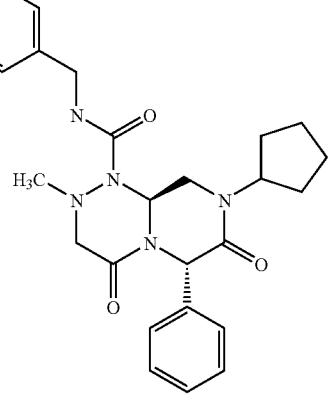 | 480 | 481 |

TABLE 2B-continued
THE [4,4,0]REVERSE TURN MIMETICS LIBRARY
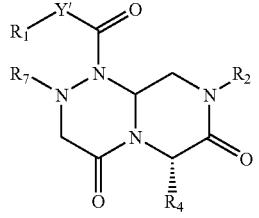
| No | MOLSTRUCTURE | Mol. Weight | M + H (MS) |
|---|---|---|---|
| 2505 | | 545 | 546 |
| 2506 | | 540 | 541 |

TABLE 2B-continued
THE [4,4,0]REVERSE TURN MIMETICS LIBRARY
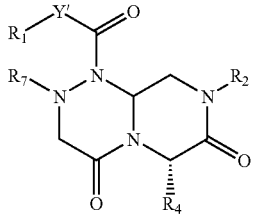
| No | MOLSTRUCTURE | Mol. Weight | M + H (MS) |
|---|---|---|---|
| 2507 | | 490 | 491 |
| 2508 | | 476 | 477 |
| 2509 | | 524 | 525 |

TABLE 2B-continued
THE [4,4,0]REVERSE TURN MIMETICS LIBRARY

| No | MOLSTRUCTURE | Mol. Weight | M + H (MS) |
|---|---|---|---|
| 2510 | | 490 | 491 |
| 2511 | | 490 | 491 |
| 2512 | | 508 | 509 |

TABLE 2B-continued
THE [4,4,0]REVERSE TURN MIMETICS LIBRARY
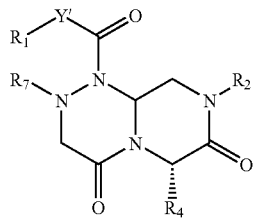
| No | MOLSTRUCTURE | Mol. Weight | M + H (MS) |
|---|---|---|---|
| 2513 |  | 476 | 477 |
| 2514 |  | 492 | 493 |

TABLE 2B-continued
THE [4,4,0]REVERSE TURN MIMETICS LIBRARY
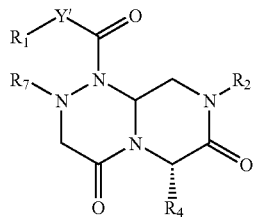
| No | MOLSTRUCTURE | Mol. Weight | M + H (MS) |
|---|---|---|---|
| 2515 | 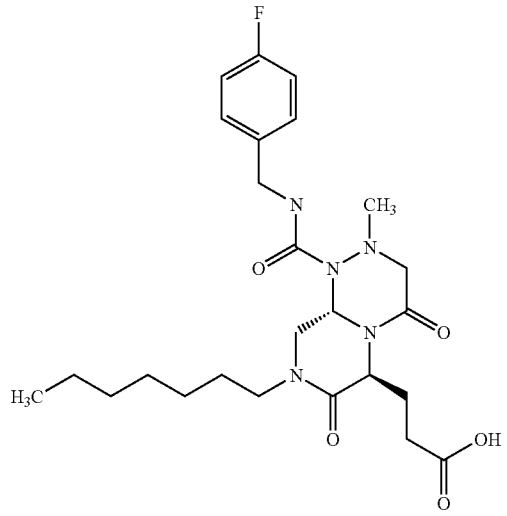 | 506 | 507 |
| 2516 | 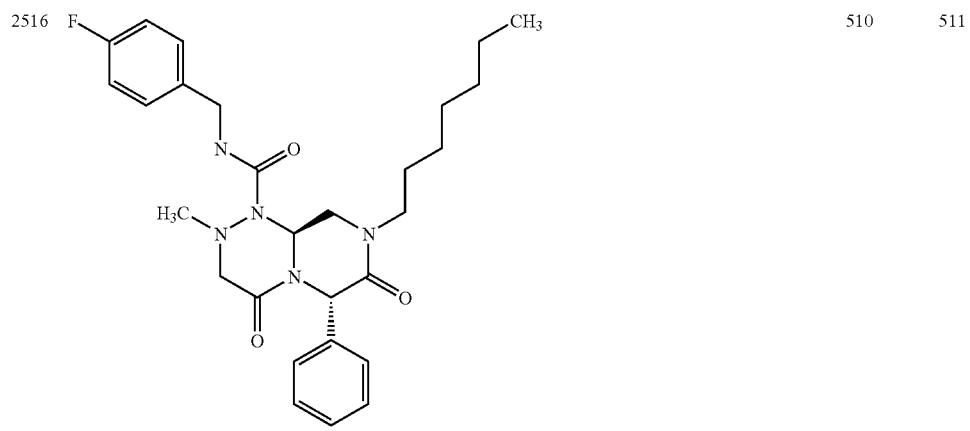 | 510 | 511 |

TABLE 2B-continued
THE [4,4,0]REVERSE TURN MIMETICS LIBRARY
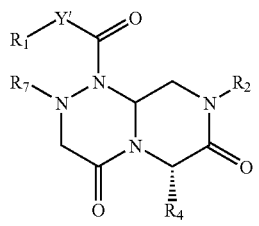
| No | MOLSTRUCTURE | Mol. Weight | M + H (MS) |
|---|---|---|---|
| 2517 | | 575 | 576 |
| 2518 | | 510 | 511 |

TABLE 2B-continued
THE [4,4,0]REVERSE TURN MIMETICS LIBRARY
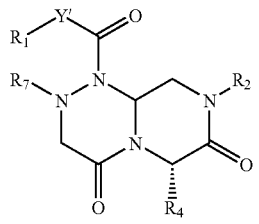
| No | MOLSTRUCTURE | Mol. Weight | M + H (MS) |
|---|---|---|---|
| 2519 | 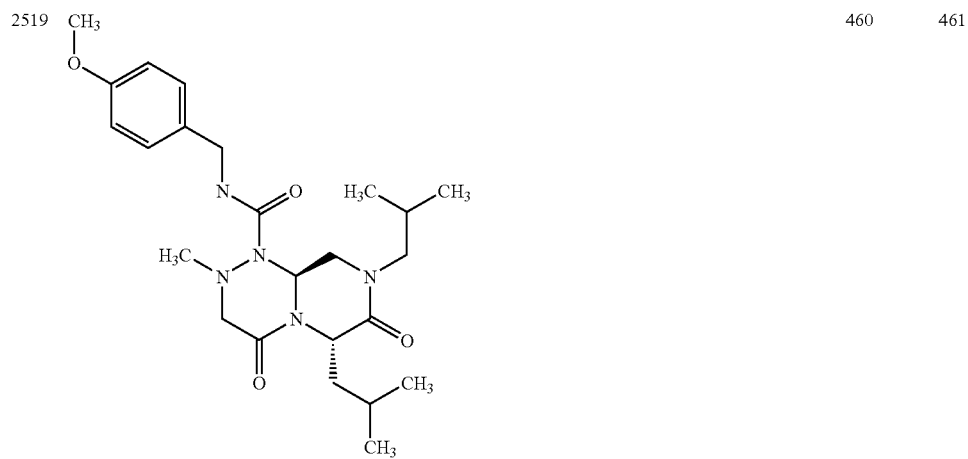 | 460 | 461 |
| 2520 | 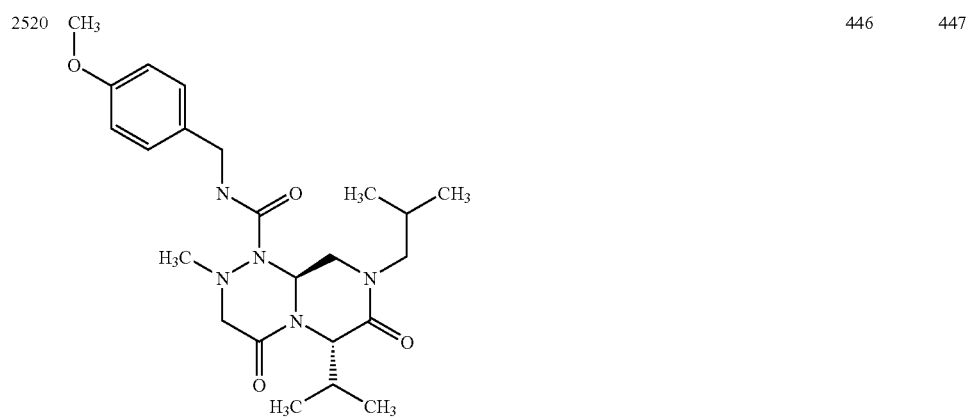 | 446 | 447 |

TABLE 2B-continued
THE [4,4,0]REVERSE TURN MIMETICS LIBRARY
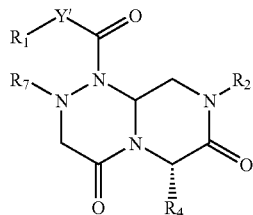
| No | MOLSTRUCTURE | Mol. Weight | M + H (MS) |
|---|---|---|---|
| 2521 | 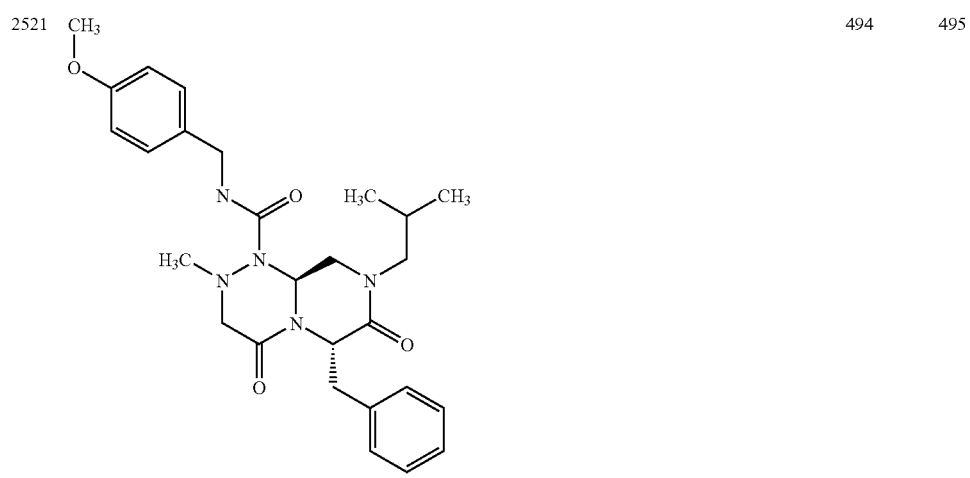 | 494 | 495 |
| 2522 | 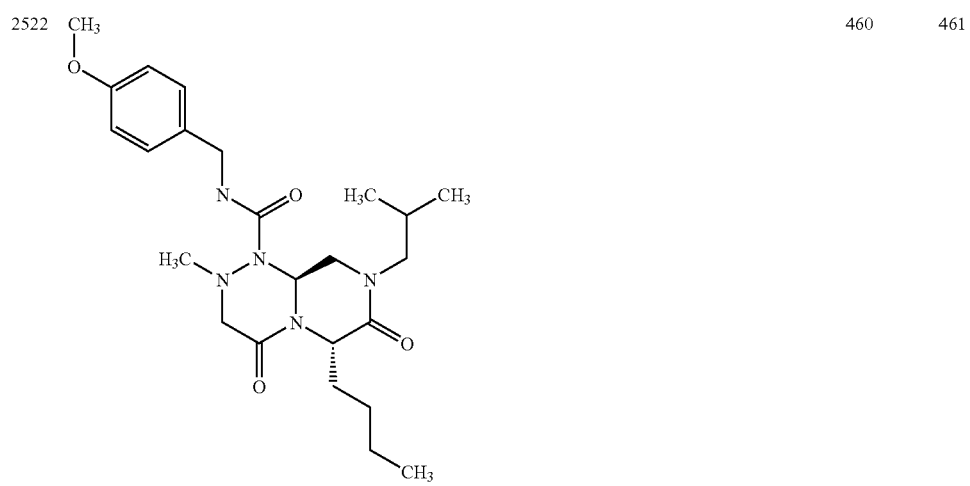 | 460 | 461 |

TABLE 2B-continued
THE [4,4,0]REVERSE TURN MIMETICS LIBRARY
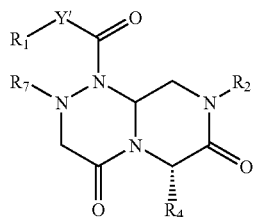
| No | MOLSTRUCTURE | Mol. Weight | M + H (MS) |
|---|---|---|---|
| 2523 | 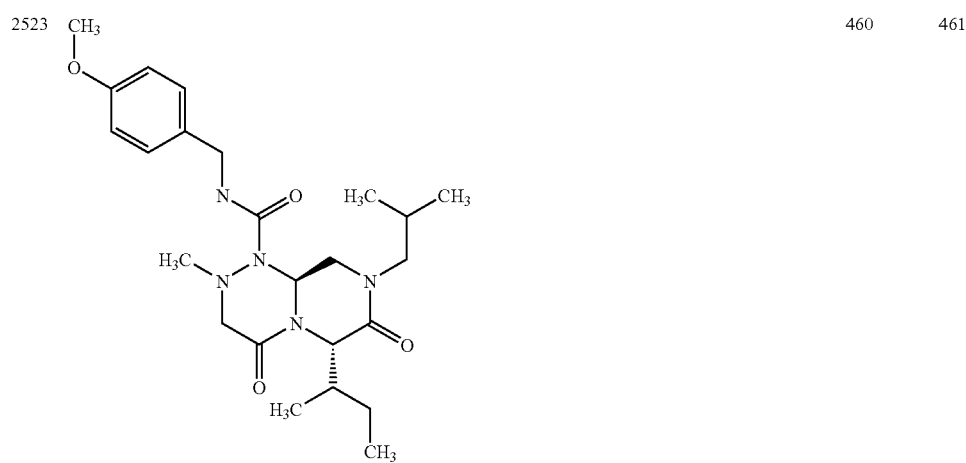 | 460 | 461 |
| 2524 | 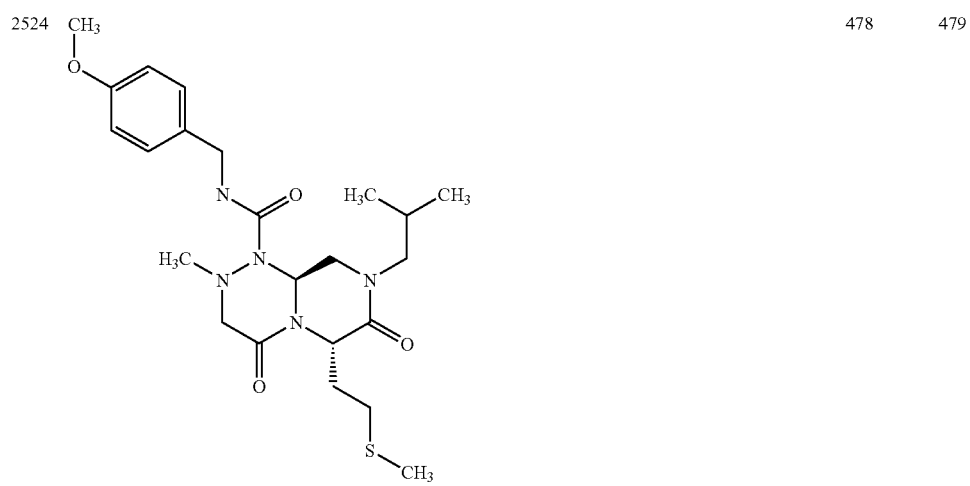 | 478 | 479 |

TABLE 2B-continued
THE [4,4,0]REVERSE TURN MIMETICS LIBRARY
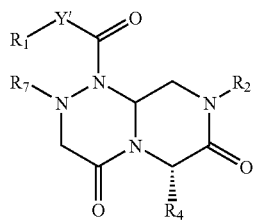
| No | MOLSTRUCTURE | Mol. Weight | M + H (MS) |
|----|--------------|-------------|------------|
| 2525 | | 446 | 447 |
| 2526 | | 462 | 463 |

TABLE 2B-continued
THE [4,4,0]REVERSE TURN MIMETICS LIBRARY
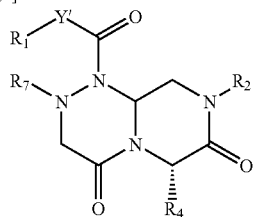
| No | MOLSTRUCTURE | Mol. Weight | M + H (MS) |
|---|---|---|---|
| 2527 | | 476 | 477 |
| 2528 | | 480 | 481 |

TABLE 2B-continued
THE [4,4,0]REVERSE TURN MIMETICS LIBRARY
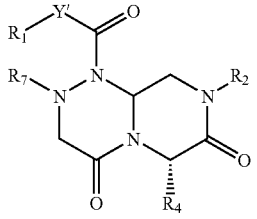
| No | MOLSTRUCTURE | Mol. Weight | M + H (MS) |
|---|---|---|---|
| 2529 | | 545 | 546 |
| 2530 | | 612 | 613 |

TABLE 2B-continued
THE [4,4,0]REVERSE TURN MIMETICS LIBRARY
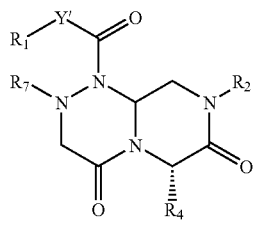
| No | MOLSTRUCTURE | Mol. Weight | M + H (MS) |
|---|---|---|---|
| 2531 | 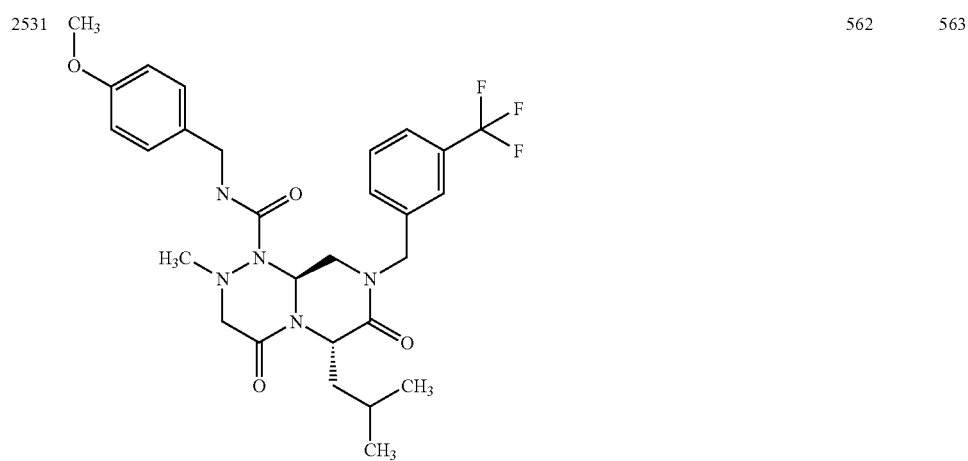 | 562 | 563 |
| 2532 | 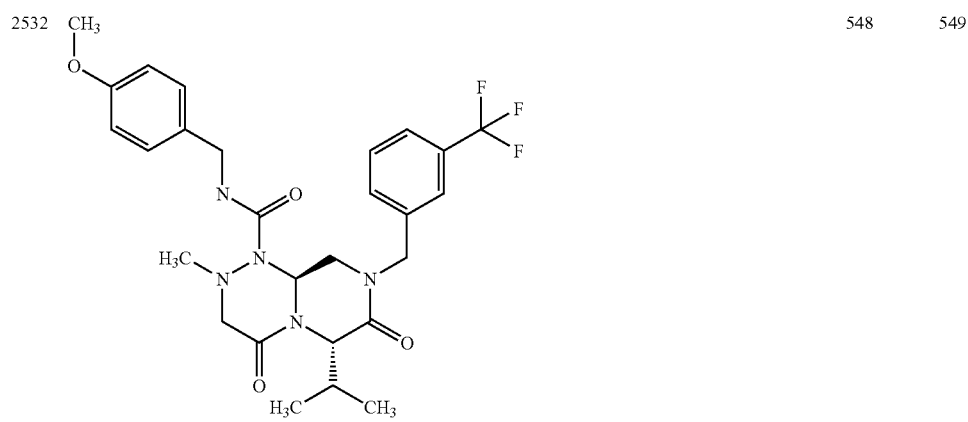 | 548 | 549 |

TABLE 2B-continued
THE [4,4,0]REVERSE TURN MIMETICS LIBRARY
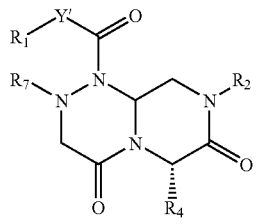
| No | MOLSTRUCTURE | Mol. Weight | M + H (MS) |
|----|--------------|-------------|------------|
| 2533 | 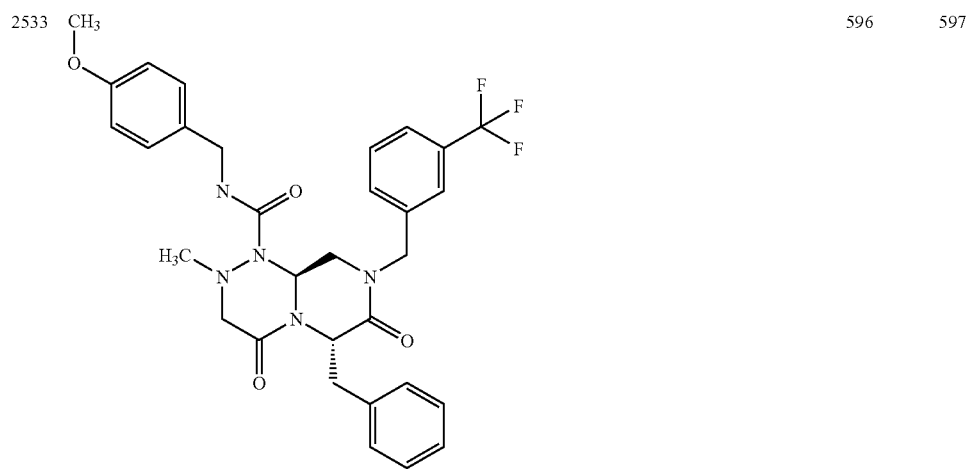 | 596 | 597 |
| 2534 | 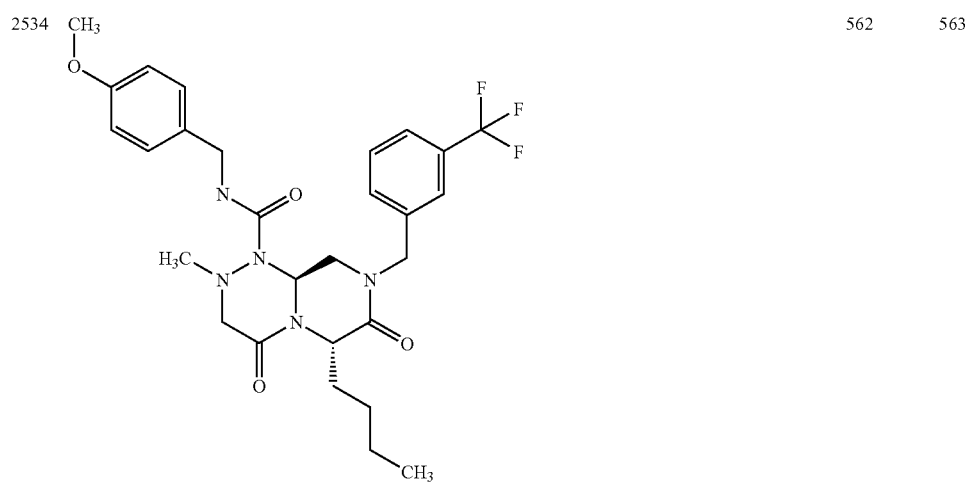 | 562 | 563 |

TABLE 2B-continued
THE [4,4,0]REVERSE TURN MIMETICS LIBRARY
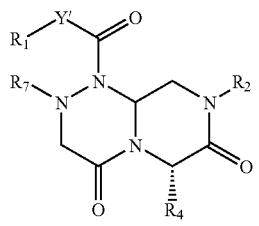
| No | MOLSTRUCTURE | Mol. Weight | M + H (MS) |
|---|---|---|---|
| 2535 | 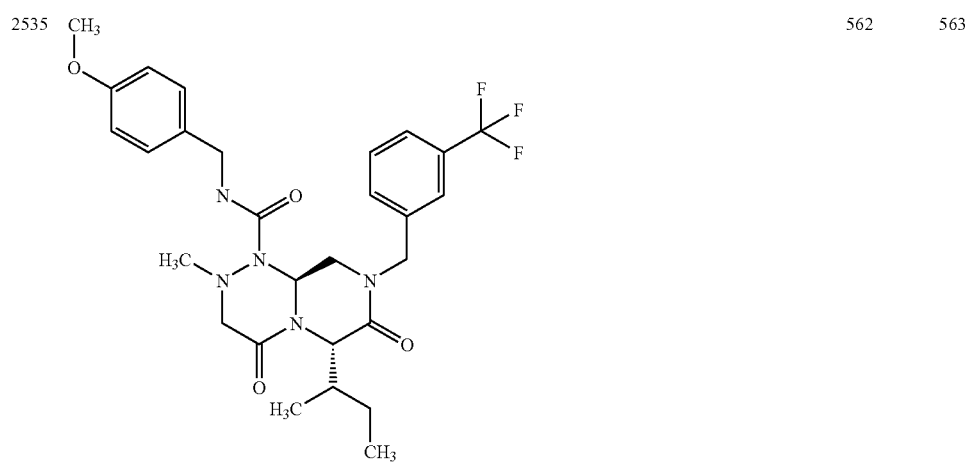 | 562 | 563 |
| 2536 |  | 580 | 581 |

TABLE 2B-continued
THE [4,4,0]REVERSE TURN MIMETICS LIBRARY
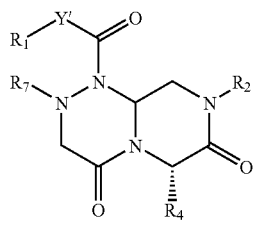
| No | MOLSTRUCTURE | Mol. Weight | M + H (MS) |
|---|---|---|---|
| 2537 | | 548 | 549 |
| 2538 | | 564 | 565 |

TABLE 2B-continued
THE [4,4,0]REVERSE TURN MIMETICS LIBRARY
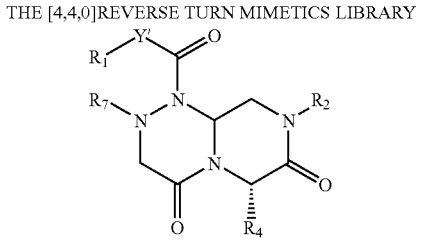
| No | MOLSTRUCTURE | Mol. Weight | M + H (MS) |
|---|---|---|---|
| 2539 | | 578 | 579 |
| 2540 | | 582 | 583 |

TABLE 2B-continued
THE [4,4,0]REVERSE TURN MIMETICS LIBRARY
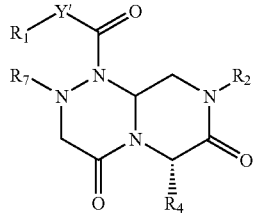
| No | MOLSTRUCTURE | Mol. Weight | M + H (MS) |
|----|--------------|-------------|------------|
| 2541 | | 647 | 648 |
| 2542 | | 572 | 573 |

TABLE 2B-continued
THE [4,4,0]REVERSE TURN MIMETICS LIBRARY
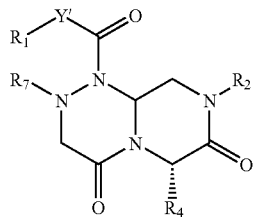
| No | MOLSTRUCTURE | Mol. Weight | M + H (MS) |
|---|---|---|---|
| 2543 | | 522 | 523 |
| 2544 | | 508 | 509 |

TABLE 2B-continued
THE [4,4,0]REVERSE TURN MIMETICS LIBRARY
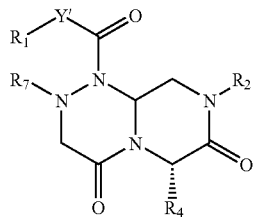
| No | MOLSTRUCTURE | Mol. Weight | M + H (MS) |
|---|---|---|---|
| 2545 | | 556 | 557 |
| 2546 | | 522 | 523 |

TABLE 2B-continued
THE [4,4,0]REVERSE TURN MIMETICS LIBRARY
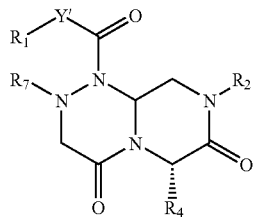
| No | MOLSTRUCTURE | Mol. Weight | M + H (MS) |
|----|--------------|-------------|------------|
| 2547 | | 522 | 523 |
| 2548 | | 540 | 541 |

TABLE 2B-continued
THE [4,4,0]REVERSE TURN MIMETICS LIBRARY
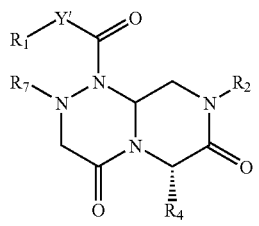
| No | MOLSTRUCTURE | Mol. Weight | M + H (MS) |
|---|---|---|---|
| 2549 | | 508 | 509 |
| 2550 | | 524 | 525 |

TABLE 2B-continued
THE [4,4,0]REVERSE TURN MIMETICS LIBRARY
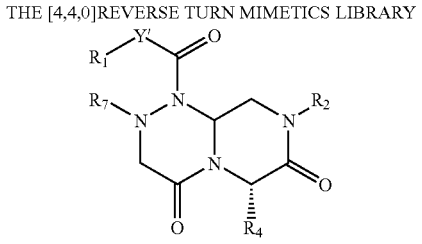
| No | MOLSTRUCTURE | Mol. Weight | M + H (MS) |
|---|---|---|---|
| 2551 | 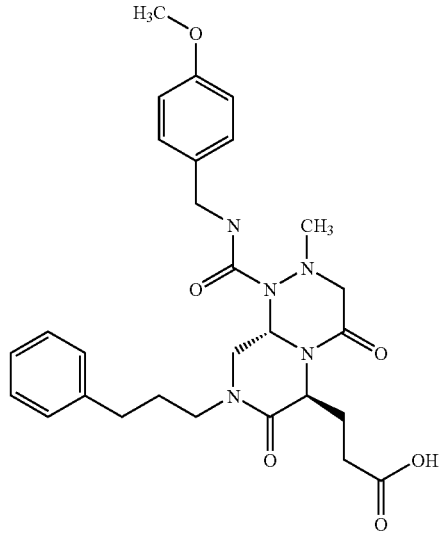 | 538 | 539 |
| 2552 | 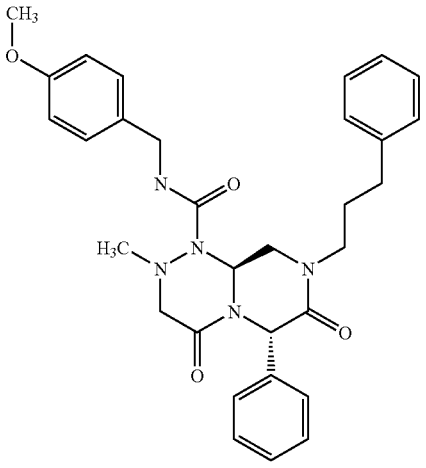 | 542 | 543 |

TABLE 2B-continued
THE [4,4,0]REVERSE TURN MIMETICS LIBRARY
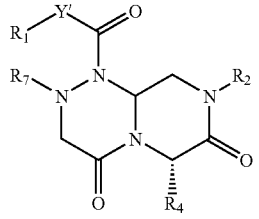
| No | MOLSTRUCTURE | Mol. Weight | M + H (MS) |
|----|--------------|-------------|------------|
| 2553 | | 607 | 608 |
| 2554 | | 562 | 563 |

TABLE 2B-continued
THE [4,4,0]REVERSE TURN MIMETICS LIBRARY
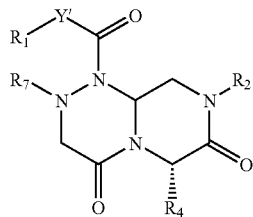
| No | MOLSTRUCTURE | Mol. Weight | M + H (MS) |
|---|---|---|---|
| 2555 | 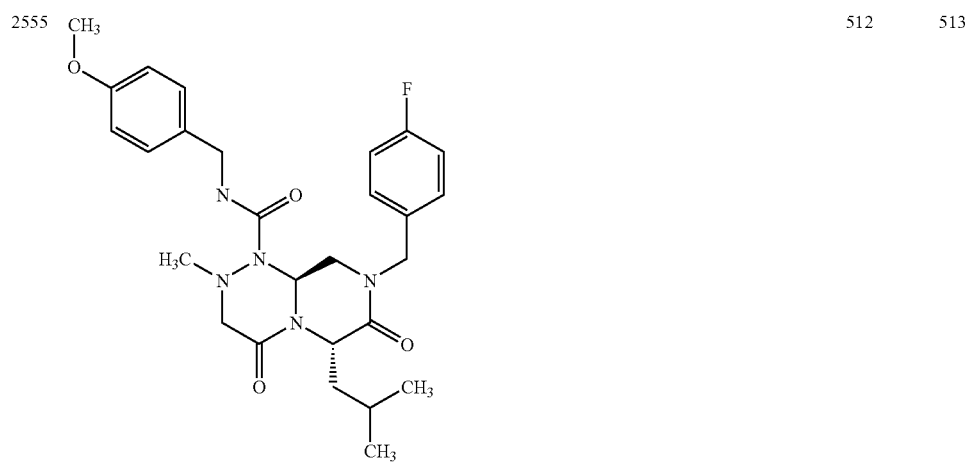 | 512 | 513 |
| 2556 |  | 498 | 499 |

TABLE 2B-continued
THE [4,4,0]REVERSE TURN MIMETICS LIBRARY
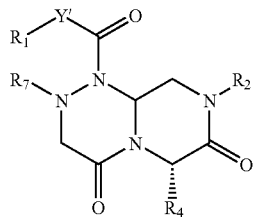
| No | MOLSTRUCTURE | Mol. Weight | M + H (MS) |
|---|---|---|---|
| 2557 | | 546 | 547 |
| 2558 | | 512 | 513 |

1447 1448
TABLE 2B-continued
THE [4,4,0]REVERSE TURN MIMETICS LIBRARY
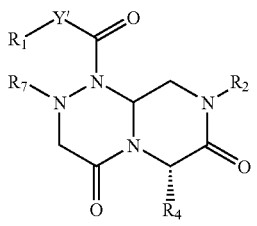
| No | MOLSTRUCTURE | Mol. Weight | M + H (MS) |
|---|---|---|---|
| 2559 |  | 512 | 513 |
| 2560 | 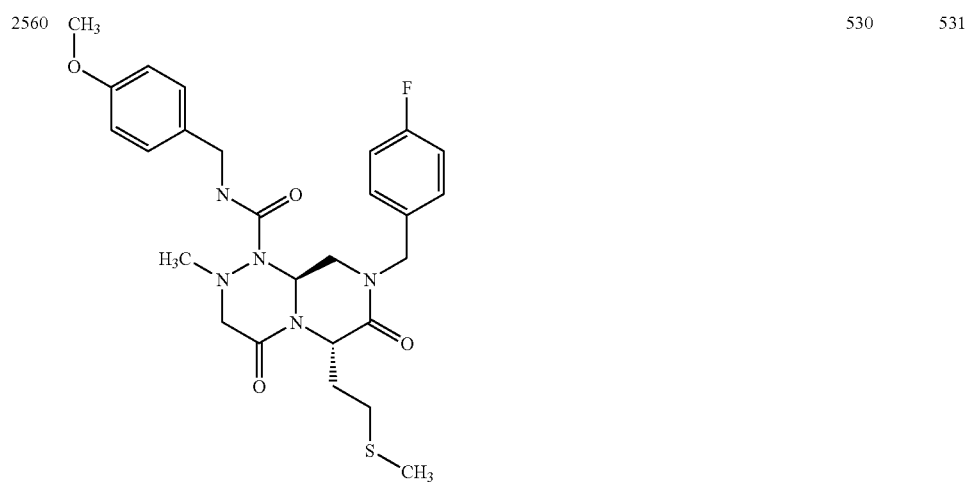 | 530 | 531 |

TABLE 2B-continued
THE [4,4,0]REVERSE TURN MIMETICS LIBRARY
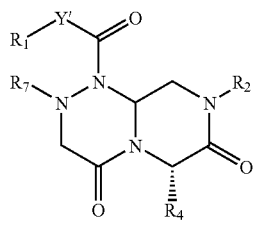
| No | MOLSTRUCTURE | Mol. Weight | M + H (MS) |
|---|---|---|---|
| 2561 | | 498 | 499 |
| 2562 | | 514 | 515 |

TABLE 2B-continued
THE [4,4,0]REVERSE TURN MIMETICS LIBRARY
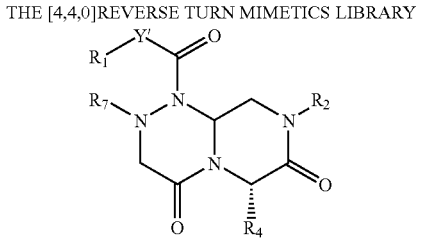
| No | MOLSTRUCTURE | Mol. Weight | M + H (MS) |
|---|---|---|---|
| 2563 | | 528 | 529 |
| 2564 | | 532 | 533 |

TABLE 2B-continued
THE [4,4,0]REVERSE TURN MIMETICS LIBRARY
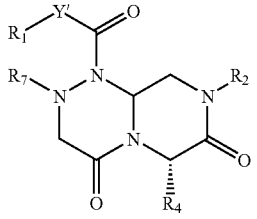
| No | MOLSTRUCTURE | Mol. Weight | M + H (MS) |
|---|---|---|---|
| 2565 | | 597 | 598 |
| 2566 | | 538 | 539 |

TABLE 2B-continued
THE [4,4,0]REVERSE TURN MIMETICS LIBRARY
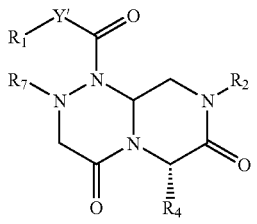
| No | MOLSTRUCTURE | Mol. Weight | M + H (MS) |
|----|--------------|-------------|------------|
| 2567 | | 488 | 489 |
| 2568 | | 474 | 475 |

TABLE 2B-continued
THE [4,4,0]REVERSE TURN MIMETICS LIBRARY
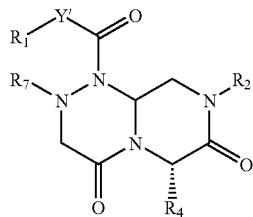
| No | MOLSTRUCTURE | Mol. Weight | M + H (MS) |
|---|---|---|---|
| 2569 |  | 522 | 523 |
| 2570 |  | 488 | 489 |

TABLE 2B-continued
THE [4,4,0]REVERSE TURN MIMETICS LIBRARY
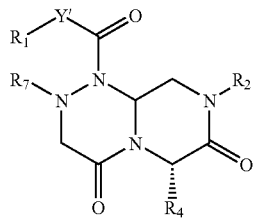
| No | MOLSTRUCTURE | Mol. Weight | M + H (MS) |
|----|--------------|-------------|------------|
| 2571 |  | 488 | 489 |
| 2572 | 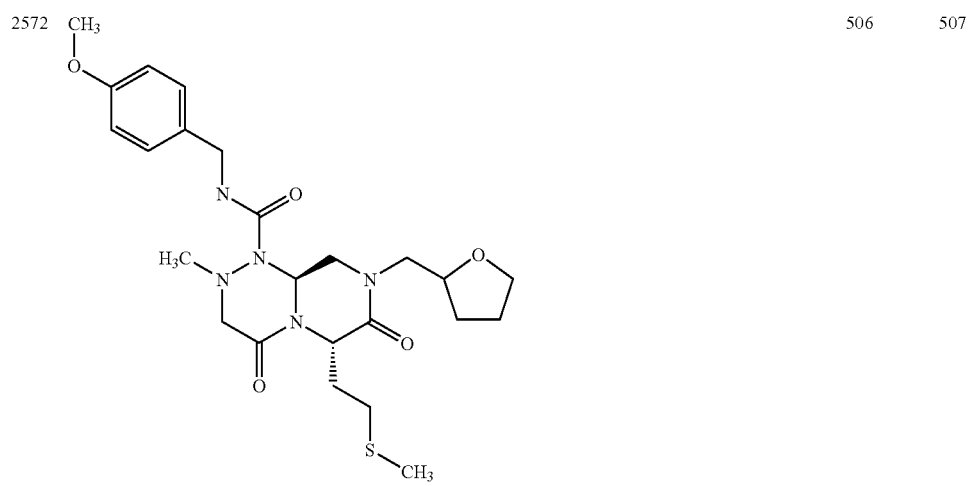 | 506 | 507 |

TABLE 2B-continued
THE [4,4,0]REVERSE TURN MIMETICS LIBRARY
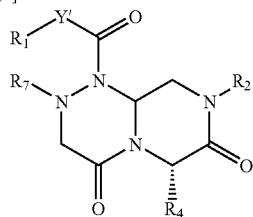
| No | MOLSTRUCTURE | Mol. Weight | M + H (MS) |
|---|---|---|---|
| 2573 | | 474 | 475 |
| 2574 | | 490 | 491 |

TABLE 2B-continued
THE [4,4,0]REVERSE TURN MIMETICS LIBRARY
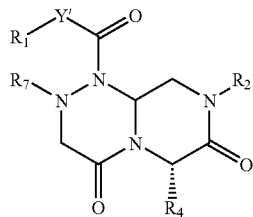
| No | MOLSTRUCTURE | Mol. Weight | M + H (MS) |
|---|---|---|---|
| 2575 | | 504 | 505 |
| 2576 | | 508 | 509 |

TABLE 2B-continued
THE [4,4,0]REVERSE TURN MIMETICS LIBRARY
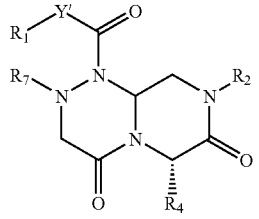
| No | MOLSTRUCTURE | Mol. Weight | M + H (MS) |
|---|---|---|---|
| 2577 | | 573 | 574 |
| 2578 | | 524 | 525 |

TABLE 2B-continued
THE [4,4,0]REVERSE TURN MIMETICS LIBRARY
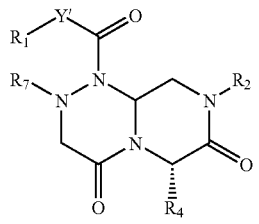
| No | MOLSTRUCTURE | Mol. Weight | M + H (MS) |
|---|---|---|---|
| 2579 | | 474 | 475 |
| 2580 | | 460 | 461 |

TABLE 2B-continued
THE [4,4,0]REVERSE TURN MIMETICS LIBRARY
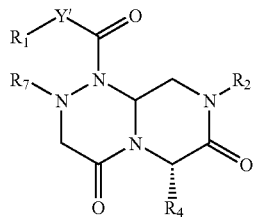
| No | MOLSTRUCTURE | Mol. Weight | M + H (MS) |
|----|--------------|-------------|------------|
| 2581 | | 508 | 509 |
| 2582 | | 474 | 475 |

TABLE 2B-continued
THE [4,4,0]REVERSE TURN MIMETICS LIBRARY
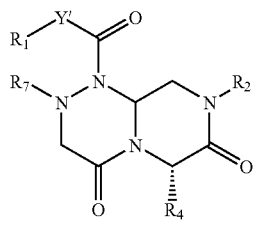
| No | MOLSTRUCTURE | Mol. Weight | M + H (MS) |
|---|---|---|---|
| 2583 | 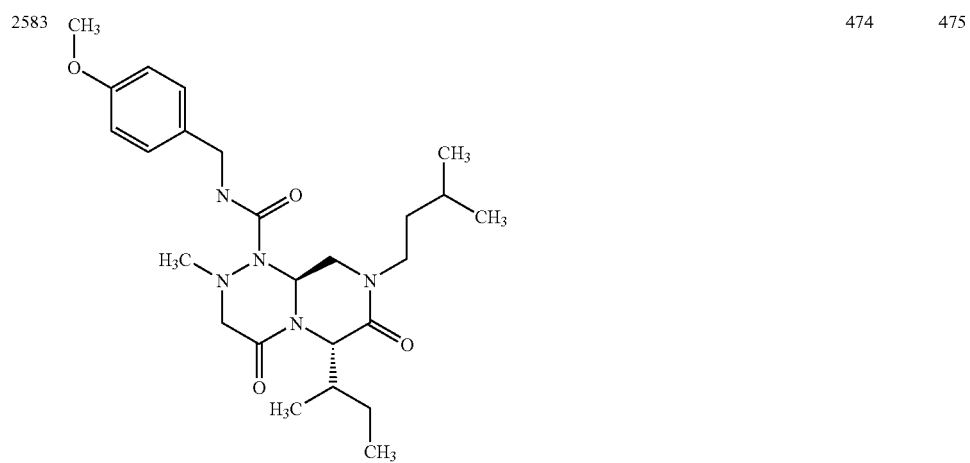 | 474 | 475 |
| 2584 |  | 492 | 493 |

TABLE 2B-continued
THE [4,4,0]REVERSE TURN MIMETICS LIBRARY
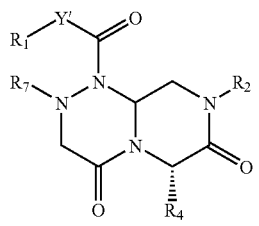
| No | MOLSTRUCTURE | Mol. Weight | M + H (MS) |
|---|---|---|---|
| 2585 | | 460 | 461 |
| 2586 | | 476 | 477 |

TABLE 2B-continued
THE [4,4,0]REVERSE TURN MIMETICS LIBRARY
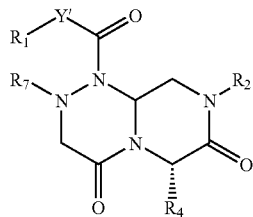
| No | MOLSTRUCTURE | Mol. Weight | M + H (MS) |
|---|---|---|---|
| 2587 | | 490 | 491 |
| 2588 | | 494 | 495 |

TABLE 2B-continued
THE [4,4,0]REVERSE TURN MIMETICS LIBRARY
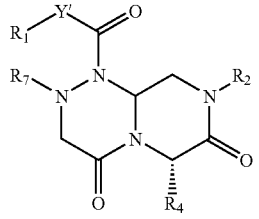
| No | MOLSTRUCTURE | Mol. Weight | M + H (MS) |
|---|---|---|---|
| 2589 | | 559 | 560 |
| 2590 | | 588 | 589 |

TABLE 2B-continued
THE [4,4,0]REVERSE TURN MIMETICS LIBRARY
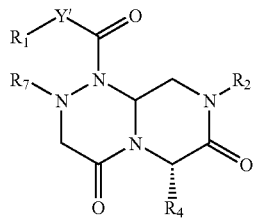
| No | MOLSTRUCTURE | Mol. Weight | M + H (MS) |
|---|---|---|---|
| 2591 | | 538 | 539 |
| 2592 | | 424 | 425 |

TABLE 2B-continued
THE [4,4,0]REVERSE TURN MIMETICS LIBRARY
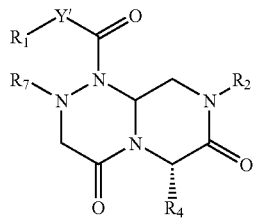
| No | MOLSTRUCTURE | Mol. Weight | M + H (MS) |
|----|--------------|-------------|------------|
| 2593 | | 572 | 573 |
| 2594 | | 538 | 539 |

TABLE 2B-continued
THE [4,4,0]REVERSE TURN MIMETICS LIBRARY
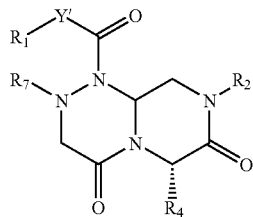
| No | MOLSTRUCTURE | Mol. Weight | M + H (MS) |
|---|---|---|---|
| 2595 |  | 538 | 539 |
| 2596 |  | 556 | 557 |

TABLE 2B-continued
THE [4,4,0]REVERSE TURN MIMETICS LIBRARY
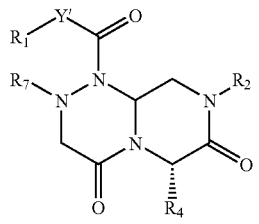
| No | MOLSTRUCTURE | Mol. Weight | M + H (MS) |
|---|---|---|---|
| 2597 | | 524 | 525 |
| 2598 | | 540 | 541 |

TABLE 2B-continued
THE [4,4,0]REVERSE TURN MIMETICS LIBRARY
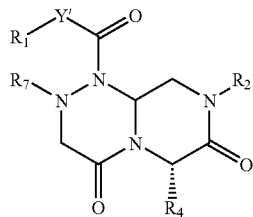
| No | MOLSTRUCTURE | Mol. Weight | M + H (MS) |
|---|---|---|---|
| 2599 | 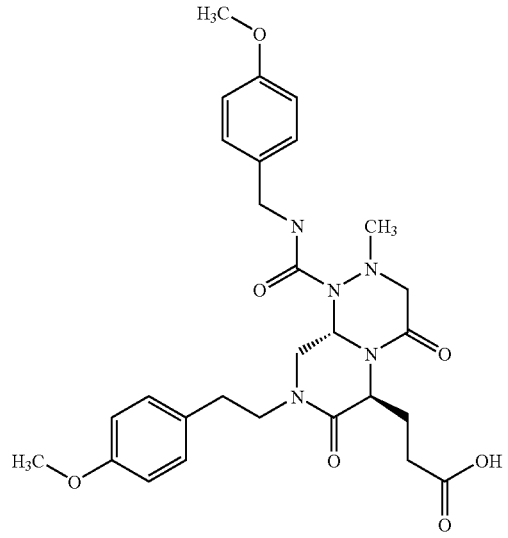 | 554 | 555 |
| 2600 | 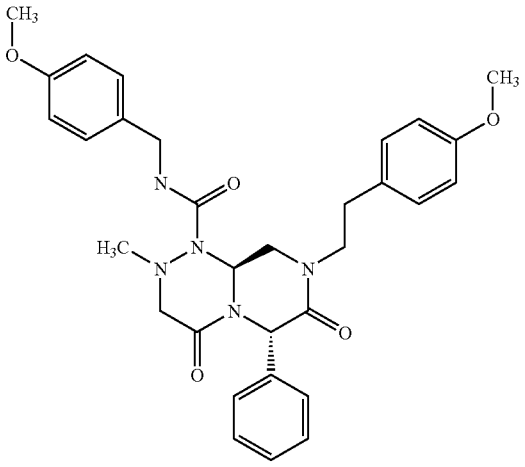 | 558 | 559 |

TABLE 2B-continued
THE [4,4,0]REVERSE TURN MIMETICS LIBRARY
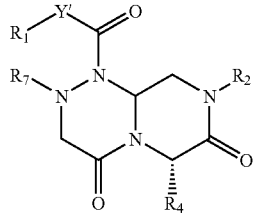
| No | MOLSTRUCTURE | Mol. Weight | M + H (MS) |
|---|---|---|---|
| 2601 | | 623 | 624 |
| 2602 | | 526 | 527 |

TABLE 2B-continued
THE [4,4,0]REVERSE TURN MIMETICS LIBRARY
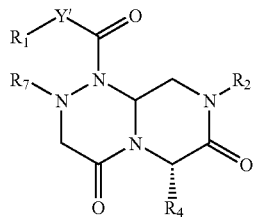
| No | MOLSTRUCTURE | Mol. Weight | M + H (MS) |
|----|--------------|-------------|------------|
| 2603 | | 476 | 477 |
| 2604 | | 462 | 463 |

TABLE 2B-continued
THE [4,4,0]REVERSE TURN MIMETICS LIBRARY
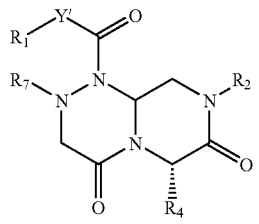
| No | MOLSTRUCTURE | Mol. Weight | M + H (MS) |
|---|---|---|---|
| 2605 | 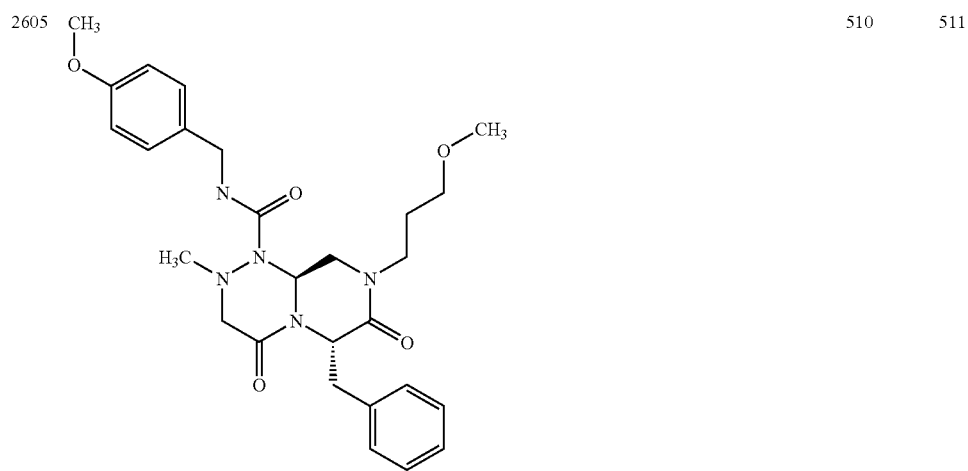 | 510 | 511 |
| 2606 | 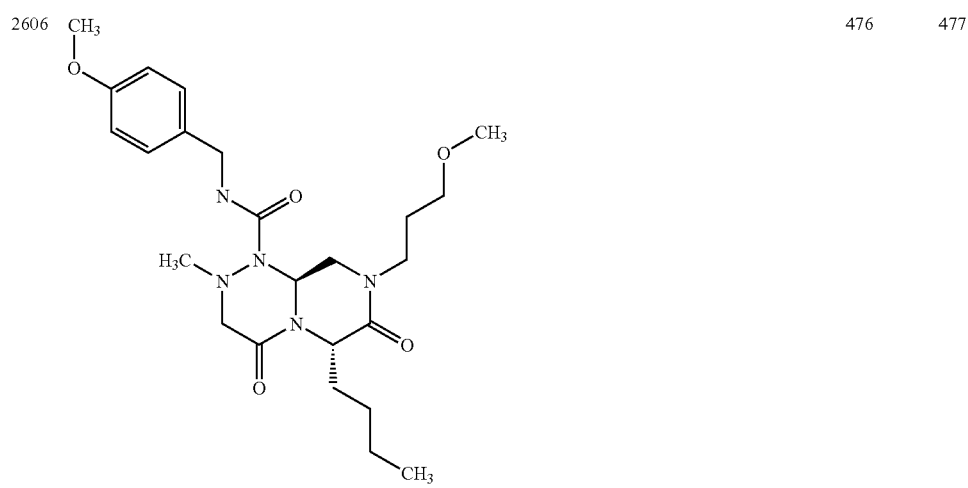 | 476 | 477 |

TABLE 2B-continued
THE [4,4,0]REVERSE TURN MIMETICS LIBRARY
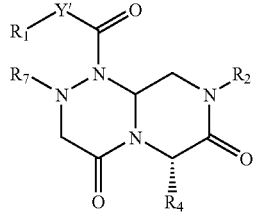
| No | MOLSTRUCTURE | Mol. Weight | M + H (MS) |
|---|---|---|---|
| 2607 | | 476 | 477 |
| 2608 | | 494 | 495 |
| 2609 | | 462 | 463 |

TABLE 2B-continued
THE [4,4,0]REVERSE TURN MIMETICS LIBRARY
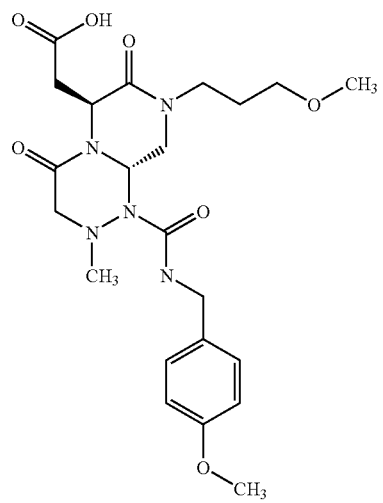
| No | MOLSTRUCTURE | Mol. Weight | M + H (MS) |
|---|---|---|---|
| 2610 | 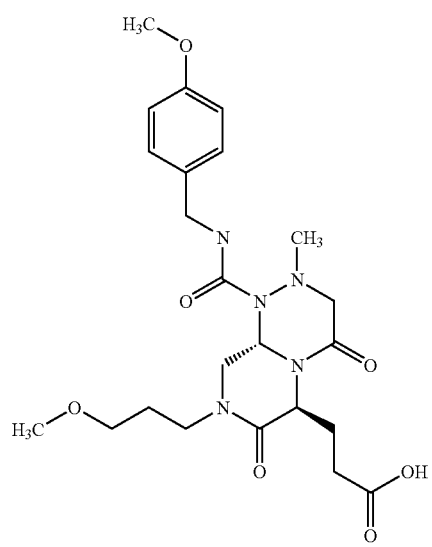 | 478 | 479 |
| 2611 | | 492 | 493 |

TABLE 2B-continued
THE [4,4,0]REVERSE TURN MIMETICS LIBRARY
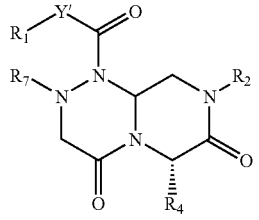
| No | MOLSTRUCTURE | Mol. Weight | M + H (MS) |
|---|---|---|---|
| 2612 | | 496 | 497 |
| 2613 | | 561 | 562 |

TABLE 2B-continued
THE [4,4,0]REVERSE TURN MIMETICS LIBRARY
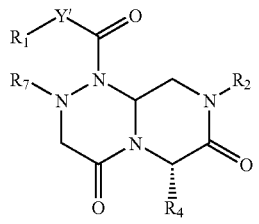
| No | MOLSTRUCTURE | Mol. Weight | M + H (MS) |
|---|---|---|---|
| 2614 | 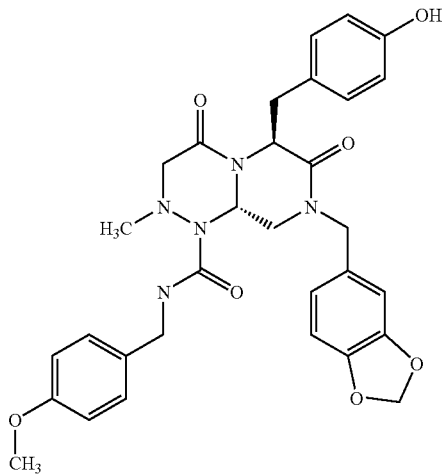 | 588 | 589 |
| 2615 | 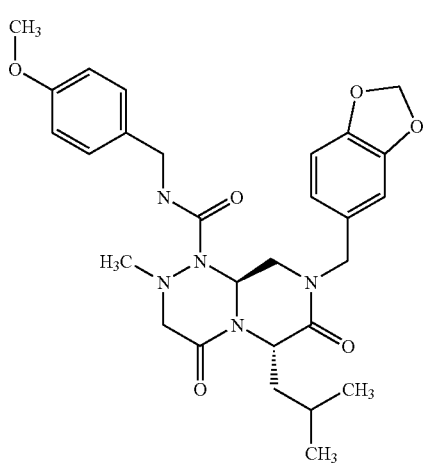 | 538 | 539 |

TABLE 2B-continued
THE [4,4,0]REVERSE TURN MIMETICS LIBRARY
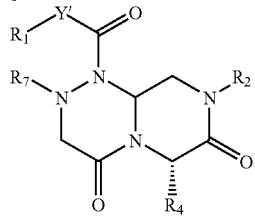
| No | MOLSTRUCTURE | Mol. Weight | M + H (MS) |
|---|---|---|---|
| 2616 | | 524 | 525 |
| 2617 | | 572 | 573 |

TABLE 2B-continued
THE [4,4,0]REVERSE TURN MIMETICS LIBRARY
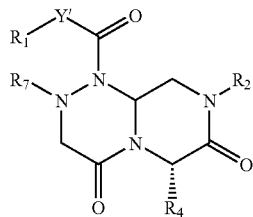
| No | MOLSTRUCTURE | Mol. Weight | M + H (MS) |
|---|---|---|---|
| 2618 | 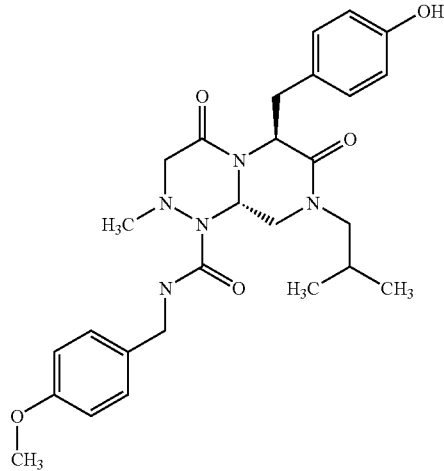 | 538 | 539 |
| 2619 | 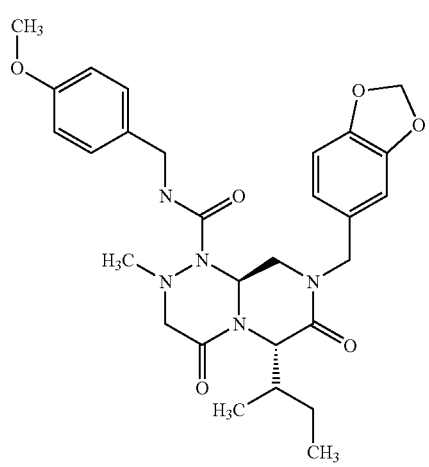 | 538 | 539 |

TABLE 2B-continued
THE [4,4,0]REVERSE TURN MIMETICS LIBRARY
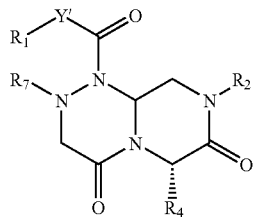
| No | MOLSTRUCTURE | Mol. Weight | M + H (MS) |
|---|---|---|---|
| 2620 | | 556 | 557 |
| 2621 | | 524 | 525 |

TABLE 2B-continued
THE [4,4,0]REVERSE TURN MIMETICS LIBRARY
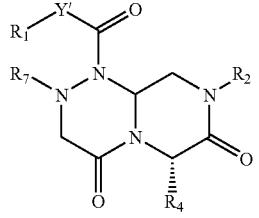
| No | MOLSTRUCTURE | Mol. Weight | M + H (MS) |
|----|--------------|-------------|------------|
| 2622 | | 540 | 541 |
| 2623 | | 554 | 555 |

//
TABLE 2B-continued
THE [4,4,0]REVERSE TURN MIMETICS LIBRARY
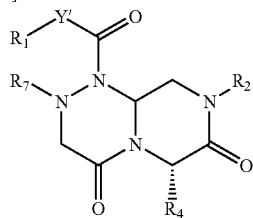
| No | MOLSTRUCTURE | Mol. Weight | M + H (MS) |
|---|---|---|---|
| 2624 | 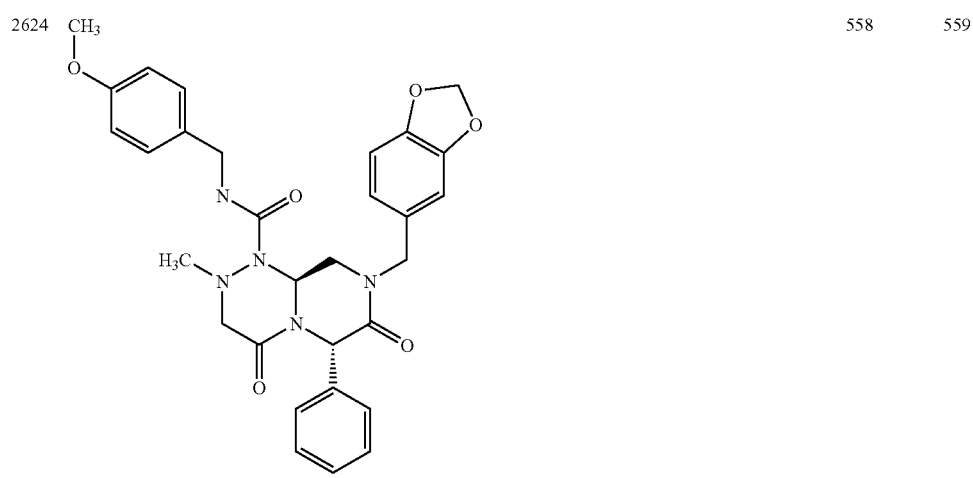 | 558 | 559 |
| 2625 | 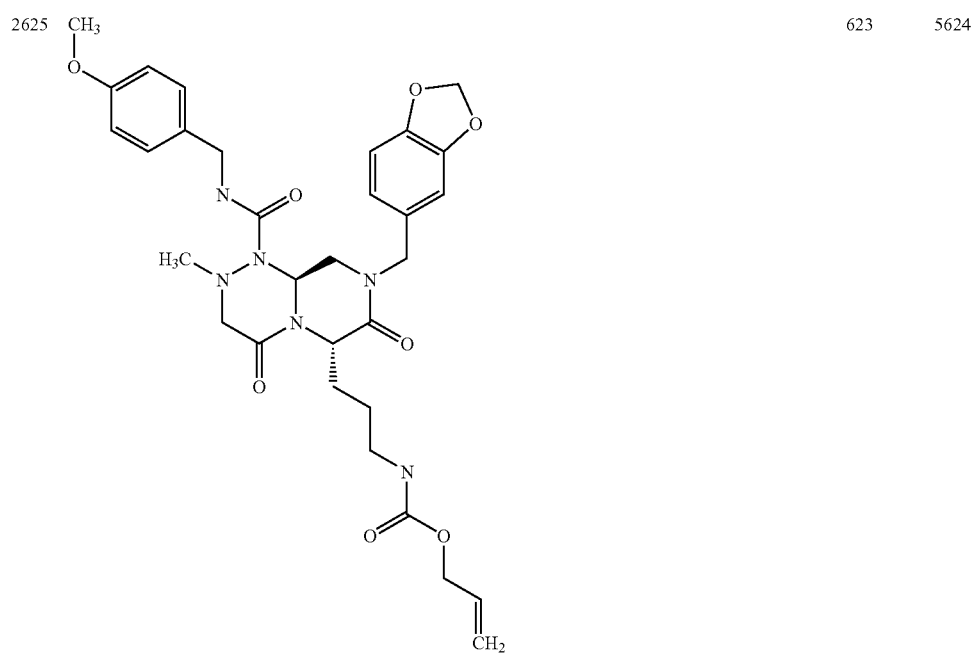 | 623 | 5624 |

TABLE 2B-continued
THE [4,4,0]REVERSE TURN MIMETICS LIBRARY
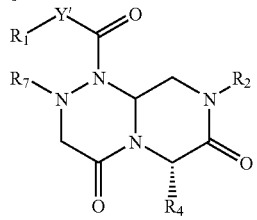
| No | MOLSTRUCTURE | Mol. Weight | M + H (MS) |
|---|---|---|---|
| 2626 | | 574 | 575 |
| 2627 | | 524 | 525 |

TABLE 2B-continued
THE [4,4,0]REVERSE TURN MIMETICS LIBRARY
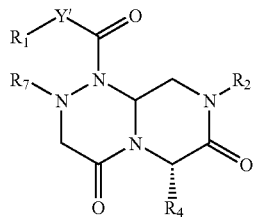
| No | MOLSTRUCTURE | Mol. Weight | M + H (MS) |
|---|---|---|---|
| 2628 | 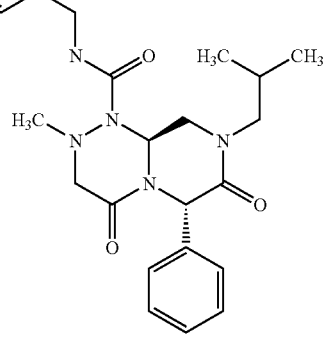 | 510 | 511 |
| 2629 | 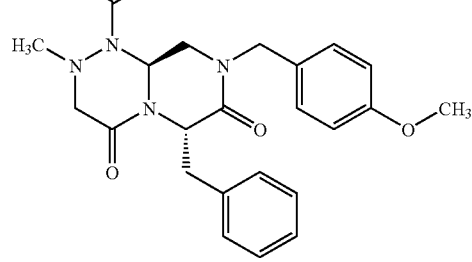 | 558 | 559 |

TABLE 2B-continued
THE [4,4,0]REVERSE TURN MIMETICS LIBRARY
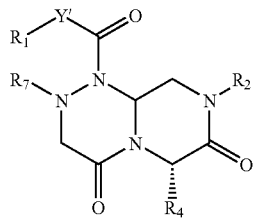
| No | MOLSTRUCTURE | Mol. Weight | M + H (MS) |
|---|---|---|---|
| 2630 | | 524 | 525 |
| 2631 | | 524 | 525 |

TABLE 2B-continued
THE [4,4,0]REVERSE TURN MIMETICS LIBRARY
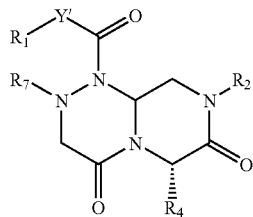
| No | MOLSTRUCTURE | Mol. Weight | M + H (MS) |
|---|---|---|---|
| 2632 | 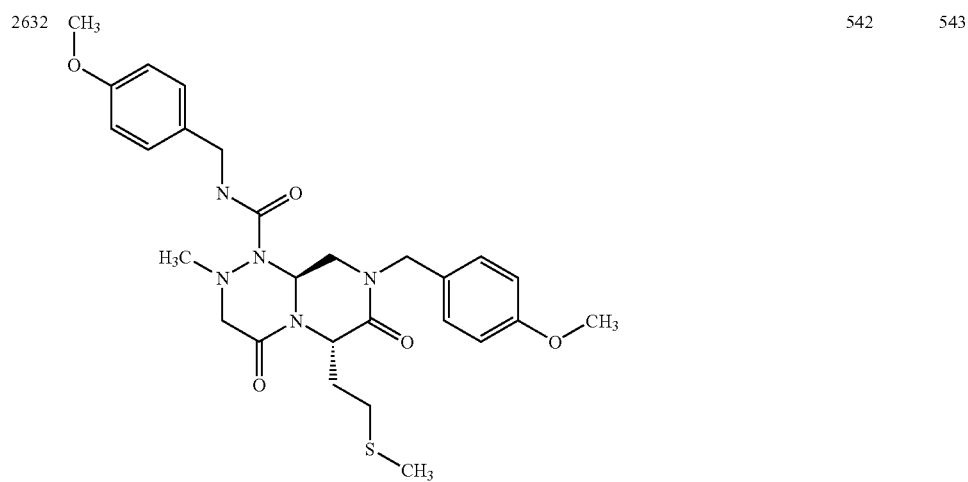 | 542 | 543 |
| 2633 |  | 510 | 511 |

TABLE 2B-continued
THE [4,4,0]REVERSE TURN MIMETICS LIBRARY
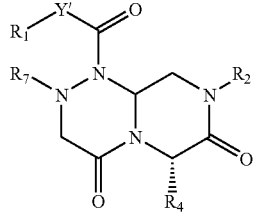
| No | MOLSTRUCTURE | Mol. Weight | M + H (MS) |
|---|---|---|---|
| 2634 | | 526 | 527 |
| 2635 | | 540 | 541 |

TABLE 2B-continued
THE [4,4,0]REVERSE TURN MIMETICS LIBRARY
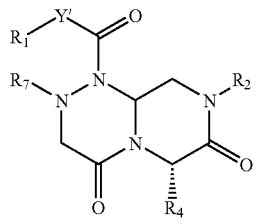
| No | MOLSTRUCTURE | Mol. Weight | M + H (MS) |
|---|---|---|---|
| 2636 | | 544 | 545 |
| 2637 | | 609 | 610 |

TABLE 2B-continued
THE [4,4,0]REVERSE TURN MIMETICS LIBRARY
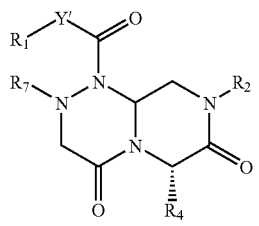
| No | MOLSTRUCTURE | Mol. Weight | M + H (MS) |
|---|---|---|---|
| 2638 | | 544 | 545 |
| 2639 | | 494 | 495 |

TABLE 2B-continued
THE [4,4,0]REVERSE TURN MIMETICS LIBRARY
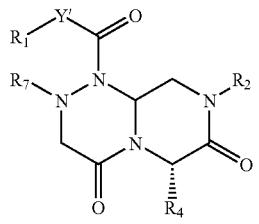
| No | MOLSTRUCTURE | Mol. Weight | M + H (MS) |
|---|---|---|---|
| 2640 | | 480 | 481 |
| 2641 | | 528 | 529 |

TABLE 2B-continued
THE [4,4,0]REVERSE TURN MIMETICS LIBRARY
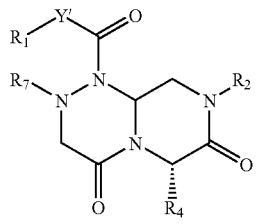
| No | MOLSTRUCTURE | Mol. Weight | M + H (MS) |
|---|---|---|---|
| 2642 | | 494 | 495 |
| 2643 | | 494 | 495 |

TABLE 2B-continued
THE [4,4,0]REVERSE TURN MIMETICS LIBRARY
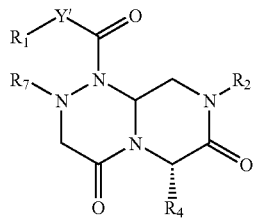
| No | MOLSTRUCTURE | Mol. Weight | M + H (MS) |
|---|---|---|---|
| 2644 | | 512 | 513 |
| 2645 | | 480 | 481 |

TABLE 2B-continued
THE [4,4,0]REVERSE TURN MIMETICS LIBRARY
| No | MOLSTRUCTURE | Mol. Weight | M + H (MS) |
|---|---|---|---|
| 2646 | | 496 | 497 |
| 2647 | | 510 | 511 |

TABLE 2B-continued
THE [4,4,0]REVERSE TURN MIMETICS LIBRARY
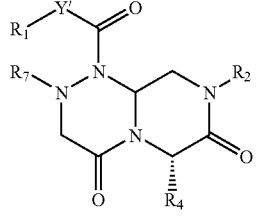
| No | MOLSTRUCTURE | Mol. Weight | M + H (MS) |
|---|---|---|---|
| 2648 | | 514 | 515 |
| 2649 | | 579 | 580 |

TABLE 2B-continued
THE [4,4,0]REVERSE TURN MIMETICS LIBRARY
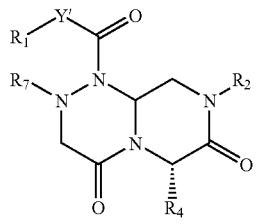
| No | MOLSTRUCTURE | Mol. Weight | M + H (MS) |
|---|---|---|---|
| 2650 | 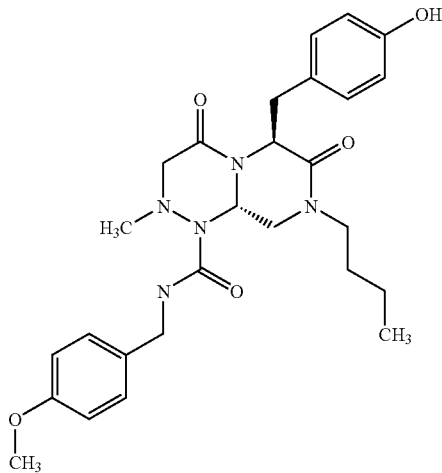 | 510 | 511 |
| 2651 | 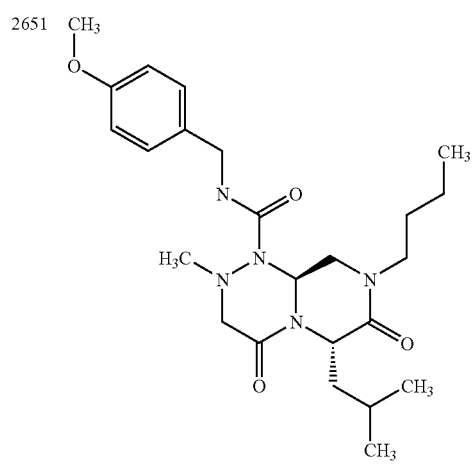 | 460 | 461 |

TABLE 2B-continued
THE [4,4,0]REVERSE TURN MIMETICS LIBRARY
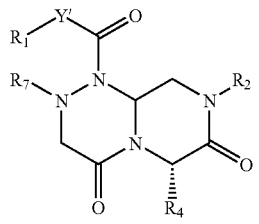
| No | MOLSTRUCTURE | Mol. Weight | M + H (MS) |
|---|---|---|---|
| 2652 | 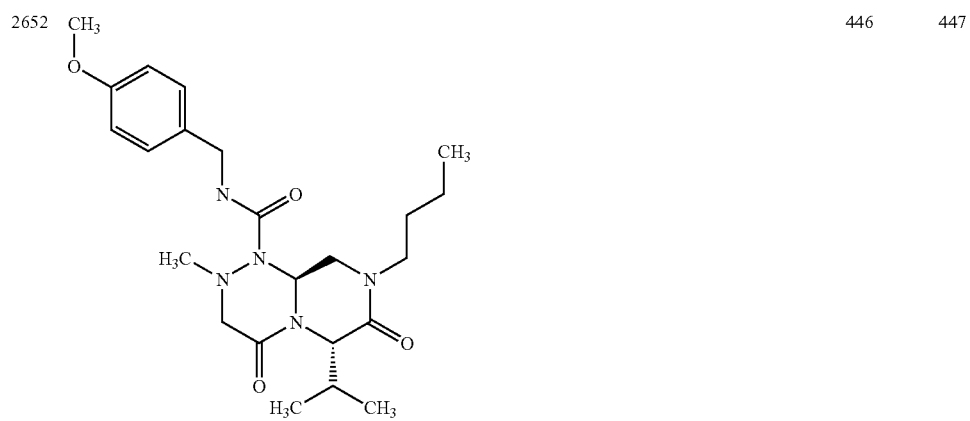 | 446 | 447 |
| 2653 | 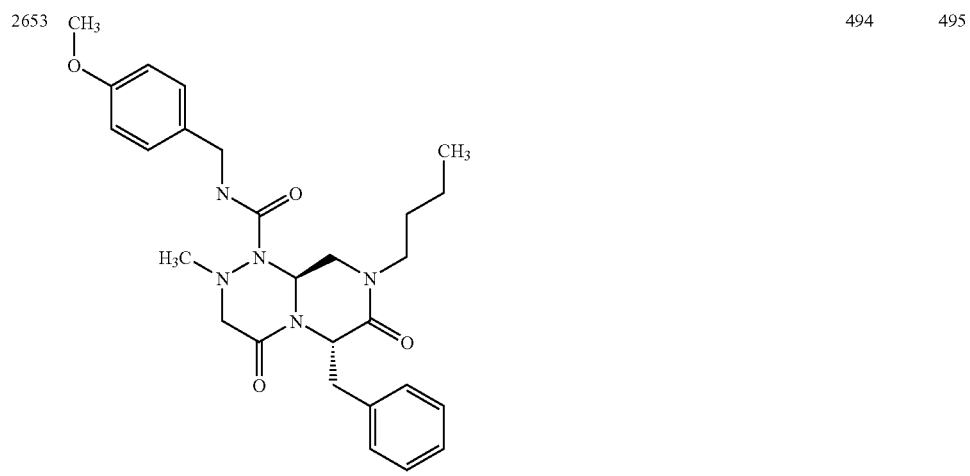 | 494 | 495 |

TABLE 2B-continued
THE [4,4,0]REVERSE TURN MIMETICS LIBRARY
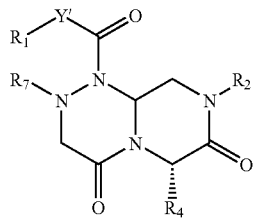
| No | MOLSTRUCTURE | Mol. Weight | M + H (MS) |
|---|---|---|---|
| 2654 | | 460 | 461 |
| 2655 | | 460 | 461 |

TABLE 2B-continued
THE [4,4,0]REVERSE TURN MIMETICS LIBRARY
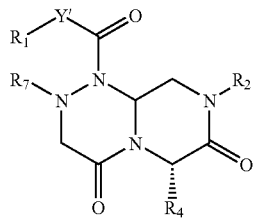
| No | MOLSTRUCTURE | Mol. Weight | M + H (MS) |
|---|---|---|---|
| 2656 | | 478 | 479 |
| 2657 | | 446 | 447 |

TABLE 2B-continued
THE [4,4,0]REVERSE TURN MIMETICS LIBRARY
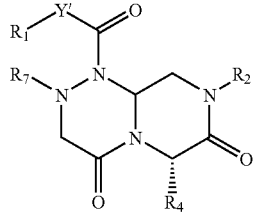
| No | MOLSTRUCTURE | Mol. Weight | M + H (MS) |
|---|---|---|---|
| 2658 | | 462 | 463 |
| 2659 | | 476 | 477 |

TABLE 2B-continued
THE [4,4,0]REVERSE TURN MIMETICS LIBRARY
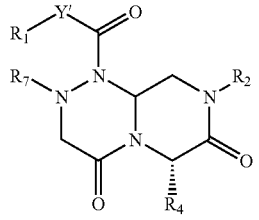
| No | MOLSTRUCTURE | Mol. Weight | M + H (MS) |
|---|---|---|---|
| 2660 |  | 480 | 481 |
| 2661 |  | 545 | 546 |

TABLE 2B-continued
THE [4,4,0]REVERSE TURN MIMETICS LIBRARY
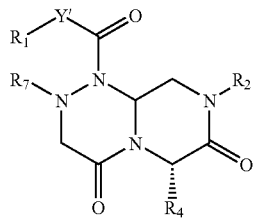
| No | MOLSTRUCTURE | Mol. Weight | M + H (MS) |
|---|---|---|---|
| 2662 | 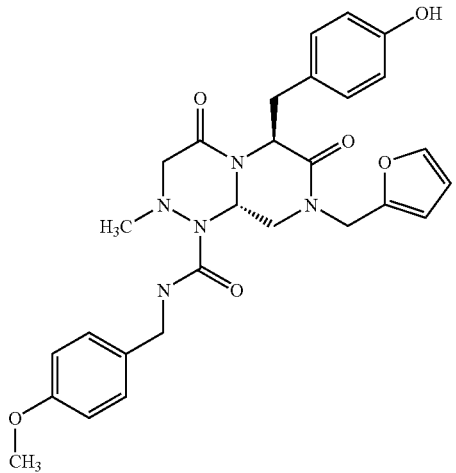 | 534 | 535 |
| 2663 | 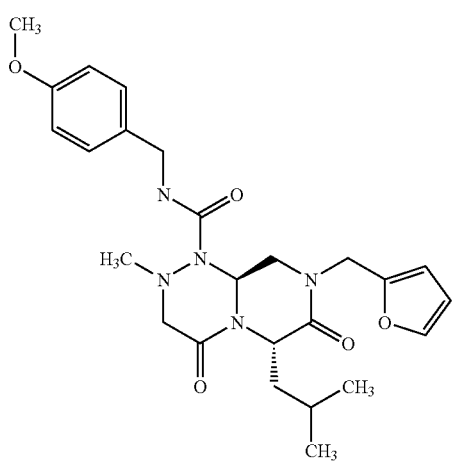 | 484 | 485 |

TABLE 2B-continued
THE [4,4,0]REVERSE TURN MIMETICS LIBRARY
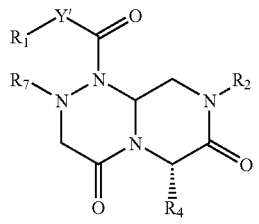
| No | MOLSTRUCTURE | Mol. Weight | M + H (MS) |
|----|--------------|-------------|------------|
| 2664 | | 470 | 471 |
| 2665 | | 518 | 519 |

TABLE 2B-continued
THE [4,4,0]REVERSE TURN MIMETICS LIBRARY
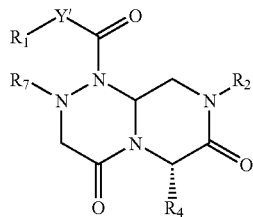
| No | MOLSTRUCTURE | Mol. Weight | M + H (MS) |
|---|---|---|---|
| 2666 | 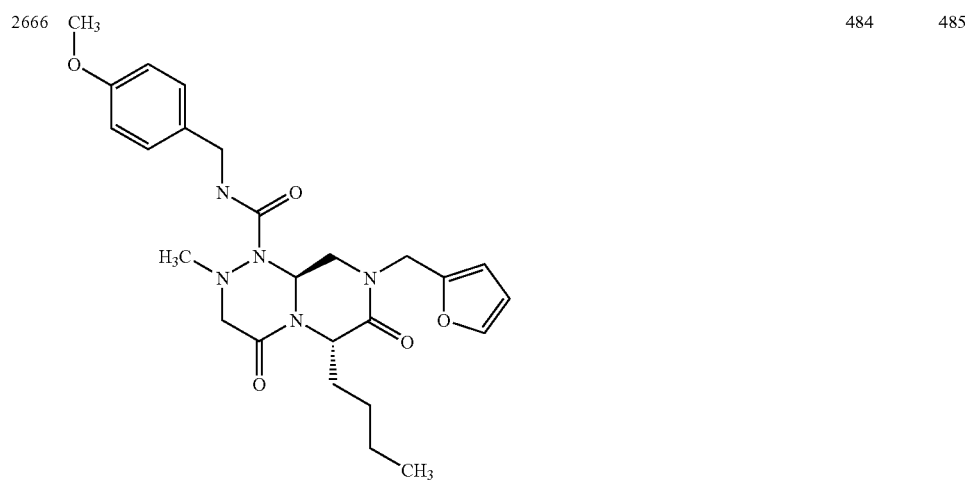 | 484 | 485 |
| 2667 | 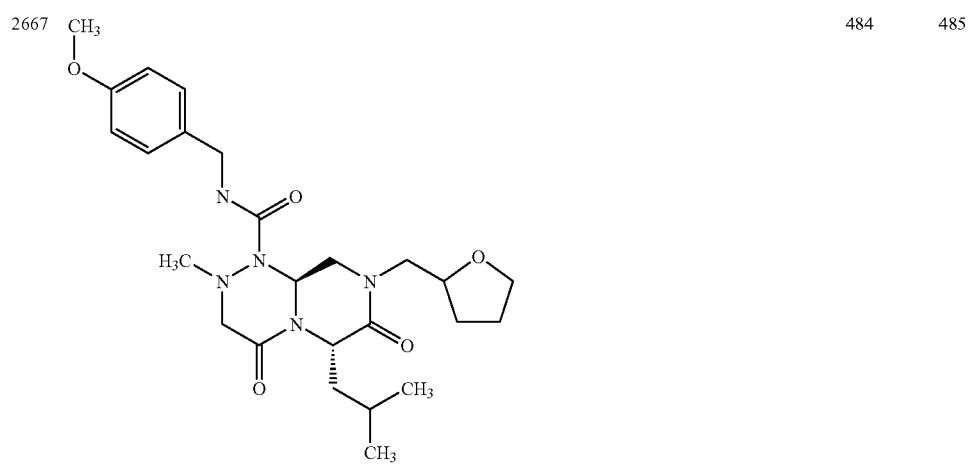 | 484 | 485 |

TABLE 2B-continued
THE [4,4,0]REVERSE TURN MIMETICS LIBRARY
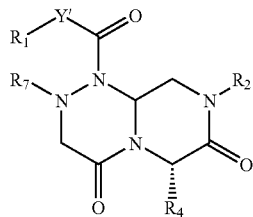
| No | MOLSTRUCTURE | Mol. Weight | M + H (MS) |
|----|--------------|-------------|------------|
| 2668 | | 502 | 503 |
| 2669 | | 470 | 471 |

TABLE 2B-continued
THE [4,4,0]REVERSE TURN MIMETICS LIBRARY
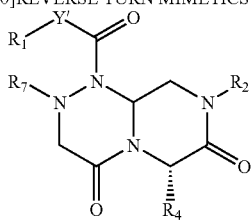
| No | MOLSTRUCTURE | Mol. Weight | M + H (MS) |
|---|---|---|---|
| 2670 | 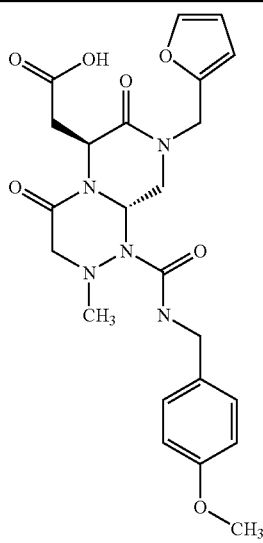 | 486 | 487 |
| 2671 | 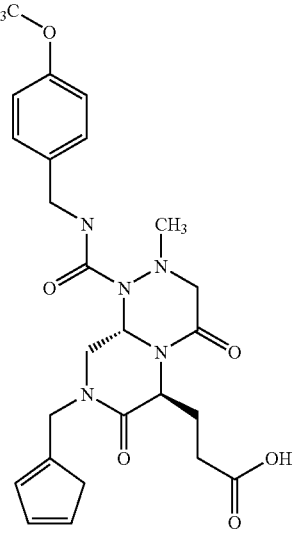 | 500 | 501 |

TABLE 2B-continued
THE [4,4,0]REVERSE TURN MIMETICS LIBRARY
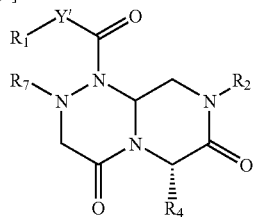
| No | MOLSTRUCTURE | Mol. Weight | M + H (MS) |
|---|---|---|---|
| 2672 | | 504 | 505 |
| 2673 | | 569 | 570 |

TABLE 2B-continued
THE [4,4,0]REVERSE TURN MIMETICS LIBRARY
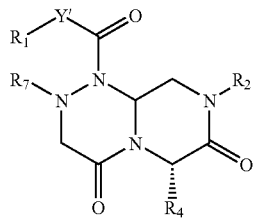
| No | MOLSTRUCTURE | Mol. Weight | M + H (MS) |
|---|---|---|---|
| 2674 | 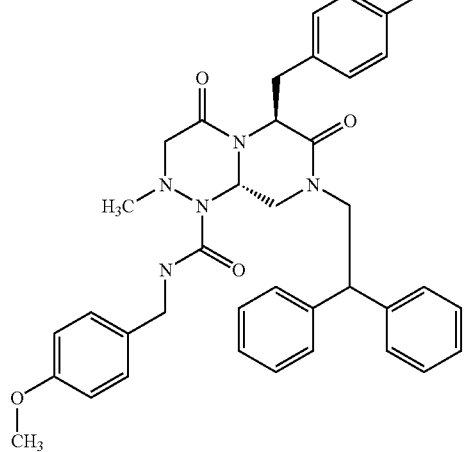 | 634 | 635 |
| 2675 | 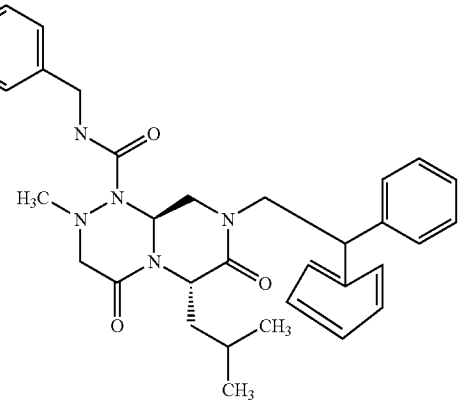 | 584 | 585 |

TABLE 2B-continued
THE [4,4,0]REVERSE TURN MIMETICS LIBRARY
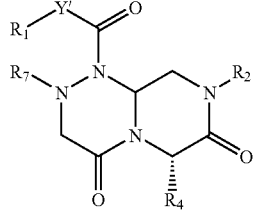
| No | MOLSTRUCTURE | Mol. Weight | M + H (MS) |
|---|---|---|---|
| 2676 | | 570 | 571 |
| 2677 | | 618 | 619 |

TABLE 2B-continued
THE [4,4,0]REVERSE TURN MIMETICS LIBRARY
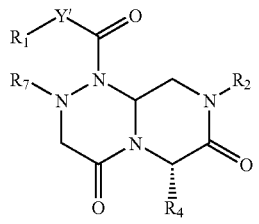
| No | MOLSTRUCTURE | Mol. Weight | M + H (MS) |
|----|--------------|-------------|------------|
| 2678 | 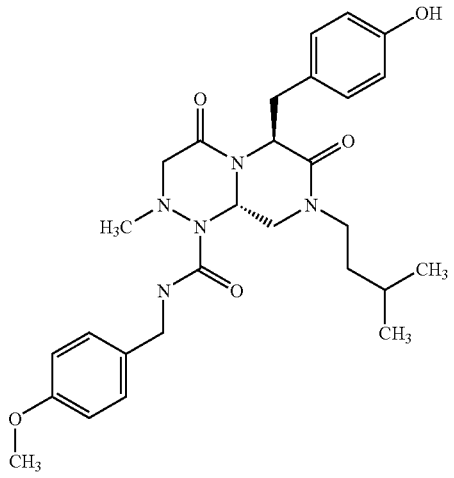 | 584 | 585 |
| 2679 | 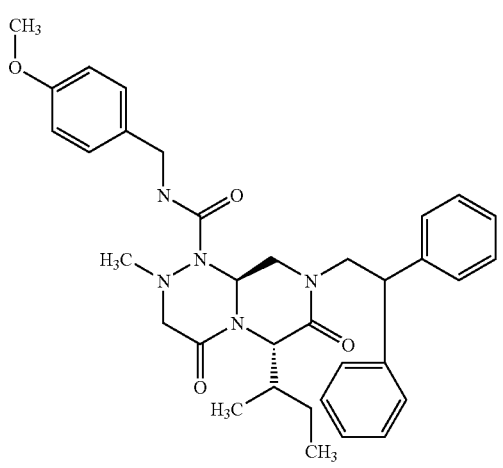 | 584 | 585 |

TABLE 2B-continued
THE [4,4,0]REVERSE TURN MIMETICS LIBRARY
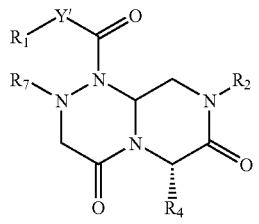
| No | MOLSTRUCTURE | Mol. Weight | M + H (MS) |
|---|---|---|---|
| 2680 | | 602 | 603 |
| 2681 | | 570 | 571 |

TABLE 2B-continued
THE [4,4,0]REVERSE TURN MIMETICS LIBRARY
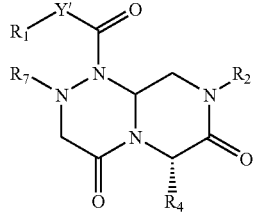
| No | MOLSTRUCTURE | Mol. Weight | M + H (MS) |
|---|---|---|---|
| 2682 | | 586 | 587 |
| 2683 | | 600 | 601 |

TABLE 2B-continued
THE [4,4,0]REVERSE TURN MIMETICS LIBRARY
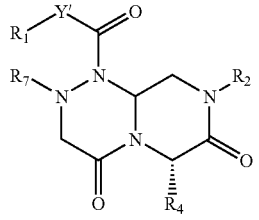
| No | MOLSTRUCTURE | Mol. Weight | M + H (MS) |
|---|---|---|---|
| 2684 | | 604 | 605 |
| 2685 | | 669 | 670 |

TABLE 2B-continued
THE [4,4,0]REVERSE TURN MIMETICS LIBRARY
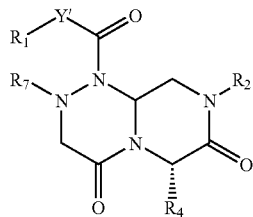
| No | MOLSTRUCTURE | Mol. Weight | M + H (MS) |
|----|--------------|-------------|------------|
| 2686 | 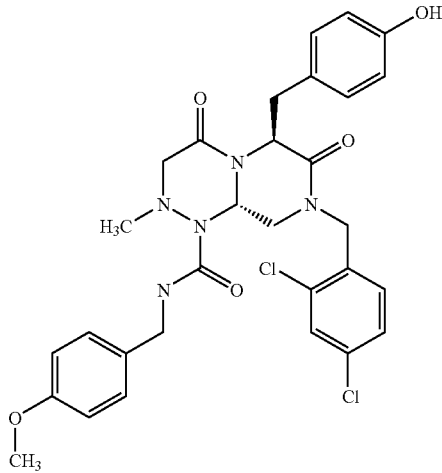 | 613 | 614 |
| 2687 | 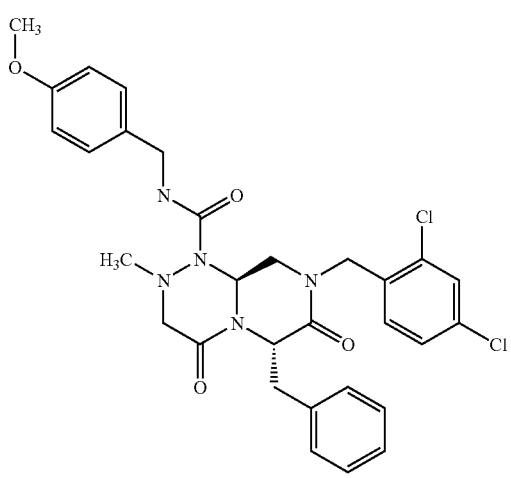 | 563 | 564 |

TABLE 2B-continued
THE [4,4,0]REVERSE TURN MIMETICS LIBRARY
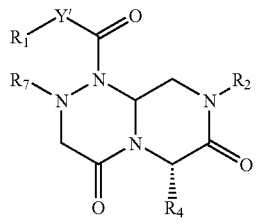
| No | MOLSTRUCTURE | Mol. Weight | M + H (MS) |
|---|---|---|---|
| 2688 | | 548 | 549 |
| 2689 | | 597 | 598 |

TABLE 2B-continued
THE [4,4,0]REVERSE TURN MIMETICS LIBRARY
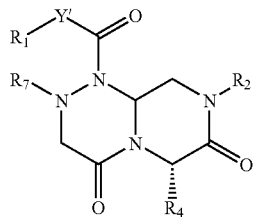
| No | MOLSTRUCTURE | Mol. Weight | M + H (MS) |
|---|---|---|---|
| 2690 | 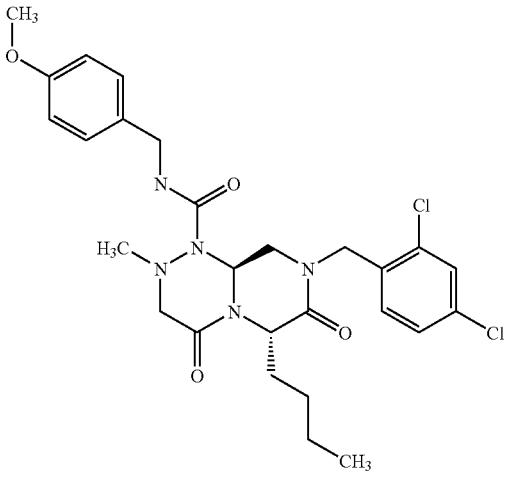 | 563 | 564 |
| 2691 | 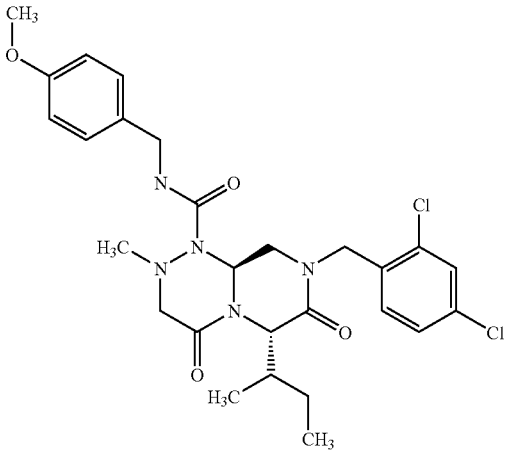 | 563 | 564 |

TABLE 2B-continued
THE [4,4,0]REVERSE TURN MIMETICS LIBRARY
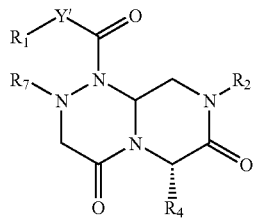
| No | MOLSTRUCTURE | Mol. Weight | M + H (MS) |
|---|---|---|---|
| 2692 | | 581 | 582 |
| 2693 | | 548 | 549 |

TABLE 2B-continued
THE [4,4,0]REVERSE TURN MIMETICS LIBRARY
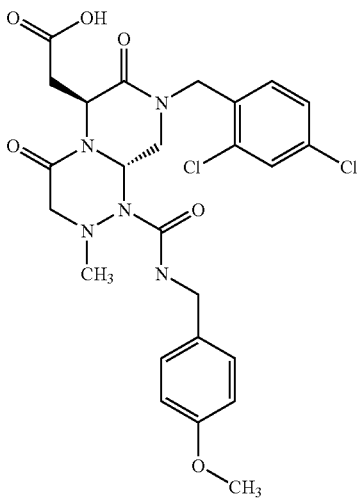
| No | MOLSTRUCTURE | Mol. Weight | M + H (MS) |
|---|---|---|---|
| 2694 | 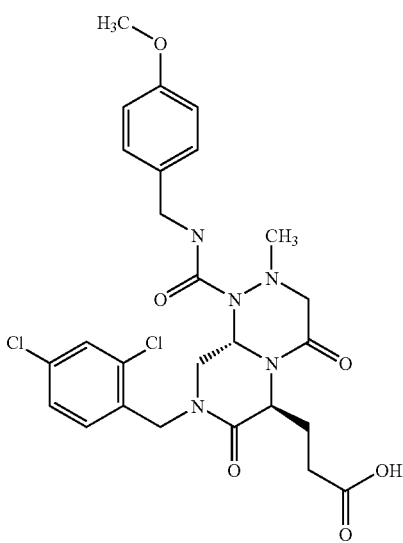 | 564 | 565 |
| 2695 | | 578 | 579 |

TABLE 2B-continued
THE [4,4,0]REVERSE TURN MIMETICS LIBRARY
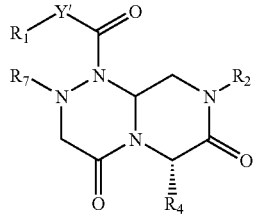
| No | MOLSTRUCTURE | Mol. Weight | M + H (MS) |
|---|---|---|---|
| 2696 | | 583 | 583 |
| 2697 | | 648 | 649 |

TABLE 2B-continued
THE [4,4,0]REVERSE TURN MIMETICS LIBRARY
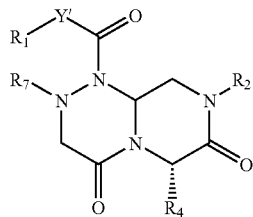
| No | MOLSTRUCTURE | Mol. Weight | M + H (MS) |
|---|---|---|---|
| 2698 | 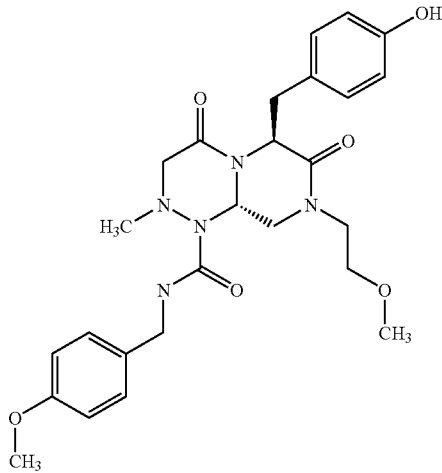 | 512 | 513 |
| 2699 | 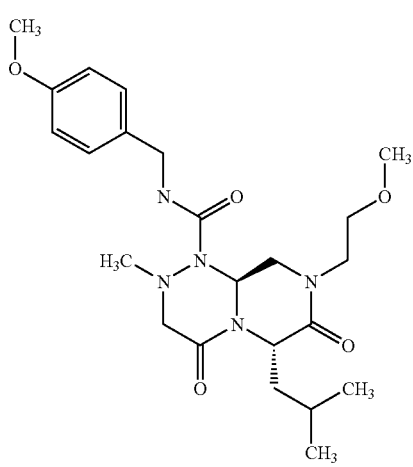 | 462 | 463 |

TABLE 2B-continued
THE [4,4,0]REVERSE TURN MIMETICS LIBRARY
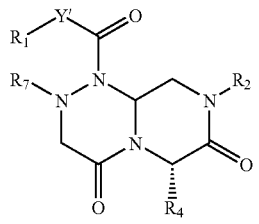
| No | MOLSTRUCTURE | Mol. Weight | M + H (MS) |
|----|--------------|-------------|------------|
| 2700 | | 448 | 449 |
| 2701 | | 496 | 497 |

TABLE 2B-continued
THE [4,4,0]REVERSE TURN MIMETICS LIBRARY
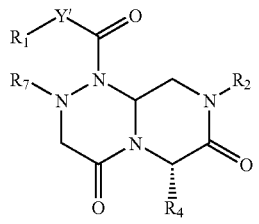
| No | MOLSTRUCTURE | Mol. Weight | M + H (MS) |
|---|---|---|---|
| 2702 | 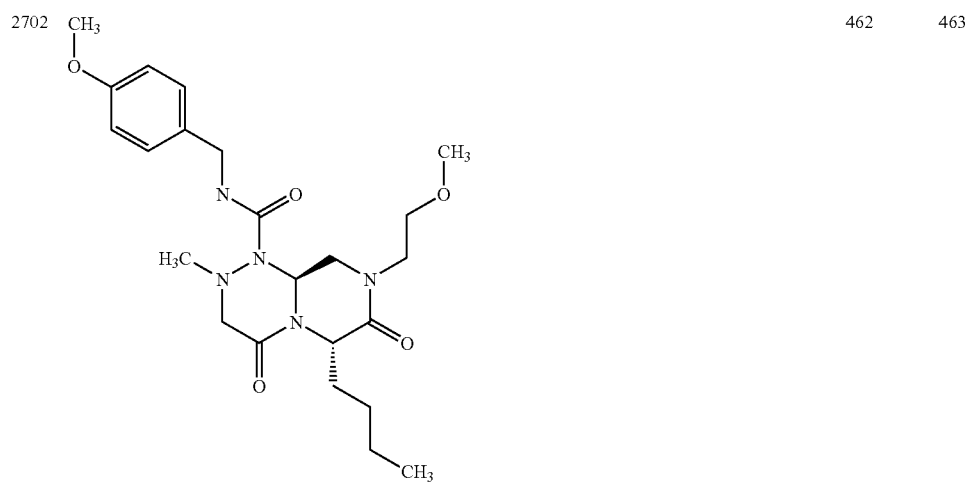 | 462 | 463 |
| 2703 | 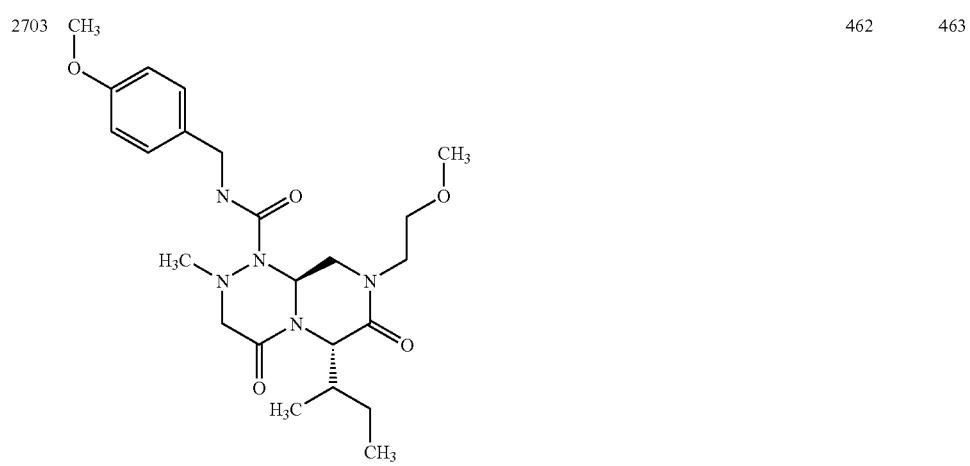 | 462 | 463 |

TABLE 2B-continued
THE [4,4,0]REVERSE TURN MIMETICS LIBRARY
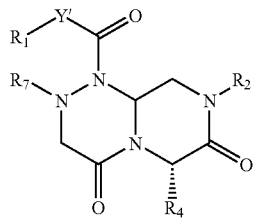
| No | MOLSTRUCTURE | Mol. Weight | M + H (MS) |
|---|---|---|---|
| 2704 | | 480 | 481 |
| 2705 | | 448 | 449 |

TABLE 2B-continued
THE [4,4,0]REVERSE TURN MIMETICS LIBRARY
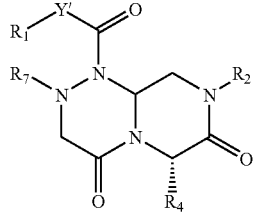
| No | MOLSTRUCTURE | Mol. Weight | M + H (MS) |
|---|---|---|---|
| 2706 | | 463 | 464 |
| 2707 | | 478 | 479 |

TABLE 2B-continued
THE [4,4,0]REVERSE TURN MIMETICS LIBRARY
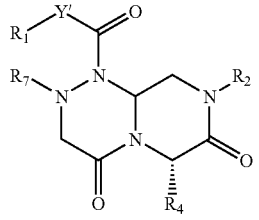
| No | MOLSTRUCTURE | Mol. Weight | M + H (MS) |
|---|---|---|---|
| 2708 | | 482 | 483 |
| 2709 | | 547 | 548 |

TABLE 2B-continued
THE [4,4,0]REVERSE TURN MIMETICS LIBRARY
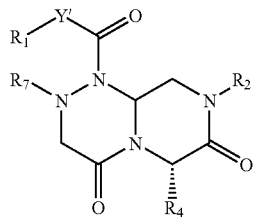
| No | MOLSTRUCTURE | Mol. Weight | M + H (MS) |
|---|---|---|---|
| 2710 | 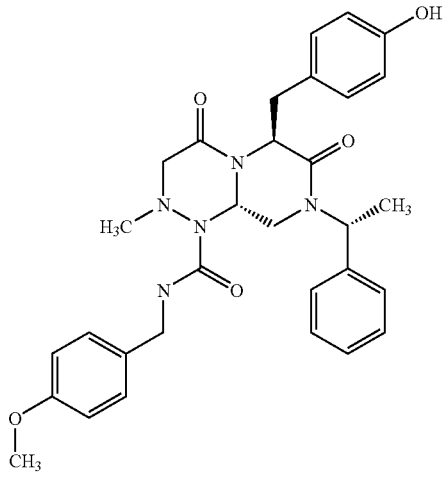 | 558 | 559 |
| 2711 | 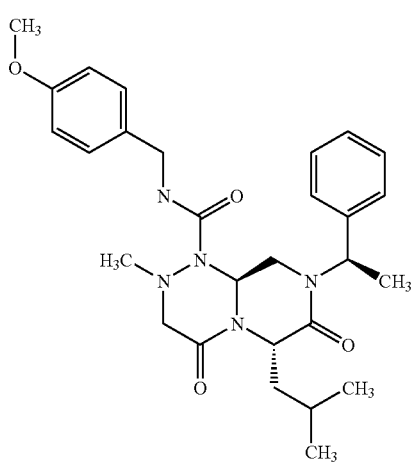 | 508 | 509 |

TABLE 2B-continued
THE [4,4,0]REVERSE TURN MIMETICS LIBRARY
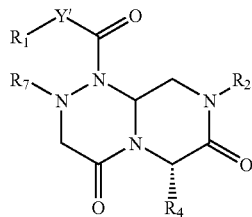
| No | MOLSTRUCTURE | Mol. Weight | M + H (MS) |
|---|---|---|---|
| 2712 | | 494 | 495 |
| 2713 | | 542 | 543 |

TABLE 2B-continued
THE [4,4,0]REVERSE TURN MIMETICS LIBRARY
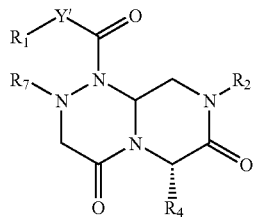
| No | MOLSTRUCTURE | Mol. Weight | M + H (MS) |
|---|---|---|---|
| 2714 | 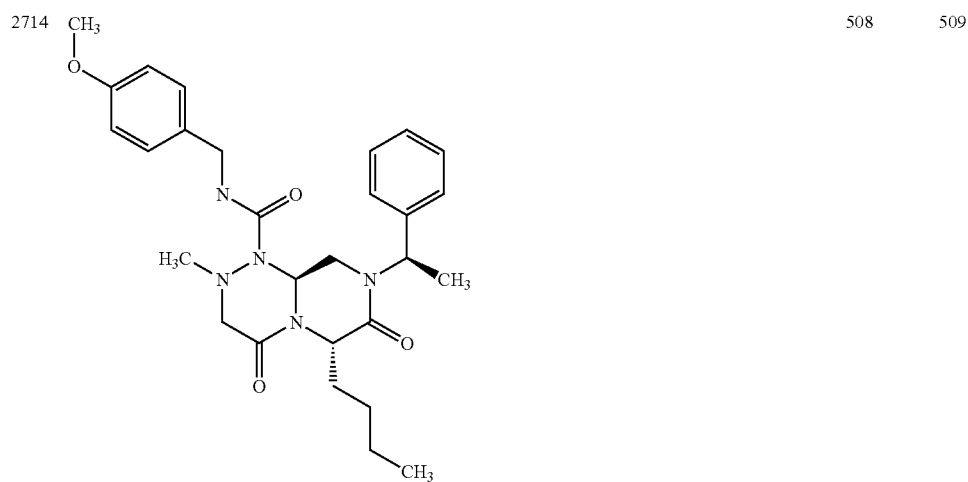 | 508 | 509 |
| 2715 | 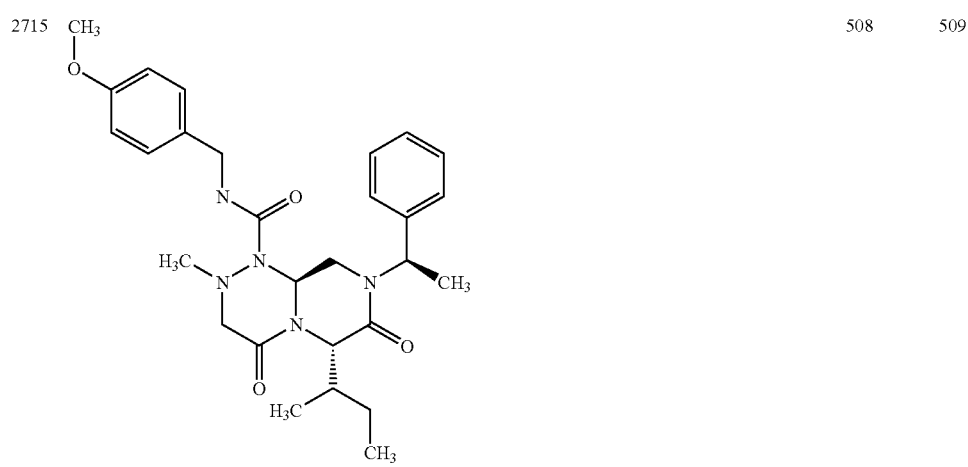 | 508 | 509 |

TABLE 2B-continued
THE [4,4,0]REVERSE TURN MIMETICS LIBRARY
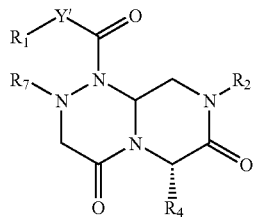
| No | MOLSTRUCTURE | Mol. Weight | M + H (MS) |
|---|---|---|---|
| 2716 | 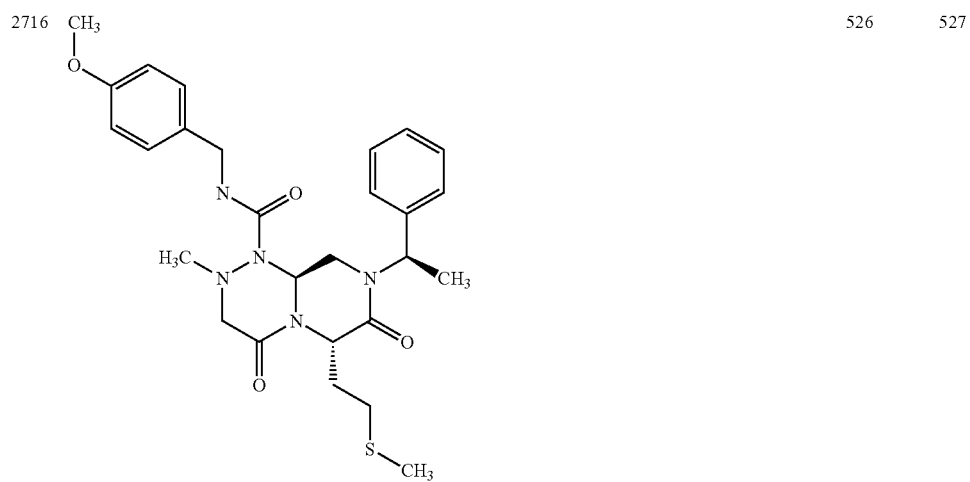 | 526 | 527 |
| 2717 | 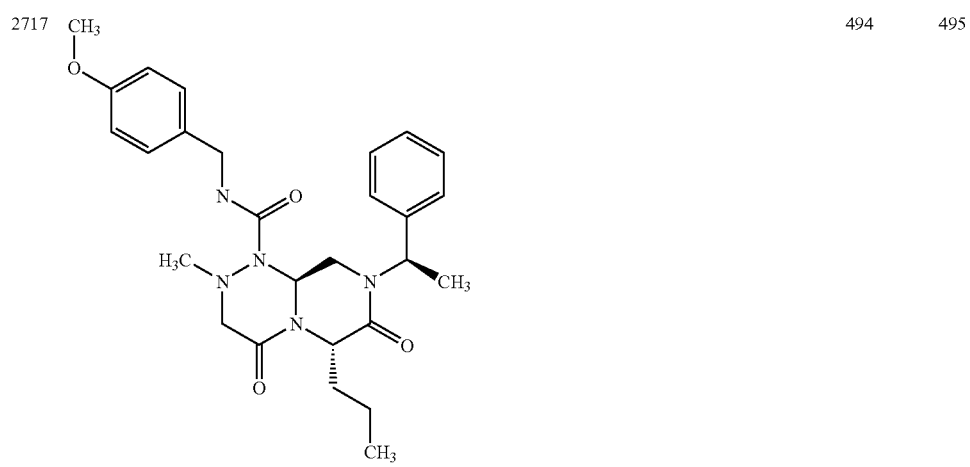 | 494 | 495 |

TABLE 2B-continued
THE [4,4,0]REVERSE TURN MIMETICS LIBRARY
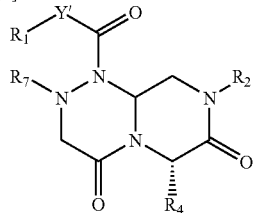
| No | MOLSTRUCTURE | Mol. Weight | M + H (MS) |
|---|---|---|---|
| 2718 | | 510 | 511 |
| 2719 | | 524 | 525 |

TABLE 2B-continued
THE [4,4,0]REVERSE TURN MIMETICS LIBRARY
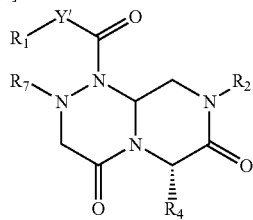
| No | MOLSTRUCTURE | Mol. Weight | M + H (MS) |
|---|---|---|---|
| 2720 | | 528 | 529 |
| 2721 | | 593 | 594 |

TABLE 2B-continued
THE [4,4,0]REVERSE TURN MIMETICS LIBRARY
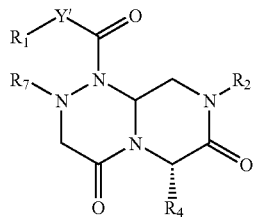
| No | MOLSTRUCTURE | Mol. Weight | M + H (MS) |
|---|---|---|---|
| 2722 | 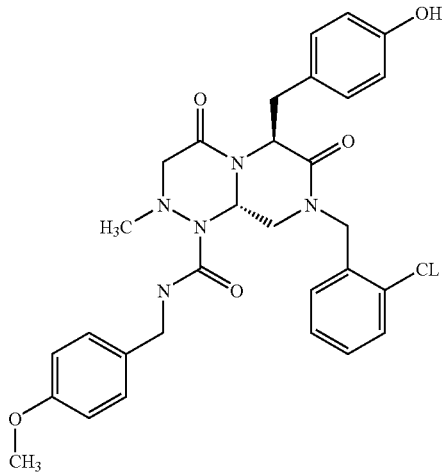 | 578 | 579 |
| 2723 | 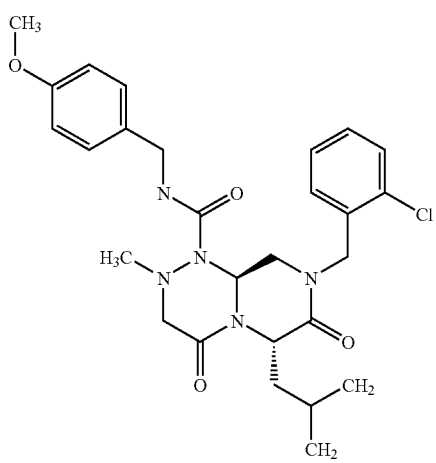 | 528 | 529 |

TABLE 2B-continued
THE [4,4,0]REVERSE TURN MIMETICS LIBRARY
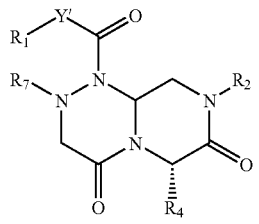
| No | MOLSTRUCTURE | Mol. Weight | M + H (MS) |
|---|---|---|---|
| 2724 | | 514 | 515 |
| 2725 | | 562 | 563 |

TABLE 2B-continued
THE [4,4,0]REVERSE TURN MIMETICS LIBRARY
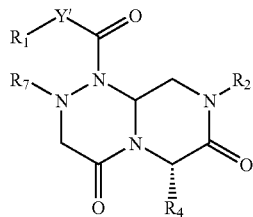
| No | MOLSTRUCTURE | Mol. Weight | M + H (MS) |
|---|---|---|---|
| 2726 | 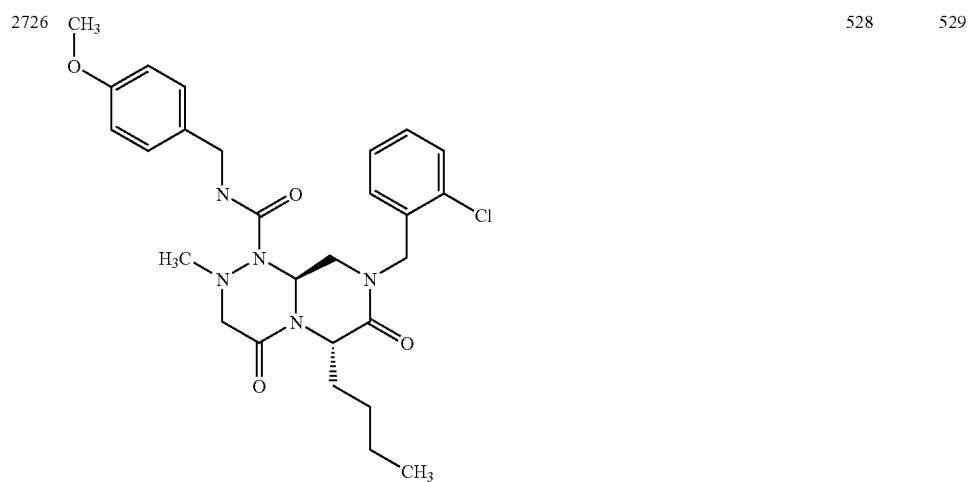 | 528 | 529 |
| 2727 | 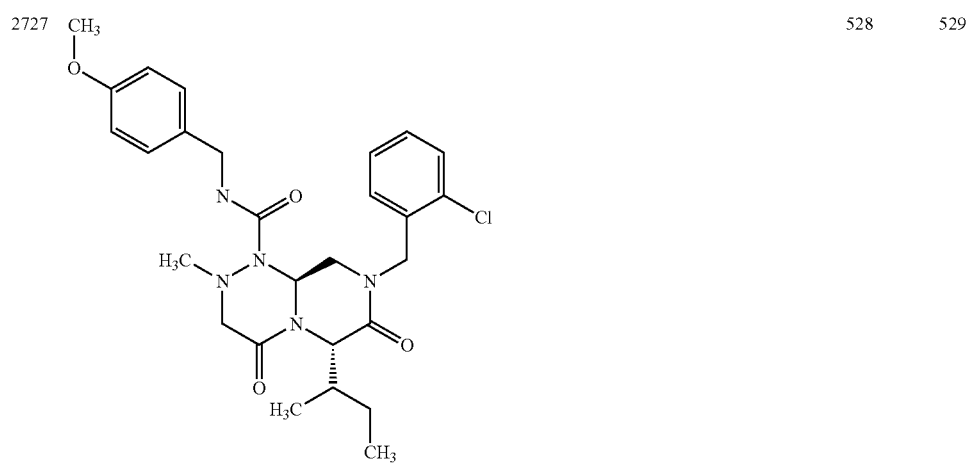 | 528 | 529 |

TABLE 2B-continued
THE [4,4,0]REVERSE TURN MIMETICS LIBRARY
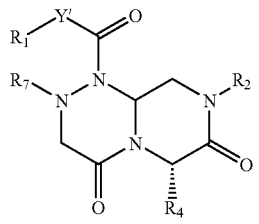
| No | MOLSTRUCTURE | Mol. Weight | M + H (MS) |
|---|---|---|---|
| 2728 | | 546 | 547 |
| 2729 | | 514 | 515 |

TABLE 2B-continued
THE [4,4,0]REVERSE TURN MIMETICS LIBRARY
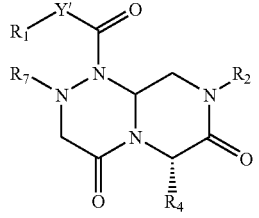
| No | MOLSTRUCTURE | Mol. Weight | M + H (MS) |
|---|---|---|---|
| 2730 | | 530 | 531 |
| 2731 | | 544 | 545 |

TABLE 2B-continued
THE [4,4,0]REVERSE TURN MIMETICS LIBRARY
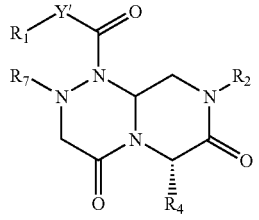
| No | MOLSTRUCTURE | Mol. Weight | M + H (MS) |
|---|---|---|---|
| 2732 | CH₃ structure | 548 | 549 |
| 2733 | CH₃ structure | 613 | 614 |

TABLE 2B-continued
THE [4,4,0]REVERSE TURN MIMETICS LIBRARY
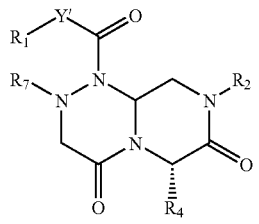
| No | MOLSTRUCTURE | Mol. Weight | M + H (MS) |
|---|---|---|---|
| 2734 | 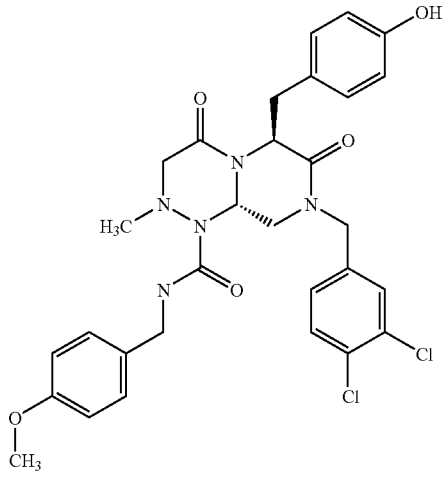 | 613 | 614 |
| 2735 | 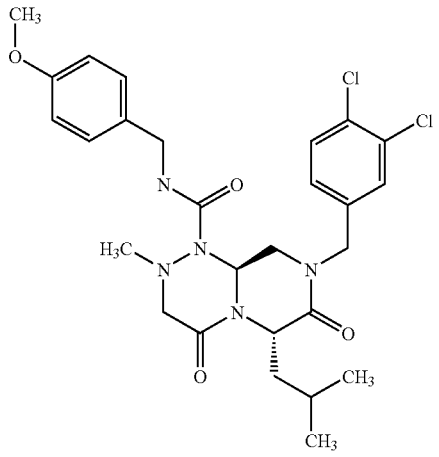 | 563 | 564 |

TABLE 2B-continued
THE [4,4,0]REVERSE TURN MIMETICS LIBRARY
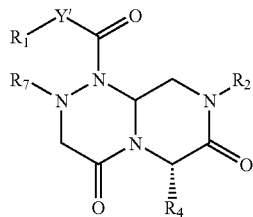
| No | MOLSTRUCTURE | Mol. Weight | M + H (MS) |
|---|---|---|---|
| 2736 | | 548 | 549 |
| 2737 | | 597 | 598 |

TABLE 2B-continued
THE [4,4,0]REVERSE TURN MIMETICS LIBRARY
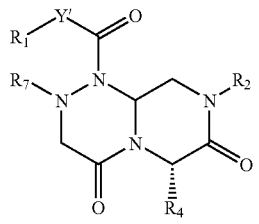
| No | MOLSTRUCTURE | Mol. Weight | M + H (MS) |
|---|---|---|---|
| 2738 | 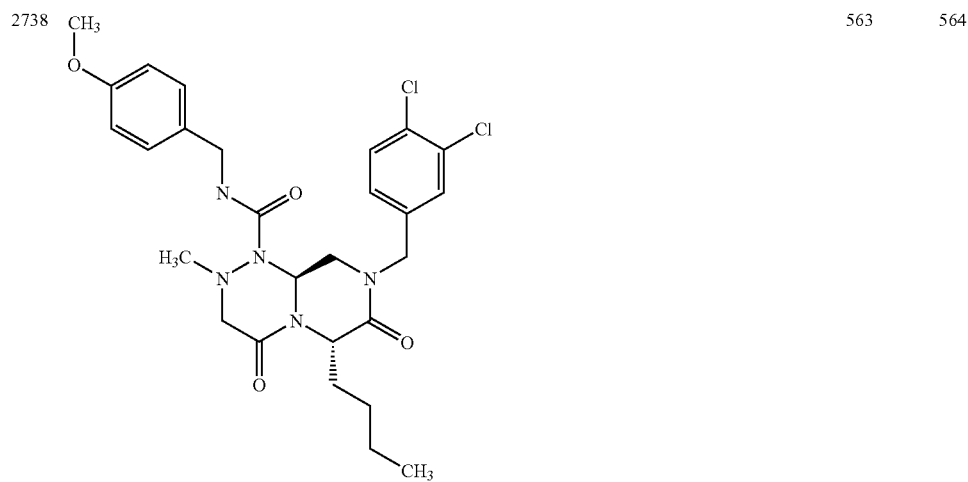 | 563 | 564 |
| 2739 | 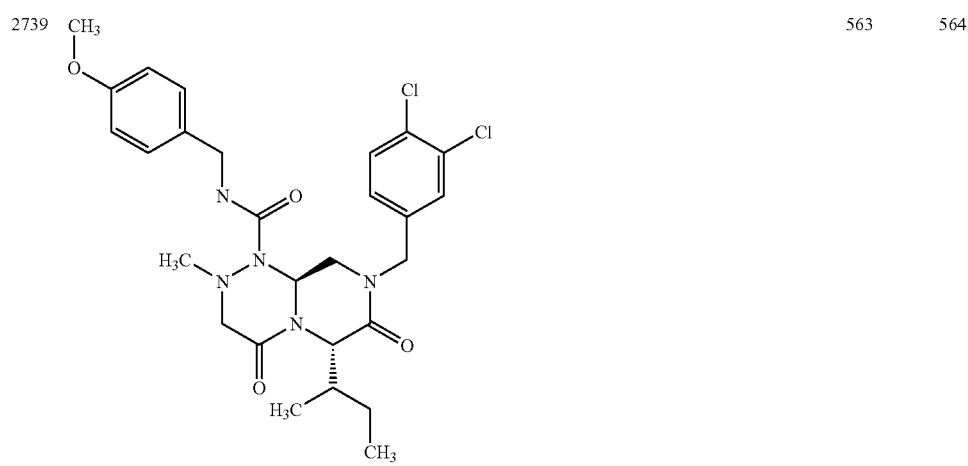 | 563 | 564 |

TABLE 2B-continued
THE [4,4,0]REVERSE TURN MIMETICS LIBRARY
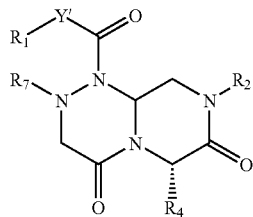
| No | MOLSTRUCTURE | Mol. Weight | M + H (MS) |
|---|---|---|---|
| 2740 | 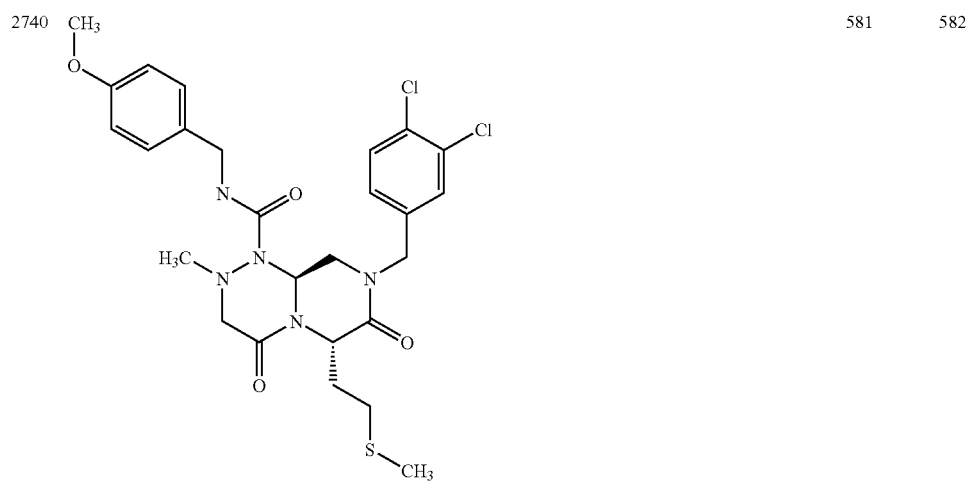 | 581 | 582 |
| 2741 |  | 548 | 549 |

TABLE 2B-continued
THE [4,4,0]REVERSE TURN MIMETICS LIBRARY
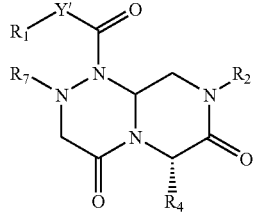
| No | MOLSTRUCTURE | Mol. Weight | M + H (MS) |
|----|--------------|-------------|------------|
| 2742 | | 564 | 565 |
| 2743 | | 573 | 579 |

TABLE 2B-continued
THE [4,4,0]REVERSE TURN MIMETICS LIBRARY
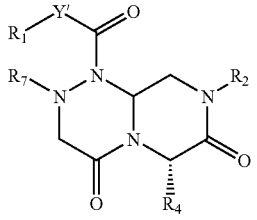
| No | MOLSTRUCTURE | Mol. Weight | M + H (MS) |
|---|---|---|---|
| 2744 | | 582 | 583 |
| 2745 | | 648 | 649 |

TABLE 2B-continued
THE [4,4,0]REVERSE TURN MIMETICS LIBRARY
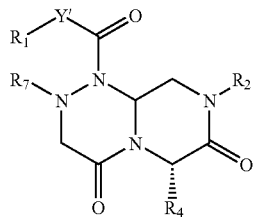
| No | MOLSTRUCTURE | Mol. Weight | M + H (MS) |
|---|---|---|---|
| 2746 | 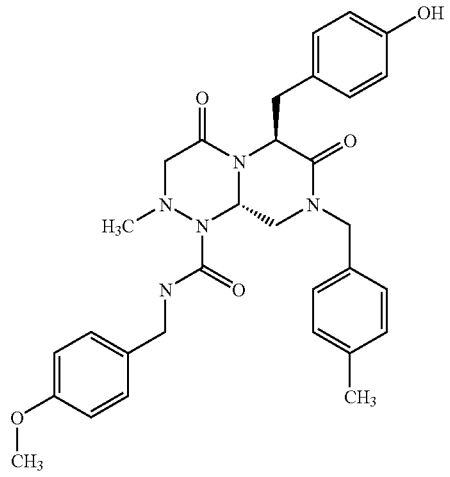 | 558 | 559 |
| 2747 | 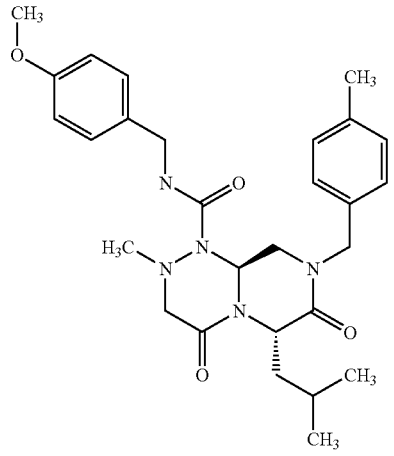 | 508 | 509 |

TABLE 2B-continued
THE [4,4,0]REVERSE TURN MIMETICS LIBRARY
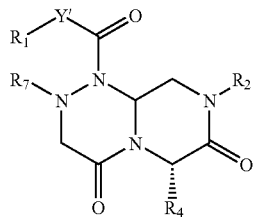
| No | MOLSTRUCTURE | Mol. Weight | M + H (MS) |
|---|---|---|---|
| 2748 | | 494 | 495 |
| 2749 | | 542 | 543 |

TABLE 2B-continued
THE [4,4,0]REVERSE TURN MIMETICS LIBRARY
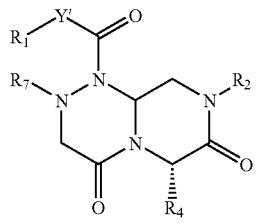
| No | MOLSTRUCTURE | Mol. Weight | M + H (MS) |
|----|--------------|-------------|------------|
| 2750 | 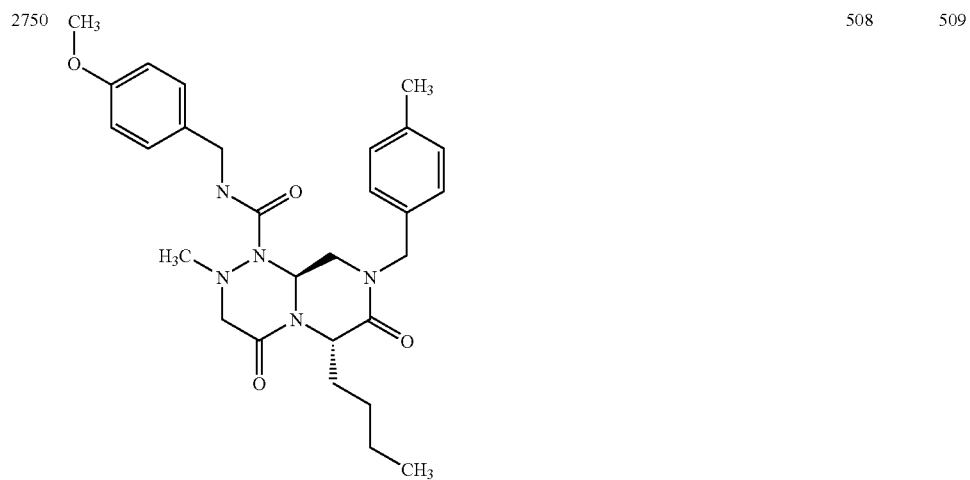 | 508 | 509 |
| 2751 | 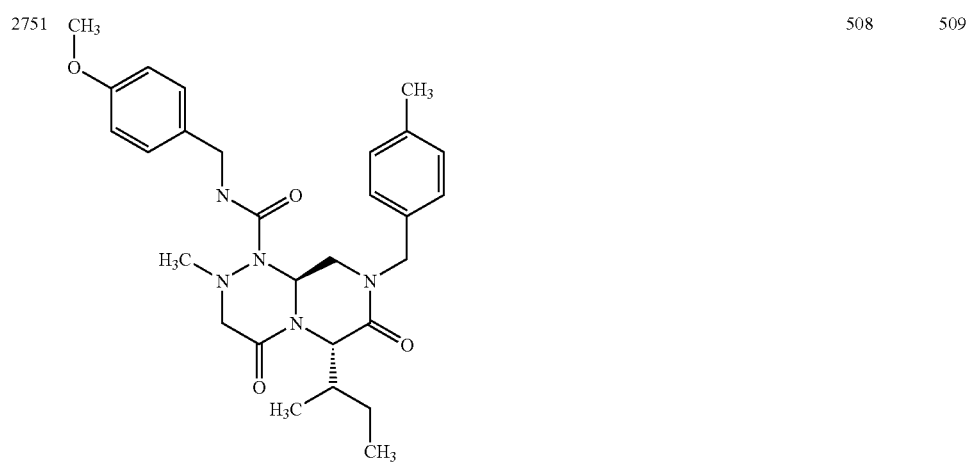 | 508 | 509 |

TABLE 2B-continued
THE [4,4,0]REVERSE TURN MIMETICS LIBRARY
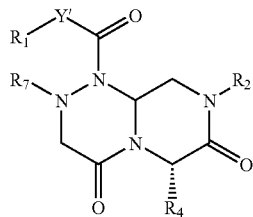
| No | MOLSTRUCTURE | Mol. Weight | M + H (MS) |
|---|---|---|---|
| 2752 | 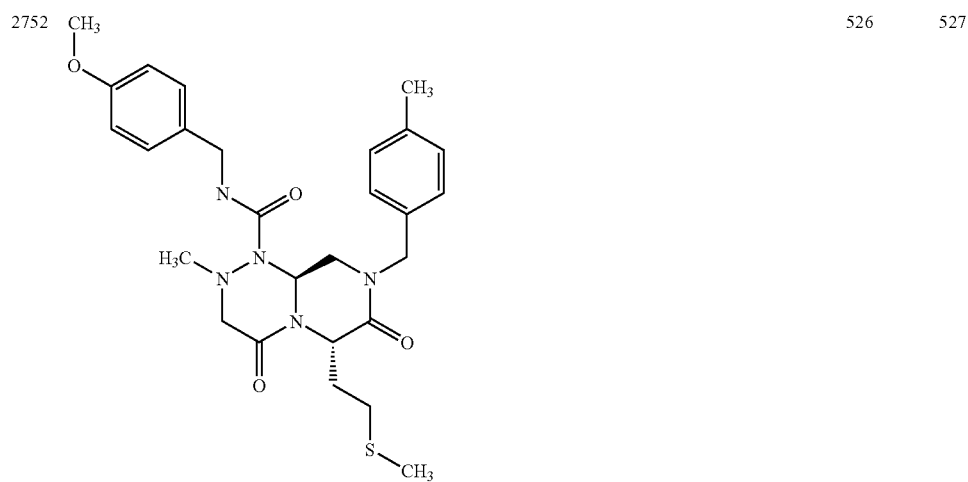 | 526 | 527 |
| 2753 |  | 494 | 495 |

TABLE 2B-continued
THE [4,4,0]REVERSE TURN MIMETICS LIBRARY

| No | MOLSTRUCTURE | Mol. Weight | M + H (MS) |
|---|---|---|---|
| 2754 |  | 510 | 511 |
| 2755 | | 524 | 525 |

TABLE 2B-continued
THE [4,4,0]REVERSE TURN MIMETICS LIBRARY
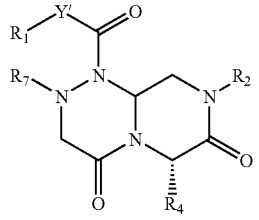
| No | MOLSTRUCTURE | Mol. Weight | M + H (MS) |
|---|---|---|---|
| 2756 | | 528 | 528 |
| 2757 | | 593 | 594 |

TABLE 2B-continued
THE [4,4,0]REVERSE TURN MIMETICS LIBRARY
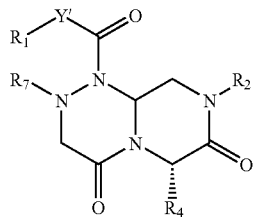
| No | MOLSTRUCTURE | Mol. Weight | M + H (MS) |
|---|---|---|---|
| 2758 | 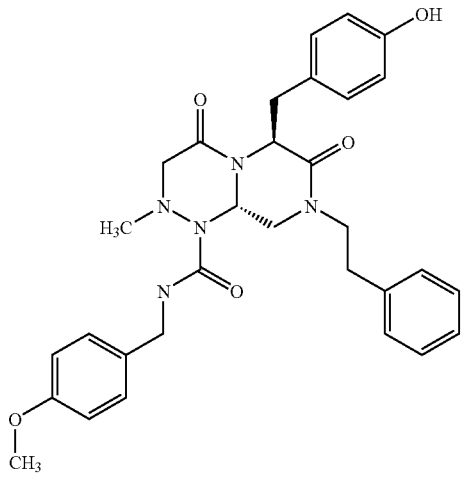 | 558 | 559 |
| 2759 | 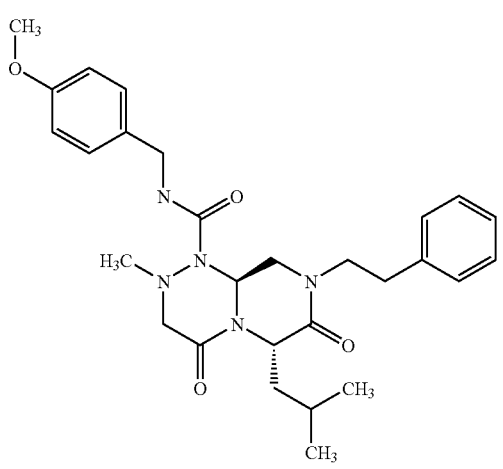 | 508 | 509 |

TABLE 2B-continued
THE [4,4,0]REVERSE TURN MIMETICS LIBRARY
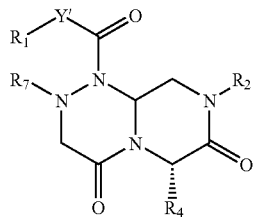
| No | MOLSTRUCTURE | Mol. Weight | M + H (MS) |
|---|---|---|---|
| 2760 | 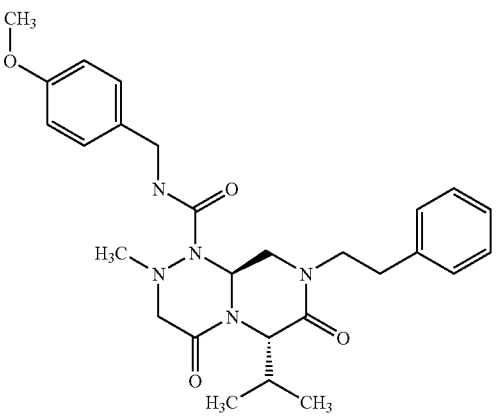 | 494 | 495 |
| 2761 | 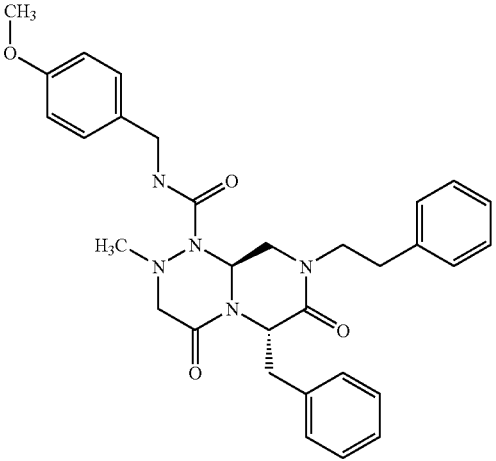 | 542 | 543 |

TABLE 2B-continued
THE [4,4,0]REVERSE TURN MIMETICS LIBRARY
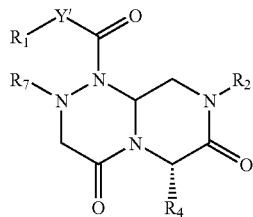
| No | MOLSTRUCTURE | Mol. Weight | M + H (MS) |
|---|---|---|---|
| 2762 | 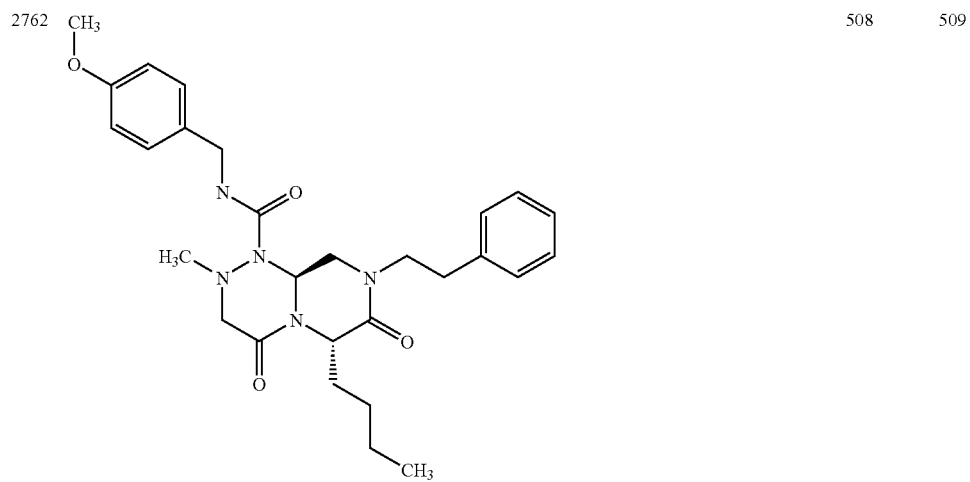 | 508 | 509 |
| 2763 | 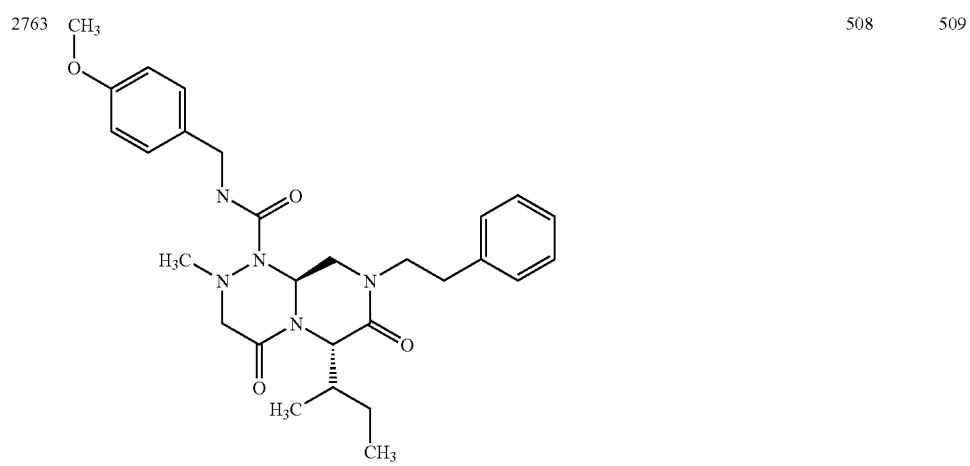 | 508 | 509 |

TABLE 2B-continued
THE [4,4,0]REVERSE TURN MIMETICS LIBRARY
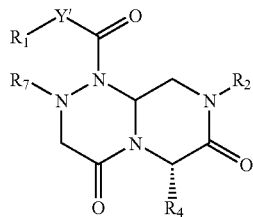
| No | MOLSTRUCTURE | Mol. Weight | M + H (MS) |
|---|---|---|---|
| 2764 | 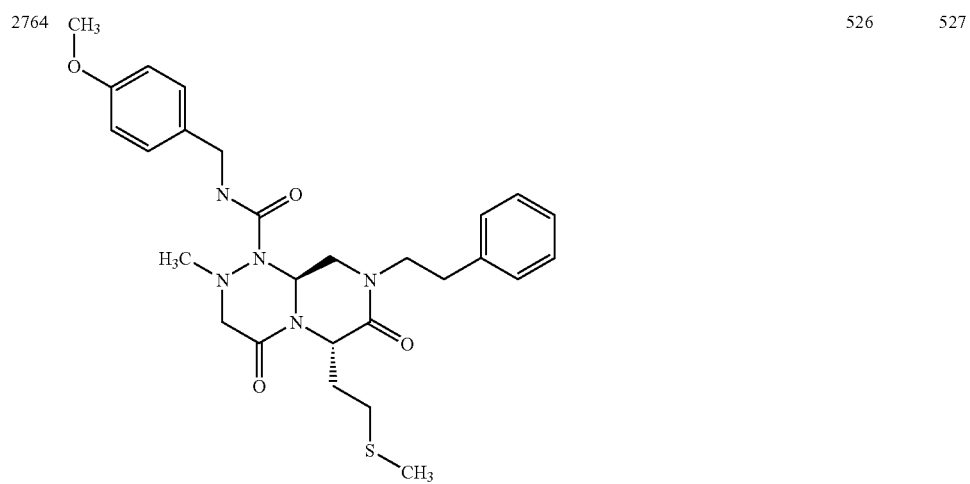 | 526 | 527 |
| 2765 | 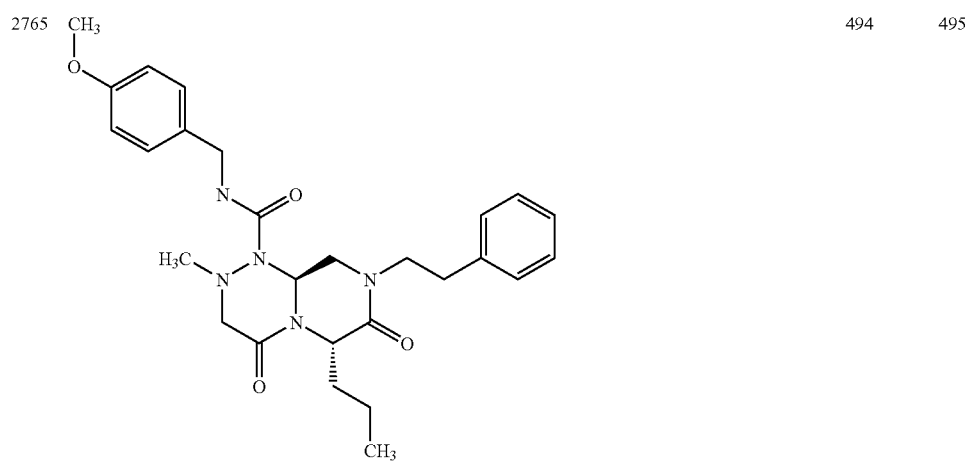 | 494 | 495 |

TABLE 2B-continued
THE [4,4,0]REVERSE TURN MIMETICS LIBRARY
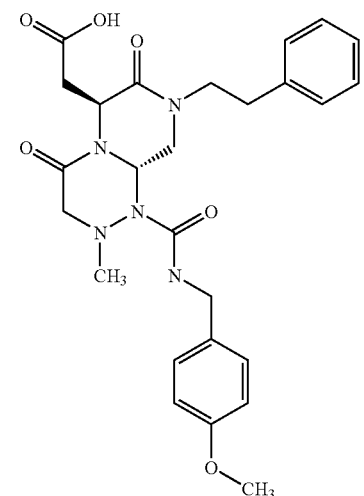
| No | MOLSTRUCTURE | Mol. Weight | M + H (MS) |
|---|---|---|---|
| 2766 | 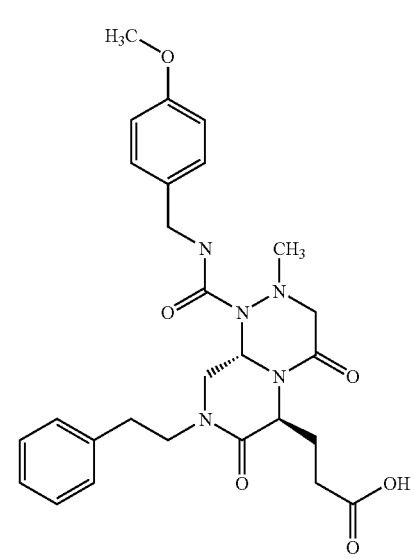 | 510 | 511 |
| 2767 | | 524 | 525 |

TABLE 2B-continued
THE [4,4,0]REVERSE TURN MIMETICS LIBRARY
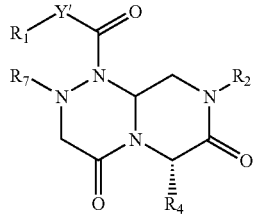
| No | MOLSTRUCTURE | Mol. Weight | M + H (MS) |
|---|---|---|---|
| 2768 | | 528 | 529 |
| 2769 | | 593 | 594 |

TABLE 2B-continued
THE [4,4,0]REVERSE TURN MIMETICS LIBRARY
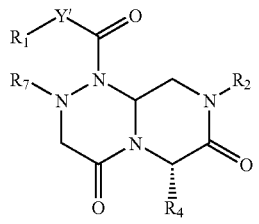
| No | MOLSTRUCTURE | Mol. Weight | M + H (MS) |
|---|---|---|---|
| 2770 | 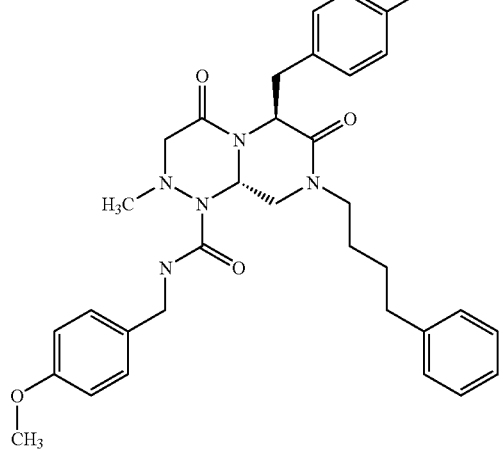 | 586 | 587 |
| 2771 | 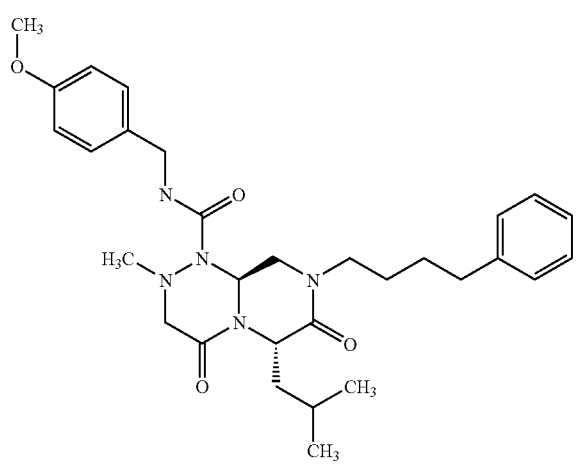 | 536 | 537 |

TABLE 2B-continued
THE [4,4,0]REVERSE TURN MIMETICS LIBRARY
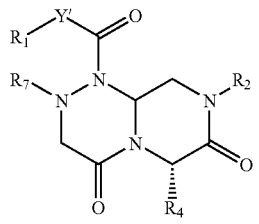
| No | MOLSTRUCTURE | Mol. Weight | M + H (MS) |
|----|--------------|-------------|------------|
| 2772 | | 522 | 523 |
| 2773 | | 570 | 571 |

TABLE 2B-continued
THE [4,4,0]REVERSE TURN MIMETICS LIBRARY
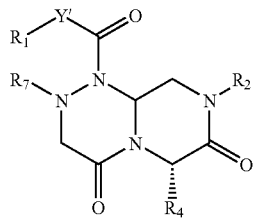
| No | MOLSTRUCTURE | Mol. Weight | M + H (MS) |
|---|---|---|---|
| 2774 | 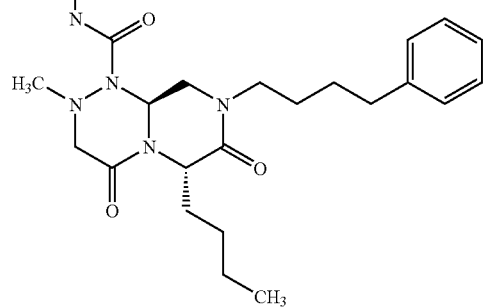 | 536 | 537 |
| 2775 | 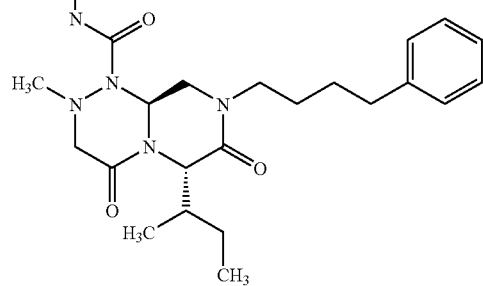 | 536 | 537 |

TABLE 2B-continued
THE [4,4,0]REVERSE TURN MIMETICS LIBRARY
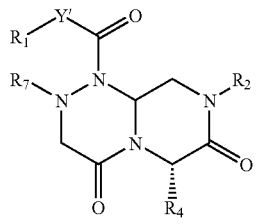
| No | MOLSTRUCTURE | Mol. Weight | M + H (MS) |
|---|---|---|---|
| 2776 | 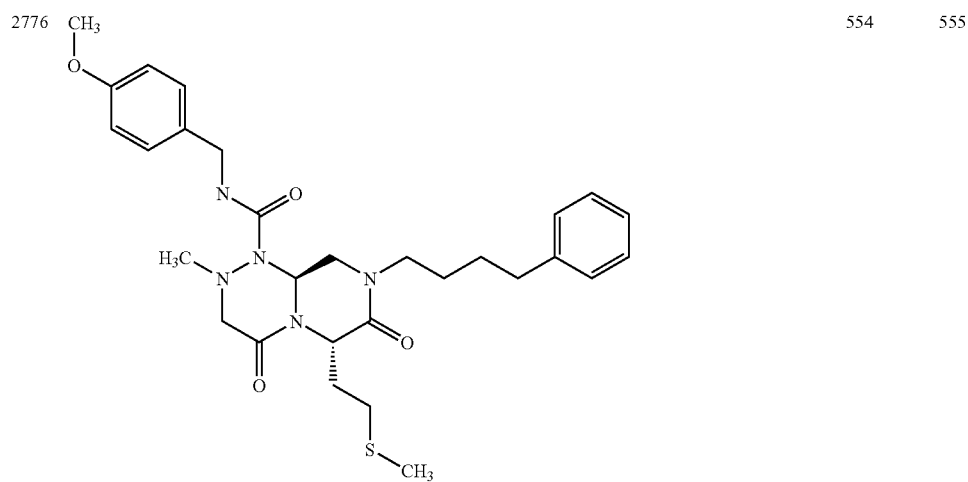 | 554 | 555 |
| 2777 | 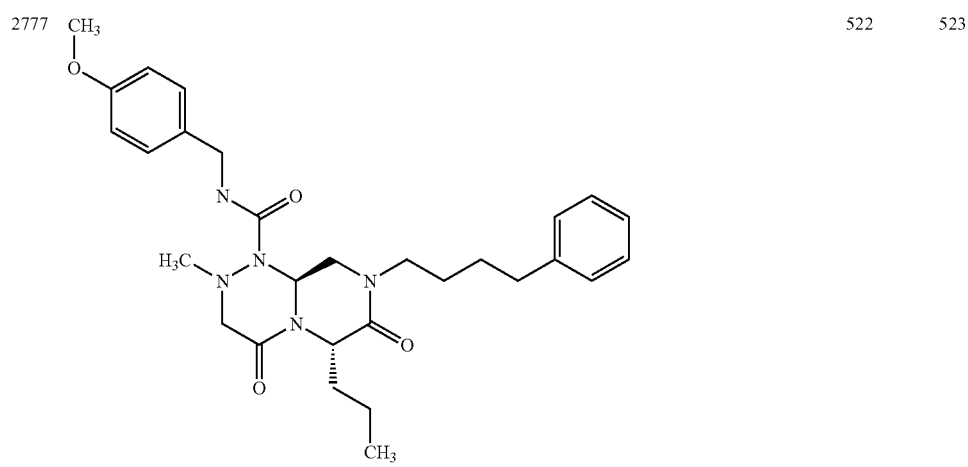 | 522 | 523 |

TABLE 2B-continued
THE [4,4,0]REVERSE TURN MIMETICS LIBRARY

| No | MOLSTRUCTURE | Mol. Weight | M + H (MS) |
|---|---|---|---|
| 2778 |  | 538 | 539 |
| 2779 | | 552 | 553 |

TABLE 2B-continued
THE [4,4,0]REVERSE TURN MIMETICS LIBRARY
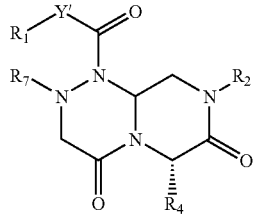
| No | MOLSTRUCTURE | Mol. Weight | M + H (MS) |
|---|---|---|---|
| 2780 | | 556 | 557 |
| 2781 | | 621 | 622 |

TABLE 2B-continued
THE [4,4,0]REVERSE TURN MIMETICS LIBRARY
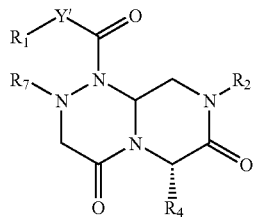
| No | MOLSTRUCTURE | Mol. Weight | M + H (MS) |
|---|---|---|---|
| 2782 | 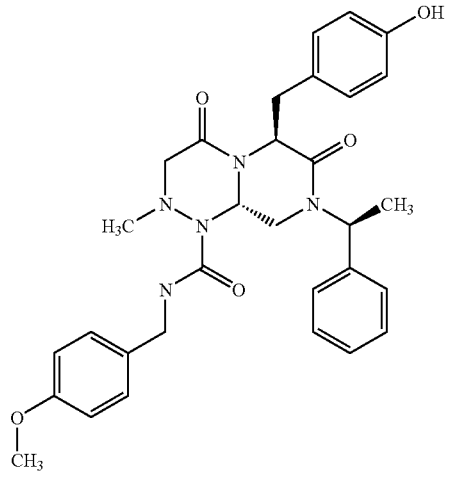 | 558 | 559 |
| 2783 | 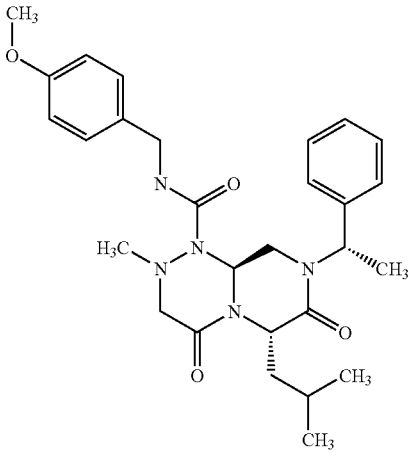 | 508 | 509 |

TABLE 2B-continued
THE [4,4,0]REVERSE TURN MIMETICS LIBRARY
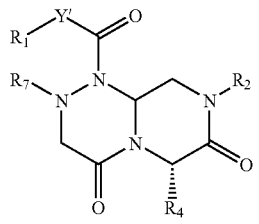
| No | MOLSTRUCTURE | Mol. Weight | M + H (MS) |
|---|---|---|---|
| 2784 | | 494 | 495 |
| 2785 | | 542 | 543 |

TABLE 2B-continued
THE [4,4,0]REVERSE TURN MIMETICS LIBRARY
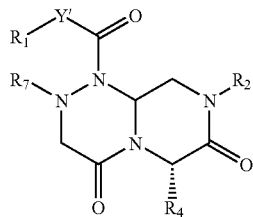
| No | MOLSTRUCTURE | Mol. Weight | M + H (MS) |
|---|---|---|---|
| 2786 | | 508 | 509 |
| 2787 | | 508 | 509 |

TABLE 2B-continued
THE [4,4,0]REVERSE TURN MIMETICS LIBRARY
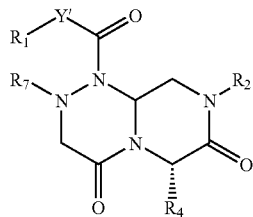
| No | MOLSTRUCTURE | Mol. Weight | M + H (MS) |
|---|---|---|---|
| 2788 | | 526 | 527 |
| 2789 | | 494 | 495 |

TABLE 2B-continued
THE [4,4,0]REVERSE TURN MIMETICS LIBRARY
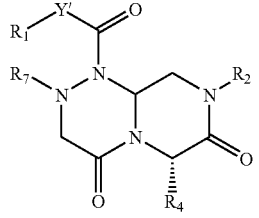
| No | MOLSTRUCTURE | Mol. Weight | M + H (MS) |
|---|---|---|---|
| 2790 | | 510 | 511 |
| 2791 | | 524 | 525 |

TABLE 2B-continued
THE [4,4,0]REVERSE TURN MIMETICS LIBRARY

| No | MOLSTRUCTURE | Mol. Weight | M + H (MS) |
|---|---|---|---|
| 2792 | | 528 | 529 |
| 2793 | | 593 | 594 |

TABLE 2B-continued
THE [4,4,0]REVERSE TURN MIMETICS LIBRARY
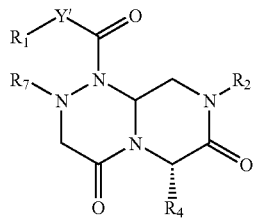
| No | MOLSTRUCTURE | Mol. Weight | M + H (MS) |
|---|---|---|---|
| 2794 | 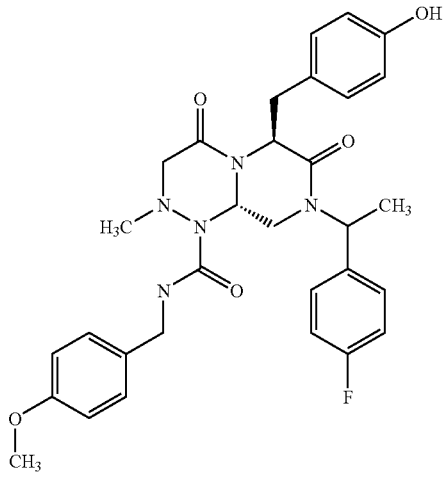 | 576 | 577 |
| 2795 | 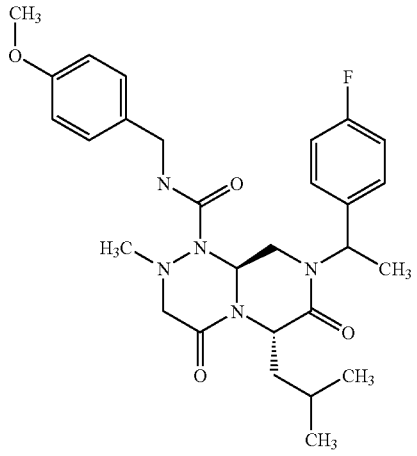 | 526 | 527 |

TABLE 2B-continued
THE [4,4,0]REVERSE TURN MIMETICS LIBRARY
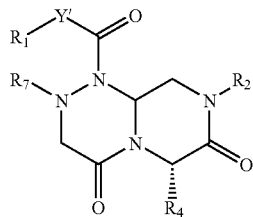
| No | MOLSTRUCTURE | Mol. Weight | M + H (MS) |
|---|---|---|---|
| 2796 | | 512 | 513 |
| 2797 | | 560 | 561 |

TABLE 2B-continued
THE [4,4,0]REVERSE TURN MIMETICS LIBRARY
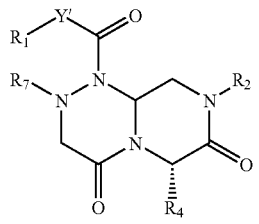
| No | MOLSTRUCTURE | Mol. Weight | M + H (MS) |
|---|---|---|---|
| 2798 | 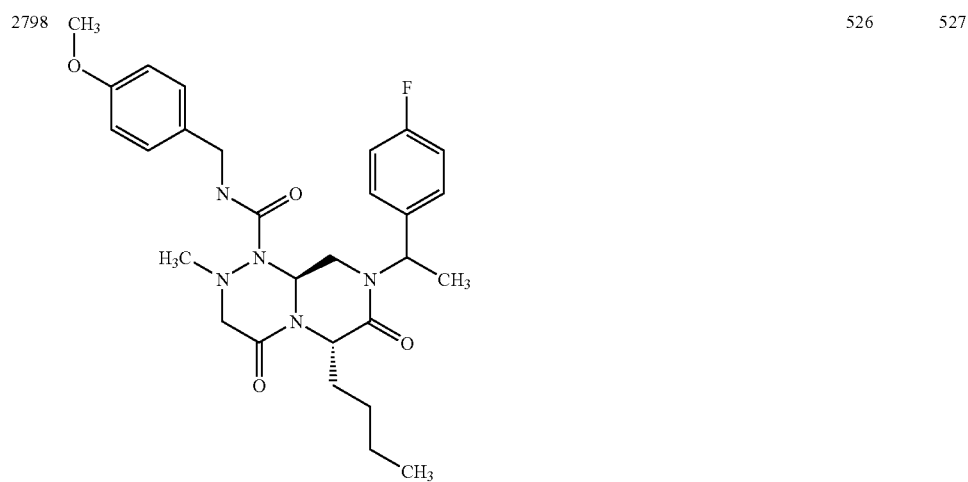 | 526 | 527 |
| 2799 |  | 526 | 527 |

TABLE 2B-continued
THE [4,4,0]REVERSE TURN MIMETICS LIBRARY
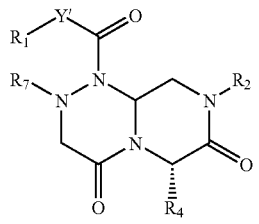
| No | MOLSTRUCTURE | Mol. Weight | M + H (MS) |
|---|---|---|---|
| 2800 | | 544 | 545 |
| 2801 | | 512 | 513 |

TABLE 2B-continued
THE [4,4,0]REVERSE TURN MIMETICS LIBRARY
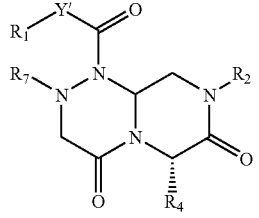
| No | MOLSTRUCTURE | Mol. Weight | M + H (MS) |
|---|---|---|---|
| 2802 | | 528 | 529 |
| 2803 | | 542 | 543 |

TABLE 2B-continued
THE [4,4,0]REVERSE TURN MIMETICS LIBRARY
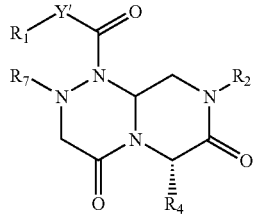
| No | MOLSTRUCTURE | Mol. Weight | M + H (MS) |
|---|---|---|---|
| 2804 | | 576 | 547 |
| 2805 | | 611 | 612 |

TABLE 2B-continued
THE [4,4,0]REVERSE TURN MIMETICS LIBRARY
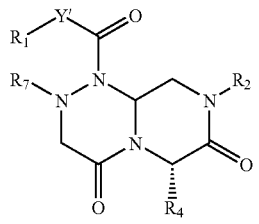
| No | MOLSTRUCTURE | Mol. Weight | M + H (MS) |
|---|---|---|---|
| 2806 | 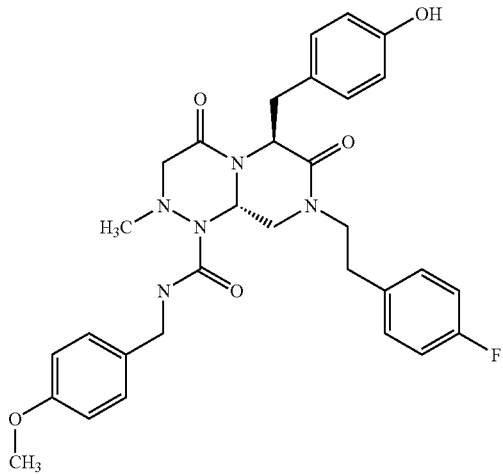 | 576 | 577 |
| 2807 | 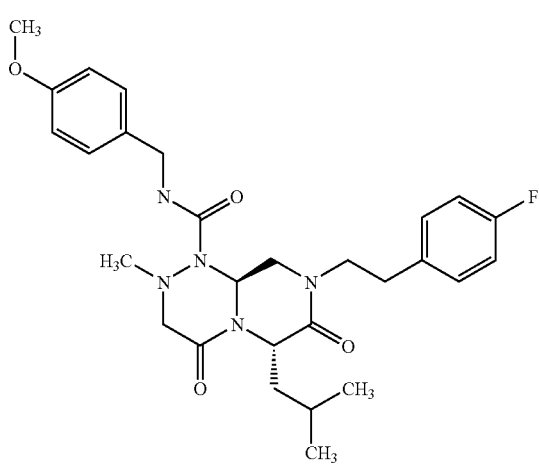 | 526 | 527 |

TABLE 2B-continued
THE [4,4,0]REVERSE TURN MIMETICS LIBRARY
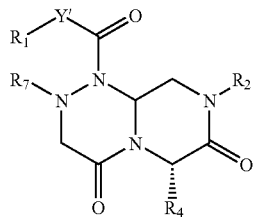
| No | MOLSTRUCTURE | Mol. Weight | M + H (MS) |
|---|---|---|---|
| 2808 | 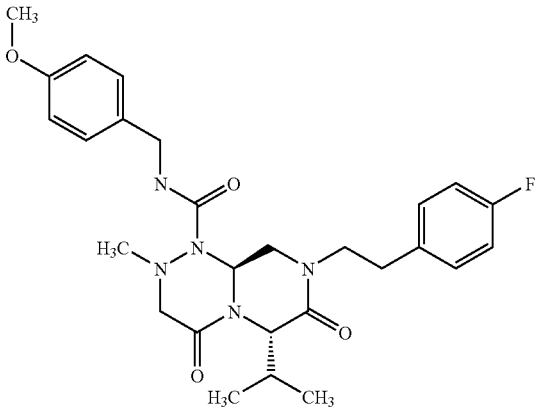 | 512 | 513 |
| 2809 | 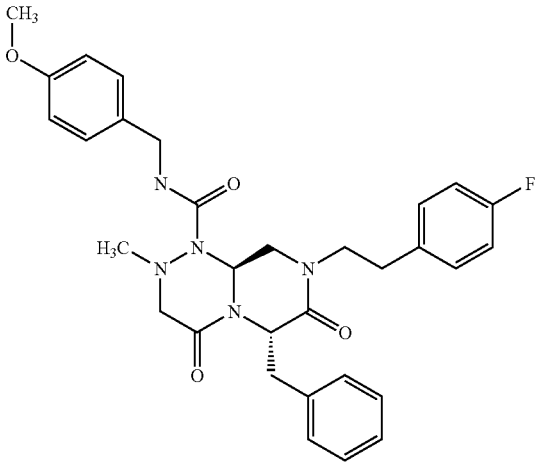 | 560 | 561 |

TABLE 2B-continued
THE [4,4,0]REVERSE TURN MIMETICS LIBRARY
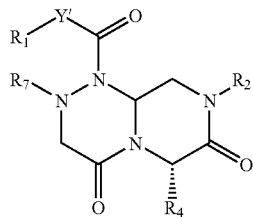
| No | MOLSTRUCTURE | Mol. Weight | M + H (MS) |
|---|---|---|---|
| 2810 | 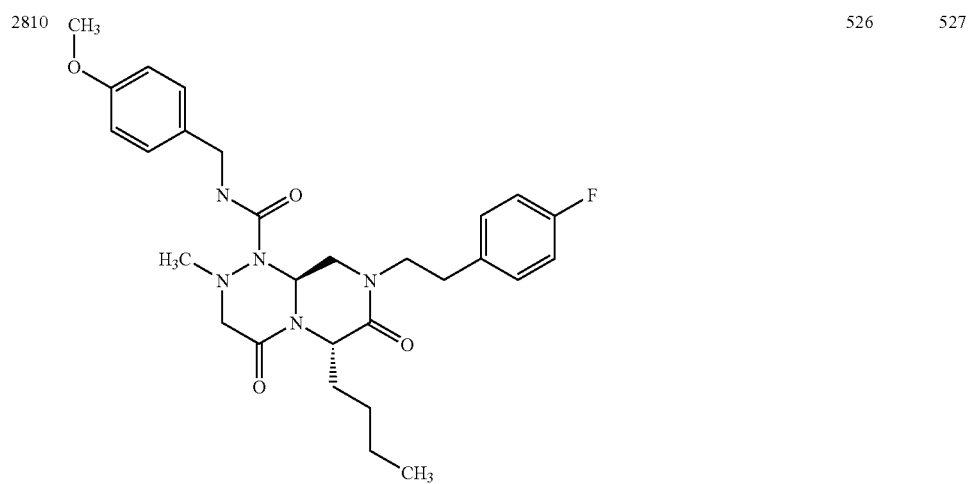 | 526 | 527 |
| 2811 | 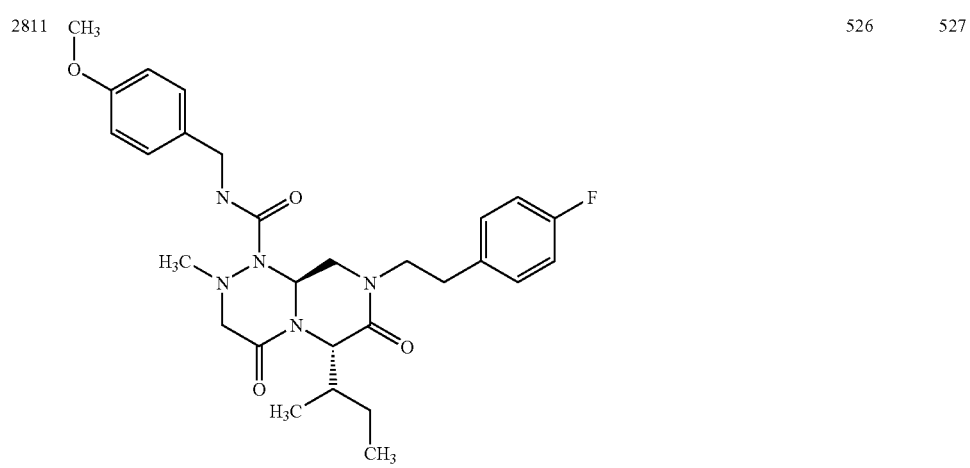 | 526 | 527 |

TABLE 2B-continued
THE [4,4,0]REVERSE TURN MIMETICS LIBRARY
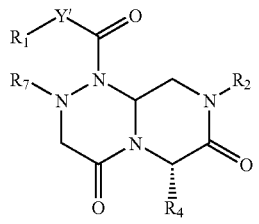
| No | MOLSTRUCTURE | Mol. Weight | M + H (MS) |
|---|---|---|---|
| 2812 | | 544 | 545 |
| 2813 | | 512 | 513 |

TABLE 2B-continued
THE [4,4,0]REVERSE TURN MIMETICS LIBRARY
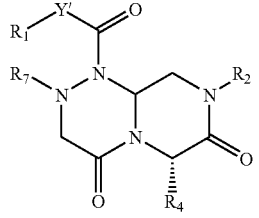
| No | MOLSTRUCTURE | Mol. Weight | M + H (MS) |
|---|---|---|---|
| 2814 | | 528 | 529 |
| 2815 | | 542 | 543 |

TABLE 2B-continued
THE [4,4,0]REVERSE TURN MIMETICS LIBRARY
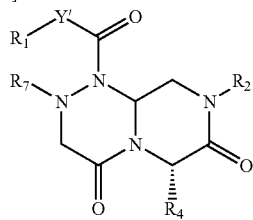
| No | MOLSTRUCTURE | Mol. Weight | M + H (MS) |
|---|---|---|---|
| 2816 | | 546 | 547 |
| 2817 | | 611 | 612 |

TABLE 2B-continued
THE [4,4,0]REVERSE TURN MIMETICS LIBRARY
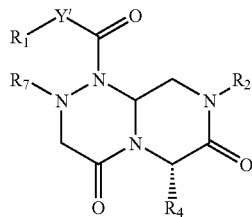
| No | MOLSTRUCTURE | Mol. Weight | M + H (MS) |
|---|---|---|---|
| 2818 | 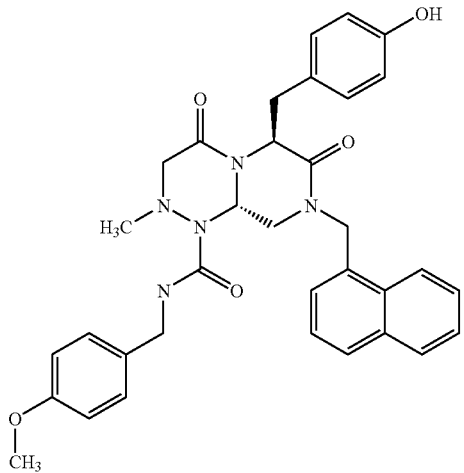 | 594 | 595 |
| 2819 | 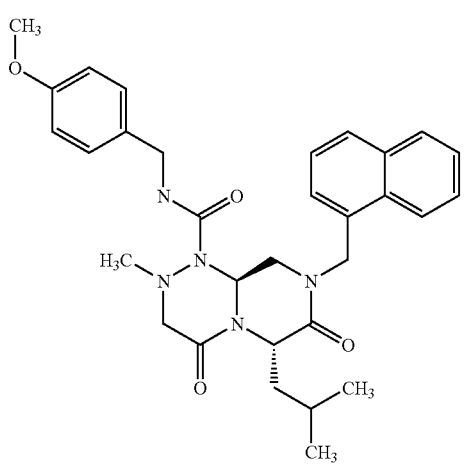 | 544 | 545 |

TABLE 2B-continued
THE [4,4,0]REVERSE TURN MIMETICS LIBRARY
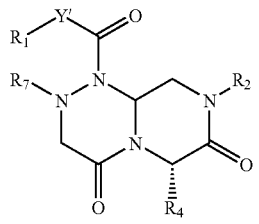
| No | MOLSTRUCTURE | Mol. Weight | M + H (MS) |
|---|---|---|---|
| 2820 | | 530 | 531 |
| 2821 | | 578 | 579 |

TABLE 2B-continued
THE [4,4,0]REVERSE TURN MIMETICS LIBRARY
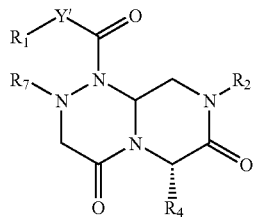
| No | MOLSTRUCTURE | Mol. Weight | M + H (MS) |
|----|--------------|-------------|------------|
| 2822 | | 544 | 545 |
| 2823 | | 544 | 545 |

TABLE 2B-continued
THE [4,4,0]REVERSE TURN MIMETICS LIBRARY
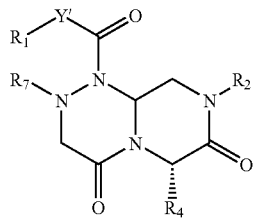
| No | MOLSTRUCTURE | Mol. Weight | M + H (MS) |
|---|---|---|---|
| 2824 | | 562 | 563 |
| 2825 | | 530 | 531 |

TABLE 2B-continued
THE [4,4,0]REVERSE TURN MIMETICS LIBRARY
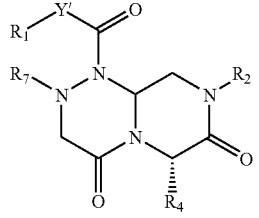
| No | MOLSTRUCTURE | Mol. Weight | M + H (MS) |
|---|---|---|---|
| 2826 | | 546 | 547 |
| 2827 | | 560 | 560 |

TABLE 2B-continued
THE [4,4,0]REVERSE TURN MIMETICS LIBRARY
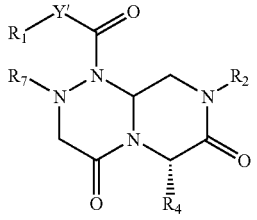
| No | MOLSTRUCTURE | Mol. Weight | M + H (MS) |
|---|---|---|---|
| 2828 | | 564 | 565 |
| 2829 | | 629 | 630 |

TABLE 2B-continued
THE [4,4,0]REVERSE TURN MIMETICS LIBRARY
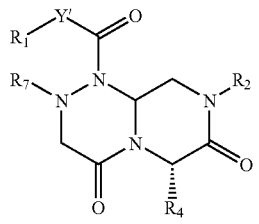
| No | MOLSTRUCTURE | Mol. Weight | M + H (MS) |
|---|---|---|---|
| 2830 | 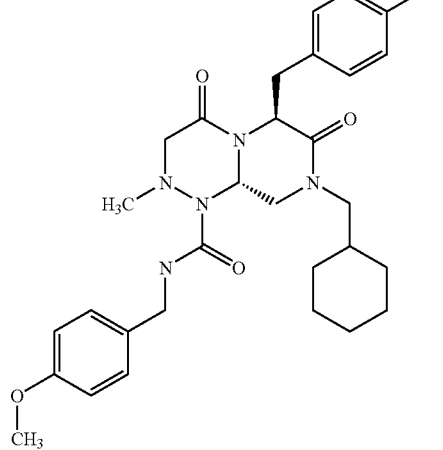 | 550 | 551 |
| 2831 | 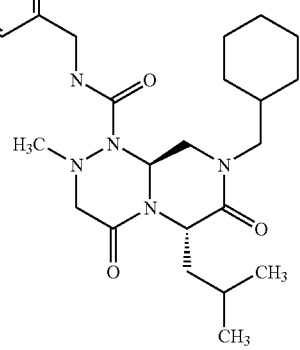 | 500 | 501 |

TABLE 2B-continued
THE [4,4,0]REVERSE TURN MIMETICS LIBRARY
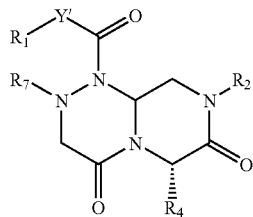
| No | MOLSTRUCTURE | Mol. Weight | M + H (MS) |
|---|---|---|---|
| 2832 | | 486 | 487 |
| 2833 | | 534 | 535 |

TABLE 2B-continued
THE [4,4,0]REVERSE TURN MIMETICS LIBRARY
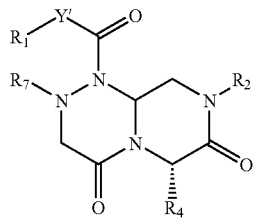
| No | MOLSTRUCTURE | Mol. Weight | M + H (MS) |
|---|---|---|---|
| 2834 | 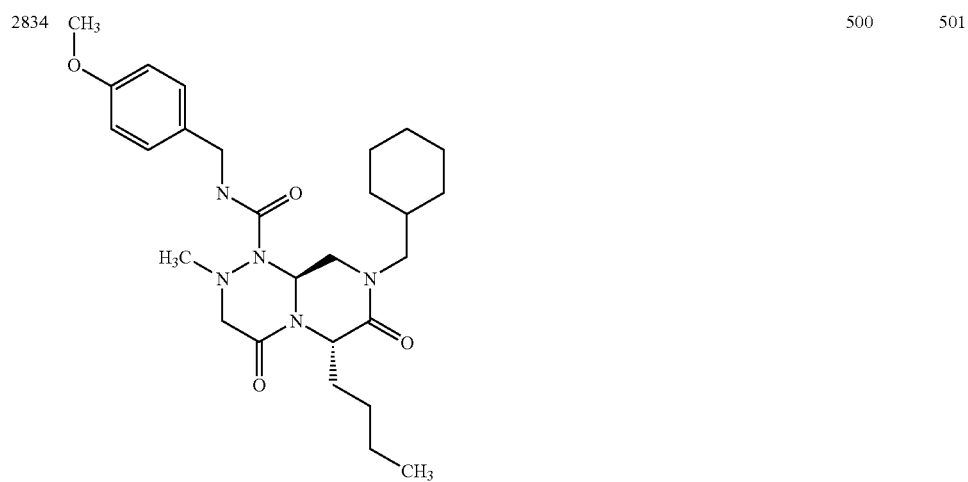 | 500 | 501 |
| 2835 | 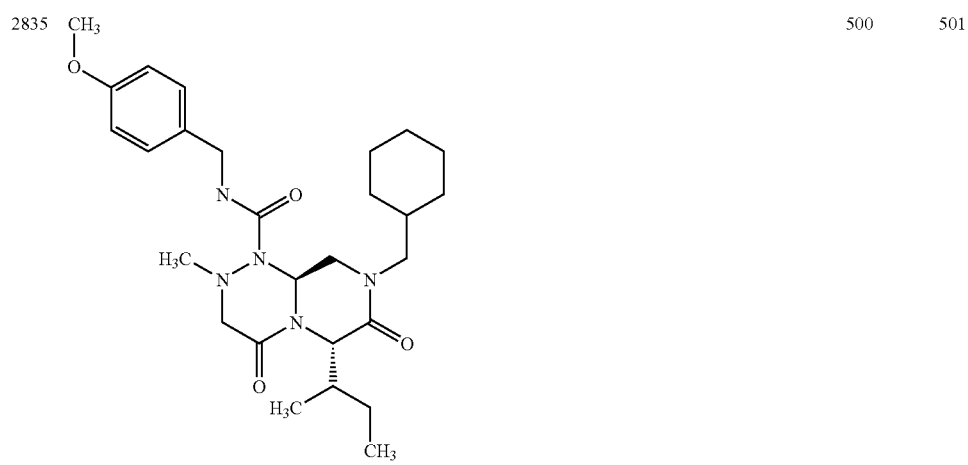 | 500 | 501 |

TABLE 2B-continued
THE [4,4,0]REVERSE TURN MIMETICS LIBRARY
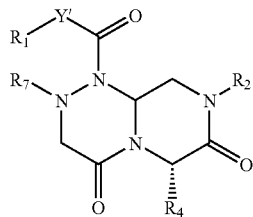
| No | MOLSTRUCTURE | Mol. Weight | M + H (MS) |
|---|---|---|---|
| 2836 | | 518 | 519 |
| 2837 | | 486 | 487 |

TABLE 2B-continued
THE [4,4,0]REVERSE TURN MIMETICS LIBRARY
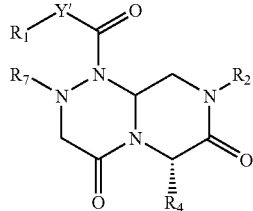
| No | MOLSTRUCTURE | Mol. Weight | M + H (MS) |
|----|---|---|---|
| 2838 | | 502 | 503 |
| 2839 | | 516 | 517 |

TABLE 2B-continued
THE [4,4,0]REVERSE TURN MIMETICS LIBRARY
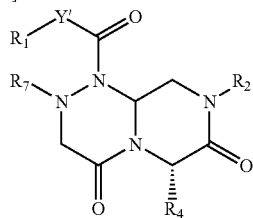
| No | MOLSTRUCTURE | Mol. Weight | M + H (MS) |
|---|---|---|---|
| 2840 | | 520 | 521 |
| 2841 | | 585 | 586 |

TABLE 2B-continued
THE [4,4,0]REVERSE TURN MIMETICS LIBRARY
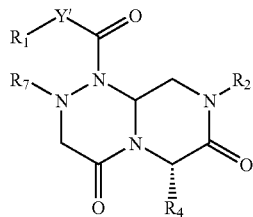
| No | MOLSTRUCTURE | Mol. Weight | M + H (MS) |
|---|---|---|---|
| 2842 | 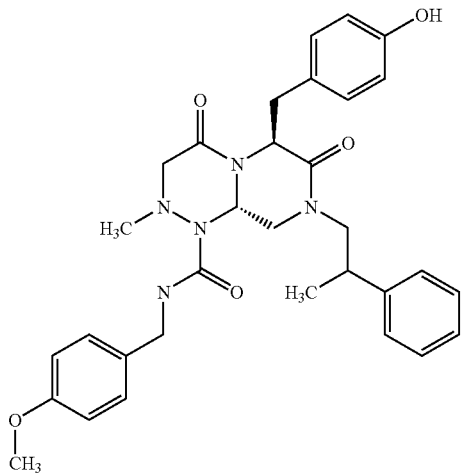 | 572 | 573 |
| 2843 | 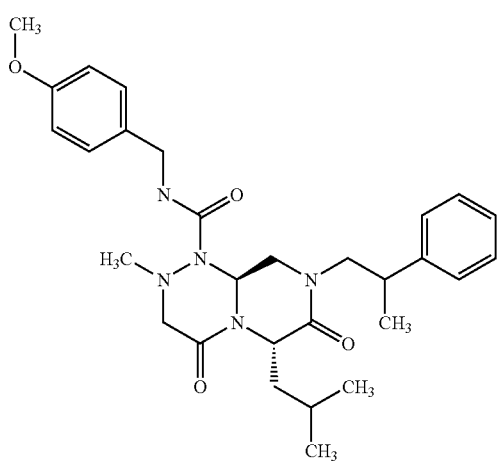 | 522 | 523 |

TABLE 2B-continued
THE [4,4,0]REVERSE TURN MIMETICS LIBRARY
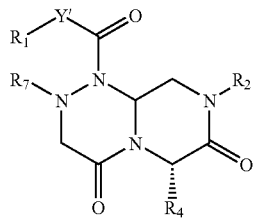
| No | MOLSTRUCTURE | Mol. Weight | M + H (MS) |
|---|---|---|---|
| 2844 | 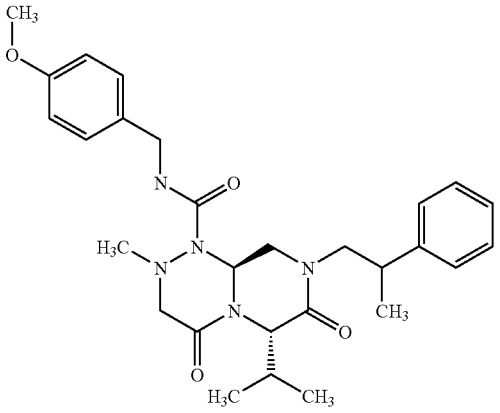 | 508 | 509 |
| 2845 | 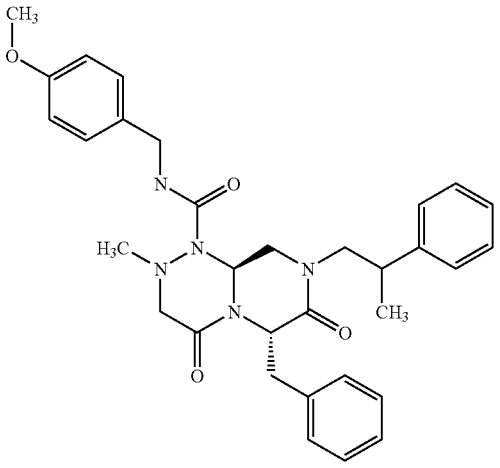 | 556 | 557 |

TABLE 2B-continued
THE [4,4,0]REVERSE TURN MIMETICS LIBRARY
| No | MOLSTRUCTURE | Mol. Weight | M + H (MS) |
|---|---|---|---|
| 2846 | | 522 | 523 |
| 2847 | | 522 | 523 |

TABLE 2B-continued
THE [4,4,0]REVERSE TURN MIMETICS LIBRARY
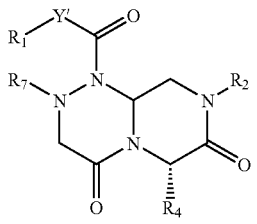
| No | MOLSTRUCTURE | Mol. Weight | M + H (MS) |
|---|---|---|---|
| 2848 | 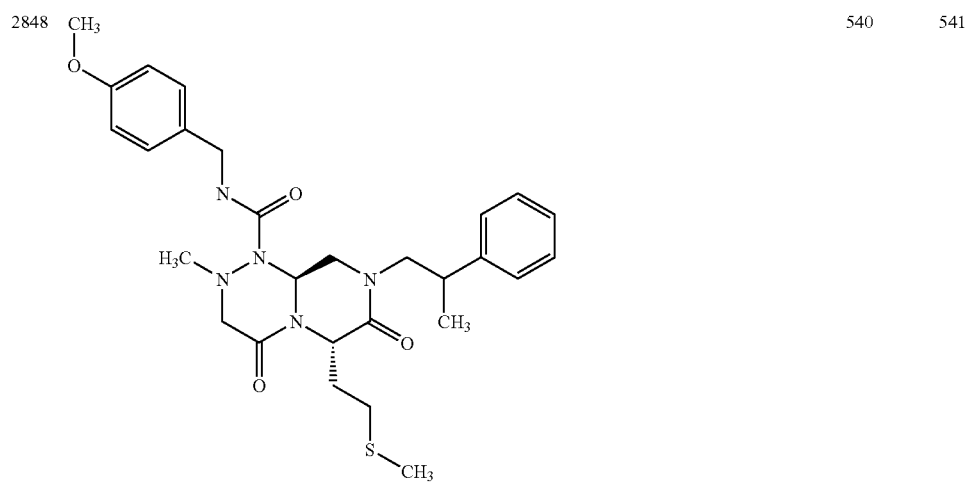 | 540 | 541 |
| 2849 | 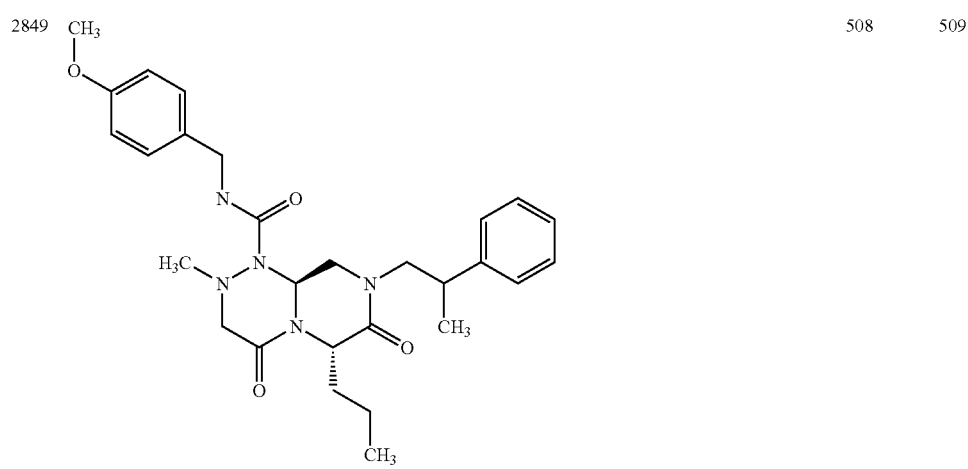 | 508 | 509 |

TABLE 2B-continued
THE [4,4,0]REVERSE TURN MIMETICS LIBRARY
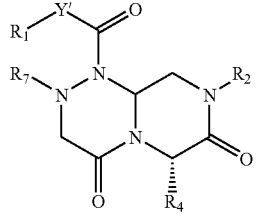
| No | MOLSTRUCTURE | Mol. Weight | M + H (MS) |
|---|---|---|---|
| 2850 | | 520 | 525 |
| 2851 | | 538 | 539 |

TABLE 2B-continued
THE [4,4,0]REVERSE TURN MIMETICS LIBRARY
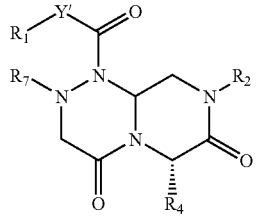
| No | MOLSTRUCTURE | Mol. Weight | M + H (MS) |
|---|---|---|---|
| 2852 | | 542 | 543 |
| 2853 | | 607 | 608 |

TABLE 2B-continued
THE [4,4,0]REVERSE TURN MIMETICS LIBRARY
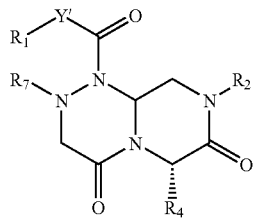
| No | MOLSTRUCTURE | Mol. Weight | M + H (MS) |
|---|---|---|---|
| 2854 | 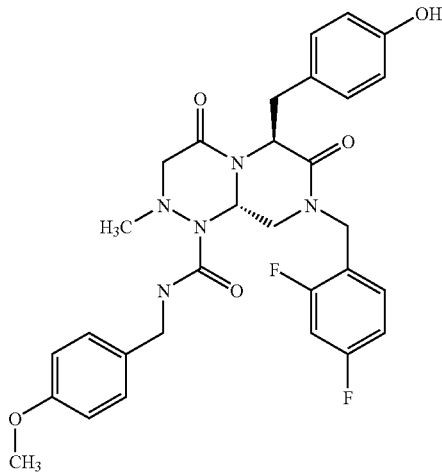 | 580 | 581 |
| 2855 | 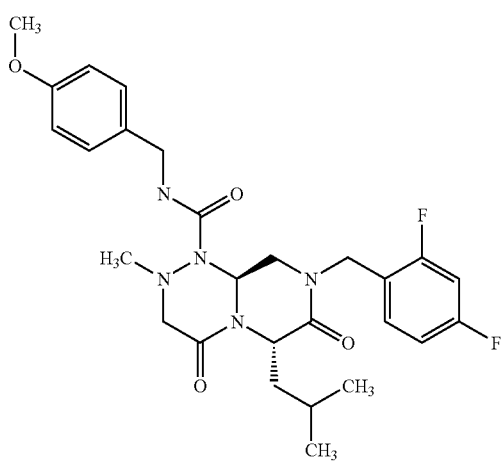 | 530 | 531 |

TABLE 2B-continued
THE [4,4,0]REVERSE TURN MIMETICS LIBRARY
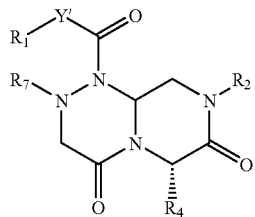
| No | MOLSTRUCTURE | Mol. Weight | M + H (MS) |
|---|---|---|---|
| 2856 | | 516 | 517 |
| 2857 | | 564 | 565 |

TABLE 2B-continued
THE [4,4,0]REVERSE TURN MIMETICS LIBRARY
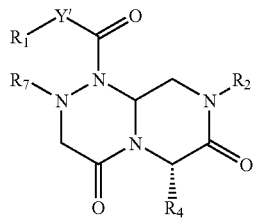
| No | MOLSTRUCTURE | Mol. Weight | M + H (MS) |
|---|---|---|---|
| 2858 | | 530 | 531 |
| 2859 | | 530 | 531 |

TABLE 2B-continued
THE [4,4,0]REVERSE TURN MIMETICS LIBRARY
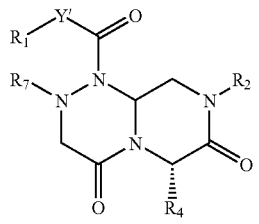
| No | MOLSTRUCTURE | Mol. Weight | M + H (MS) |
|---|---|---|---|
| 2860 | 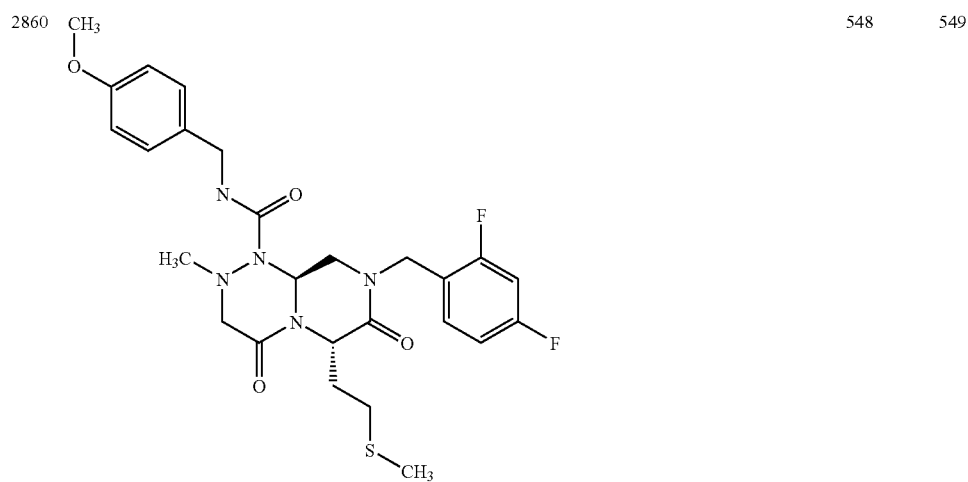 | 548 | 549 |
| 2861 | 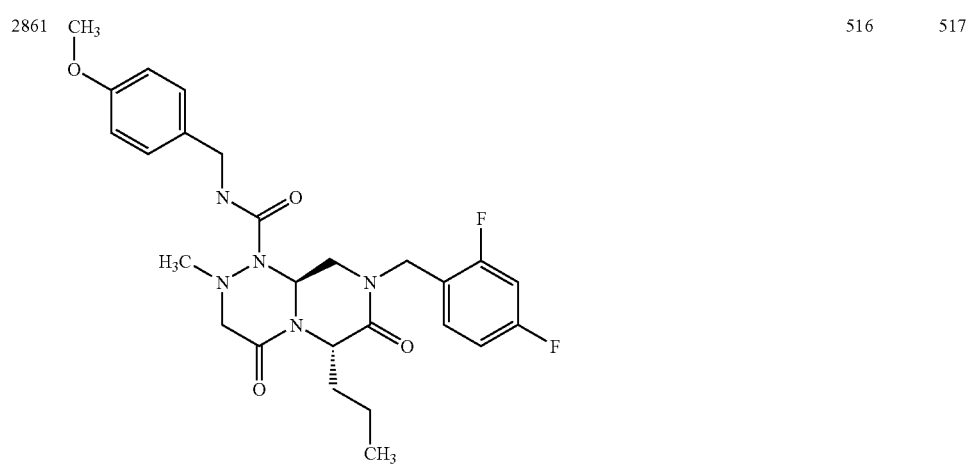 | 516 | 517 |

TABLE 2B-continued
THE [4,4,0]REVERSE TURN MIMETICS LIBRARY
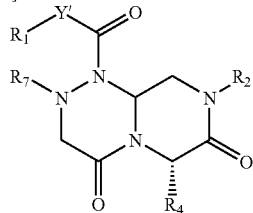
| No | MOLSTRUCTURE | Mol. Weight | M + H (MS) |
|---|---|---|---|
| 2862 | | 532 | 533 |
| 2863 | | 546 | 547 |

TABLE 2B-continued
THE [4,4,0]REVERSE TURN MIMETICS LIBRARY
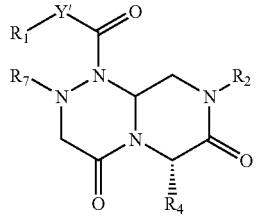
| No | MOLSTRUCTURE | Mol. Weight | M + H (MS) |
|---|---|---|---|
| 2864 | 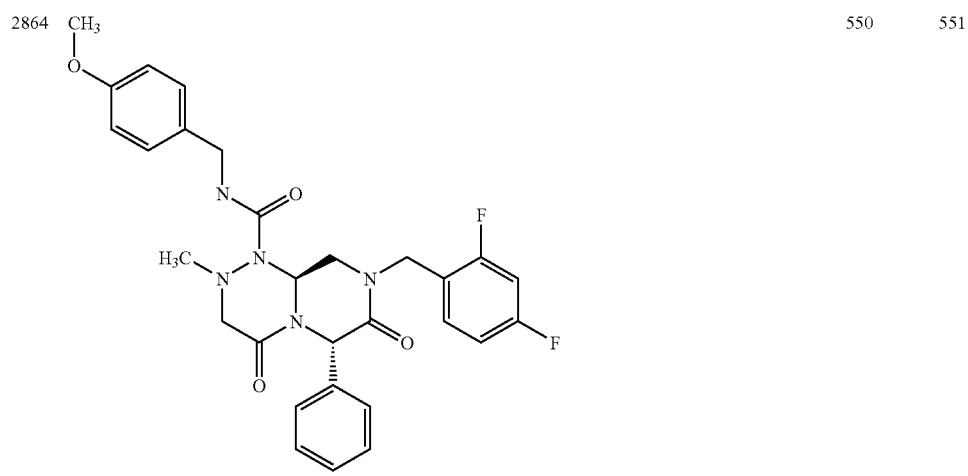 | 550 | 551 |
| 2865 | 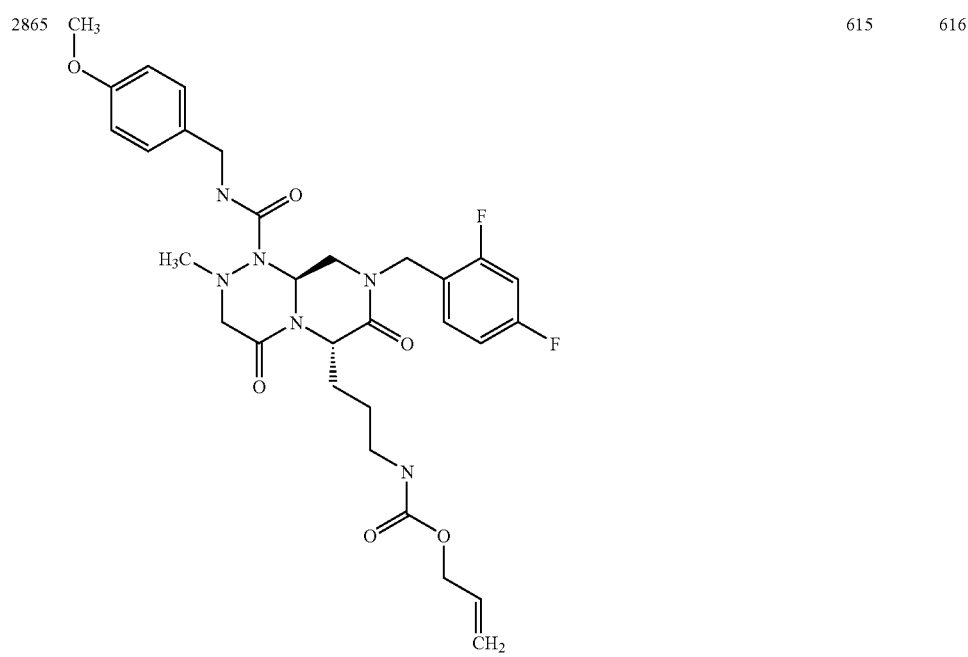 | 615 | 616 |

TABLE 2B-continued
THE [4,4,0]REVERSE TURN MIMETICS LIBRARY
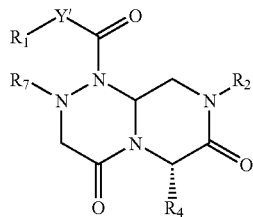
| No | MOLSTRUCTURE | Mol. Weight | M + H (MS) |
|---|---|---|---|
| 2866 | 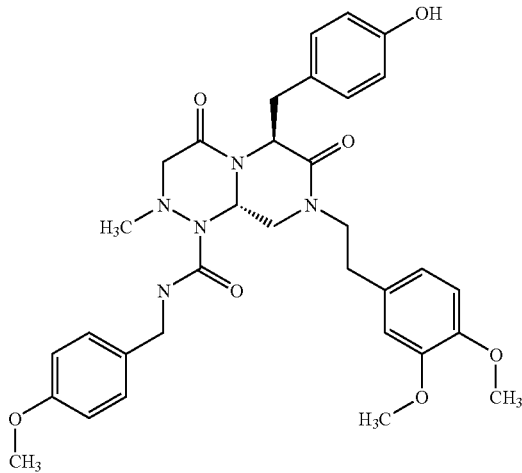 | 618 | 619 |
| 2867 | 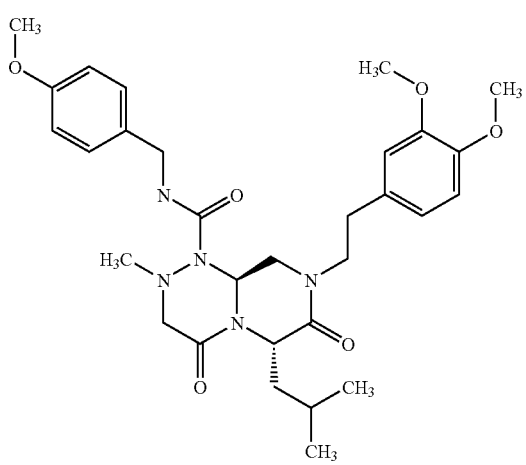 | 568 | 569 |

TABLE 2B-continued
THE [4,4,0]REVERSE TURN MIMETICS LIBRARY
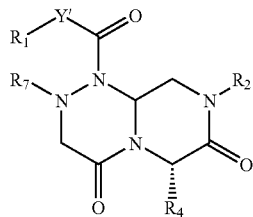
| No | MOLSTRUCTURE | Mol. Weight | M + H (MS) |
|---|---|---|---|
| 2868 | 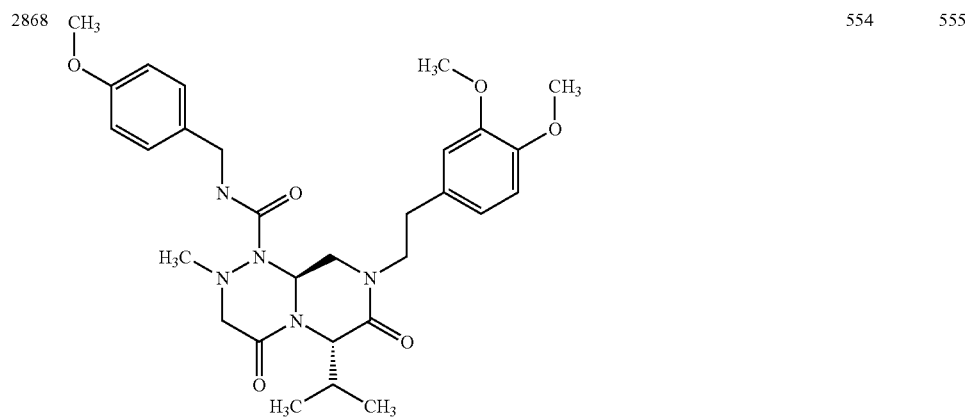 | 554 | 555 |
| 2869 | 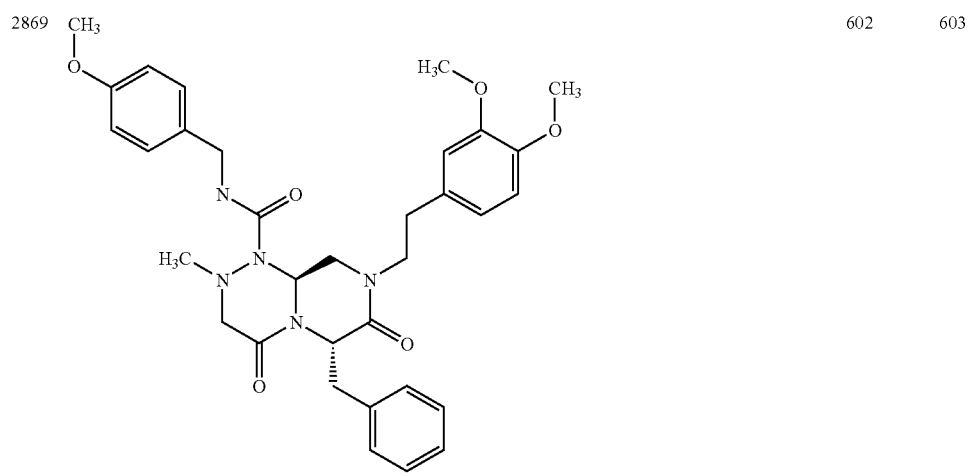 | 602 | 603 |

TABLE 2B-continued
THE [4,4,0]REVERSE TURN MIMETICS LIBRARY
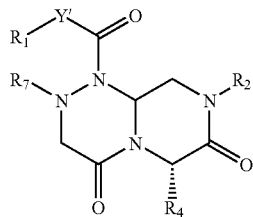
| No | MOLSTRUCTURE | Mol. Weight | M + H (MS) |
|---|---|---|---|
| 2870 | 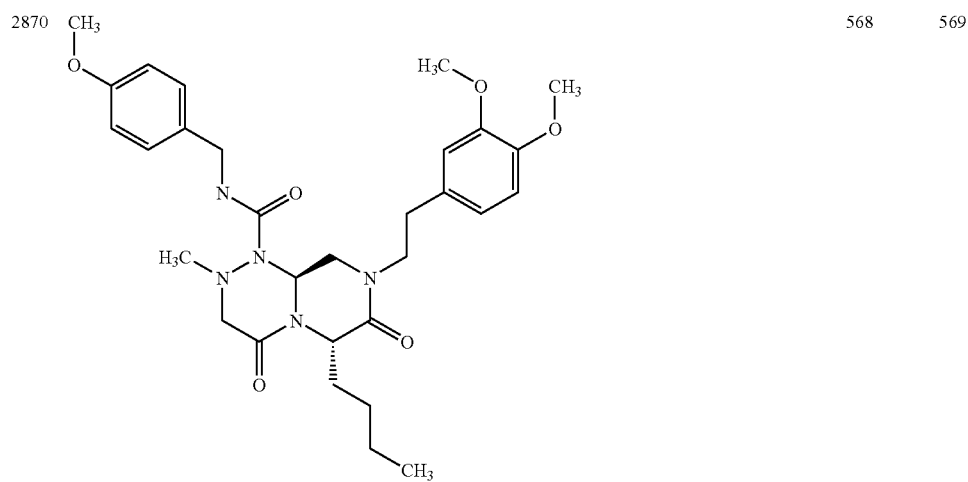 | 568 | 569 |
| 2871 | 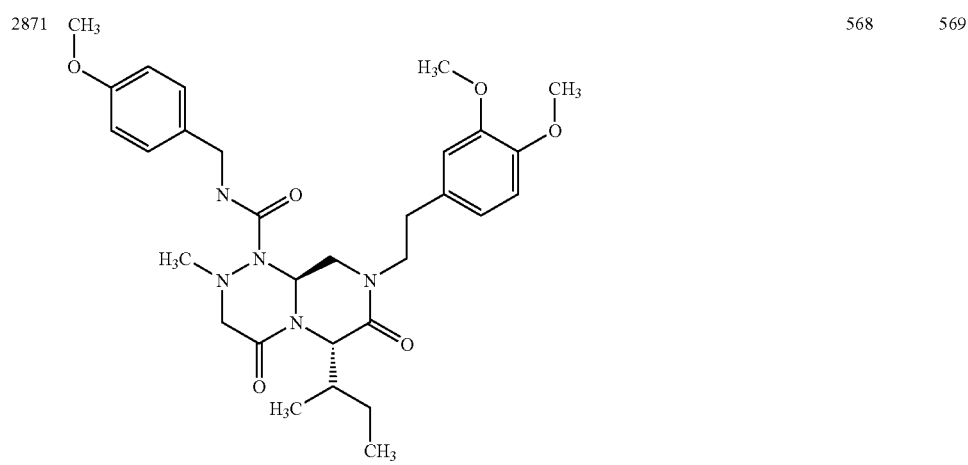 | 568 | 569 |

TABLE 2B-continued
THE [4,4,0]REVERSE TURN MIMETICS LIBRARY
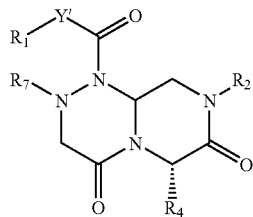
| No | MOLSTRUCTURE | Mol. Weight | M + H (MS) |
|---|---|---|---|
| 2872 | 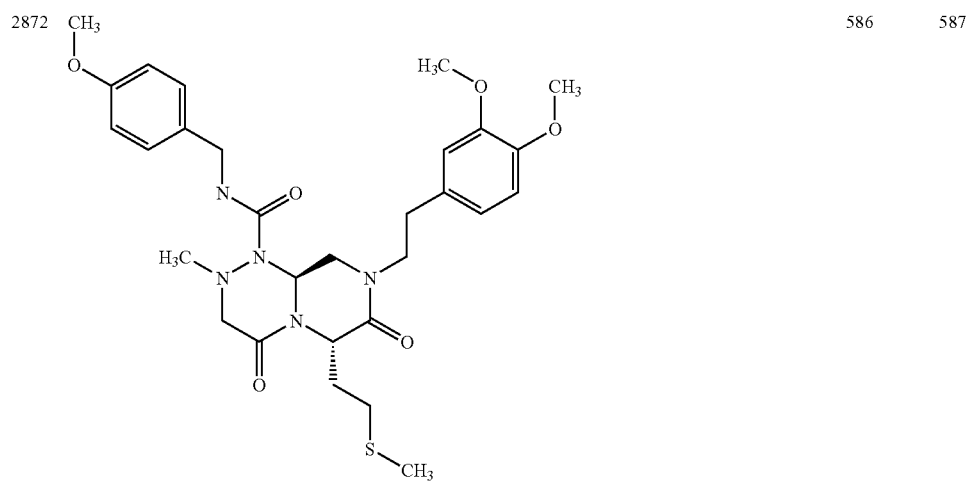 | 586 | 587 |
| 2873 | 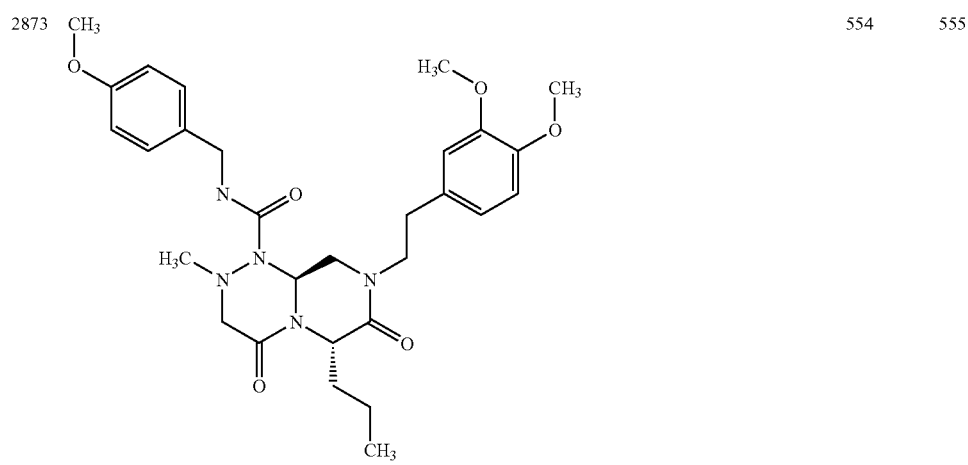 | 554 | 555 |

TABLE 2B-continued
THE [4,4,0]REVERSE TURN MIMETICS LIBRARY
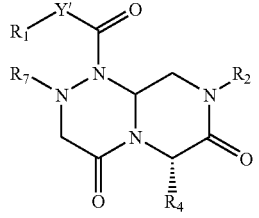
| No | MOLSTRUCTURE | Mol. Weight | M + H (MS) |
|---|---|---|---|
| 2874 | | 570 | 571 |
| 2875 | | 584 | 585 |

TABLE 2B-continued
THE [4,4,0]REVERSE TURN MIMETICS LIBRARY
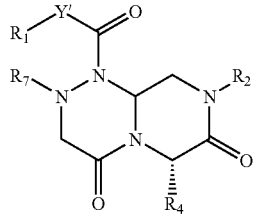
| No | MOLSTRUCTURE | Mol. Weight | M + H (MS) |
|---|---|---|---|
| 2876 | 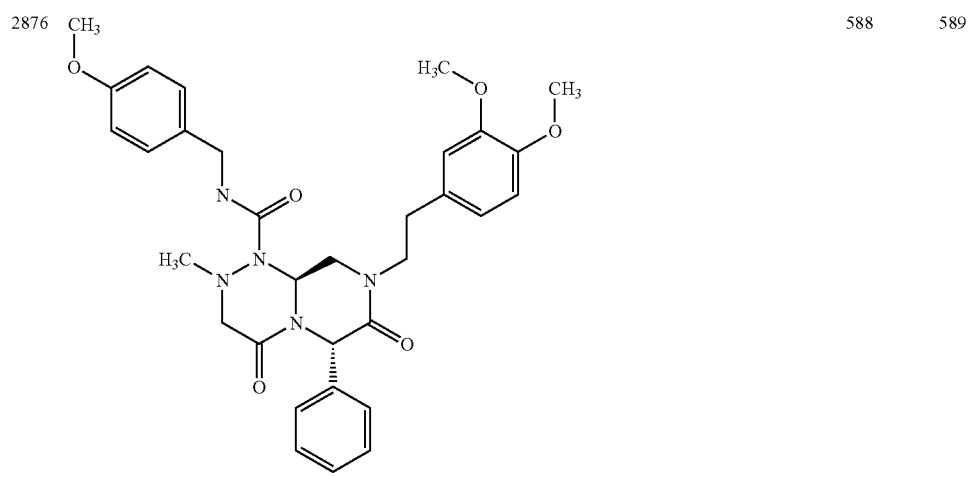 | 588 | 589 |
| 2877 | 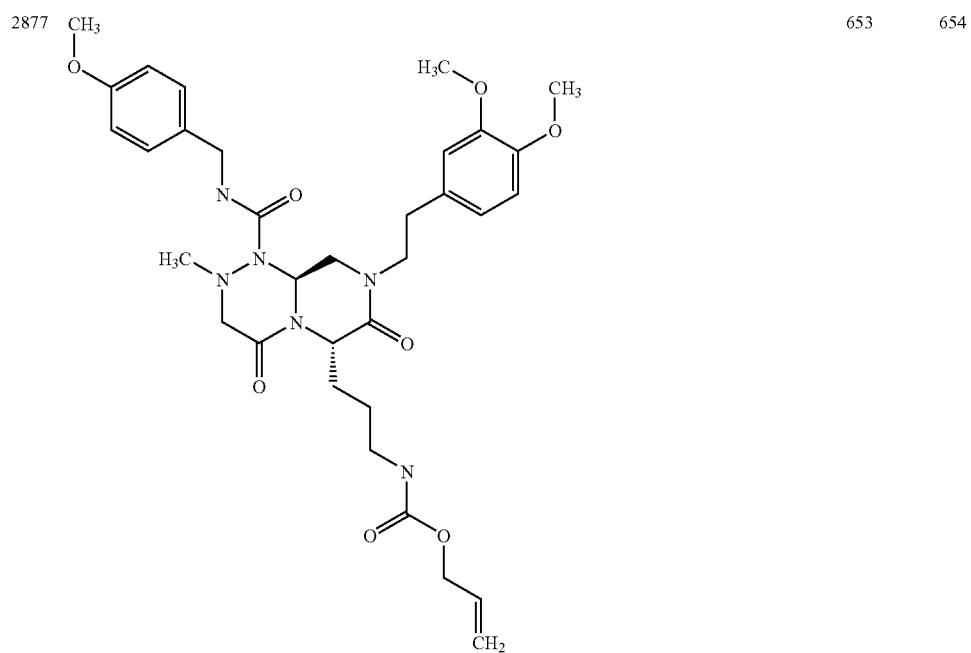 | 653 | 654 |

TABLE 2B-continued
THE [4,4,0]REVERSE TURN MIMETICS LIBRARY
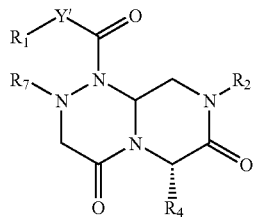
| No | MOLSTRUCTURE | Mol. Weight | M + H (MS) |
|---|---|---|---|
| 2878 | 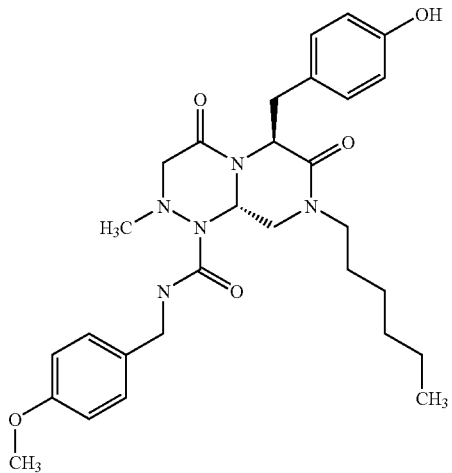 | 538 | 539 |
| 2879 | 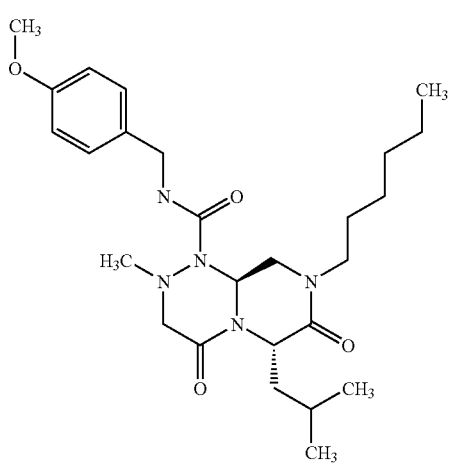 | 488 | 489 |

TABLE 2B-continued
THE [4,4,0]REVERSE TURN MIMETICS LIBRARY
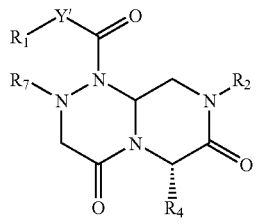
| No | MOLSTRUCTURE | Mol. Weight | M + H (MS) |
|---|---|---|---|
| 2880 | | 474 | 475 |
| 2881 | | 522 | 523 |

TABLE 2B-continued
THE [4,4,0]REVERSE TURN MIMETICS LIBRARY
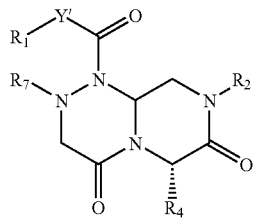
| No | MOLSTRUCTURE | Mol. Weight | M + H (MS) |
|---|---|---|---|
| 2882 | 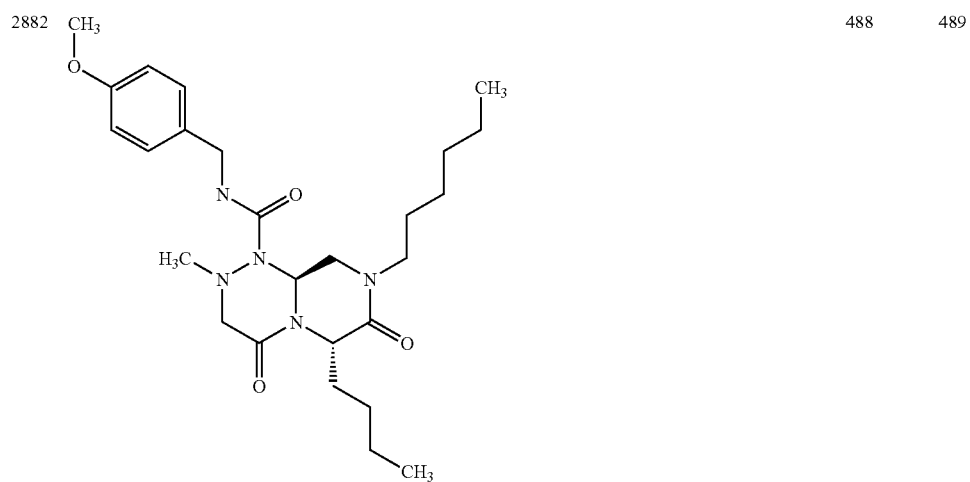 | 488 | 489 |
| 2883 | 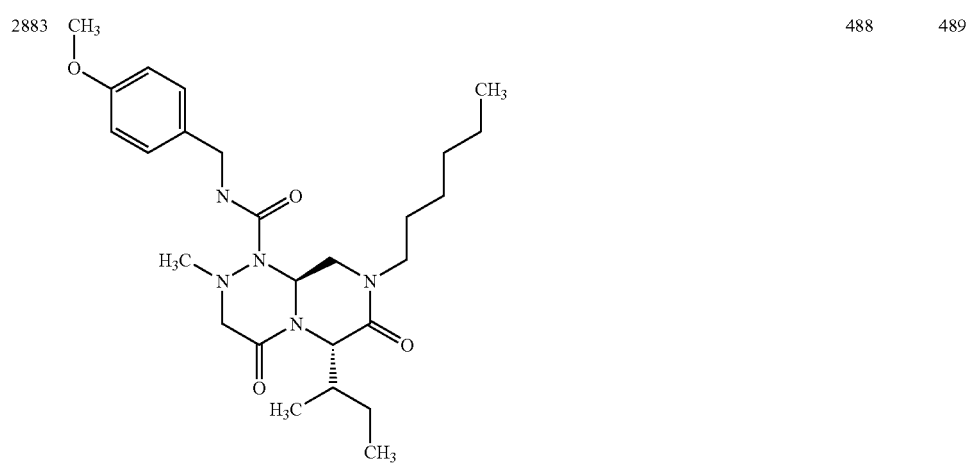 | 488 | 489 |

TABLE 2B-continued
THE [4,4,0]REVERSE TURN MIMETICS LIBRARY
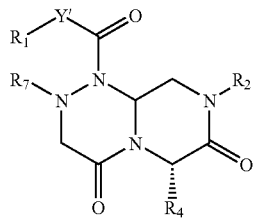
| No | MOLSTRUCTURE | Mol. Weight | M + H (MS) |
|---|---|---|---|
| 2884 | 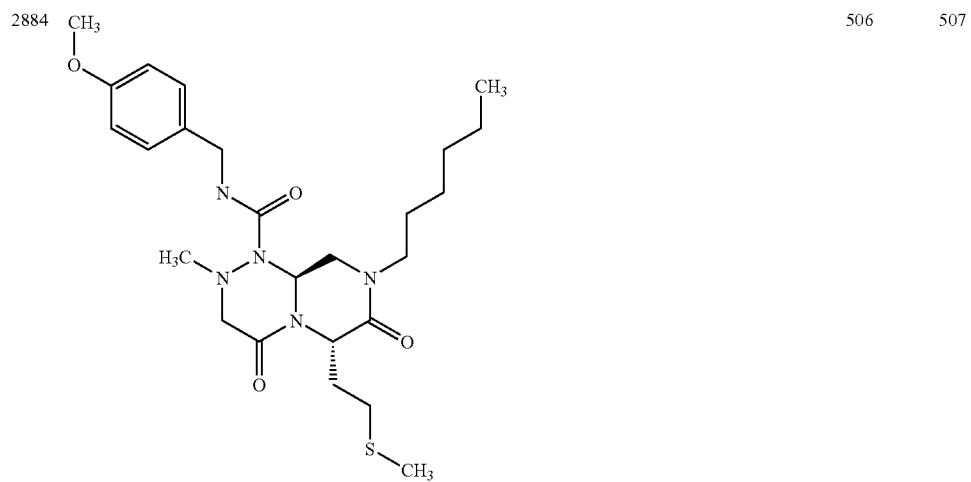 | 506 | 507 |
| 2885 | 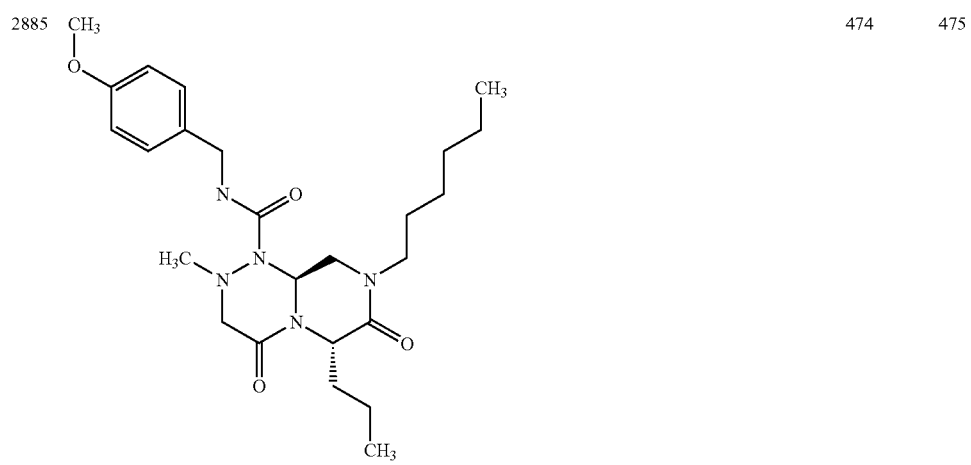 | 474 | 475 |

TABLE 2B-continued
THE [4,4,0]REVERSE TURN MIMETICS LIBRARY
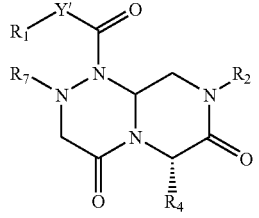
| No | MOLSTRUCTURE | Mol. Weight | M + H (MS) |
|---|---|---|---|
| 2886 | | 490 | 491 |
| 2887 | | 504 | 505 |

TABLE 2B-continued
THE [4,4,0]REVERSE TURN MIMETICS LIBRARY
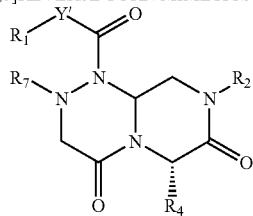
| No | MOLSTRUCTURE | Mol. Weight | M + H (MS) |
|---|---|---|---|
| 2888 | | 508 | 509 |
| 2889 | | 573 | 574 |

TABLE 2B-continued
THE [4,4,0]REVERSE TURN MIMETICS LIBRARY
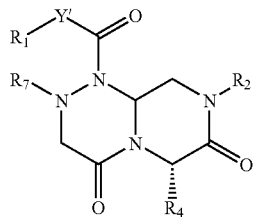
| No | MOLSTRUCTURE | Mol. Weight | M + H (MS) |
|---|---|---|---|
| 2890 | 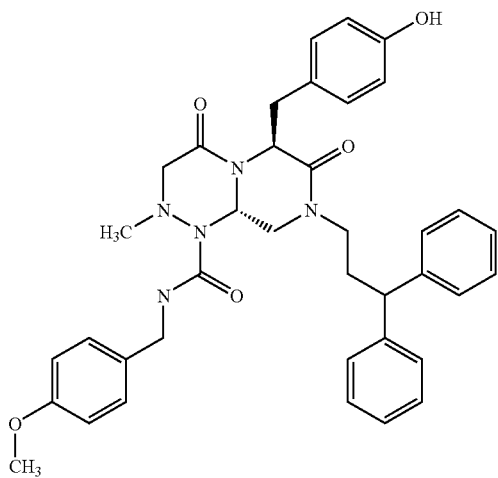 | 648 | 649 |
| 2891 | 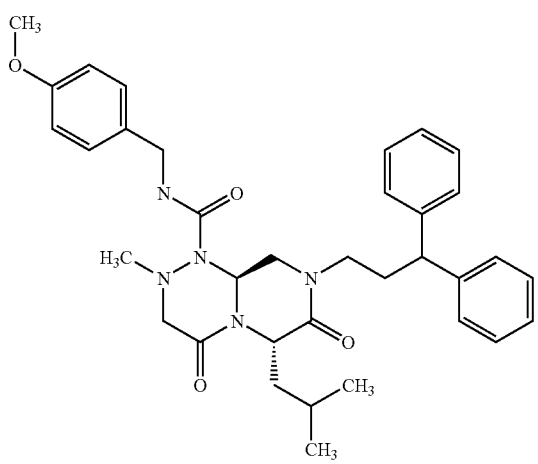 | 598 | 599 |

TABLE 2B-continued
THE [4,4,0]REVERSE TURN MIMETICS LIBRARY
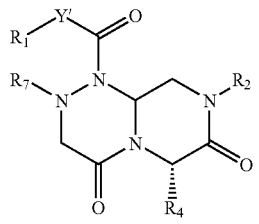
| No | MOLSTRUCTURE | Mol. Weight | M + H (MS) |
|---|---|---|---|
| 2892 | | 584 | 585 |
| 2893 | | 632 | 633 |

TABLE 2B-continued
THE [4,4,0]REVERSE TURN MIMETICS LIBRARY
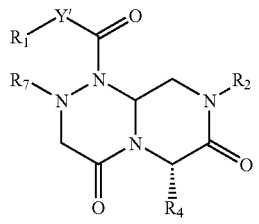
| No | MOLSTRUCTURE | Mol. Weight | M + H (MS) |
|---|---|---|---|
| 2894 | | 598 | 599 |
| 2895 | | 598 | 599 |

TABLE 2B-continued
THE [4,4,0]REVERSE TURN MIMETICS LIBRARY
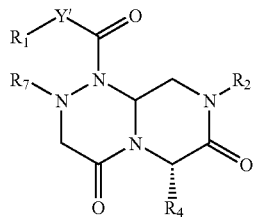
| No | MOLSTRUCTURE | Mol. Weight | M + H (MS) |
|---|---|---|---|
| 2896 | 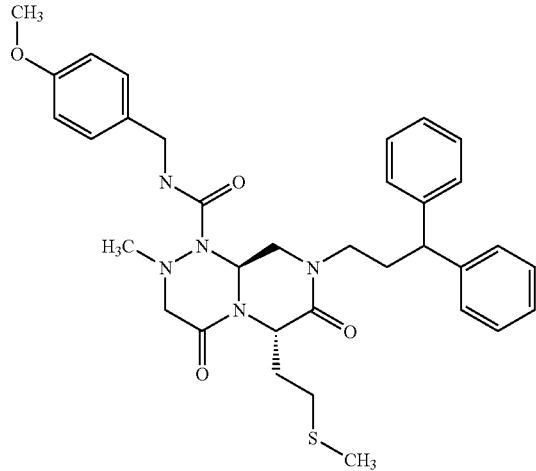 | 616 | 617 |
| 2897 | 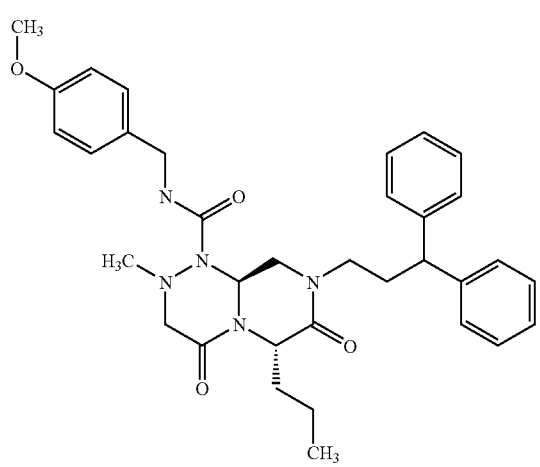 | 584 | 585 |

TABLE 2B-continued
THE [4,4,0]REVERSE TURN MIMETICS LIBRARY
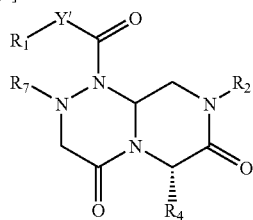
| No | MOLSTRUCTURE | Mol. Weight | M + H (MS) |
|---|---|---|---|
| 2898 | 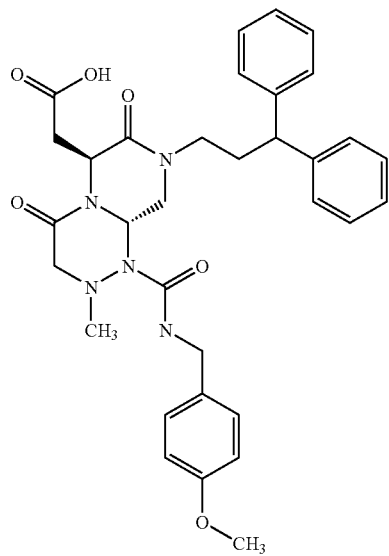 | 600 | 601 |
| 2899 | 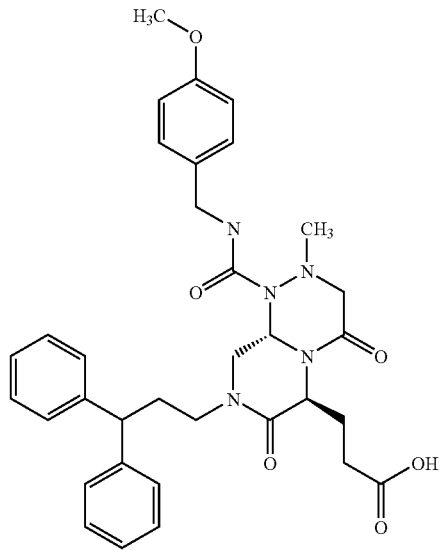 | 614 | 615 |

TABLE 2B-continued
THE [4,4,0]REVERSE TURN MIMETICS LIBRARY
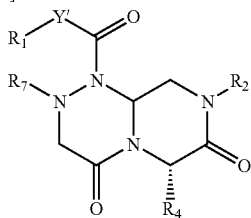
| No | MOLSTRUCTURE | Mol. Weight | M + H (MS) |
|---|---|---|---|
| 2900 | | 618 | 619 |
| 2901 | | 683 | 684 |

TABLE 2B-continued
THE [4,4,0]REVERSE TURN MIMETICS LIBRARY
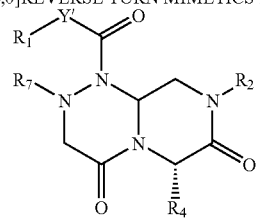
| No | MOLSTRUCTURE | Mol. Weight | M + H (MS) |
|---|---|---|---|
| 2902 | | 622 | 623 |
| 2903 | Chiral | 585 | 586 |
| 2904 | Chiral | 619 | 620 |

TABLE 2B-continued
THE [4,4,0]REVERSE TURN MIMETICS LIBRARY
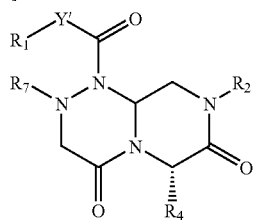
| No | MOLSTRUCTURE | Mol. Weight | M + H (MS) |
|---|---|---|---|
| 2905 | Chiral | 619 | 620 |
| 2906 | Chiral | 585 | 586 |

TABLE 2B-continued
THE [4,4,0]REVERSE TURN MIMETICS LIBRARY
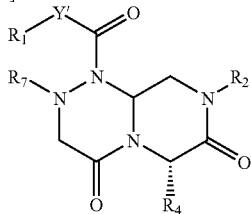
| No | MOLSTRUCTURE | Mol. Weight | M + H (MS) |
|---|---|---|---|
| 2907 | Chiral | 568 | 569 |
| 2908 | Chiral | 583 | 584 |
| 2909 | Chiral | 568 | 569 |

TABLE 2B-continued
THE [4,4,0]REVERSE TURN MIMETICS LIBRARY
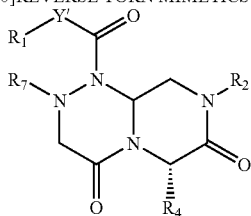
| No | MOLSTRUCTURE | Mol. Weight | M + H (MS) |
|---|---|---|---|
| 2910 | Chiral | 462 | 463 |
| 2911 | Chiral | 589 | 590 |
| 2912 | Chiral | 589 | 590 |

TABLE 2B-continued
THE [4,4,0]REVERSE TURN MIMETICS LIBRARY
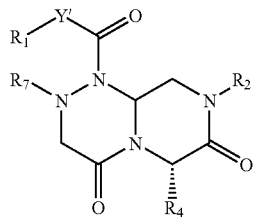
| No | MOLSTRUCTURE | | Mol. Weight | M + H (MS) |
|---|---|---|---|---|
| 2913 | 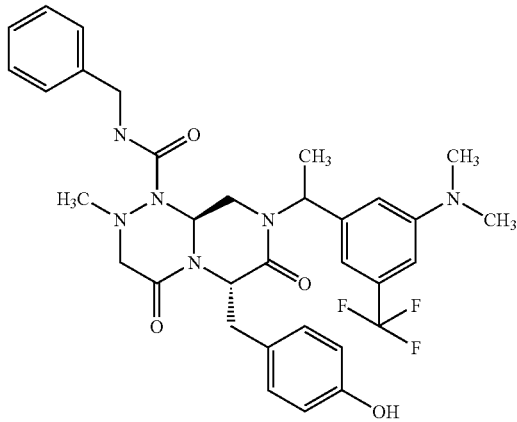 | Chiral | 639 | 640 |
| 2914 | 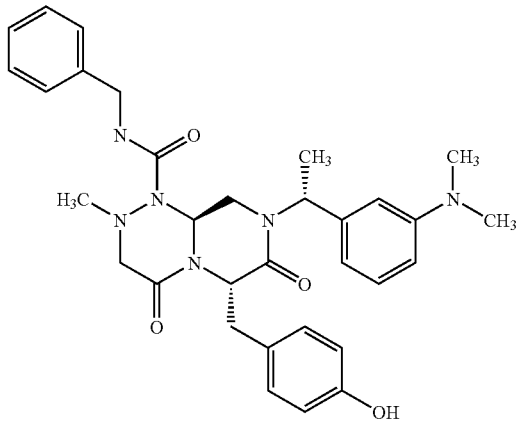 | Chiral | 571 | 572 |

TABLE 2B-continued
THE [4,4,0]REVERSE TURN MIMETICS LIBRARY
| No | MOLSTRUCTURE | Mol. Weight | M + H (MS) |
|---|---|---|---|
| 2915 | Chiral 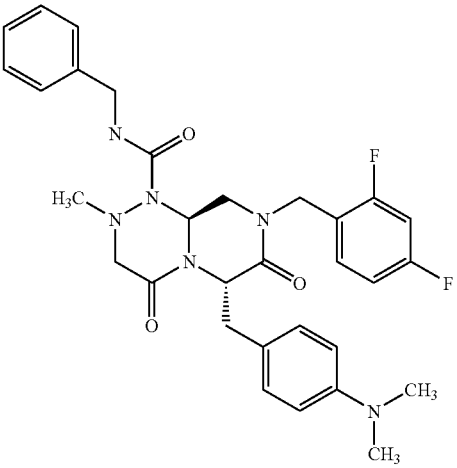 | 577 | 578 |
| 2916 | Chiral 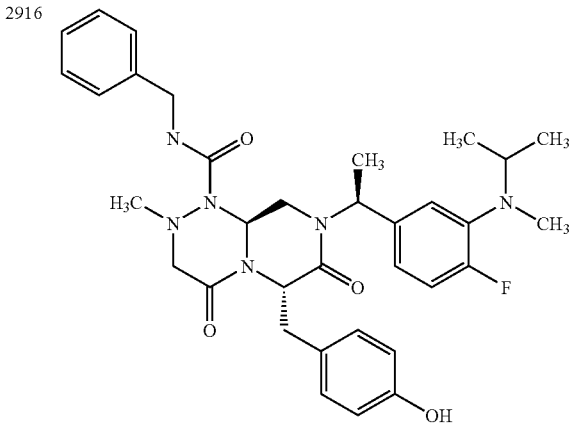 | 617 | 618 |
| 2917 | Chiral 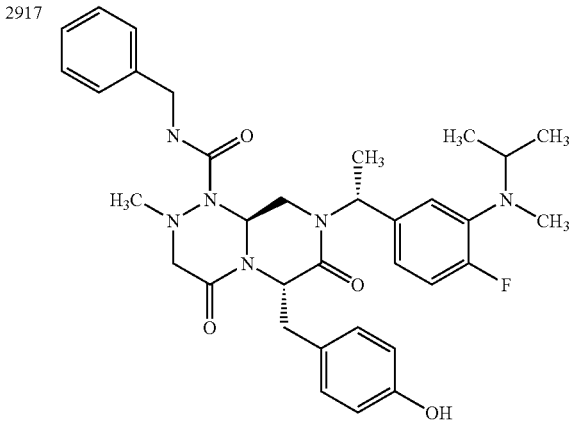 | 617 | 618 |

TABLE 2B-continued

THE [4,4,0]REVERSE TURN MIMETICS LIBRARY

| No | MOLSTRUCTURE | Mol. Weight | M + H (MS) |
|---|---|---|---|
| 2918 | Chiral | 583 | 584 |
| 2919 | Chiral | 617 | 618 |
| 2920 | Chiral | 617 | 618 |

TABLE 2B-continued

THE [4,4,0]REVERSE TURN MIMETICS LIBRARY

| No | MOLSTRUCTURE | Mol. Weight | M + H (MS) |
|----|--------------|-------------|------------|
| 2921 | | 617 | 618 |
| 2922 | | 599 | 600 |
| 2923 | | 599 | 600 |

TABLE 2B-continued
THE [4,4,0]REVERSE TURN MIMETICS LIBRARY
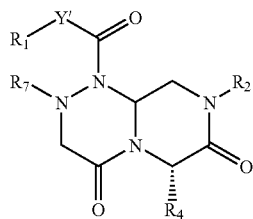
| No | MOLSTRUCTURE | Mol. Weight | M + H (MS) |
|---|---|---|---|
| 2924 | Chiral | 639 | 640 |
| 2925 | Chiral | 591 | 592 |

TABLE 2B-continued
THE [4,4,0]REVERSE TURN MIMETICS LIBRARY
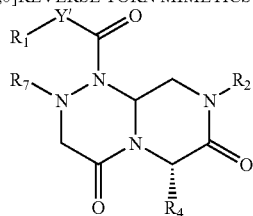
| No | MOLSTRUCTURE | Mol. Weight | M + H (MS) |
|---|---|---|---|
| 2926 | | 591 | 592 |
| 2927 | Chiral | 564 | 565 |
| 2928 | Chiral | 554 | 555 |

TABLE 2B-continued
THE [4,4,0]REVERSE TURN MIMETICS LIBRARY
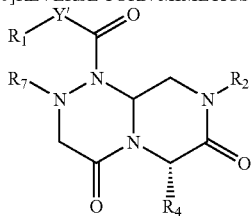
| No | MOLSTRUCTURE | Mol. Weight | M + H (MS) |
|---|---|---|---|
| 2929 | Chiral | 597 | 598 |
| 2930 | Chiral | 659 | 660 |
| 2931 | Chiral | 599 | 600 |

TABLE 2B-continued
THE [4,4,0]REVERSE TURN MIMETICS LIBRARY
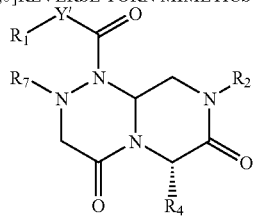
| No | MOLSTRUCTURE | Mol. Weight | M + H (MS) |
|---|---|---|---|
| 2932 | Chiral | 599 | 600 |
| 2933 | Chiral | 689 | 690 |
| 2934 | Chiral | 569 | 570 |

TABLE 2B-continued

THE [4,4,0]REVERSE TURN MIMETICS LIBRARY

| No | MOLSTRUCTURE | | Mol. Weight | M + H (MS) |
|---|---|---|---|---|
| 2935 | | Chiral | 569 | 570 |
| 2936 | | Chiral | 571 | 572 |
| 2937 | | Chiral | 571 | 572 |

TABLE 2B-continued
THE [4,4,0]REVERSE TURN MIMETICS LIBRARY
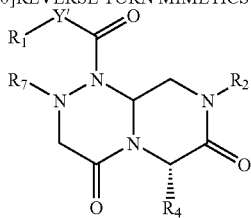
| No | MOLSTRUCTURE | | Mol. Weight | M + H (MS) |
|---|---|---|---|---|
| 2938 | | Chiral | 633 | 634 |
| 2939 | | Chiral | 564 | 565 |
| 2940 | | Chiral | 571 | 572 |

TABLE 2B-continued
THE [4,4,0]REVERSE TURN MIMETICS LIBRARY
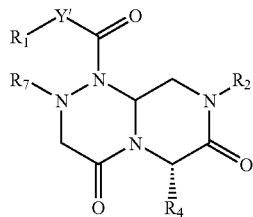
| No | MOLSTRUCTURE | | Mol. Weight | M + H (MS) |
|---|---|---|---|---|
| 2941 | 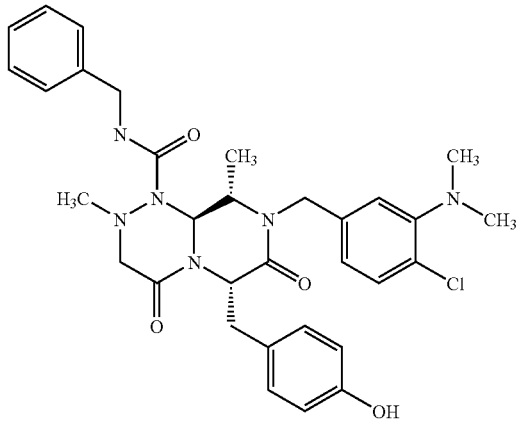 | Chiral | 605 | 606 |
| 2942 | 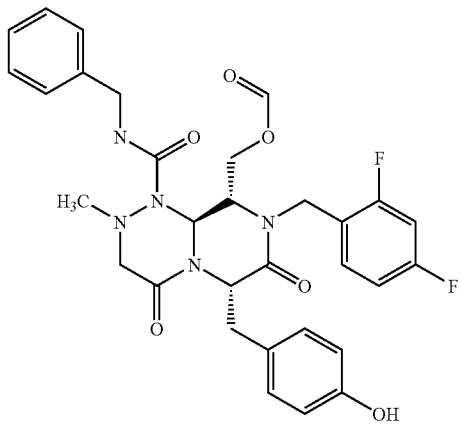 | Chiral | 608 | 609 |

TABLE 2B-continued
THE [4,4,0]REVERSE TURN MIMETICS LIBRARY
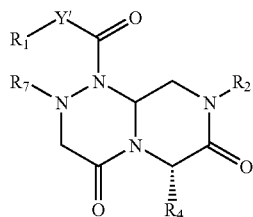
| No | MOLSTRUCTURE | | Mol. Weight | M + H (MS) |
|---|---|---|---|---|
| 2943 | | Chiral | 580 | 581 |
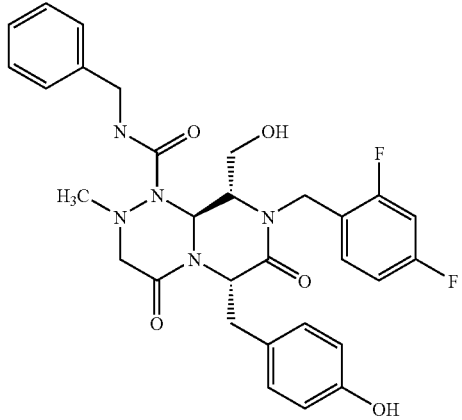
| 2944 | | Chiral | 605 | 606 |
|---|---|---|---|---|
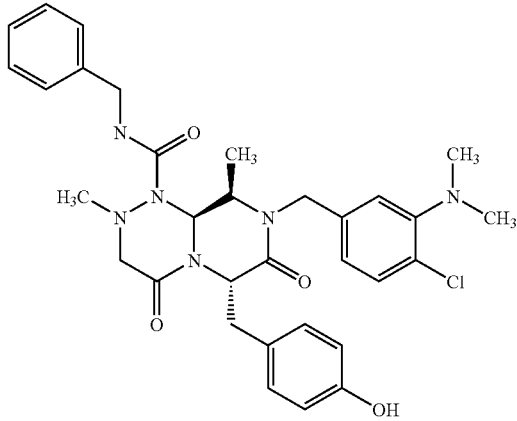

TABLE 2B-continued
THE [4,4,0]REVERSE TURN MIMETICS LIBRARY
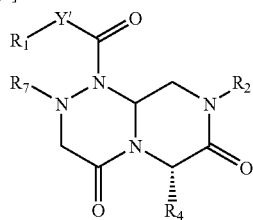
| No | MOLSTRUCTURE | | Mol. Weight | M + H (MS) |
|---|---|---|---|---|
| 2945 | 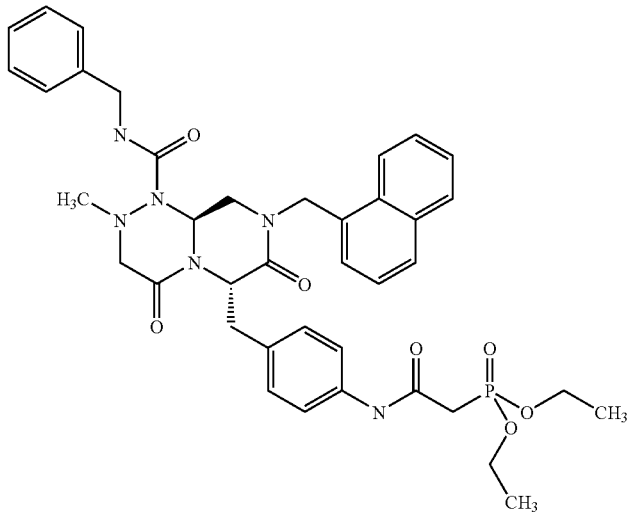 | Chiral | 741 | 742 |
| 2946 | 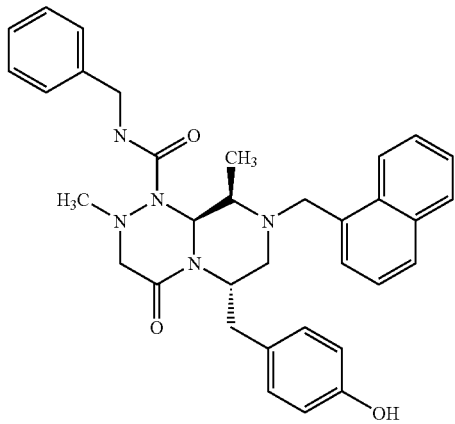 | Chiral | 550 | 551 |

TABLE 2B-continued
THE [4,4,0]REVERSE TURN MIMETICS LIBRARY
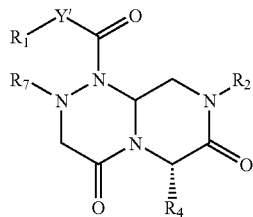
| No | MOLSTRUCTURE | | Mol. Weight | M + H (MS) |
|---|---|---|---|---|
| 2947 | 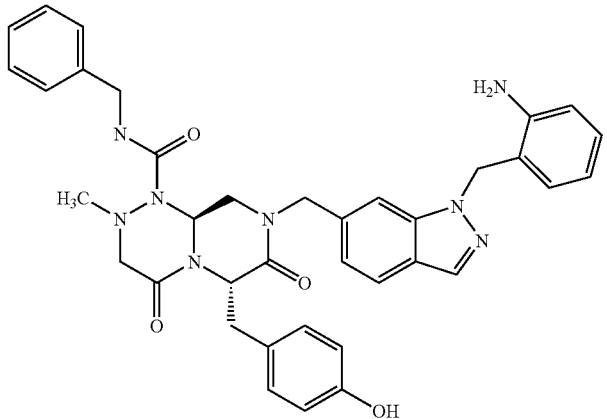 | Chiral | 659 | 660 |
| 2948 | 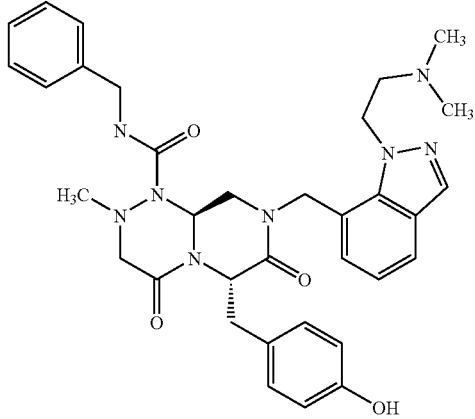 | Chiral | 625 | 626 |

TABLE 2B-continued
THE [4,4,0]REVERSE TURN MIMETICS LIBRARY
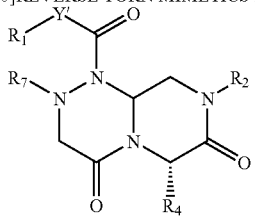
| No | MOLSTRUCTURE | Mol. Weight | M + H (MS) |
|---|---|---|---|
| 2949 | Chiral | 659 | 660 |
| 2950 | Chiral | 554 | 555 |
| 2951 | Chiral | 648 | 649 |

TABLE 2B-continued
THE [4,4,0]REVERSE TURN MIMETICS LIBRARY
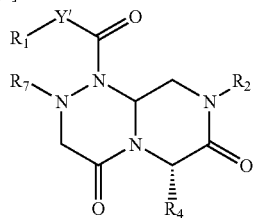
| No | MOLSTRUCTURE | | Mol. Weight | M + H (MS) |
|---|---|---|---|---|
| 2952 | 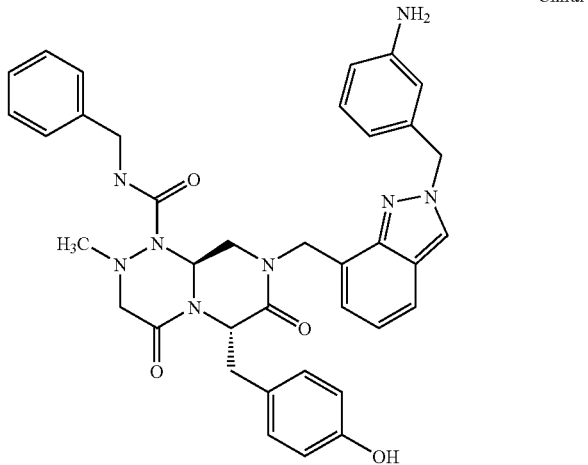 | Chiral | 659 | 660 |
| 2953 | 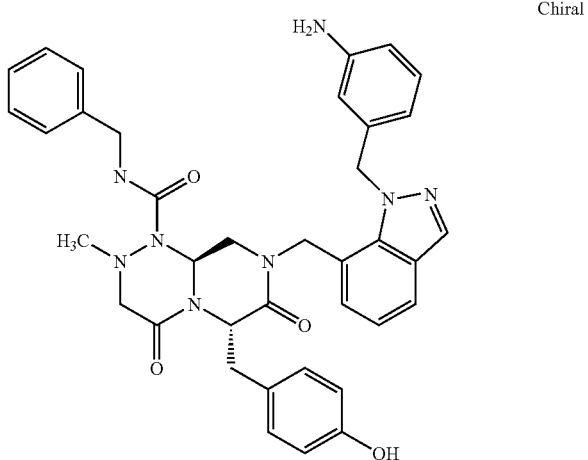 | Chiral | 659 | 660 |

TABLE 2B-continued
THE [4,4,0]REVERSE TURN MIMETICS LIBRARY
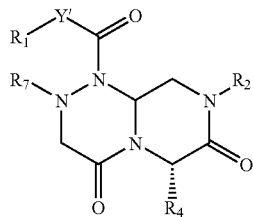
| No | MOLSTRUCTURE | | Mol. Weight | M + H (MS) |
|---|---|---|---|---|
| 2954 | 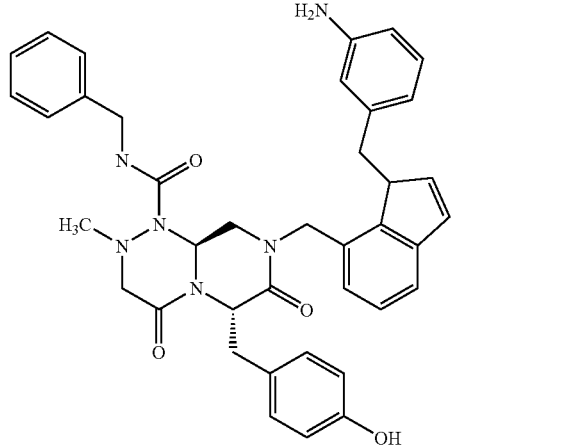 | Chiral | 659 | 660 |
| 2955 | 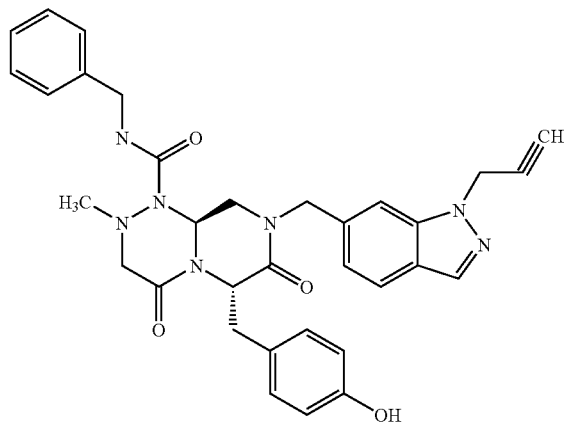 | Chiral | 592 | 593 |

TABLE 2B-continued
THE [4,4,0]REVERSE TURN MIMETICS LIBRARY
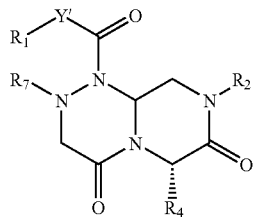
| No | MOLSTRUCTURE | | Mol. Weight | M + H (MS) |
|---|---|---|---|---|
| 2956 | 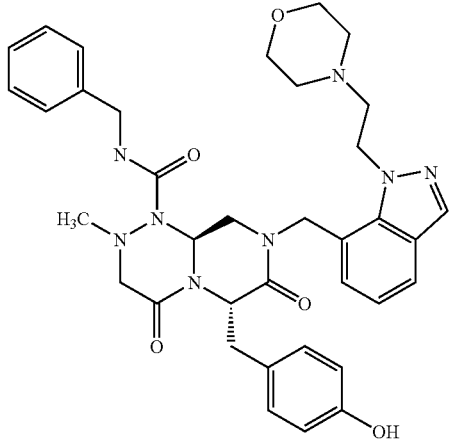 | Chiral | 667 | 668 |
| 2957 | 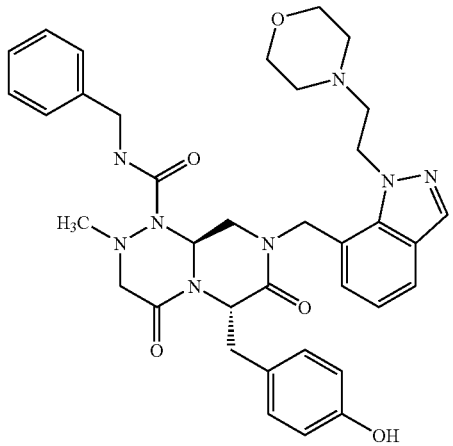 | Chiral | 667 | 668 |

TABLE 2B-continued
THE [4,4,0]REVERSE TURN MIMETICS LIBRARY
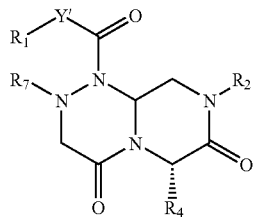
| No | MOLSTRUCTURE | Mol. Weight | M + H (MS) |
|----|---|---|---|
| 2958 | Chiral 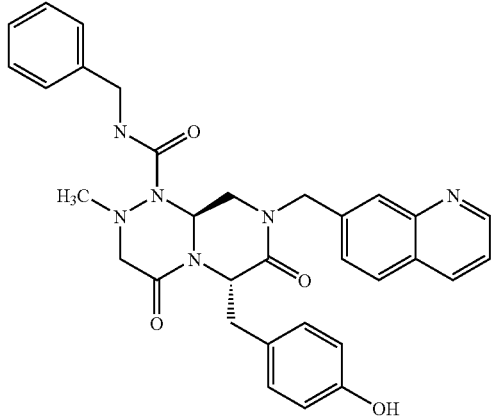 | 565 | 566 |
| 2959 | Chiral 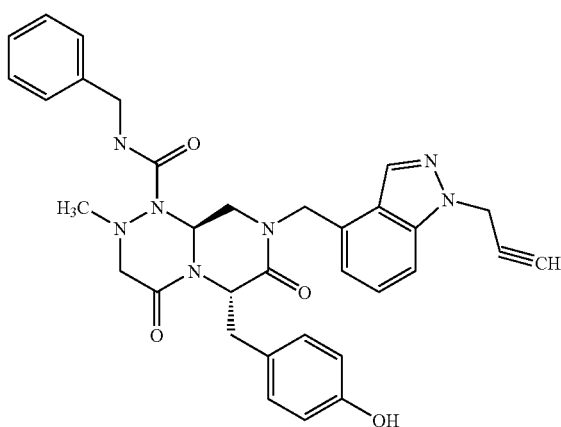 | 592 | 593 |

TABLE 2B-continued
THE [4,4,0]REVERSE TURN MIMETICS LIBRARY
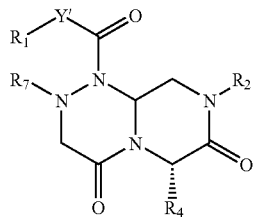
| No | MOLSTRUCTURE | Mol. Weight | M + H (MS) |
|---|---|---|---|
| 2960 | Chiral 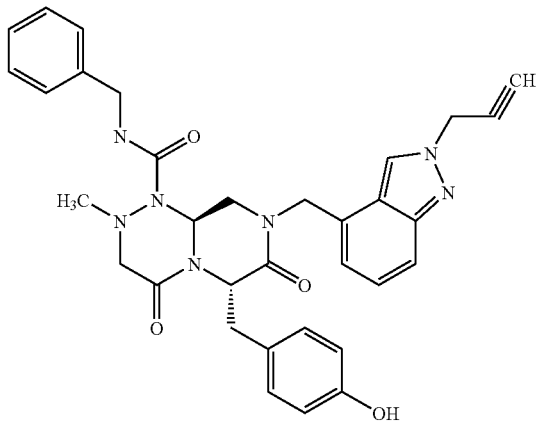 | 592 | 593 |
| 2961 | Chiral 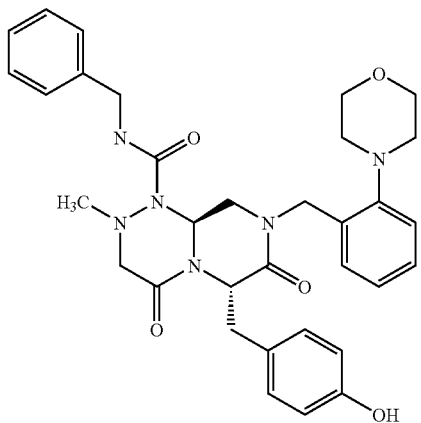 | 599 | 600 |

TABLE 2B-continued
THE [4,4,0]REVERSE TURN MIMETICS LIBRARY
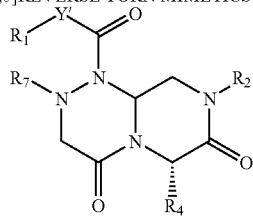
| No | MOLSTRUCTURE | | Mol. Weight | M + H (MS) |
|---|---|---|---|---|
| 2962 | | Chiral | 667 | 668 |
| 2963 | | Chiral | 702 | 703 |
| 2964 | | Chiral | 688 | 689 |

TABLE 2B-continued
THE [4,4,0]REVERSE TURN MIMETICS LIBRARY
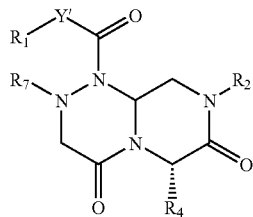
| No | MOLSTRUCTURE | | Mol. Weight | M + H (MS) |
|---|---|---|---|---|
| 2965 | 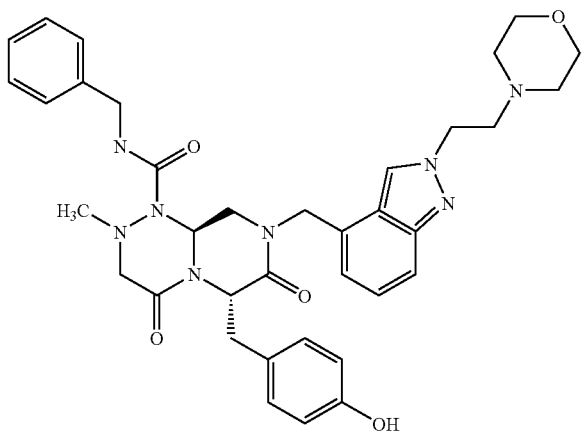 | Chiral | 667 | 668 |
| 2966 | 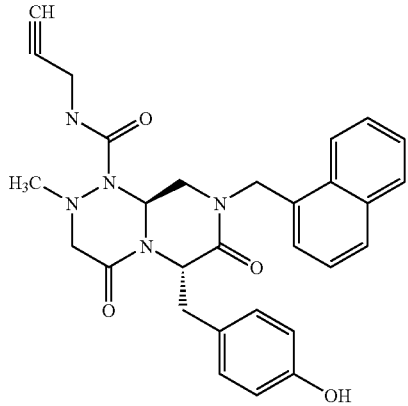 | Chiral | 512 | 513 |

TABLE 2B-continued
THE [4,4,0]REVERSE TURN MIMETICS LIBRARY
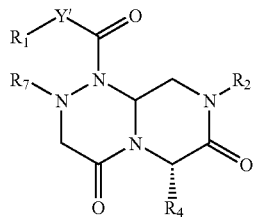
| No | MOLSTRUCTURE | | Mol. Weight | M + H (MS) |
|---|---|---|---|---|
| 2967 | 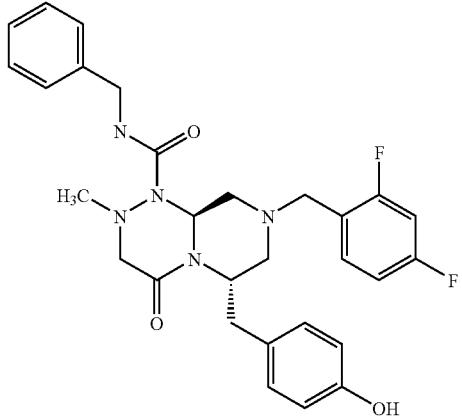 | Chiral | 536 | 537 |
| 2968 | 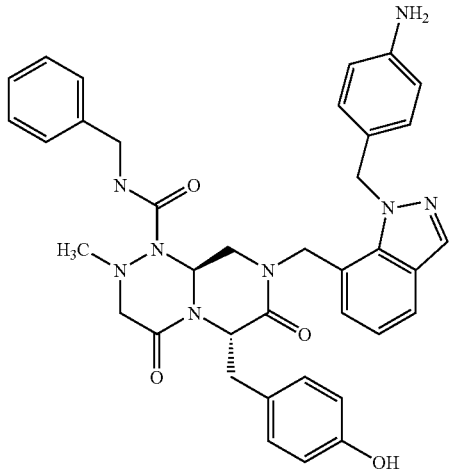 | Chiral | 659 | 660 |

TABLE 2B-continued
THE [4,4,0]REVERSE TURN MIMETICS LIBRARY
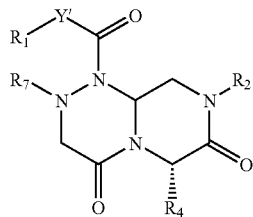
| No | MOLSTRUCTURE | | Mol. Weight | M + H (MS) |
|---|---|---|---|---|
| 2969 | 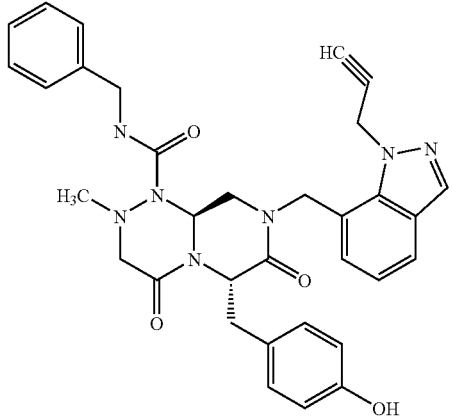 | Chiral | 592 | 593 |
| 2970 | 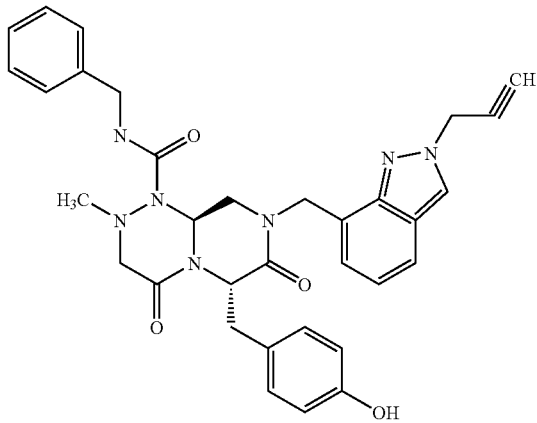 | Chiral | 592 | 593 |

TABLE 2B-continued
THE [4,4,0]REVERSE TURN MIMETICS LIBRARY
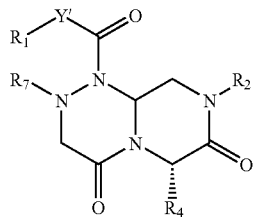
| No | MOLSTRUCTURE | Mol. Weight | M + H (MS) |
|---|---|---|---|
| 2971 | 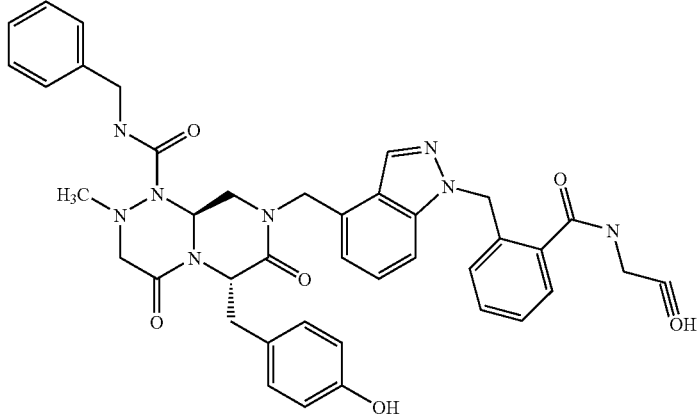 | Chiral 725 | 726 |
| 2972 | 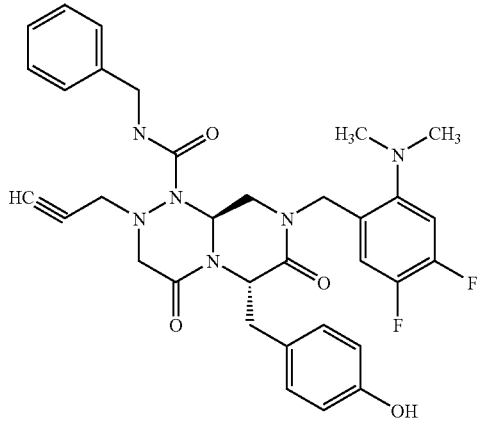 | Chiral 617 | 618 |

TABLE 2B-continued
THE [4,4,0]REVERSE TURN MIMETICS LIBRARY
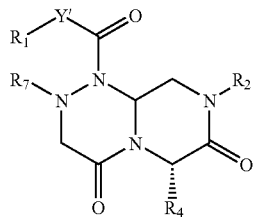
| No | MOLSTRUCTURE | | Mol. Weight | M + H (MS) |
|---|---|---|---|---|
| 2973 | | Chiral | 615 | 616 |
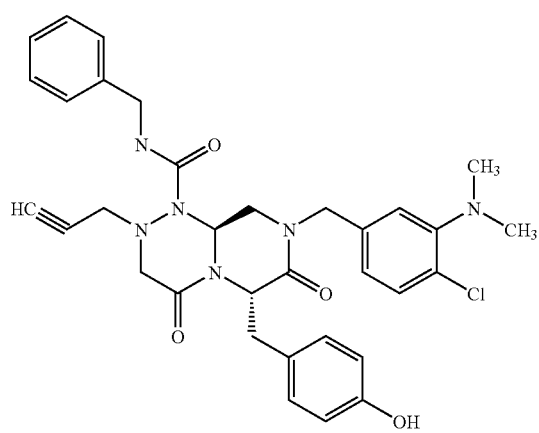
| 2974 | | Chiral | 588 | 589 |
|---|---|---|---|---|
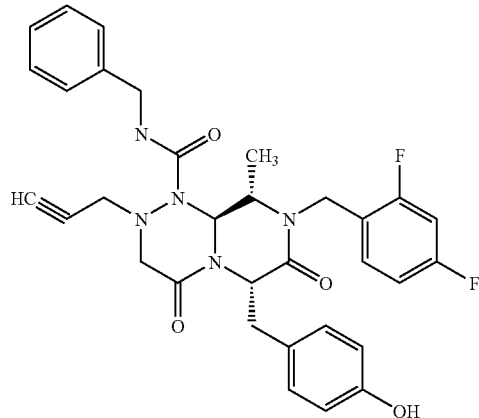

TABLE 2B-continued
THE [4,4,0]REVERSE TURN MIMETICS LIBRARY
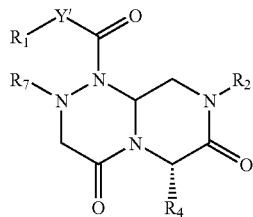
| No | MOLSTRUCTURE | | Mol. Weight | M + H (MS) |
|---|---|---|---|---|
| 2975 | 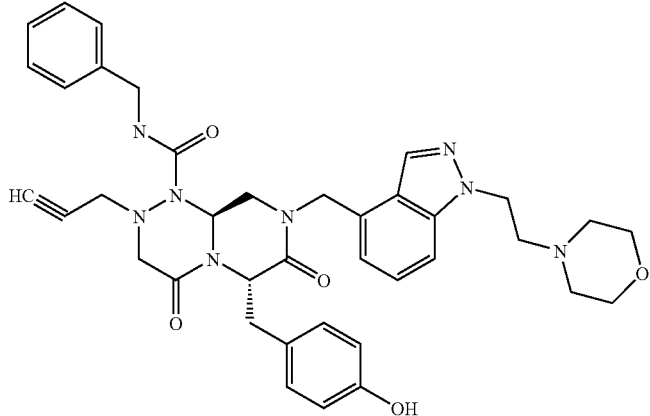 | Chiral | 691 | 692 |
| 2976 | 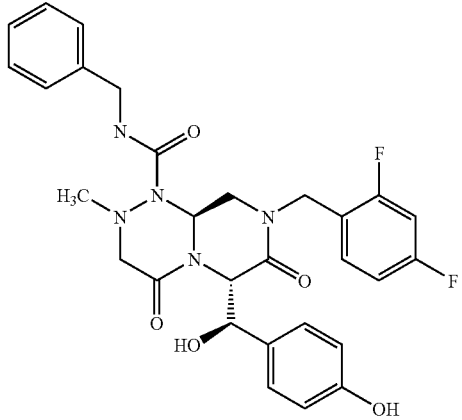 | Chiral | 566 | 567 |

TABLE 2B-continued
THE [4,4,0]REVERSE TURN MIMETICS LIBRARY
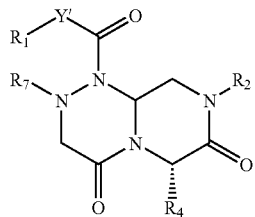
| No | MOLSTRUCTURE | | Mol. Weight | M + H (MS) |
|----|--------------|--|-------------|------------|
| 2977 | 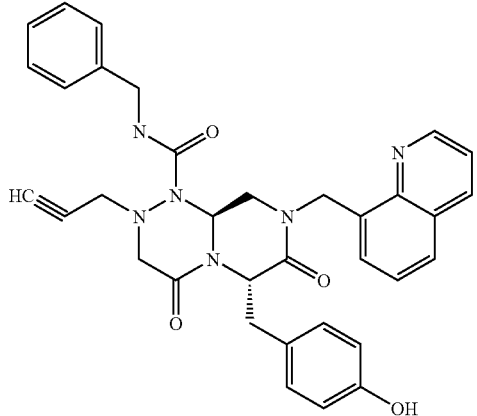 | Chiral | 589 | 590 |
| 2978 | 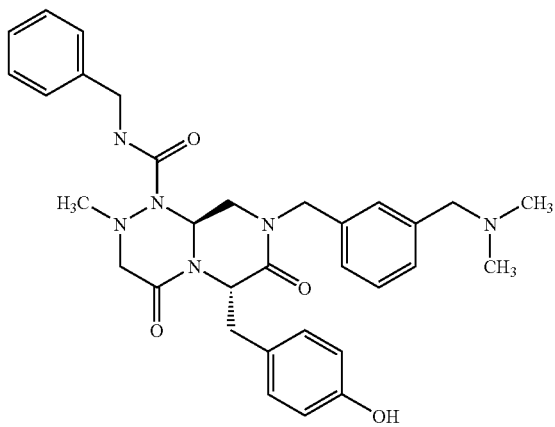 | Chiral | 571 | 572 |

TABLE 2B-continued
THE [4,4,0]REVERSE TURN MIMETICS LIBRARY
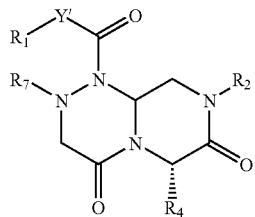
| No | MOLSTRUCTURE | | Mol. Weight | M + H (MS) |
|----|---|---|---|---|
| 2979 | | Chiral | 501 | 502 |
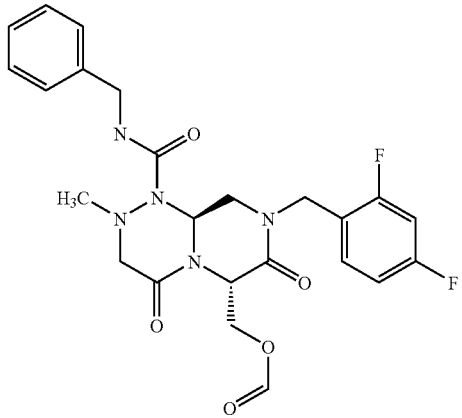
| 2980 | | Chiral | 599 | 600 |
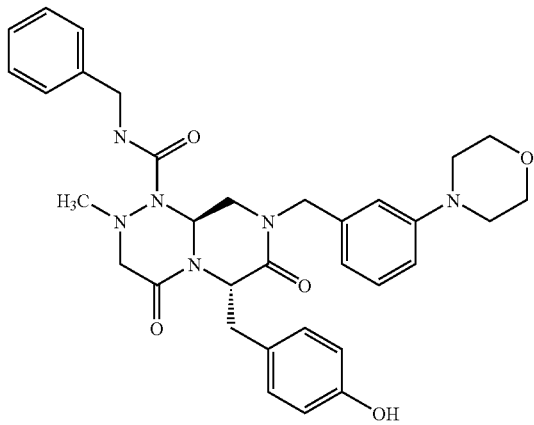

TABLE 2B-continued
THE [4,4,0]REVERSE TURN MIMETICS LIBRARY
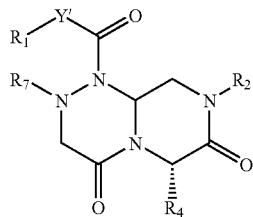
| No | MOLSTRUCTURE | Mol. Weight | M + H (MS) |
|----|--------------|-------------|------------|
| 2981 | Chiral 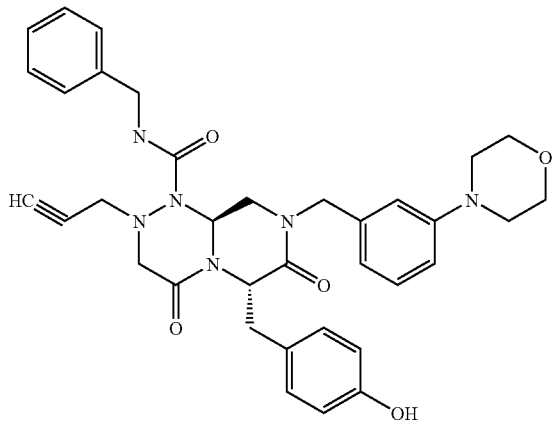 | 623 | 624 |
| 2982 | Chiral 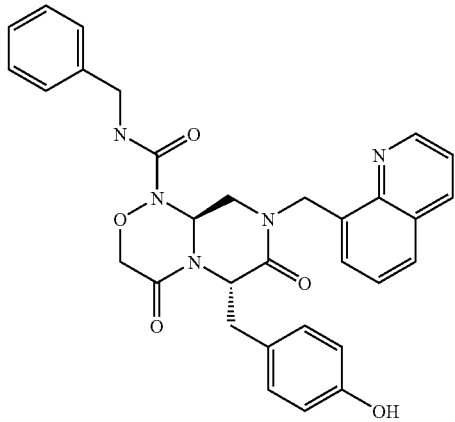 | 552 | 553 |

TABLE 2B-continued
THE [4,4,0]REVERSE TURN MIMETICS LIBRARY
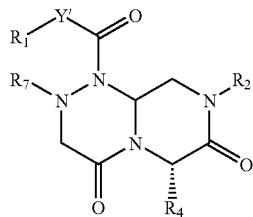
| No | MOLSTRUCTURE | | Mol. Weight | M + H (MS) |
|----|--------------|---|-------------|------------|
| 2983 | | Chiral | 641 | 642 |
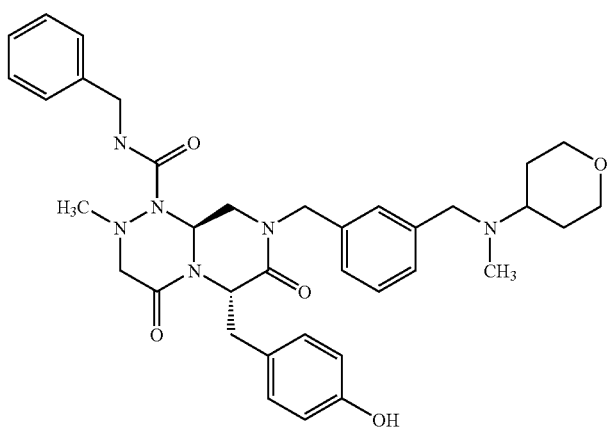
| 2984 | | Chiral | 579 | 580 |
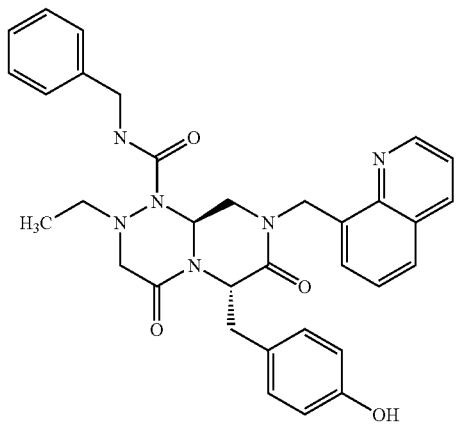

TABLE 2B-continued
THE [4,4,0]REVERSE TURN MIMETICS LIBRARY
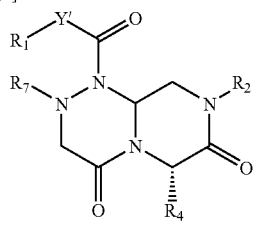
| No | MOLSTRUCTURE | Mol. Weight | M + H (MS) |
|---|---|---|---|
| 2985 | Chiral | 593 | 594 |
| 2986 | | 613 | 614 |
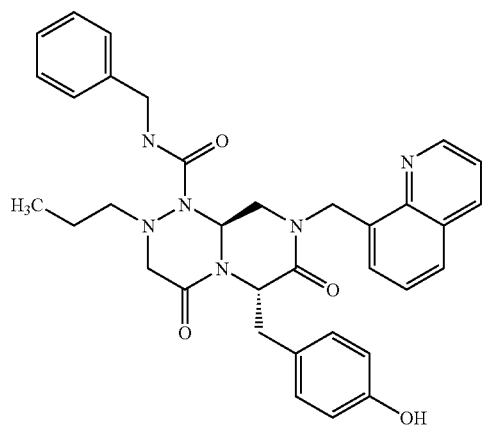

TABLE 2B-continued
THE [4,4,0]REVERSE TURN MIMETICS LIBRARY
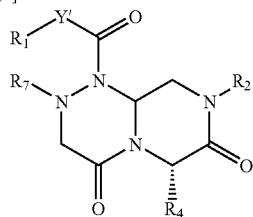
| No | MOLSTRUCTURE | Mol. Weight | M + H (MS) |
|----|--------------|-------------|------------|
| 2987 | | 627 | 628 |
| 2988 | | 605 | 606 |

TABLE 2B-continued
THE [4,4,0]REVERSE TURN MIMETICS LIBRARY
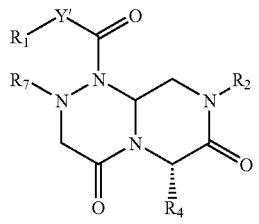
| No | MOLSTRUCTURE | Mol. Weight | M + H (MS) |
|---|---|---|---|
| 2989 | | 619 | 620 |
| 2990 | Chiral | 625 | 626 |
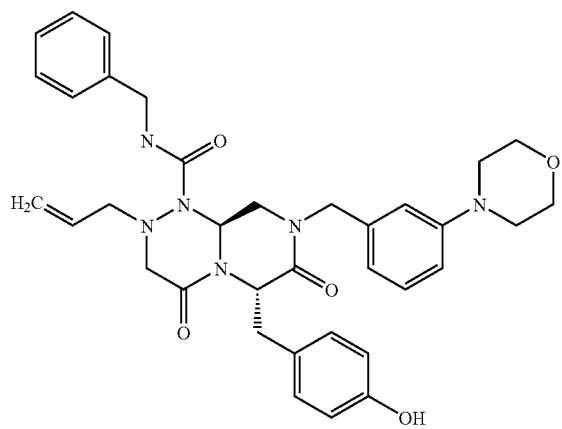

TABLE 2B-continued
THE [4,4,0]REVERSE TURN MIMETICS LIBRARY
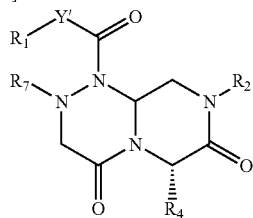
| No | MOLSTRUCTURE | Mol. Weight | M + H (MS) |
|---|---|---|---|
| 2991 | Chiral 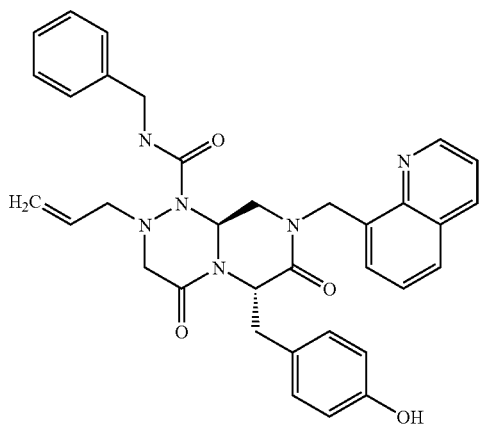 | 591 | 592 |
| 2992 | Chiral 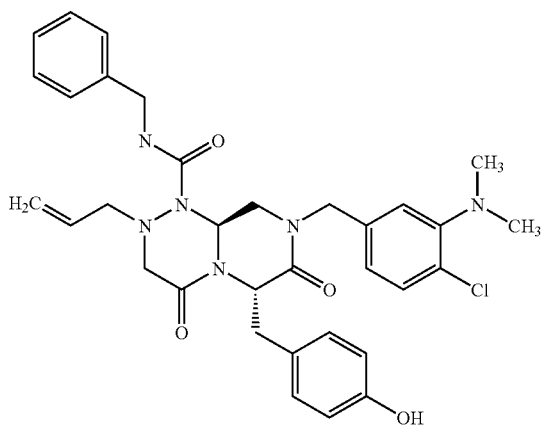 | 617 | 618 |

TABLE 2B-continued
THE [4,4,0]REVERSE TURN MIMETICS LIBRARY
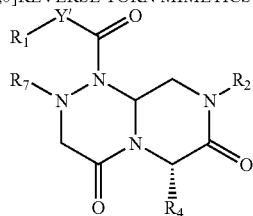
| No | MOLSTRUCTURE | | Mol. Weight | M + H (MS) |
|---|---|---|---|---|
| 2993 | | Chiral | 643 | 644 |
| 2994 | | Chiral | 667 | 668 |
| 2995 | | Chiral | 669 | 670 |

TABLE 2B-continued
THE [4,4,0]REVERSE TURN MIMETICS LIBRARY
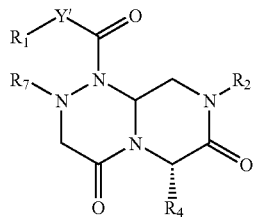
| No | MOLSTRUCTURE | | Mol. Weight | M + H (MS) |
|---|---|---|---|---|
| 2996 | 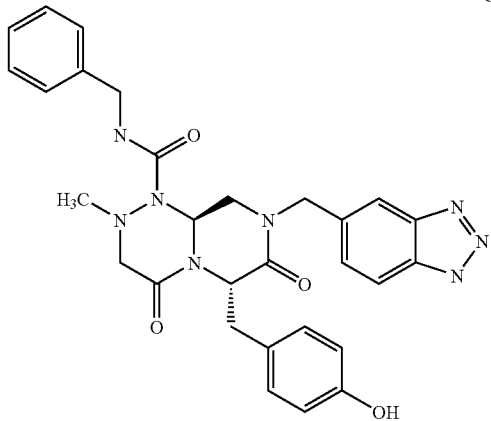 | Chiral | 555 | 556 |
| 2997 | 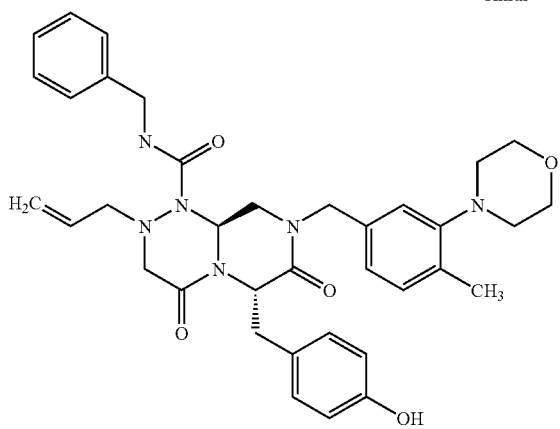 | Chiral | 639 | 640 |

TABLE 2B-continued
THE [4,4,0]REVERSE TURN MIMETICS LIBRARY
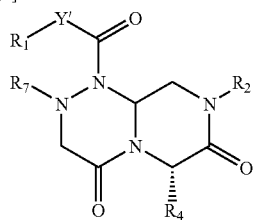
| No | MOLSTRUCTURE | Mol. Weight | M + H (MS) |
|---|---|---|---|
| 2998 | 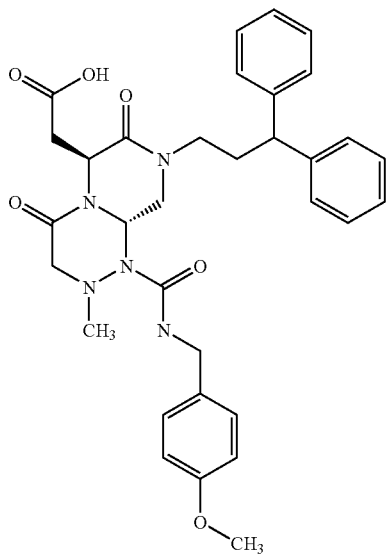 | 637 | 638 |
| 2999 | 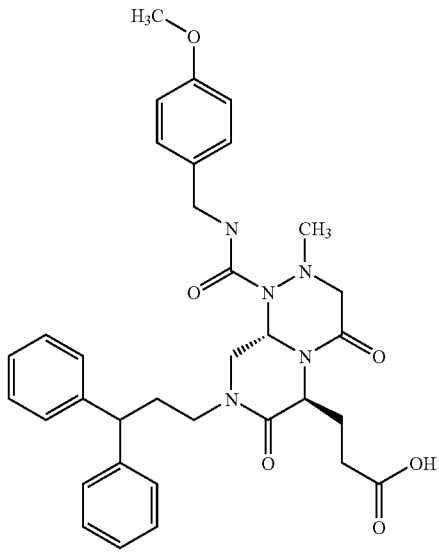 | 596 | 597 |

TABLE 2B-continued
THE [4,4,0]REVERSE TURN MIMETICS LIBRARY
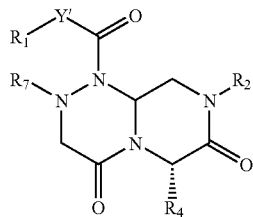
| No | MOLSTRUCTURE | Mol. Weight | M + H (MS) |
|---|---|---|---|
| 3000 | Chiral 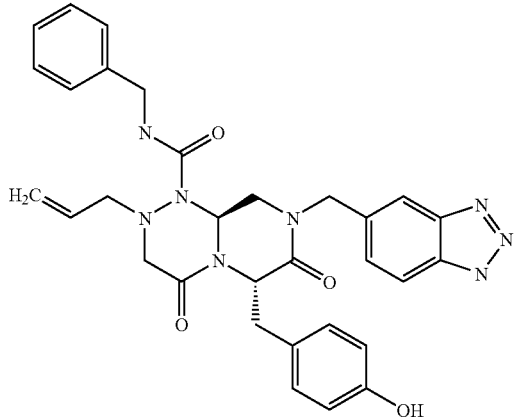 | 581 | 582 |
| 3001 | Chiral 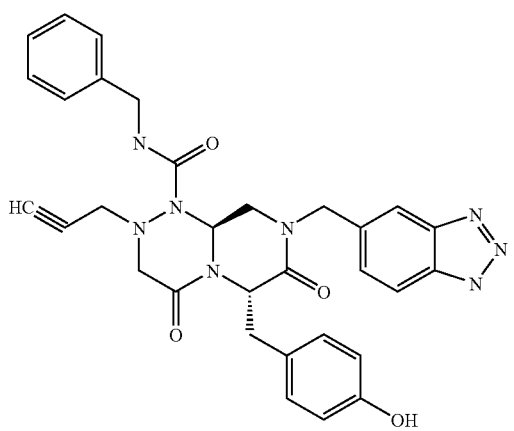 | 579 | 580 |

TABLE 2B-continued
THE [4,4,0]REVERSE TURN MIMETICS LIBRARY
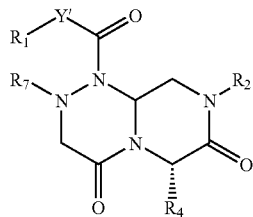
| No | MOLSTRUCTURE | Mol. Weight | M + H (MS) |
|---|---|---|---|
| 3002 | Chiral 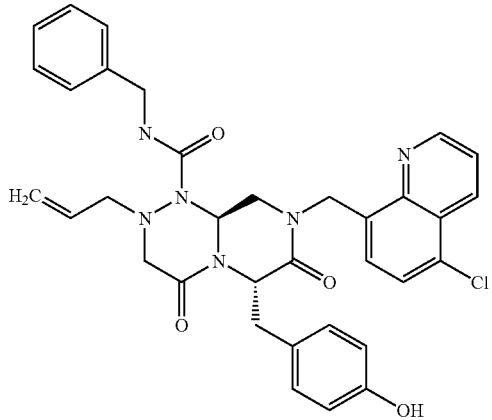 | 625 | 626 |
| 3003 | Chiral 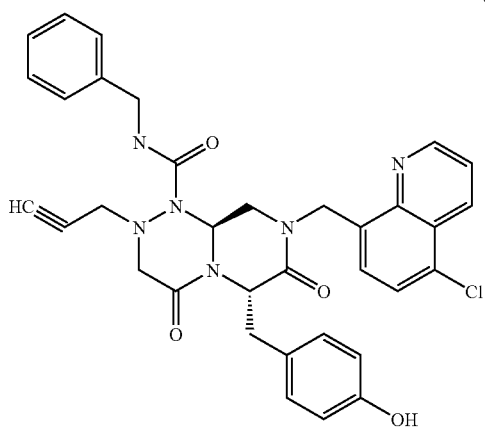 | 623 | 624 |

TABLE 2B-continued
THE [4,4,0]REVERSE TURN MIMETICS LIBRARY
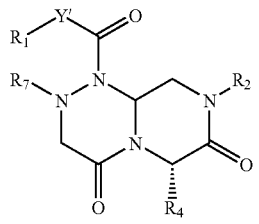
| No | MOLSTRUCTURE | Mol. Weight | M + H (MS) |
|----|--------------|-------------|------------|
| 3004 | Chiral 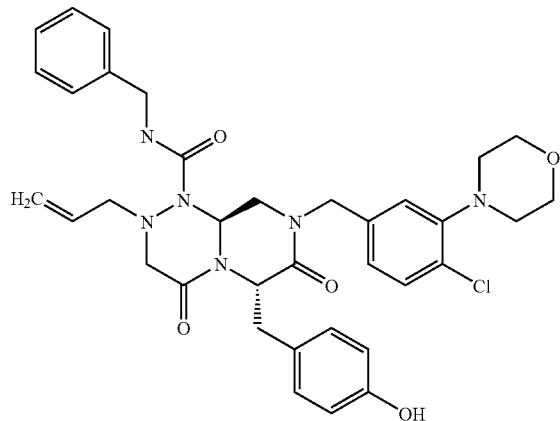 | 659 | 660 |
| 3005 | Chiral 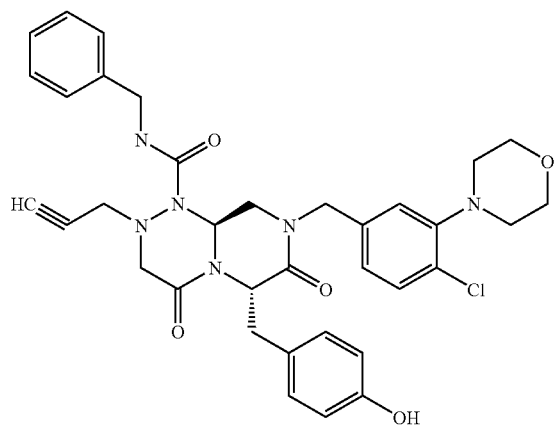 | 657 | 658 |

TABLE 2B-continued
THE [4,4,0]REVERSE TURN MIMETICS LIBRARY
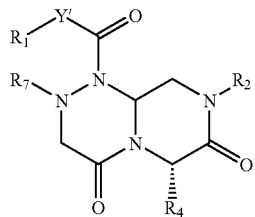
| No | MOLSTRUCTURE | Mol. Weight | M + H (MS) |
|---|---|---|---|
| 3006 | Chiral 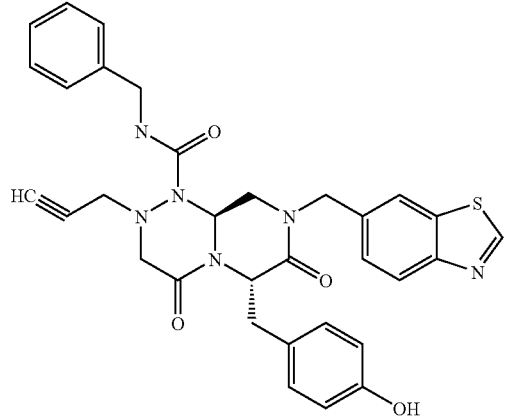 | 595 | 596 |
| 3007 | Chiral 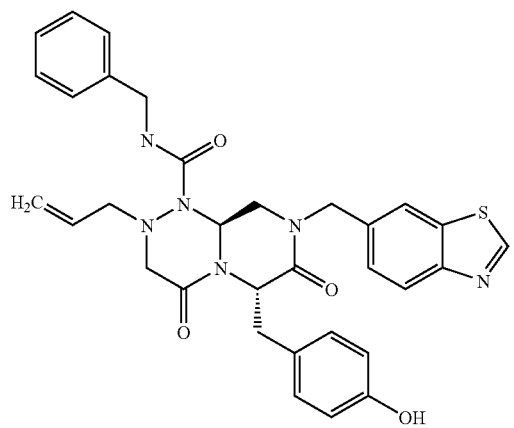 | 597 | 598 |

TABLE 2B-continued
THE [4,4,0]REVERSE TURN MIMETICS LIBRARY
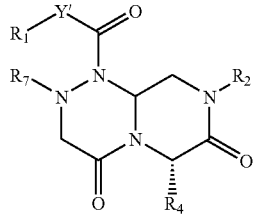
| No | MOLSTRUCTURE | Mol. Weight | M + H (MS) |
|---|---|---|---|
| 3008 | Chiral 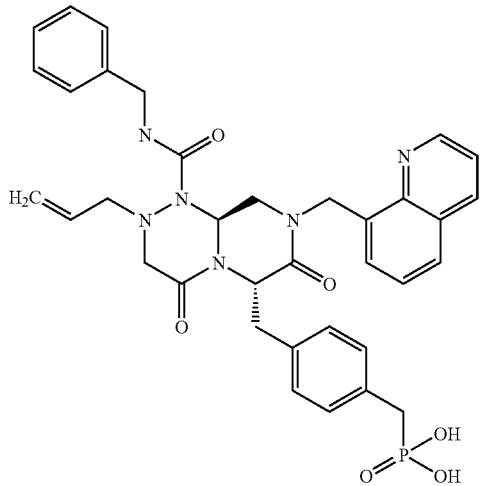 | 669 | 670 |
| 3009 | Chiral 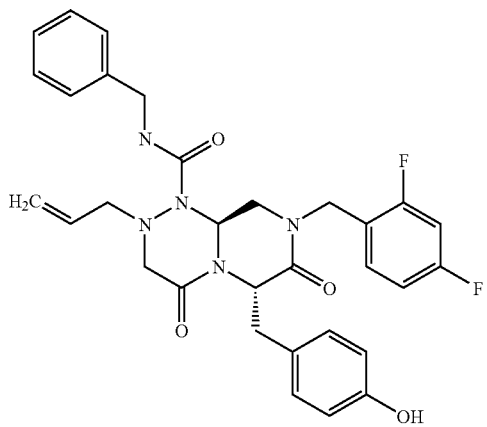 | 576 | 577 |

TABLE 2B-continued
THE [4,4,0]REVERSE TURN MIMETICS LIBRARY
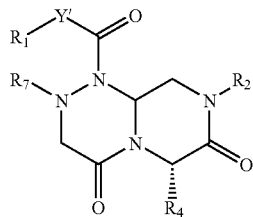
| No | MOLSTRUCTURE | Mol. Weight | M + H (MS) |
|----|--------------|-------------|------------|
| 3010 | Chiral 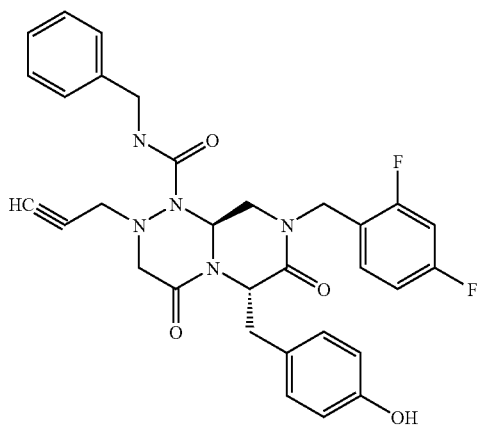 | 574 | 575 |
| 3011 | Chiral 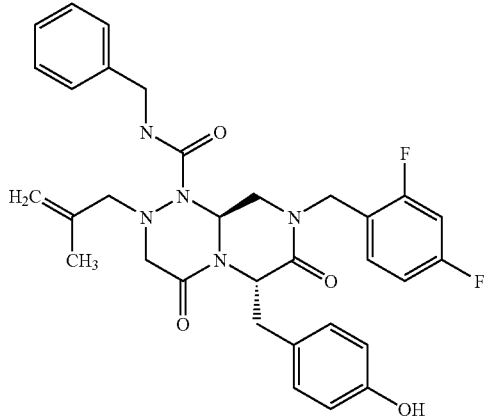 | 590 | 591 |

TABLE 2B-continued
THE [4,4,0]REVERSE TURN MIMETICS LIBRARY
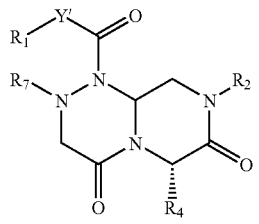
| No | MOLSTRUCTURE | Mol. Weight | M + H (MS) |
|----|--------------|-------------|------------|
| 3012 | Chiral 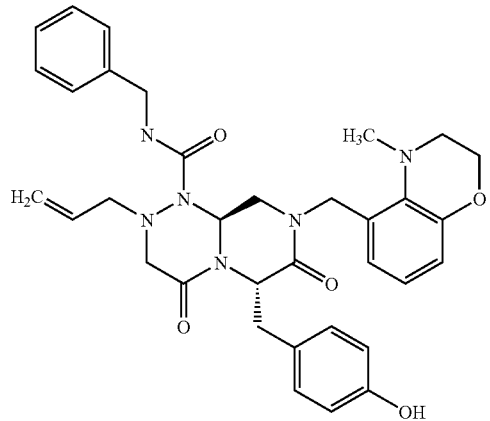 | 611 | 612 |
| 3013 | Chiral 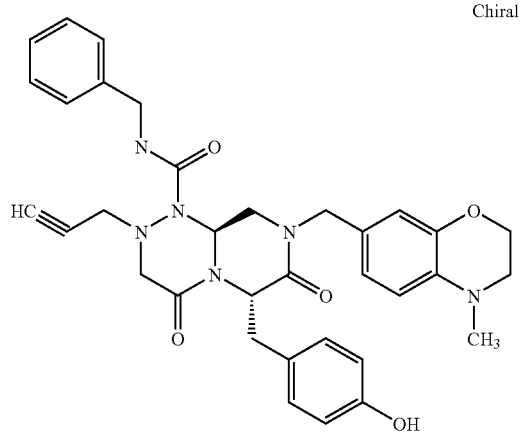 | 609 | 610 |

TABLE 2B-continued
THE [4,4,0]REVERSE TURN MIMETICS LIBRARY
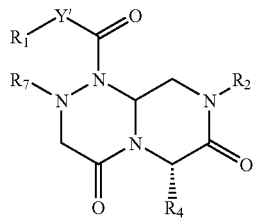
| No | MOLSTRUCTURE | | Mol. Weight | M + H (MS) |
|---|---|---|---|---|
| 3014 | 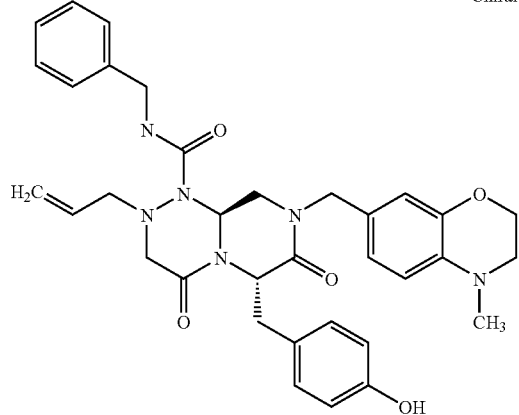 | Chiral | 611 | 612 |
| 3015 | 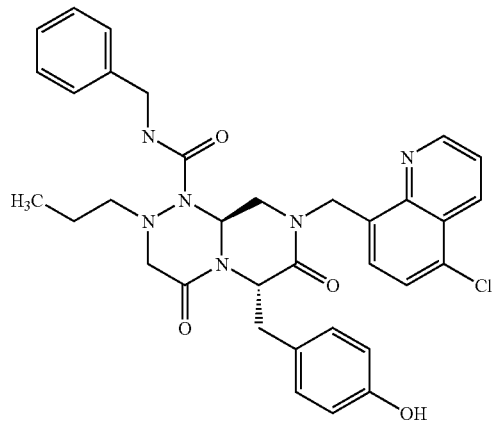 | Chiral | 627 | 628 |

TABLE 2B-continued
THE [4,4,0]REVERSE TURN MIMETICS LIBRARY
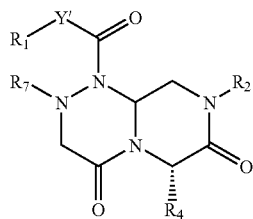
| No | MOLSTRUCTURE | Mol. Weight | M + H (MS) |
|----|--------------|-------------|------------|
| 3016 | Chiral 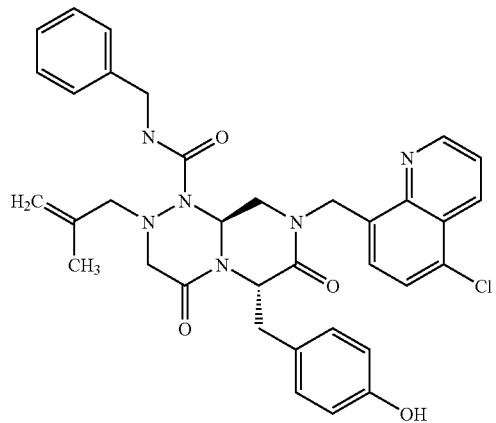 | 639 | 640 |
| 3017 | Chiral 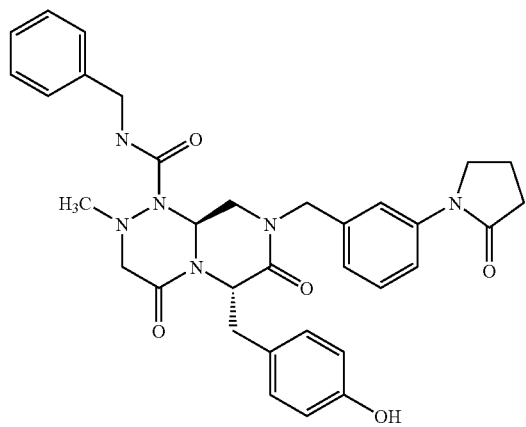 | 597 | 598 |

TABLE 2B-continued
THE [4,4,0]REVERSE TURN MIMETICS LIBRARY
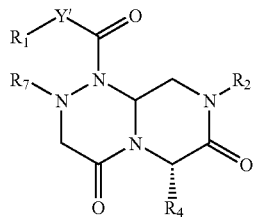
| No | MOLSTRUCTURE | Mol. Weight | M + H (MS) |
|---|---|---|---|
| 3018 | Chiral 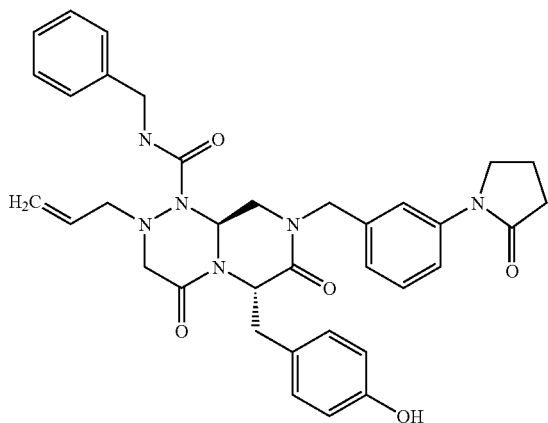 | 623 | 624 |
| 3019 | Chiral 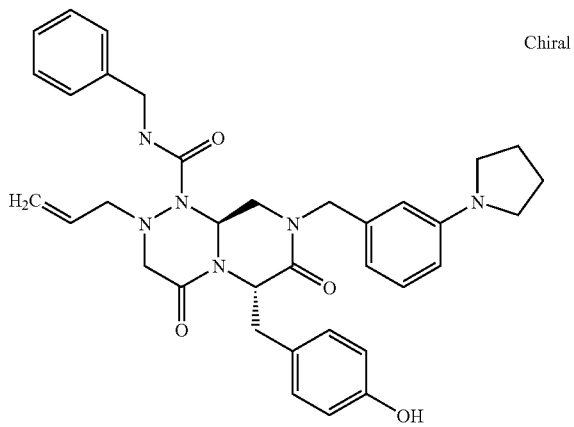 | 609 | 610 |

TABLE 2B-continued
THE [4,4,0]REVERSE TURN MIMETICS LIBRARY
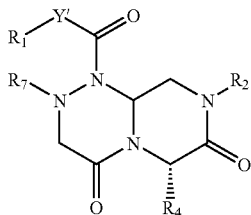
| No | MOLSTRUCTURE | Mol. Weight | M + H (MS) |
|----|--------------|-------------|------------|
| 3020 | Chiral | 681 | 682 |
| 3021 | Chiral | 679 | 680 |

TABLE 2B-continued
THE [4,4,0]REVERSE TURN MIMETICS LIBRARY
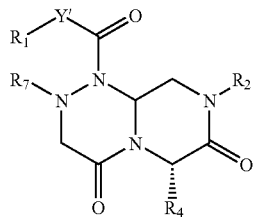
| No | MOLSTRUCTURE | Mol. Weight | M + H (MS) |
|----|--------------|-------------|------------|
| 3022 | Chiral 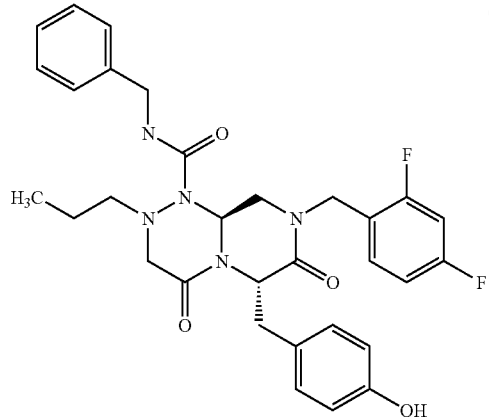 | 578 | 579 |
| 3023 | Chiral 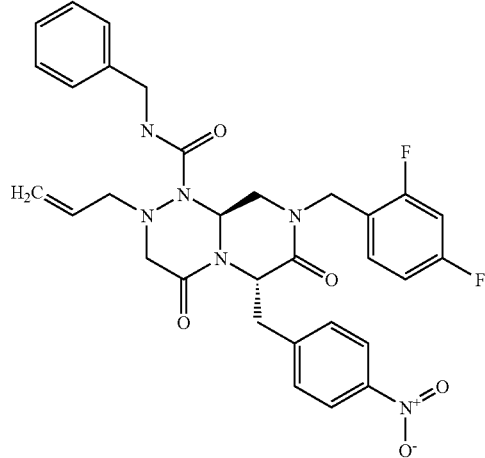 | 605 | 606 |

TABLE 2B-continued
THE [4,4,0]REVERSE TURN MIMETICS LIBRARY
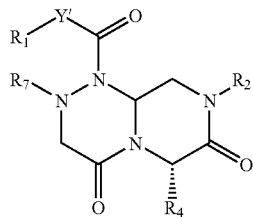
| No | MOLSTRUCTURE | Mol. Weight | M + H (MS) |
|---|---|---|---|
| 3024 | 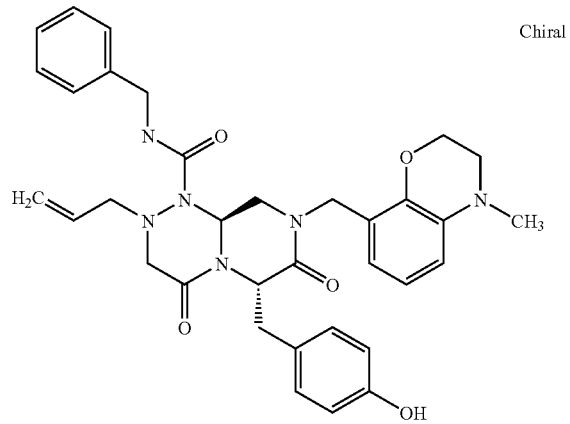 Chiral | 611 | 612 |
| 3025 | 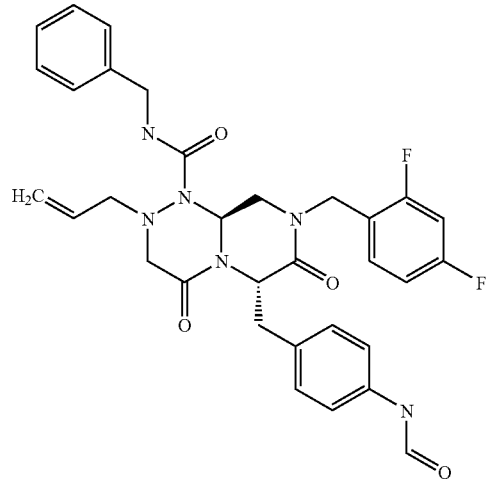 Chiral | 603 | 604 |

TABLE 2B-continued
THE [4,4,0]REVERSE TURN MIMETICS LIBRARY
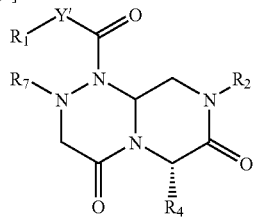
| No | MOLSTRUCTURE | Mol. Weight | M + H (MS) |
|----|--------------|-------------|------------|
| 3026 | Chiral | 605 | 606 |
| 3027 | | 589 | 590 |

TABLE 2B-continued
THE [4,4,0]REVERSE TURN MIMETICS LIBRARY
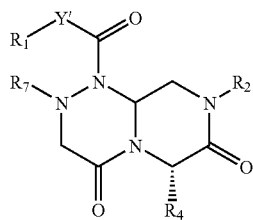
| No | MOLSTRUCTURE | Mol. Weight | M + H (MS) |
|---|---|---|---|
| 3028 | 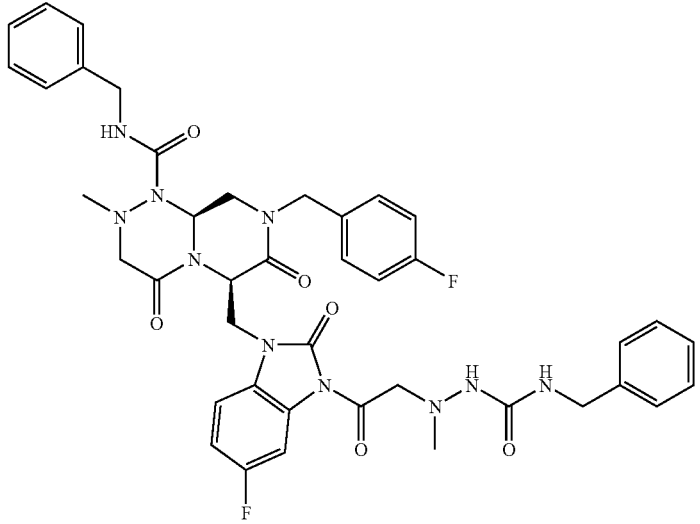 | 808 | 809 |
| 3029 | 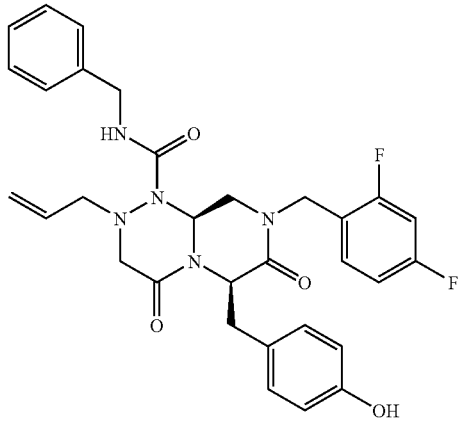 | 575 | 576 |

TABLE 2B-continued
THE [4,4,0]REVERSE TURN MIMETICS LIBRARY
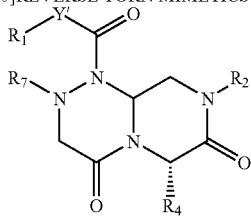
| No | MOLSTRUCTURE | Mol. Weight | M + H (MS) |
|---|---|---|---|
| 3030 | | 605 | 606 |
| 3031 | | 741 | 742 |
| 3032 | | 618 | 619 |

TABLE 2B-continued
THE [4,4,0]REVERSE TURN MIMETICS LIBRARY
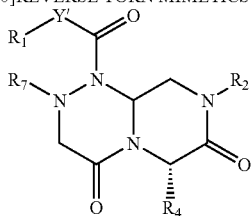
| No | MOLSTRUCTURE | Mol. Weight | M + H (MS) |
|---|---|---|---|
| 3033 | | 742 | 743 |
| 3034 | | 539 | 540 |
| 3035 | | 565 | 566 |

TABLE 2B-continued
THE [4,4,0]REVERSE TURN MIMETICS LIBRARY
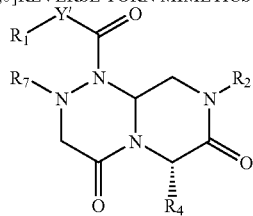
| No | MOLSTRUCTURE | Mol. Weight | M + H (MS) |
|---|---|---|---|
| 3036 | | 565 | 566 |
| 3037 | | 624 | 625 |
| 3038 | | 541 | 542 |

TABLE 2B-continued
THE [4,4,0]REVERSE TURN MIMETICS LIBRARY
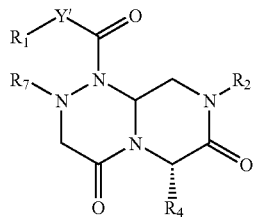
| No | MOLSTRUCTURE | Mol. Weight | M + H (MS) |
|---|---|---|---|
| 3039 | | 734 | 735 |
| 3040 | | 575 | 576 |

TABLE 2B-continued
THE [4,4,0]REVERSE TURN MIMETICS LIBRARY
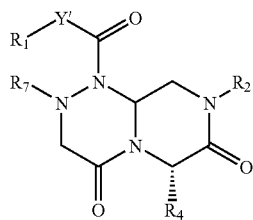
| No | MOLSTRUCTURE | Mol. Weight | M + H (MS) |
|----|--------------|-------------|------------|
| 3041 | 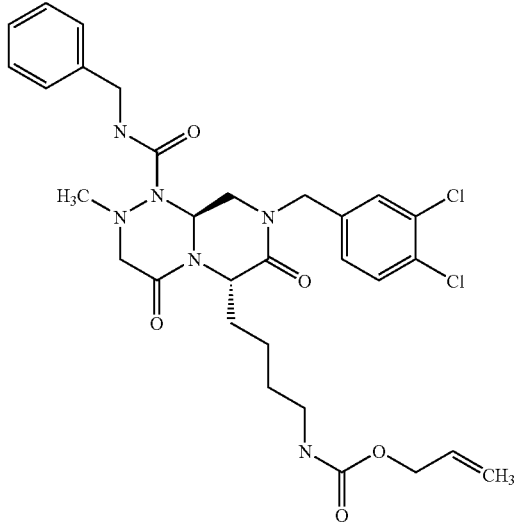 | 617 | 618 |
| 3042 | 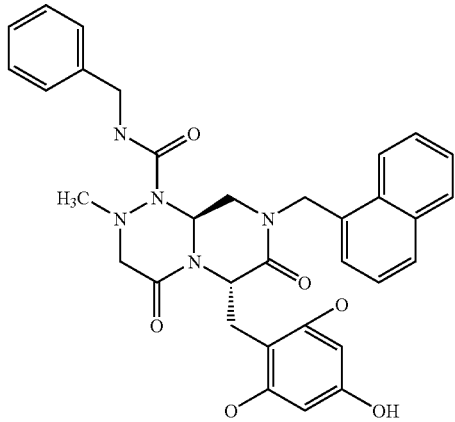 | 566 | 567 |

TABLE 2B-continued
THE [4,4,0]REVERSE TURN MIMETICS LIBRARY
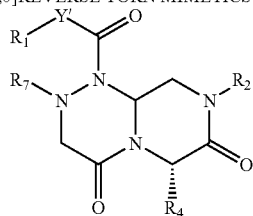
| No | MOLSTRUCTURE | Mol. Weight | M + H (MS) |
|---|---|---|---|
| 3043 | | 550 | 551 |
| 3044 | | 647 | 648 |
| 3045 | | 690 | 691 |

TABLE 2B-continued
THE [4,4,0]REVERSE TURN MIMETICS LIBRARY
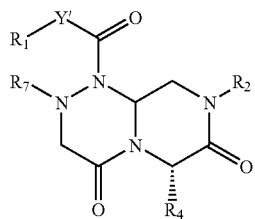
| No | MOLSTRUCTURE | Mol. Weight | M + H (MS) |
|---|---|---|---|
| 3046 | | 555 | 556 |
| 3047 | | 636 | 637 |
| 3048 | | 664 | 665 |

TABLE 2B-continued
THE [4,4,0]REVERSE TURN MIMETICS LIBRARY
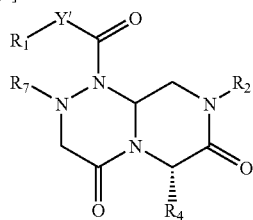
| No | MOLSTRUCTURE | Mol. Weight | M + H (MS) |
|---|---|---|---|
| 3049 | | 594 | 595 |
| 3050 | Chiral | 655 | 656 |
| 3051 | Chiral | 653 | 654 |

TABLE 2B-continued
THE [4,4,0]REVERSE TURN MIMETICS LIBRARY
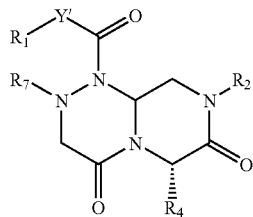
| No | MOLSTRUCTURE | | Mol. Weight | M + H (MS) |
|---|---|---|---|---|
| 3052 | 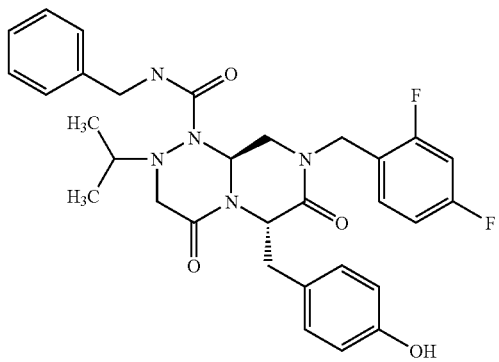 | Chiral | 578 | 579 |
| 3053 | 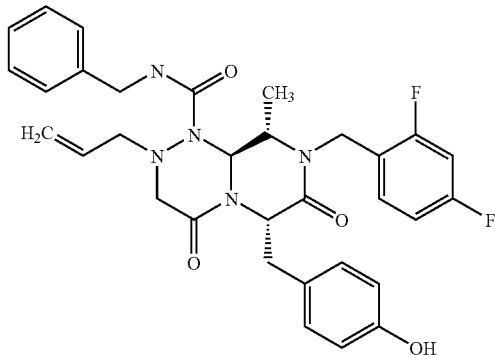 | Chiral | 590 | 591 |
| 3054 | 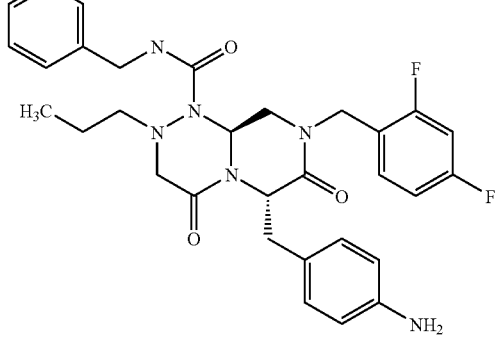 | | 577 | 578 |

TABLE 2B-continued
THE [4,4,0]REVERSE TURN MIMETICS LIBRARY
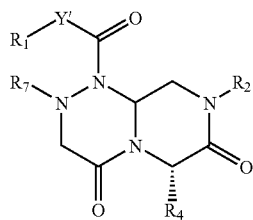
| No | MOLSTRUCTURE | Mol. Weight | M + H (MS) |
|----|--------------|-------------|------------|
| 3055 | | 617 | 618 |
| 3056 | | 576 | 577 |
| 3057 | | 645 | 646 |

TABLE 2B-continued
THE [4,4,0]REVERSE TURN MIMETICS LIBRARY
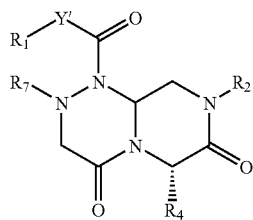
| No | MOLSTRUCTURE | Mol. Weight | M + H (MS) |
|---|---|---|---|
| 3058 | | 609 | 610 |
| 3059 | | 526 | 527 |
| 3060 | | 528 | 529 |

TABLE 2B-continued
THE [4,4,0]REVERSE TURN MIMETICS LIBRARY
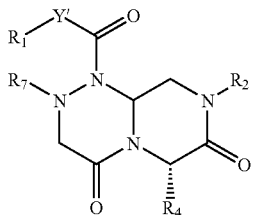
| No | MOLSTRUCTURE | Mol. Weight | M + H (MS) |
|---|---|---|---|
| 3061 | | 512 | 513 |
| 3062 | | 542 | 543 |
| 3063 | | 592 | 593 |

TABLE 2B-continued
THE [4,4,0]REVERSE TURN MIMETICS LIBRARY
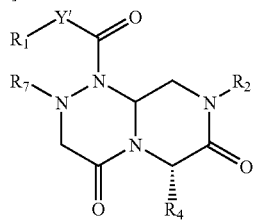
| No | MOLSTRUCTURE | Mol. Weight | M + H (MS) |
|---|---|---|---|
| 3064 | | 597 | 598 |
| 3065 | | 554 | 555 |
| 3066 | | 554 | 555 |

TABLE 2B-continued
THE [4,4,0]REVERSE TURN MIMETICS LIBRARY
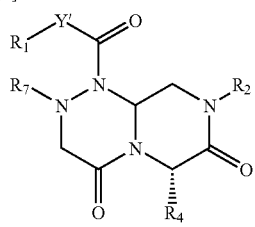
| No | MOLSTRUCTURE | Mol. Weight | M + H (MS) |
|---|---|---|---|
| 3067 | | 554 | 555 |
| 3068 | | 639 | 640 |
| 3069 | | 576 | 577 |

TABLE 2B-continued
THE [4,4,0]REVERSE TURN MIMETICS LIBRARY
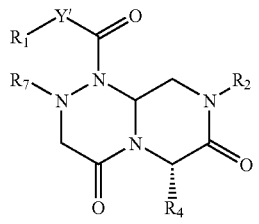
| No | MOLSTRUCTURE | Mol. Weight | M + H (MS) |
|---|---|---|---|
| 3070 | 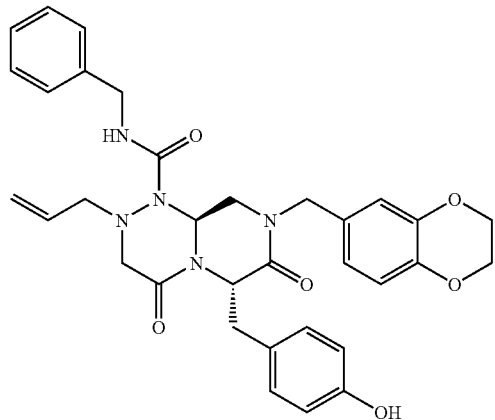 | 598 | 599 |
| 3071 | 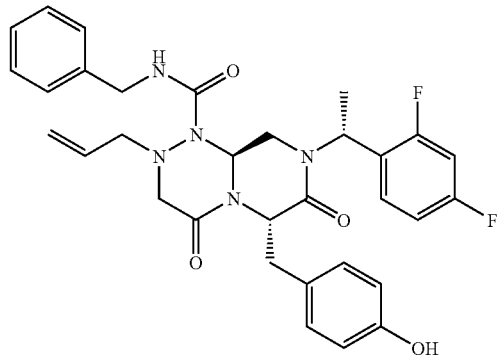 | 590 | 591 |
| 3072 | 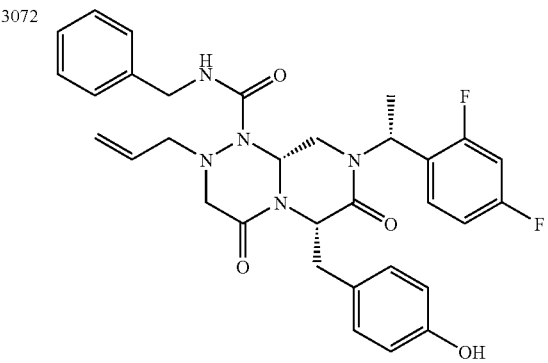 | 590 | 591 |

TABLE 2B-continued
THE [4,4,0]REVERSE TURN MIMETICS LIBRARY
| No | MOLSTRUCTURE | Mol. Weight | M + H (MS) |
|---|---|---|---|
| 3073 | | 639 | 640 |
| 3074 | | 639 | 640 |
| 3075 | | 639 | 640 |

TABLE 2B-continued
THE [4,4,0]REVERSE TURN MIMETICS LIBRARY
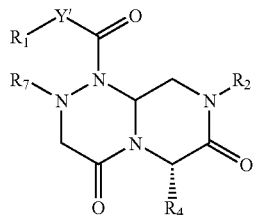
| No | MOLSTRUCTURE | Mol. Weight | M + H (MS) |
|---|---|---|---|
| 3076 | | 583 | 584 |
| 3077 | | 590 | 591 |
| 3078 | | 579 | 580 |

TABLE 2B-continued
THE [4,4,0]REVERSE TURN MIMETICS LIBRARY
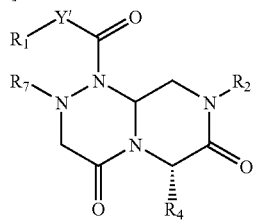
| No | MOLSTRUCTURE | Mol. Weight | M + H (MS) |
|---|---|---|---|
| 3079 | | 564 | 565 |
| 3080 | | 569 | 570 |
| 3081 | | 667 | 668 |

TABLE 2B-continued
THE [4,4,0]REVERSE TURN MIMETICS LIBRARY
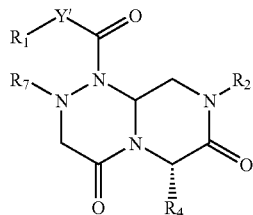
| No | MOLSTRUCTURE | Mol. Weight | M + H (MS) |
|----|--------------|-------------|------------|
| 3082 | | 564 | 565 |
| 3083 | | 613 | 614 |
| 3084 | | 721 | 722 |

TABLE 2B-continued
THE [4,4,0]REVERSE TURN MIMETICS LIBRARY
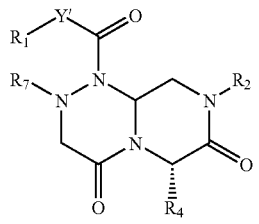
| No | MOLSTRUCTURE | Mol. Weight | M + H (MS) |
|---|---|---|---|
| 3085 | | 613 | 614 |
| 3086 | | 579 | 580 |
| 3087 | | 660 | 661 |

TABLE 2B-continued
THE [4,4,0]REVERSE TURN MIMETICS LIBRARY
| No | MOLSTRUCTURE | Mol. Weight | M + H (MS) |
|---|---|---|---|
| 3088 | 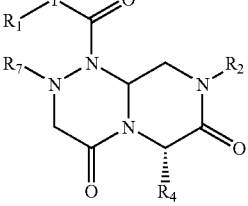 | 568 | 569 |
| 3089 | 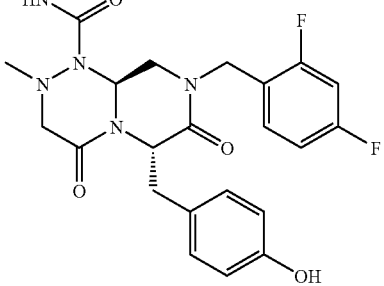 | 628 | 629 |
| 3090 | 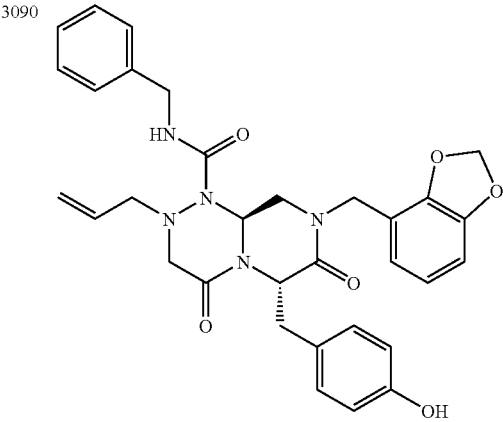 | 584 | 585 |

TABLE 2B-continued
THE [4,4,0]REVERSE TURN MIMETICS LIBRARY
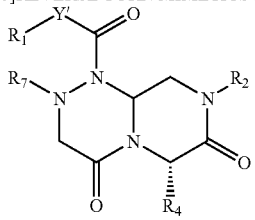
| No | MOLSTRUCTURE | Mol. Weight | M + H (MS) |
|---|---|---|---|
| 3091 | | 598 | 599 |
| 3092 | | 667 | 668 |
| 3093 | | 582 | 583 |

TABLE 2B-continued
THE [4,4,0]REVERSE TURN MIMETICS LIBRARY
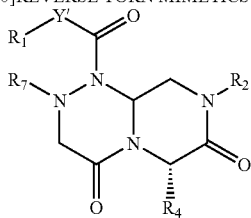
| No | MOLSTRUCTURE | Mol. Weight | M + H (MS) |
|---|---|---|---|
| 3094 | | 624 | 625 |
| 3095 | | 609 | 610 |
| 3096 | | 570 | 571 |

TABLE 2B-continued
THE [4,4,0]REVERSE TURN MIMETICS LIBRARY
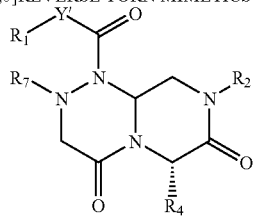
| No | MOLSTRUCTURE | Mol. Weight | M + H (MS) |
|---|---|---|---|
| 3097 | | 694 | 695 |
| 3098 | | 694 | 695 |
| 3099 | | 694 | 695 |

TABLE 2B-continued
THE [4,4,0]REVERSE TURN MIMETICS LIBRARY
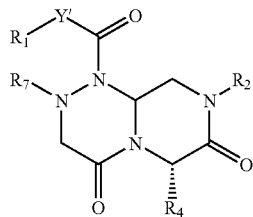
| No | MOLSTRUCTURE | Mol. Weight | M + H (MS) |
|---|---|---|---|
| 3100 | | 694 | 695 |
| 3101 | | 694 | 695 |

TABLE 2B-continued
THE [4,4,0]REVERSE TURN MIMETICS LIBRARY
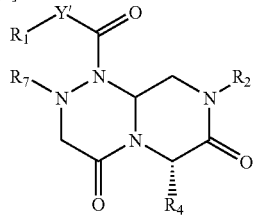
| No | MOLSTRUCTURE | Mol. Weight | M + H (MS) |
|---|---|---|---|
| 3102 | | 694 | 695 |
| 3103 | | 639 | 640 |
| 3104 | | 615 | 616 |

TABLE 2B-continued
THE [4,4,0]REVERSE TURN MIMETICS LIBRARY
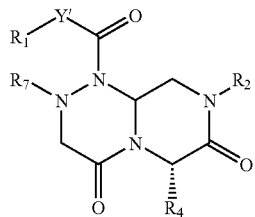
| No | MOLSTRUCTURE | Mol. Weight | M + H (MS) |
|----|--------------|-------------|------------|
| 3105 | | 631 | 632 |
| 3106 | | 680 | 681 |
| 3107 | | 682 | 683 |

TABLE 2B-continued
THE [4,4,0]REVERSE TURN MIMETICS LIBRARY
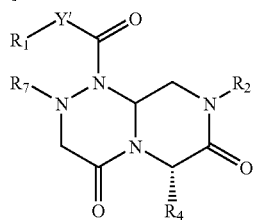
| No | MOLSTRUCTURE | Mol. Weight | M + H (MS) |
|----|--------------|-------------|------------|
| 3108 | | 637 | 638 |
| 3109 | | 673 | 674 |
| 3110 | | 689 | 690 |

TABLE 2B-continued
THE [4,4,0]REVERSE TURN MIMETICS LIBRARY
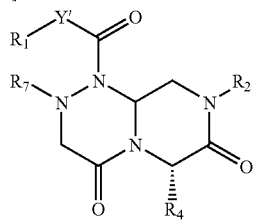
| No | MOLSTRUCTURE | Mol. Weight | M + H (MS) |
|---|---|---|---|
| 3111 | | 631 | 632 |
| 3112 | | 615 | 616 |
| 3113 | | 669 | 670 |

TABLE 2B-continued
THE [4,4,0]REVERSE TURN MIMETICS LIBRARY
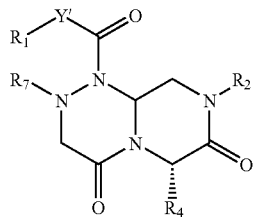
| No | MOLSTRUCTURE | Mol. Weight | M + H (MS) |
|---|---|---|---|
| 3114 | | 640 | 641 |
| 3115 | | 696 | 697 |
| 3116 | | 611 | 612 |

TABLE 2B-continued
THE [4,4,0]REVERSE TURN MIMETICS LIBRARY
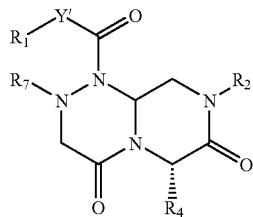
| No | MOLSTRUCTURE | Mol. Weight | M + H (MS) |
|---|---|---|---|
| 3117 | | 725 | 726 |
| 3118 | | 612 | 613 |
| 3119 | | 708 | 709 |

TABLE 2B-continued
THE [4,4,0]REVERSE TURN MIMETICS LIBRARY
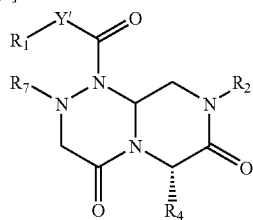
| No | MOLSTRUCTURE | Mol. Weight | M + H (MS) |
|---|---|---|---|
| 3120 | | 615 | 616 |
| 3121 | | 464 | 465 |
| 3122 | | 478 | 479 |

TABLE 2B-continued
THE [4,4,0]REVERSE TURN MIMETICS LIBRARY
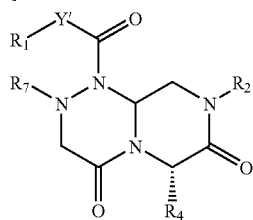
| No | MOLSTRUCTURE | Mol. Weight | M + H (MS) |
|---|---|---|---|
| 3123 | | 558 | 559 |
| 3124 | | 572 | 573 |
| 3125 | | 490 | 491 |

TABLE 2B-continued
THE [4,4,0]REVERSE TURN MIMETICS LIBRARY
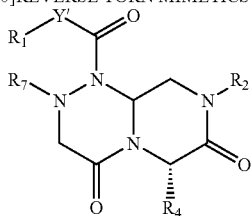
| No | MOLSTRUCTURE | Mol. Weight | M + H (MS) |
|---|---|---|---|
| 3126 | | 504 | 505 |
| 3127 | | 437 | 438 |
| 3128 | | 541 | 542 |
| 3129 | | 571 | 572 |

TABLE 2B-continued
THE [4,4,0]REVERSE TURN MIMETICS LIBRARY
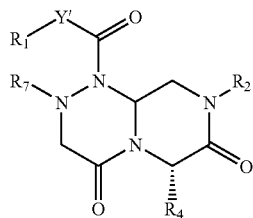
| No | MOLSTRUCTURE | Mol. Weight | M + H (MS) |
|---|---|---|---|
| 3130 | | 599 | 600 |
| 3131 | | 569 | 570 |
| 3132 | | 567 | 568 |
| 3133 | | 468 | 469 |

TABLE 2B-continued
THE [4,4,0]REVERSE TURN MIMETICS LIBRARY
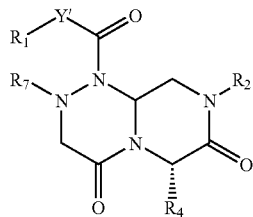
| No | MOLSTRUCTURE | Mol. Weight | M + H (MS) |
|----|--------------|-------------|------------|
| 3134 | | 453 | 454 |
| 3135 | | 616 | 617 |
| 3136 | | 574 | 575 |

TABLE 2B-continued
THE [4,4,0]REVERSE TURN MIMETICS LIBRARY
| No | MOLSTRUCTURE | Mol. Weight | M + H (MS) |
|---|---|---|---|
| 3137 | | 590 | 591 |
| 3138 | | 688 | 689 |
In addition, synthesis of the peptide mimetics of the library of the present invention may be accomplished using the General Scheme of [4,3,0] Reverse-Turn Mimetic Library as follows:
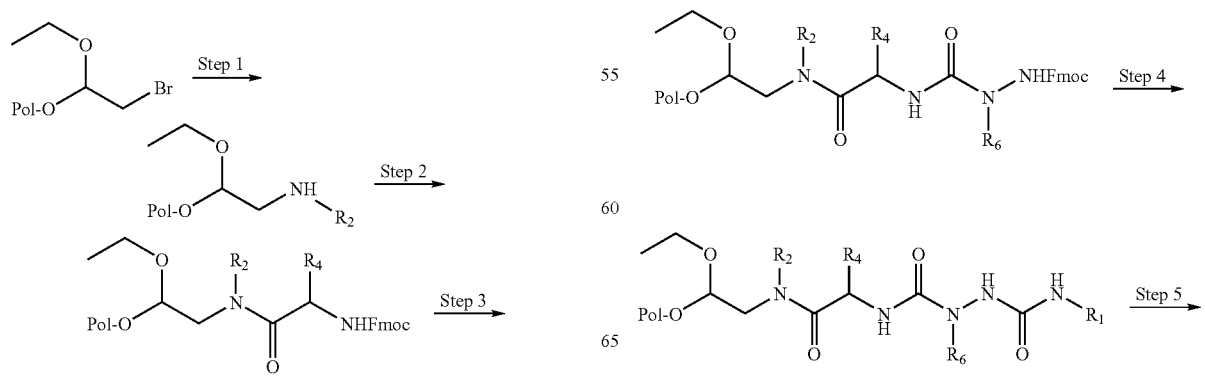

-continued

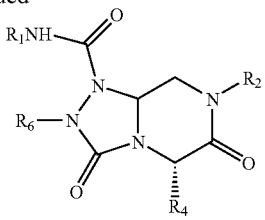

Synthesis of the peptide mimetics of the bicyclic template libraries of the present invention was accomplished using FlexChem Reactor Block which has 96 well plate by known techniques. In the above scheme 'Pol' represents Bromoacetal resin (Advanced ChemTech) and detailed procedure is illustrated below.

Step 1

The bromoacetal resin (1.6 mmol/g) and a solution of R1 amine in DMSO (2M solution) were placed in 96 well Robbins block (FlexChem). The reaction mixture was shaken at 60° C. using rotating oven [Robbins Scientific] for 12 hours. The resin was washed with DMF, MeOH, and then DCM Step 2

A solution of commercial available Fmoc-Amino Acids (4 equiv.), PyBob (4 equiv.), HOAt (4 equiv.), and DIEA (12 equiv.) in DMF was added to the resin. After the reaction mixture was shaken for 12 hours at room temperature, the resin was washed with DMF, MeOH, and then DCM.

Step 3

To the resin swollen by DMF before reaction was added 25% piperidine in DMF. After the reaction mixture was shaken for 30 min at room temperature. This deprotection step was repeated again and then washed with DMF, Methanol, then DCM. A solution of hydrazine carbamoyl chloride (4 equiv.), HOBt (4 equiv.), and DIC (4 equiv.) in DMF was added to the resin. After the reaction mixture was shaken for 12 hours at room temperature, the resin was washed with DMF, MeOH, and then DCM.

Step 4

To the resin swollen by DMF before reaction was added 25% piperidine in DMF. After the reaction mixture was shaken for 30 min at room temperature. This deprotection step was repeated again and then washed with DMF, Methanol, then DCM. To the resin swollen by DCM before reaction was added $R_1$-isocynate (5 equiv.) in DCM. After the reaction mixture was shaken for 12 hours at room temperature the resin was washed with DMF, MeOH, then DCM.

Step 5

The resin was treated with formic acid (1.2 mL each well) for 18 hours at room temperature. After the resin was removed by filtration, the filtrate was condensed under reduced pressure using SpeedVac [SAVANT] to give the product as oil. These products were diluted with 50% water/acetonitrile and then lyophilized after freezing.

Table 3 shows a [4,3,0] reverse turn mimetics library which can be prepared according to the present invention, of which representative preparation is given in Example 5.

TABLE 3

THE [4,3,0] REVERSE TURN MIMETICS LIBRARY

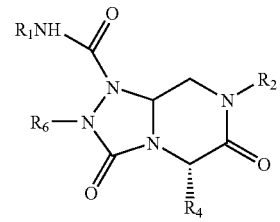

| No | $R_2$ | $R_4$ | $R_6$ | $R_1$ | Mol. Weight | M + H |
|---|---|---|---|---|---|---|
| 610 | Isoamyl | 4-HO-phenyl | Methyl | Phenyl | 466 | 467 |
| 611 | Isoamyl | 4-HO-phenyl | Methyl | 4-Me-phenyl | 480 | 481 |
| 612 | Isoamyl | 4-HO-phenyl | Methyl | 3,5-Me$_2$-phenyl | 494 | 495 |
| 613 | Isoamyl | 4-HO-phenyl | Methyl | 4-MeO-phenyl | 496 | 497 |
| 614 | Isoamyl | 4-HO-phenyl | Methyl | 4-CF$_3$-phenyl | 534 | 535 |
| 615 | Isoamyl | 4-HO-phenyl | Methyl | Cyclohexyl | 472 | 473 |
| 616 | Isoamyl | 4-HO-phenyl | Methyl | Benzyl | 480 | 481 |
| 617 | Isoamyl | 4-HO-phenyl | Methyl | 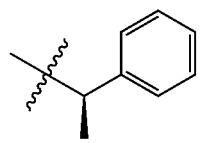 | 494 | 495 |
| 618 | Isoamyl | 4-HO-phenyl | Methyl | 4-MeO-benzyl | 510 | 511 |
| 619 | Isoamyl | 4-HO-phenyl | Methyl | Phenethyl | 494 | 495 |
| 620 | Isoamyl | 4-HO-phenyl | Methyl | Pentyl | 460 | 461 |
| 621 | Isoamyl | 4-HO-phenyl | Methyl | Hexyl | 474 | 475 |
| 622 | Benzyl | 4-HO-phenyl | Methyl | Phenyl | 486 | 487 |
| 623 | Benzyl | 4-HO-phenyl | Methyl | 4-Me-phenyl | 500 | 501 |
| 624 | Benzyl | 4-HO-phenyl | Methyl | 3,5-Me$_2$-phenyl | 514 | 515 |
| 625 | Benzyl | 4-HO-phenyl | Methyl | 4-MeO-phenyl | 516 | 517 |

TABLE 3-continued

THE [4,3,0] REVERSE TURN MIMETICS LIBRARY

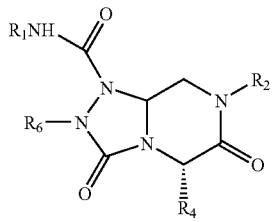

| No | R$_2$ | R$_4$ | R$_6$ | R$_1$ | Mol. Weight | M + H |
|---|---|---|---|---|---|---|
| 626 | Benzyl | 4-HO-phenyl | Methyl | 4-CF$_3$-phenyl | 554 | 555 |
| 627 | Benzyl | 4-HO-phenyl | Methyl | Cyclohexyl | 492 | 493 |
| 628 | Benzyl | 4-HO-phenyl | Methyl | Benzyl | 500 | 501 |
| 629 | Benzyl | 4-HO-phenyl | Methyl | 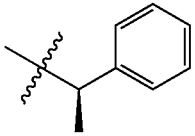 | 514 | 515 |
| 630 | Benzyl | 4-HO-phenyl | Methyl | 4-MeO-benzyl | 530 | 531 |
| 631 | Benzyl | 4-HO-phenyl | Methyl | Phenethyl | 514 | 515 |
| 632 | Benzyl | 4-HO-phenyl | Methyl | Pentyl | 480 | 481 |
| 633 | Benzyl | 4-HO-phenyl | Methyl | Hexyl | 494 | 495 |
| 634 | Naphth-1-ylmethyl | 4-HO-phenyl | Methyl | Phenyl | 536 | 537 |
| 635 | Naphth-1-ylmethyl | 4-HO-phenyl | Methyl | 4-Me-phenyl | 550 | 551 |
| 636 | Naphth-1-ylmethyl | 4-HO-phenyl | Methyl | 3,5-Me$_2$-phenyl | 564 | 565 |
| 637 | Naphth-1-ylmethyl | 4-HO-phenyl | Methyl | 4-MeO-phenyl | 566 | 567 |
| 638 | Naphth-1-ylmethyl | 4-HO-phenyl | Methyl | 4-CF$_3$-phenyl | 604 | 605 |
| 639 | Naphth-1-ylmethyl | 4-HO-phenyl | Methyl | Cyclohexyl | 542 | 543 |
| 640 | Naphth-1-ylmethyl | 4-HO-phenyl | Methyl | Benzyl | 550 | 551 |
| 641 | Naphth-1-ylmethyl | 4-HO-phenyl | Methyl | 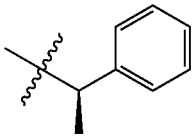 | 564 | 565 |
| 642 | Naphth-1-ylmethyl | 4-HO-phenyl | Methyl | 4-MeO-benzyl | 580 | 581 |
| 643 | Naphth-1-ylmethyl | 4-HO-phenyl | Methyl | Phenethyl | 564 | 565 |
| 644 | Naphth-1-ylmethyl | 4-HO-phenyl | Methyl | Pentyl | 530 | 531 |
| 645 | Naphth-1-ylmethyl | 4-HO-phenyl | Methyl | Hexyl | 544 | 545 |
| 646 | Cyclohexylmethyl | 4-HO-phenyl | Methyl | Phenyl | 492 | 493 |
| 647 | Cyclohexylmethyl | 4-HO-phenyl | Methyl | 4-Me-phenyl | 506 | 507 |
| 648 | Cyclohexylmethyl | 4-HO-phenyl | Methyl | 3,5-Me$_2$-phenyl | 520 | 521 |
| 649 | Cyclohexylmethyl | 4-HO-phenyl | Methyl | 4-MeO-phenyl | 522 | 523 |
| 650 | Cyclohexylmethyl | 4-HO-phenyl | Methyl | 4-CF$_3$-phenyl | 560 | 561 |
| 651 | Cyclohexylmethyl | 4-HO-phenyl | Methyl | Cyclohexyl | 468 | 469 |
| 652 | Cyclohexylmethyl | 4-HO-phenyl | Methyl | Benzyl | 506 | 507 |
| 653 | Cyclohexylmethyl | 4-HO-phenyl | Methyl | 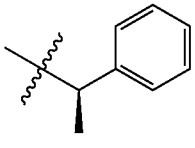 | 520 | 521 |
| 654 | Cyclohexylmethyl | 4-HO-phenyl | Methyl | 4-MeO-benzyl | 536 | 537 |
| 655 | Cyclohexylmethyl | 4-HO-phenyl | Methyl | Phenethyl | 520 | 521 |
| 656 | Cyclohexylmethyl | 4-HO-phenyl | Methyl | Pentyl | 486 | 487 |
| 657 | Cyclohexylmethyl | 4-HO-phenyl | Methyl | Hexyl | 500 | 501 |
| 658 | 4-methylbenzyl | 4-HO-phenyl | Methyl | Phenyl | 500 | 501 |
| 659 | 4-methylbenzyl | 4-HO-phenyl | Methyl | 4-Me-phenyl | 514 | 515 |
| 660 | 4-methylbenzyl | 4-HO-phenyl | Methyl | 3,5-Me$_2$-phenyl | 528 | 529 |
| 661 | 4-methylbenzyl | 4-HO-phenyl | Methyl | 4-MeO-phenyl | 530 | 531 |
| 662 | 4-methylbenzyl | 4-HO-phenyl | Methyl | 4-CF$_3$-phenyl | 568 | 569 |
| 663 | 4-methylbenzyl | 4-HO-phenyl | Methyl | Cyclohexyl | 506 | 507 |
| 664 | 4-methylbenzyl | 4-HO-phenyl | Methyl | Benzyl | 514 | 515 |

TABLE 3-continued

THE [4,3,0] REVERSE TURN MIMETICS LIBRARY

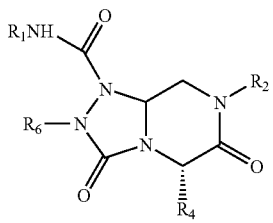

| No | $R_2$ | $R_4$ | $R_6$ | $R_1$ | Mol. Weight | M + H |
|---|---|---|---|---|---|---|
| 665 | 4-methylbenzyl | 4-HO-phenyl | Methyl | | 528 | 529 |
| 666 | 4-methylbenzyl | 4-HO-phenyl | Methyl | 4-MeO-benzyl | 544 | 545 |
| 667 | 4-methylbenzyl | 4-HO-phenyl | Methyl | Phenethyl | 528 | 529 |
| 668 | 4-methylbenzyl | 4-HO-phenyl | Methyl | Pentyl | 494 | 495 |
| 669 | 4-methylbenzyl | 4-HO-phenyl | Methyl | Hexyl | 508 | 509 |
| 670 | Methoxypropyl | 4-HO-phenyl | Methyl | Phenyl | 468 | 469 |
| 671 | Methoxypropyl | 4-HO-phenyl | Methyl | 4-Me-phenyl | 482 | 483 |
| 672 | Methoxypropyl | 4-HO-phenyl | Methyl | 3,5-Me$_2$-phenyl | 496 | 497 |
| 673 | Methoxypropyl | 4-HO-phenyl | Methyl | 4-MeO-phenyl | 498 | 499 |
| 674 | Methoxypropyl | 4-HO-phenyl | Methyl | 4-CF$_3$-phenyl | 536 | 537 |
| 675 | Methoxypropyl | 4-HO-phenyl | Methyl | Cyclohexyl | 474 | 475 |
| 676 | Methoxypropyl | 4-HO-phenyl | Methyl | Benzyl | 482 | 483 |
| 677 | Methoxypropyl | 4-HO-phenyl | Methyl | | 496 | 497 |
| 678 | Methoxypropyl | 4-HO-phenyl | Methyl | 4-MeO-benzyl | 512 | 513 |
| 679 | Methoxypropyl | 4-HO-phenyl | Methyl | Phenethyl | 496 | 497 |
| 680 | Methoxypropyl | 4-HO-phenyl | Methyl | Pentyl | 462 | 463 |
| 681 | Methoxypropyl | 4-HO-phenyl | Methyl | Hexyl | 476 | 477 |
| 682 | Phenethyl | 4-HO-phenyl | Methyl | Phenyl | 500 | 501 |
| 683 | Phenethyl | 4-HO-phenyl | Methyl | 4-Me-phenyl | 514 | 515 |
| 684 | Phenethyl | 4-HO-phenyl | Methyl | 3,5-Me$_2$-phenyl | 528 | 529 |
| 685 | Phenethyl | 4-HO-phenyl | Methyl | 4-MeO-phenyl | 530 | 531 |
| 686 | Phenethyl | 4-HO-phenyl | Methyl | 4-CF$_3$-phenyl | 568 | 569 |
| 687 | Phenethyl | 4-HO-phenyl | Methyl | Cyclohexyl | 506 | 507 |
| 688 | Phenethyl | 4-HO-phenyl | Methyl | Benzyl | 514 | 515 |
| 689 | Phenethyl | 4-HO-phenyl | Methyl | | 528 | 529 |
| 690 | Phenethyl | 4-HO-phenyl | Methyl | 4-MeO-benzyl | 544 | 545 |
| 691 | Phenethyl | 4-HO-phenyl | Methyl | Phenethyl | 528 | 529 |
| 692 | Phenethyl | 4-HO-phenyl | Methyl | Pentyl | 494 | 495 |
| 693 | Phenethyl | 4-HO-phenyl | Methyl | Hexyl | 508 | 509 |
| 694 | 2,2-bisphenylethyl | 4-HO-phenyl | Methyl | Phenyl | 576 | 577 |
| 695 | 2,2-bisphenylethyl | 4-HO-phenyl | Methyl | 4-Me-phenyl | 590 | 591 |
| 696 | 2,2-bisphenylethyl | 4-HO-phenyl | Methyl | 3,5-Me$_2$-phenyl | 604 | 605 |
| 697 | 2,2-bisphenylethyl | 4-HO-phenyl | Methyl | 4-MeO-phenyl | 606 | 607 |
| 698 | 2,2-bisphenylethyl | 4-HO-phenyl | Methyl | 4-CF$_3$-phenyl | 644 | 645 |
| 699 | 2,2-bisphenylethyl | 4-HO-phenyl | Methyl | Cyclohexyl | 582 | 583 |
| 700 | 2,2-bisphenylethyl | 4-HO-phenyl | Methyl | Benzyl | 586 | 587 |

TABLE 3-continued

THE [4,3,0] REVERSE TURN MIMETICS LIBRARY

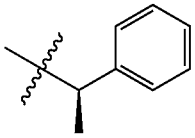

| No | R₂ | R₄ | R₆ | R₁ | Mol. Weight | M + H |
|---|---|---|---|---|---|---|
| 701 | 2,2-bisphenylethyl | 4-HO-phenyl | Methyl | 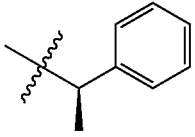 | 604 | 605 |
| 702 | 2,2-bisphenylethyl | 4-HO-phenyl | Methyl | 4-MeO-benzyl | 620 | 621 |
| 703 | 2,2-bisphenylethyl | 4-HO-phenyl | Methyl | Phenethyl | 604 | 605 |
| 704 | 2,2-bisphenylethyl | 4-HO-phenyl | Methyl | Pentyl | 570 | 571 |
| 705 | 2,2-bisphenylethyl | 4-HO-phenyl | Methyl | Hexyl | 584 | 585 |
| 706 | Naphth-1-ylmethyl | Benzyl | Methyl | Phenyl | 520 | 521 |
| 707 | Naphth-1-ylmethyl | Benzyl | Methyl | 4-Me-phenyl | 534 | 535 |
| 708 | Naphth-1-ylmethyl | Benzyl | Methyl | 3,5-Me₂-phenyl | 548 | 549 |
| 709 | Naphth-1-ylmethyl | Benzyl | Methyl | 4-MeO-phenyl | 550 | 551 |
| 710 | Naphth-1-ylmethyl | Benzyl | Methyl | 4-CF₃-phenyl | 588 | 589 |
| 711 | Naphth-1-ylmethyl | Benzyl | Methyl | Cyclohexyl | 526 | 527 |
| 712 | Naphth-1-ylmethyl | Benzyl | Methyl | Benzyl | 534 | 535 |
| 713 | Naphth-1-ylmethyl | Benzyl | Methyl | 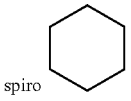 | 548 | 549 |
| 714 | Naphth-1-ylmethyl | Benzyl | Methyl | 4-MeO-benzyl | 564 | 565 |
| 715 | Naphth-1-ylmethyl | Benzyl | Methyl | Phenethyl | 548 | 549 |
| 716 | Naphth-1-ylmethyl | Benzyl | Methyl | Pentyl | 514 | 515 |
| 717 | Naphth-1-ylmethyl | Benzyl | Methyl | Hexyl | 528 | 529 |
| 718 | Naphth-1-ylmethyl | 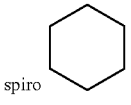 spiro | Methyl | Phenyl | 498 | 499 |
| 719 | Naphth-1-ylmethyl | 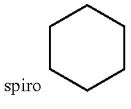 spiro | Methyl | 4-Me-phenyl | 512 | 513 |
| 720 | Naphth-1-ylmethyl | 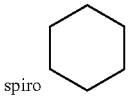 spiro | Methyl | 3,5-Me₂-phenyl | 526 | 527 |
| 721 | Naphth-1-ylmethyl | 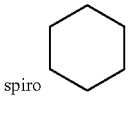 spiro | Methyl | 4-MeO-phenyl | 528 | 529 |
| 722 | Naphth-1-ylmethyl | 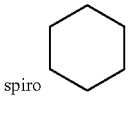 spiro | Methyl | 4-CF₃-phenyl | 566 | 567 |

TABLE 3-continued

THE [4,3,0] REVERSE TURN MIMETICS LIBRARY

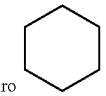

| No | R$_2$ | R$_4$ | R$_6$ | R$_1$ | Mol. Weight | M + H |
|---|---|---|---|---|---|---|
| 723 | Naphth-1-ylmethyl | spiro-cyclohexyl | Methyl | Cyclohexyl | 504 | 505 |
| 724 | Naphth-1-ylmethyl | spiro-cyclohexyl | Methyl | Benzyl | 512 | 513 |
| 725 | Naphth-1-ylmethyl | spiro-cyclohexyl | Methyl |  | 526 | 527 |
| 726 | Naphth-1-ylmethyl | spiro-cyclohexyl | Methyl | 4-MeO-benzyl | 542 | 543 |
| 727 | Naphth-1-ylmethyl | spiro-cyclohexyl | Methyl | Phenethyl | 526 | 527 |
| 728 | Naphth-1-ylmethyl | spiro-cyclohexyl | Methyl | Pentyl | 492 | 493 |
| 729 | Naphth-1-ylmethyl | spiro-cyclohexyl | Methyl | Hexyl | 506 | 507 |
| 730 | Naphth-1-ylmethyl | Naphth-1-ylmethyl | Methyl | Phenyl | 570 | 571 |
| 731 | Naphth-1-ylmethyl | Naphth-1-ylmethyl | Methyl | 4-Me-phenyl | 584 | 585 |
| 732 | Naphth-1-ylmethyl | Naphth-1-ylmethyl | Methyl | 3,5-Me$_2$-phenyl | 598 | 599 |
| 733 | Naphth-1-ylm6thyl | Naphth-1-ylmethyl | Methyl | 4-MeO-phenyl | 600 | 601 |
| 734 | Naphth-1-ylmethyl | Naphth-1-ylmethyl | Methyl | 4-CF$_3$-phenyl | 638 | 639 |
| 735 | Naphth-1-ylmethyl | Naphth-1-ylmethyl | Methyl | Cyclohexyl | 576 | 577 |
| 736 | Naphth-1-ylmethyl | Naphth-1-ylmethyl | Methyl | Benzyl | 584 | 585 |
| 737 | Naphth-1-ylmethyl | Naphth-1-ylmethyl | Methyl |  | 598 | 599 |
| 738 | Naphth-1-ylmethyl | Naphth-1-ylmethyl | Methyl | 4-MeO-benzyl | 614 | 615 |
| 739 | Naphth-1-ylmethyl | Naphth-1-ylmethyl | Methyl | Phenethyl | 598 | 599 |
| 740 | Naphth-1-ylmethyl | Naphth-1-ylmethyl | Methyl | Pentyl | 564 | 565 |
| 741 | Naphth-1-ylmethyl | Naphth-1-ylmethyl | Methyl | Hexyl | 578 | 579 |
| 742 | Naphth-1-ylmethyl | Cyclohexylmethyl | Methyl | Phenyl | 526 | 527 |
| 743 | Naphth-1-ylmethyl | Cyclohexylmethyl | Methyl | 4-Me-phenyl | 540 | 541 |

TABLE 3-continued

THE [4,3,0] REVERSE TURN MIMETICS LIBRARY

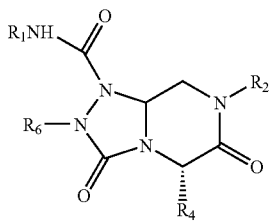

| No | R₂ | R₄ | R₆ | R₁ | Mol. Weight | M + H |
|---|---|---|---|---|---|---|
| 744 | Naphth-1-ylmethyl | Cyclohexylmethyl | Methyl | 3,5-Me₂-phenyl | 554 | 555 |
| 745 | Naphth-1-ylmethyl | Cyclohexylmethyl | Methyl | 4-MeO-phenyl | 556 | 557 |
| 746 | Naphth-1-ylmethyl | Cyclohexylmethyl | Methyl | 4-CF₃-phenyl | 594 | 595 |
| 747 | Naphth-1-ylmethyl | Cyclohexylmethyl | Methyl | Cyclohexyl | 532 | 533 |
| 748 | Naphth-1-ylmethyl | Cyclohexylmethyl | Methyl | Benzyl | 540 | 541 |
| 749 | Naphth-1-ylmethyl | Cyclohexylmethyl | Methyl |  | 554 | 555 |
| 750 | Naphth-1-ylmethyl | Cyclohexylmethyl | Methyl | 4-MeO-benzyl | 570 | 571 |
| 751 | Naphth-1-ylmethyl | Cyclohexylmethyl | Methyl | Phenethyl | 554 | 555 |
| 752 | Naphth-1-ylmethyl | Cyclohexylmethyl | Methyl | Pentyl | 520 | 521 |
| 753 | Naphth-1-ylmethyl | Cyclohexylmethyl | Methyl | Hexyl | 534 | 535 |
| 754 | Naphth-1-ylmethyl | 4-chlorobenzyl | Methyl | Phenyl | 554 | 555 |
| 755 | Naphth-1-ylmethyl | 4-chlorobenzyl | Methyl | 4-Me-phenyl | 568 | 569 |
| 756 | Naphth-1-ylmethyl | 4-chlorobenzyl | Methyl | 3,5-Me₂-phenyl | 582 | 583 |
| 757 | Naphth-1-ylmethyl | 4-chlorobenzyl | Methyl | 4-MeO-phenyl | 584 | 585 |
| 758 | Naphth-1-ylmethyl | 4-chlorobenzyl | Methyl | 4-CF₃-phenyl | 622 | 623 |
| 759 | Naphth-1-ylmethyl | 4-chlorobenzyl | Methyl | Cyclohexyl | 560 | 561 |
| 760 | Naphth-1-ylmethyl | 4-chlorobenzyl | Methyl | Benzyl | 568 | 569 |
| 761 | Naphth-1-ylmethyl | 4-chlorobenzyl | Methyl |  | 582 | 583 |
| 762 | Naphth-1-ylmethyl | 4-chlorobenzyl | Methyl | 4-MeO-benzyl | 598 | 599 |
| 763 | Naphth-1-ylmethyl | 4-chlorobenzyl | Methyl | Phenethyl | 582 | 583 |
| 764 | Naphth-1-ylmethyl | 4-chlorobenzyl | Methyl | Pentyl | 548 | 549 |
| 765 | Naphth-1-ylmethyl | 4-chlorobenzyl | Methyl | Hexyl | 562 | 563 |
| 766 | Naphth-1-ylmethyl | Methyl | Methyl | Phenyl | 444 | 445 |
| 767 | Naphth-1-ylmethyl | Methyl | Methyl | 4-Me-phenyl | 458 | 459 |
| 768 | Naphth-1-ylmethyl | Methyl | Methyl | 3,5-Me₂-phenyl | 472 | 473 |
| 769 | Naphth-1-ylmethyl | Methyl | Methyl | 4-MeO-phenyl | 474 | 475 |
| 770 | Naphth-1-ylmethyl | Methyl | Methyl | 4-CF₃-phenyl | 512 | 513 |
| 771 | Naphth-1-ylmethyl | Methyl | Methyl | Cyclohexyl | 450 | 451 |
| 772 | Naphth-1-ylmethyl | Methyl | Methyl | Benzyl | 458 | 459 |
| 773 | Naphth-1-ylmethyl | Methyl | Methyl |  | 472 | 473 |
| 774 | Naphth-1-ylmethyl | Methyl | Methyl | 4-MeO-benzyl | 488 | 489 |
| 775 | Naphth-1-ylmethyl | Methyl | Methyl | Phenethyl | 472 | 473 |
| 776 | Naphth-1-ylmethyl | Methyl | Methyl | Pentyl | 438 | 439 |
| 777 | Naphth-1-ylmethyl | Methyl | Methyl | Hexyl | 452 | 453 |
| 778 | Naphth-1-ylmethyl | Isobutyl | Methyl | Phenyl | 486 | 487 |
| 779 | Naphth-1-ylmethyl | Isobutyl | Methyl | 4-Me-phenyl | 500 | 501 |
| 780 | Naphth-1-ylmethyl | Isobutyl | Methyl | 3,5-Me₂-phenyl | 514 | 515 |
| 781 | Naphth-1-ylmethyl | Isobutyl | Methyl | 4-MeO-phenyl | 516 | 517 |
| 782 | Naphth-1-ylmethyl | Isobutyl | Methyl | 4-CF₃-phenyl | 554 | 555 |
| 783 | Naphth-1-ylmethyl | Isobutyl | Methyl | Cyclohexyl | 492 | 493 |

TABLE 3-continued

THE [4,3,0] REVERSE TURN MIMETICS LIBRARY

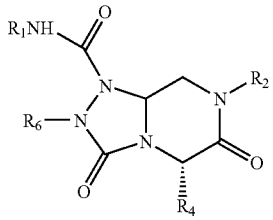

| No | R₂ | R₄ | R₆ | R₁ | Mol. Weight | M + H |
|---|---|---|---|---|---|---|
| 784 | Naphth-1-ylmethyl | Isobutyl | Methyl | Benzyl | 500 | 501 |
| 785 | Naphth-1-ylmethyl | Isobutyl | Methyl | | 514 | 515 |
| 786 | Naphth-1-ylmethyl | Isobutyl | Methyl | 4-MeO-benzyl | 530 | 531 |
| 787 | Naphth-1-ylmethyl | Isobutyl | Methyl | Phenethyl | 514 | 515 |
| 788 | Naphth-1-ylmethyl | Isobutyl | Methyl | Pentyl | 480 | 481 |
| 789 | Naphth-1-ylmethyl | Isobutyl | Methyl | Hexyl | 494 | 495 |
| 790 | Naphth-1-ylmethyl | Methylthioethyl | Methyl | Phenyl | 504 | 505 |
| 791 | Naphth-1-ylmethyl | Methylthioethyl | Methyl | 4-Me-phenyl | 518 | 519 |
| 792 | Naphth-1-ylmethyl | Methylthioethyl | Methyl | 3,5-Me₂-phenyl | 532 | 533 |
| 793 | Naphth-1-ylmethyl | Methylthioethyl | Methyl | 4-MeO-phenyl | 534 | 535 |
| 794 | Naphth-1-ylmethyl | Methylthioethyl | Methyl | 4-CF₃-phenyl | 572 | 573 |
| 795 | Naphth-1-ylmethyl | Methylthioethyl | Methyl | Cyclohexyl | 510 | 511 |
| 796 | Naphth-1-ylmethyl | Methylthioethyl | Methyl | Benzyl | 518 | 519 |
| 797 | Naphth-1-ylmethyl | Methylthioethyl | Methyl | | 532 | 533 |
| 798 | Naphth-1-ylmethyl | Methylthioethyl | Methyl | 4-MeO-benzyl | 548 | 549 |
| 799 | Naphth-1-ylmethyl | Methylthioethyl | Methyl | Phenethyl | 532 | 533 |
| 800 | Naphth-1-ylmethyl | Methylthioethyl | Methyl | Pentyl | 498 | 499 |
| 801 | Naphth-1-ylmethyl | Methylthioethyl | Methyl | Hexyl | 512 | 513 |

In a further aspect of this invention, the present invention provides methods for screening the libraries for bioactivity and isolating bioactive library members.

In yet another aspect, the present invention provides a method for carrying out a binding assay. The method includes providing a composition that includes a first co-activator, an interacting protein, and a test compound. The amino acid structure of the first co-activator includes a binding motif of LXXLL, LXXLI or FxxFF wherein X is any amino acid. The method further includes detecting an alteration in binding between the first co-activator and the interacting protein due to the presence of the compound, and then characterizing the test compound in terms of its effect on the binding.

The assay may be carried out by any means that can measure the effect of a test compound on the binding between two proteins. Many such assays are known in the art and can be utilized in the method of the present invention, including the so-called Two-Hybrid and Split-Hybrid systems.

The Two-Hybrid system, and various means to carry out an assay using this system, are described in, e.g., U.S. Pat. No. 6,410,245. The Split-Hybrid system has been described by, e.g., Hsiu-Ming Shiu et al. *Proc. Natl. Acad. Sci. USA,* 93:13896-13901, November 1996; and John D. Crispino, et al. *Molecular Cell,* 3:1-20, February 1999. In the Split-Hybrid system, a fusion protein is utilized where protein X is fused to the lexA DNA binding domains (pLexA) and protein Y is fused to the transcription activator VP16 (pSHM.1-LacZ). Interaction between lexA-X and VP16-Y leads to the expression of the Tetracycline repressor protein (TetR). TetR prevents transcription of the HIS3 reporter gene, making the cells unable to grow on media lacking histidine. Disruption of protein-protein interaction will restore the ability of the cells to grow on such media by shutting down expression of the tetracycline repressor. Accordingly, compounds of the present invention may be added to the growing cells, and if the addition of the compound restores the ability of the cells to grow on the media, the compound may be seen as an effective disruptor of the protein-protein interaction.

The yeast strains required to make the Split-Hybrid system work can be employed with two hybrid LexA/VP16 constructs such as those described by Stanley M. Hollenberg, et al. *Molecular and Cellular Biology* 15(7):3813-3822, July 1995. A useful modification of the Split-Hybrid system was utilized by Takemaru, K. I. and Moon, R. T. *J. of Cell Biol;* 149:249-254, 2000.

Other assay formats are also suitable. For example, reporter gene assays for AP-1, ELISA, for example, blocking the production of IL-2 by a T-cell line after stimulation with CD3 and CD28 to look for inhibitors of IL-2 transcription. Direct binding assays (between coactivators and their partners) can be performed by surface plasmon resonance spectroscopy (Biacore, Sweden, manufactures suitable instruments) or ELISA.

Exemplary transcriptional regulators include, without limitation, VP16, VP64, p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet Dev.* 9:499-504. Other exemplary transcription factors include, without limitation, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15, 348-15,353.

In a preferred embodiment, the transcriptional coactivator is a human transcriptional coactivator. In another preferred embodiment, the transcriptional coactivator is a member of the p300/CBP family of co-activators which have histone acetyltransferase activity. p300 is described for example by Eckner et al, 1994 and CBP by Bannister and Kouzarides, 1996. For the purposes of the present invention, reference to p300/CBP refers to human allelic and synthetic variants of p300, and to other mammalian variants and allelic and synthetic variants thereof, as well as fragments of said human and mammalian forms of p300. In one aspect of the assay, the interacting protein is a transcription factor or a second co-activator.

In one aspect of the assay, the interacting protein is any one of RIP140; SRC-1 (NCoA-1); TIF2 (GRIP-1; SRC-2); p (CIP; RAC3; ACTR; AIB-1; TRAM-1; SRC-3); CBP (p300); TRAPs (DRIPs); PGC-1; CARM-1; PRIP (ASC-2; AIB3; RAP250; NRC); GT-198; and SHARP (CoAA; p68; p72). In another aspect of the assay, the interacting protein is any one of TAL 1; p73; MDm2; TBP; HIF-1; Ets-1; RXR; p65; AP-1; Pit-1; HNF-4; Stat2; HPV E2; BRCA1; p45 (NF-E2); c-Jun; c-myb; Tax; Sap 1; YY1; SREBP; ATF-1; ATF-4; Cubitus; Interruptus; Gli3; MRF; AFT-2; JMY; dMad; PyLT: HPV E6; CITTA; Tat; SF-1; E2F; junB; RNA helicase A; C/EBP β; GATA-1; Neuro D; Microphthalimia; E1A; TFIIB; p53; P/CAF; Twist; Myo D; pp9O RSK; c-Fos; and SV40 Large T. In another aspect of the assay, the interacting protein is any one of ERAP140; RIP140; RIP160; Trip1; SWI1 (SNF); ARA70; RAP46; TIF1; TIF2; GRIP1; and TRAP. In another aspect of the invention, the interacting protein is any one of VP16; VP64; p300; CBP; PCAF; SRC1 PvALF; AtHD2A; ERF-2; OsGAI; HALF-1; C1; AP-1; ARF-5; ARF-6; ARF-7; ARF-8; CPRF1; CPRF4; MYC-RP/GP; and TRAB1. In another aspect of the invention, the first co-activator is CBP or p300.

The test compound is selected from compounds as described herein. For example, compounds having the formula (I), (II), (III), (IV), (VI) and (VIa). Typically, a test compound will be evaluated at several different concentrations, where these concentrations will be selected, in part, based on the conditions of the assay, e.g., the concentrations of the first co-activator and the interacting protein. Concentrations in the range of about 0.1 to 10 μM are typical. In one aspect, the assay evaluates the relative efficacy of two compounds to affect the binding interaction between two proteins, where at least one of those two compounds is a compound of the present invention. The more effective compound can than serve as a reference compound in a study of the relationship between compound structure and compound activity.

The libraries of the present invention were screened for bioactivity by various techniques and methods. In general, the screening assay may be performed by (1) contacting the mimetics of a library with a biological target of interest, such as a receptor, to allow binding between the mimetics of the library and the target to occur, and (2) detecting the binding event by an appropriate assay, such as the calorimetric assay disclosed by Lam et al. (*Nature* 354:82-84, 1991) or Griminski et al. (*Biotechnology* 12:1008-1011, 1994) (both of which are incorporated herein by reference). In a preferred embodiment, the library members are in solution and the target is immobilized on a solid phase. Alternatively, the library may be immobilized on a solid phase and may be probed by contacting it with the target in solution.

Table 4 below shows compounds for bioactivity test selected from the library of the present invention and $IC_{50}$ values thereof, which are measured by the Reporter gene assay as described in Example 6.

TABLE 4

| | $IC_{50}$ (μM) OF SELECTED LIBRARY COMPOUNDS | | |
|---|---|---|---|
| No | STRUCTURE | M.W. | $IC_{50}$ (μM) |
| 1 | 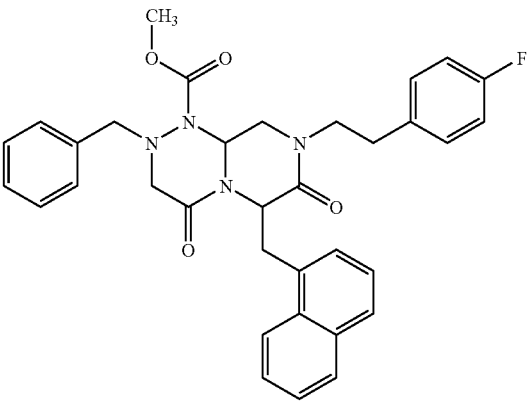 | 580.7 | 12.8 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 2 | 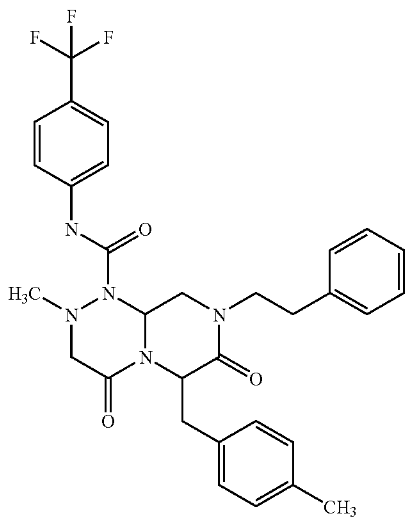 | 579.6 | 12.6 |
| 3 | 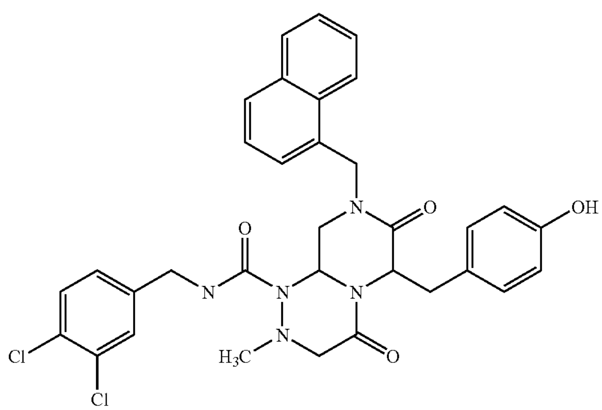 | 632.5 | 13.9 |
| 4 | 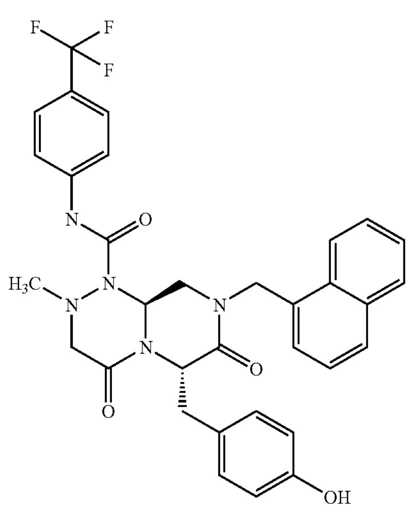 | 617.6 | 11.8 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 5 | 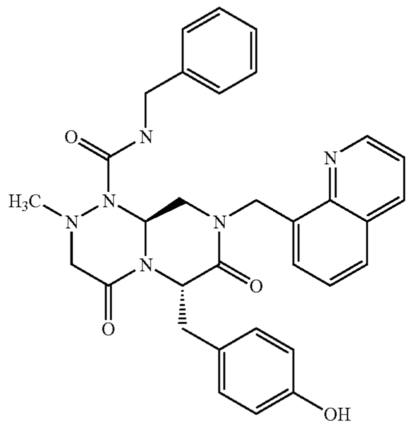 | 564.6 | 6.8 |
| 6 | 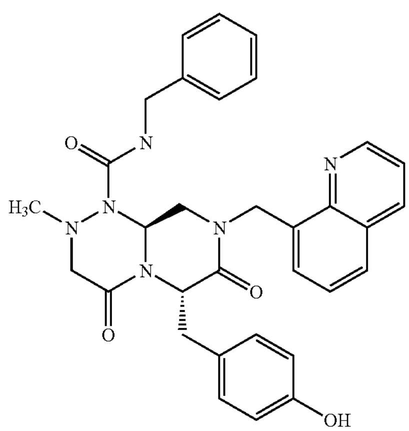 | 564.6 | 6.1 |
| 7 | 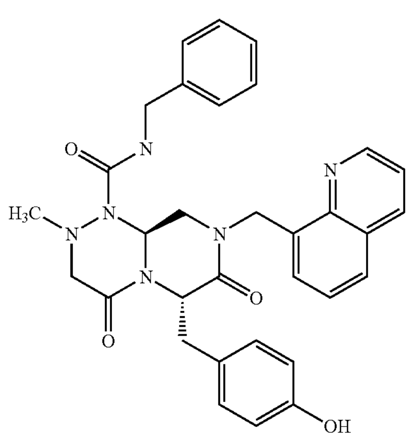 | 564.6 | 2.2 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 8 | 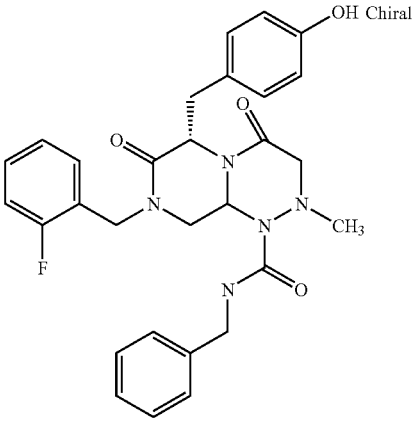 | 531.6 | 14.5 |
| 9 | 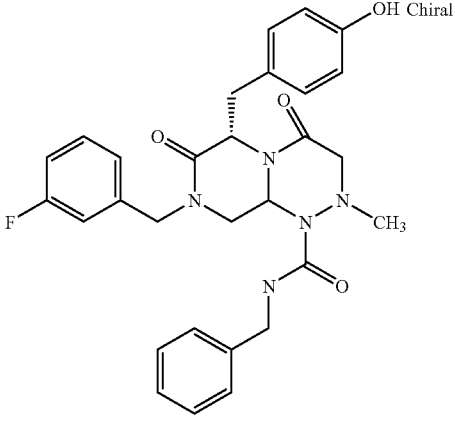 | 531.6 | 6.7 |
| 10 | 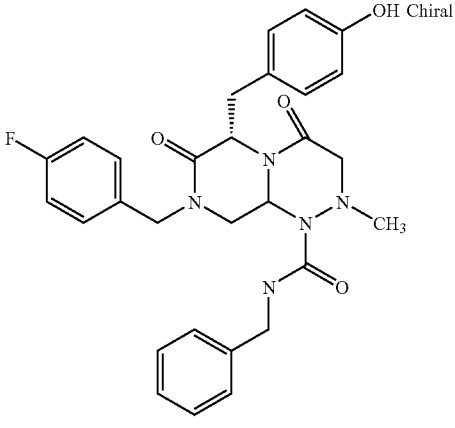 | 531.6 | 4.0 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 11 | 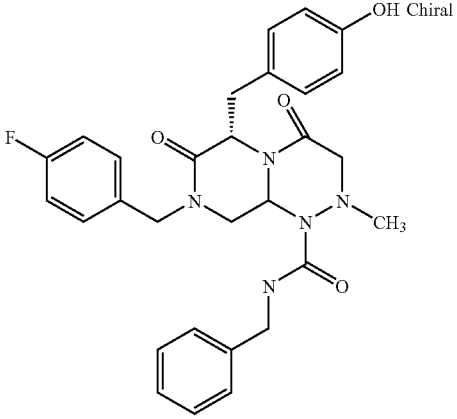 | 531.6 | 4.6 |
| 12 | 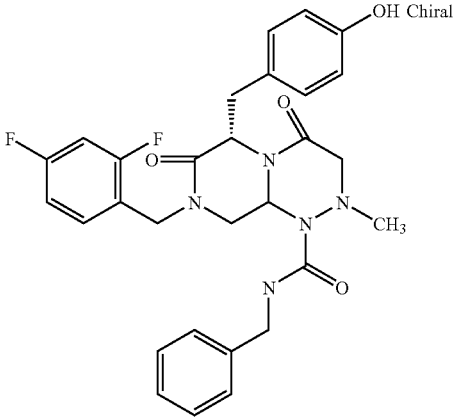 | 549.6 | 9.0 |
| 13 | 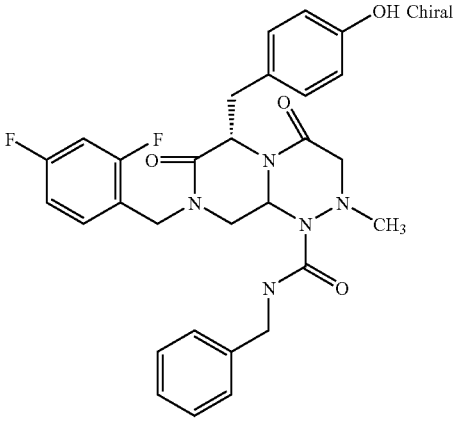 | 549.6 | 6.4 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 14 | 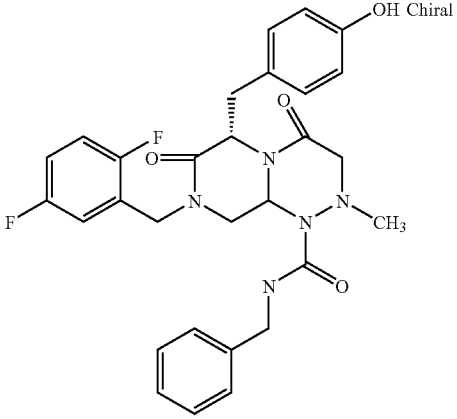 | 549.6 | 17.7 |
| 15 | 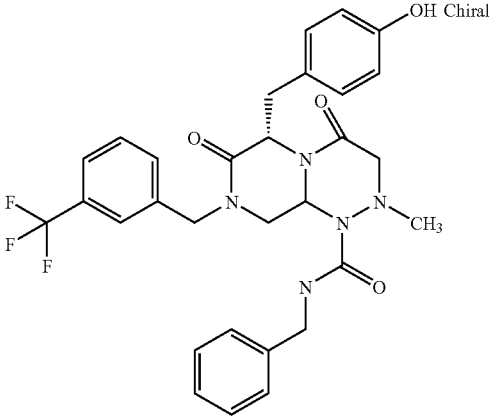 | 581.6 | 4.2 |
| 16 | 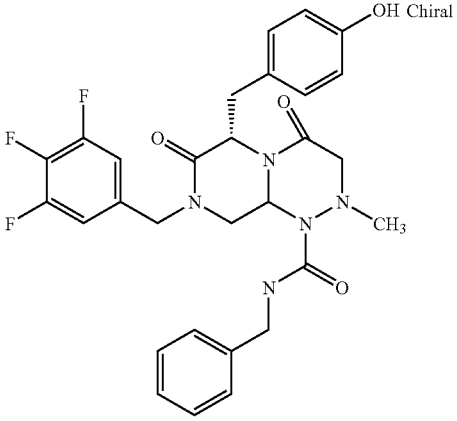 | 567.6 | 3.8 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 17 | 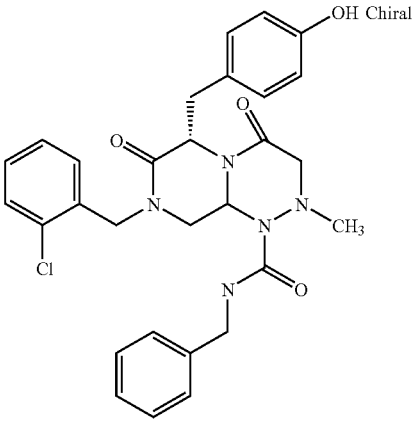 | 548.0 | 14.3 |
| 18 | 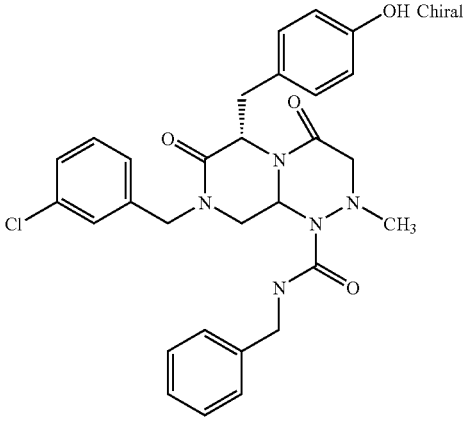 | 548.0 | 3.3 |
| 19 | 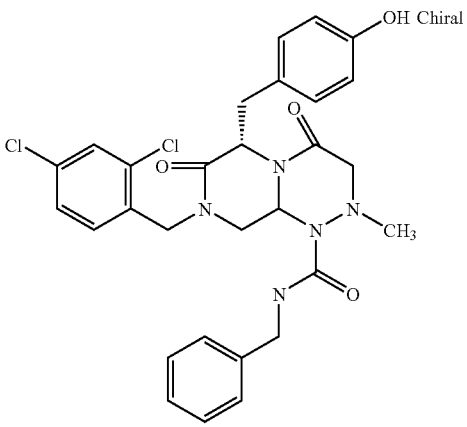 | 582.5 | 11.5 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 20 | 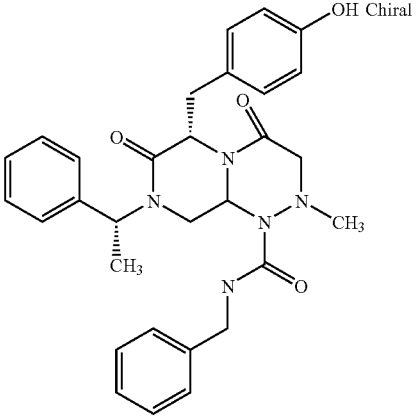 | 527.6 | 5.1 |
| 21 | 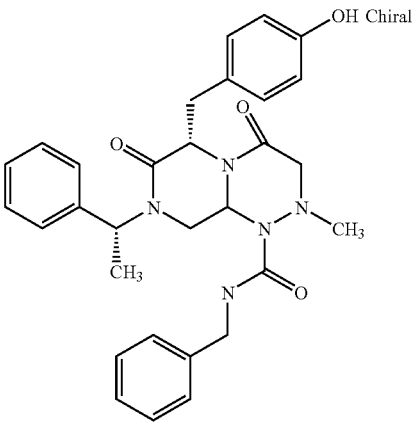 | 527.6 | 5.0 |
| 22 | 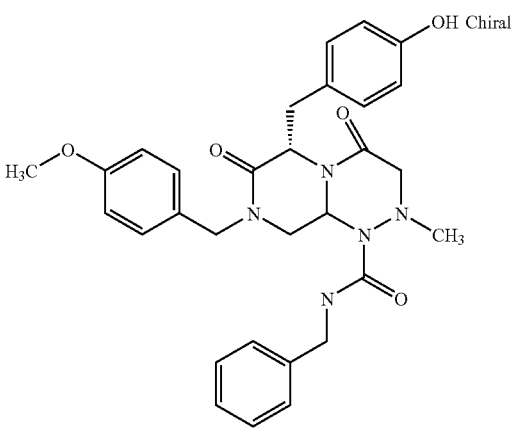 | 543.6 | 10.4 |

TABLE 4-continued
IC$_{50}$ (μM) OF SELECTED LIBRARY COMPOUNDS
| No | STRUCTURE | M.W. | IC$_{50}$ (μM) |
|----|-----------|------|----------------|
| 23 | 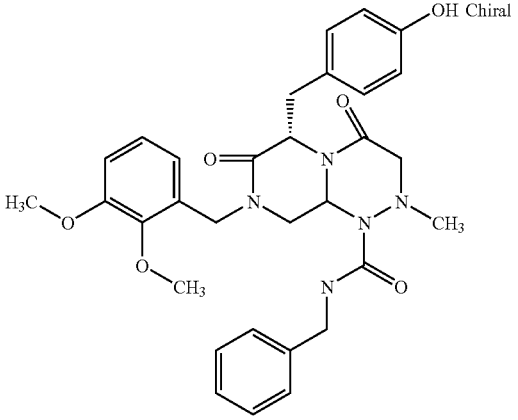 | 573.6 | 10.7 |
| 24 | 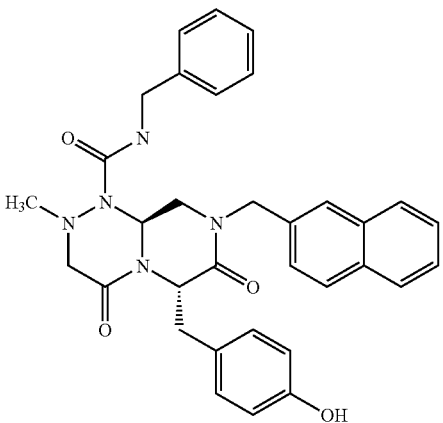 | 563.7 | 5.0 |
| 25 | 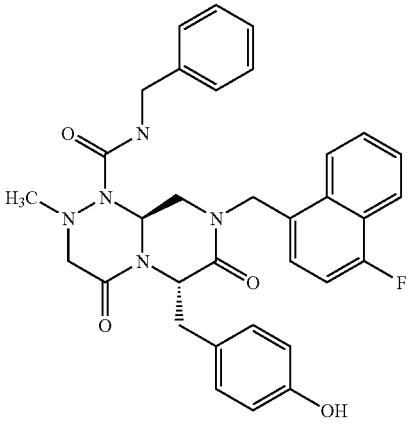 | 581.6 | 3.0 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 26 | 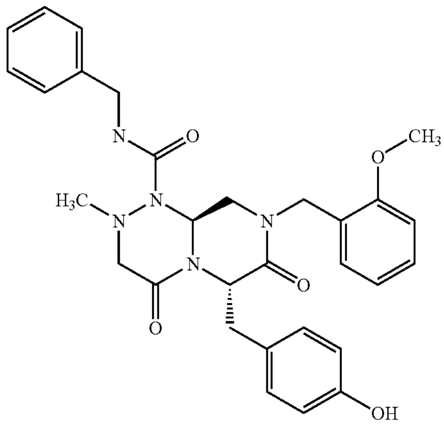 | 543.6 | 7.1 |
| 27 | 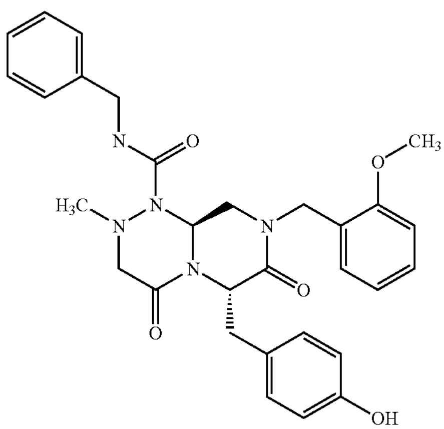 | 543.6 | 5.2 |
| 28 | 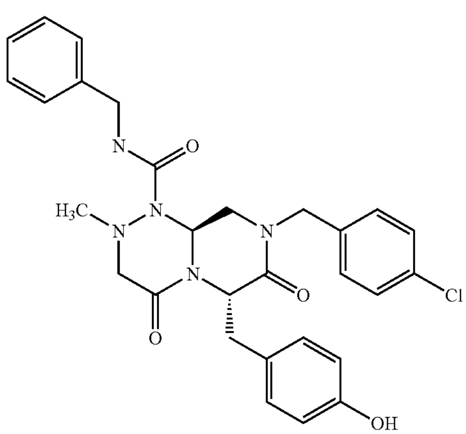 | 548.0 | 7.5 |

TABLE 4-continued
IC$_{50}$ (μM) OF SELECTED LIBRARY COMPOUNDS
| No | STRUCTURE | M.W. | IC$_{50}$ (μM) |
|----|-----------|------|----------------|
| 29 | 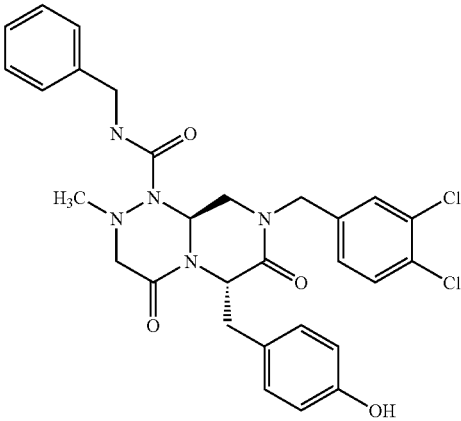 | 582.5 | 3.8 |
| 30 | 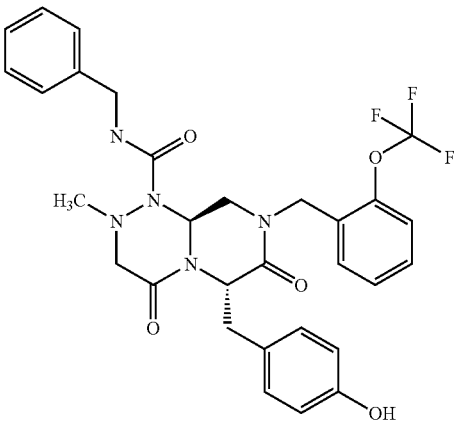 | 597.6 | 7.5 |
| 31 | 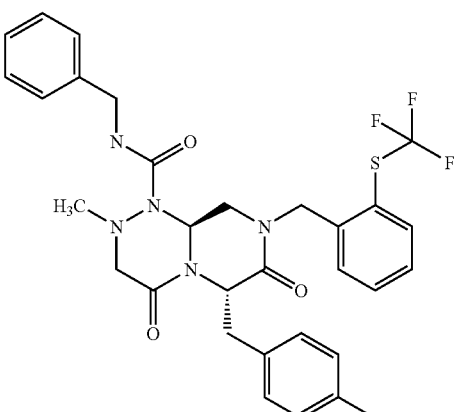 | 613.7 | 11.9 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 32 | 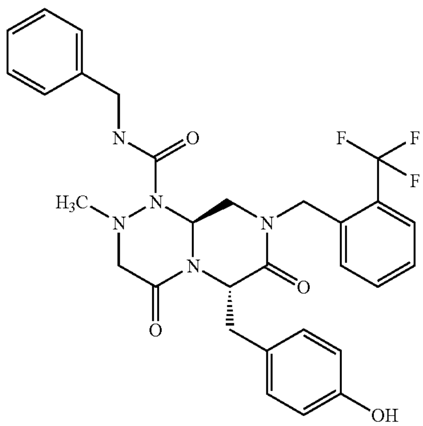 | 581.6 | 4.1 |
| 33 | 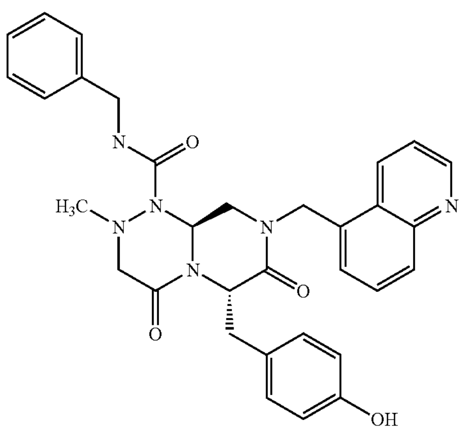 | 564.6 | 13.0 |
| 34 | 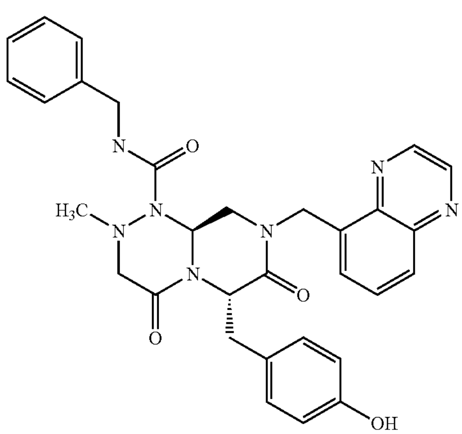 | 565.6 | 4.4 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 35 | 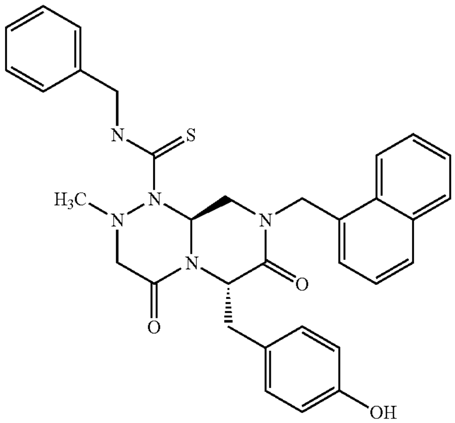 | 579.7 | 11.4 |
| 36 | 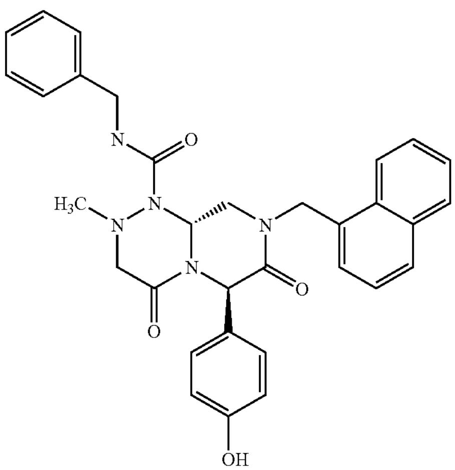 | 549.6 | 12.5 |
| 37 | 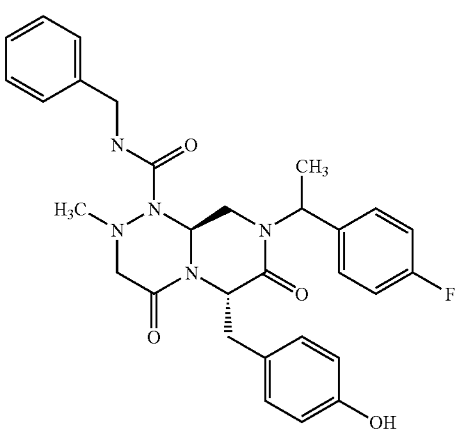 | 545.6 | 2.3 |

TABLE 4-continued
IC$_{50}$ (μM) OF SELECTED LIBRARY COMPOUNDS
| No | STRUCTURE | M.W. | IC$_{50}$ (μM) |
|----|-----------|------|----------------|
| 38 | 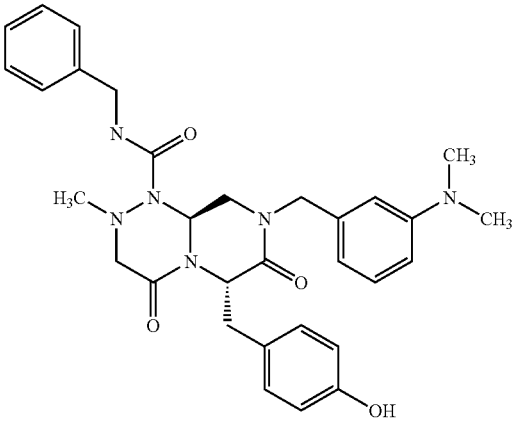 | 556.7 | 7.1 |
| 39 | 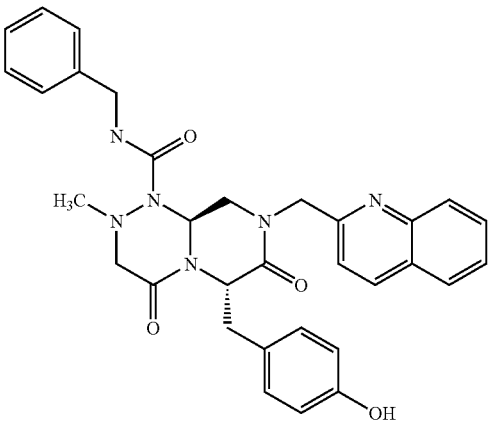 | 564.6 | 9.7 |
| 40 | 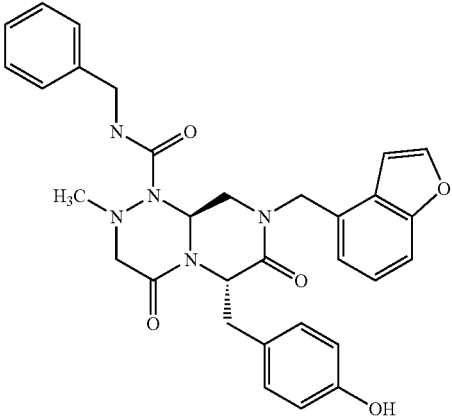 | 553.6 | 7.0 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 41 | 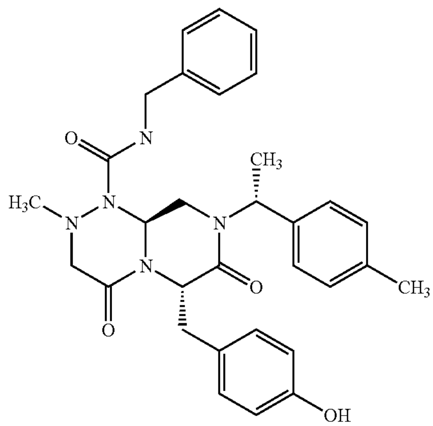 | 541.6 | 13.6 |
| 42 | 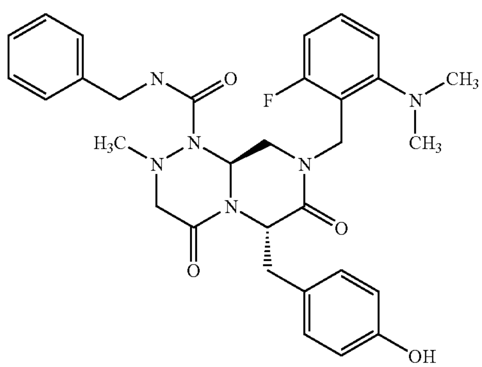 | 574.7 | 18.2 |
| 43 | 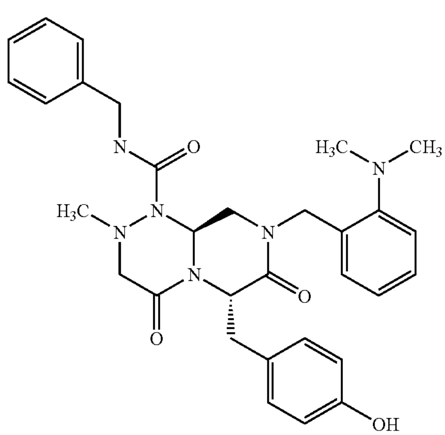 | 556.7 | 5.2 |

TABLE 4-continued

IC₅₀ (μM) OF SELECTED LIBRARY COMPOUNDS

| No | STRUCTURE | M.W. | IC$_{50}$ (μM) |
|---|---|---|---|
| 44 | 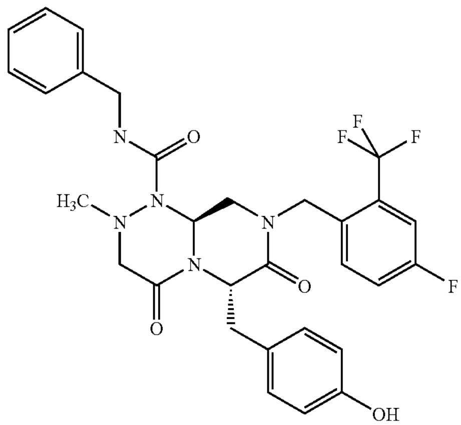 | 599.6 | 1.3 |
| 45 | 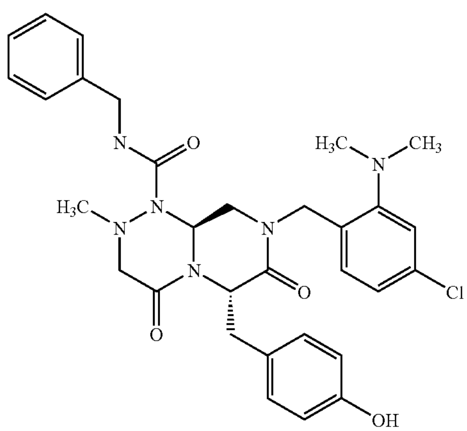 | 591.1 | 2.2 |
| 46 | 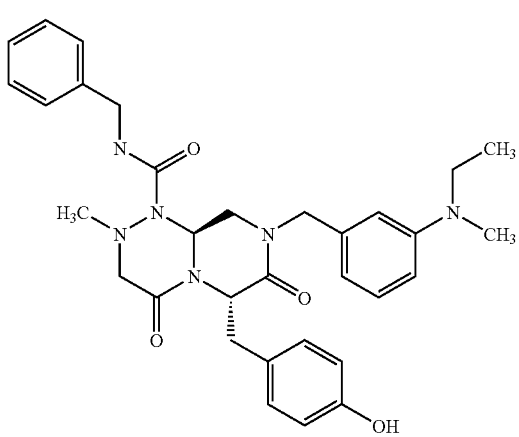 | 570.7 | 4.4 |

TABLE 4-continued
IC₅₀ (μM) OF SELECTED LIBRARY COMPOUNDS
| No | STRUCTURE | M.W. | IC₅₀ (μM) |
|---|---|---|---|
| 47 | 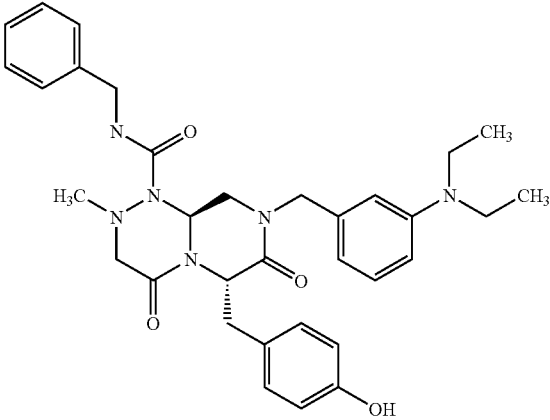 | 584.7 | 3.5 |
| 48 | 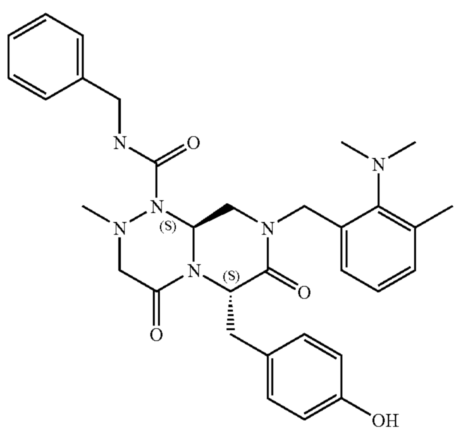 | 570.7 | 10.9 |
| 49 | 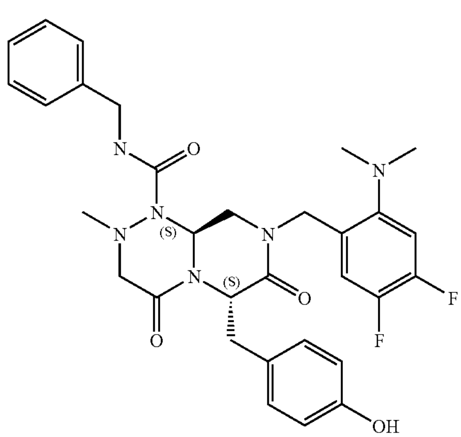 | 592.6 | 1.4 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 50 | 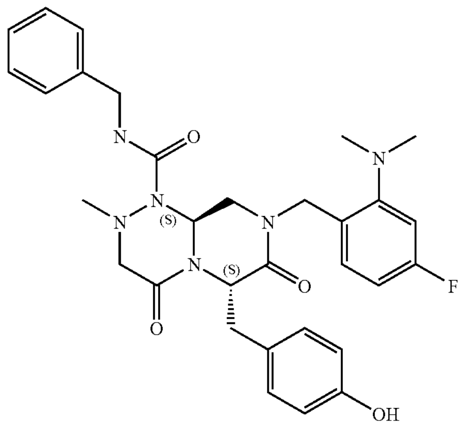 | 574.6 | 1.3 |
| 51 | 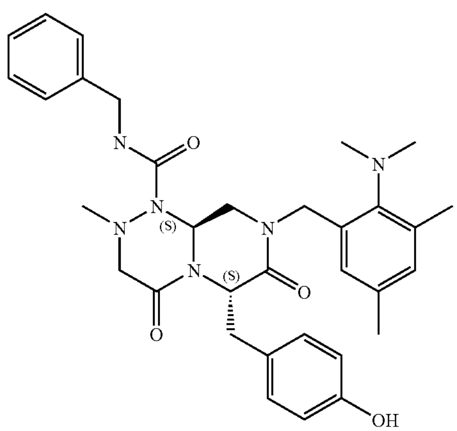 | 584.7 | 4.8 |
| 52 | 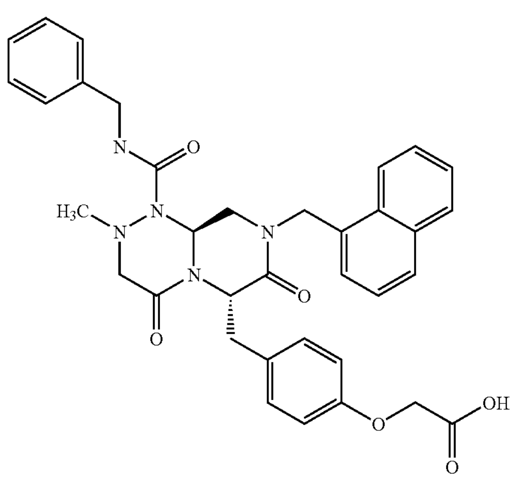 | 621.69 | 25 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 53 | 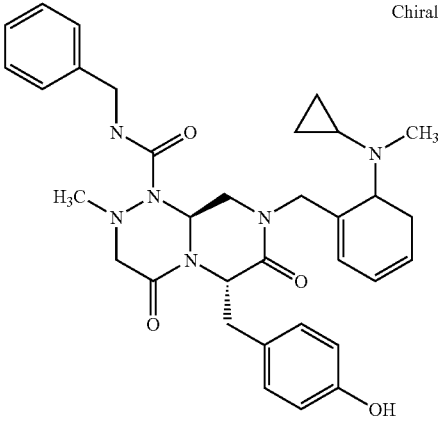 | 584.72 | 9.0 ± 1.5 |
| 54 | 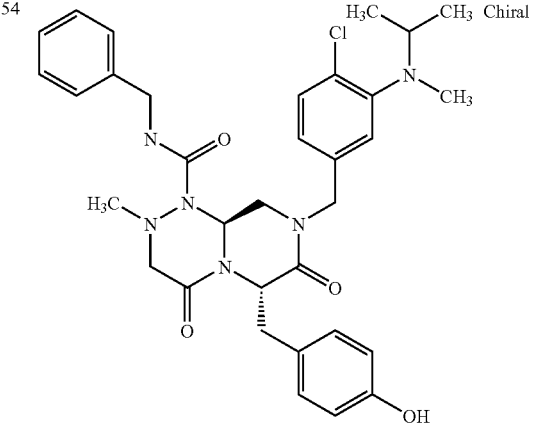 | 619.16 | 23.6 ± 5.6 |
| 55 | 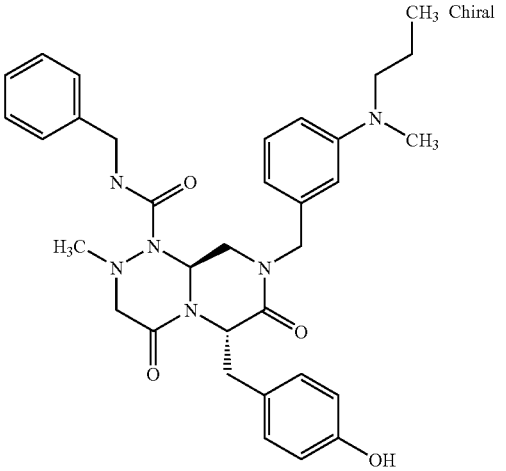 | 584.72 | 7.2 ± 1.4 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 56 | 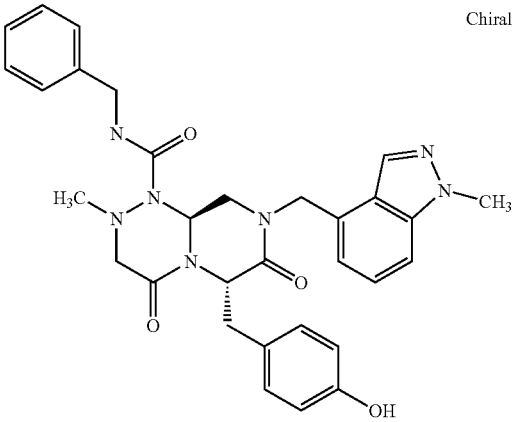 Chiral | 567.65 | 9.3 ± 1.6 |
| 57 | 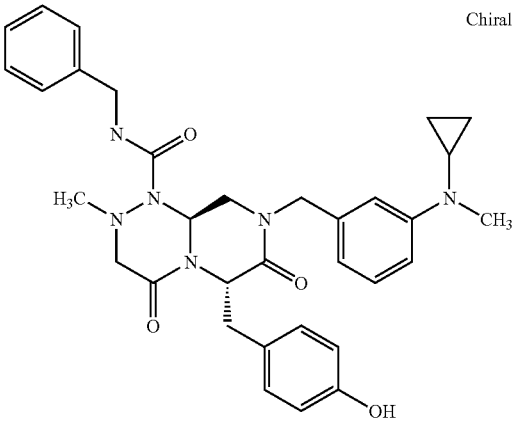 Chiral | 582.70 | 9.4 ± 1.5 |
| 58 | 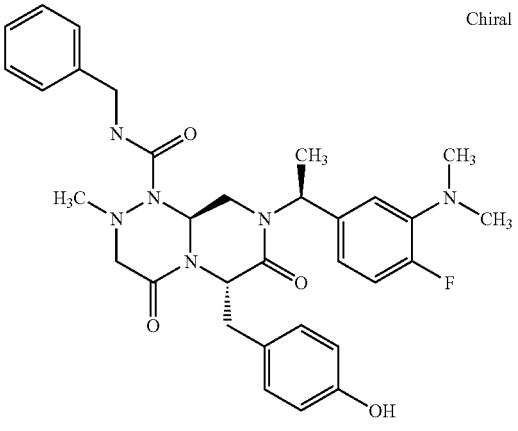 Chiral | 588.68 | 49.1 ± 8.1 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 59 | Chiral | 588.68 | 5.3 ± 1.3 |
| 60 | Chiral | 638.69 | 6.9 ± 1.7 |
| 61 | Chiral | 570.69 | 25.6 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 62 | 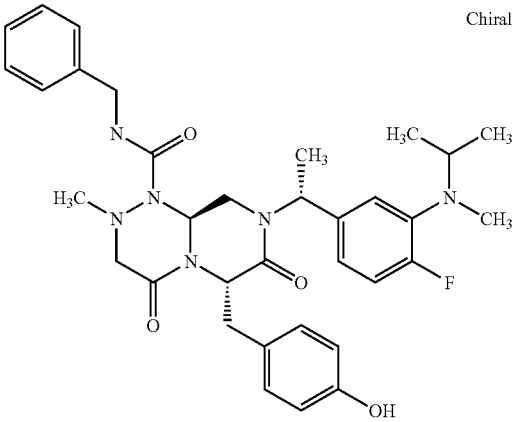 Chiral | 616.73 | 9.7 ± 1.7 |
| 63 | 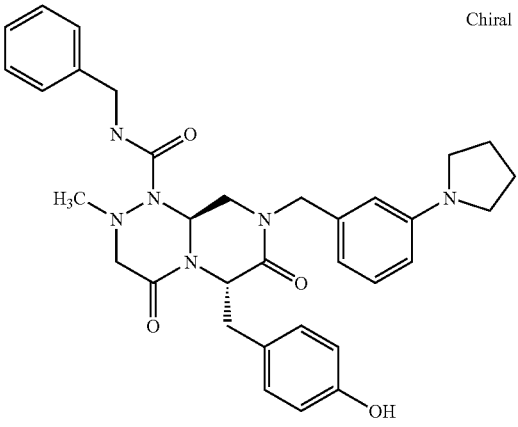 Chiral | 582.70 | 4.1 ± 0.5 |
| 64 | 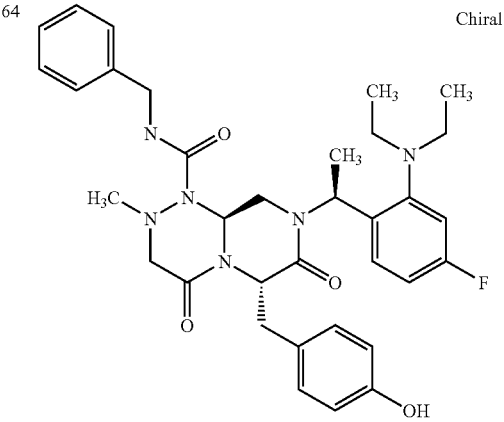 Chiral | 616.73 | 25.3 ± 6.6 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 65 | 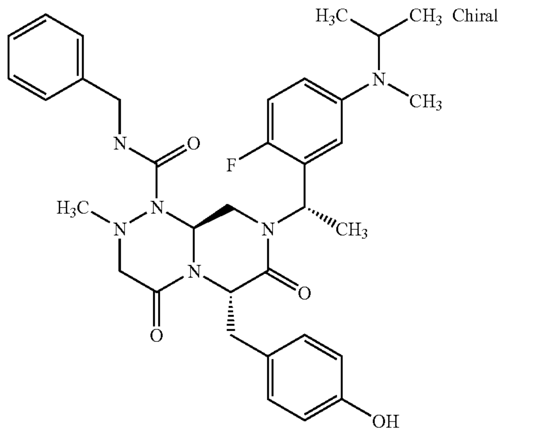 | 616.73 | 19 ± 7.1 |
| 66 | 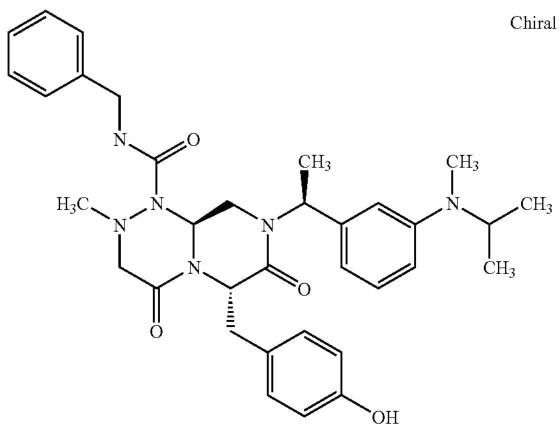 | 598.74 | 11.8 |
| 67 | 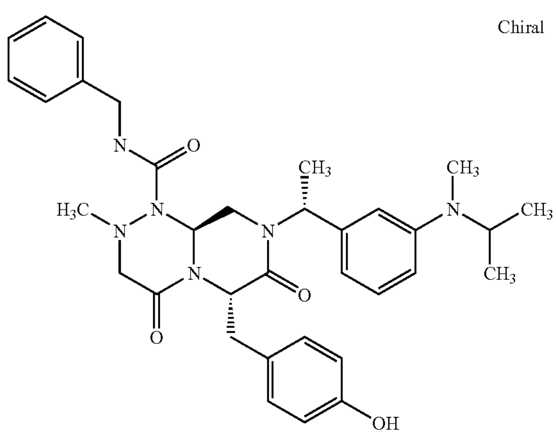 | 598.74 | 6.8 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 68 | 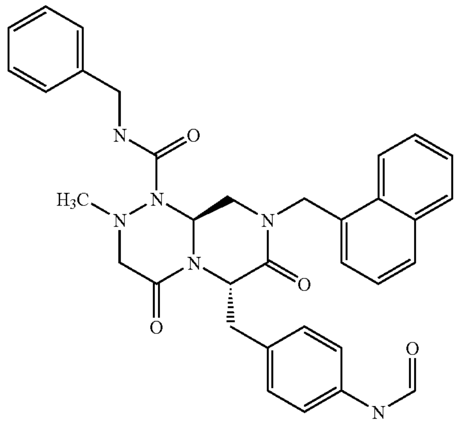 | 590.68 | 4.3 ± 0.8 |
| 69 | Chiral | 563.60 | 1.4 ± 0.7 |
| 70 | Chiral | 553.62 | 8.8 ± 1.9 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 71 | Chiral | 596.73 | 6.5 ± 0.7 |
| 72 | Chiral | 658.76 | 1.6 ± 0.1 |
| 73 | Chiral | 658.76 | 3.6 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 74 | 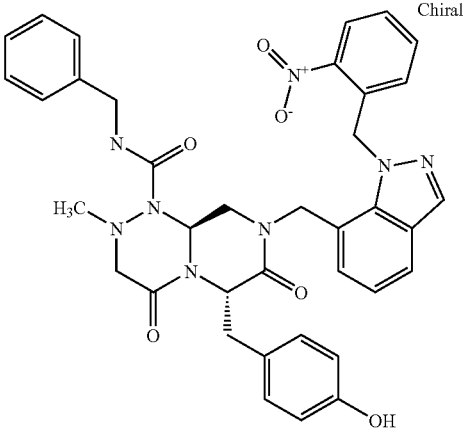 | 688.74 | 2.1 ± 0.2 |
| 75 | 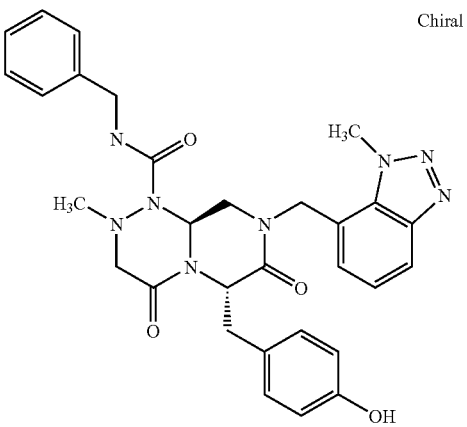 | 568.64 | 50.5 ± 18.4 |
| 76 | 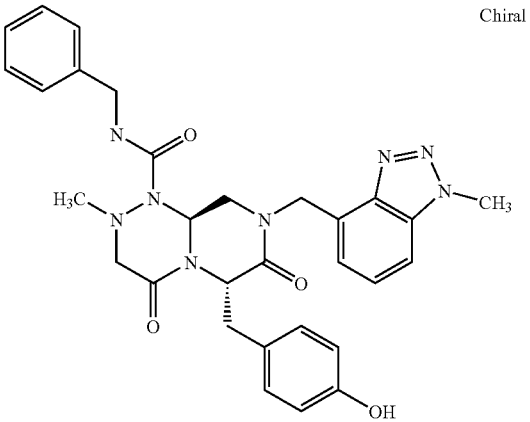 | 568.64 | 10.7 ± 2.5 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 77 | Chiral | 570.67 | 7.2 ± 2.5 |
| 78 | Chiral | 570.69 | 4.3 ± 0.9 |
| 79 | Chiral | 632.76 | 16.5 ± 4.8 |

TABLE 4-continued
IC₅₀ (μM) OF SELECTED LIBRARY COMPOUNDS
| No | STRUCTURE | M.W. | IC$_{50}$ (μM) |
|----|-----------|------|----------------|
| 80 | 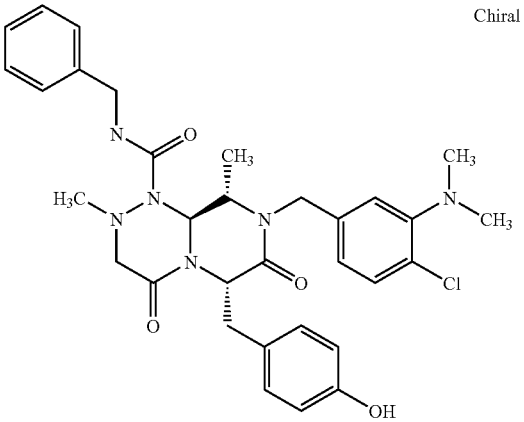 Chiral | 605.14 | 7.9 ± 2.0 |
| 81 | 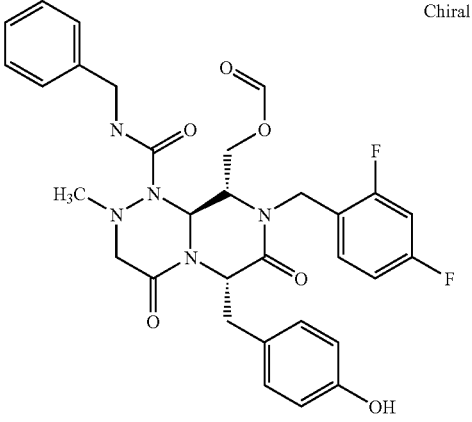 Chiral | 607.61 | 66.1 ± 6.8 |
| 82 | 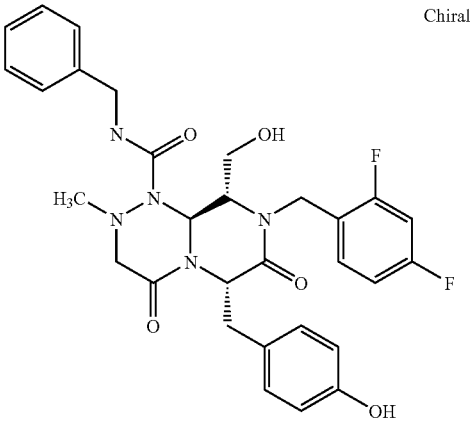 Chiral | 579.60 | 68.1 ± 8.9 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 83 | Chiral | 605.14 | 46.4 ± 3.7 |
| 84 | Chiral | 740.79 | 46.7 ± 6.7 |
| 85 | Chiral | 549.67 | 15.6 ± 2.2 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 86 | Chiral | 658.76 | 9.9 ± 2.6 |
| 87 | Chiral | 624.74 | 8.1 ± 0.8 |
| 88 | Chiral | 658.76 | 2.2 ± 0.2 |

TABLE 4-continued
IC₅₀ (μM) OF SELECTED LIBRARY COMPOUNDS
| No | STRUCTURE | M.W. | IC₅₀ (μM) |
|---|---|---|---|
| 89 | 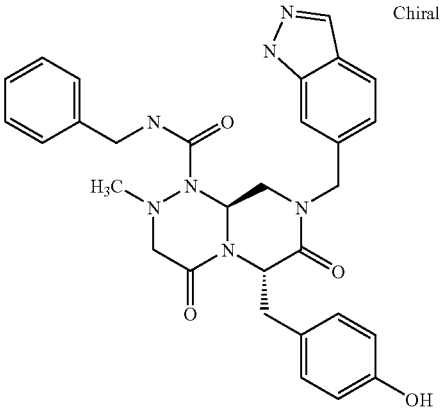 | 553.62 | 13.9 ± 0.9 |
| 90 | 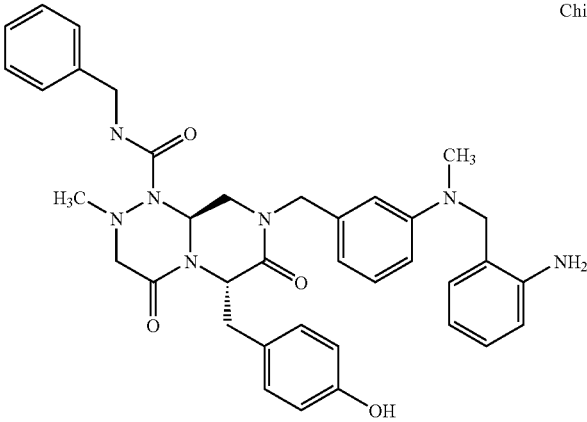 | 647.78 | 3.9 |
| 91 | 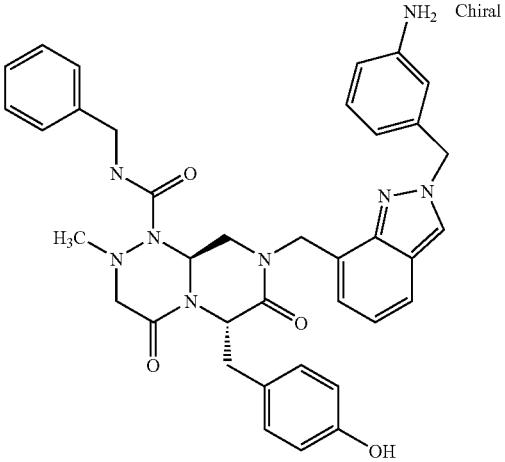 | 658.76 | 2.9 ± 0.2 |

TABLE 4-continued
IC₅₀ (μM) OF SELECTED LIBRARY COMPOUNDS
| No | STRUCTURE | M.W. | IC$_{50}$ (μM) |
|---|---|---|---|
| 92 | 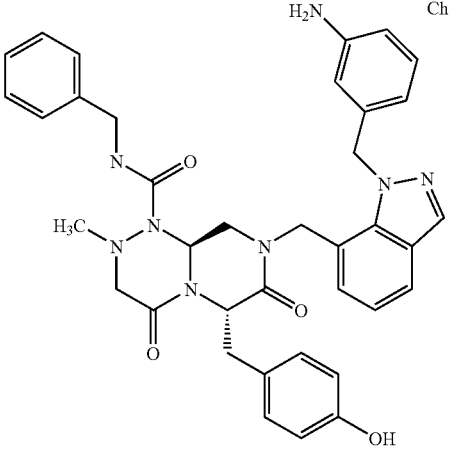 | 658.76 | 3.8 ± 1.2 |
| 93 | 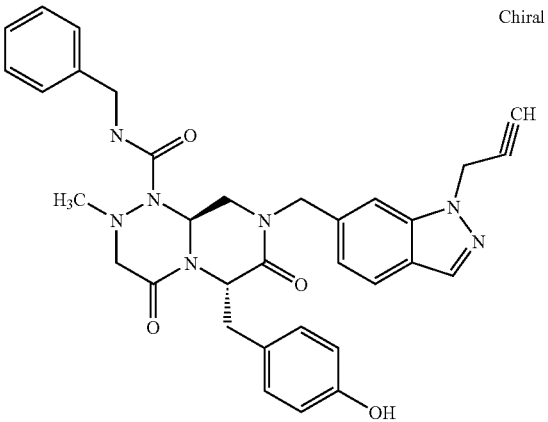 | 591.67 | 6.8 ± 1.3 |
| 94 | 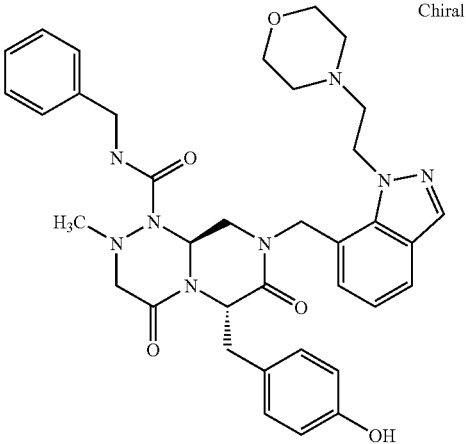 | 666.78 | 7.6 ± 0.6 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 95 | Chiral | 564.64 | 13.3 ± 1.4 |
| 96 | Chiral | 591.67 | 8.1 ± 0.9 |
| 97 | Chiral | 598.70 | 12.6 ± 1.2 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 98 | 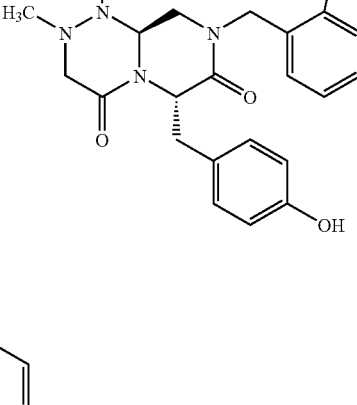 Chiral | 666.78 | 14.4 ± 2.2 |
| 99 | 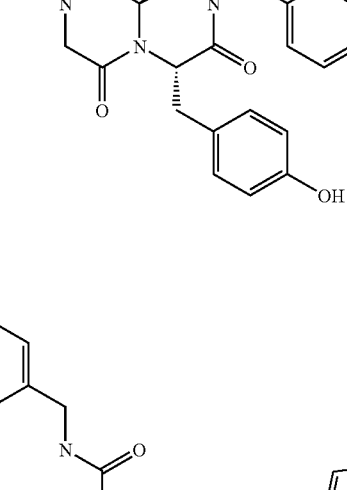 Chiral | 701.78 | 2.4 ± 0.3 |
| 100 | 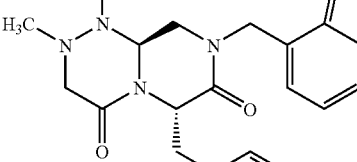 Chiral | 666.78 | 2.7 ± 0.3 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 101 | 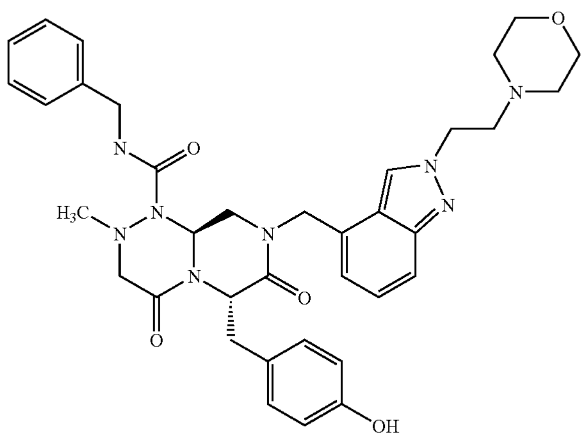 | 666.78 | 3.9 |
| 102 | 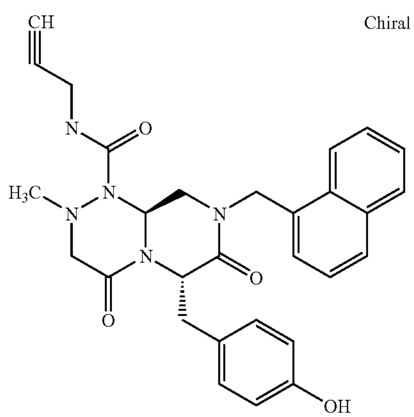 | 511.58 | 62.0 ± 17.0 |
| 103 | 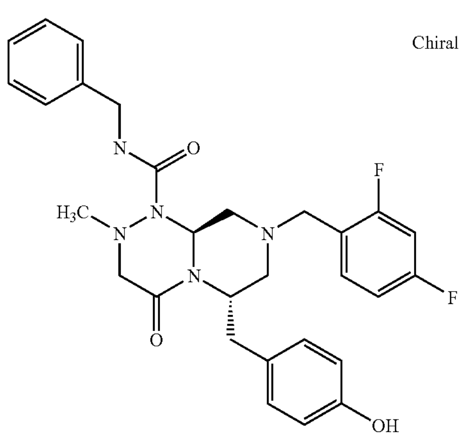 | 535.59 | 14.5 ± 1.7 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 104 | 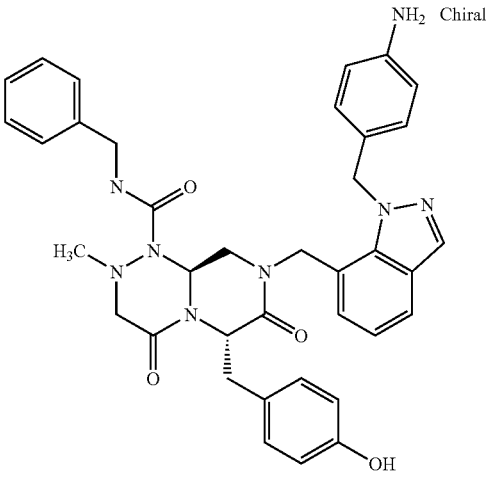 | 658.76 | 4.6 ± 0.4 |
| 105 | 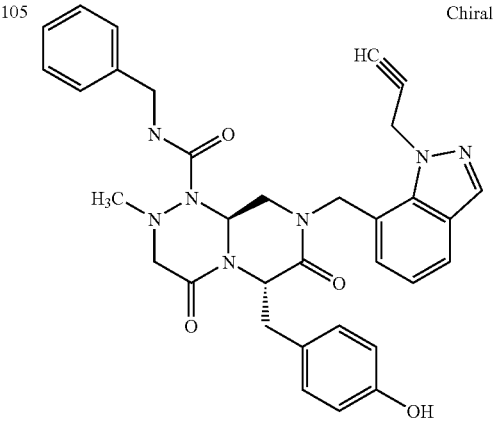 | 591.67 | 16.6 ± 2.7 |
| 106 | 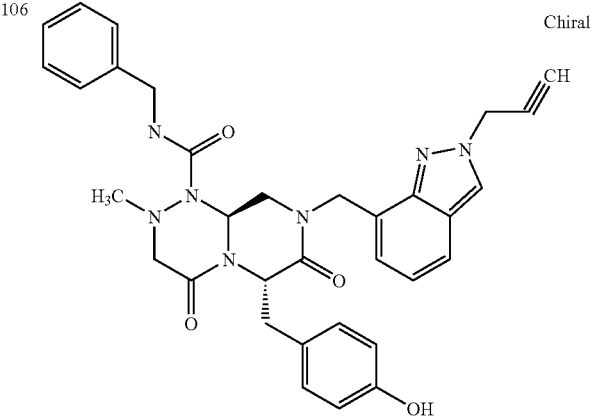 | 591.67 | 2.6 ± 0.2 |

TABLE 4-continued
IC$_{50}$ (μM) OF SELECTED LIBRARY COMPOUNDS
| No | STRUCTURE | M.W. | IC$_{50}$ (μM) |
|----|-----------|------|----------------|
| 107 | 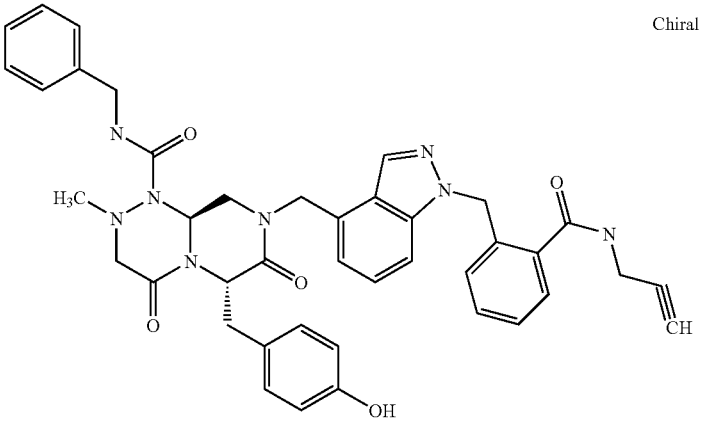 Chiral | 724.82 | 2.7 ± 0.3 |
| 108 | 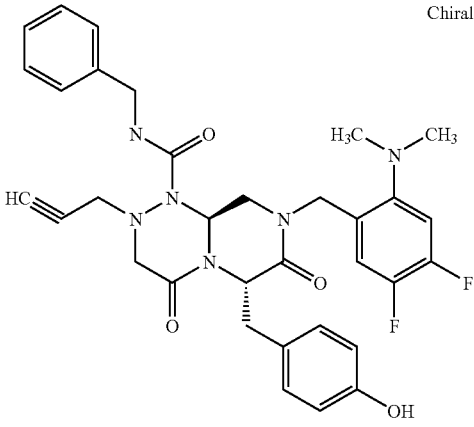 Chiral | 616.67 | 1.6 ± 0.1 |
| 109 | 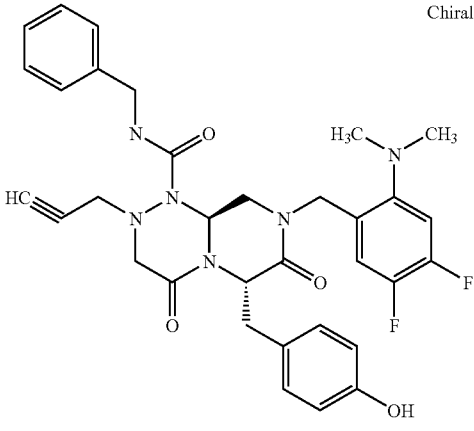 Chiral | 616.67 | 2.1 |

TABLE 4-continued
IC$_{50}$ (μM) OF SELECTED LIBRARY COMPOUNDS
| No | STRUCTURE | M.W. | IC$_{50}$ (μM) |
|----|-----------|------|----------------|
| 110 | 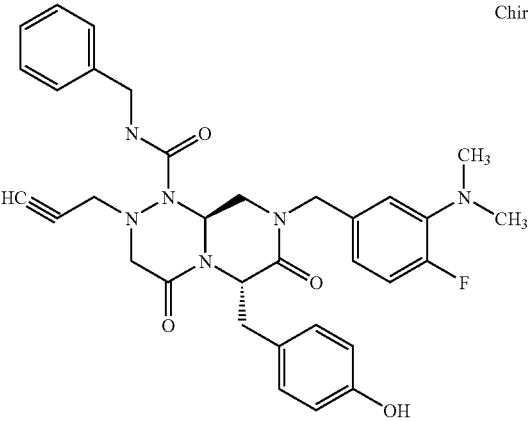 Chiral | 615.13 | 3.8 ± 0.6 |
| 111 | 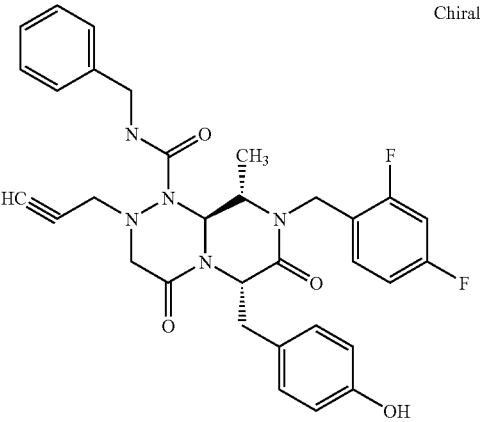 Chiral | 587.62 | 7.2 ± 0.8 |
| 112 | 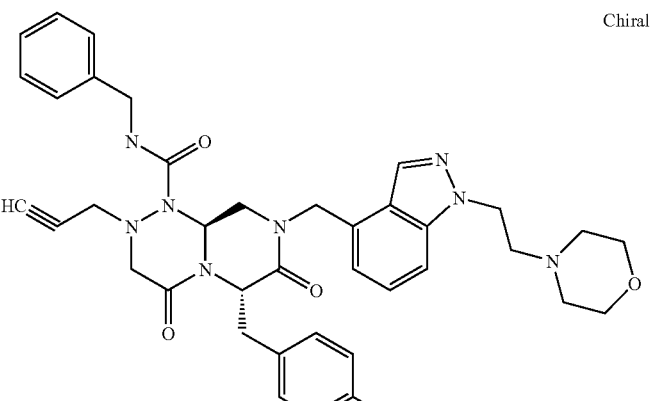 Chiral | 690.80 | 4.1 ± 0.8 |

TABLE 4-continued
IC$_{50}$ (μM) OF SELECTED LIBRARY COMPOUNDS
| No | STRUCTURE | M.W. | IC$_{50}$ (μM) |
|----|-----------|------|----------------|
| 113 | 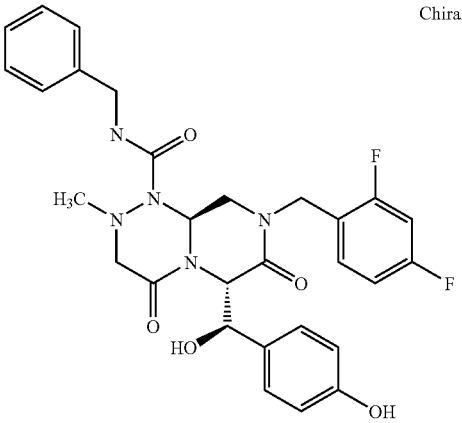 Chiral | 565.57 | 7.3 ± 1.1 |
| 114 | 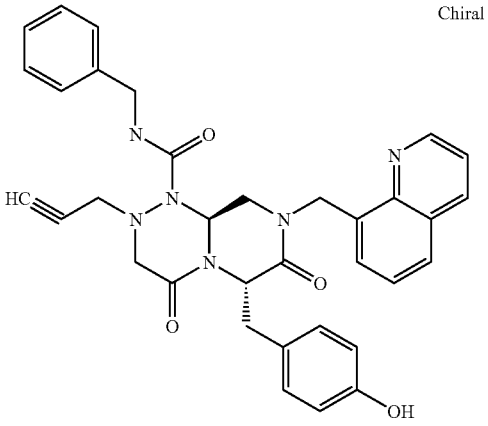 Chiral | 588.67 | 0.4 ± 0.04 |
| 115 | 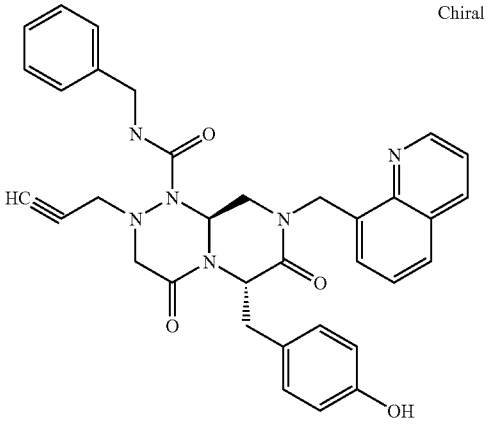 Chiral | 588.67 | 0.8 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 116 | Chiral | 570.69 | 8.0 ± 0.7 |
| 117 | Chiral | 598.70 | 6.9 ± 0.6 |
| 118 | Chiral | 622.72 | 0.8 ± 0.1 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 119 | Chiral | 551.60 | 8.8 ± 1.3 |
| 120 | Chiral | 640.78 | 34.4 ± 4.9 |
| 121 | Chiral | 578.67 | 3.0 ± 0.4 |

TABLE 4-continued

IC$_{50}$ (µM) OF SELECTED LIBRARY COMPOUNDS

| No | STRUCTURE | M.W. | IC$_{50}$ (µM) |
|---|---|---|---|
| 122 | Chiral | 592.70 | 2.1 ± 0.4 |
| 123 | Chiral | 612.73 | 11.7 ± 1.0 |
| 124 | Chiral | 626.75 | 6.4 ± 0.4 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 125 | Chiral | 605.14 | 9.8 ± 0.7 |
| 126 | Chiral | 619.16 | 10.3 ± 1.5 |
| 127 | Chiral | 624.74 | 1.8 ± 0.2 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 128 | Chiral | 590.68 | 0.4 ± 0.1 |
| 129 | Chiral | 617.15 | 2.4 ± 0.5 |
| 130 | Chiral | 642.75 | 6.1 ± 0.4 |

TABLE 4-continued
IC$_{50}$ (μM) OF SELECTED LIBRARY COMPOUNDS
| No | STRUCTURE | | M.W. | IC$_{50}$ (μM) |
|---|---|---|---|---|
| 131 | 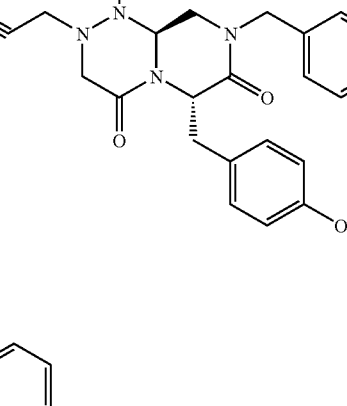 | Chiral | 666.78 | 2.2 ± 0.3 |
| 132 | 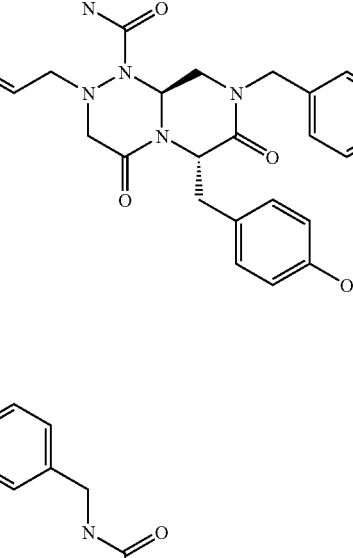 | Chiral | 668.79 | 2.3 ± 0.5 |
| 133 | 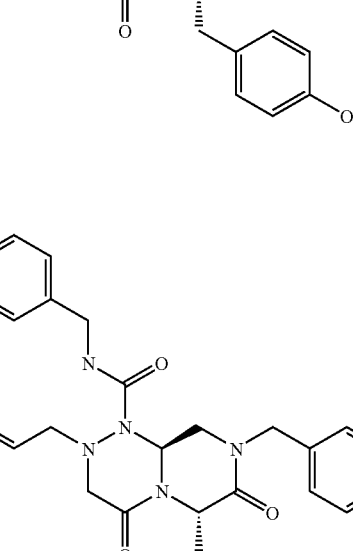 | Chiral | 638.77 | 3.5 ± 0.7 |

TABLE 4-continued
IC₅₀ (μM) OF SELECTED LIBRARY COMPOUNDS
| No | STRUCTURE | | M.W. | IC₅₀ (μM) |
|---|---|---|---|---|
| 134 | 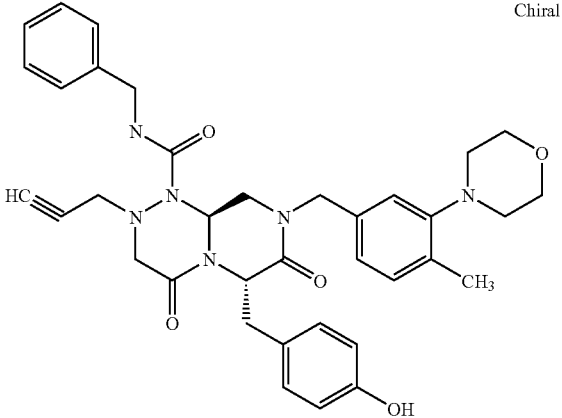 | Chiral | 636.75 | 4.5 ± 0.9 |
| 135 | 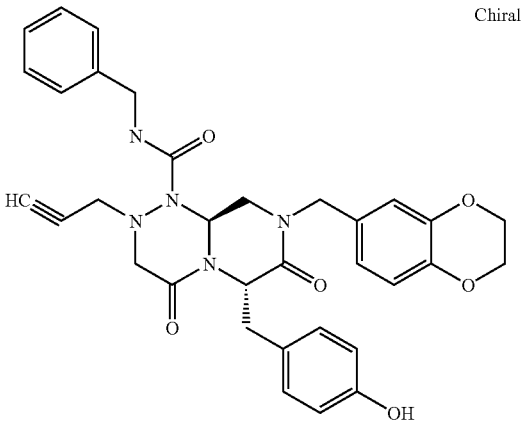 | Chiral | 595.65 | 2.4 ± 0.7 |
| 136 | 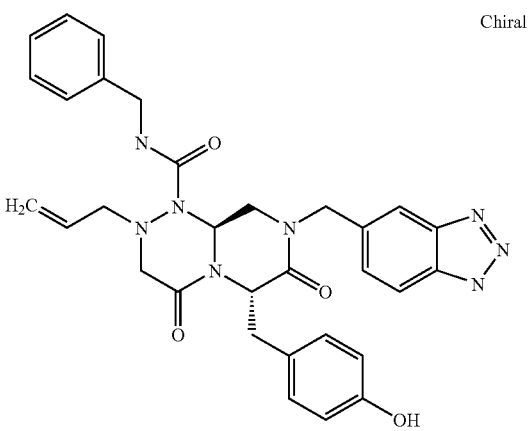 | Chiral | 580.65 | 28.0 ± 2.9 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 137 | Chiral | 625.13 | 0.6 ± 0.1 |
| 138 | Chiral | 623.11 | 1.0 ± 0.2 |
| 139 | Chiral | 659.18 | 1.1 ± 0.1 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 140 | Chiral 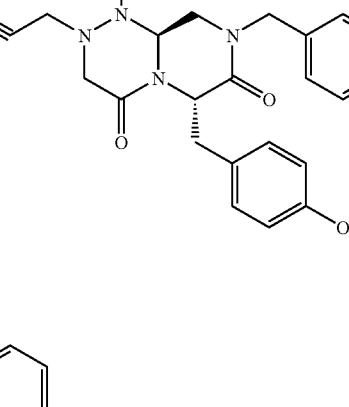 | 657.17 | 2.7 ± 0.3 |
| 141 | Chiral 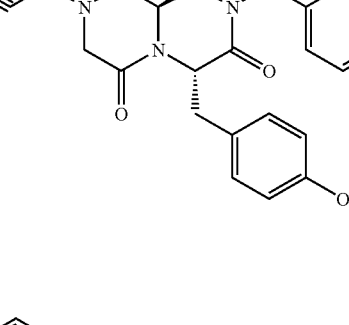 | 594.69 | 1.8 ± 0.3 |
| 142 | Chiral 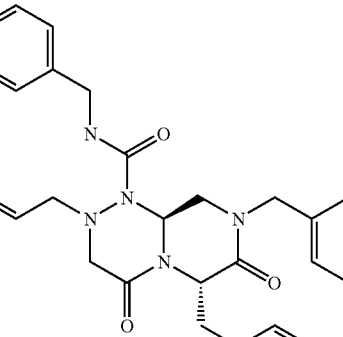 | 596.71 | 1.6 ± 0.4 |

TABLE 4-continued

IC₅₀ (μM) OF SELECTED LIBRARY COMPOUNDS

| No | STRUCTURE | M.W. | IC$_{50}$ (μM) |
|----|-----------|------|----------------|
| 143 | Chiral | 575.61 | 1.3 ± 0.2 |
| 144 | Chiral | 573.60 | 2.1 ± 0.2 |
| 145 | Chiral | 610.71 | 0.3 ± 0.04 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 146 | Chiral | 608.70 | 16.7 ± 1.4 |
| 147 | Chiral | 610.71 | 9.4 ± 1.0 |
| 148 | Chiral | 627.14 | 2.6 ± 0.3 |

TABLE 4-continued

IC$_{50}$ (μM) OF SELECTED LIBRARY COMPOUNDS

| No  | STRUCTURE | M.W. | IC$_{50}$ (μM) |
|-----|-----------|------|----------------|
| 149 | Chiral    | 639.15 | 31.0 ± 6.4 |
| 150 | Chiral    | 596.68 | 12.7 ± 0.7 |
| 151 | Chiral    | 596.68 | 9.2 ± 0.1 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 152 | Chiral | 622.72 | 1.2 ± 0.3 |
| 153 | Chiral | 622.72 | 1.9 ± 0.3 |
| 154 | Chiral | 608.74 | 3.2 ± 0.4 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 155 | 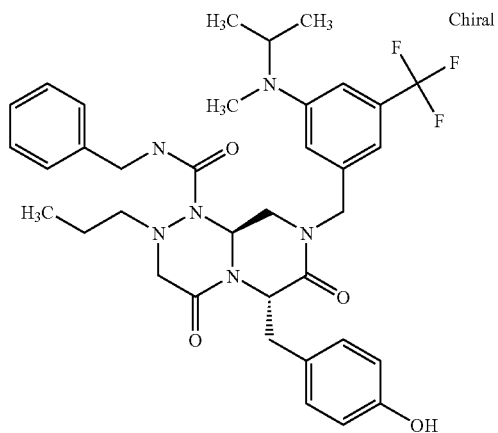 Chiral | 680.77 | 30.5 ± 4.1 |
| 156 | 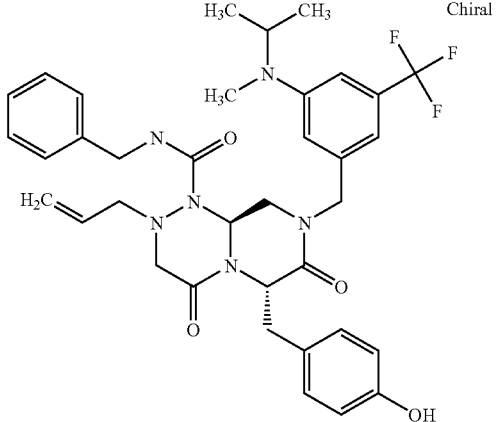 Chiral | 678.75 | 13.3 ± 1.6 |
| 157 | 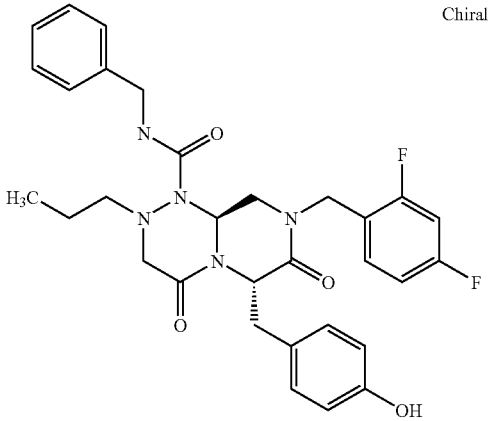 Chiral | 577.63 | 4.2 ± 0.1 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 158 | Chiral | 610.71 | 0.9 ± 0.02 |
| 159 | Chiral | 602.64 | 2.7 ± 0.2 |
| 160 | Chiral | 604.66 | 10.6 ± 0.5 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 161 | 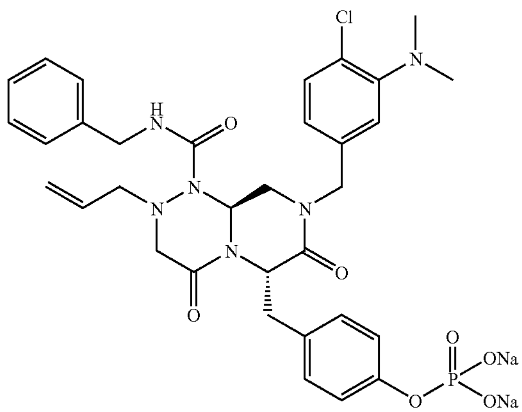 | 741 | 1.8 ± 0.2 |
| 162 | 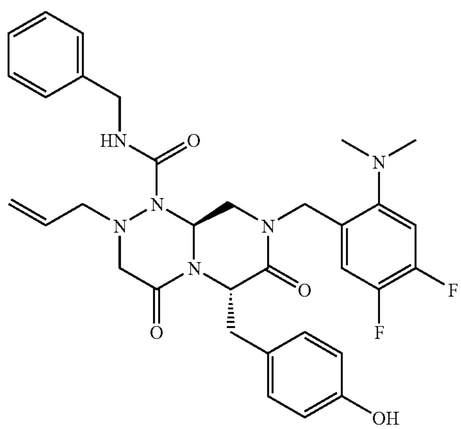 | 618 | 1.8 ± 0.6 |
| 163 | 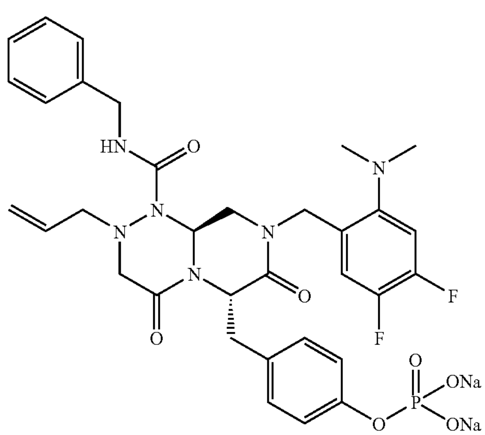 | 742 | 1.7 ± 0.5 |

TABLE 4-continued

IC$_{50}$ (μM) OF SELECTED LIBRARY COMPOUNDS

| No | STRUCTURE | M.W. | IC$_{50}$ (μM) |
|----|-----------|------|----------------|
| 164 | 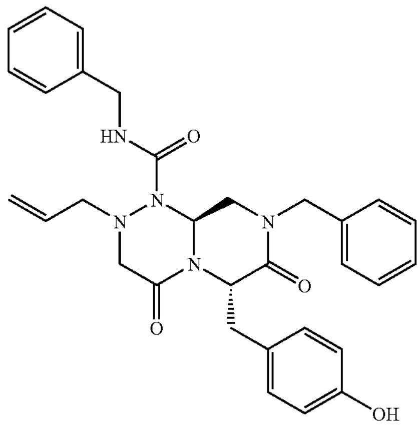 | 539 | 1.1 ± 0.2 |
| 165 | 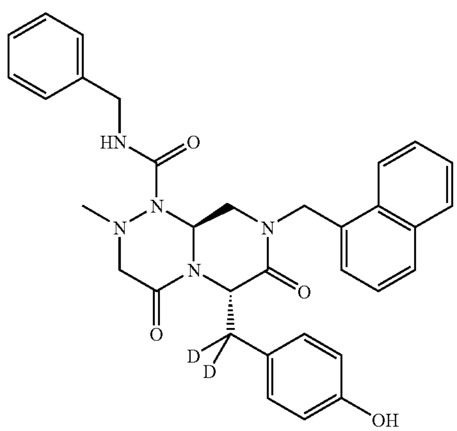 | 565 | 3.9 ± 0.3 |
| 166 | 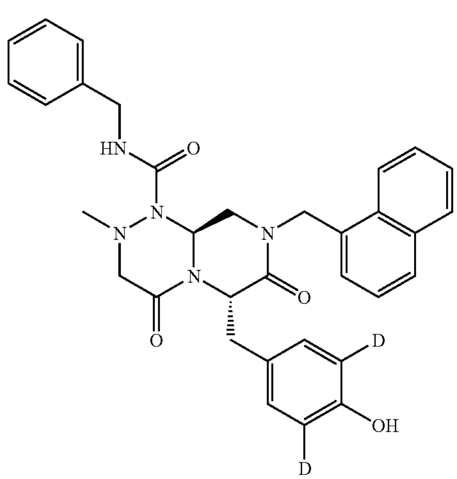 | 565 | 3.3 ± 0.2 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 167 | 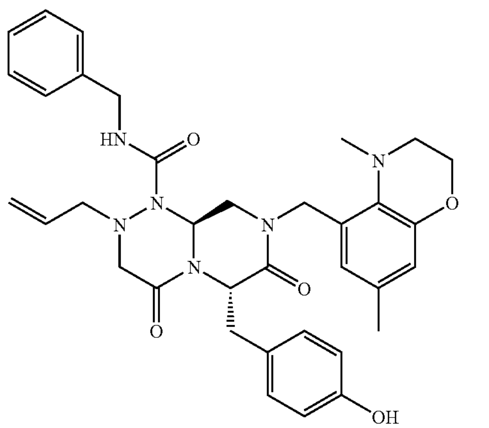 | 624 | 1.3 ± 0.1 |
| 168 | 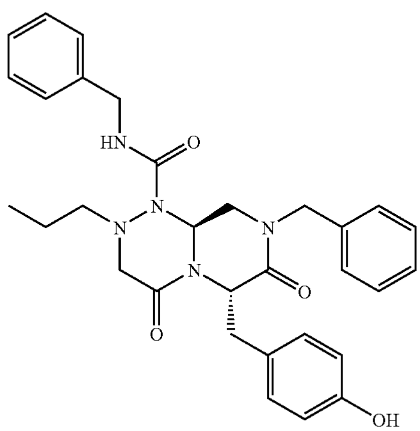 | 541 | 3.5 ± 0.3 |
| 169 | 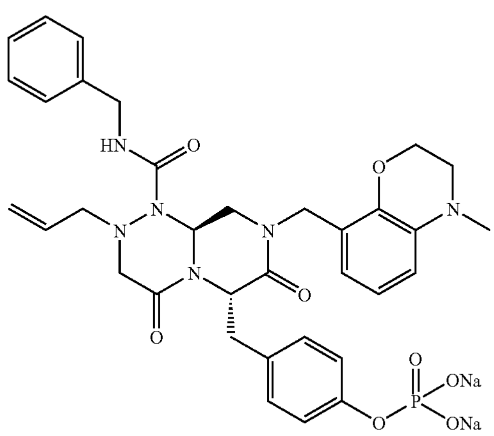 | 734 | 1.0 ± 0.1 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 170 | 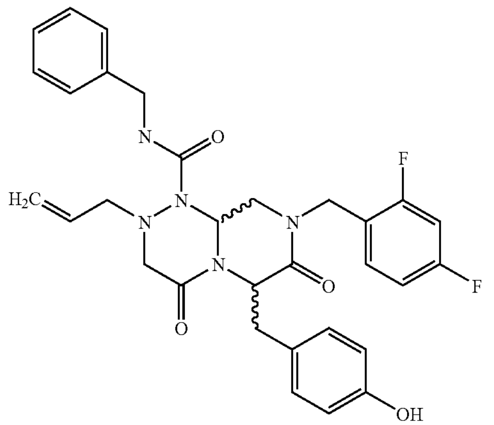 | 575 | 1.5 ± 0.5 |
| 171 | 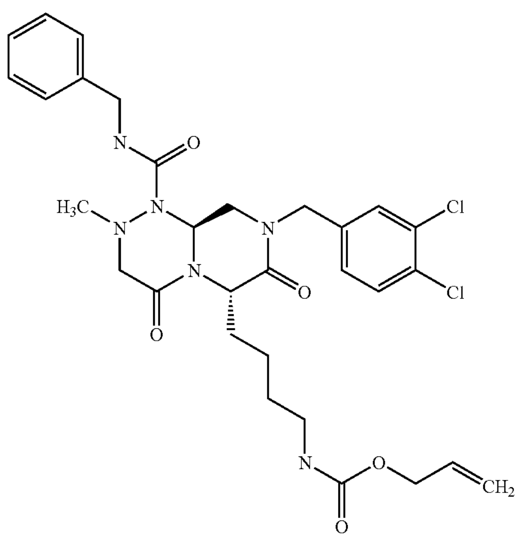 | 617 | 44.7 ± 6.6 |
| 172 | Chiral | 566 | 2.9 ± 0.4 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 173 | 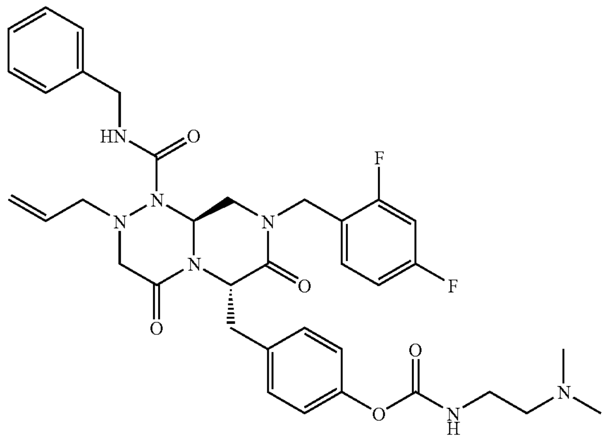 | 690 | 1.8 ± 0.2 |
| 174 | 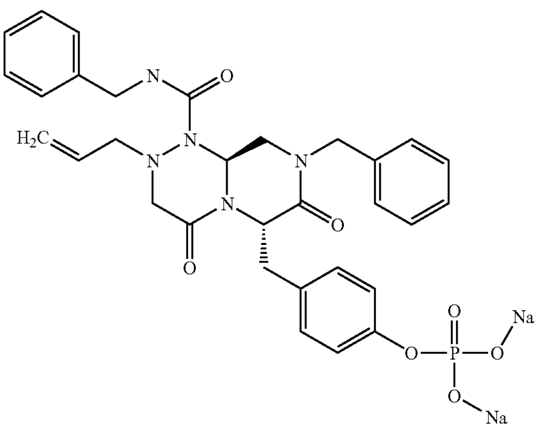 | 664 | 1.0 ± 0.1 |
| 175 | 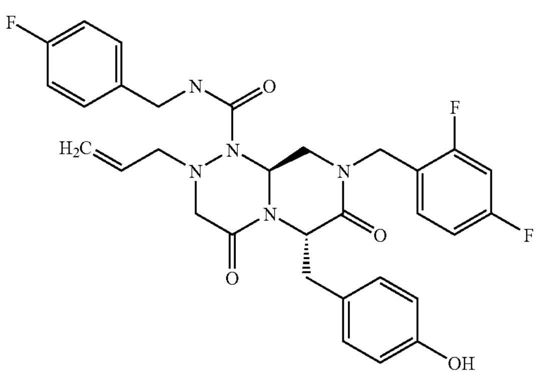 | 594 | 5.4 ± 0.5 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 176 | Chiral | 578 | 4.0 ± 0.4 |
| 177 | Chiral | 590 | 5.3 ± 0.4 |
| 178 | 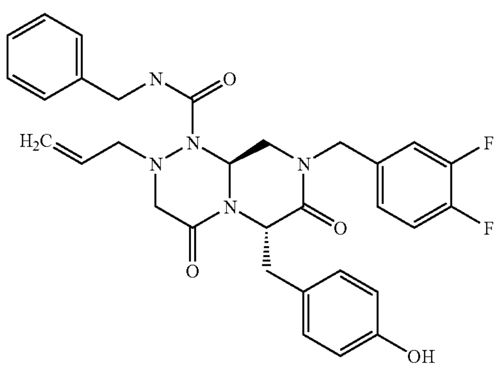 | 576 | 1.2 ± 0.1 |
| 179 | 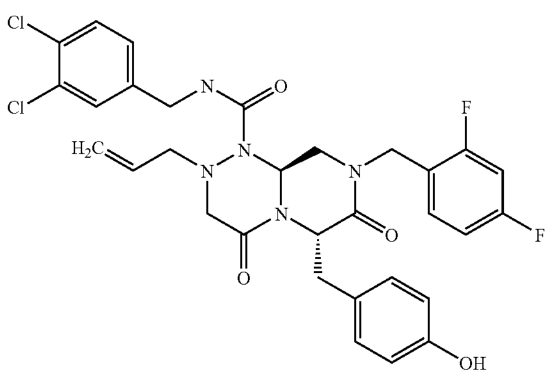 | 645 | 2.3 ± 0.2 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 180 | 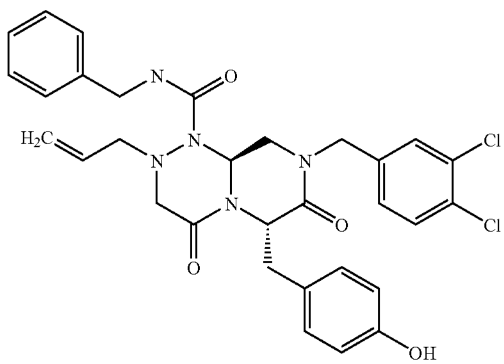 | 609 | 1.3 ± 0.1 |
| 181 | 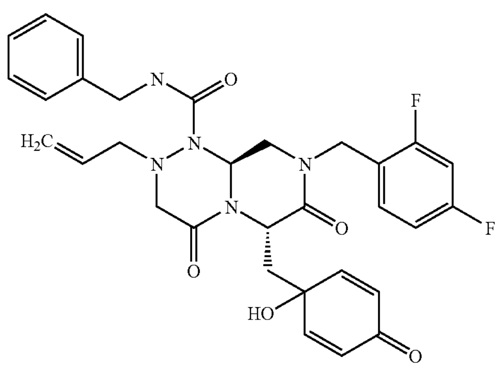 | 592 | 6.7 ± 0.6 |
| 182 | 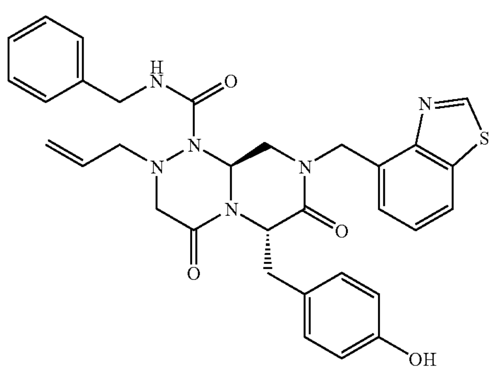 | 597 | 0.6 ± 0.04 |
| 183 | 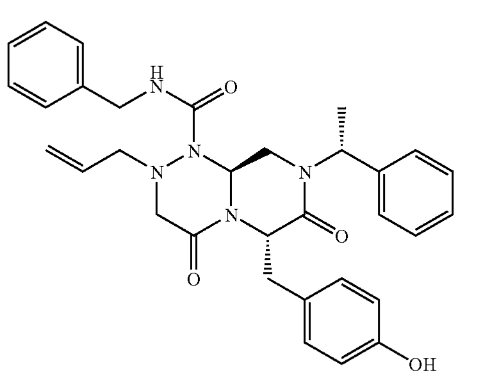 | 554 | 12.8 ± 0.9 |

TABLE 4-continued

IC$_{50}$ (µM) OF SELECTED LIBRARY COMPOUNDS

| No | STRUCTURE | M.W. | IC$_{50}$ (µM) |
|---|---|---|---|
| 184 | 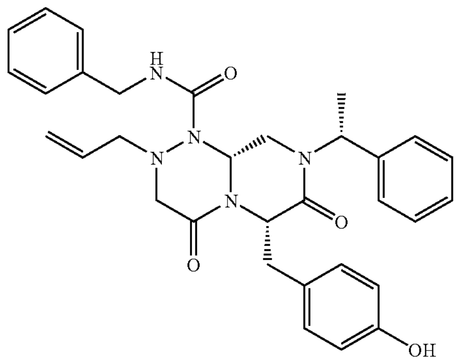 | 554 | 1.2 ± 0.1 |
| 185 | 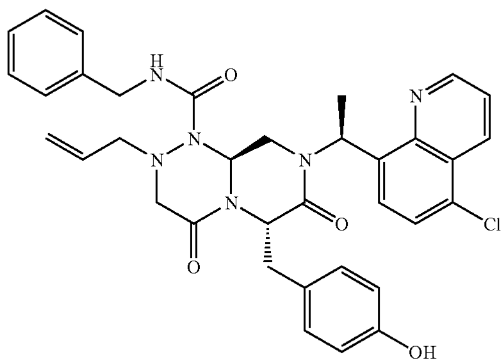 | 639 | 23.4 ± 1.9 |
| 186 | 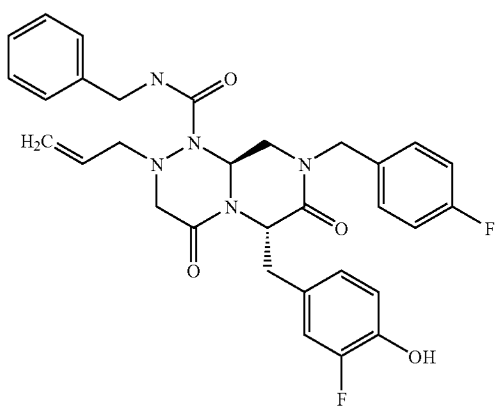 | 576 | 3.6 ± 0.3 |
| 187 | 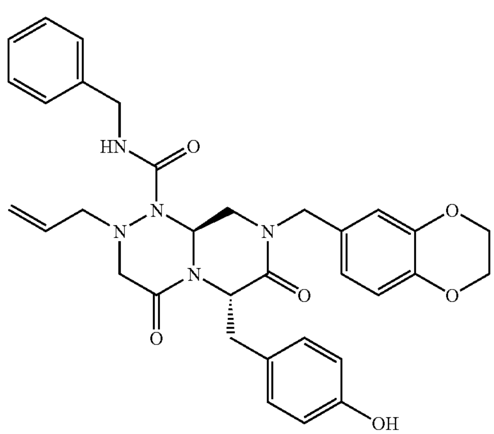 | 598 | 1.1 ± 0.2 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 188 | 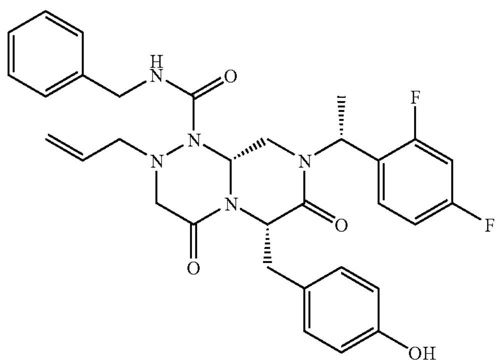 | 590 | 4.4 ± 0.2 |
| 189 | 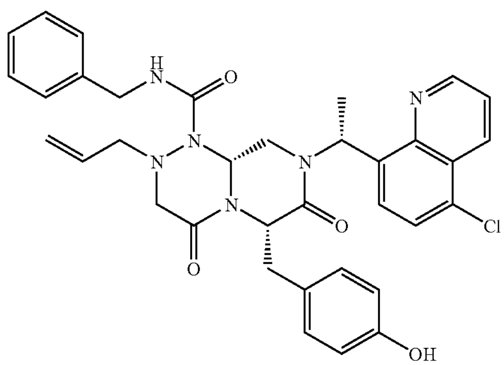 | 639 | 8.7 ± 0.4 |
| 190 | 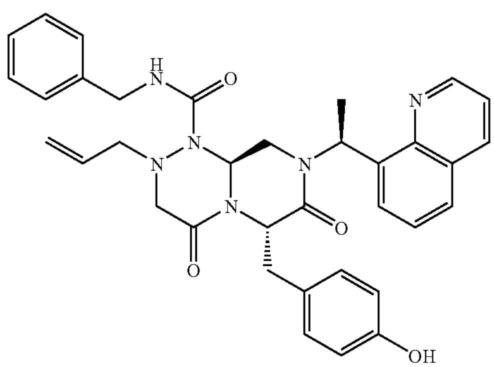 | 639 | 13.9 ± 0.8 |
| 191 | 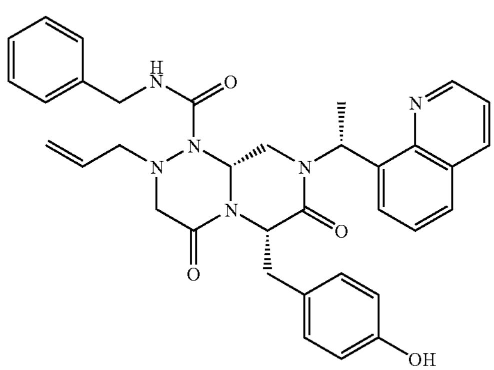 | 639 | 5.2 ± 0.4 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 192 | 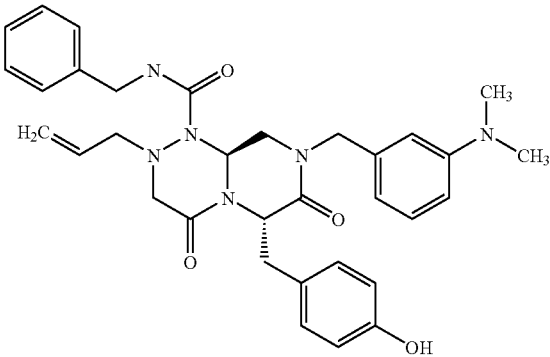 | 583 | 1.3 ± 0.3 |
| 193 | 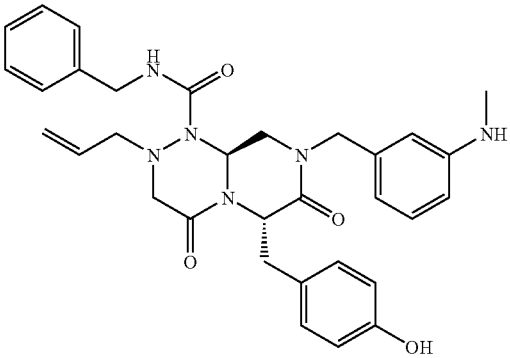 | 569 | 2.5 ± 0.5 |
| 194 | 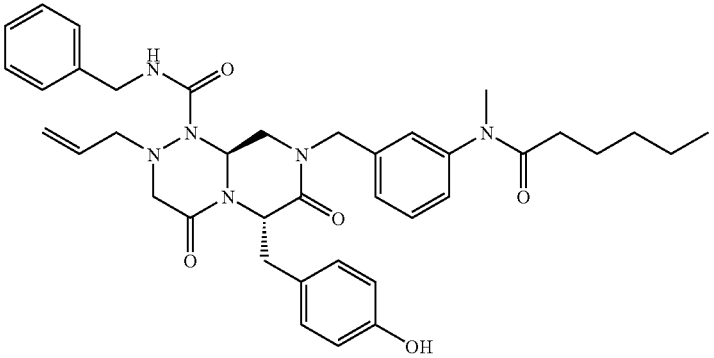 | 667 | 3.2 ± 0.4 |
| 195 | 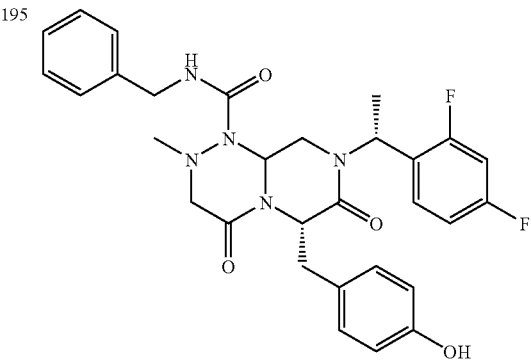 | 564 | 22.3 ± 2.3 |

TABLE 4-continued
IC$_{50}$ (μM) OF SELECTED LIBRARY COMPOUNDS
| No | STRUCTURE | M.W. | IC$_{50}$ (μM) |
|----|-----------|------|----------------|
| 196 | 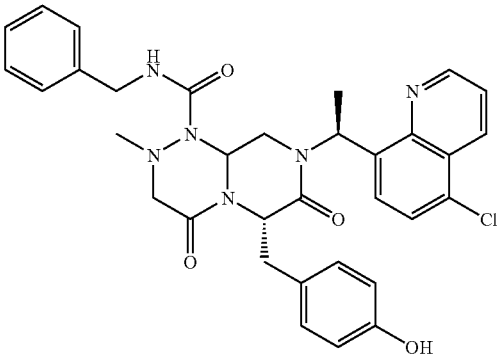 | 613 | 27.4 ± 2.8 |
| 197 | 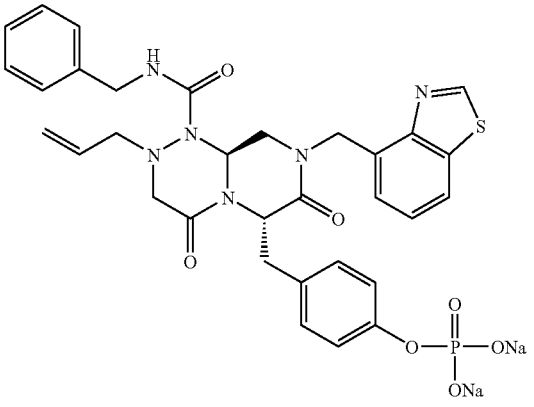 | 721 | 0.7 ± 0.2 |
| 198 | 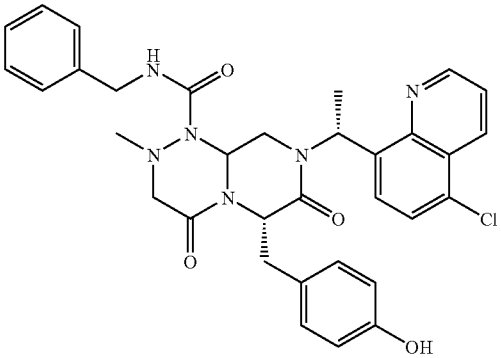 | 613 | 5.8 ± 0.3 |
| 199 | 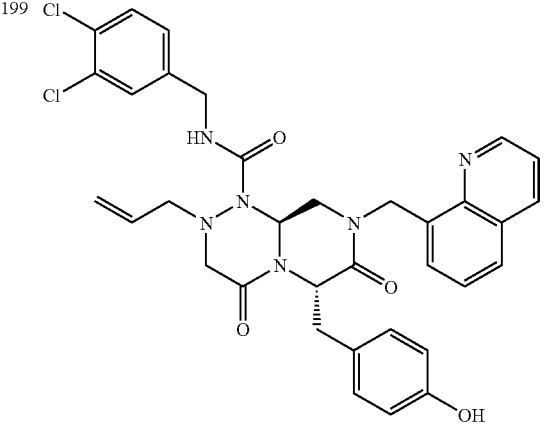 | 660 | 1.0 ± 0.2 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 200 | 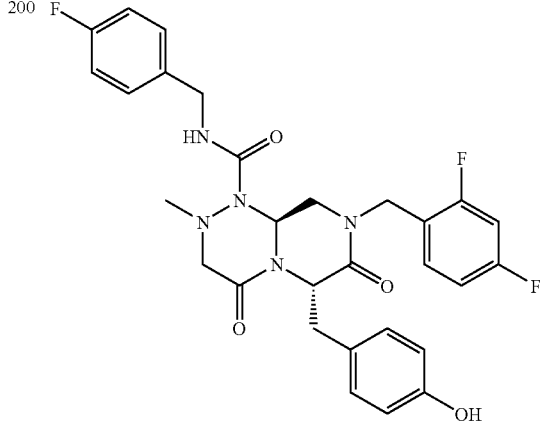 | 568 | 8.6 ± 0.4 |
| 201 | 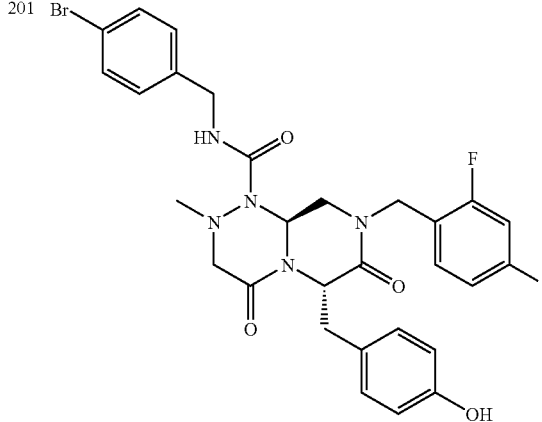 | 628 | 5.8 ± 0.4 |
| 202 | 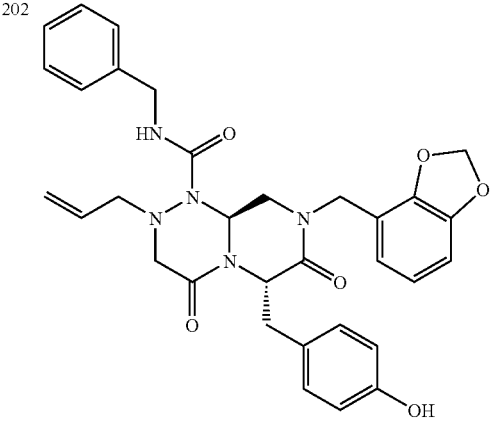 | 584 | 0.7 ± 0.1 |

TABLE 4-continued
IC$_{50}$ (µM) OF SELECTED LIBRARY COMPOUNDS
| No | STRUCTURE | M.W. | IC$_{50}$ (µM) |
|---|---|---|---|
| 203 | 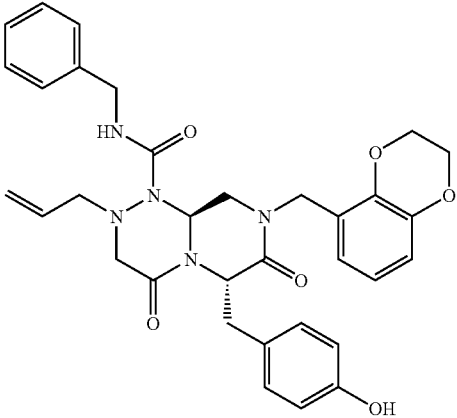 | 598 | 0.7 ± 0.1 |
| 204 | 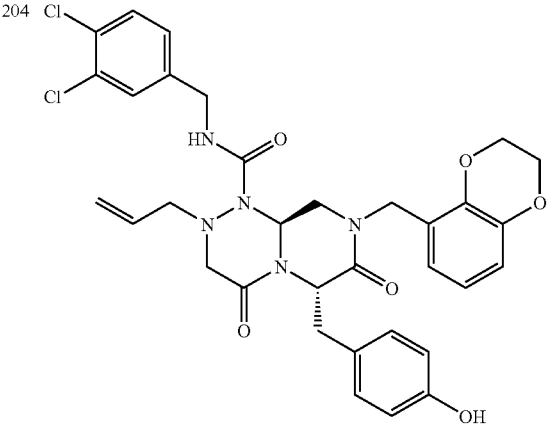 | 667 | 1.9 ± 0.1 |
| 205 | 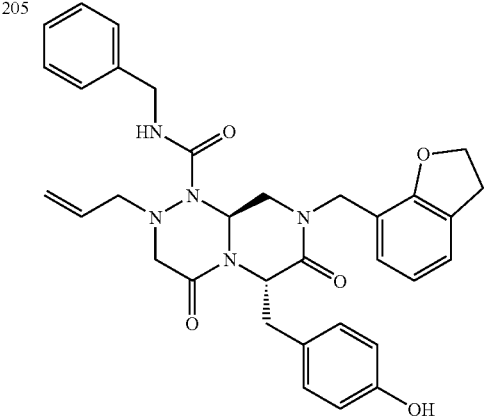 | 582 | 3.5 ± 0.8 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 206 | 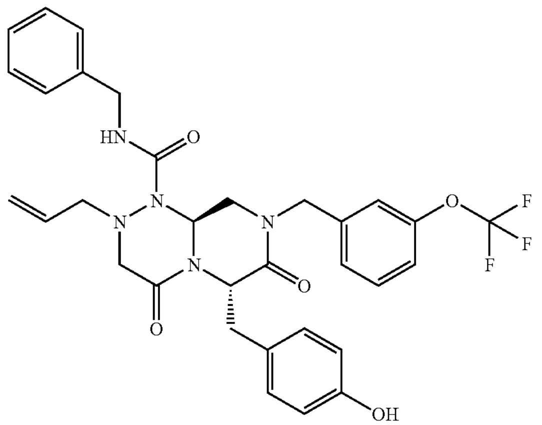 | 624 | 1.3 ± 0.1 |
| 207 | 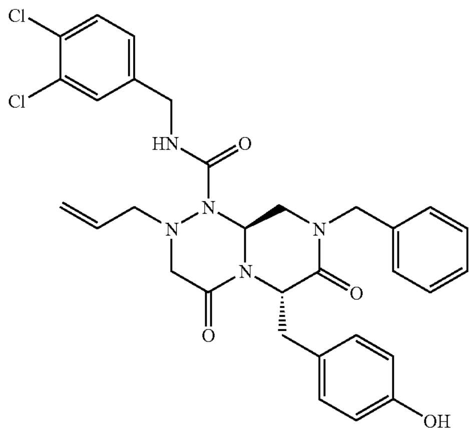 | 609 | 1.5 ± 0.1 |
| 208 | 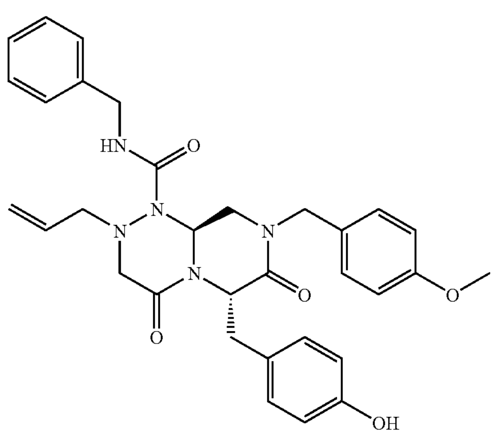 | 570 | 1.6 ± 0.4 |

TABLE 4-continued
IC$_{50}$ (µM) OF SELECTED LIBRARY COMPOUNDS
| No | STRUCTURE | M.W. | IC$_{50}$ (µM) |
|----|-----------|------|----------------|
| 209 | 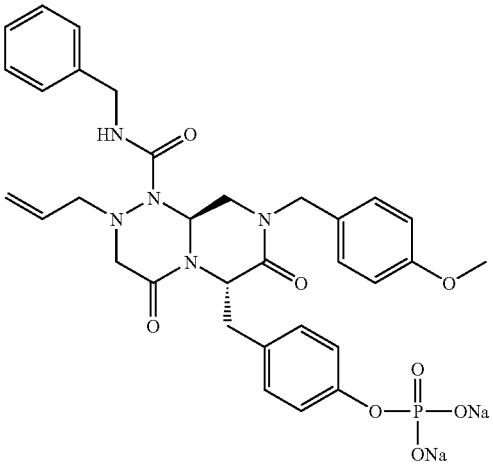 | 694 | 1.9 ± 0.5 |
| 210 | 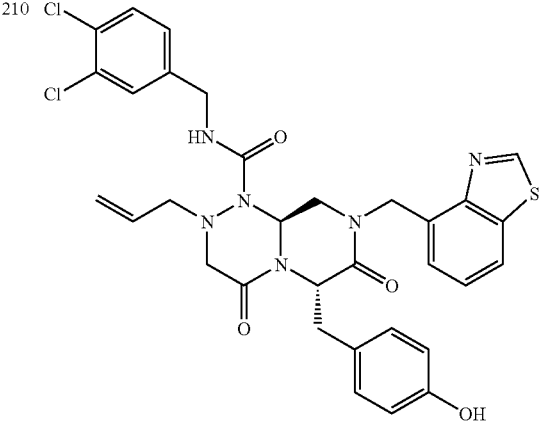 | 694 | 0.9 ± 0.1 |
| 211 | 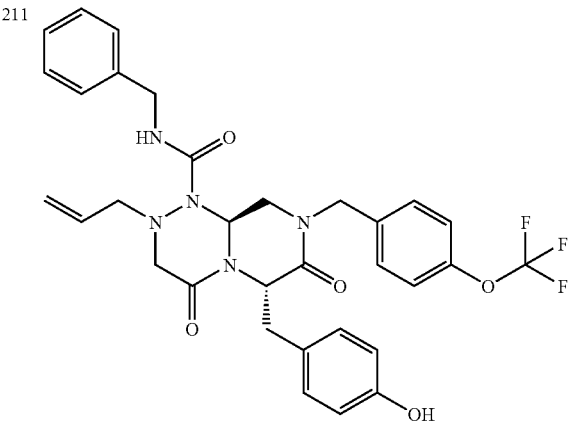 | 694 | 2.3 ± 0.2 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 212 | 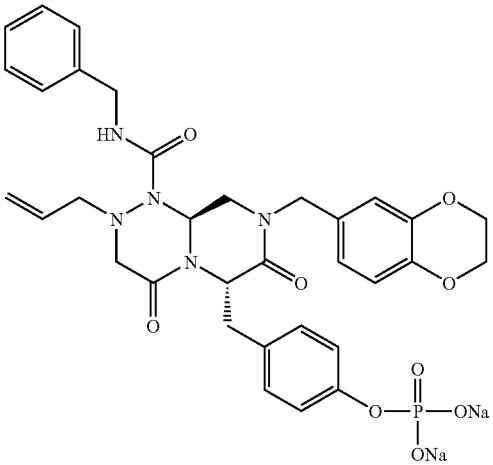 | 694 | 1.3 ± 0.3 |
| 213 | 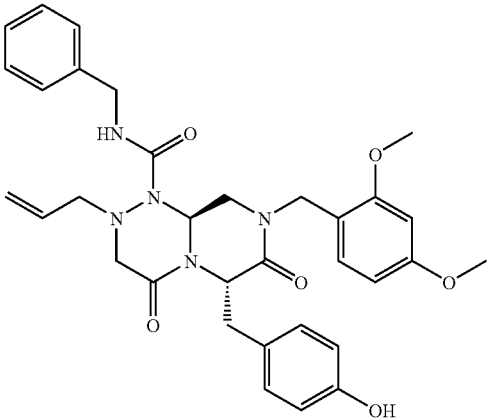 | 694 | 1.7 ± 0.3 |
| 214 | 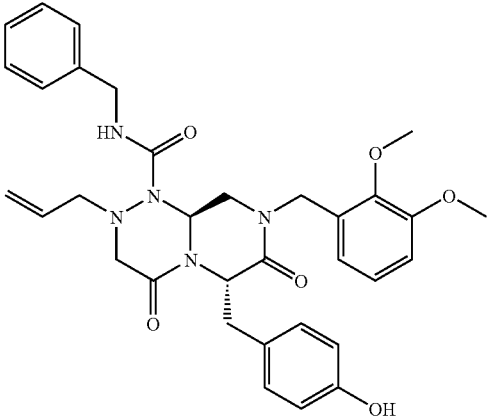 | 694 | 0.6 ± 0.2 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 215 | 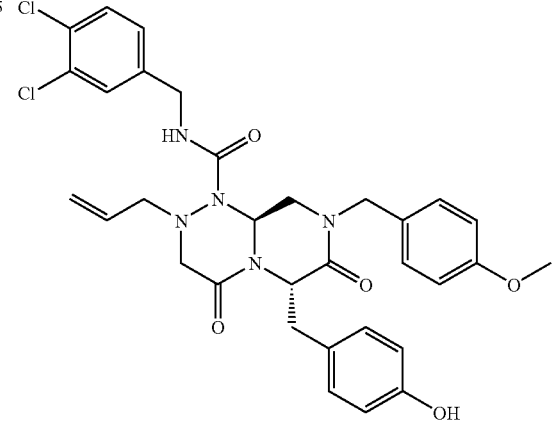 | 639 | 18 ± 5.1 |
| 216 | 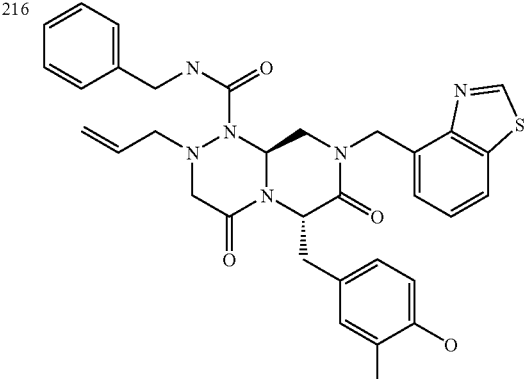 | 615 | 1.6 ± 0.2<br>(1.8 ± 0.3) |
| 217 | 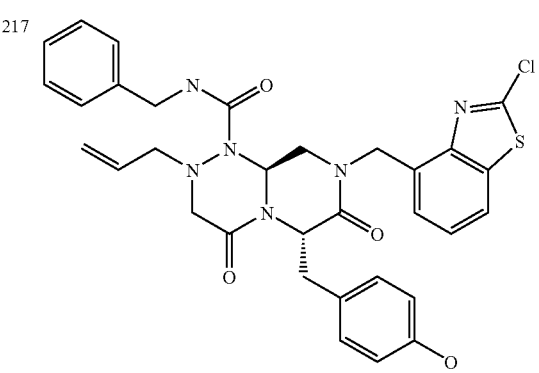 | 631 | lower than 1.6 |

TABLE 4-continued
IC$_{50}$ (μM) OF SELECTED LIBRARY COMPOUNDS
| No | STRUCTURE | M.W. | IC$_{50}$ (μM) |
|---|---|---|---|
| 218 | 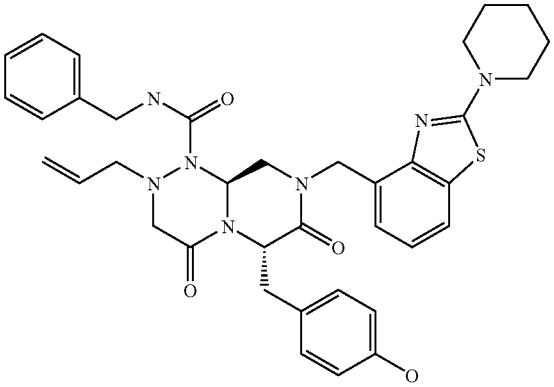 | 680 | 1.6 ± 1.2 |
| 219 | 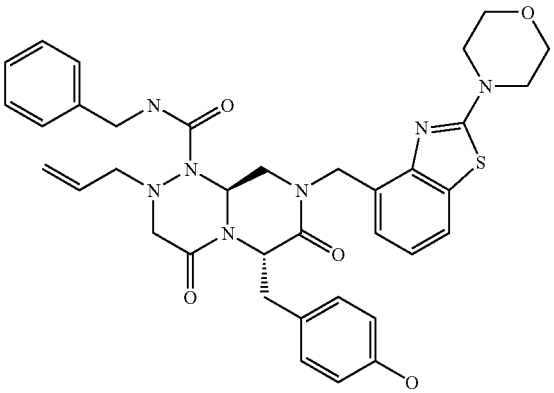 | 682 | 2.2 ± 0.7 |
| 220 | 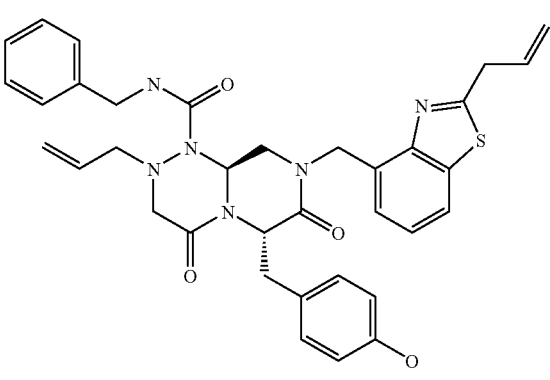 | 637 | 1.1 ± 0.3 |
| 221 | 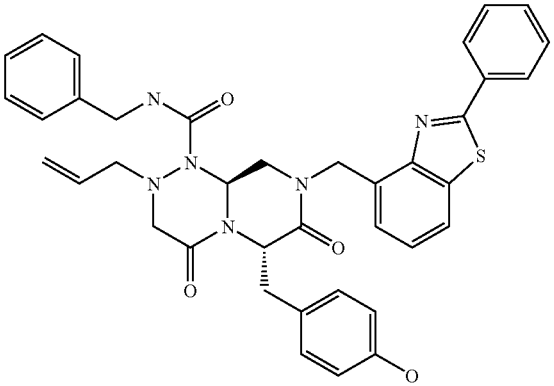 | 673 | 4.7 ± 3.5 |

TABLE 4-continued

IC$_{50}$ (μM) OF SELECTED LIBRARY COMPOUNDS

| No | STRUCTURE | M.W. | IC$_{50}$ (μM) |
|---|---|---|---|
| 222 | 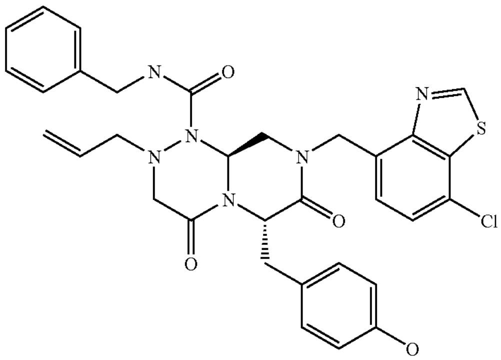 | 631 | 3.8 ± 2.7 |
| 223 | 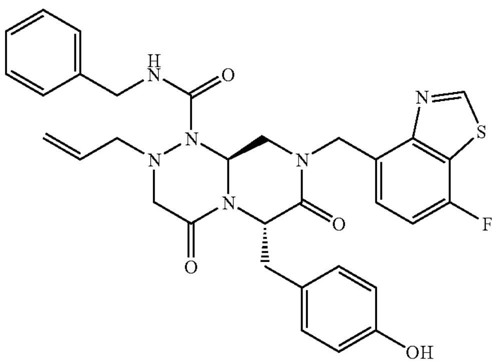 | 615 | 0.6 ± 0.1 |
| 224 | 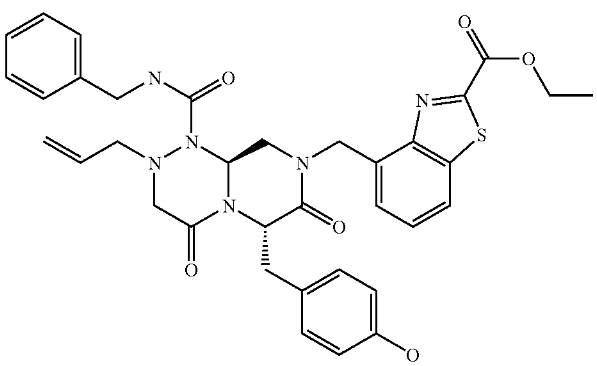 | 669 | 5.4 ± 1.0 |
| 225 | 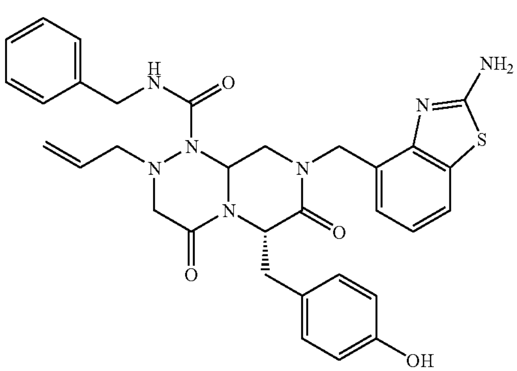 | 611 | 0.1 ± 0.1 |

It has been found according to the present invention that compounds of general formula (I), and especially the compounds of general formula (VI), can inhibit CBP-mediated transcriptional activation in cancer cells due to their specific binding to CBP. This conclusion is supported by immunoprecipitation of CBP of SW480 cells with compounds of the present invention.

The compounds of the present invention can also inhibit the survivin expression in SW480 cells, and therefore, inhibit the oncogenic activity in cancer cells. The compounds of the present invention can be used for inhibiting cancer cells, and thus, would be useful for the regulation of cell growth. Supporting such results, the compounds of the present invention further shows that it can induce the caspase-3 activation in SW480 cells, and therefore, induce the apoptotic activity in cells. The compounds of the present invention can be also advantageously used for inducing apoptosis in cells.

To confirm the oncogenic activity in cancer cell in in vitro MTS cytotoxicity assay was tested by following method.

(1) Cytotoxicity Test

SW480 or HCT116 cells were placed into 96 well microplate ($10^4$ cells/well) and incubated for 24 hours at 37° C. The cells were treated with TCF4 compound at various concentrations for 24 hours. 20 µl of MTS solution (Promega) was added into each well and incubated for 2 hours at 37° C. Cell viability was measured by reading the absorbance at 490 nm using microplate reader (Molecular Device) and cytotoxicity of a compound at each concentration was calculated.

(2) Growth Inhibition Assay

SW480 or HCT116 cells were placed into 96 well microplate ($10^4$ cells/well) and incubated for 24 hours at 37° C. 20 µl of [3-(4,5-dimethylthiazol-2-yl)-5-(3-carboxyphenyl)-2-(4-sulfophenyl)-2H-tetrazolium, inner salt](MTS) solution (Promega) was added into each well and the absorbance after 2 hour incubation at 37° C. (negative control) was read. And then, the cells were treated with TCF4 compound at various concentrations for 48 hours. 20 µl of MTS solution (Promega) was added into each well and incubated for 2 hour at 37° C. Cell viability was measured by reading the absorbance at 490 nm using a microplate reader (Molecular device) and cytotoxicity of a compound at each concentration was calculated.

The results of oncogenic activity for selected library compounds were shown in the Table 5. The compound numbers is Table 5 are unrelated to the compound numbers in Table 4.

TABLE 5

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
| --- | --- | --- | --- |
| | | SW480 | HCT116 |
| 1 | 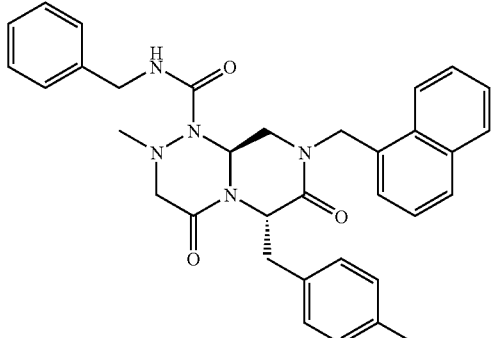 | 2.28 | 1.78 |
| 2 | 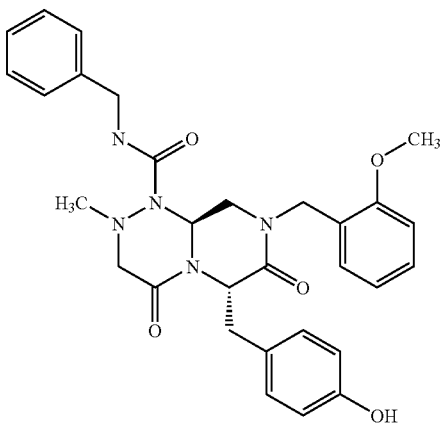 | 2.58 | 2.23 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 3 | 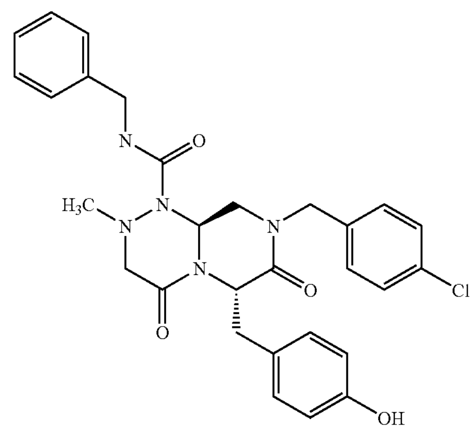 | 2.73 | 2.39 |
| 4 | 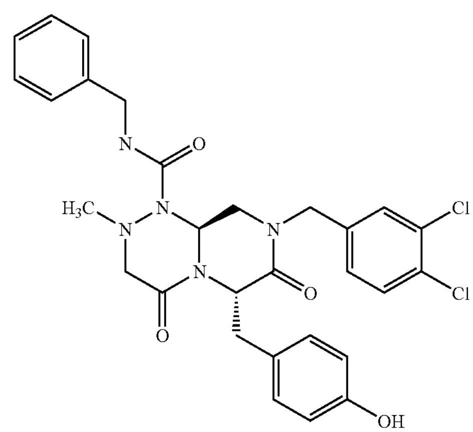 | 1.99 | 1.91 |
| 5 | 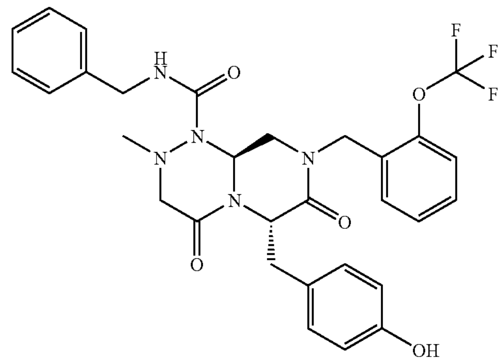 | 2.32 | 2.06 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 6 | 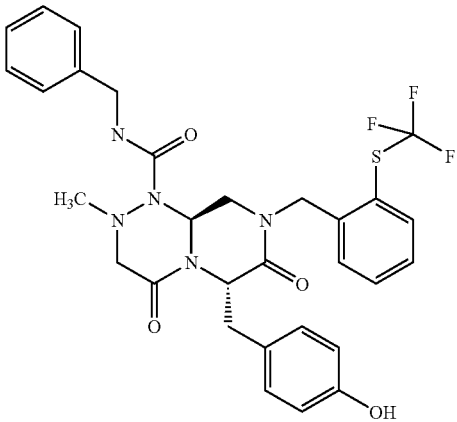 | 3.96 | 3.91 |
| 7 | 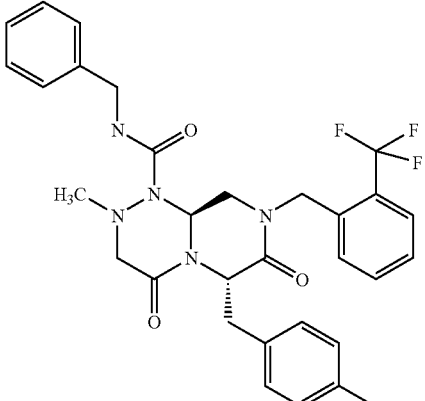 | 1.22 | 0.73 |
| 8 | 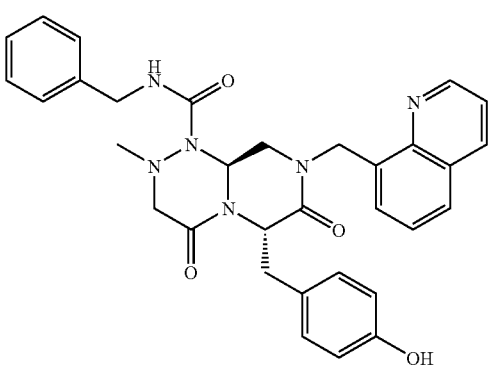 | <0.3 | <0.3 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 9 | 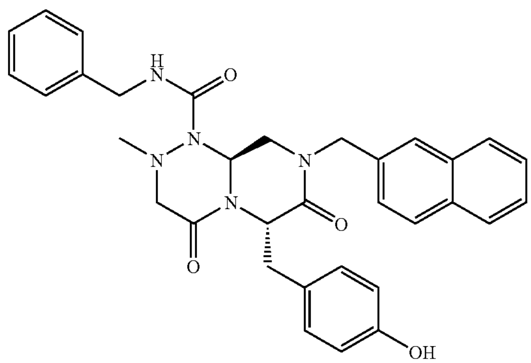 | 2.36 | 1.92 |
| 10 | 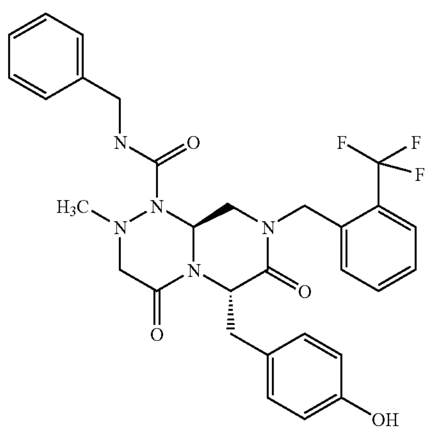 | 2.34 | 1.66 |
| 11 | 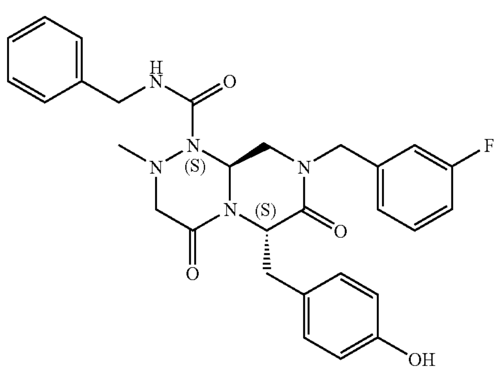 | 1.97 | 1.30 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 12 | 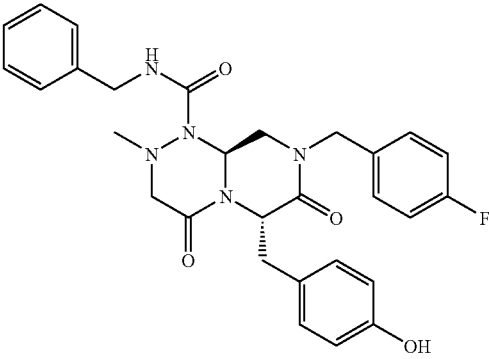 | 2.54 | 1.48 |
| 13 | 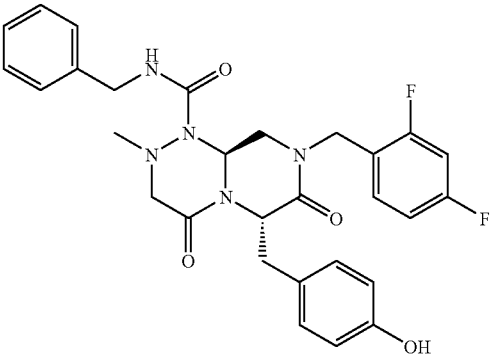 | 1.65 | 1.59 |
| 14 | 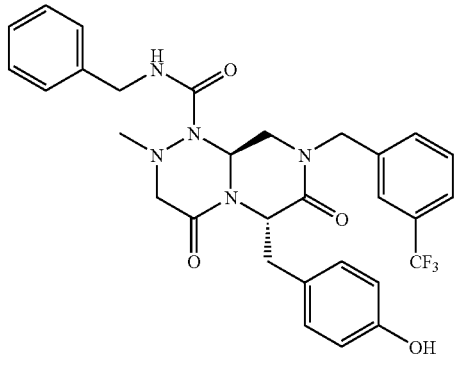 | 2.70 | 2.10 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 15 | 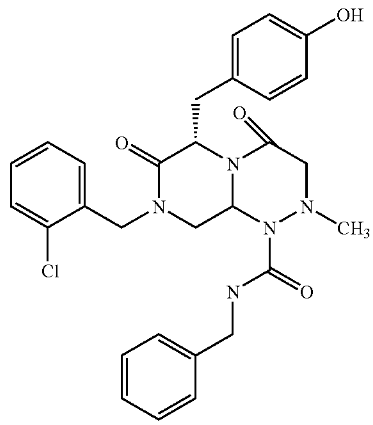 | 1.68 | 1.34 |
| 16 | 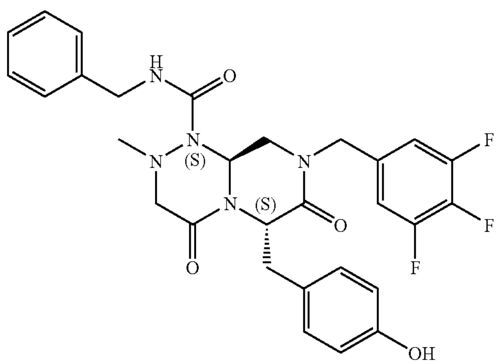 | 4.18 | 2.95 |
| 17 | 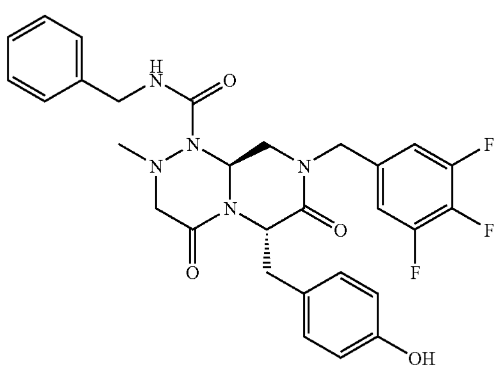 | 1.12 | 0.74 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 18 | 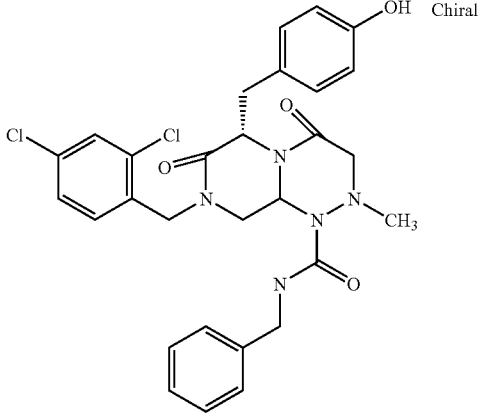 | 4.63 | 3.52 |
| 19 | 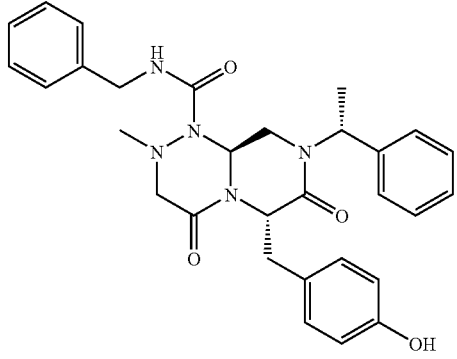 | 2.66 | 1.17 |
| 20 | 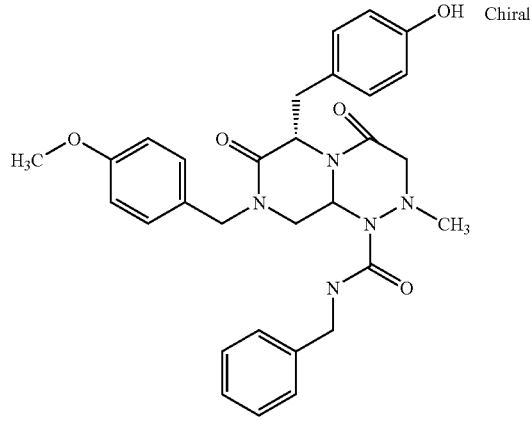 | 5.02 | 2.75 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 21 | | 5.25 | 1.67 |
| 22 | | 6.58 | 3.26 |
| 23 | | 3.9 | 25.41 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 24 | | 13.79 | 1.67 |
| 25 | | 24.53 | 1.81 |
| 26 | | 23.89 | 3.06 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 27 | 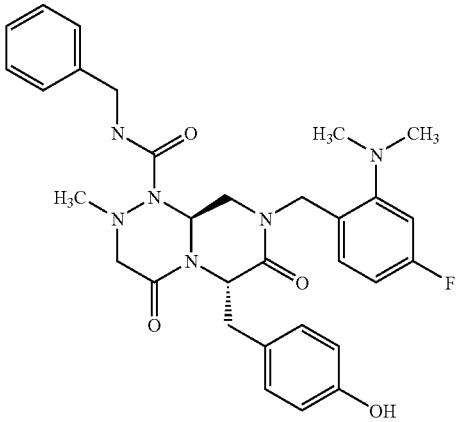 | 11.7 | 1.13 |
| 28 | 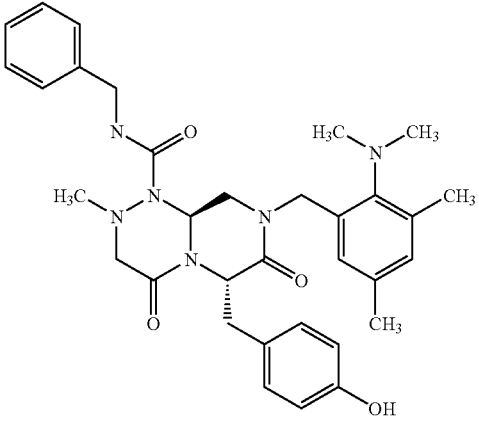 | 3.57 | 5.47 |
| 29 | 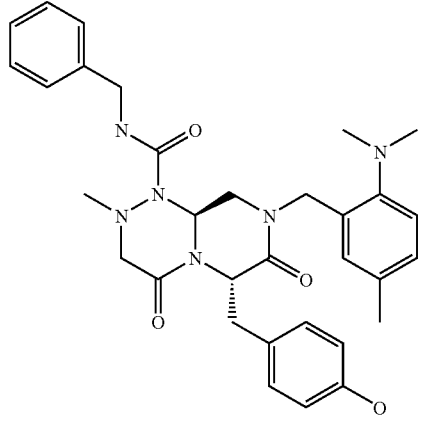 | 15.98 | 7.93 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 30 | | 14.05 | 5.4 |
| 31 | Chiral | 8.1 ± 0.7 | 5.0 ± 1.0 |
| 32 | Chiral | 47.2 ± 12.1 | 16.9 ± 1.9 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
| --- | --- | --- | --- |
| | | SW480 | HCT116 |
| 33 | Chiral | ND up to 50 uM | 28.6 ± 2.0 |
| 34 | Chiral | 13.8 ± 2.4 | 6.4 ± 1.3 |
| 35 | Chiral | 4.7 ± 0.5 | 5.0 ± 0.7 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 36 | 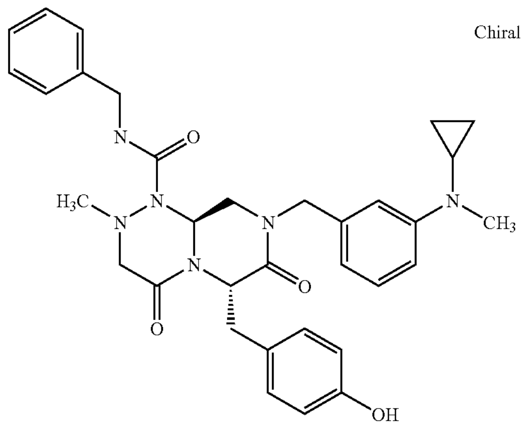 | 21.9 ± 2.3 | 12.7 ± 1.3 |
| 37 | 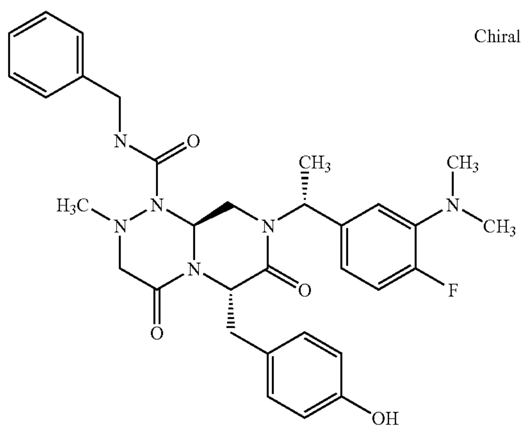 | 10.4 ± 0.8 | 9.2 ± 0.9 |
| 38 | 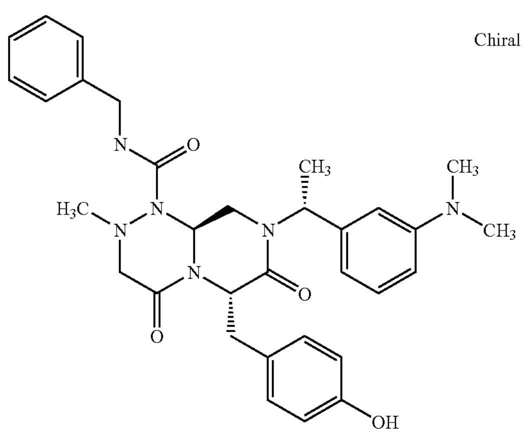 | 8.5 | 6.9 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 39 | 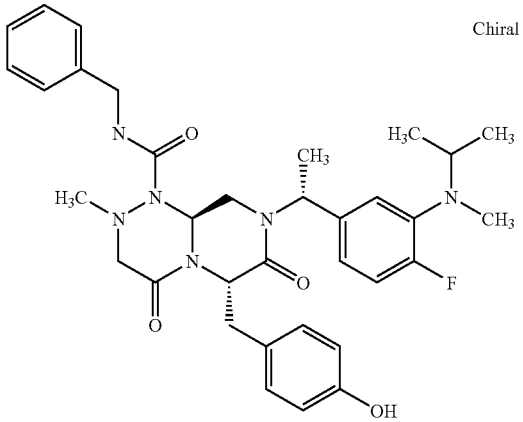 | 22.8 ± 6.5 | 19.7 ± 3.3 |
| 40 | 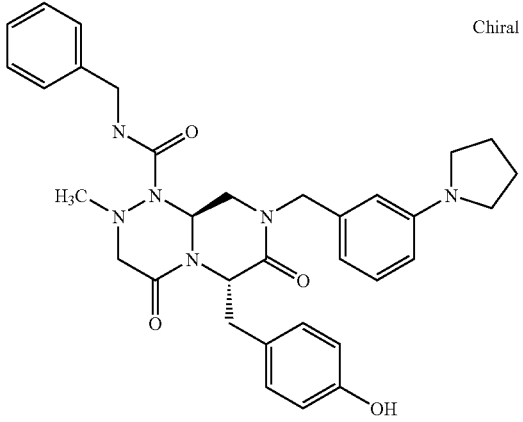 | 6.4 ± 0.5 | 5.8 ± 0.4 |
| 41 | 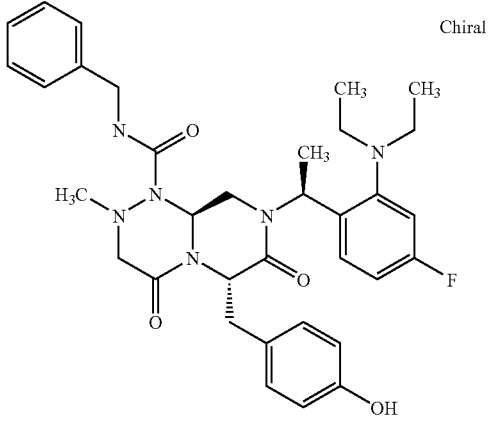 | 34.4 ± 9.6 | 14.7 ± 2.6 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 42 | 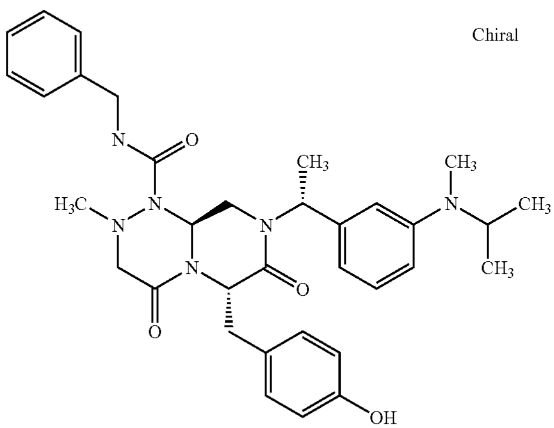 | 24.7 | 10.8 |
| 43 | 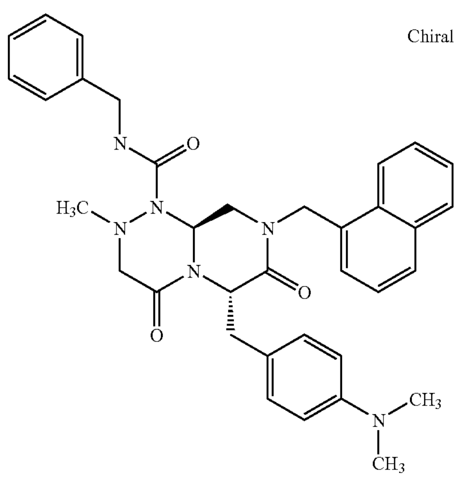 | ND up to 50 uM | 39.1 |
| 44 | 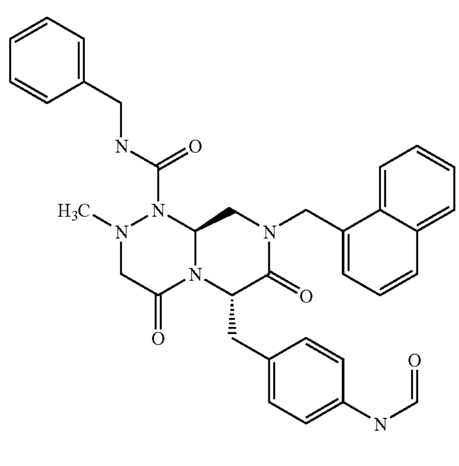 | 3.8 ± 0.4 | 4.2 ± 0.5 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 45 | 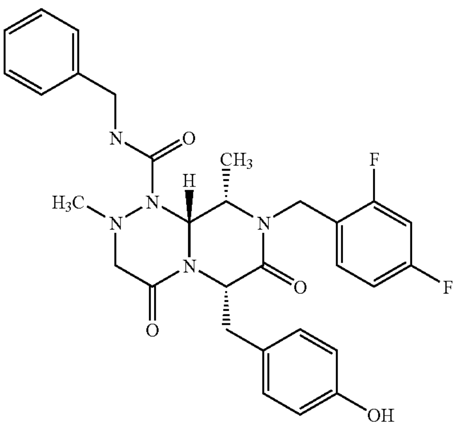 | 2.5 ± 0.2 | 2.9 ± 0.4 |
| 46 | Chiral | 5.5 ± 0.5 | 9.2 ± 0.9 |
| 47 | Chiral | 6.2 | 12.2 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 48 | Chiral | 20.7 ± 2.8 | 15.5 ± 2.3 |
| 49 | Chiral | 1.4 ± 0.1 | 1.0 ± 0.2 |
| 50 | Chiral | 4.6 | 2.6 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 51 | 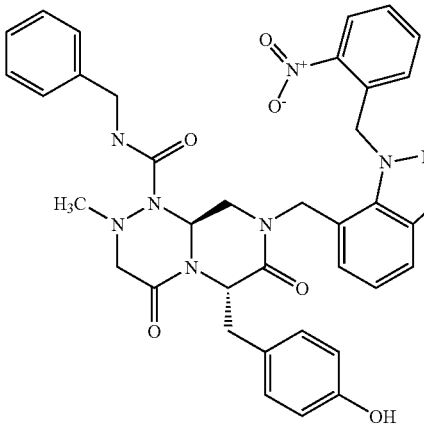 Chiral | 3.0 ± 0.1 | 2.8 |
| 52 | 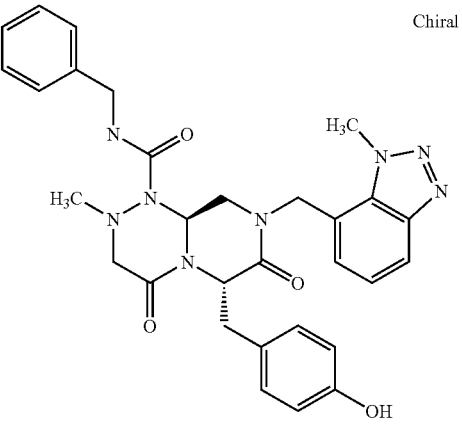 Chiral | 19.3 ± 2.1 | 9.7 ± 0.9 |
| 53 | 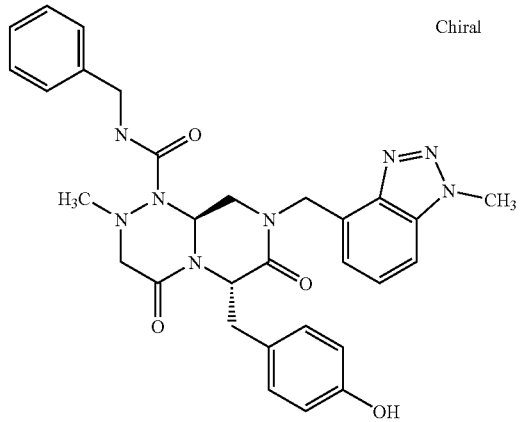 Chiral | 11.4 ± 0.9 | 4.7 ± 0.4 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 54 | 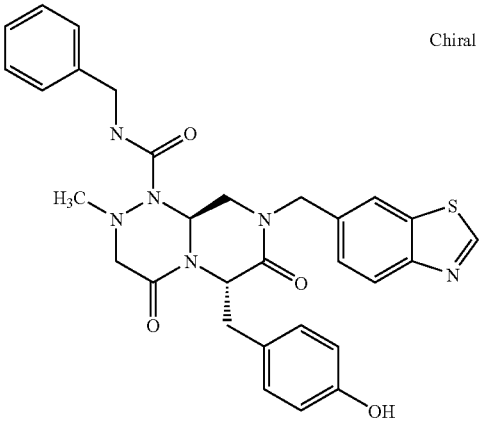 | 7.1 ± 0.5 | 4.9 ± 0.7 |
| 55 | 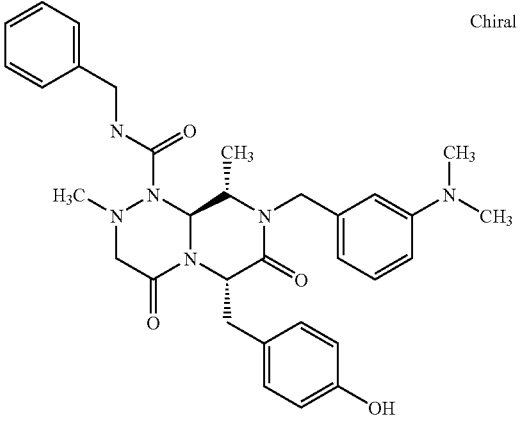 | 4.6 ± 0.5 | 4.1 ± 0.7 |
| 56 | 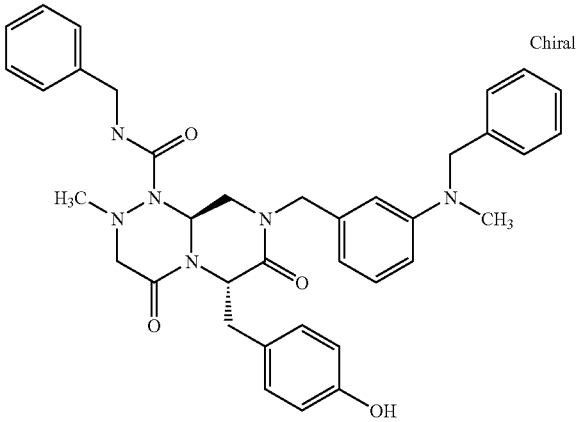 | 10.8 | 9.1 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 57 | 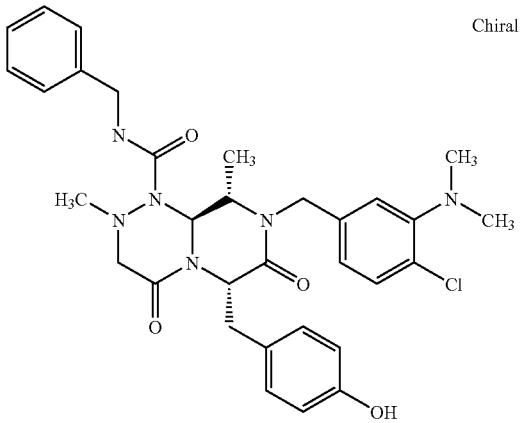 Chiral | 3.1 ± 0.3 | 5.1 ± 0.3 |
| 58 | 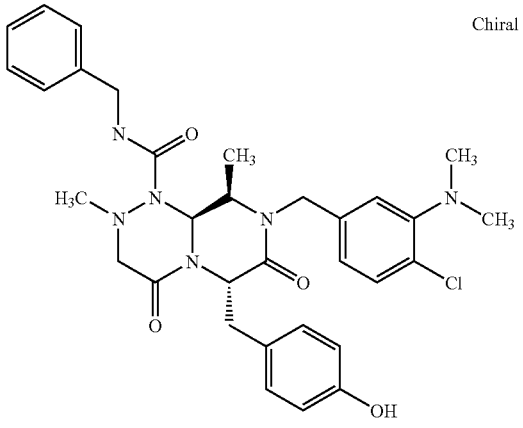 Chiral | 47.9 ± 7.2 | 22.3 ± 4.1 |
| 59 | 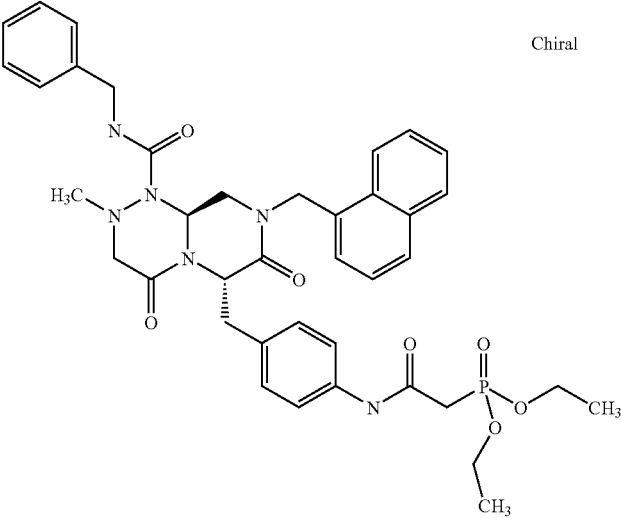 Chiral | ND up to 50 uM | 55.1 ± 33.7 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 60 | | $8.3 \pm 1.4$ | $6.3 \pm 2.6$ |
| 61 | | $11.3 \pm 6.0$ | $3.6 \pm 0.3$ |
| 62 | | $35.3 \pm 4.6$ | $23.5 \pm 2.7$ |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
| --- | --- | --- | --- |
| | | SW480 | HCT116 |
| 63 | Chiral | 18.8 ± 4.8 | 1.3 ± 0.1 |
| 64 | Chiral | 12.0 ± 0.7 | 19.0 ± 1.6 |
| 65 | Chiral | 7.3 | 4.7 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 66 | 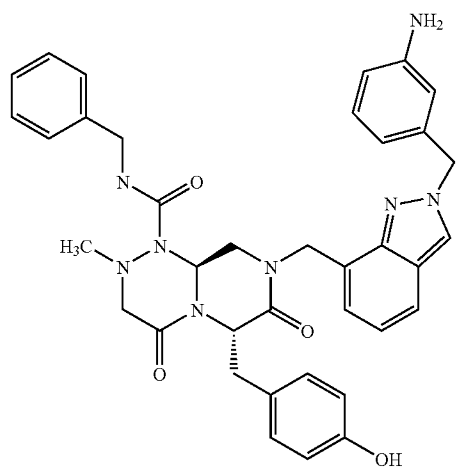 | 3.0 ± 0.3 | 5.8 ± 0.3 |
| 67 | 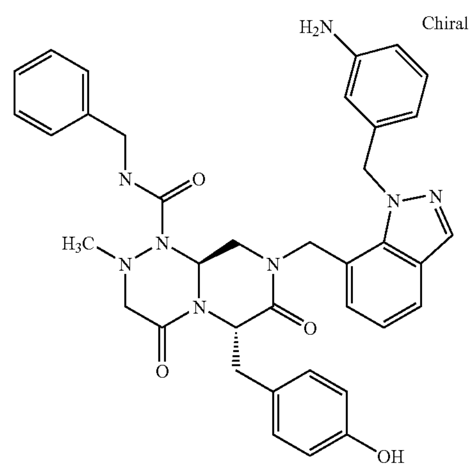 | 0.6 ± 0.2 | 0.3 ± 0.03 |
| 68 | 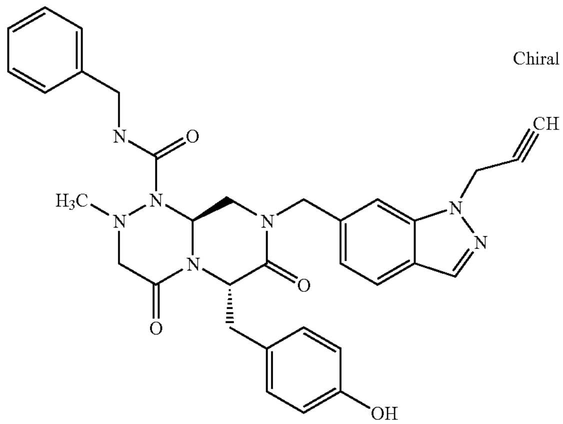 | 3.7 ± 0.2 | 3.8 ± 0.6 |

TABLE 5-continued
ONCOGENIC ACTIVITY BY MTS OR SULFORHODAMINE B ASSAY FOR SELECTED LIBRARY COMPOUNDS
| | | Growth Inhibition (GI50, uM) | |
|---|---|---|---|
| Compound | Structure | SW480 | HCT116 |
| 69 | 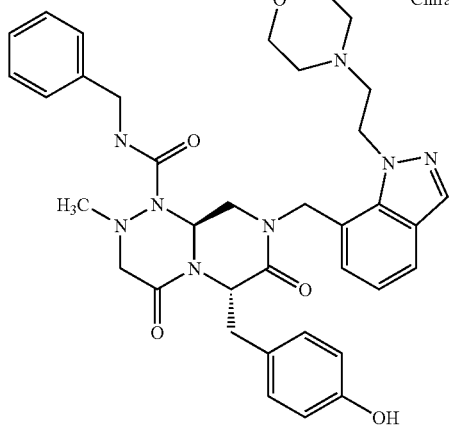 | 17.9 ± 3.1 | 9.7 ± 1.0 |
| 70 | 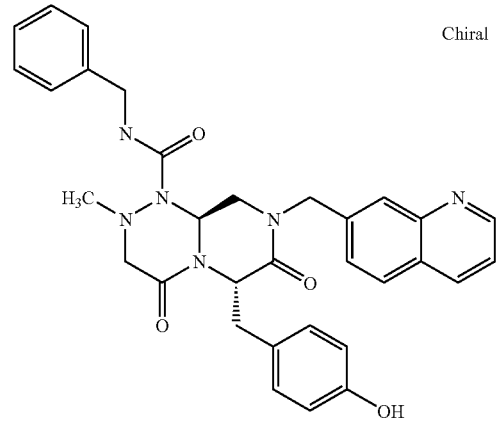 | 7.4 ± 0.6 | 7.2 ± 0.7 |
| 71 | 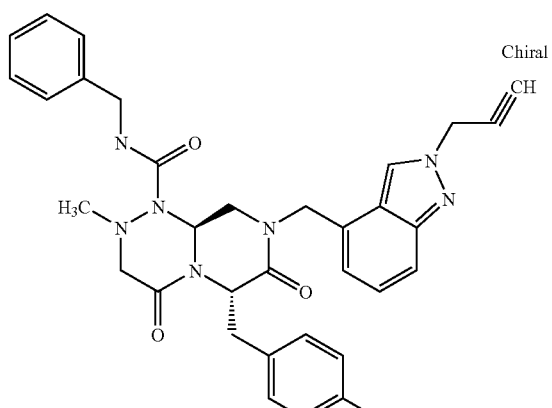 | 4.6 ± 0.5 | 3.6 ± 0.7 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 72 | 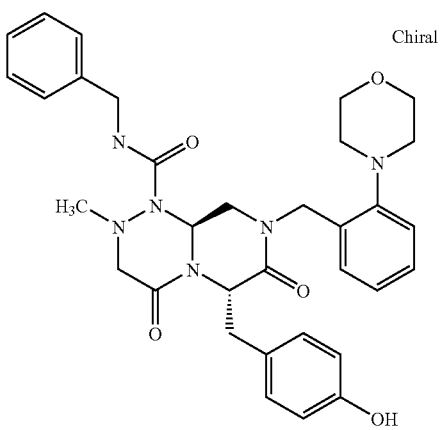 | 10.9 ± 0.6 | 10.3 ± 1.6 |
| 73 | 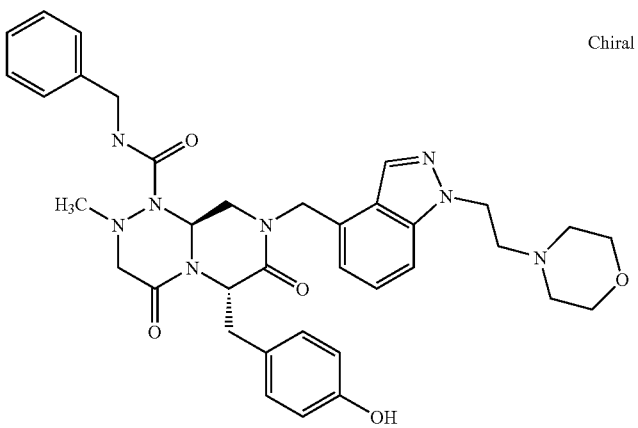 | 9.2 ± 0.8 | 15.8 ± 2.6 |
| 74 | 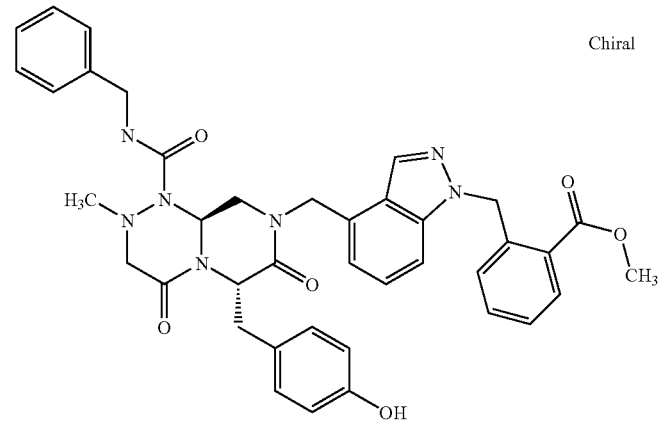 | 1.3 ± 0.4 | 2.4 ± 0.3 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 75 | 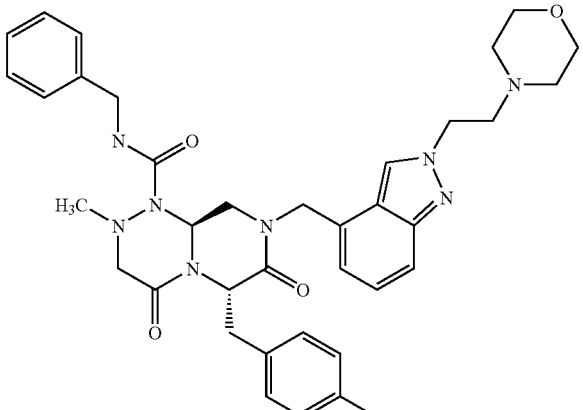 | 2.0 ± 0.1 | 4.5 ± 0.4 |
| 76 | 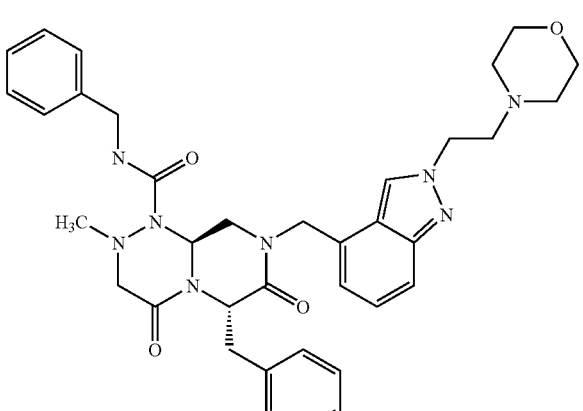 | 4 | 6.1 |
| 77 | 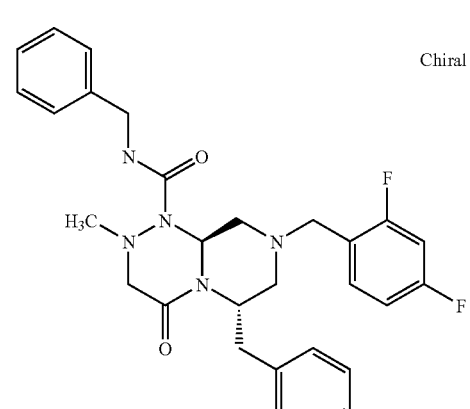 | 26.5 ± 6.5 | 10.7 ± 0.8 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
| --- | --- | --- | --- |
| | | SW480 | HCT116 |
| 78 | 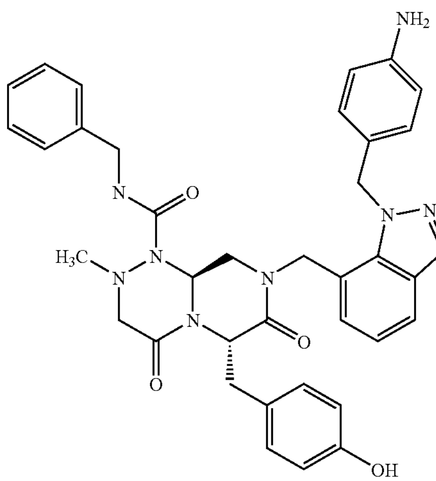 | 2.2 ± 0.2 | 3.7 ± 0.3 |
| 79 | 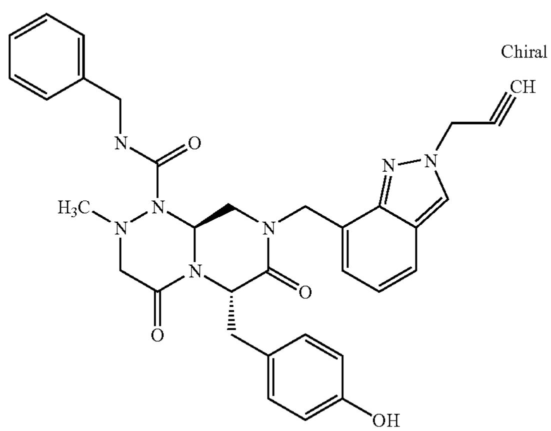 | 2.8 ± 0.2 | 5.2 ± 0.4 |
| 80 | 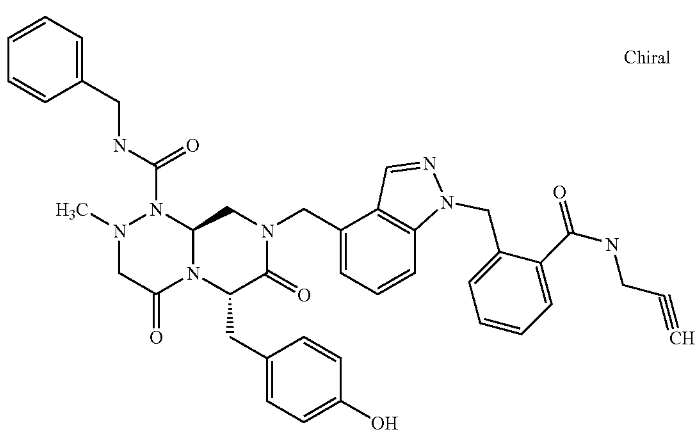 | 4.0 ± 0.6 | 3.9 ± 0.6 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 81 | 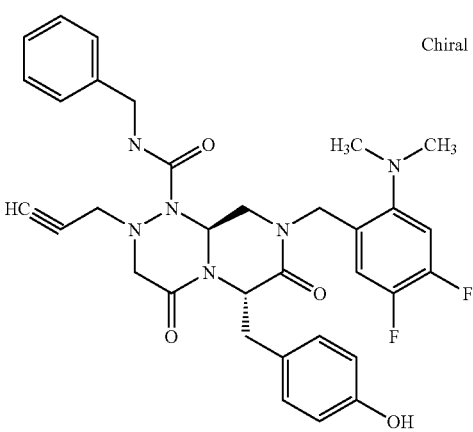 Chiral | 0.5 ± 0.3 | 1.8 ± 0.1 |
| 82 | 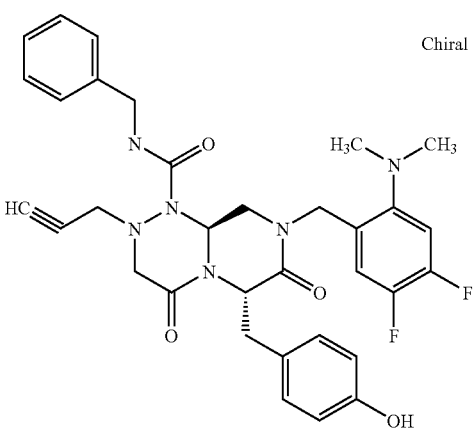 Chiral | 1.5 | 1.4 |
| 83 | 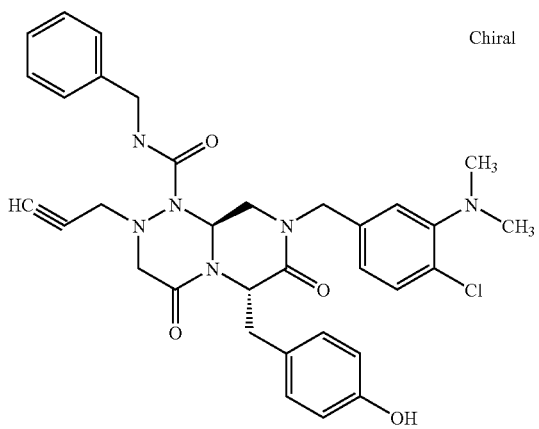 Chiral | 2.3 ± 0.3 | 2.5 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 84 | Chiral | 8.4 ± 1.1 | 9.9 ± 1.0 |
| 85 | Chiral | 1.4 ± 0.5 | 2.7 ± 0.3 |
| 86 | Chiral | 9.6 ± 1.6 | 6.5 ± 0.6 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 87 | 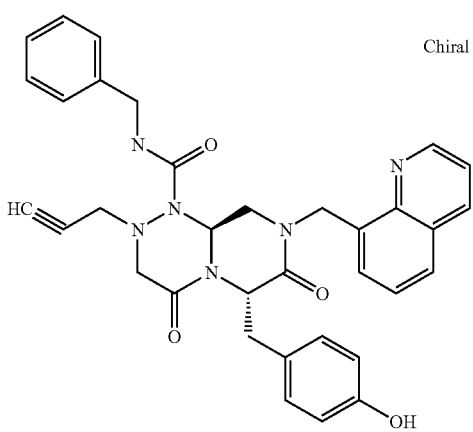 | 0.6 ± 0.2 | 0.5 ± 0.1 |
| 88 | 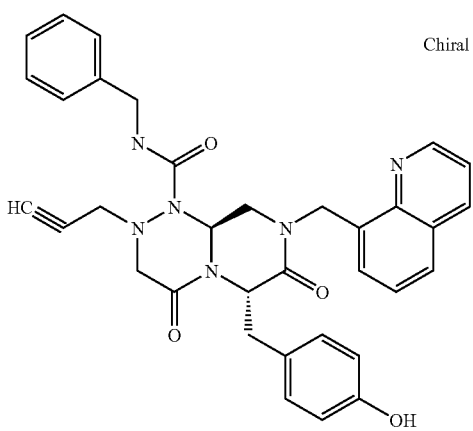 | 0.3 | 0.4 |
| 89 | 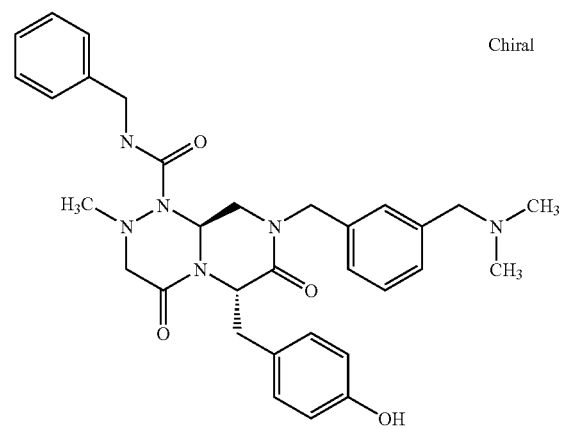 | 14.6 ± 1.4 | 7.5 ± 1.0 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 90 | 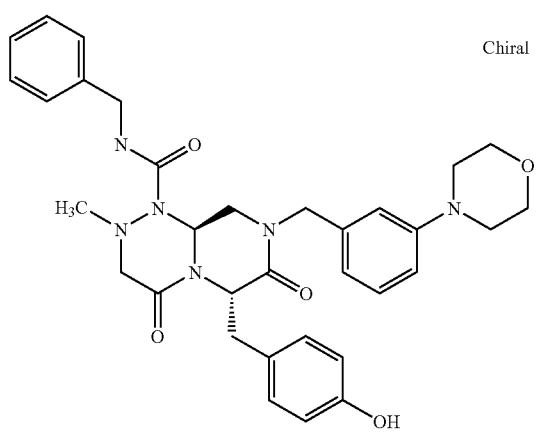 | 12.6 ± 0.9 | 14.7 ± 1.0 |
| 91 | 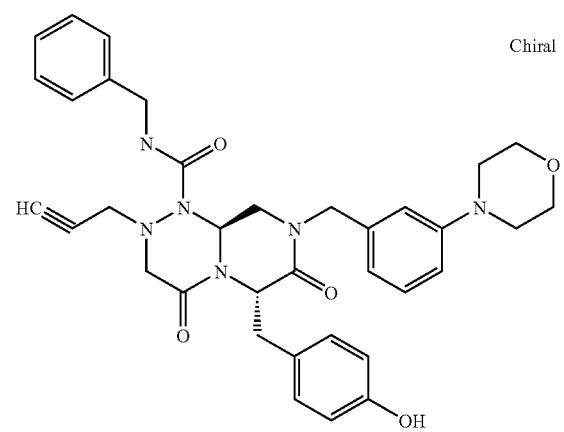 | 1.5 ± 0.1 | 3.2 ± 0.2 |
| 92 | 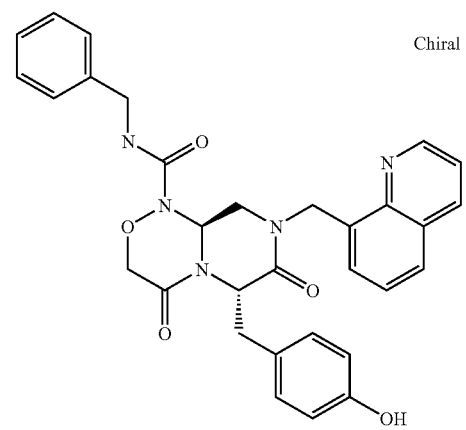 | 12.9 ± 1.0 | 14.9 ± 2.2 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 93 | 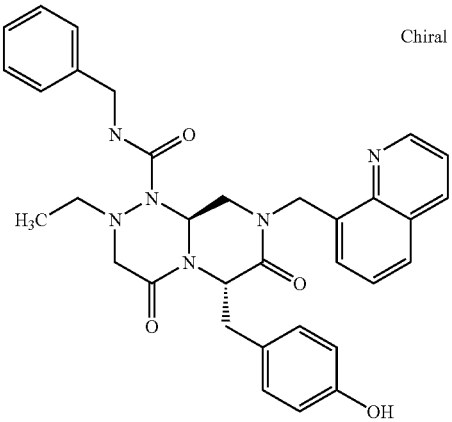 Chiral | 1.9 ± 0.4 | 1.1 ± 0.1 |
| 94 | 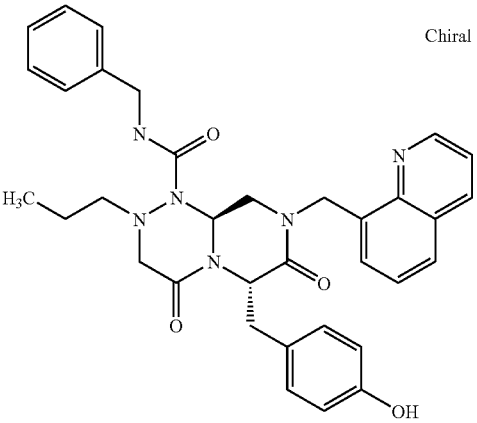 Chiral | 1.1 ± 0.3 | 0.7 ± 0.07 |
| 95 | 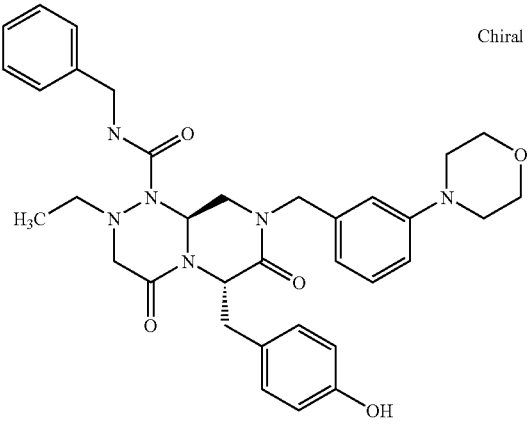 Chiral | 16.2 ± 2.6 | 7.1 ± 1.2 |

TABLE 5-continued
ONCOGENIC ACTIVITY BY MTS OR SULFORHODAMINE B ASSAY FOR SELECTED LIBRARY COMPOUNDS
| | | Growth Inhibition (GI50, uM) | |
|---|---|---|---|
| Compound | Structure | SW480 | HCT116 |
| 96 | 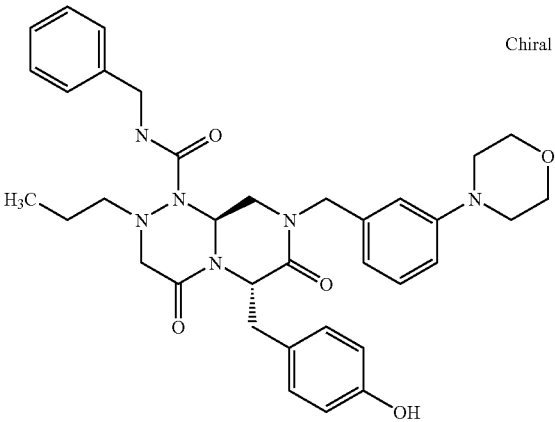 Chiral | 3.7 ± 0.4 | 3.4 ± 0.4 |
| 97 | 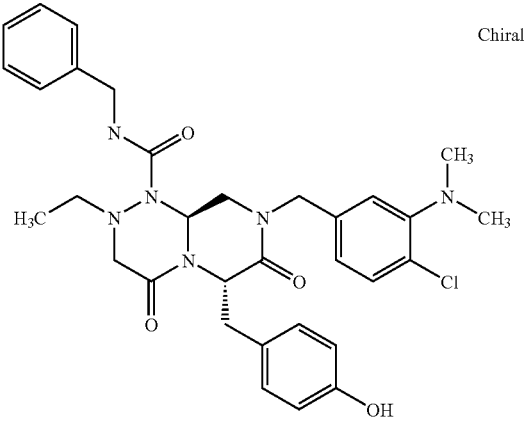 Chiral | 7.1 ± 1.0 | 5.2 ± 0.5 |
| 98 | 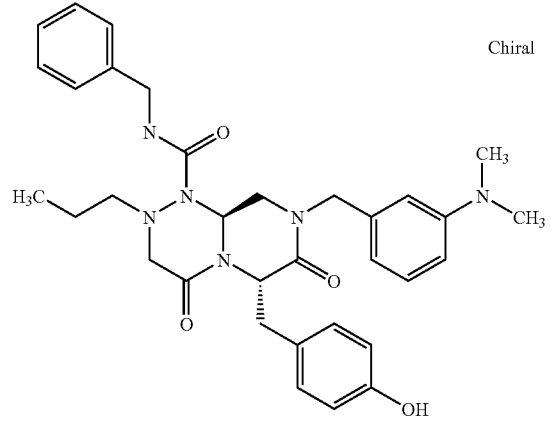 Chiral | 7.0 ± 1.1 | 4.4 ± 0.5 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 99 | 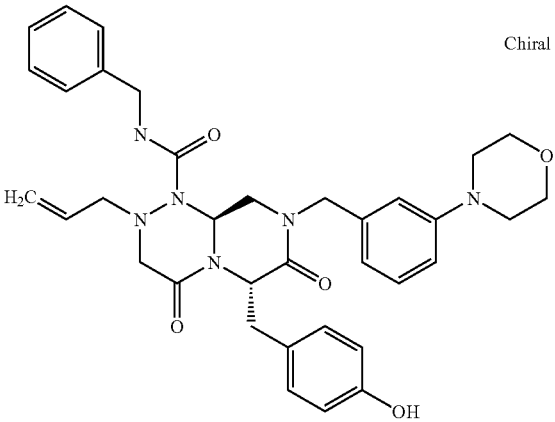 Chiral | 1.0 ± 0.05 | 0.7 ± 0.1 |
| 100 | 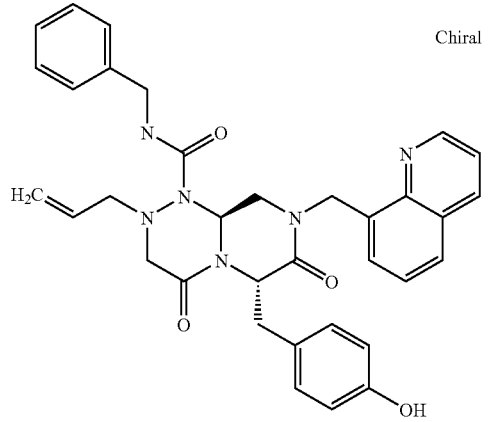 Chiral | 0.3 ± 0.03 | 0.4 ± 0.1 |
| 101 | 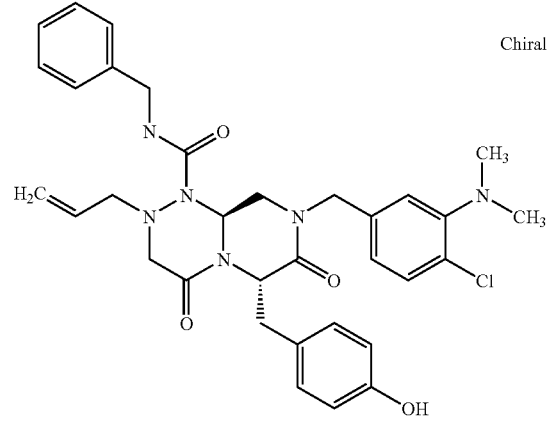 Chiral | 1.1 ± 0.07 | 0.9 ± 0.1 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 102 | 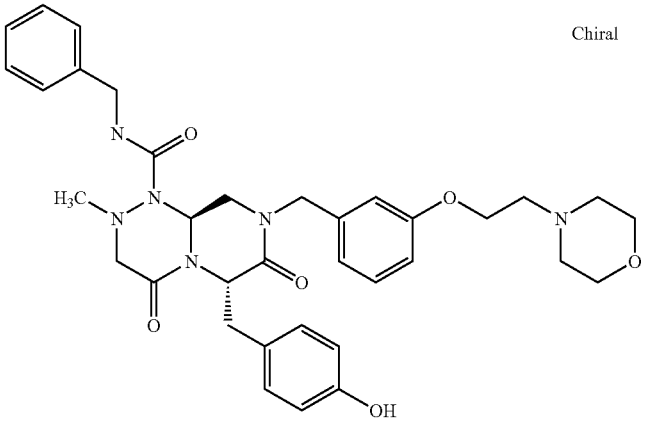 Chiral | 2.5 ± 0.4 | 4.9 ± 1.2 |
| 103 | 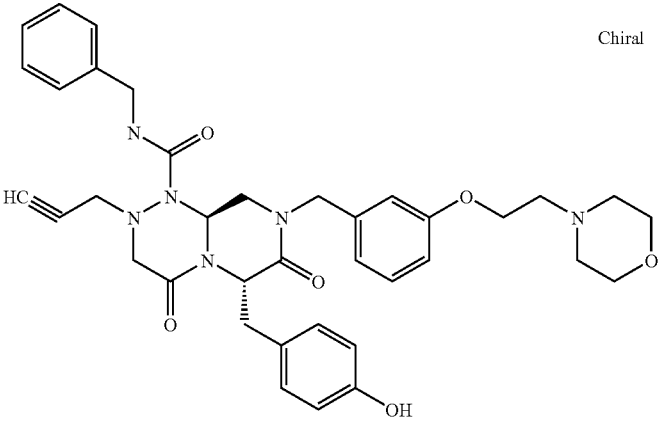 Chiral | 1.1 ± 0.1 | 1.5 ± 0.2 |
| 104 | 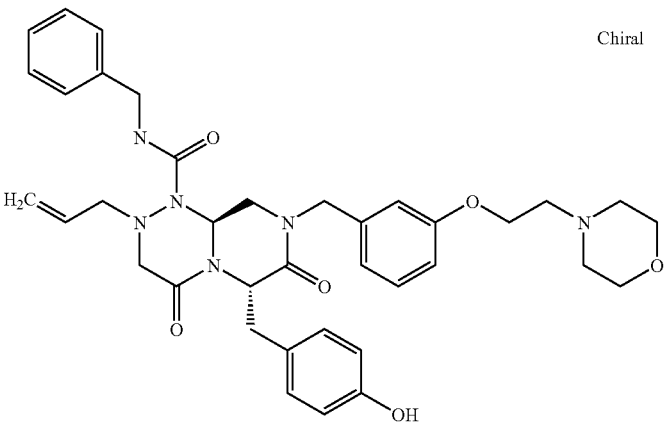 Chiral | <0.4 | <0.4 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 105 | 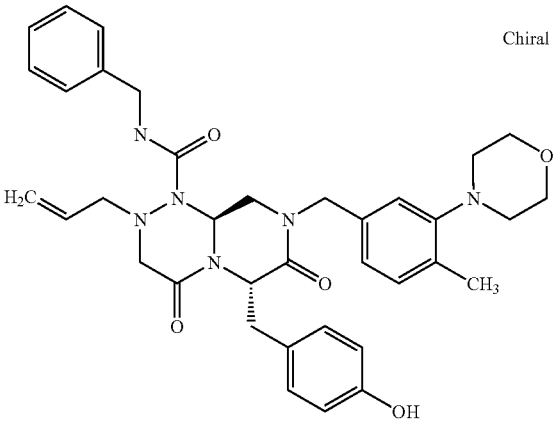 Chiral | 2.8 ± 0.2 | 2.1 ± 0.3 |
| 106 | 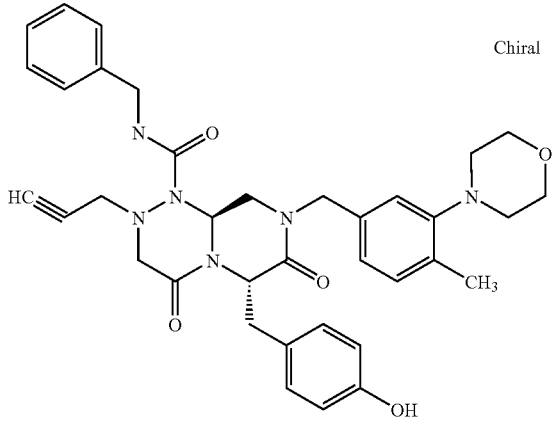 Chiral | 4.5 ± 0.3 | 2.8 ± 0.4 |
| 107 | 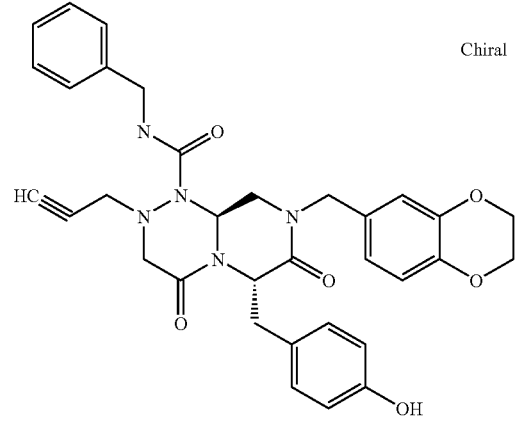 Chiral | 1.6 ± 0.1 | 1.6 ± 0.1 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 108 | 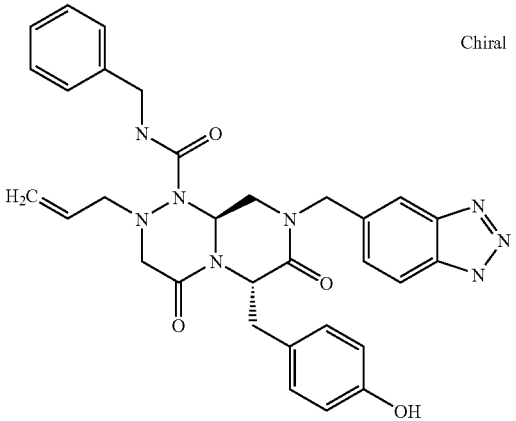 | 24.9 ± 2.2 | 37.9 ± 5.7 |
| 109 | 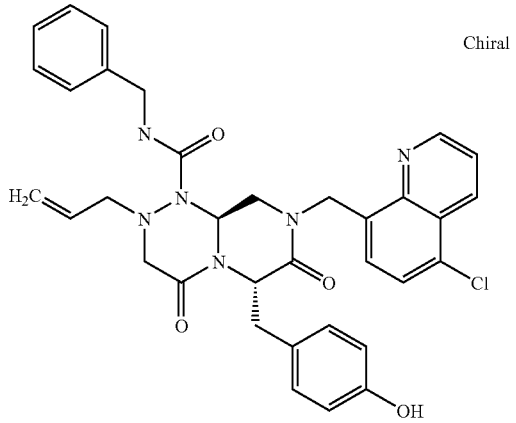 | 1.3 ± 0.3 | 1.1 ± 0.1 |
| 110 | 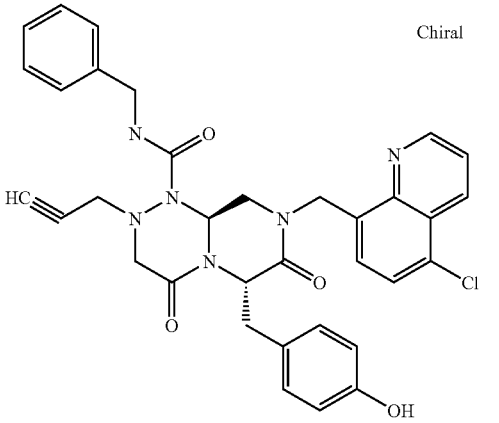 | 2.1 ± 0.3 | 1.9 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 111 | | 2.7 ± 0.8 | 2.1 ± 0.2 |
| 112 | | 5.1 ± 0.5 | 4.7 ± 0.3 |
| 113 | | 6.8 ± 1.4 | 3.7 ± 0.6 |

TABLE 5-continued
ONCOGENIC ACTIVITY BY MTS OR SULFORHODAMINE B ASSAY FOR SELECTED LIBRARY COMPOUNDS
| | | Growth Inhibition (GI50, uM) | |
|---|---|---|---|
| Compound | Structure | SW480 | HCT116 |
| 114 | 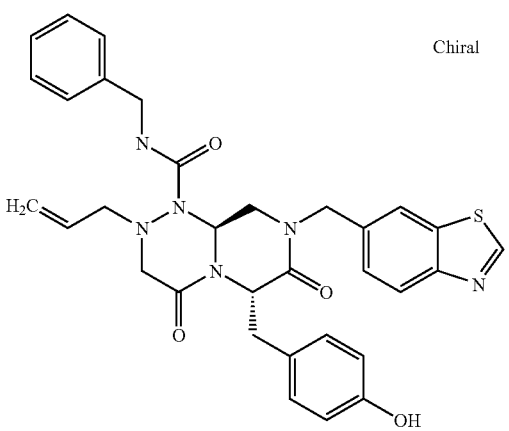 Chiral | 1.7 ± 0.7 | 1.9 ± 0.2 |
| 115 | 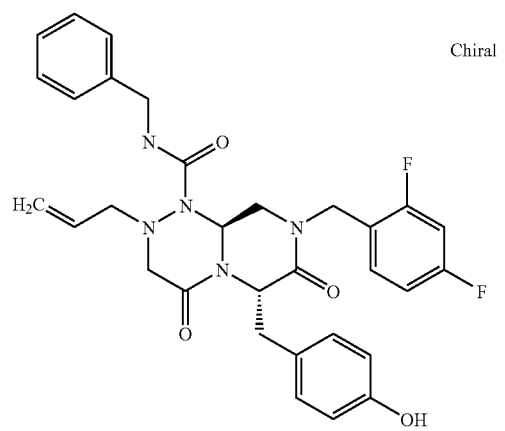 Chiral | 2.0 ± 0.7 | 1.1 ± 0.04 |
| 116 | 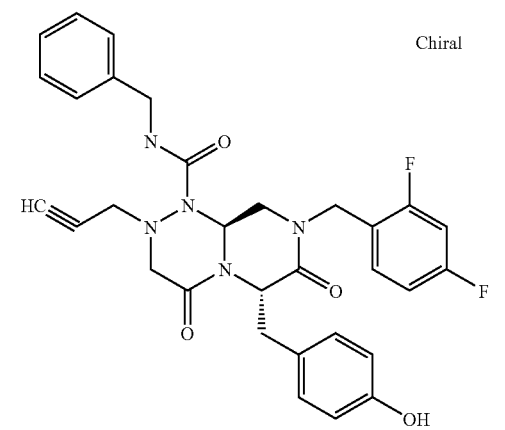 Chiral | 2.8 ± 0.9 | 1.7 ± 0.1 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 117 | 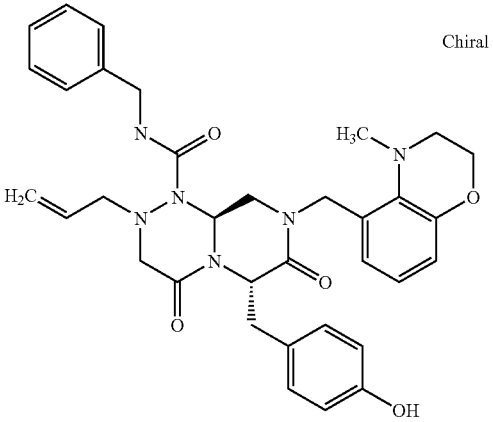 | 0.6 ± 0.1 | 0.3 ± 0.02 |
| 118 | 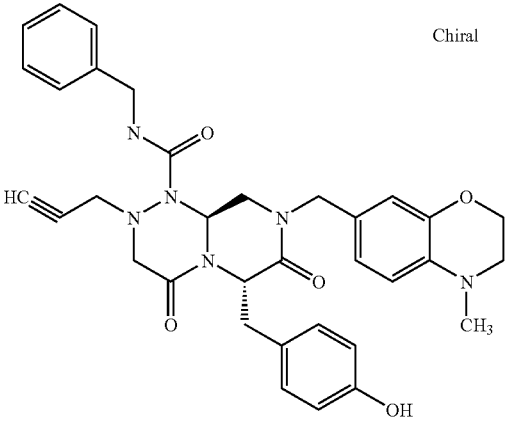 | 21.2 ± 1.5 | 23.2 ± 2.8 |
| 119 | 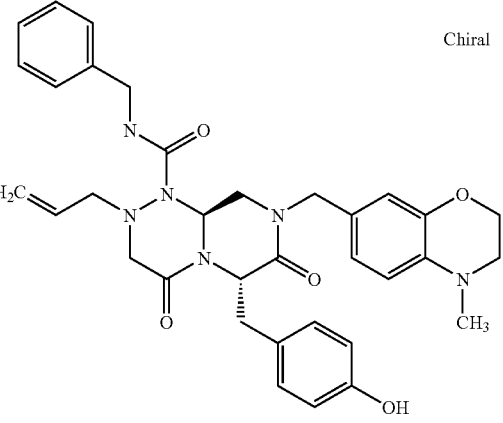 | 10.0 ± 1.3 | 9.5 ± 1.1 |

TABLE 5-continued
ONCOGENIC ACTIVITY BY MTS OR SULFORHODAMINE B ASSAY FOR SELECTED LIBRARY COMPOUNDS
| | | Growth Inhibition (GI50, uM) | |
|---|---|---|---|
| Compound | Structure | SW480 | HCT116 |
| 120 | 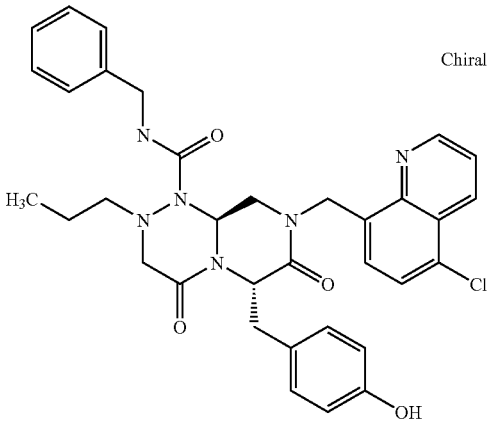 | 1.8 ± 0.2 | 2.6 ± 0.1 |
| 121 | 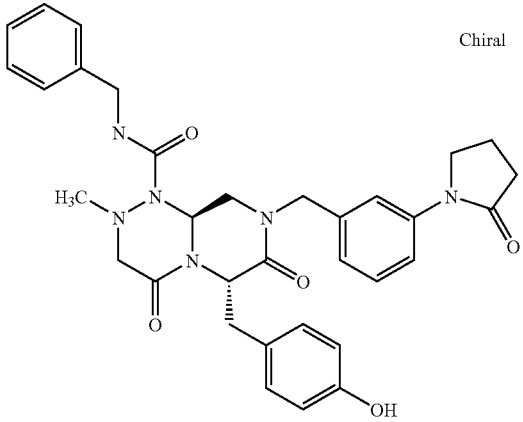 | 8.2 ± 0.5 | 13.1 ± 0.6 |
| 122 | 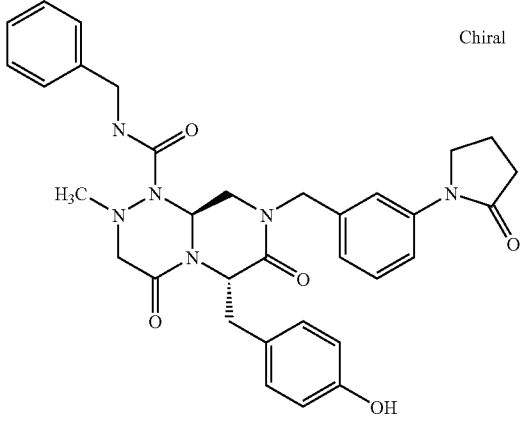 | 15.9 ± 5.2 | 14.8 ± 1.3 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 123 | 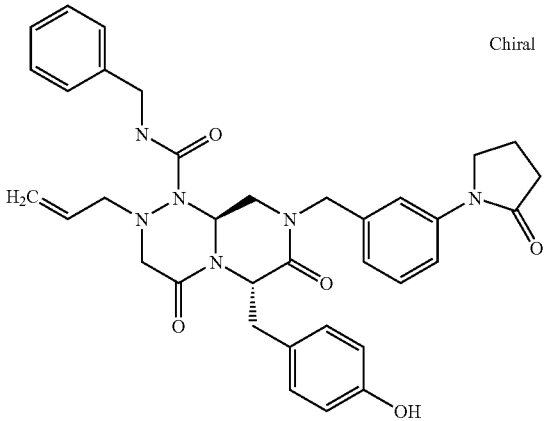 | 1.1 ± 0.3 | 1.7 ± 0.3 |
| 124 | 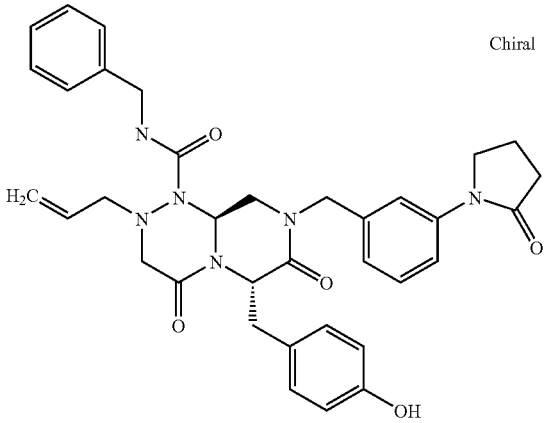 | 2.3 ± 0.2 | 1.4 ± 0.1 |
| 125 | 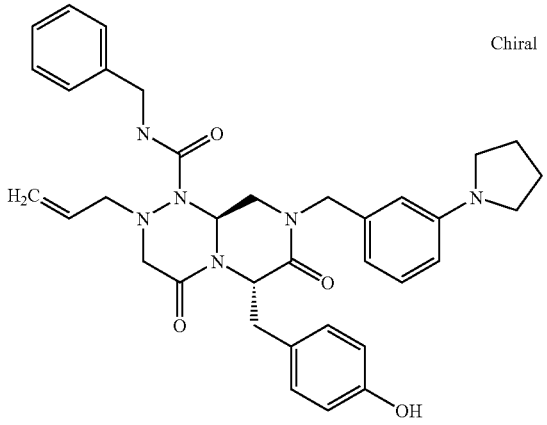 | 2.2 ± 0.3 | 1.9 ± 0.2 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 126 | 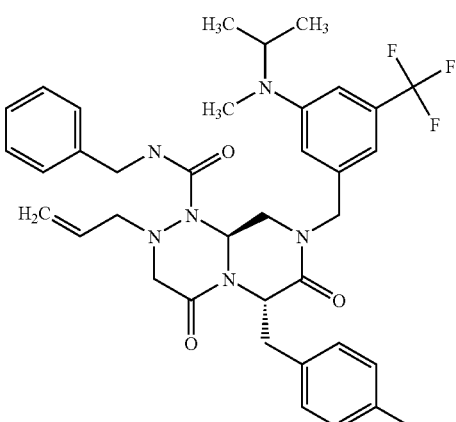 | 19.4 ± 3.0 | 11.6 ± 3.0 |
| 127 | 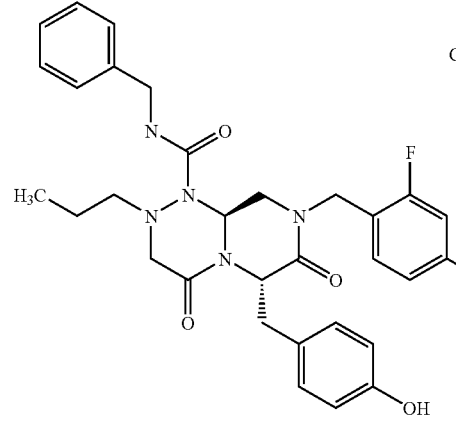 | 4.9 ± 0.7 | 4.3 ± 0.7 |
| 128 | 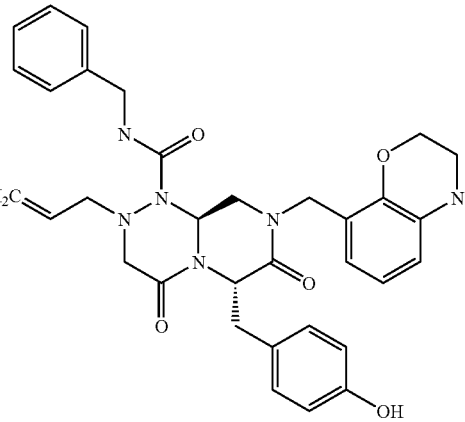 | 0.9 ± 0.1 | 1.0 ± 0.03 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 129 | 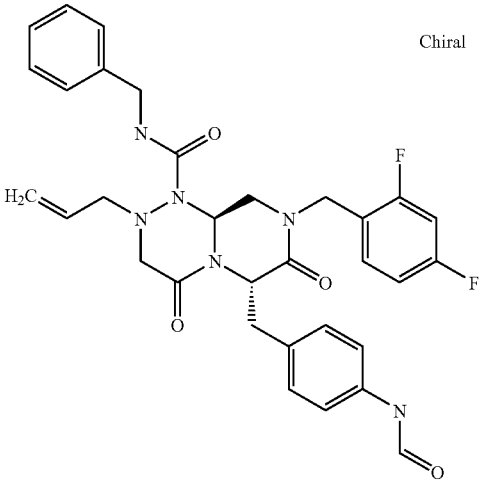 Chiral | 2.9 ± 0.5 | 3.1 ± 0.3 |
| 130 | 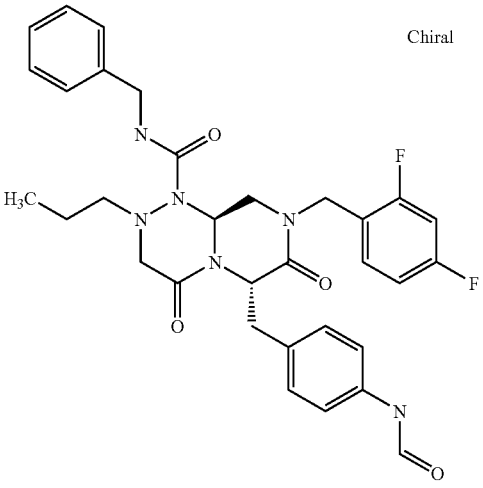 Chiral | 17.3 ± 1.2 | 10.7 ± 1.7 |
| 131 | 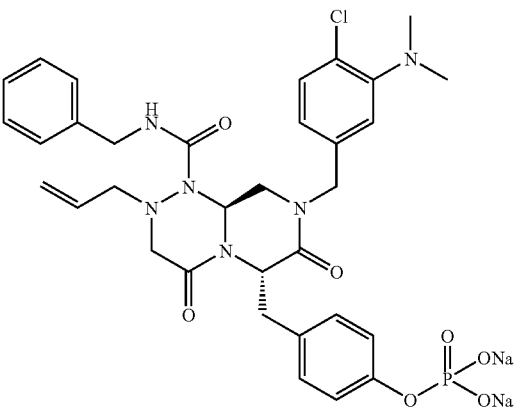 | 2.3 ± 0.1 | 1.7 ± 0.5 |

TABLE 5-continued
ONCOGENIC ACTIVITY BY MTS OR SULFORHODAMINE B ASSAY FOR SELECTED LIBRARY COMPOUNDS
| | | Growth Inhibition (GI50, uM) | |
|---|---|---|---|
| Compound | Structure | SW480 | HCT116 |
| 132 | 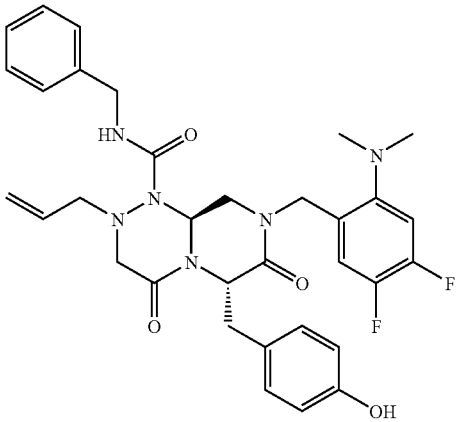 | 2.5 ± 0.1 | 2.2 ± 1.2 |
| 133 | 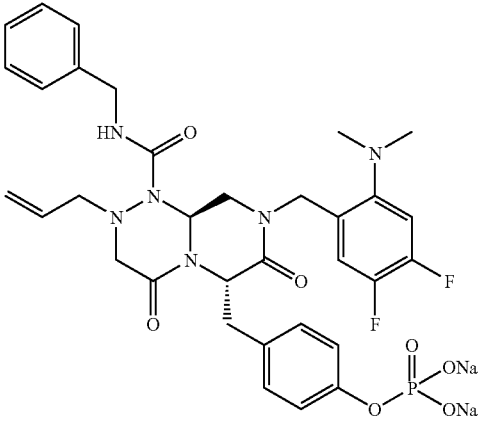 | 2.3 ± 0.1 | 2.1 ± 1.8 |
| 134 | 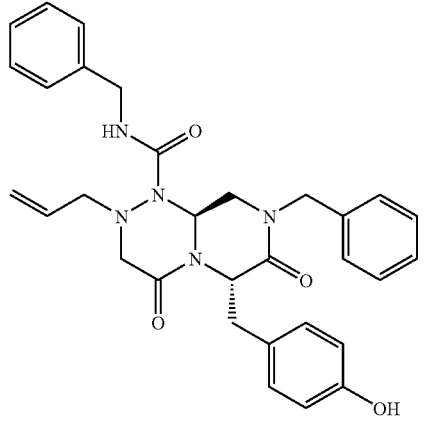 | 1.4 ± 0.4 | 0.8 ± 0.7 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 135 | | 3.2 ± 0.4 | 3.1 ± 0.8 |
| 136 | | 3.4 ± 0.4 | 3.0 ± 0.9 |
| 137 | | 1.4 ± 0.4 | 1.3 ± 0.3 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 138 | 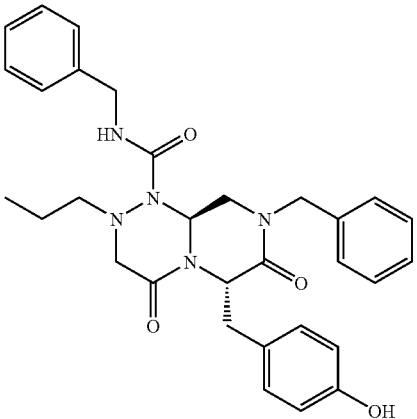 | 4.0 ± 0.4 | 3.9 ± 0.7 |
| 139 | 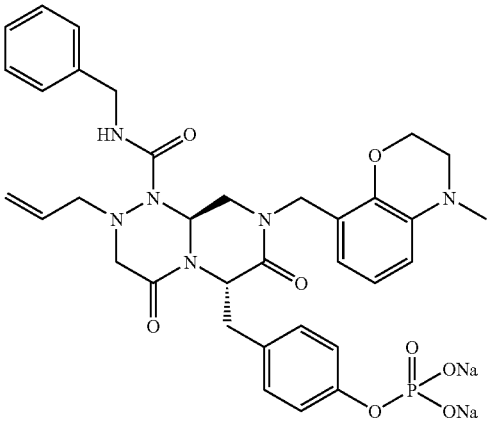 | 1.2 ± 0.1 | 1.0 ± 0.2 |
| 140 | 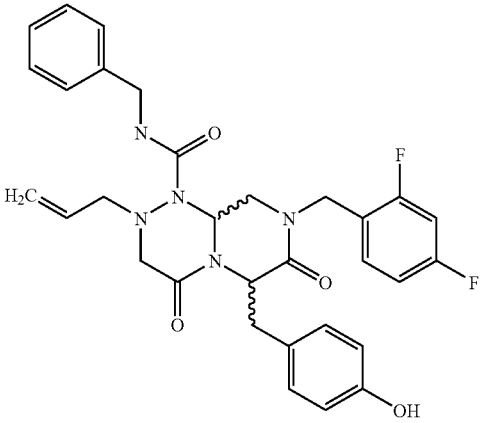 | 1.6 ± 0.5 | 1.7 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
| --- | --- | --- | --- |
| | | SW480 | HCT116 |
| 141 | | 35 ± 11 | 21 ± 2.6 |
| 142 | | 3.2 ± 0.3 | 3.3 ± 0.4 |
| 143 | | 1.2 ± 0.1 | 1.2 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 144 | | 0.5 ± 0.03 | 0.6 ± 0.1 |
| 145 | | 6.4 ± 0.1 | 5.9 ± 0.3 |
| 146 | (Chiral) | 3.7 ± 0.5 | 4.0 ± 0.5 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 147 | Chiral | 6.1 ± 0.4 | 5.5 ± 0.4 |
| 148 | 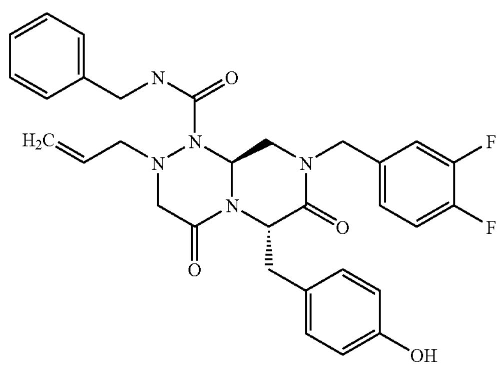 | 1.3 ± 0.1 | 1.0 ± 0.3 |
| 149 | 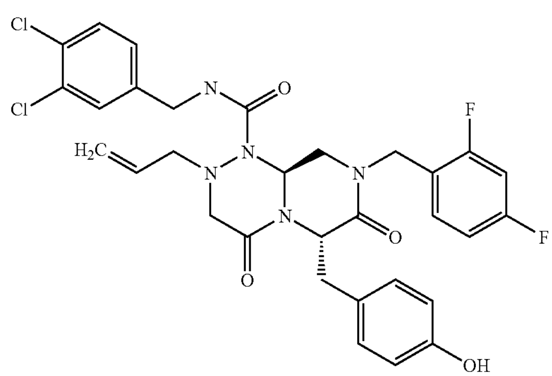 | 2.3 ± 0.1 | 2.3 ± 0.4 |
| 150 | 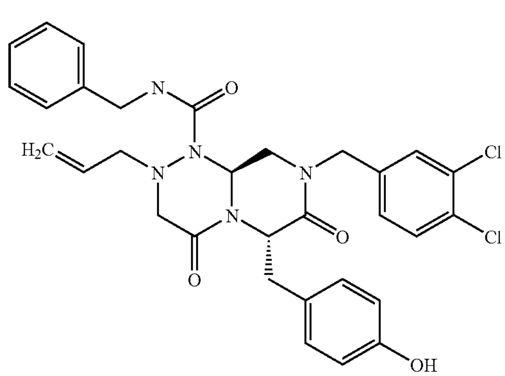 | 1.3 ± 0.1 | 1.4 ± 0.2 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
|---|---|---|---|
| | | SW480 | HCT116 |
| 151 | 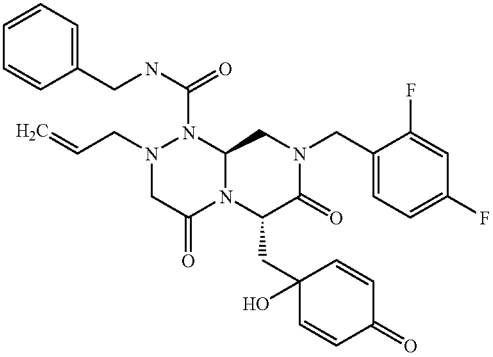 | 11.2 ± 1.3 | 8.6 ± 0.9 |
| 152 | 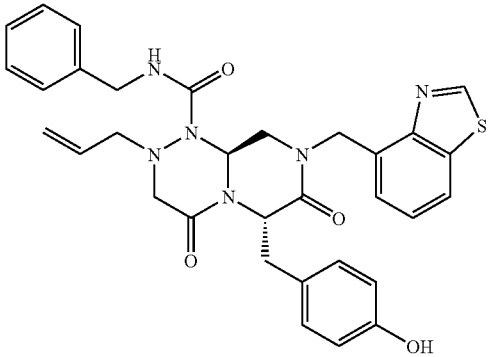 | 0.7 ± 0.1 | 0.6 ± 0.1 |
| 153 | 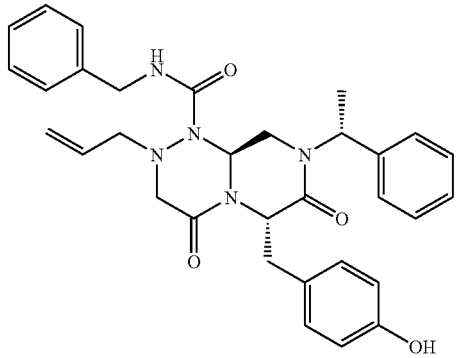 | 12.8 ± 1.6 | 14.3 ± 7.0 |
| 154 | 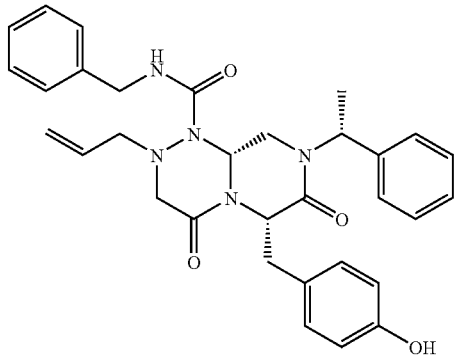 | 0.7 ± 0.2 | 0.7 ± 0.2 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
| --- | --- | --- | --- |
| | | SW480 | HCT116 |
| 155 | 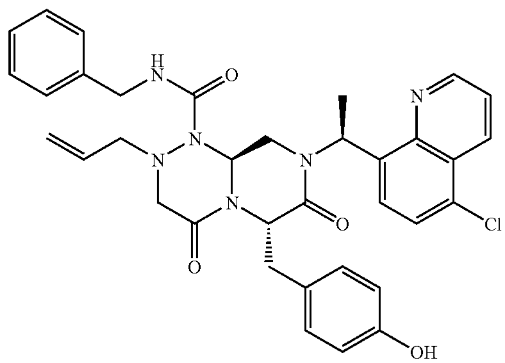 | 26.3 ± 2.5 | 23.3 ± 1.2 |
| 156 | 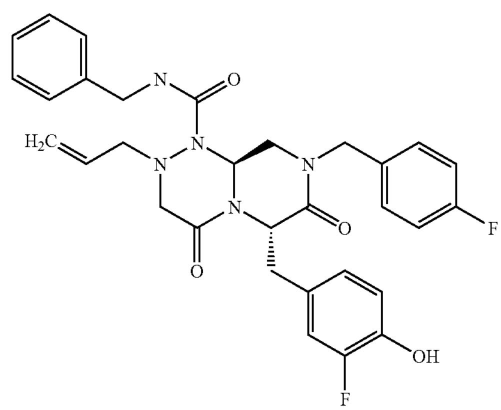 | 3.7 ± 0.3 | 3.8 ± 0.2 |
| 157 | 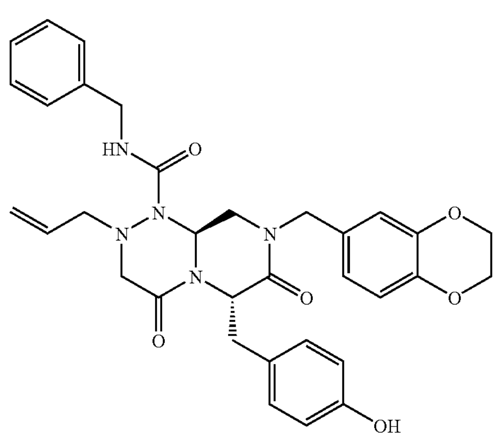 | 1.0 ± 0.2 | 1.2 ± 0.1 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 58 | 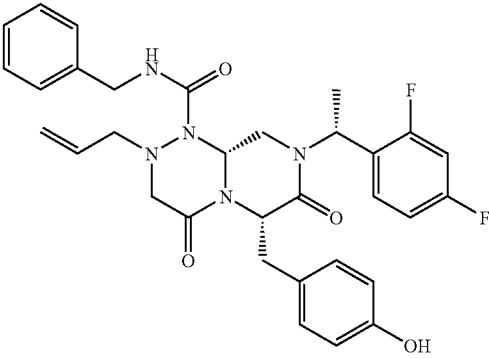 | 4.4 ± 0.1 | 3.8 ± 0.5 |
| 159 | 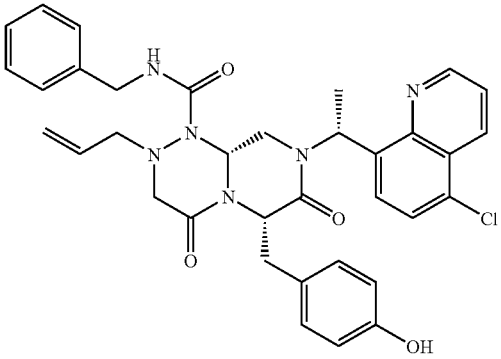 | 9.1 ± 0.5 | 8.2 ± 0.4 |
| 160 | 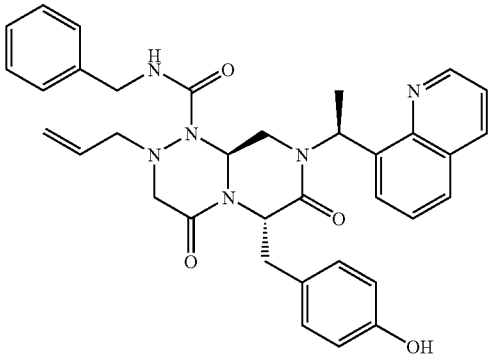 | 13.7 ± 0.5 | 10.1 ± 01.3 |
| 161 | 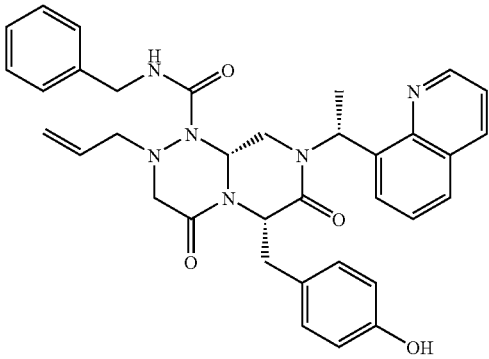 | 4.2 ± 0.4 | 4.1 ± 0.5 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 162 | 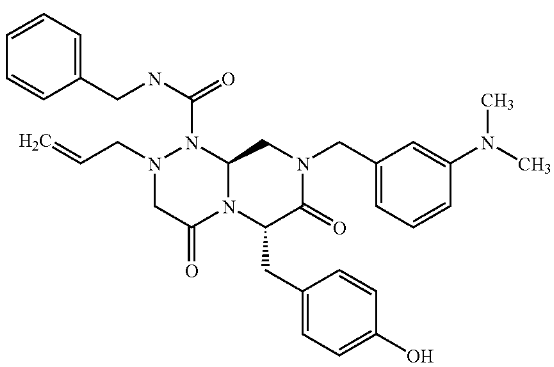 | 1.0 ± 0.3 | 1.3 ± 0.7 |
| 163 | 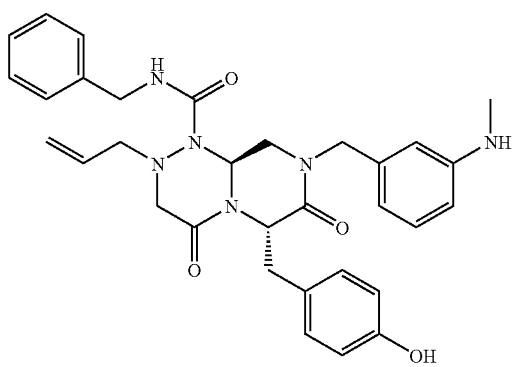 | 2.4 ± 0.2 | 2.3 ± 0.4 |
| 164 | 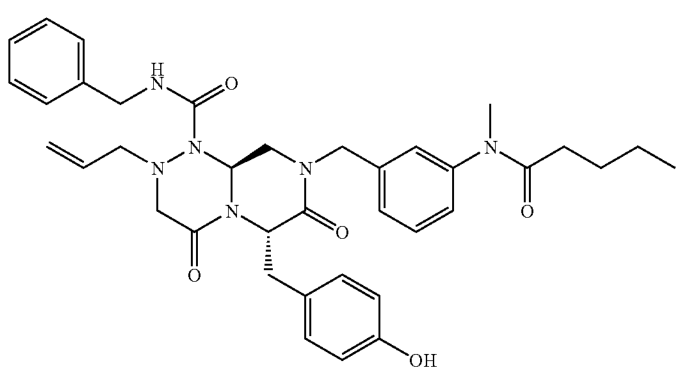 | 3.0 ± 0.3 | 2.9 ± 0.4 |
| 165 | 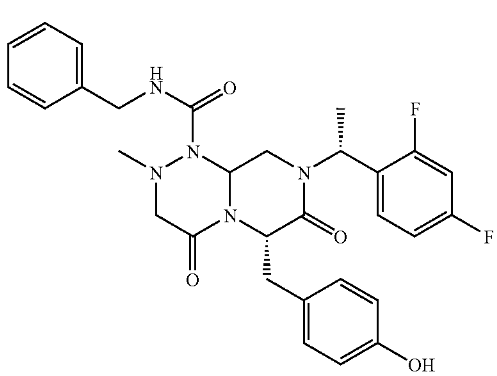 | 22.8 ± 0.9 | 24.4 ± 1.9 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 166 | | 27.9 ± 4.7 | 25.2 ± 3.2 |
| 167 | | 0.3 ± 0.02 | 0.2 ± 0.02 |
| 168 | | 6.2 ± 0.8 | 6.5 ± 0.3 |

TABLE 5-continued
ONCOGENIC ACTIVITY BY MTS OR SULFORHODAMINE B ASSAY FOR SELECTED LIBRARY COMPOUNDS
| | | Growth Inhibition (GI50, uM) | |
|---|---|---|---|
| Compound | Structure | SW480 | HCT116 |
| 169 | 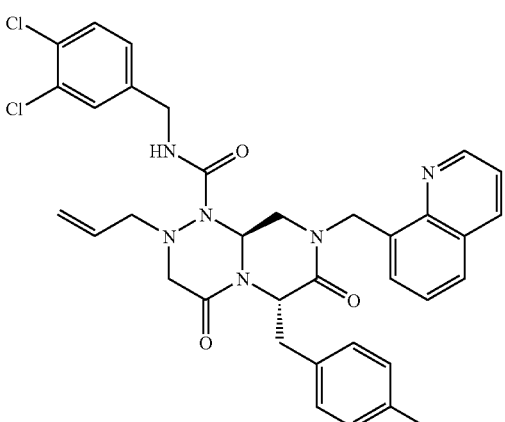 | 0.8 ± 0.1 | 1.0 ± 0.2 |
| 170 | 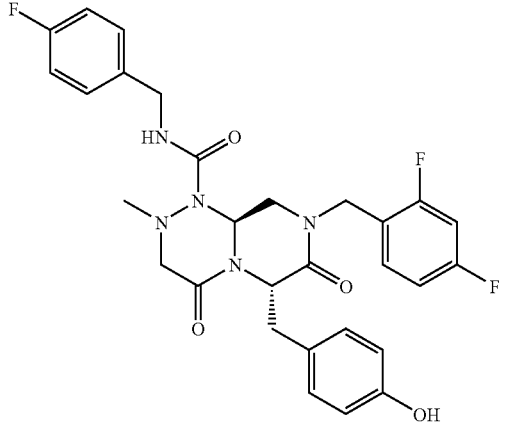 | 8.9 ± 0.8 | 8.6 ± 0.8 |
| 171 | 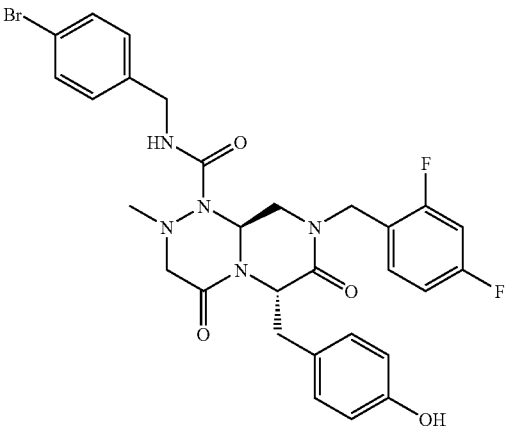 | 6.2 ± 1.0 | 6.0 ± 0.4 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 172 | | 0.8 ± 0.1 | 0.9 ± 0.1 |
| 173 | | 0.6 ± 0.1 | 0.8 ± 0.1 |
| 174 | | 1.9 ± 0.2 | 1.8 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 175 | | 3.0 ± 0.4 | 2.5 ± 0.1 |
| 176 | | 1.7 ± 0.2 | 1.7 ± 0.1 |
| 177 | | 1.8 ± 0.1 | 1.6 ± 0.1 |

TABLE 5-continued
ONCOGENIC ACTIVITY BY MTS OR SULFORHODAMINE B ASSAY FOR SELECTED LIBRARY COMPOUNDS
| Compound | Structure | Growth Inhibition (GI50, uM) | |
| --- | --- | --- | --- |
| | | SW480 | HCT116 |
| 178 | 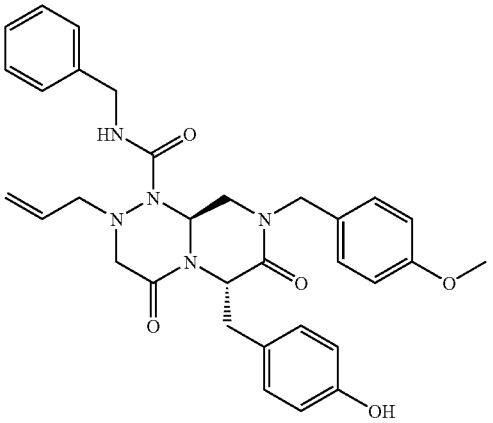 | 1.6 ± 0.2 | 1.5 ± 4.4 |
| 179 | 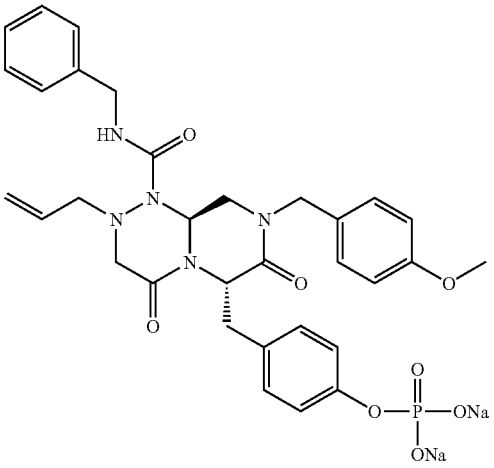 | 1.5 ± 0.1 | 1.6 ± 0.1 |
| 180 | 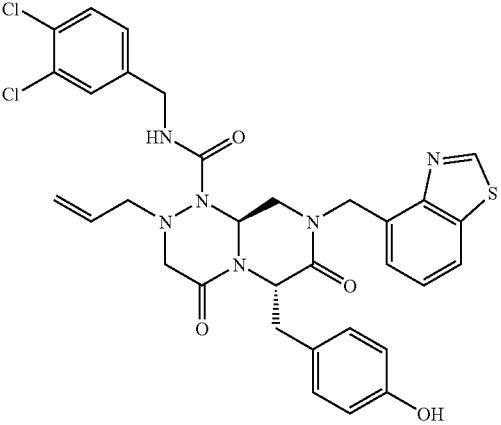 | 1.0 ± 0.1 | 1.1 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
| --- | --- | --- | --- |
| | | SW480 | HCT116 |
| 181 | 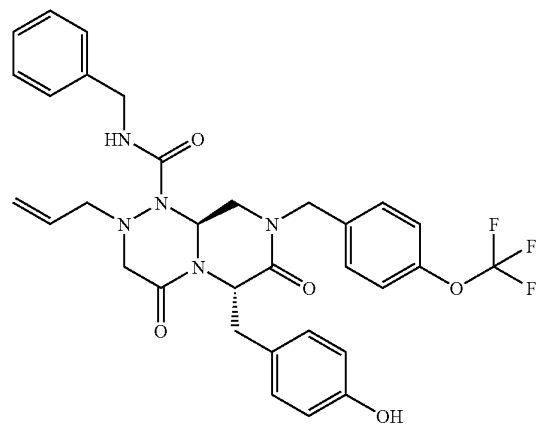 | 2.3 ± 0.1 | 2.3 ± 0.1 |
| 182 | 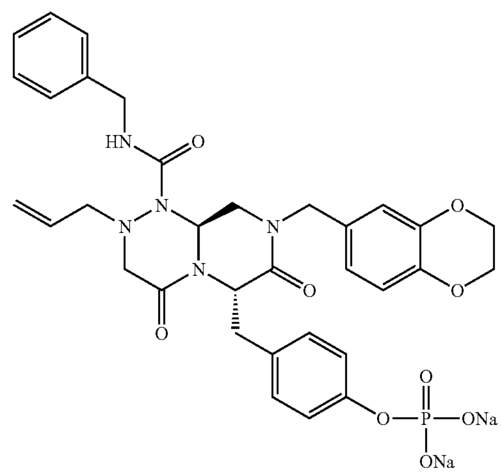 | 1.0 ± 0.1 | 0.8 ± 0.1 |
| 183 | 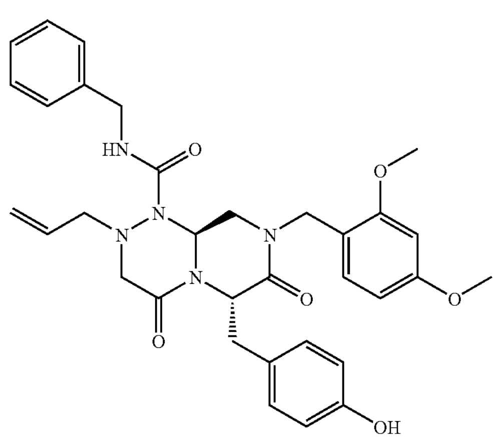 | 1.6 ± 0.3 | 1.5 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 184 | 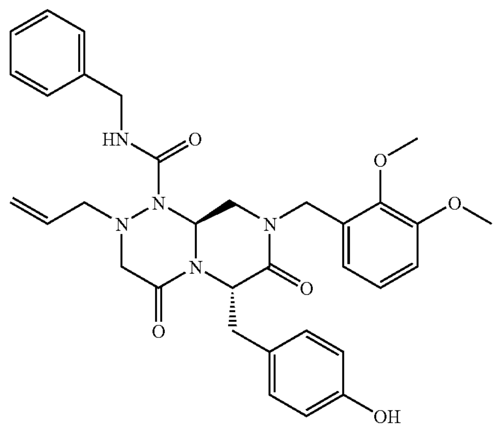 | 0.7 ± 0.4 | 0.7 ± 0.1 |
| 185 | 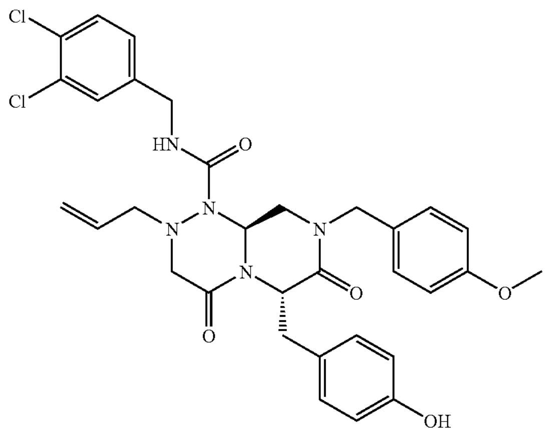 | 4.9 ± 0.4 | 4.5 ± 0.2 |
| 186 | 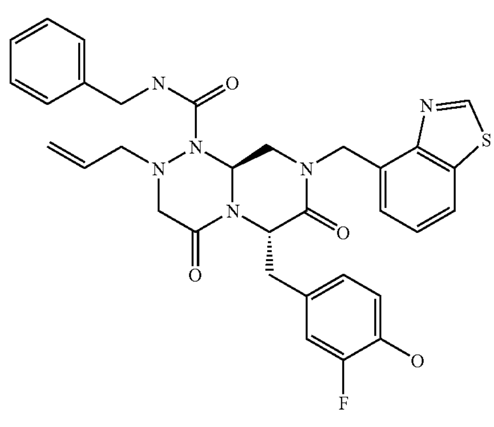 | 1.7 ± 0.1 | 2.0 ± 0.2 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 187 | | 1.0 ± 0.1 | 1.0 ± 0.1 |
| 188 | | 1.6 ± 0.2 | 1.8 ± 0.2 |
| 189 | | 1.0 ± 0.1 | 1.2 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 190 | | 1.1 ± 0.3 | 1.0 ± 0.1 |
| 191 | | 1.2 ± 0.1 | 1.4 ± 0.1 |
| 192 | | 1.1 ± 0.1 | 1.3 ± 0.1 |

TABLE 5-continued

ONCOGENIC ACTIVITY BY MTS OR SULFORHODAMINE B ASSAY FOR SELECTED LIBRARY COMPOUNDS

| Compound | Structure | Growth Inhibition (GI50, uM) | |
|---|---|---|---|
| | | SW480 | HCT116 |
| 193 | | 0.8 ± 0.1 | 1.1 ± 0.1 |
| 194 | | 0.2 ± 0.02 | 0.2 ± 0.02 |
| 195 | | 3.1 ± 0.4 | 3.0 ± 0.3 |

In other aspects the present invention provides pharmaceutical compositions containing a compound having the general formula (I), or the general formula (II), or the general formula (III), or the general formula (IV), or the general formula (VI). These compositions may be used in various methods (e.g., treating cancer or Alzheimer's disease) of the present invention as described in detail below.

The pharmaceutical composition of the present invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. In addition, pH may be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a compound having general formula (I), (II), (III), (IV), or (VI) in the required amount in an appropriate solvent with one or a combination of ingredients enumerated above, as required, followed by filtered sterilization. Generally, dispersions are prepared by incorporating the active compound into a sterile vehicle that contains a dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposbmal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For instance, in certain embodiments, a pharmaceutical composition of the present invention is one suitable for oral administration in unit dosage form such as a tablet or capsule that contains from about 1 mg to about 1 g of the compound of this invention. In some other embodiments, a pharmaceutical composition of the present invention is one suitable for intravenous, subcutaneous or intramuscular injection. A patient may receive, for example, an intravenous, subcutaneous or intramuscular dose of about 1 μg/kg to about 1 g/kg of the compound of the present invention. The intravenous, subcutaneous and intramuscular dose may be given by means of a bolus injection or by continuous infusion over a period of time. Alternatively a patient will receive a daily oral dose approximately equivalent to the daily parenteral dose, the composition being administered 1 to 4 times per day.

The following table illustrates representative pharmaceutical dosage forms containing the compound or pharmaceutically-acceptable salt thereof for therapeutics or prophylactic use in humans:

| Tablet 1 | mg/tablet |
|---|---|
| Compound | 100 |
| Lactose Ph. Eur. | 179 |
| Croscarmellose sodium | 12.0 |
| Polyvinylpyrrolidone | 6 |
| Magnesium stearate | 3.0 |

| Tablet 2 | mg/tablet |
|---|---|
| Compound | 50 |
| Lactose Ph. Eur. | 229 |
| Croscarmellose sodium | 12.0 |
| Polyvinylpyrrolidone | 6 |
| Magnesium stearate | 3.0 |

| Tablet 3 | mg/tablet |
|---|---|
| Compound | 1.0 |
| Lactose Ph. Eur. | 92 |
| Croscarmellose sodium | 4.0 |
| Polyvinylpyrrolidone | 2.0 |
| Magnesium stearate | 1.0 |

| Capsule | mg/capsule |
|---|---|
| Compound | 10 |
| Lactose Ph. Eur. | 389 |
| Croscarmellose sodium | 100 |
| Magnesium stearate | 1.0 |

| Injection I | (50 mg/ml) |
|---|---|
| Compound | 0.5% w/v |
| Isotonic aqueous solution | to 100% |

The pharmaceutical composition containing the compound of general formulae (I) or (II) or (III) or (IV) or (VI) can be used for treatment of disorders modulated by Wnt signaling pathway, especially cancer, more especially colorectal cancer.

In one aspect, the present invention provides compounds that inhibit the binding of a radiolabeled enkephalin derivative to the δ and μ opiate receptors. Accordingly, the reverse-turn mimetics of the present invention may be used as receptor agonists and as potential analgesic agents.

In another aspect, the present invention provides methods for inhibiting tumor growth. Such methods comprise the step of administering to a subject (e.g., a mammalian subject) having a tumor a compound with general formula (I), especially general formula (VI) in an amount effective to inhibit tumor growth. A compound or composition inhibits tumor growth if the tumor sizes are statistically significantly smaller in subjects with the treatment of the compound or composition than those without the treatment.

The inhibitory effect of a particular compound or composition of the present invention on tumor growth may be characterized by any appropriate methods known in the art. For instance, the effect of the compound or composition on survivin expression may be measured. Compounds or compositions down-regulate survivin expression are likely to have inhibitory effects on tumor growth. In addition, assays using tumor cell lines (e.g., soft agar assays using SW480 cells) and animal models for tumor growth (e.g., nude mice grafted with tumor cells and Min mouse model) may also be used to evaluate the inhibitory effect on tumor growth of a given compound or composition as described in detail in the examples. Other exemplary animal models or xenografts for tumor growth include those for breast cancer (Guo et al., *Cancer Res.* 62: 4678-84, 2002; Lu et al., *Breast Cancer Res. Treat.* 57: 183-92, 1999), pancreatic cancer (Bouvet et al., *Cancer Res.* 62: 1534-40, 2002), ovarian tumor (Nilsson et al., *Cancer Chemother. Pharmacol.* 49: 93-100, 2002; Bao et al., *Gynecol. Oncol.* 78: 373-9, 2000), melanoma (Demidem et al., *Cancer Res.* 61: 2294-300, 2001), colorectal cancer (Brown et al., *Dig. Dis. Sci.* 45: 1578-84, 2000; Tsunoda et al., *Anticancer Res.* 19: 1149-52, 1999; Cao et al., *Clin. Cancer Res.* 5: 267-74, 1999; Shawler et al., *J. Immunother. Emphasis Tumor Immunol.* 17: 201-8, 1995; McGregor et al., *Dis. Colon. Rectum.* 36: 834-9, 1993; Verstijnen et al., *Anticancer Res.* 8: 1193-200, 1988), hepatocellular cancer (Labonte et al., *Hepatol. Res.* 18: 72-85, 2000), and gastric cancer (Takahashi et al., *Int. J. Cancer* 85: 243-7, 2000).

The compound or composition that inhibits tumor growth may be administered into a subject with a tumor via an appropriate route depending on, for example, the tissue in which the tumor resides. The appropriate dosage may be determined using knowledge and techniques known in the art as described above. The effect of the treatment of the compound or composition on tumor growth may also be monitored using methods known in the art. For instance, various methods may be used for monitoring the progression and/or growth of colorectal cancer, including colonoscopy, sigmoidoscopy, biopsy, computed tomograph, ultrasound, magnetic resonance imaging, and positron emission tomography. Methods for monitoring the progression and/or growth of ovarian cancer include, for example, ultrasound, computed tomography, magnetic resonance imaging, chest X-ray, laparoscopy, and tissue sampling.

In a related aspect, the present invention provides a method for treating or preventing cancer. Such methods comprise the step of administering to a subject in need thereof a compound or composition having general formula (I), especially the compound of general formular (VI), in an amount effective to treat or prevent cancer in the subject. Treating cancer is understood to encompass reducing or eliminating cancer progression (e.g., cancer growth and metastasis). Preventing cancer is understood to encompass preventing or delaying the onset of cancer. Various types of cancer may be treated or prevented by the present invention. They include, but are not limited to, lung cancer, breast cancer, colorectal cancer, stomach cancer, pancreatic cancer, liver cancer, uterus cancer, ovarian cancer, gliomas, melanoma, lymphoma, and leukemia.

A subject in need of treatment may be a human or non-human primate or other animal with various types of cancer.

A subject in need of prevention may be a human or non-human primate or other animal that is at risk for developing cancer. Methods for diagnosing cancer and screening for individuals with high risk of cancer are known in the art and may be used in the present invention. For instance, colorectal cancer may be diagnosized by fecal occult blood test, sigmoidoscopy, colonoscopy, barium enema with air contrast, and virtual colonoscopy. An individual with high risk of colorectal cancer may have one or more colorectal cancer risk factors such as a strong family history of colorectal cancer or polyps, a known family history of hereditary colorectal cancer syndromes, a personal history of adenomatous polyps, and a personal history of chronic inflammatory bowel disease.

A compound with general formula (I) useful in cancer treatment or prevention may be identified by appropriate methods known in the art. Methods that may be used to select compounds for inhibitory effect on tumor growth as described above may also be used. The route of administration, the dosage of a given compound, the effectiveness of the treatment may be determined using knowledge and techniques known in the art. Factors that may be considered in making such a determination include, for example, type and stage of the cancer to be treated.

The compound with general formula (I) useful in cancer treatment and prevention may be administered in combination with an anti-neoplastic agent. An anti-neoplastic agent refers to a compound that inhibits tumor growth. Exemplary anti-neoplastic agents include Fluorouracil; 5-fluoro-2,4(1H, 3H)-pyrimidinedione (5-FU), taxol, cisplatin, mitomycin C, tegafur, raltitrexed, capecitabine, and irinotecan (Arango et al., *Cancer Research* 61, 2001 4910-4915). A compound with general formula (I) administered in combination with an anti-neoplastic agent does not necessarily require that the compound and the anti-neoplastic agent be administered concurrently. The compound and the agent may be administered separately as long as at a time point, they both have effects on same cancer cells.

In a further related aspect, the present invention provides methods for promoting apoptosis in cancer cells. Such methods comprise the step of contacting cancer cells with a compound having general formula (I), especially a compound having general formula (VI), in an amount effective to promote apoptosis in these cells. A compound promotes apoptosis if the number of cancer cells undergoing apoptosis is statistically significantly larger in the presence of the compound than that in the absence of the compound. Such compounds may be identified by methods known in the art (e.g., measuring caspase activities and/or cell death) using cultured cancer cell lines, xenografts, or animal cancer models. Preferably, the compound is more active in promoting apoptosis in cancer cells than in normal cells. Cancer cells treatable by the present method may be from various tissue origins.

In another aspect of the present invention, a method for treating a disorder modulated by Wnt signaling pathway in which the method comprises administering to a patient a safe and effective amount of the compounds having general formula (I), especially the compound of general formula (VI) is disclosed. Pharmaceutical composition containing the compound of the present invention can be also used for this purpose. In this connection, it is found in the present invention that the compounds having general formula (I), especially the compound of general formula (VI) or the pharmaceutical composition containing thereof can be useful for the treatment of disorder modulated by TCF4-β catenin-CBP complex, which is believed to be responsible for initiating the overexpression of cancer cells related to Wnt signaling pathway. Thus, it is another aspect of the present invention to provide a method for the treatment of disorder modulated by TCF4-β catenin-CBP complex, using the compounds having the general formula (I), especially the compound of general formula (VI).

The present invention also provides compounds and methods for inhibiting survivin expression. Survivin is a target gene of the TCF/beta-catenin pathway, and more specifically is a target gene of the TCF/beta-catenin/CBP pathway. It is a member of the IAP (Inhibitor of Apoptosis Protein) family of proteins. Biological activity associated with survivin includes: highly expressed at $G_2/M$, regulating cell cycle entry and exit; associated with microtubule, centrosomes, centromeres and midbody depending upon the phases of the cell cycle; and anti-apoptosis via interacting directly or indirectly with caspases (e.g., caspase 3, 7 and 9). In connection with cancer, survivin is widely and highly expressed in tumor cells, but expressed to little or no extent in normal tissue cells. Also, it has been observed that cancer patients whose tumors expressed survivin had a decreased overall survival. Furthermore, the degree of surviving expression has been correlated with other cancer markers, e.g., Ki67, PNCA, p53, APC, etc.

The effect of a particular compound of the present invention on survivin expression may be characterized by methods known in the art. Such methods include methods for characterizing survivin expression at the transcriptional or translational level. Exemplary methods for characterizing survivin expression at the transcriptional level are: cDNA microarry, reverse transcription-polymerase chain reaction (RT-PCR), chromatin immunoprecipitation (ChIP), and assays for reporter activities driven by survivin promoter. Exemplary methods for characterizing survivin expression at the translational level are: Western blot analysis, immunochemistry and caspase activities. Detailed descriptions of the above exemplary methods may be found in the examples below.

As described above, the present invention provides methods for inhibiting survivin expression. Such methods comprise the step of contacting a survivin-expressing cell with a compound of the present invention in an amount effective to inhibit survivin expression. A compound inhibits survivin expression if survivin expression in a cell is decreased in the presence of the compound compared to survivin expression in the absence of the compound. Survivin-expressing cells include tumor cells that express, such as cells in or from lung cancer, breast cancer, stomach cancer, pancreatic cancer, liver cancer, uterus cancer, ovarian cancer, gliomas, melanoma, colorectal cancer, lymphoma and leukemia. The step of contacting the survivin-expressing cells with the compound may be performed in vitro, ex vivo, or in vivo. A compound useful in inhibiting survivin expression may be identified, and the effects of a particular compound of the present invention may be characterized, by appropriate methods known in the art, as described in detail above.

Compounds of the present invention have been shown to inhibit the expression of survivin. Blanc-Brude et al., *Nat. Medicine* 8:987 (2002), have shown that survivin is a critical regulator of smooth muscle cell apoptosis which is important in pathological vessel-wall remodeling. Accordingly, another aspect of the present invention provides a method of treating or preventing restenosis associated with angioplasty comprising administering to a subject in need thereof a safe and effective amount of a reverse-turn mimetic of the present invention. In one embodiment the invention treats the restenosis, i.e., administration of a reverse-turn mimetic of the present invention to a subject having restenosis achieves a reduction in the severity, extent, or degree, etc. of the restenosis. In another embodiment the invention prevents the restenosis, i.e., administration of a reverse-turn mimetic of the present invention to a subject that is anticipated to develop new or additional restenosis achieves a reduction in the anticipated severity, extent, or degree, etc. of the restenosis. Optionally, the subject is a mammalian subject.

Compounds of the present invention have been shown to inhibit TCF/B-catenin transcription. Rodova et al., *J. Biol. Chem.* 277:29577 (2002), have shown that PKD-1 promoter is a target of the B-catenin/TCF pathway. Accordingly, another aspect of the present invention provides a method of treating or preventing polycystic kidney disease comprising administering to a subject in need thereof a safe and effective amount of a reverse-turn mimetic of the present invention. In one embodiment the invention treats the polycystic kidney disease, i.e., administration of a reverse-turn mimetic of the present invention to a subject having polycystic kidney disease achieves a reduction in the severity, extent, or degree, etc. of the polycystic kidney disease. In another embodiment the invention prevents polycystic kidney disease, i.e., administration of a reverse-turn mimetic of the present invention to a subject that is anticipated to develop new or additional polycystic kidney disease achieves a reduction in the anticipated severity, extent, or degree, etc. of the polycystic kidney disease. Optionally, the subject is a mammalian subject.

Compounds of the present invention have been shown to inhibit the expression of Wnt signaling. Hanai et al., *J. Cell Bio.* 158:529 (2002), have shown that endostatin, a known anti-angiogenic factor, inhibits Wnt signaling. Accordingly, another aspect of the present invention provides a method of treating or preventing aberrant angiogenesis disease comprising administering to a subject in need thereof a safe and effective amount of a reverse-turn mimetic of the present invention. In one embodiment the invention treats the aberrant angiogenesis disease, i.e., administration of a reverse-turn mimetic of the present invention to a subject having aberrant angiogenesis disease achieves a reduction in the severity, extent, or degree, etc. of the aberrant angiogenesis disease. In another embodiment the invention prevents aberrant angiogenesis disease, i.e., administration of a reverse-turn mimetic of the present invention to a subject that is anticipated to develop new or additional aberrant angiogenesis disease achieves a reduction in the anticipated severity, extent, or degree, etc. of the aberrant angiogenesis disease. Optionally, the subject is a mammalian subject.

Compounds of the present invention have been shown to inhibit the expression of Wnt signalling. Sen et al., *P.N.A.S. (USA)* 97:2791 (2000), have shown that mammals with rheumatoid arthritis demonstrate increased expression of Wnt and Fz in RA synovial tissue. Accordingly, another aspect of the present invention provides a method of treating or preventing rheumatoid arthritis disease comprising administering to a subject in need thereof a safe and effective amount of a reverse-turn mimetic of the present invention. In one embodiment the invention treats the rheumatoid arthritis disease, i.e., administration of a reverse-turn mimetic of the present invention to a subject having rheumatoid arthritis disease achieves a reduction in the severity, extent, or degree, etc. of the rheumatoid arthritis disease. In another embodiment the invention prevents rheumatoid arthritis disease, i.e., administration of a reverse-turn mimetic of the present invention to a subject that is anticipated to develop new or additional rheumatoid arthritis disease achieves a reduction in the anticipated severity, extent, or degree, etc. of the rheumatoid arthritis disease. Optionally, the subject is a mammalian subject.

Compounds of the present invention have been shown to inhibit the expression of Wnt signalling. Uthoff et al., *Int. J. Oncol.* 19:803 (2001), have shown that differential upregulation of disheveled and fz (Wnt pathway molecules) occurs in ulcerative colitis (compared to Chron's disease patients). Accordingly, another aspect of the present invention provides a method of treating or preventing ulcerative colitis comprising administering to a subject in need thereof a safe and effective amount of a reverse-turn mimetic the present invention. In one embodiment the invention treats the ulcerative colitis, i.e., administration of a reverse-turn mimetic of the present invention to a subject having ulcerative colitis achieves a reduction in the severity, extent, or degree, etc. of the ulcerative colitis. In another embodiment the invention prevents ulcerative colitis, i.e., administration of a reverse-turn mimetic of the present invention to a subject that is anticipated to develop new or additional ulcerative colitis achieves a reduction in the anticipated severity, extent, or degree, etc. of the ulcerative colitis. Optionally, the subject is a mammalian subject.

Compounds of the present invention have been shown to inhibit Wnt TCF/catenin signalling. Accordingly, another aspect of the invention provides a method of treating or preventing tuberious sclerosis complex (TSC) comprising administering to a subject in need thereof a safe and effective amount of a reverse-turn mimetic the present invention. Subjects having TSC typically develop multiple focal lesions in the brain, heart, kidney and other tissues (see, e.g., Gomez, M. R. *Brain Dev.* 17(suppl): 55-57 (1995)). Studies in mammalian cells have shown that overexpression of TSC1 (which expresses hamartin) and TSC2 (which expresses tuberin) negatively regulates cell proliferation and induces $G_1$/S arrest (see, e.g., Miloloza, A. et al., *Hum. Mol. Genet.* 9: 1721-1727 (2000)). Other studies have shown that hamartin and tuberin function at the level of the p catenin degradation complex, and more specifically that these proteins negatively regulate beta-catenin stability and activity by participating in the beta-catenin degradation complex (see, e.g., Mak, B. C., et al. *J. Biol. Chem.* 278(8): 5947-5951, (2003)). Beta-catenin is a 95-kDa protein that participates in cell adhesion through its association with members of the membrane-bound cadherin family, and in cell proliferation and differentiation as a key component of the Wnt/Wingless pathway (see, e.g., Daniels, D. L., et al., *Trends Biochem. Sci.* 26: 672-678 (2001)). Misregulation of this pathway has been shown to be oncogenic in humans and rodents. The present invention provides compounds that modulate β-catenin activity, and particularly its interactions with other proteins, and accordingly may be used in the treatment of TSC. Thus, in one embodiment the invention treats TSC, i.e., administration of a reverse-turn mimetic of the present invention to a subject having TSC achieves a reduction in the severity, extent, or degree, etc. of the TSC. In another embodiment the invention prevents TSC, i.e., administration of a reverse-turn mimetic of the present invention to a subject that is anticipated to develop new or additional TSC achieves a reduction in the anticipated severity, extent, or degree, etc. of the TSC. Optionally, the subject is a mammalian subject.

Compounds of the present invention have been shown to inhibit the expression of Wnt signalling. The Kaposi's sarcoma-associated herpesvirus (KSHV) latency-associated nuclear antigen (LANA) is expressed in all KSHV-associated tumors, including Kaposi's sarcoma (KS) and β-cell malignancies such as primary effusion lymphoma (PEL) and multicentric Castleman's disease. Fujimuro, M. et al., *Nature Medicine* 9(3):300-306 (2003), have shown that LANA acts to stabilize β-catenin, apparently by redistribtution of the negative regular GSK-3β. The present invention provides compounds and methods for inhibiting β-catenin protein interactions, e.g., β-catenin/TCF complex formation. Thus, the compounds of the present invention thwart the LANA-induced accumulation of β-catenin/TCF complex and, at least in part, the consequences of KSHV infection. Accordingly, another aspect of the present invention provides a method of treating or preventing conditions due to infection by Karposi's sarcoma-associated herpesvirus (KSHV). Such conditions include KSHV-associated tumors, including Kaposi's sarcoma (KS) and primary effusion lymphoma (PEL). The method comprises administering to a subject in need thereof a safe and effective amount of a reverse-turn mimetic the present invention. In one embodiment the invention treats the KSHV-associated tumor, i.e., administration of a reverse-turn mimetic of the present invention to a subject having a KSHV-associated tumor achieves a reduction in the severity, extent, or degree, etc. of the tumor. In another embodiment the invention prevents a KSHV-associated tumor, i.e., administration of a reverse-turn mimetic of the present invention to a subject that is anticipated to develop new or additional KSHV-associated tumors achieves a reduction in the anticipated severity, extent, or degree, etc. of the tumor. Optionally, the subject is a mammalian subject.

LEF/TCF DNA-binding proteins act in concert with activated β-catenin (the product of Wnt signaling) to transactivate downstream target genes. DasGupta, R. and Fuchs, E. *Development* 126(20):4557-68 (1999) demonstrated the importance of activated LEF/TCF complexes at distinct times in hair development and cycling when changes in cell fate and differentiation commitments take place. Furthermore, in skin morphogenesis, β-catenin has been shown to be essential for hair follicle formation, its overexpression causing the "furry" phenotype in mice (Gat, U., et al. *Cell* 95:605-614 (1998) and Fuchs, E. *Harvey Lect.* 94:47-48 (1999). See also Xia, X. et al. *Proc. Natl. Aad. Sci. USA* 98:10863-10868 (2001). Compounds of the present invention have been shown to inhibit the expression of Wnt signaling, and interfere with formation of β-catenin complexes. Accordingly, the present invention provides a method for modulating hair growth comprising administering to a subject in need thereof a safe and effective amount of a reverse-turn mimetic the present invention, where the amount is effective to modulate hair growth in the subject. Optionally, the subject is a mammalian subject.

The present invention provides compounds useful in treating or preventing Alzheimer's disease. Alzheimer's disease (AD) is a neurodegenerative disease with progressive dementia. This disease is accompanied by three main structural changes in the brain, namely, i) intracellular protein deposits (also known as neurofibrillary tangles, or NFT), ii) extracellular protein deposits termed amyloid plaques that are surrounded by dystrophic neuritis, and iii) diffuse loss of neurons.

The compounds or compositions of the present invention rescue defects in neuronal differentiation caused by a presenilin-1 mutation and may decrease the number, or rate at which neuronal precursor populations differentiate to neurons in Alzheimer's brains. Presenilins are transmembrane proteins whose functions are related to trafficking, turnover and cleavage of Notch and Amyloid Precursor Protein. Missense mutations in presenilin 1 (PS-1) are associated with early-onset familial Alzheimer's disease (Fraser et al., *Biochem. Soc. Symp.* 67, 89 (2001)). The compounds of the present invention may be applicable not only to individuals with PS-1 familial Alzheimer's mutations, but also to general Alzheimer's patients.

In addition, the present invention provides a method for treating or preventing Alzheimer's disease comprising administering to a subject in need thereof a safe and effective amount of a reverse-turn mimetic of the present invention, where the amount is effective to treat or prevent Alzheimer's disease in the subject. Treating Alzheimer's disease is understood to encompass reducing or eliminating the manifestation of symptoms characteistic of Alzheimer's disease, or delaying the progression of this disease. Preventing Alzheimer's disease is understood to encompass preventing or delaying the onset of this disease.

A subject in need of treatment may be a human or non-human primate or other animal that is at various stages of Alzheimer's disease. Methods for diagnosing Alzheimer's disese are known in the art (see, e.g., Dinsmore, *J. Am. Osteopath. Assoc.* 99(9 *Suppl.*):S1-6, 1999; Kurz et al., *J. Neural Transm. Suppl.* 62: 127-33, 2002; Storey et al., *Front Viosci.* 7: e155-84, 2002; Marin et al., *Geriatrics* 57: 36-40, 2002; Kril and Halliday, *Int. Rev. Neurobiol.* 48:167-217, 2001; Gurwitz, *Trends Neurosci.* 23: 386, 2000; Muller-Spahn and Hock, *Eur. Arch. Psychiatry Clin. Neurosci.* 249 *Suppl.* 3: 37-42; Fox and Rossor, *Rev. Neuro. (Paris)* 155 *Suppl.* 4: S33-7, 1999), including the use of neuropsychological measures, functional imaging measures, biological markers, and autopsy of brain tissue. A subject in need of prevention may be a human or non-human primate or other animal that is at risk for developing Alzheimer's disease, such as an individual having a mutation of certain genes responsible for this disease (e.g., genes encoding amyloid precursor protein, presenilin 1, and presenilin 2), and/or a gene involved in the pathogenesis of this disease (e.g., apolipoprotein E gene) (Rocchi et al., *Brain Res. Bull.* 61: 1-24, 2003).

Compounds with structures as set forth in formula (I) may be screened for their activities in treating or preventing Alzheimer's disease by any appropriate methods known in the art. Such screening may be initially performed using in vitro cultured cells (e.g, PC-12 cells as described in Example 8). Compounds capable of rescuing defects in neuronal differentiation caused by a presenilin 1 mutation may be further screened using various animal models for Alzheimer's disease. Alternatively, compounds with structures as set forth in formula (I) may be directedly tested in animal models for Alzheimer's disease. Many model systems are known in the art and may be used in the present invention (see, e.g., Rowan et al., *Philos. Trans. R. Soc. Lond. B. Biol. Sci.* 358: 821-8, 2003; Lemere et al., *Neurochem. Res.* 28: 1017-27, 2003; Sant'Angelo et al., *Neurochem. Res.* 28: 1009-15, 2003; Weiner *Harv. Rev. Psychiatry* 4: 306-16, 1997). The effects of the selected compounds on treating or preventing Alzheimer's disease may be characterized or monitored by methods known in the art for evaluating the progress of Alzheimer's disease, including those described above for diagnosing this disease.

The present invention also provides methods for promoting neurite outgrowth. Such methods comprise the step of contacting a neuron with a compound according to formula (I) in an amount-effective to promote neurite outgrowth. These methods are useful in treating neurodegenerative diseases (e.g., glaucoma, macular degeneration, Parkinson's Disease, and Alzheimer's disease) and injuries to nervous system. A compound promotes neurite outgrowth if the neurite lengths of neurons are statistically significantly longer in the presence of the compound than those in the absence of the compound. Such a compound may be identified using in vitro cultured cells (e.g, PC-12 cells, neuroblastoma B104 cell) (Bitar et al., *Cell Tissue Res.* 298: 233-42, 1999; Pellitteri et al., *Eur. J. Histochem.* 45: 367-76, 2001; Satoh et al., *Biochem. Biophys. Res. Commun.* 258: 50-3-1999; Hirata and Fujisawa, *J. Neurobiol.* 32:415-25, 1997; Chauvet et al., *Glia* 18: 211-23, 1996; Vetter and Bishop, *Curr. Biol.* 5: 168-78, 1994; Koo et al., *Proc. Natl. Acad. Sci. USA* 90: 4748-52, 1993; Skubitz et al., *J. Cell Biol.* 115:1137-48, 1991; O'Shea et al., *Neuron* 7:

231-7, 1991; Rydel and Greene, *Proc. Natl. Acad. Sci. USA* 85:1257-61, 1988) or using explants (Kato et al., *Brain Res.* 31: 143-7, 1983; Vanhems et al., *Eur. J. Neurosci.* 2: 776-82, 1990; Carri et al., *Int. J. Dev. Neurosci.* 12: 567-78, 1994). Contacting a neuron with a compound according to the present invention may be carried out in vitro or in vivo. The resulting treated neuron, if generated in vitro, may be transplanted into a tissue in need thereof (Lacza et al., *Brain Res. Brain Res. Protoc.* 11: 145-54, 2003; Chu et al., *Neurosci. Lett* 343: 129-33, 2003; Fukunaga et al., *Cell Transplant* 8: 435-41, 1999).

The present invention also provides methods for promoting differentiation of a neural stem cell comprising contacting a neural stem cell with a compound according to formula (I) in an amount effective to promote differentiation of a neural stem cell. Such methods are also useful in treating neurodegenerative diseases (e.g., glaucoma, macular degeneration, Parkinson's Disease, and Alzheimer's disease) and injuries to nervous system. "Neural stem cell" refers to a clonogenic, undifferentiated, multipotent cell capable of differentiating into a neuron, an astrocyte or an oligodendrocyte under appropriate conditions. A compound promotes differentiation of neural stem cells if neural stem cells exhibit a statistically significantly higher degree of differentiation in the presence of the compound than in the absence of the compound. Such a compound may be identified using assays involving in-vitro cultured stem cells or animal models (Albranches et al., *Biotechnol. Lett.* 25: 725-30, 2003; Deng et al., *Exp. Neurol.* 182: 373-82, 2003; Munoz-Elias et al., *Stem Cells* 21: 437-48, 2003; Kudo et al., *Biochem. Pharmacol.* 66: 289-95, 2003; Wan et al., *Chin. Med. J.* 116: 428-31, 2003, Kawamorita et al., *Hum. Cell* 15: 178-82, 2002; Stavridis and Smith, *Biochem. Soc. Trans.* 31: 45-9, 2003; Pachernik et al., *Reprod. Nutr. Dev.* 42: 317-26, 2002; Fukunaga et al., supra). The neural stem cell may be a cultured stem cell, a stem cell freshly isolated from its source tissue, or a stem cell within its source organism. Thus, contacting the neural stem cell with a compound according to the present invention may be carried out either in vitro (for a cultured or freshly isolated stem cell) or in vivo (for a stem cell within its source organism). The resulting differentiated neural cell, if generated in vitro, may be transplanted into a tissue in need thereof (Lacza et al., supra; Chu et al., supra; Fukunaga et al., supra). Such a tissue includes a brain tissue or other nervous tissue that suffers from a trauma or a neurodegenerative disease.

The following non-limiting examples illustrate the compounds, compositions, and methods of use of this invention.

EXAMPLES

Preparation Example 1

Preparation Of (N-Fmoc-N'—$R_3$-hydrazino)-acetic acid (1) Preparation of N-Fmoc-N'-Methyl Hydrazine

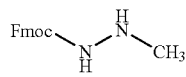

2 L, two-neck, round-bottomed-flask was fitted with a glass stopper and a calcium tube. A solution of methylhydrazine sulfate (20 g, 139 mmol, where $R_3$ is methyl) in THF (300 mL) was added and a solution of DiBoc (33 g, 153 mmol) in THF was added. Saturated sodium bicarbonate aqueous solution (500 mL) was added dropwise via addition funnel over 2 hours with vigorous stirring. After 6 hours, a solution of Fmoc-Cl (39 g, 153 mmol) in THF was added slowly. The resulting suspension was stirred for 6 hours at 0° C. The mixture was extracted with ethyl acetate (EA, 500 mL) and the organic layer was retained. The solution was dried with sodium sulfate and evaporated in vacuo. The next step proceeded without purification.

A 1 L, two-necked, round-bottom-flask was fitted with a glass stopper and a calcium tube. A solution of the product from the previous step in MeOH (300 mL) was added and conc. HCl (30 mL, 12 N) was added slowly via addition funnel with magnetic stirring in ice water bath and stirred overnight. The mixture was extracted with EA (1000 mL) and the organic layer was retained. The solution was dried with sodium sulfate and evaporated in vacuo. The residue was purified by recrystallization with n-hexane and EA to give N-Fmoc-N'-methyl hydrazine (32.2 g, 83%). $^1$HNMR (DMSO-D6) δ 7.90~7.88 (d, J=6 Hz, 2H), δ 7.73~7.70 (d, J=9 Hz, 2H), 7.44~7.31 (m, 4H), 4.52~4.50 (d, J=6 Hz, 2H), 4.31~4.26 (t, J=6 Hz, 1H), 2.69 (s, 1H).

(2) Preparation of (N-Fmoc-N'-methyl-hydrazino)-acetic acid t-butyl ester

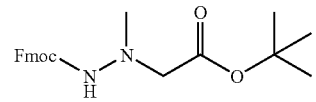

1 L, two-necked, round-bottom-flask was fitted with a glass stopper and reflux condenser connected to a calcium tube. A solution of N-Fmoc-N'-methyl hydrazine (20 g, 75 mmol) in toluene (300 mL) was added. A solution of t-butylbromo acetate (22 g, 111 mmol) in toluene (50 mL) was added slowly. $Cs_2CO_3$ (49 g, 149 mmol) was added slowly. NaI (11 g, 74 mmol) was added slowly with vigorous stirring. The reaction mixture was stirred at reflux temperature over 1 day. The product mixture was filtered and extracted with EA (500 mL). The solution was dried over sodium sulfate and evaporated in vacuo. The product was purified by chromatography with hexane:EA=2:1 solution to give (N-Fmoc-N'-methyl-hydrazino)-acetic acid t-butyl ester (19.8 g, 70%).

$^1$H-NMR (CDCl$_3$-d) δ 7.78~7.75 (d, J=9 Hz, 2H), δ 7.61~7.59 (d, J=6 Hz, 2H), 7.43~7.26 (m, 4H), 4.42~4.40 (d, J=6 Hz, 2H), 4.23 (b, 1H), 3.57 (s, 2H), 2.78 (s, 3H), 1.50 (s, 9H).

(3) Preparation of (N-Fmoc-N'-methyl-hydrazino)-acetic acid

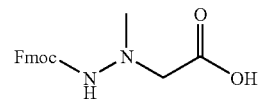

1 L, two-neck, round-bottomed-flask was fitted with a glass stopper and reflux condenser connected to a calcium tube. (N-Fmoc-N'-methyl-hydrazino)-acetic acid t-butyl ester (20 g, 52 mmol) was added. A solution of HCl (150 mL, 4 M solution in dioxane) was added slowly with vigorous stirring in an ice water bath. The reaction mixture was stirred at RT over 1 day. The solution was concentrated completely under reduced pressure at 40° C. A saturated aq. NaHCO$_3$ solution (100 mL) was added and the aqueous layer was washed with diethyl ether (100 mL). Conc. HCl was added dropwise slowly at 0° C. (pH 2-3). The mixture was extracted and the organic layer was retained (500 mL, MC). The solution was dried with sodium sulfate and evaporated in vacuo. The residue was purified by recrystallization with n-hexane and ethyl acetate to give (N-Fmoc-N'-methyl-hydrazino)-acetic acid (12 g, 72%). $^1$H-NMR (DMSO-$d_6$) δ 12.38 (s, 1H), 8.56 (b, 1H), 7.89~7.86 (d, J=9 Hz, 2H), 7.70~7.67 (d, J=9 Hz, 2H), 7.43~7.29 (m, 4H), 4.29~4.27 (d, J=6 Hz, 2H), 4.25~4.20 (t, J=6 Hz, 1H), 3.47 (s, 2H), 2.56 (s, 3H).

Preparation Example 2

Preparation of (N-Moc-N'—R$_7$-hydrazino)-acetic acid (1) Preparation of (N'-Methoxycarbonyl-hydrazino)-acetic acid ethyl ester

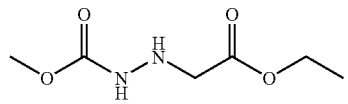

MOC—NH—NH$_2$ (50 g, 0.55 mol) was dissolved in DMF (300 ml), and then-ethyl bromoacetate (68 ml, 0.555 mol) and potassium carbonate (77 g, 0.555 mol) were added to the reaction vessel. The mixture was warmed to 50° C. for 5 hours. After the reaction was completed, the mixture was filtered, and diluted with EtOAc, and washed with brine (3 times). The crude product was purified by column (eluent: Hex/EtOAc=4/1) to provide 72 of colorless oil.

(2) [N—R$_7$—N'-methoxycarbonyl-hydrazino]-acetic acid ethyl ester

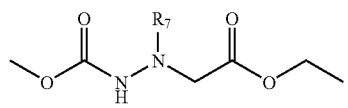

The ethyl ester (10 g, 0.05 mol), potassium carbonate (6.9 g, 0.05 mol), and R$_7$-bromide (14.1 g, 0.06 mol) were dissolved in DMF (200 ml), and The mixture was warmed to 50° C. for 5 hours. After the reaction was completed, the mixture was filtered, and diluted with EA, and washed with brine (3 times). The crude product was purified by Chromatography (eluent: Hex/EtOAc=4/1).

(3) [N—R$_7$—N'-methoxycarbonyl-hydrazino]-acetic acid

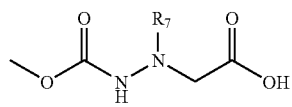

The alkylated ethyl ester (9.5 g, 0.03 mol) was dissolved in THF/water (1/1, ml), and added 2N NaOH (28.3 ml) solution at 0° C. The mixture was stirred at RT for 2 hours. After the starting ester was not detected on UV, the solution was diluted with EA, then separated. The aqueous layer was acidified to pH 3~4 by 1 N HCl, and the compound was extracted by DCM (3 times). The combined organic layer was dried over MgSO4, and evaporated to give a yellow solid.

Example 1

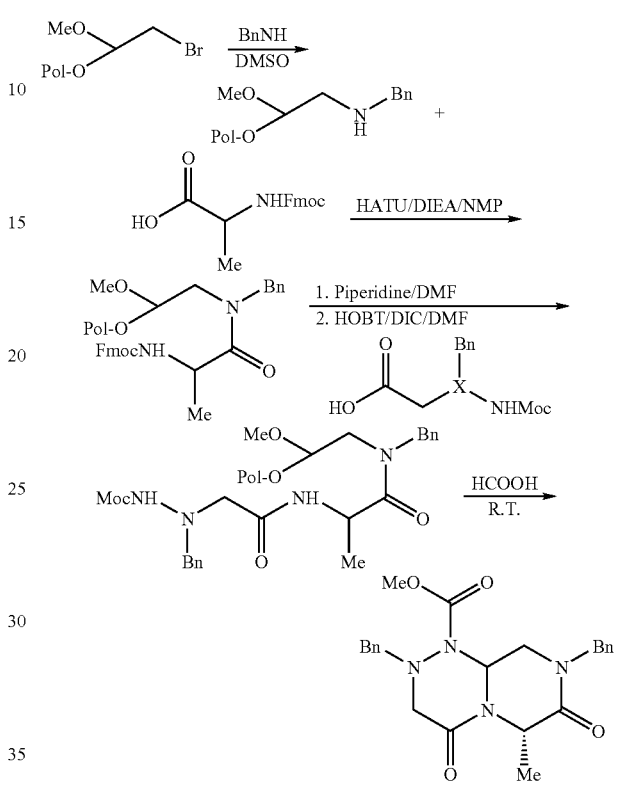

(1) Preparation of N$^β$-Moc-N$^α$-benzyl-hydrazinoglycine

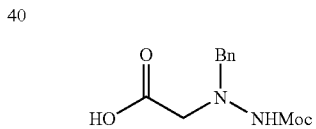

This compound was prepared according to literature procedure. (Cheguillaume et. al., *Synlett* 2000, 3, 331)

(2) Preparation of 1-Methoxycarbonyl-2,8-dibenzyl-6-methyl-4,7-dioxo-hexahydro-pyrazino[2,1-c][1,2,4]triazine Bromoacetal resin (60 mg, 0.98 mmol/g) and a solution of benzyl amine in DMSO (2.5 ml, 2 M) were placed in vial with screw cap. The reaction mixture was shaken at 60° C. using rotating oven [Robbins Scientific] for 12 hours. The resin was collected by filtration, and washed with DMF, then DCM, to provide a first component piece.

A solution of Fmoc-alanine (4 equiv., commercially available, the second component piece), HATU (PerSeptive Biosystems, 4 equiv.), and DIEA (4 equiv.) in NMP (Advanced ChemTech) was added to the resin. After the reaction mixture was shaken for 4 hours at room temperature, the resin was collected by filtration and washed with DMF, DCM, and then DMF.

To the resin was added 20% piperidine in DMF. After the reaction mixture was shaken for 8 min at room temperature, the resin was collected by filtration and washed with DMF, DCM, and then DMF.

A solution of N^β-Moc-N^α-benzyl-hydrazinoglycine (4 equiv., compound (3) in preparative example 2, where $R_7$ is benzyl, 3rd component piece), HOBT [Advanced ChemTech] (4 equiv.), and DIC (4 equiv.) in DMF was added to the resin prepared above. After the reaction mixture was shaken for 3 hours at room temperature, the resin was collected by filtration and washed with DMF, DCM, and then MeOH. The resin was dried in vacuo at room temperature.

The resin was treated with formic acid (2.5 ml) for 18 hours at room temperature. After the resin was removed by filtration, the filtrate was condensed under reduced pressure to give the product as an oil. $^1$H-NMR (400 MHz, CDCl$_3$) δ ppm; 1.51 (d, 3H), 2.99 (m, 1H), 3.39 (d, 1H), 3.69 (m, 1H), 3.75 (m, 1H), 3.82 (s, 3H), 4.02 (d, 1H), 4.24 (d, 1H), 4.39 (d, 1H), 4.75 (d, 1H), 5.14 (q, 1H), 5.58 (dd, 1H), 7.10-7.38 (m, 10H).

Example 2

-continued

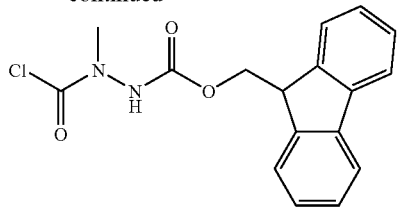

An ice-cooled biphasic mixture of N-methyl hydrazine carboxylic acid 9H-fluoren-9-ylmethyl ester (107 mg, 0.4 mmol) in 15 ml of CH$_2$Cl$_2$ and 15 ml of saturated aq. NaHCO$_3$ was rapidly stirred while 1.93 M phosgene in toluene (1.03 ml, 2 mmol) was added as a single portion. The reaction mixture was stirred for 30 min, the organic phase was

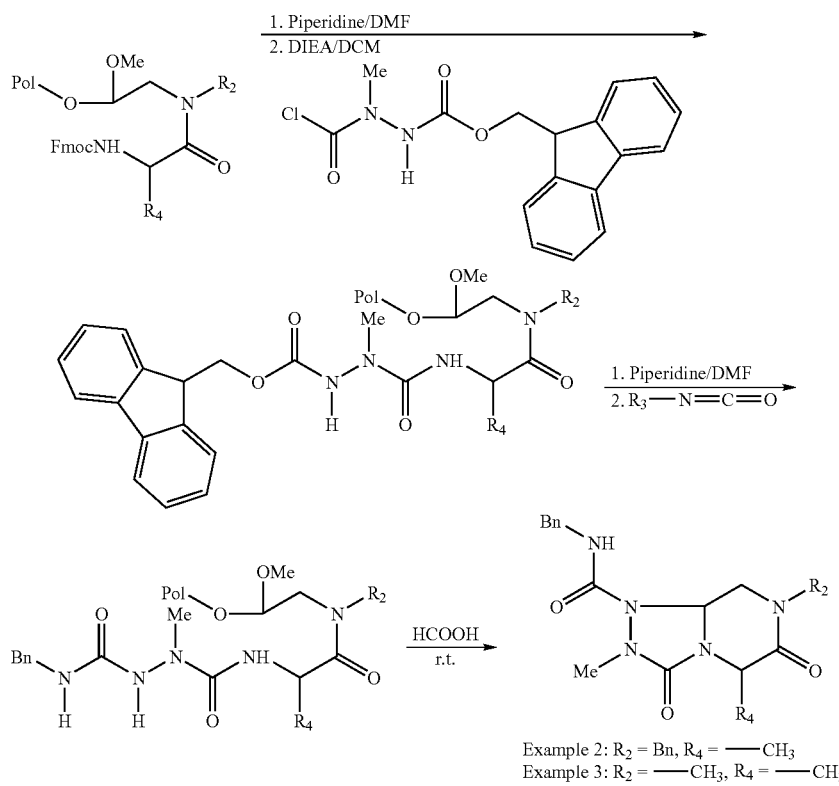

Example 2: $R_2$ = Bn, $R_4$ = —CH$_3$
Example 3: $R_2$ = —CH$_3$, $R_4$ = —CH$_3$ (1) Preparation of N'-Fmoc-N-methyl-hydrazinocarbonyl chloride

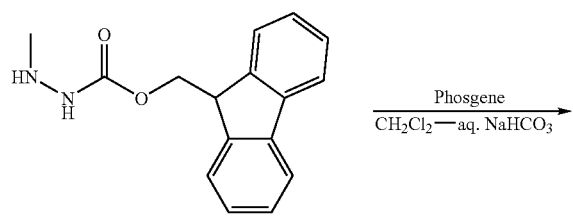

collected, and the aqueous phase was extracted with CH$_2$Cl$_2$. The combined organic layers were dried over MgSO$_4$, filtered, and concentrated in vacuo to afford 128 mg (97%) of carbamoyl chloride as a foamy solid. [Caution: Phosgene vapor is highly toxic. Use it in a hood]. This product was used for the following solid phase synthesis without further purification.

(2) Preparation of 2,5-Dimethyl-7-benzyl-3,6-dioxo-hexahydro-[1,2,4]triazolo[4,5-a]pyrazine-1-carboxylic acid benzylamide Bromoacetal resin (30 mg, 0.98 mmol/g) and a solution of benzyl amine in DMSO (1.5 ml, 2 M) were placed in vial with screw cap. The reaction mixture was shaken at 60° C. using rotating oven [Robbins Scientific] for 12 hours. The resin was collected by filtration, and washed with DMF, then DCM, to provide the first component piece.

A solution of Fmoc-alanine (3 equiv., second component piece, commercially available), HATU (PerSeptive Biosystems, 3 equiv.), and DIEA (3 equiv.) in NMP (Advanced ChemTech) was added to the resin. After the reaction mixture was shaken for 4 hours at room temperature, the resin was collected by filtration and washed with DMF, DCM, and then DMF, to thereby add the second component piece to the first component piece.

To the resin was added 20% piperidine in DMF. After the reaction mixture was shaken for 8 min at room temperature, the resin was collected by filtration and washed with DMF, DCM, and then DMF.

A solution of N'-Fmoc-N-methyl-hydrazinocarbonyl chloride (combined third and fourth component pieces, 5 equiv.) obtained in the above step (1), DIEA (5 equiv.) in DCM was added to the resin prepared above. After the reaction mixture was shaken for 4 hours at room temperature, the resin was collected by filtration and washed with DMF, DCM, and DMF.

To the resin was added 20% piperidine in DMF (10 ml for 1 g of the resin). After the reaction mixture was shaken for 8 min at room temperature, the resin was collected by filtration and washed with DMF, DCM, and then DMF.

The resin was treated with a mixture of benzyl isocyanate (4 equiv.) and DIEA (4 equiv.) in DCM for 4 hours at room temperature. Then, the resin was collected by filteration and washed with DMF, DCM, and then MeOH. The resin was dried in vacuo at room temperature.

The resin was treated with formic acid for 14 hours at room temperature. After the resin was removed by filtration, the filtrate was condensed under reduced pressure to give the product as an oil.

$^1$H-NMR (400 MHz, CDCl$_3$) δ ppm; 1.48 (d, 3H), 2.98 (s, 3H), 3.18 (m, 1H), 3.46 (m, 1H), 4.37-4.74 (m, 5H), 5.66 (dd, 1H), 6.18 (m, 1H), 7.10-7.40 (m, 10H).

Example 3

Preparation of 2,5,7-Trimethyl-3,6-dioxo-hexahydro-[1,2,4]triazolo[4,5-a]pyrazine-1-carboxylic acid benzylamide The title compound is prepared according to the same procedure as described in Example 2, but reacting bromoacetal resin with a solution of methyl amine instead of benzyl amine. $^1$H-NMR (400 MHz, CDCl$_3$) δ ppm; 1.48 (d, 3H), 2.99 (s, 3H), 3.03 (s, 3H), 3.38 (m, 1H), 3.53 (dd, 1H), 4.36 (dd, 1H), 4.52 (q, 1H), 4.59 (dd, 1H), 5.72 (dd, 1H), 6.19 (br.t, 1H), 7.10-7.38 (m, 5H).

Example 4

Preparation of 2-Methyl-5-(p-hydroxyphenylmethyl)-7-naphthylmethyl-3,6-dioxo-hexahydro-[1,2,4]triazolo[4,5-a]pyrazine-1'-carboxylic acid benzylamide Bromoacetal resin (30 mg, 0.98 mmol/g) and a solution of naphthylmethyl amine in DMSO (1.5 ml, 2 M) were placed in vial with screw cap. The reaction mixture was shaken at 60° C. using rotating oven [Robbins Scientific] for 12 hours. The resin was collected by filtration, and washed with DMF, then DCM to provide the first component piece.

A solution of Fmoc-Tyr(OBut)-OH (3 equiv.), HATU (PerSeptive Biosystems, 3 equiv.), and DIEA (3 equiv.) in NMP (Advanced ChemTech) was added to the resin. After the reaction mixture was shaken for 4 hours at room temperature, the resin was collected by filtration and washed with DMF, DCM, and then DMF, to thereby add the second component piece to the first component piece.

To the resin was added 20% piperidine in DMF. After the reaction mixture was shaken for 8 min at room temperature, the resin was collected by filtration and washed with DMF, DCM, and then DMF.

A solution of N'-Fmoc-N-methyl-hydrazinocarbonyl chloride (5 equiv.), DIEA (5 equiv.) in DCM was added to the resin prepared above. After the reaction mixture was shaken for 4 hours at room temperature, the resin was collected by filtration and washed with DMF, DCM, and DMF.

To the resin was added 20% piperidine in DMF (10 ml for 1 g of the resin). After the reaction mixture was shaken for 8 min at room temperature, the resin was collected by filtration and washed with DMF, DCM, and then DMF.

The resin was treated with a mixture of benzyl isocyanate (4 equiv.) and DIEA (4 equiv.) in DCM for 4 hours at room temperature. Then, the resin was collected by filteration and washed with DMF, DCM, and then MeOH. The resin was dried in vacuo at room temperature.

The resin was treated with formic acid for 14 hours at room temperature. After the resin was removed by filtration, the filtrate was condensed under reduced pressure to give the product as an oil.

$^1$H-NMR (400 MHz, CDCl$_3$) δ ppm; 2.80-2.98 (m, 5H), 3.21-3.37 (m, 2H), 4.22-4.52 (m, 2H), 4.59 (t, 1H), 4.71 (d, 1H), 5.02 (dd, 1H), 5.35 (d, 1H), 5.51 (d, 1H), 6.66 (t, 2H), 6.94 (dd, 2H), 7.21-8.21 (m, 12H).

Example 5

Preparation of 2-Methyl-6-(p-hydroxyphenylmethyl)-8-naphthyl-4,7-dioxo-hexahydro-pyrazino[2,1-c][1,2,4]triazine-1-carboxylic acid benzylamide Bromoacetal resin (60 mg, 0.98 mmol/g) and a solution of naphthyl amine in DMSO (2.5 ml, 2 M) were placed in vial with screw cap. The reaction mixture was shaken at 60° C. using rotating oven [Robbins Scientific] for 12 hours. The resin was collected by filtration, and washed with DMF, then DCM.

A solution of Fmoc-Tyr(OBut)-OH (4 equiv.), HATU [PerSeptive Biosystems] (4 equiv.), and DIEA (4 equiv.) in NMP (Advanced ChemTech) was added to the resin. After the reaction mixture was shaken for 4 hours at room temperature, the resin was collected by filtration and washed with DMF, DCM, and then DMF.

To the resin was added 20% piperidine in DMF. After the reaction mixture was shaken for 8 min at room temperature, the resin was collected by filtration and washed with DMF, DCM, and then DMF.

A solution of N$^\beta$-Fmoc-N$^\alpha$-benzyl-hyrazinoglycine (4 equiv.), HOBT [Advanced ChemTech] (4 equiv.), and DIC (4 equiv.) in DMF was added to the resin prepared above. After the reaction mixture was shaken for 3 hours at room temperature, the resin was collected by filtration and washed with DMF, and then DCM. To the resin was added 20% piperidine in DMF (10 ml for 1 g of the resin). After the reaction mixture was shaken for 8 min at room temperature, the resin was collected by filtration and washed with DMF, DCM, and then DMF.

The resin was treated with a mixture of benzyl isocyanate (4 equiv.) and DIEA (4 equiv.) in DCM for 4 hours at room temperature. Then, the resin was collected by filtration and washed with DMF, DCM, and then MeOH. After the resin was dried in vacuo at room temperatur, the resin was treated with formic acid (2.5 ml) for 18 hours at room temperature. The resin was removed by filtration, and the filtrate was condensed under reduced pressure to give the product as an oil.

$^1$H-NMR (400 MHz, CDCl$_3$) δ ppm; 2.73 (s, 3H), 3.13 (d, 1H), 3.21-3.38 (m, 3H), 3.55 (d, 1H), 3.75 (t, 1H), 4.22 (dd, 1H), 4.36 (dd, 1H), 4.79 (d, 1H), 5.22 (t, 1H), 5.47 (m, 2H), 6.68 (d, 2H), 6.99 (d, 2H), 7.21-8.21 (m, 12H); MS (m/z, ESI) 564.1 (MH$^+$) 586.3 (MNa$^+$).

Example 6

Bioassay for the Measurement of IC$_{50}$ Against SW480 Cells and Cytotoxicity Test on the Cell Lines The test compound (Compound A) used in this example was prepared in Example 4.

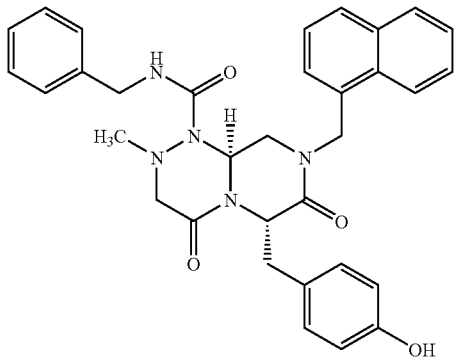

a. Reporter Gene Assay

SW480 cells were transfected with the usage of Superfect™ transfect reagent (Qiagen, 301307). Cells were trypsinized briefly 1 day before transfection and plated on 6 well plate (5×10$^5$ cells/well) so that they were 50-80% confluent on the day of transfection.

Four microgram (TOPFlash) and one microgram (pRL-null) of DNAs were diluted in 150 μl of serum-free medium, and 30 μl of Superfect™ transfect reagent was added. The DNA-Superfect mixture was incubated at room temperature for 15 min, and then, 1 ml of 10% FBS DMEM was added to this complex for an additional 3 hours of incubation. While complexes were forming, cells were washed with PBS twice without antibiotics.

The DNA-Superfec™ transfect reagent complexes were applied to the cells before incubating at 37° C. at 5% CO$_2$ for 3 hours. After incubation, recovery medium with 10% FBS was added to bring the final volume to 1.18 ml. After 3 hours incubation, the cells were harvested and reseeded to 96 well plate (3×10$^4$ cells/well). After overnight incubation at 37° C. at 5% CO$_2$, the cells were treated with Compound A for 24 hours. Finally, the activity was checked by means of luciferase assay (Promega, E1960).

Figure 3:
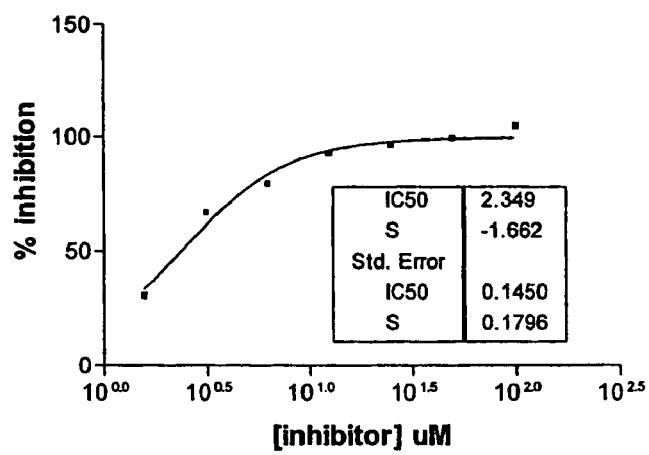
FIG. 3 shows a graph based on the measurement of $IC_{50}$ for Compound A of the present invention using SW480 cells, wherein cell growth inhibition on SW480 cells was measured at various concentrations of Compound A prepared in Example 4 to obtain the $IC_{50}$ value. Specifically, the degree of inhibition in firefly and renilla luciferase activities by Compound A was determined. As a result, the $IC_{50}$ of Compound A against SW480 cell growth was found as disclosed in Table 4. Detailed procedures are the same as disclosed in Example 6.

FIG. 3 illustrates the results of the measurement of IC$_{50}$ of Compound A for SW480 cells.

b. Sulforhodamine B (SRB) Assay

Growth inhibitory effect of Compound A on the cells listed below was measured by the sulforhodamine B assay. SW480 cells in 100 μl media were plated in each well of 96-well plate and allowed to attach for 24 hours. Compound A was added to the wells to produce the desired final concentrations, and the plates were incubated at 37° C. for 48 hours. The cells were then fixed by gentle addition of 100 μl of cold (4° C.) 10% trichloroacetic acid to each well, followed by incubation at 4° C. for 1 hour. Plates were washed with deionized water five times and allowed to air dry. The cells were then stained by addition of 100 μl SRB solution (0.4% SRB (w/v) in 1% acetic acid (v/v)) to wells for 15 min. After staining, the plates were quickly washed five times with 1% acetic acid to remove any unbound dye, and allowed to air dry. Bound dye was solubilized with 10 mmol/L Tris base (pH 10.5) prior to reading the plates. The optical density (OD) was read on a plate reader at a wavelength of 515 nm with Molecular Device. Inhibition of growth was expressed as relative viability (% of control) and GI$_{50}$ was calculated from concentration-response curves after log/probit transformation.

Table 6 shows in vitro cyclotoxicity (SRB) assay data for Compound A obtained in Example 4. The values in Table 6 are in μg/ml.

TABLE 6

| Origin | Cell | Example 4 | Cisplatin | 5-FU |
|---|---|---|---|---|
| Colon | T84 | 1.134 | >10 | 1.816 |
|  | LOVO | 0.532 | >10 | 1.029 |
|  | HT29 | 1.694 | >10 | 5.334 |
|  | DLD-1 | 1.775 | >10 | >10 |
|  | COLO205 | 1.136 | >10 | 1.130 |
|  | CACO-2 | 1.201 | >10 | 0.451 |
|  | SW480-Kribb | 1.137 | >10 | >10 |
|  | SW480-CWP | 0.980 | 4.502 | >10 |
|  | SW620 | 1.426 | >10 | 5.570 |
|  | KM12 | 1.451 | >10 | 2.729 |
|  | HCT15 | 2.042 | >10 | 1.179 |
|  | HCT116 | 0.96 | >10 | 1.039 |
|  | HCC2998 | 1.047 | >10 | 5.486 |
|  | 786-0 | 1.417 | 3.347 | 0.584 |
| Leukemia | HL60 | 1.243 | >10 | 7.010 |
|  | RPMI8226 | 1.1.177 | >10 | >10 |
|  | K562/VIN | 1.640 | >10 | 7.071 |
|  | K562/ADR | 7.682 | >10 | >10 |
|  | K562 | 1.247 | >10 | 6.133 |
| Prostate | PC3 | 1.207 | >10 | >10 |
|  | HT1080 | 1.469 | >10 | 0.798 |
| Lung | A549 | 1.386 | >10 | 1.007 |
|  | NCI H460 | 1.498 | >10 | 1.397 |
|  | NCI H23 | 1.296 | 5.176 | 2.254 |
| Renal | 293 | 0.731 | 6.641 | 2.015 |
|  | CAKI-1 | 0.467 | >10 | 0.925 |
|  | ACHN | 1.263 | 5.019 | 5.062 |
| Melanoma | RPMI7951 | 0.936 | 5.010 | 0.920 |
|  | M14 | 2.289 | 3.447 | 1.225 |
|  | HMV-II | 4.834 | 3.190 | 0.695 |
|  | HMV-I | 1.153 | 5.478 | 2.110 |
|  | G361 | 0.584 | 4.827 | 1.539 |
|  | CRL 1579 | 1.830 | 0.699 | >10 |
|  | A431 | 1.083 | 3.722 | 0.404 |
|  | A253 | 1.398 | 2.084 | 2.926 |
|  | UACC62 | 0.563 | >10 | 1.093 |
|  | SK-MEL-28 | 1.291 | >10 | >10 |
|  | SK-MEL-5 | 0.888 | >10 | 2.434 |
|  | LOX-IMVI | 1.526 | >10 | >10 |
|  | A375 | 1.391 | >10 | 1.464 |
| Breast | MCF7/ADR | 9.487 | 9.907 | >10 |
|  | MCF7 | 7.355 | >10 | 1.751 |

Example 7

Min Mouse Model

Selected compounds of the present invention (Compound B and Compound C) were evaluated in the min mouse model to evaluate their efficacy as anit-cancer agents.

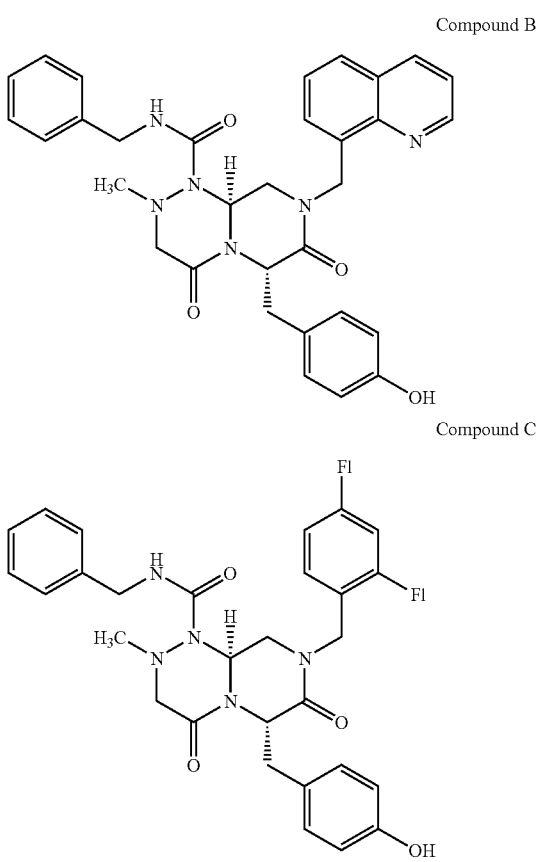

Compound B

Compound C

The min mouse model is a widely used model to test for this type of efficacy. The numbers of polyp formed in small intestine and colon of these mice after various treatments were measured (Table 7). The data shown that both compounds, when administered at about 300 mpk, reduce the number of polyp in min mice compared to those in the control mice treated with vehicle only.

TABLE 7

MIN MOUSE MODEL DATA

| Group | Polyp Number (Mean ± S.D.) | | | P (total) Vs. VH | % Inhibition vs. VH |
| --- | --- | --- | --- | --- | --- |
| | Small Intestine | Colon | Total | | |
| Wild Type | 0.0 ± 0.0 | 0.0 ± 0.0 | 0.0 ± 0.0 | — | — |
| Vehicle | 65.8 ± 15.9 | 1.8 ± 1.5 | 67.7 ± 15.3 | — | — |
| Compound C −100 mpk | 69.2 ± 20.8 | 1.7 ± 1.5 | 71.4 ± 23.0 | — | — |
| Compound C −300 mpk | 46.1 ± 17.1 | 1.1 ± 1.2 | 47.0 ± 16.9 | <0.01 | 31 |
| Compound B −300 mpk | 45.2 ± 22.1 | 1.4 ± 0.9 | 46.8 ± 17.0 | <0.01 | 31 |
| Sulindac −160 ppm | 48.0 ± 20.7 | 0.5 ± 0.5 | 48.5 ± 20.9 | <0.05 | 28 |

Example 8

Chemogenomic Inhibition of CBP/β-Catenin Interaction Rescues Defects in Neuronal Differentiation Caused by a Presenilin-1 Mutation The following compound (Compound D) was used in this example:

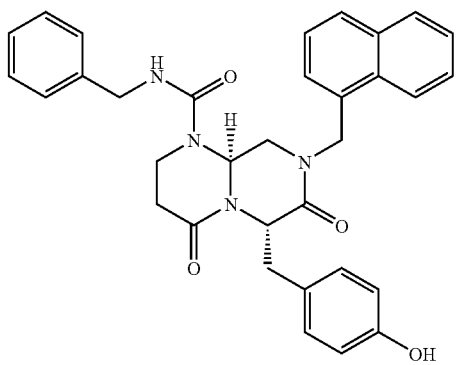

Materials and Methods

Plasmids. TOPFLASH and FOPFLASH reporter constructs were transformed into DH5α competent cells by standard protocol. Plasmids used for transfection assays were isolated and purified using EndoFree Maxi Kit (Qiagen, Valencia, Calif.).

PC-12 Cell Culture. PC-12 cells were maintained in RPMI 1640 supplemented with 10% horse serum, 5% fetal bovine serum, 4.5 g/L glucose, 2 mM L-glutamine, 1.0 mM sodium pyruvate and 10 μg/ml penicillin-streptomycin.

Cell Differentiation. Cell culture dishes were pre-coated overnight with 0.25 mg/ml collagen (Cohesion, Calif), 10 μg/ml Poly-L-Lysine (Sigma-Aldrich, St. Louis, Mo.) and 12 μg/ml Polyethyleneimine (ICN, La Mesa, Calif.). Cells were cultured on coated dishes at 15,000 cells/cm$^2$, and differentiated into a neuron-like phenotype by incubation in medium with reduced serum (1% fetal bovine serum), containing 50 ng/ml nerve-growth factor (NGF) (Sigma-Aldrich) for 10 days. NGF-containing medium was changed every 2-3 days.

Treatment with Compound D. Compound D, a small molecule inhibitor of β-catenin/CBP interaction, was dissolved in DMSO at a stock concentration of 100 mM. Differentiated PC-12/L286V cells were treated with increasing concentrations of this compound for 4 hours. Transfection was then initiated after this treatment period. For cell differentiation experiments, Compound D was added at a concentration of 10 μM, together with NGF, for the entire differentiation period.

Transfection. PC-12 cells were cultured and differentiated on 60-mm dishes. At the end of the 10-day differentiation period, cells were transfected with 2 μg reporter constructs, TOPFLASH and FOPFLASH, per 60-mm dish. Transfections were performed using Superfect (Qiagen) according to manufacturer's instructions.

Luciferase Assays. Cells were lysed, 6 hours after transfections, in 100 μl of Cell Culture Lysis Reagent (Promega, Madison, Wis.), and scraped into microcentrifuge tubes. Tubes were then centrifuged briefly (about 10 seconds) at 12000 rpm to pellet cell debris. Luciferase activity was measured on 20 μl of cell lysate and 100 μl substrate from the Luciferase Assay System (Promega). Luciferase activity was measure using Packard LumiCount. (Hewlett Packard). Quantitation of luciferase was performed in triplicates, and repeated in at least three independent experiments.

Immunofluorescence. Cells were plated at a density of 10,000 cells/cm$^2$ on sterile coated 22×22 mm coverslips in a 6-well culture plate. Differentiation was initiated, as previously described, for 10 days. The differentiated cells were then fixed in methanol for 15 minutes at −20° C. This is followed by a 15 minutes incubation with PBS+0.1% Triton X-100. The coverslips were incubated with antibodies raised against Ephrin B2 Receptor (Santa Cruz Biotechnology) and Gap-43 (Novus Biologicals) for 40 minutes at 37° C. After a series of washes with PBS-Triton X-100, secondary antibody conjugated to FITC (Jackson ImmunoResearch, Westgrove, Pa.) was applied. All slides images were acquired using a Nikon PCM2000 Laser Scanning Confocal Microscope mounted on a Nikon Eclipse E600 upright microscope (Nikon, Melville, N.Y.).

Quantitation of Neurite Outgrowth. Cell counts were taken from six randomly chosen microscopic fields (10×). In each field, total number of cells, as well as cells that displayed neurites greater than twice the length of the cell body was determined. The number of cells with such outgrowths was then expressed as a percentage of the total number of cells. Values obtained were from duplicates of three independent experiments.

RT-PCR. To analyze the mRNA levels for Ephrin B2 (EphB2) receptor, total RNA was isolated using Trizol (Invitrogen-GIBCO-BRL, Baltimore, Md.) from differentiated cells. 2 μg RNA was reverse transcribed in a total volume of 20 μl with random hexamer (50 ng), and using the Superscript II reverse transcription system (Invitrogen-GIBCO-BRL), according to manufacturer's guidelines. PCR was carried out in a 50 μl volume containing 5 μl cDNA, 100 pmol primers, 100 μM dNTPs, 1× Taq buffer and 1.5 mM $MgCl_2$. Reaction mixtures were heated to 80° C. for 10 min, after which Taq was added. cDNAs were amplified for 25 (EphB2 receptor) or 15 (GAPDH) cycles. One round of amplification consisted of 1 min at 94° C., 2 min at 60° C., and 2 min at 72° C., with a final extension time of 10 min at 72° C. The PCR products were resolved and visualized by electrophoresis in a 2% gel, stained with ethidium bromide. EphB2 receptor PCR primers used were, 5'-CACTACTGGACCGCACGATAC-3' and 5'-TCTACCGACTGGATCTGGTTCA-3'. Primer pairs for GAPDH were 5'-GGTGCTGAGTATGTCGTGGA-3' and 5'-ACAGTGTTCTGGGTGGCAGT-3'.

Results

Rat PC-12 cells are derived from the neural crest lineage and upon nerve growth factor (NGF) treatment, undergo differentiation to a neurite-bearing sympathetic-like neuron (Greene and Tischler, *Proc Natl Acad Sci USA* 73, 2424 (1976)). Utilizing a PC-12 cell based model, the effects of an early-onset FAD associated PS-1 mutation, PS-1/L286V, on TCF/β-catenin mediated transcription and neuronal differentiation were characterized. It has been demonstrated that specifically blocking transcription mediated by TCF/β-catenin/CBP alleviates PS-1 induced defects in neuronal differentiation.

PC-12 cells stably overexpressing either wild type PS-1 (PS-1/WT) or mutant PS-1 (PS-1/L286V) and a vector-transfected control cell line (Guo et al., *Neuroreport*, 8, 379 (1996)) were plated on dishes coated with collagen, poly-L-lysine and poly-etheleneimine. Differentiation was induced by treatment with 50 ng/ml of NGF for 10 days. Overexpressing PS-1/WT cells or the vector-transfected cells had extensive neurite formation (similar to PC-12 cell clones from ATCC), whereas the PS-1/L286V mutant cells had only stubby neurite formation (FIG. 4 A-C). Additionally, vector-transfected PC-12 control and PS-1/WT cells displayed extensive expression of the neuronal differentiation marker GAP-43 (Gorgels et al., *Neurosci Lett.* 83, 59(1987)) (FIG. 4 D,E), whereas the PS-1/L286V cells were essentially devoid of this marker (FIG. 4 F).

Figure 4A:
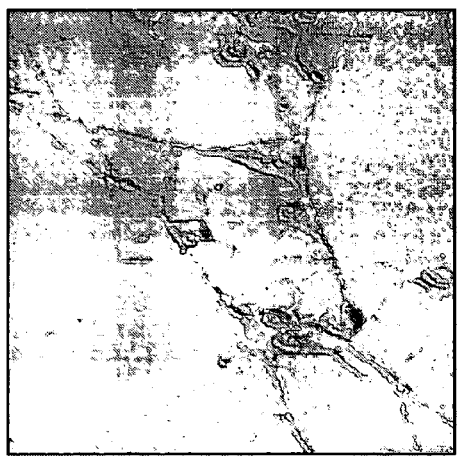
FIG. 4. PC-12 cells were cultured on coated dishes, and differentiated for 10 days in 50 ng/ml nerve growth factor (NGF) (as described in Example 7). (A, B) Vector-transfected PC-12 cells (A) and PC-12 cells overexpressing wt PS-1 (B) exhibit extensive neurite outgrowth after 10 days in NGF. (C) PC-12 cells expressing mutant PS-1/L286V do not display significant neurites under the same culture conditions. (D, E) Immunofluorescence analysis of GAP-43 (as described in Example 7), a molecular marker of neurite outgrowth, demonstrates intense staining for GAP-43 in the neurites (D) of vector-transfected and overexpressing PS-1/WT in PC-12 cells (E). (F) Lack of neurite outgrowth corresponds to weak GAP-43 immunostaining in the mutant cells. Data represent at least two independent experiments. (G) Differentiated cells were transfected with, Topflash, a TCF/β-catenin reporter construct. Cells were lysed, and luciferase activity measured 6 hours post-transfection (as described in Example 7). Data represent the mean of three independent experiments (±SD). Asterisk indicate P<0.05.
Figure 4B:
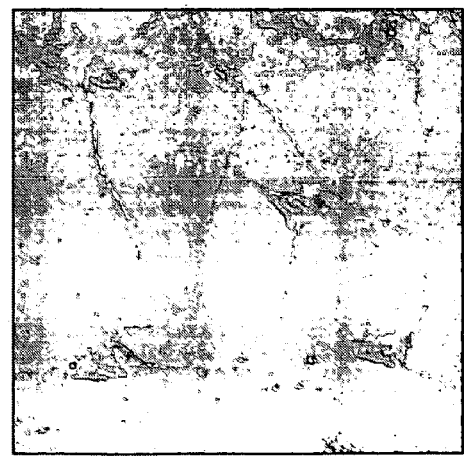
Figure 4C:
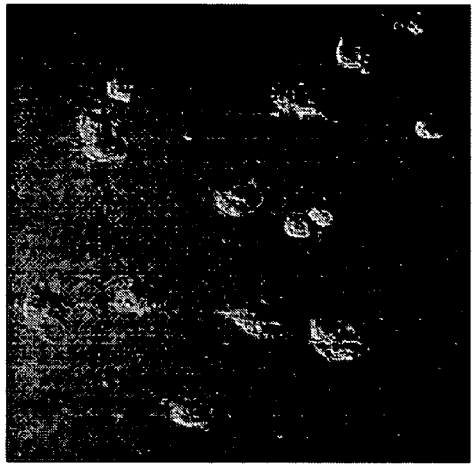
Figure 4D:
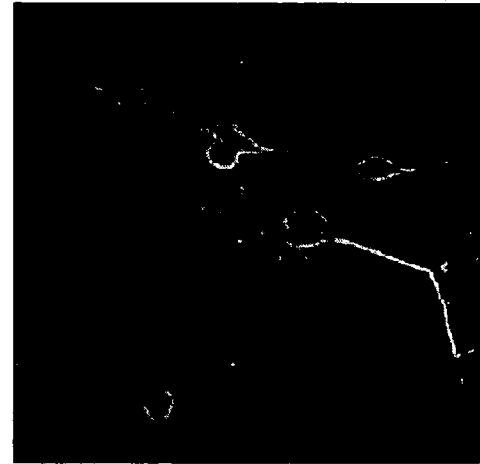
Figure 4E:
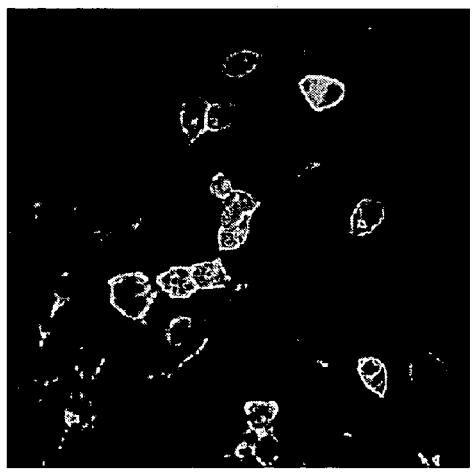
Figure 4F:
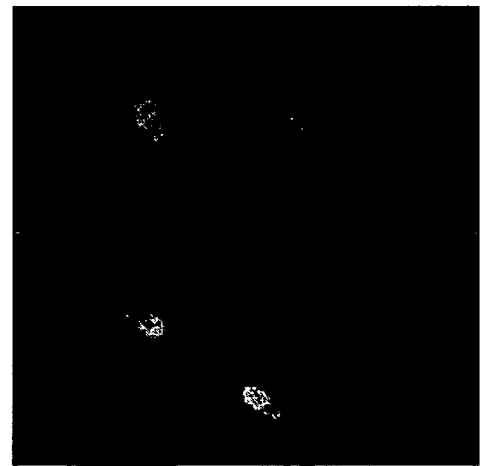
Figure 4G:
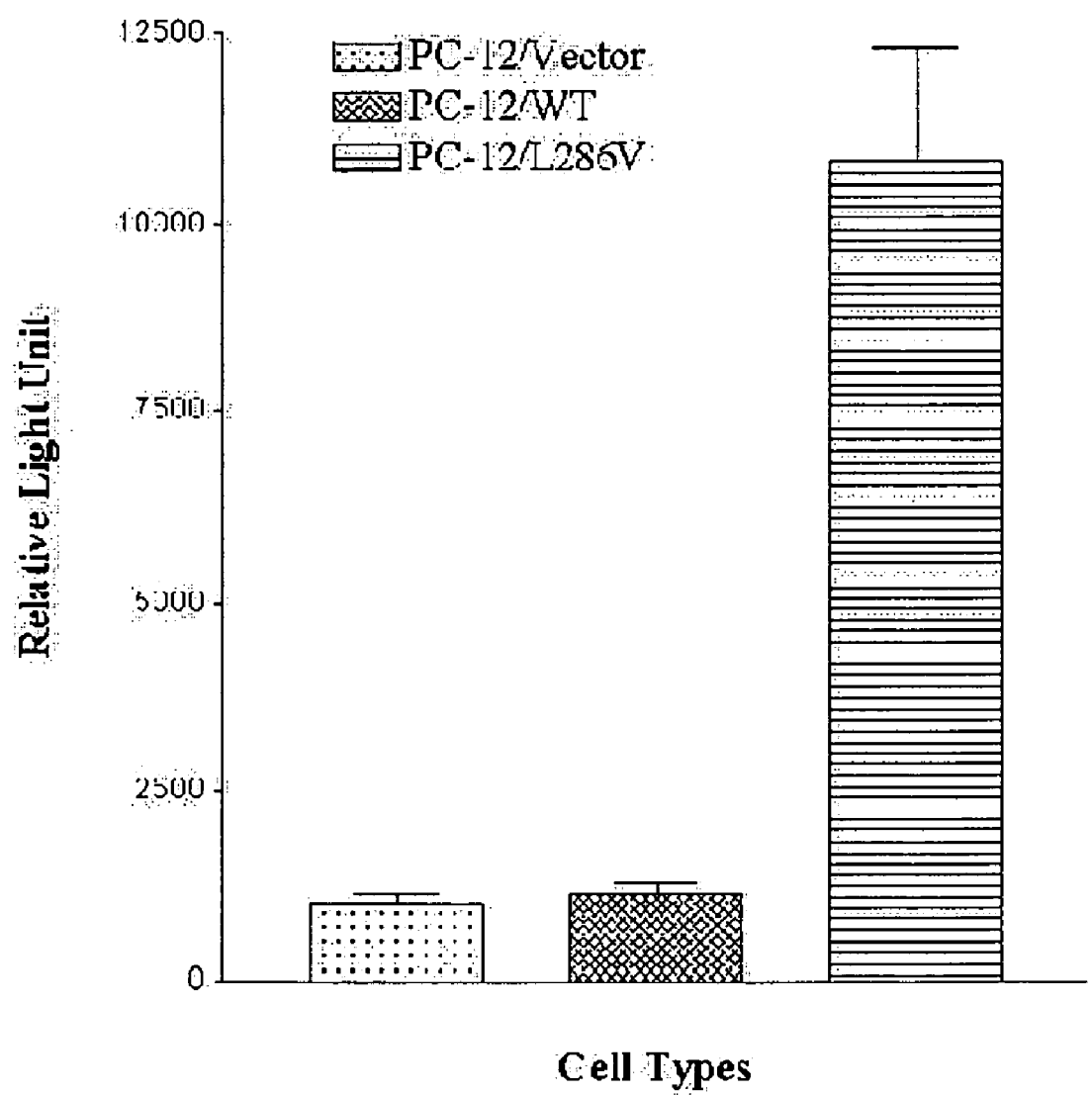

To assess the effects of the PS-1/L286V mutation on canonical Wnt/β-catenin signaling, we transiently transfected NGF treated PC-12 cells with Topflash, a Wnt/β-catenin signaling reporter construct (Morin et al., *Science* 275, 1787(1997)). As seen in FIG. 4F, the overexpressing PS-1/WT cells had similar levels of TCF/β-catenin signaling compared to the vector control cells. However, the PS-1/L286V mutant cells displayed significantly (10-fold) increased Topflash expression. In contrast, the negative control reporter construct Fopflash did not show any significant differences.

Figure 5A:
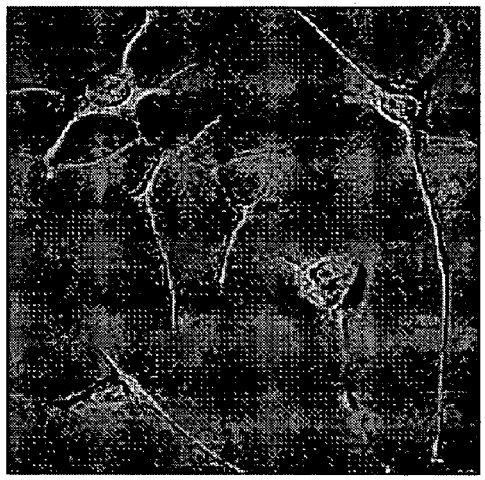
FIG. 5. Compound D phenotypically corrects deficient neuronal differentiation in PC-12 overexpressing mutant PS-1/L286V cells. Mutant cells were exposed to 10 μM Compound D, in addition to NGF, during the differentiation period (Misner et al., Proc. Natl. Acad. Sci. USA 98, 11714 (2001)). (A) Neurite elongation and extension are observed in PC-12 cells overexpressing PS-1/L286V upon treatment with Compound D. (B) GAP-43 (green) is significantly elevated in the mutant cells, and is seen in the neurites. (C) Quantitation of neurite outgrowth in PC-12 cells. Number of mutant cells with neurite lengths greater than two cell diameters was less than 10% that of the vector-transfected and overexpressing PS-1/WT in PC-12 cells. Number of mutant PS-1/L286V cells that had the defined neurite lengths was significantly increased, after treatment with 10 μM Compound D. The results are the average (±SD) of three independent determinations. Asterisk indicate P<0.05.
Figure 5B:
Figure 5C:
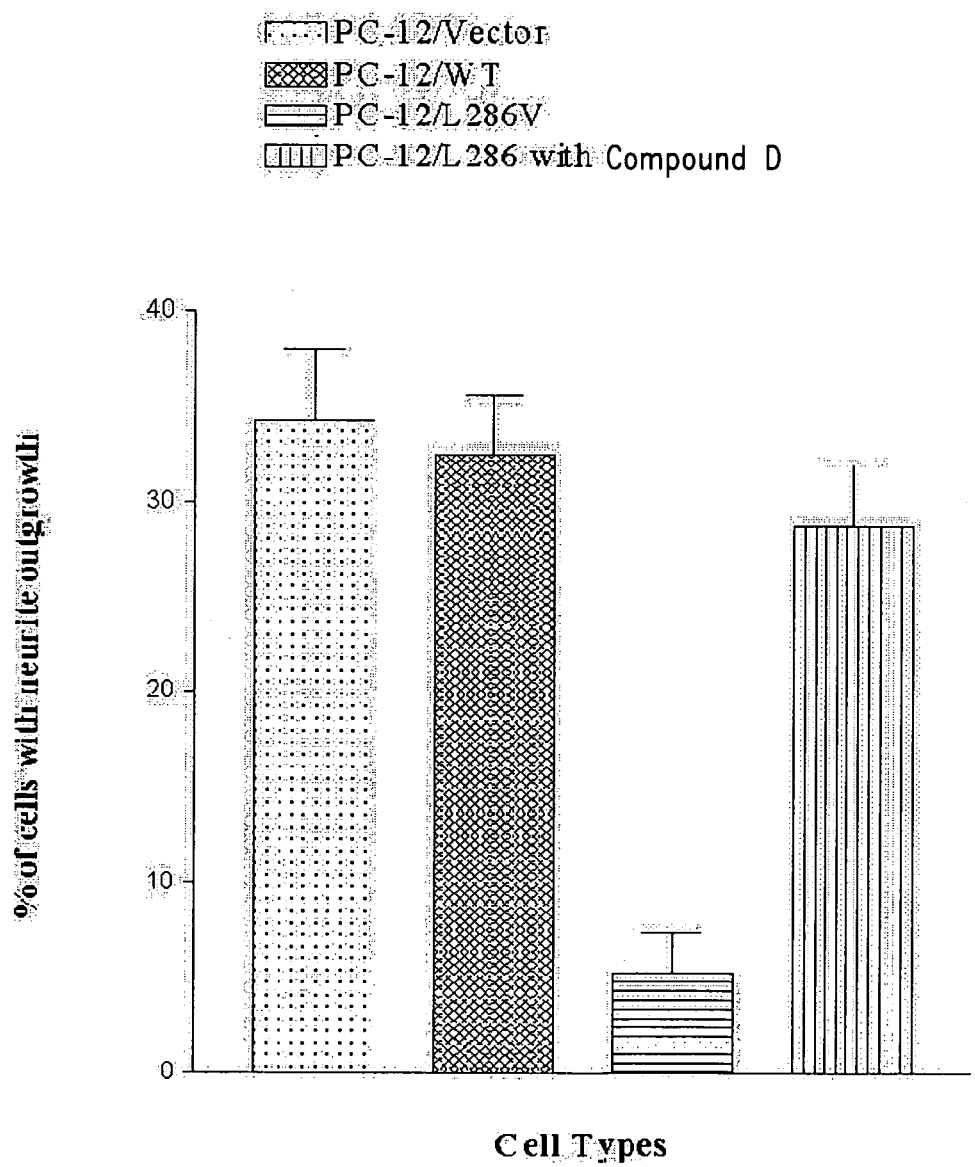
Figure 6A:
FIG. 6. Ephrin B2 (EphB2) receptor expression. Immunofluorescence analysis and RT-PCR were performed to detect EphB2 receptor expression (as described in Example 7). (A, B) EphB2 receptors are clearly demonstrated in neurites of vector-transfected and overexpressing PS-1/WT cells. The intensity of staining correlates with the high expression level. (C) In contrast, PS-1/L286V PC-12 cells have markedly reduced EphB2 receptor expression. (D) Treatment of mutant cells with Compound D leads to increased EphB2 receptor expression, which is focused at points of neurite outgrowth. (E) Expression of EphB2 receptor has previously been shown to be transcriptionally regulated (Guo et al., J. Neurosci. 17, 4212 (1997).). Lane 1, vector-transfected PC-12 cells, lane 2, overexpressing PS-1/WT-cells, lane 3, overexpressing mutant PS-1/L286V cells, lane 4, mutant cells treated with Compound D. RT-PCR analysis indicates message for EphB2 receptor in cells overexpressing mutant PS-1/L286V is decreased compared to those in both the vector-transfected and overexpressing wt PS-1 PC-12 cells. Treatment with 10 μM Compound D upregulates EphB2 message. GAPDH is used an internal control.
Figure 6B:
Figure 6C:
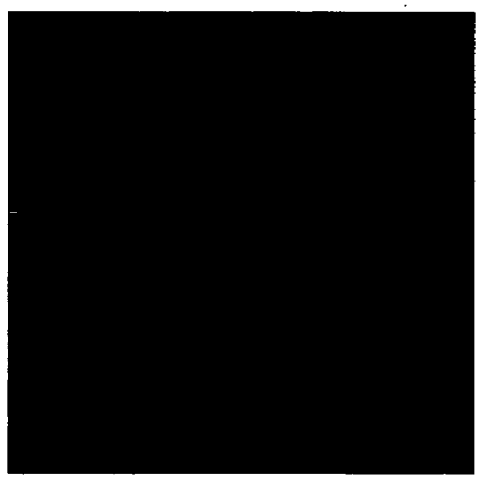
Figure 6D:
Figure 6E:
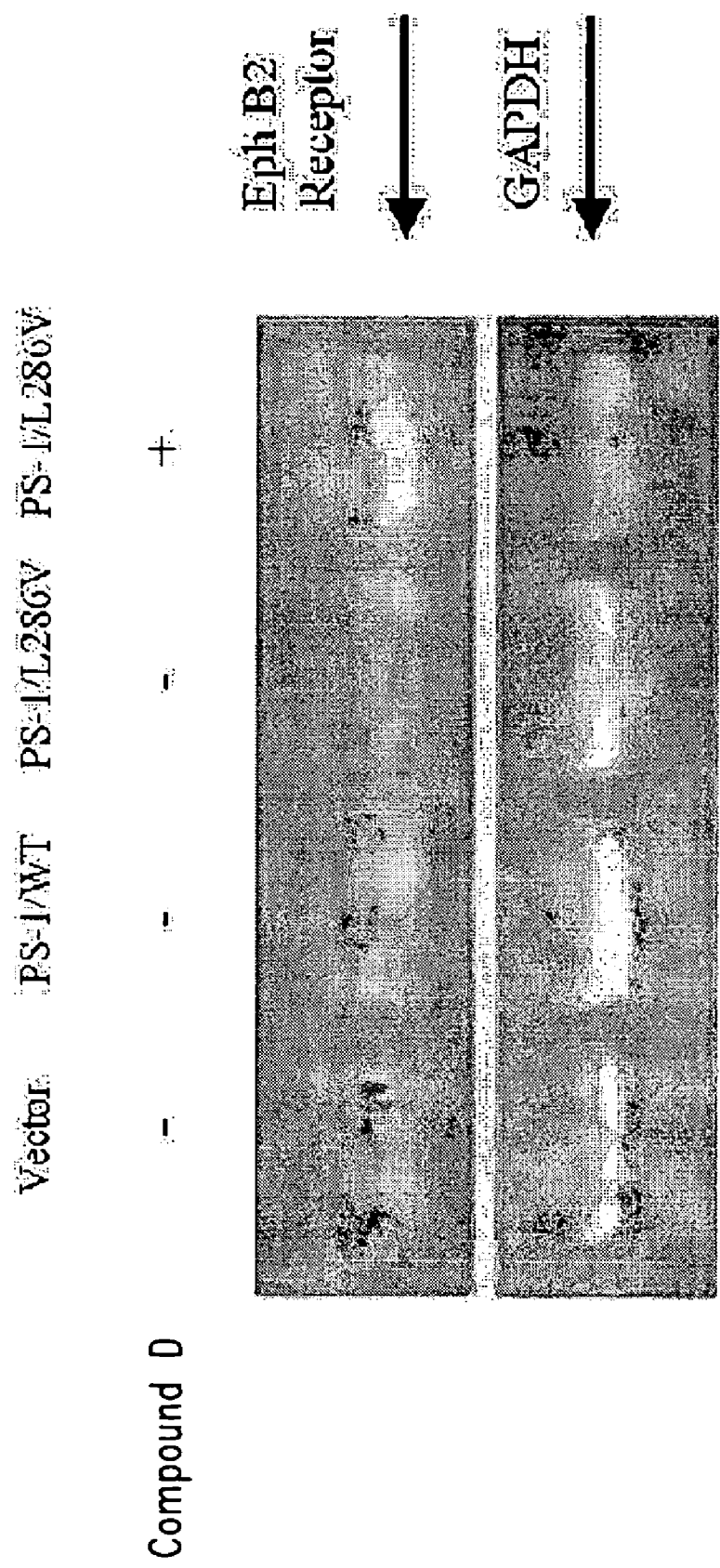

It was hypothesized that dysregulated TCF/β-catenin signaling in the PS-1/L286V mutant cells was responsible for the defective differentiation and neurite outgrowth. To test this hypothesis, a specific small molecule inhibitor of TCF/β-catenin signaling, Compound D (Emami et al., *Cancer Cell*, in press), was used. This small molecule selectively blocks the β-catenin/CBP interaction, but not the β-catenin/p300 interaction, thereby interrupting a subset of TCF/β-catenin transcription. Treatment of the PS-1/L286V mutant cells with 10 μM Compound D plus NGF decreased TCF/β-catenin reporter gene transcription, and led to essentially normal neurite outgrowth and differentiation (FIG. 5 A), similar to that seen in the overexpressing PS-1/WT cells (FIGS. 5 A, B), as compared to the untreated cells (FIG. 4 C). Furthermore, PS-1/L286V mutants treated with Compound D showed similar intense GAP-43 staining to the PS-1/WT and vector-transfected cells (FIG. 4 B). To demonstrate that Compound D treated mutant cells develop neurites similar to that of the vector control or PS-1/WT cells, cells that had neurites greater than twice the length of the cell body were counted. Treatment with Compound D substantially increased the percentage of cells bearing neurites to levels similar to that of the vector-transfected and overexpressing PS-1/WT cells (FIG. 5 C). It is concluded that blocking transcription mediated by TCF/β-catenin/CBP corrects many of the phenotypic defects in neurite outgrowth and neuronal differentiation due to the PS-1/L286V mutation.

Ephrin B2 receptors (EphB2) have been implicated in synapse formation (Wilkinson, *Nat. Rev. Neurosci.* 2, 155 (2001)) and the Ephrin A family has recently been shown to play a role in hippocampal dendritic spine morphology (Murai et al., *Nat Neurosci.* 6, 153 (2003)). Focused EphB2 expression was observed, which localized with neuronal processes in the vector and PS-1/WT-transfected cells (FIG. 6 A, B), whereas the PS-1/L286V mutant cells demonstrated very weak and diffuse EphB2 signal (FIG. 6 C). Increased TCF/β-catenin signaling in PS-1/L286V mutant cells manifested itself in decreased EphB2 expression as judged by RT-PCR (FIG. 6 E, lane 3). Furthermore, addition of 10 μM Compound D led to increased EphB2 message (FIG. 6 E, lane 4) as well as EphB2 expression in these cells (FIG. 6 D). These results are consistent with the data of Batlle and colleagues (Batlle et al., *Cell* 111, 251 (2002)) who recently showed that expression of EphB2/EphB3 receptors and their ligand ephrin-B1 is inversely controlled in colonic crypts via TCF/β-catenin transcription, and that proper regulation is important for appropriate cell proliferation, differentiation and sorting. We present evidence that the PS-1/L286V mutation via increased TCF/β-catenin signaling, decreased the expression of EphB2 receptors and this is corrected by Compound D mediated inhibition of the β-catenin/CBP interaction.

Example 9

Compound D Causes a G1/S-Phase Arrest and Activates Caspase Activity

Flow Cytometric Analysis (FACS)

For FACS analysis, approx. $5 \times 10^6$ cells from Compound D-treated or vehicle-treated were fixed with 70% chilled ethanol and stored at −20° C. for at least 30 minutes. The cells were washed once with 1×PBS and incubated with propidium iodine (PI) solution (85 μg/ml propidium iodine, 0.1% Nonidet P-40, 10 mg/ml RNAse) for 30 minutes at room temperature. 10,000 stained cells for each sample were acquired using Beckman Coulter EPICS XL-MCL Flow Cytometry and the percentage of cells in different phase of the cell cycle was determined by Expo32 ADC software (Coulter Corporation, Miami, Fla., 33196).

Caspase-3 Activity Assay

SW480, HCT116, and CCD18Co cells were plated at $10^5$ cells per well (96-well plates) for 24 hours prior to treatment. 25 μM of Compound D or control (0.5% DMSO) was added to each well. 24 hours post treatment, cells were lysed and caspase activity was measured using a caspase-3/7 activity kit (Apo-One Homogeneous caspase-3/7 assay, #G77905, Promega). Relative fluorescence units (RFU) were obtained by subtracting the unit values of the blank (control, without cells) from the experimental measured values.

Compound D Causes a $G_1$/S-Phase Arrest and Activates Caspase Activity

Figure 7A:
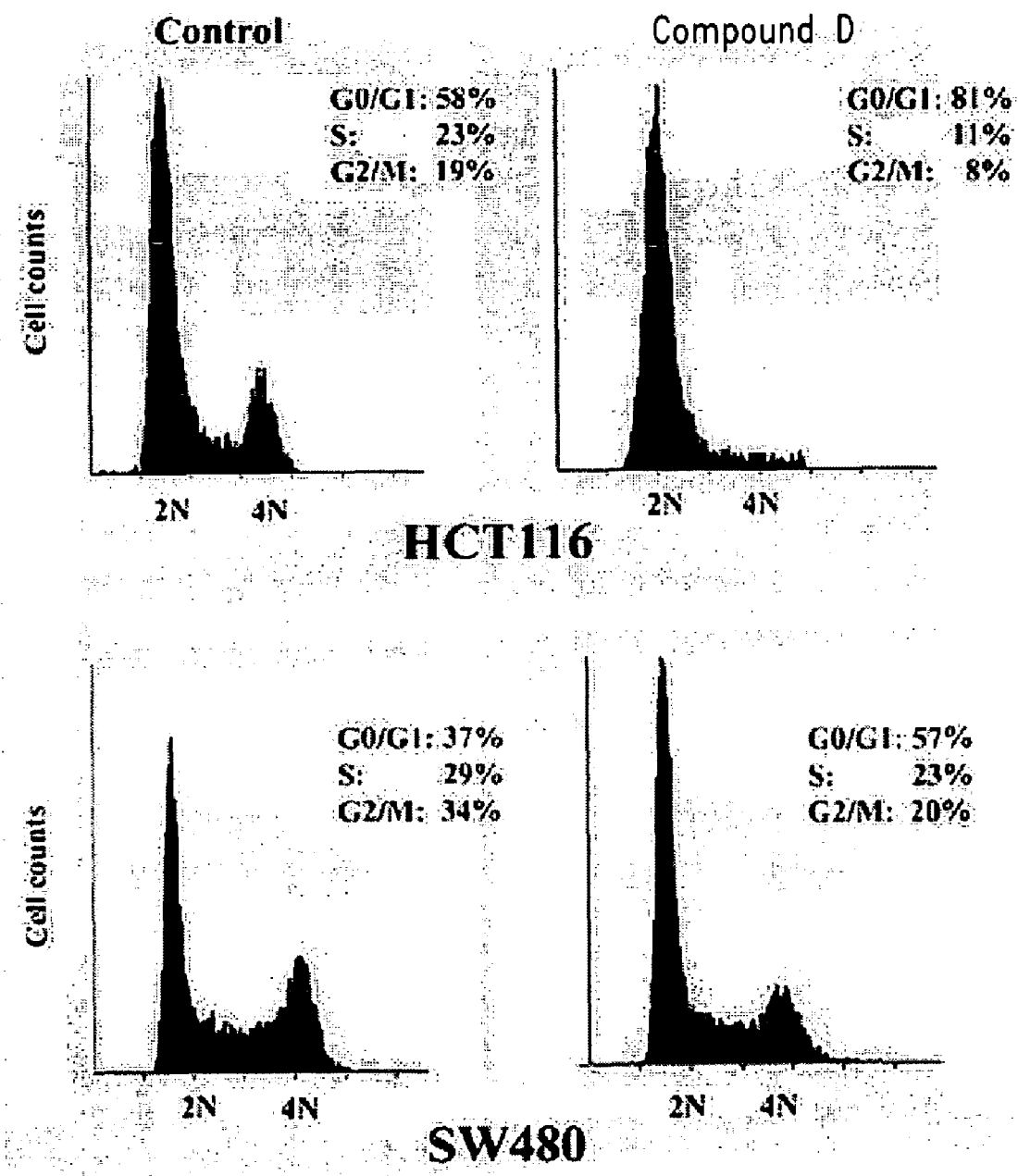
FIG. 7. A. Compound D arrests cells in $G_1$. FACS analysis was performed on SW480 (lower panel) and HCT116 (upper panel) cells treated for 24 hours with either Compound D (25 μM) (right) or control (0.5% DMSO (left). $5.5 \times 10^6$ cells were fixed and stained with propidium iodide (PI). B. Compound D selectively activates caspases in colon carcinoma cell lines. SW480 and HCT116 (left graph) cells (105) along with the normal colonocytes CCD18Co (right graph) were treated with either control (0.5% DMSO) or Compound D (25 μM). 24 hours post treatment, cells were lysed and the caspase-3/7 enzymatic activities were measured. Relative fluorescence units (RFU) were calculated by subtracting the unit values of the blank (control, without cells) from the treated samples (Compound D or control) and plotted.

It has been shown that inhibition of the expression of the cyclin D1 gene causes arrest at the $G_1$/S-phase of the cell cycle (Shintani et al., "Infrequent alternations of RB pathway (Rb-p16INK4A-cyclin D1) in adenoid cystic carcinoma of salivary glands," Anticancer Res. 20:2169-75 (2000)). HCT116 (FIG. 7A, upper panel) and SW480 (FIG. 7A, lower panel) cells were treated with Compound D (25 μM) (FIG. 7A, right) or control (0.5% DMSO) (FIG. 7A, left) for 24 hours. The cells were subsequently stained with propidium iodide (PI) and analyzed for DNA content by FACS cytofluorometry. As expected, the control cells, (FIG. 7A, left), were cycling normally whereas the Compound D treated cells (FIG. 7A, right) showed increased accumulation at $G_1$/S-phase of the cell cycle. Thus, it can be seen that Compound D causes arrest of cells at the $G_1$ phase.

Figure 7B:
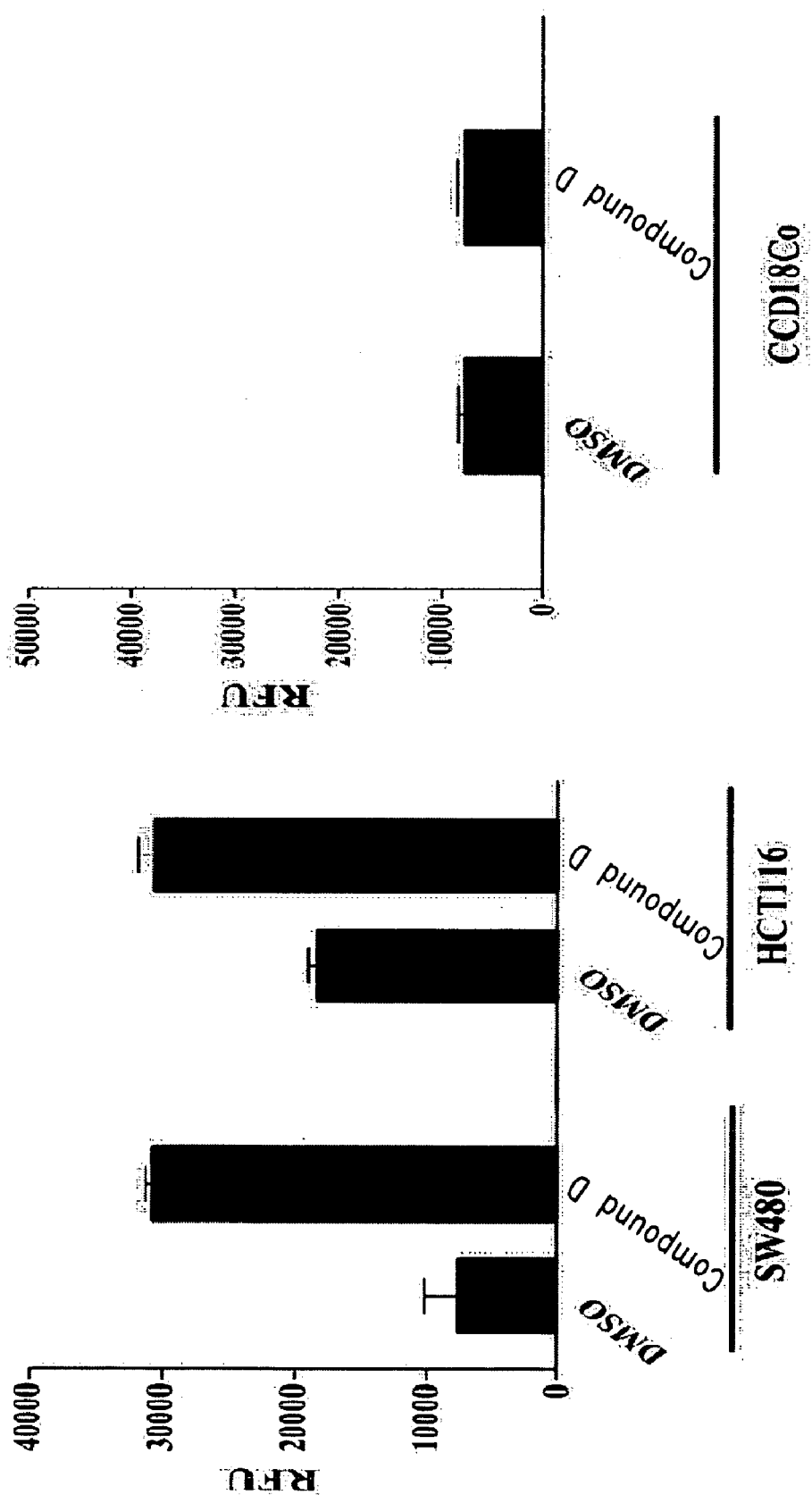

Caspases are cysteine proteases that are generally activated in a given population of cells triggered by apoptotic stimuli. To assess apoptotic induction in SW480, HCT116, and wild-type colonocytes (CCD18Co cells), the cells were treated with either Compound D (25 μM) or control (0.5% DMSO) for 24 hours, followed by an assay for caspase-3/7 activity. As shown in FIG. 7B, Compound D specifically and significantly activated the caspase-3/7 pathway in SW480 and HCT116 cells compared to CCD18Co cells.

Example 10

Compound D Reduces Proliferation of Transformed Colorectal Cells

Soft Agar Assays

The soft agar colony formation assay was conducted with SW480 cells by some modification of the procedure previously described (Moody et al., "A vasoactive intestinal peptide antagonist inhibits non-small cell lung cancer growth," Proc. Natl. Acad. Sci. USA. 90:4345-49 (1993)).

Each well (35 mm) of a 6-well plate (Nalge Nunc International, Roskide, Denmark) was coated with 1 ml of 0.8% bottom agar in DMEM medium containing 10% fetal bovine serum. After it was solidified, 1 ml of DMEM medium containing 0.4% top agar, 10% fetal bovine serum, compound doubly concentrated, and 5,000 single viable cells was added to each well. The cultures were incubated at 37° C. in humidified 5% $CO_2$ incubator. Colonies in soft agar were monitored daily and photographed after incubation for 8 days. Colonies>60 μm in diameter were counted.

Compound D Reduces Proliferation of Transformed Colorectal Cells

Figure 8:
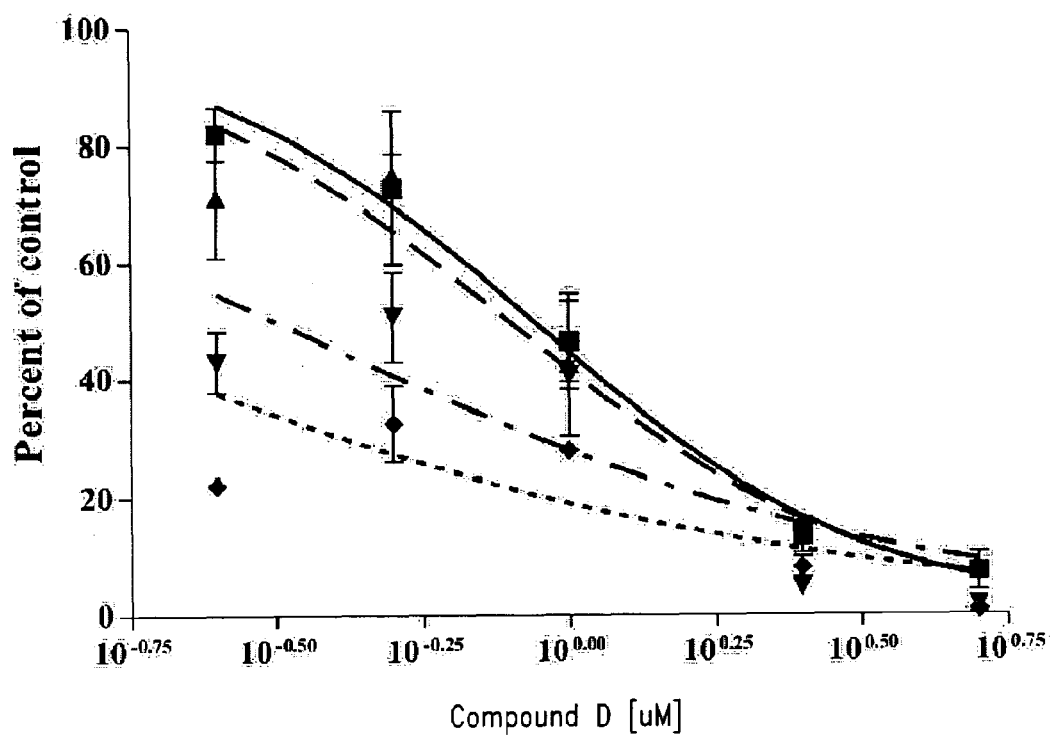
FIG. 8. Compound D reduces colony growth in soft agar in a dose dependent manner. Increasing concentrations of 5-fluorouracil (5-FU) (0.5-32 μM) and Compound D (0.25-5 μM) were added to SW480 (5000 cells/well) of triplicate wells. Cells were washed and suspended in soft agar growth medium. The number of colonies after 8 days (colonies over 60 μM diameter) were counted and plotted against the compound concentration. Mean±SE of three determinations is indicated. The colony number of control in the absence of the compound was 1,637±71.

Soft agar colony forming assays were performed using SW480 cells treated with Compound D (0.25-5 μM) and 5-fluorouracil (5-FU) (0.5-32 μM). As shown in FIG. 8A, Compound D shows a dose dependent decrease in the number of colonies formed. $IC_{50}$ value of Compound D and 5-FU was 0.87±0.11 μM and 1.98±0.17 μM, respectively. Thus, Compound D increased caspase activity and reduced growth in vitro of colorectal cells that are transformed by mutations that activate β-catenin signaling.

Example 11

Compound C Reduces Tumor Growth in Nude Mouse Model

Figures 9A, 9B:
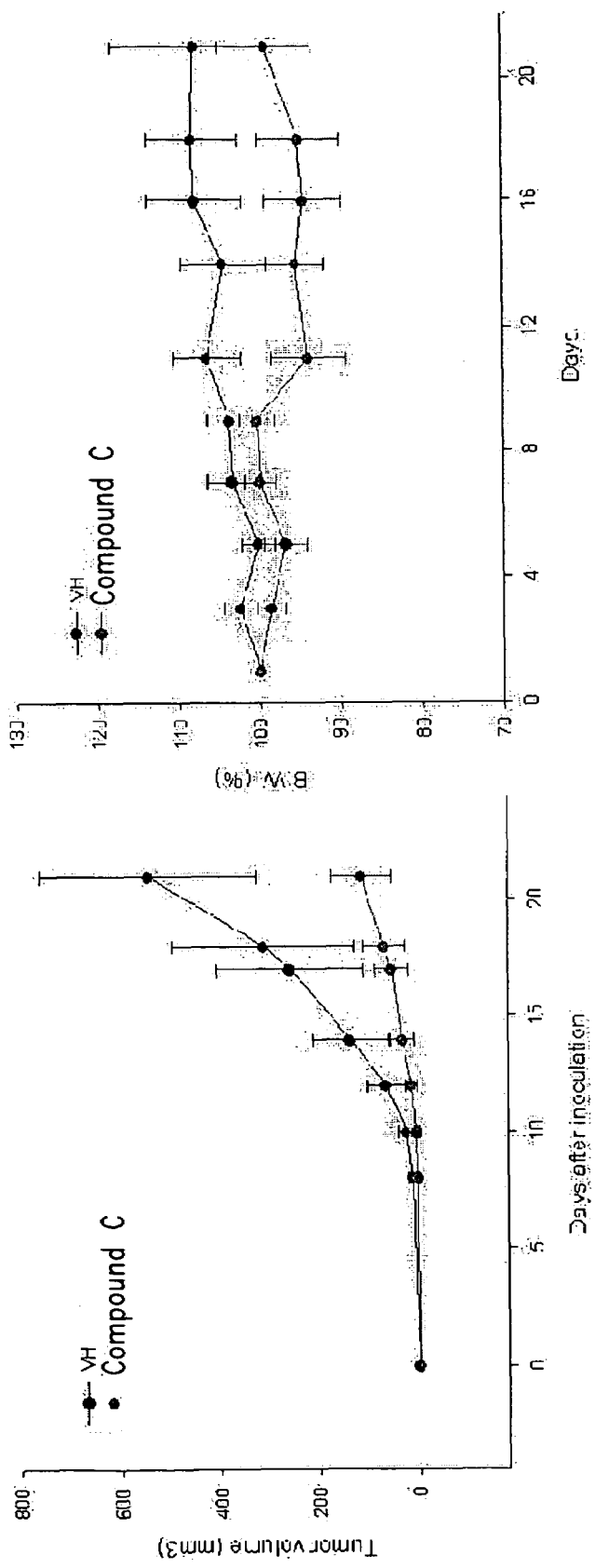
FIG. 9. A. Compound C reduces tumor-growth in nude mouse model. B. Compound C slightly reduces body weight in nude mouse model.

SW620 cells ($9 \times 10^6$ cells/mouse) were grafted into nude mice subcutaneously on Day 0. Mice received 200 mg/kg of Compound C intraperitoneally every other day until Day 21 after 4 times of 300 mg/kg every other day starting Day 1. Compound C reduces the tumor growth in the treated mice compared to the vehicle control mice (FIG. 9A), and slightly reduces body weights of the treated mice compared to those of the vehicle control mice (FIG. 9B).

Example 12

Compound D Suprresses Survivin Expression

The effect of Compound D on survivin expression was studied at both transcriptional and translational levels. The methods used at the transcriptional level include cDNA microarray analysis, RT-PCR, survivin reporter assays and chromotin immunoprecipitation (ChIP). The methods used at translational levels include Western blot analysis and immunochemistry.

Figure 10:
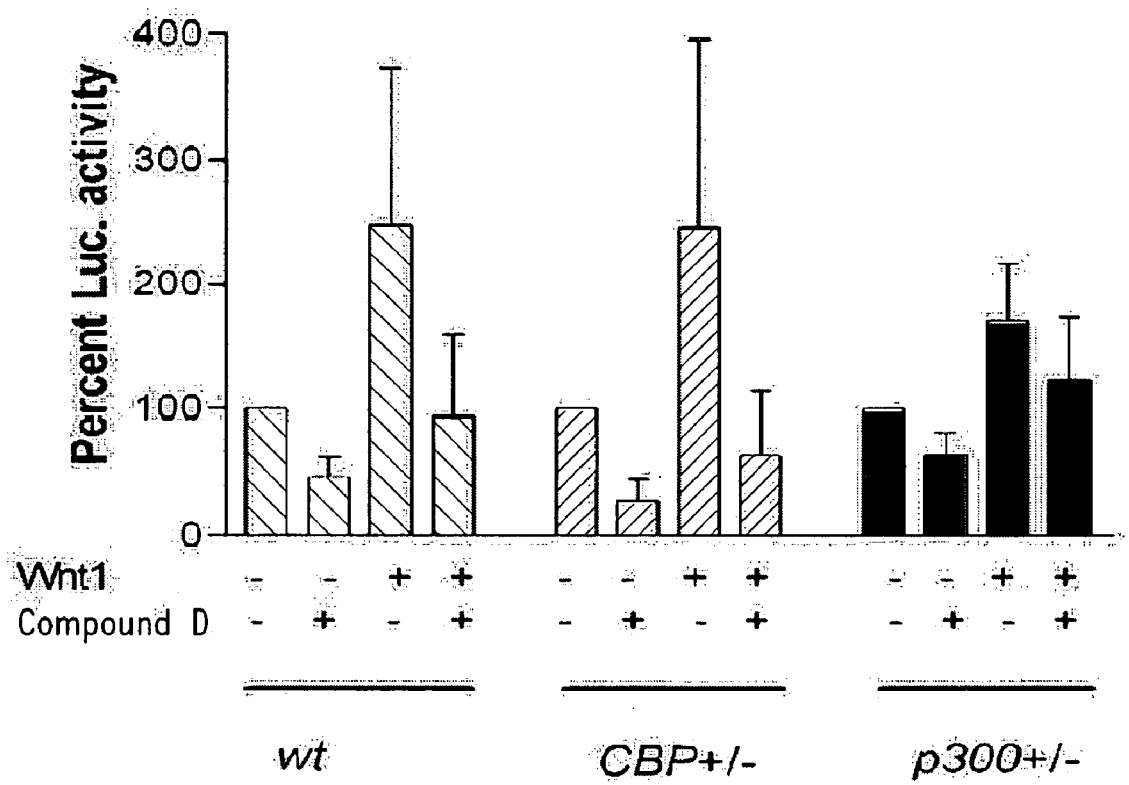
FIG. 10. The survivin transcriptional activity is upregulated by Wnt1, but knout-down by Compound D. Percent luciferase activities were measured in wildtype, CBP+/−, and p300+/−3T3 cells in the absence of Wnt1 and Compound D, or in the presence of Wnt1, Compound D or both.
Figure 11:
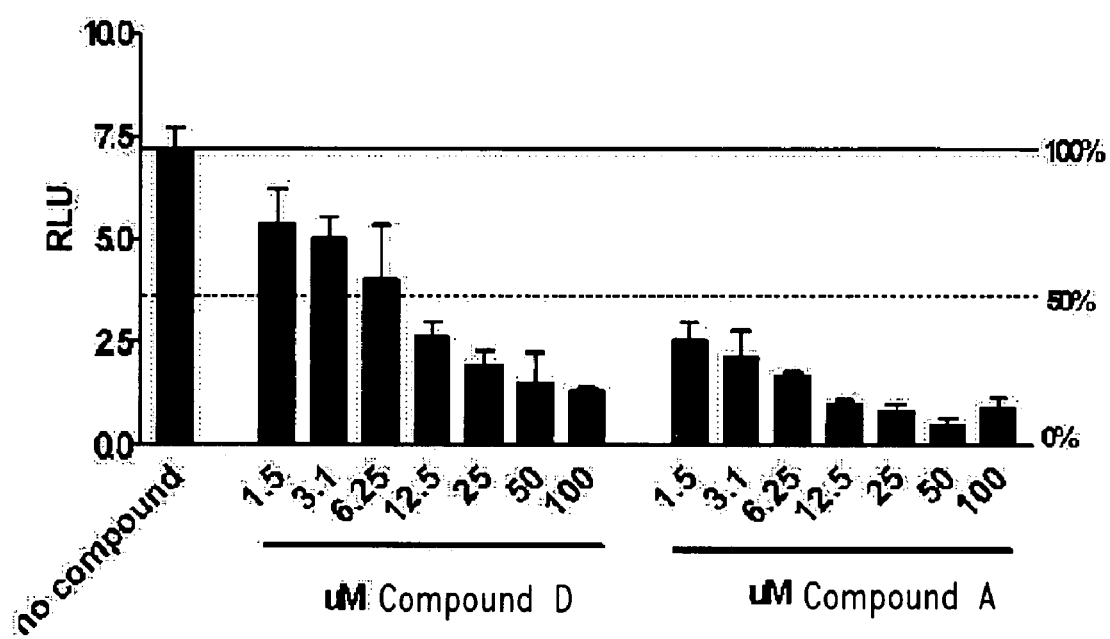
FIG. 11. Compound A (right graph) and Compound D (left graph) inhibit the activity of a survivin luciferase reporter in SW480 cells. The luciferase activities under the control of the survivin promoter were measured in SW480 cells treated with compound A or Compound D at various concentrations.

A plasmid containing luciferase under the control of survivin promoter was constructed and transfected into wild type, CBP+/−, or p300+/−3T3 cells. The results (FIG. 10) show that Wnt 1 stimulates expression of the survivin gene in all three types of cells, whereas Compound D reduces expression of the survivin gene and decreases the stimulation of the survinin gene expression by Wnt1 in those cells. Similarly, Compound D and its analog (Comound A) were shown to inhibit expression of survivin in SW480 cells (FIG. 11).

Figure 12:
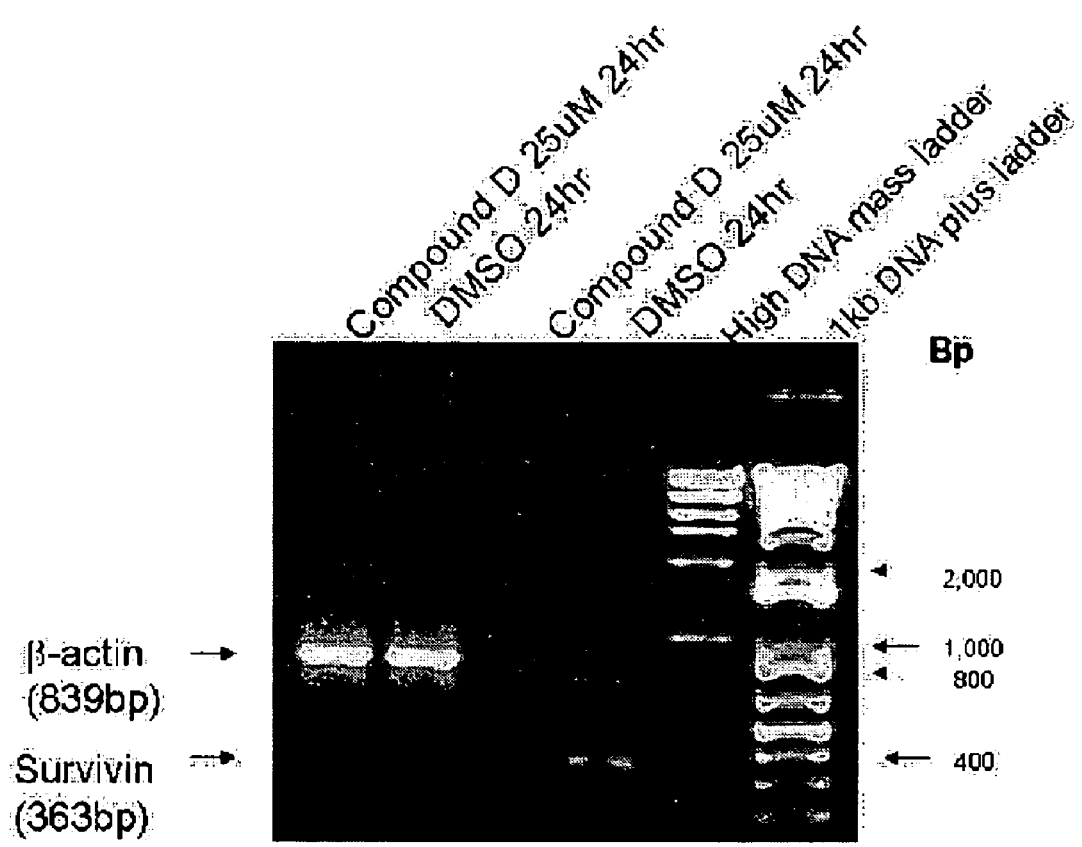
FIG. 12. RT-PCR analsis indicates that Compound D treatment decreases the expression level of the survivin gene.

Real time reverse transcription-PCR analysis was performed according to the protocol provided with the SYBR Green PCR Master Mix Kit (Perkin Elmer Biosystems, Shelton, ST). Total RNA templates for the RT-PCR reactions were extracted with the RNeasy Midi Kit (Qiagen) from cells treated with Compound D (25 μM) or control (0.5% DMSO) 24 hours after treatment. The primers used for the RT-PCR reactions were 5'-AGCCCTTTCTCAAGGACCAC-3' and 5'-GCACTTTCTTCGCAGTTTCC-3'. Table 8 shows the results of the analysis. A ratio less than 0.5 indicates a significant decrease of gene expression due to the treatment of Compound D, whereas a ratio greater than 1.5 indicates a significant increase of gene expression. A ratio about 1 indicates no change. As indicated in Table 8 and FIG. 12, the expression of the survivin gene is significantly reduced in the presence of Compound D compared to the control.

TABLE 8

Gene Expression with and without Compound D

| Gene | Ratio (Treated/DMSO Control) |
|---|---|
| Ubiquitin | 0.98 |
| GADPH | 0.98 |
| HLAC | 1.01 |
| Survivin | 0.30 |
| PONA | 0.33 |
| Antigen KI-67 | 0.45 |
| MIC-1 | 7.0 |
| GADD-153 | 7.00 |

Figure 13:
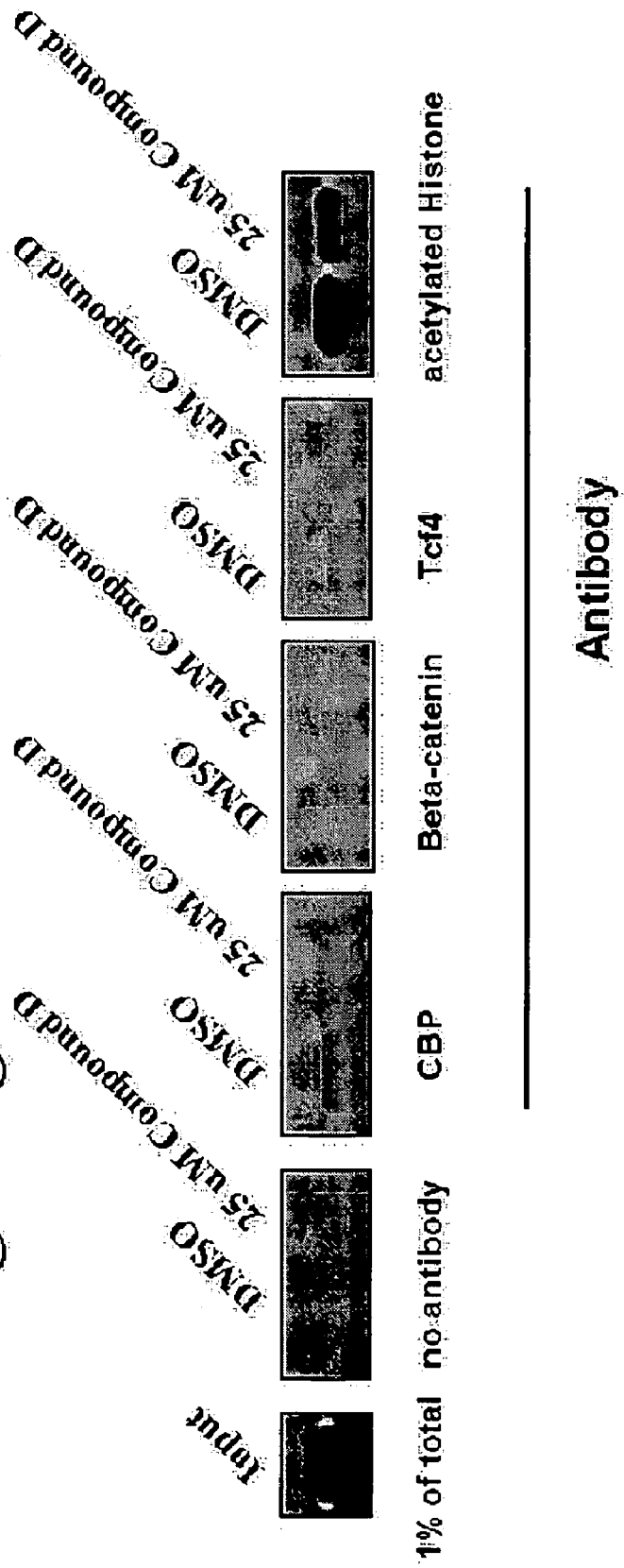
FIG. 13. Compound D decreases the association of various proteins with the survivin promoter. ChIP assays on SW480 cells treated with either Compound D (25 μM) or control (0.5% DMSO) for 18 hours were performed.

ChIP assays on SW 480 cells treated with either Compound D (25 µM) or control (0.5% DMSO) were performed. As shown in FIG. 13, the survivin promoter is occuried by CBP, β-catenin, Tcf4 and acetylated histone in control treated cells. Treatment with Compound D decreases the association of all these proteins with the survivin promoter.

Figure 14A:
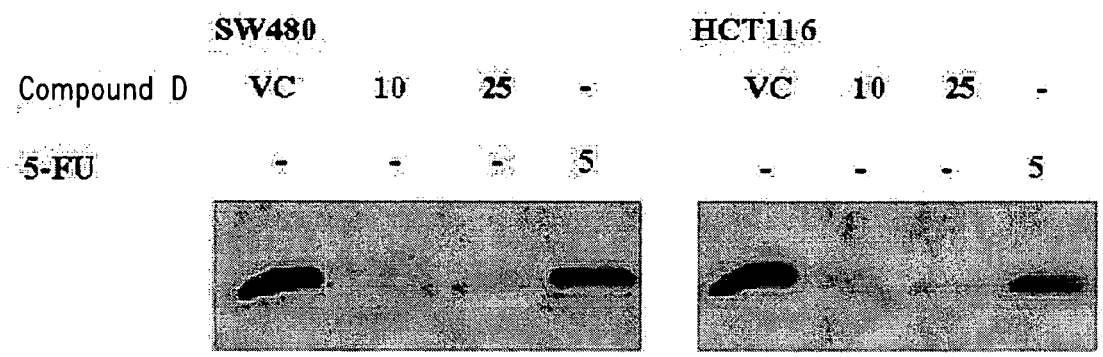
FIG. 14. Compound D decreases survivin expression at the translational level. A. Western blot analysis of extracts of cells treated with vehicle (0.5% DMSO) alone, 10 μM or 25 μM Compound D, or 5 μM 5-FU was performed using survivin 6E4 monoclonal antibody (Cell Signaling Technolgy). B. Survivin immunofluorescence microscopy. Cultured cancer cells were fixed and stained with anti-survivin green. C. Survivin immunofluorescence microscopy. SW480 cells treated with Compound D were fixed and stained with anti-survivin green.

To characterize the effect of Compound D on the survivin expression at the translational level, Western blot analysis of extracts of cells treated with vehicle (0.5% DMSO) alone, 10 µM or 25 µM Compound D, or 5 µM 5-FU was performed using survivin 6E4 monoclonal antibody (Cell Signaling Technolgy). The results (FIG. 14A) show that the treatments with Compound D at both concentrations and the treatment with 5-FU reduced the amount of the survivin protein. The treatments with Compound D at both concentrations were more effective in reducing the survivin expression than the treatment with 5-FU, and the treatment with Compound D at the higher concentration (i.e., 25 µM) was most effective.

Figure 14B:
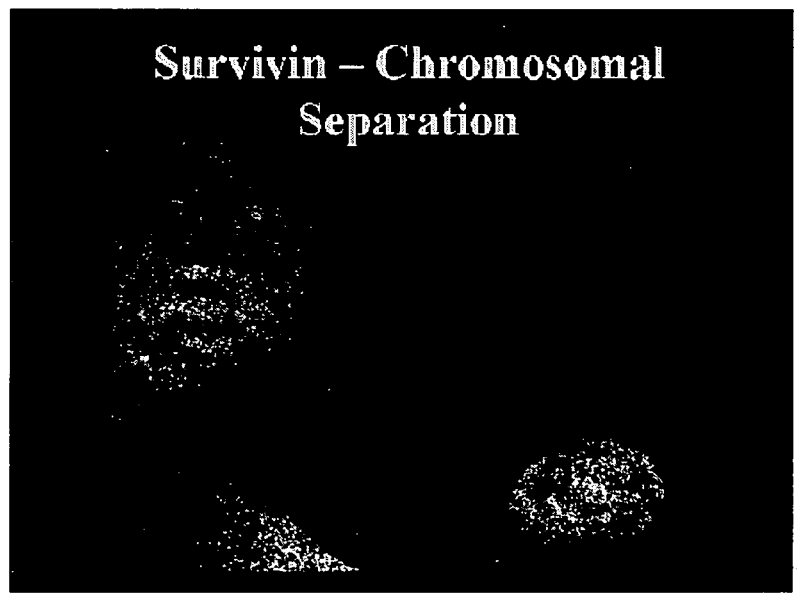
Figure 14C:

The effect of Compound D on the survivin expression at the translational level was further characterized using immunofluorescence microscopy. In the absence of Compound D, survivin localizes to the mitotic spindle apparatus, consistent with the notion that survivin is involved in chromosomal separation (FIG. 14B). This expression pattern was not observed in SW480 cells after the treatment of Compound D as little or no survivin protein was detected (FIG. 14C).

Example 13

Effects of Various Compounds on Survivin and TCF4 Expression

The effects of various compounds having general formula (I) on survivin and TCF4 expression were characterized. The results are shown in Table 9.

TABLE 9

Effects of compounds on survivin and TCF4 expression

| Structure | Survivin % inhibition 5 uM | Survivin % inhibition 25 uM | TCF4 IC50 (uM) |
|---|---|---|---|
| (structure 1) | 100 | 99 | ~2 |
| (structure 2) | 97 | 100 | ~2.2 |

TABLE 9-continued
Effects of compounds on survivin and TCF4 expression
| | Survivin % inhibition | | TCF4 IC50 |
|---|---|---|---|
| | 5 uM | 25 uM | (uM) |
| 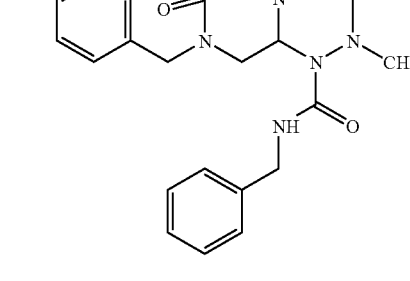 | 51 | 93 | ~6.3 |
| 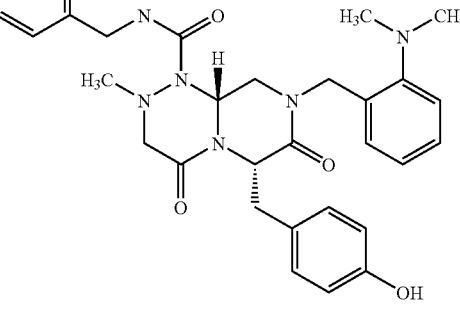 | 41 | 92 | 5.2 ± 0.7 |
| 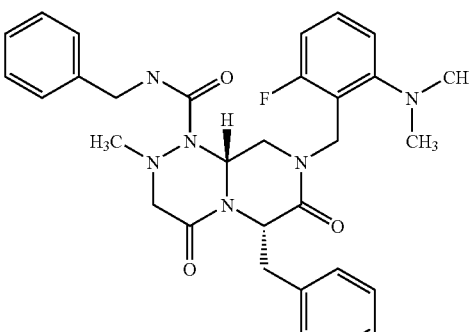 | 0 | 6 | 18.2 ± 2.4 |

TABLE 9-continued

Effects of compounds on survivin and TCF4 expression

| | Survivin % inhibition | | TCF4 IC50 |
|---|---|---|---|
| | 5 uM | 25 uM | (uM) |
| | 0 | 80 | 1.3 ± 0.1 |
| | 0 | 93 | 2.2 ± 0.2 |
| | 46 | 96 | 4.4 ± 0.6 |
| | 0 | 77 | 3.5 ± 0.3 |

TABLE 9-continued

Effects of compounds on survivin and TCF4 expression

| | Survivin % inhibition | | TCF4 IC50 |
|---|---|---|---|
| | 5 uM | 25 uM | (uM) |
| | 0 | 92 | 7.3 ± 0.6 |
| | 79 | 81 | 1.7 ± 0.2 |
| | 0 | 84 | 4.8 ± 0.4 |
| | 0 | 68 | 10.9 ± 1.3 |

TABLE 9-continued

Effects of compounds on survivin and TCF4 expression

| | Survivin % inhibition | | TCF4 IC50 |
|---|---|---|---|
| | 5 uM | 25 uM | (uM) |
| [structure] | 8 | 4 | NA |
| [structure] | 9 | 91 | 1.4 ± 0.2 |
| [structure] | 5 | 91 | 6.3 ± 0.431 |
| [structure] | 0 | 94 | 2.6 ± 0.4 |

TABLE 9-continued
Effects of compounds on survivin and TCF4 expression
| | Survivin % inhibition | | TCF4 IC50 (uM) |
|---|---|---|---|
| | 5 uM | 25 uM | |
| 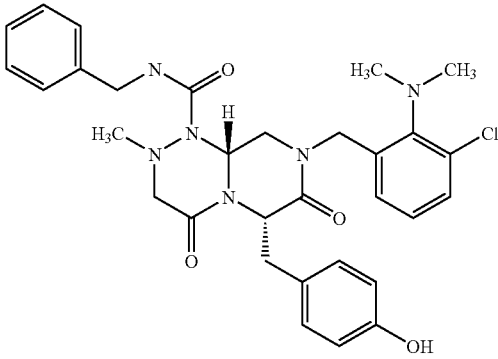 | 0 | 21 | 7.3 ± 1.1 |
| 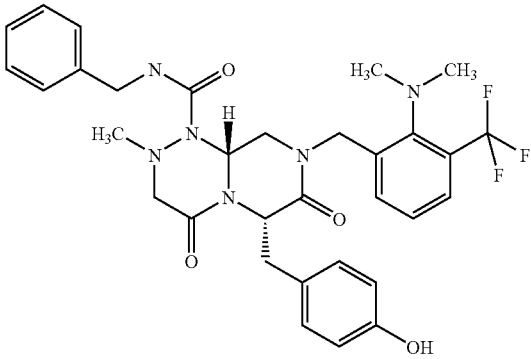 | 0 | 91 | 5.2 ± 1.1 |
| 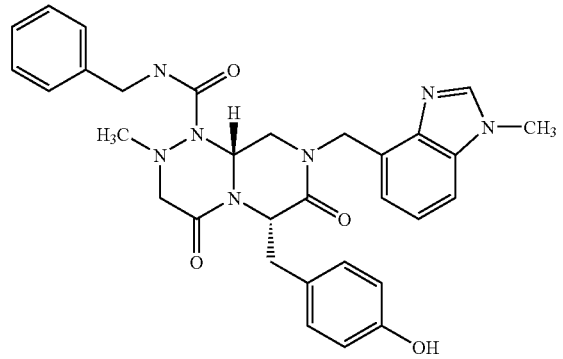 | 45 | 88 | 13.2 ± 4.1 |
| 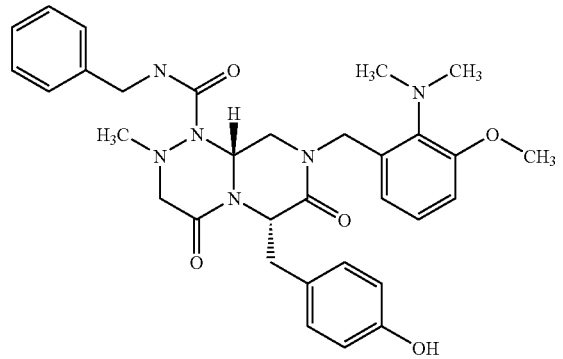 | 9 | 92 | 5.9 ± 0.5 |

TABLE 9-continued
Effects of compounds on survivin and TCF4 expression
| | Survivin % inhibition | | TCF4 IC50 |
|---|---|---|---|
| | 5 uM | 25 uM | (uM) |
| 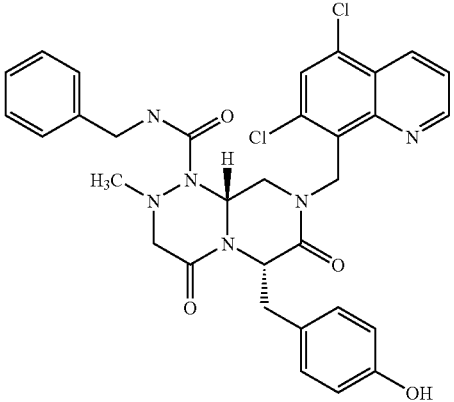 | 6 | 58 | 11.2 ± 1.5 |
| 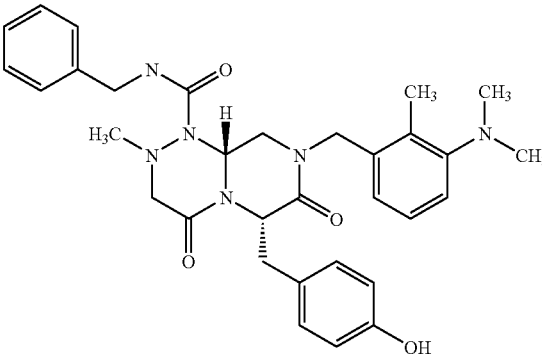 | 48 | 96 | 3.9 ± 0.55 |
| 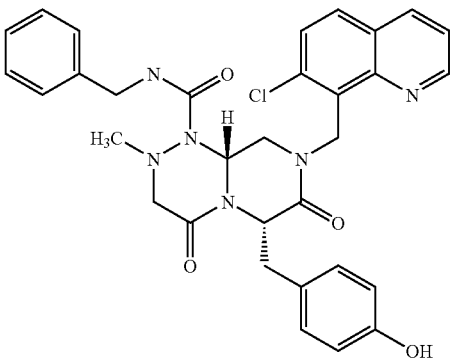 | 0 | 32 | 50.4 ± 7.0 |

TABLE 9-continued
Effects of compounds on survivin and TCF4 expression
| | Survivin % inhibition | | TCF4 IC50 (uM) |
|---|---|---|---|
| | 5 uM | 25 uM | |
| 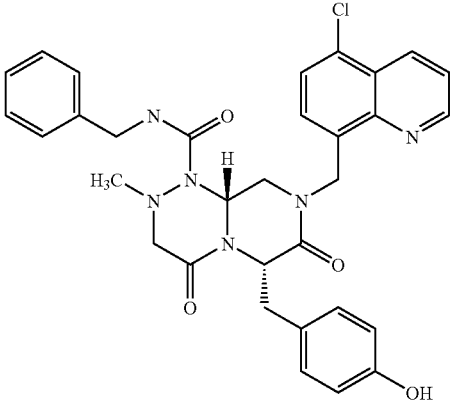 | 86 | 91 | 2.6 ± 0.6 |
| 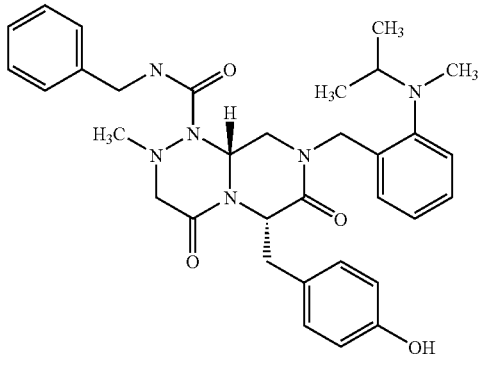 | 27 | 98 | 10.7 ± 1.7 |
| 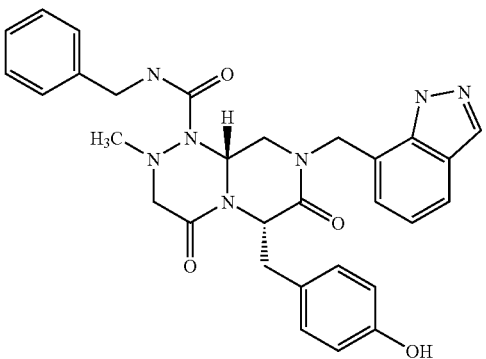 | 80 | 97 | 4.6 ± 0.7 |

TABLE 9-continued

Effects of compounds on survivin and TCF4 expression

| | Survivin % inhibition | | TCF4 IC50 |
|---|---|---|---|
| | 5 uM | 25 uM | (uM) |
| | 82 | 97 | 2.8 ± 0.4 |
| | 6 | 89 | 13.9 ± 2.3 |
| | 14 | 99 | 10.7 ± 1.9 |

TABLE 9-continued

Effects of compounds on survivin and TCF4 expression

| Structure | Survivin % inhibition | | TCF4 IC50 |
|---|---|---|---|
| | 5 uM | 25 uM | (uM) |
| [chemical structure] | 25 | 44 | 27.1 ± 4.6 |

Example 14

Compound D Promotes Apoptosis Via Suppression of Survivin Expression

Figure 15:
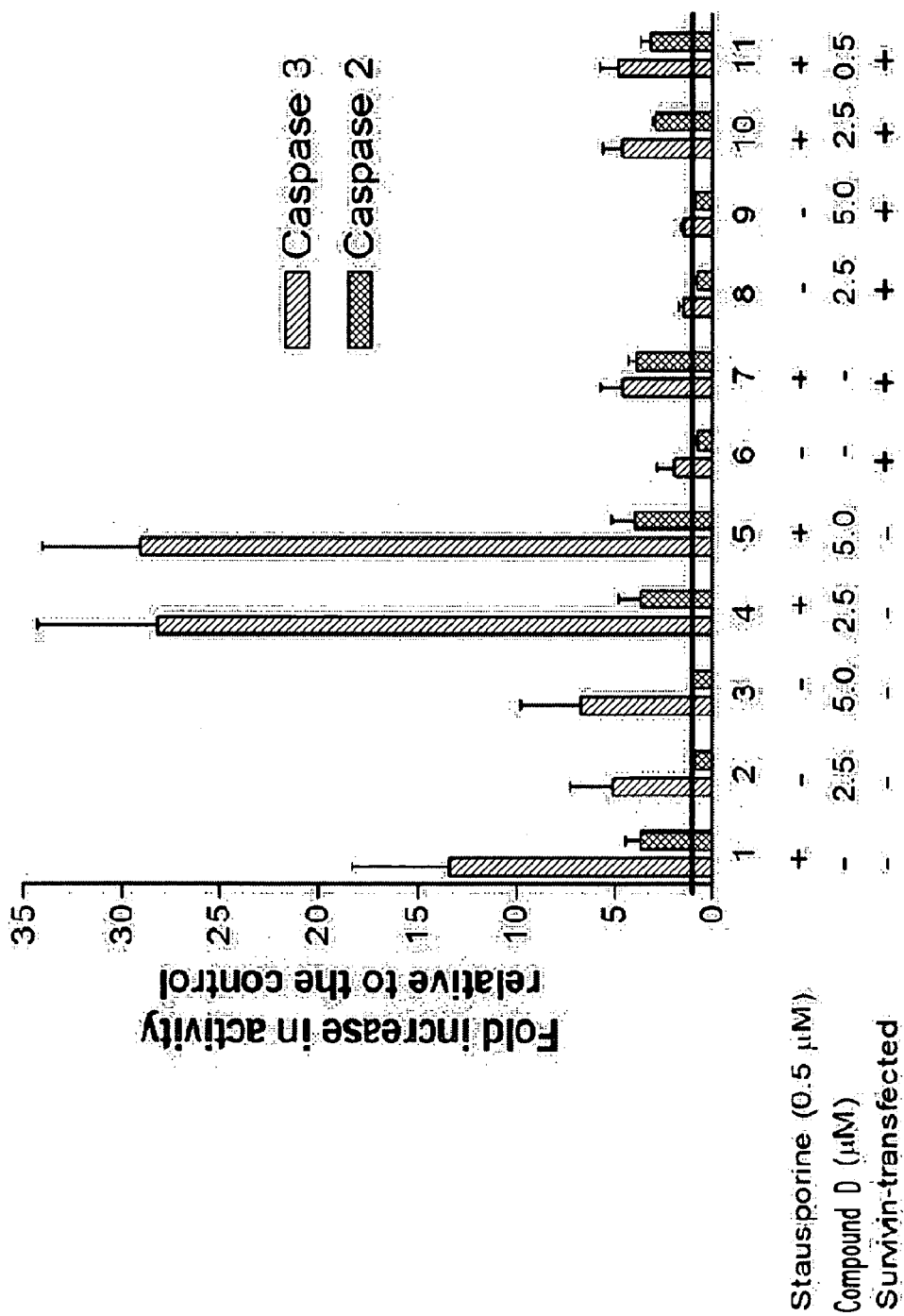
FIG. 15. Compound D activates the caspase 3 activity (but not the caspase 2 activity) via suppression of the survivin expression. Cultured cells with or without transfection of a construct containing the survivin gene were treated with stausporine (0.5 μM), Compound D (2.5 μM or 5.0 μM), or both. The caspase 2 and caspase 3 activities in these cells were measured.

To determine the effect of Compound D on apoptosis and the role of survivin in such an effect, the activities of caspases 2 and 3 in cultured tumor cells treated with either Compound D or control were measured. The results (FIG. 15) show that (1) Compound D (at 2.5 µM or 5.0 µM) activated the caspase 3 activity, but not the caspase 2 activity; (2) stausporine (0.5 µM) increased both the caspase 2 and caspase 3 activities; (3) the co-treatment of stausporine and Compound D produced a synergic stimuation of the caspase 3 activity, but not a synergic stimuation of the caspase 2 activity; and (4) transfection of the survivin gene decreased the activiation of the caspase 3 activity induced by the treatment of stausporine or Compound D, and the synergic stimulation of the caspase 3 activity induced by the co-treatment of stausporine and Compound D. The above results suggest that Compound D stimulate the caspase 3 activity via suppression of the expression of the survivin gene.

Figure 16:
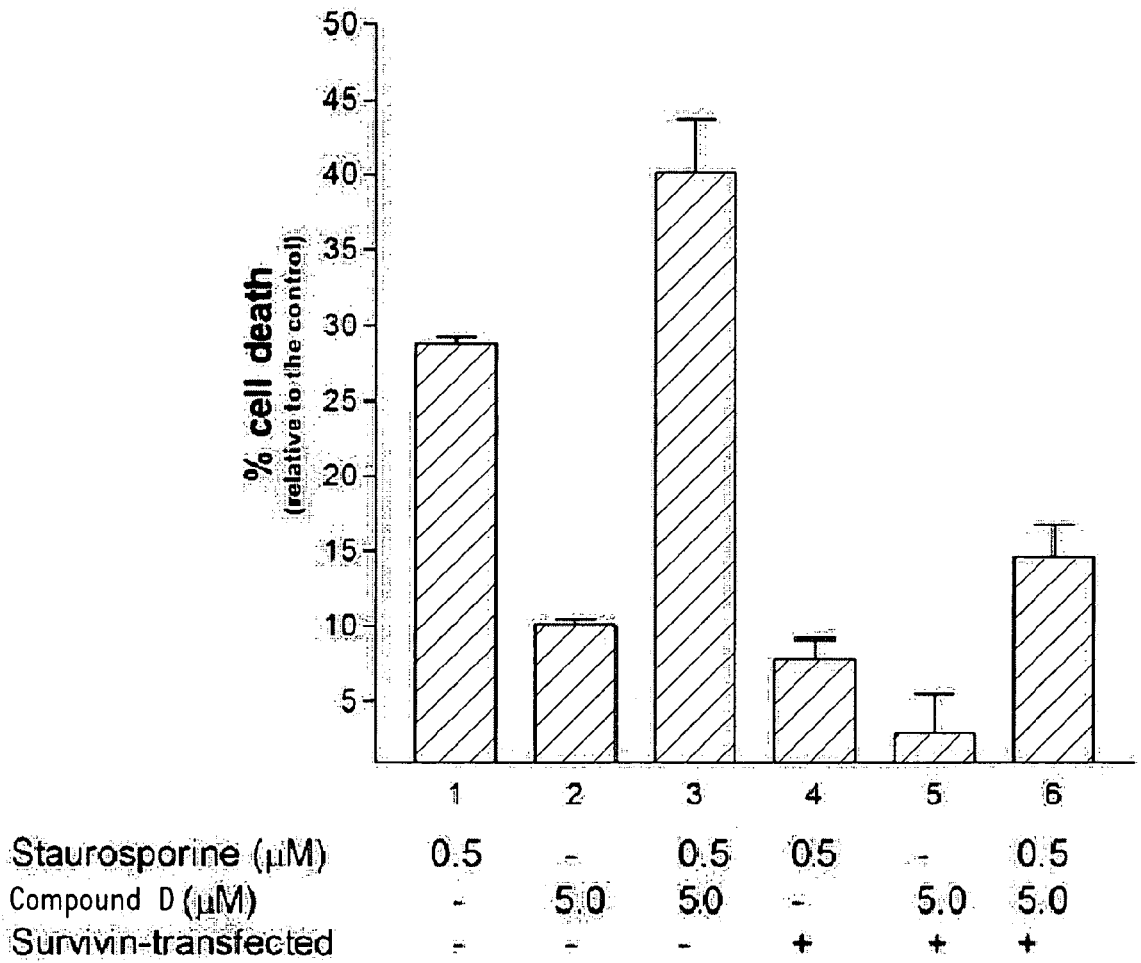
FIG. 16. Compound D promotes cell death via suppression of the survivin expression. Cultured cancer cells with or without transfection of a construct containing the survivin gene were treated with stausporine (0.5 μM), Compound D (5.0 μM), or both. The cell death of these cells was measured.

The effect of compound D on apoptosis and the role of survivin in such an effect were further characterized by measuring cell death of cultured tumor cells treated with staurosporine (0.5 µM), Compound D (5.0 µM) or both. The results (FIG. 16) showed that both Compound D and stausporine promote cell death, and that transfection of the survivin gene decreased the increase in cell death induced by the treatment of stausporine, Compound D, or both. The above results suggest that Compound D promote apoptosis via suppression of the expression of the survivin gene.

Figure 17:
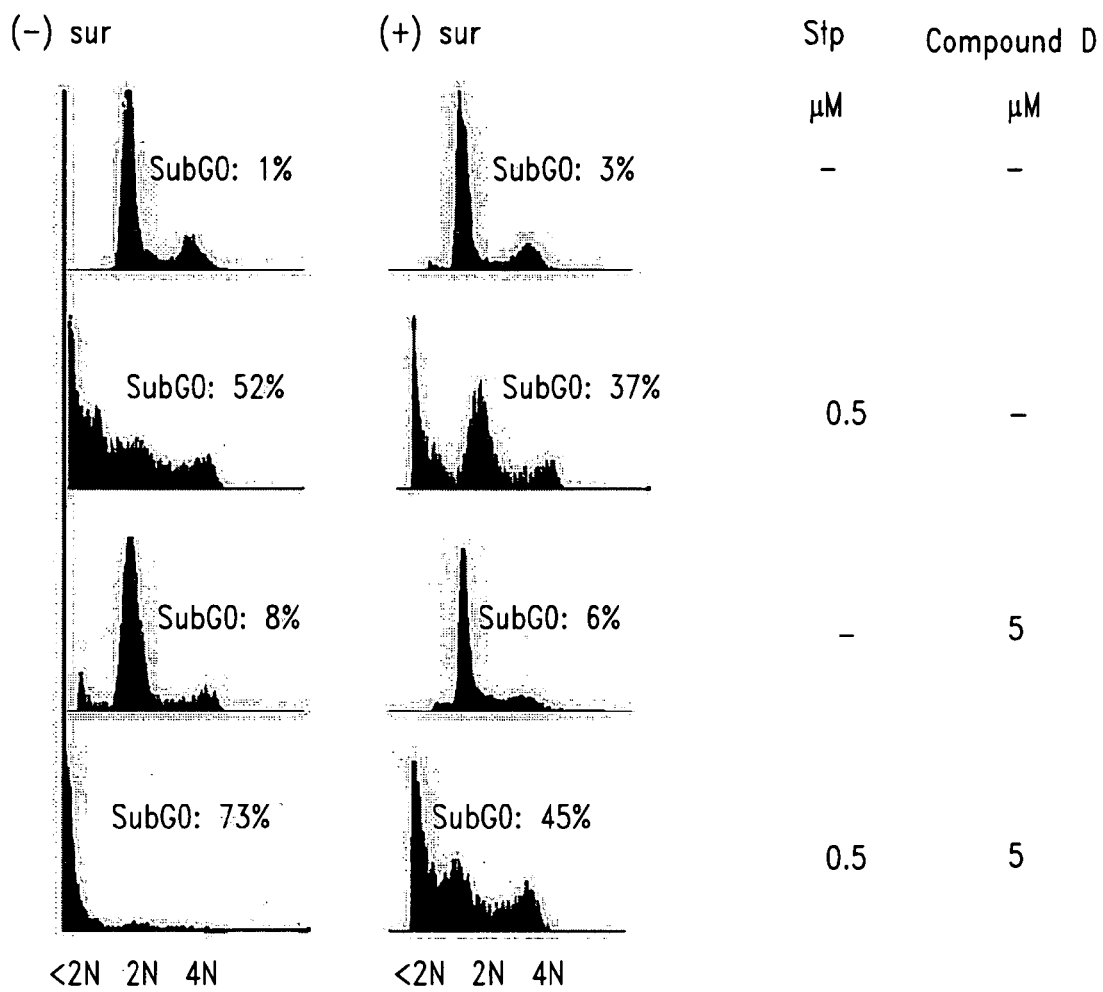
FIG. 17. Compound D increases the number of cells in $G_0$. Cultured cancer cells with or without transfection of a construct containing the survivin gene were treated with stausporine (0.5 μM), Compound D (5 μM), or both. FACS analysis was performed on these cells and the percentages of cells in $G_0$ are indicated.

To determine the effect of Compound D on cell cycle and the role of survivin in such an effect, FACS analysis was performed on cultured tumor cells with or without transfection of a construct containing the survivin gene and further treated with stausporine (0.5 µM), Compound D (5 µM), or both. The results (FIG. 17) show that both stausporine and Compound D increase the number of cells in $G_0$, and that overexpression of survivin in the cells decreases the effect of the treatment of stausporine, Compound D, or both. These results suggest that the effect of Compound D on cell cycle may be at least partially via suppression of the expression of the survivin gene.

Example 15

Preparation and Activity of Prodrugs (1) General Procedure for Preparing Prodrugs by Phosphorylation of Phenol Group The starting phenol (26.06 mmol) was dissolved in tetrahydrofuran (130 ml), followed by addition of triethylamine (TEA) (10.9 ml, 78.18 mmol) at room temperature. The reaction mixture was cooled to 5° C., and then $POCl_3$ (12.2 ml, 130.3 mmol) was added slowly. After addition was finished, the mixture was allowed to warm to room temperature, and stirred at this temperature for 5 hours. After the reaction was completed, the mixture was poured into celite-pad filter funnel to remove TEA-HCl salt. Organics was diluted with water (130 ml) at 5° C., followed by adjusting pH 7~8 using sodium bicarbonate (50 g), and the resulting basic solution was stirred overnight at room temperature. The resulting aqueous layer was washed with EtOAc (100 ml), and then lyophilized. The crude product was dissolved in methylene chloride (100 ml), followed by for 1 hour at room temperature. Inorganic salts were removed by filtration using celite pad, then solvent was evaporated. The crude product was purified by recrystallization (EA/Ether) to get 9.5 g of phosphorylated product as an off-white solid.

(2) Typical Work-up Procedure for the Free Form of Phosphate

After washing the resulting basic aqueous layer, the solution was acidified to pH 3~4 using 1 N HCl, and then the phosphate free form was extracted twice with chloroform (300 ml). The organic layer was dried over sodium sulfate, and the crude product was purified by recrystallization.

(3) Converting Method from Free Form to Di-sodium Form

A. Titration Method

Free form of phosphate can be transformed to di-sodium salt form by titration, which could use many inorganic bases. For example, sodium carbonate, sodium bicarbonate, and sodium hydroxide are used in this experiment to produce di-sodium form. Other cations can be used to make different di-salt forms.

1. Analytical Method and Instrument for Titration
a. Instrument: TitraLab (RADIOMETER COPENHAGEN)
Electrode: pHG201 pH glass electrode
(RADIOMETER COPENHAGEN, 945-462)
REF201 reference electrode with KCl salt-bridge solution
(RADIOMETER COPENHAGEN, 945-463)
Titrant: 10 M $Na_2CO_3$
Burette speed (titration speed): 15% (=1.5 ml/min)
Sample: 50 mg dissolved in distilled water (30 ml)
b. Results
pH 4 (start pH=2)

|   | | EP1 | | EP2 | |
|---|---|---|---|---|---|
| n | start pH | pH | Titrant (ml) | pH | Titrant (ml) |
| 1 | 2.10 | 4.21 | 9.50 | 8.15 | 19.03 |
| 2 | 2.08 | 4.26 | 10.28 | 8.02 | 19.12 |
| Mean | 2.09 | 4.24 | 9.89 | 8.09 | 19.08 |

B. Using Organic Sodium Donor

The basic drawback of titration using inorganic base is that the water must be used for the solvent. So searching the sodium donor dissolved freely in normal organic solvent is the easiest way to solve the problem. Several reagents such as sodium acetate and sodium ethylhexanoic acid were tested and found to be useful for making a di-sodium salt form.

Table 10 shows compounds for bioactivity test selected from the prodrugs of the present invention and $IC_{50}$ values thereof, which are measured by the reporter gene assay (RGA) and oncogenic activity by MTS or Sulforhodamine B assay as described in Example 6. The compound numbers on Table 10 are unrelated to those in Table 4 or 5.

TABLE 10

THE REPORTER GENE ASSAY AND ONCOGENIC ACTIVITY BY MTS OR SULFORHODAMINE B ASSAY FOR SELECTED PRODRUG COMPOUNDS

| | | Assay | | | | | |
|---|---|---|---|---|---|---|---|
| | | RGA, TopF $IC_{50}$, | RGA, Survivin $IC_{50}$, | MTS, SW480 (uM) | | MTS, HCT116 (uM) | |
| No | Structure | uM | uM | LD50 | GI50 | LD50 | GI50 |
| 1 | (structure) | 4.2 | 6.4 | 17.0 | 2.0 | 16.1 | 2.2 |
| 2 | (structure) | 3.5 | 5.7 | 8.2 | 3.1 | 23.2 | 6.6 |

TABLE 10-continued
THE REPORTER GENE ASSAY AND ONCOGENIC ACTIVITY BY MTS OR SULFORHODAMINE B ASSAY FOR SELECTED PRODRUG COMPOUNDS
| | | Assay | | | | | |
|---|---|---|---|---|---|---|---|
| | | RGA, TopF IC50, | RGA, Survivin IC50, | MTS, SW480 (uM) | | MTS, HCT116 (uM) | |
| No | Structure | uM | uM | LD50 | GI50 | LD50 | GI50 |
| 3 | 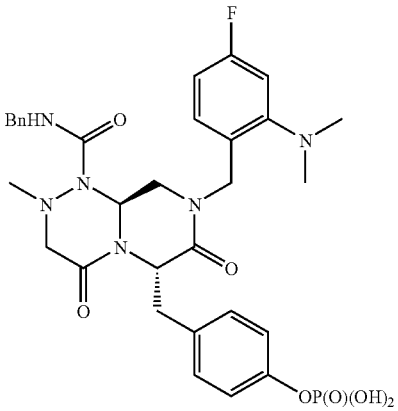 | 11.5 | | ND up to 50 uM | 3.0 | 41.9 | 3.1 |
| 4 | 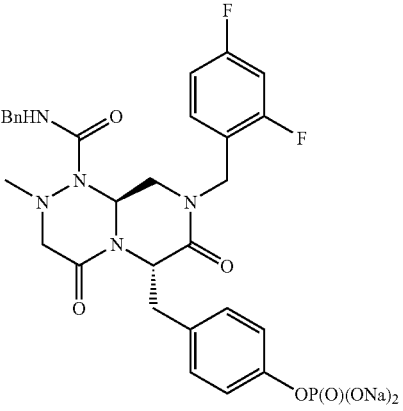 | 7.3 | 6.5 | ND up to 50 uM | 6.9 | 49.3 | 11.4 |
| 5 | 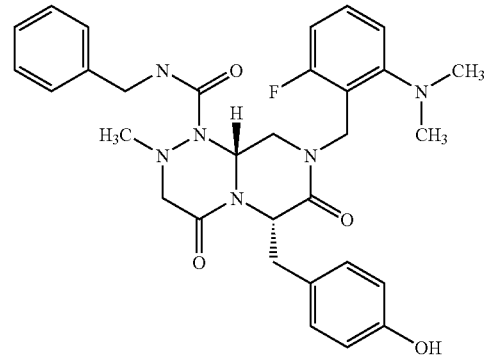 | 26.0 | 34.0 | 5.2 | | ND up to 50 uM | 16.5 |

TABLE 10-continued

THE REPORTER GENE ASSAY AND ONCOGENIC ACTIVITY BY MTS OR SULFORHODAMINE B
ASSAY FOR SELECTED PRODRUG COMPOUNDS

| No | Structure | RGA, TopF IC50, uM | RGA, Survivin IC50, uM | MTS, SW480 (uM) LD50 | MTS, SW480 (uM) GI50 | MTS, HCT116 (uM) LD50 | MTS, HCT116 (uM) GI50 |
|---|---|---|---|---|---|---|---|
| 6 | 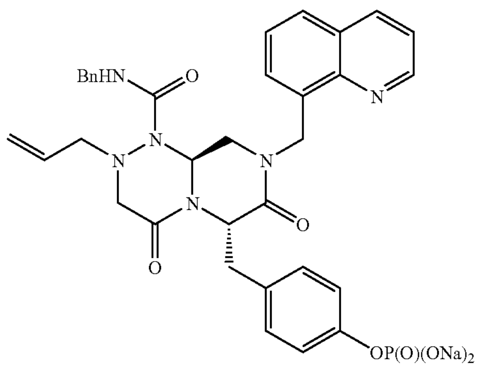 | 0.8 | 0.1 | 9.2 | 0.5 | 6.4 | 0.4 |
| 7 | 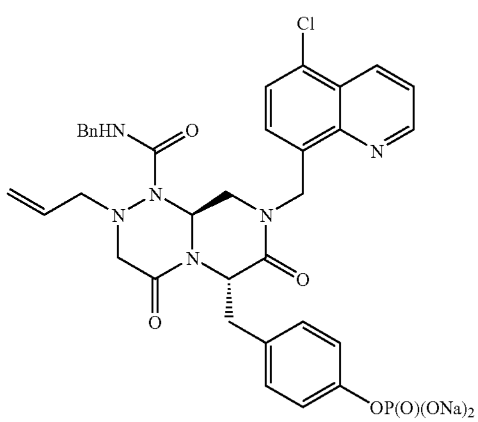 | 2.3 | 1.0 | 12.9 | 2.2 | 12.0 | 1.8 |
| 8 | 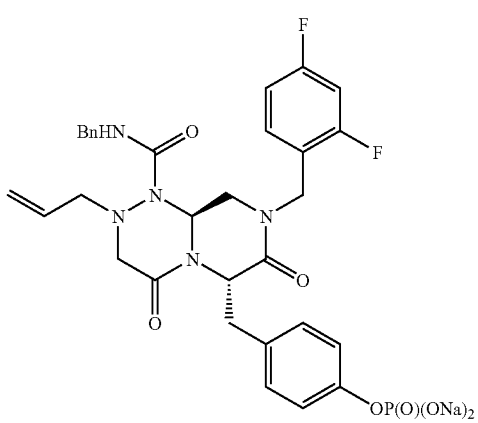 | 1.4 | 0.9 | 21.6 | 2.1 | 23.2 | 1.9 |

TABLE 10-continued

THE REPORTER GENE ASSAY AND ONCOGENIC ACTIVITY BY MTS OR SULFORHODAMINE B
ASSAY FOR SELECTED PRODRUG COMPOUNDS

| No | Structure | Assay | | | | | |
|---|---|---|---|---|---|---|---|
| | | RGA, TopF IC50, uM | RGA, Survivin IC50, uM | MTS, SW480 (uM) | | MTS, HCT116 (uM) | |
| | | | | LD50 | GI50 | LD50 | GI50 |
| 9 | 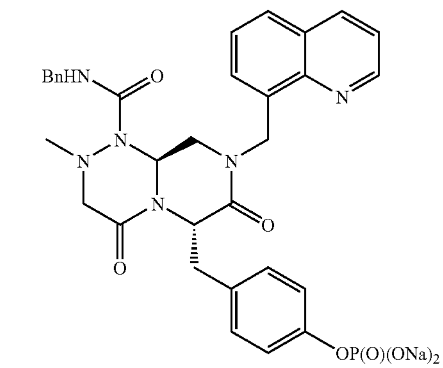 | 9.6 | 6.0 | ND up to 50 uM | 7.6 | ND up to 50 uM | 14.7 |
| 10 | 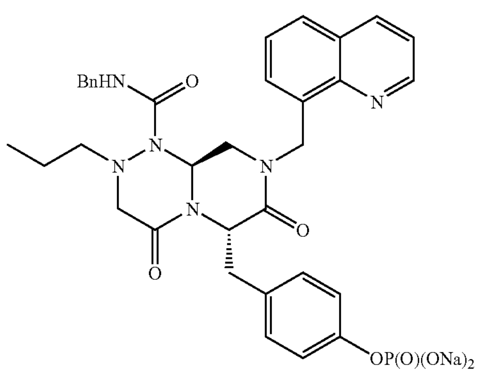 | 2.8 | 1.7 | 9.4 | 0.9 | 7.9 | 0.8 |
| 11 | 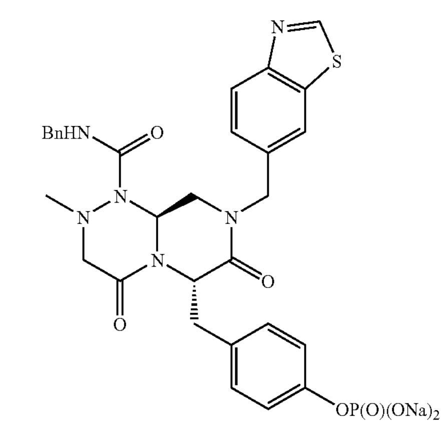 | 10.3 | 6.7 | ND up to 50 uM | 6.5 | ND up to 50 uM | 6.3 |

TABLE 10-continued

THE REPORTER GENE ASSAY AND ONCOGENIC ACTIVITY BY MTS OR SULFORHODAMINE B ASSAY FOR SELECTED PRODRUG COMPOUNDS

| | | Assay | | | | | |
|---|---|---|---|---|---|---|---|
| | | RGA, TopF IC50, | RGA, Survivin IC50, | MTS, SW480 (uM) | | MTS, HCT116 (uM) | |
| No | Structure | uM | uM | LD50 | GI50 | LD50 | GI50 |
| 12 | | 1.0 | 0.7 | ND up to 50 uM | 1.0 | 19.3 | 1.2 |
| 13 | | 1.8 | 0.9 | 21.1 | 2.3 | 20.0 | 1.7 |
| 14 | | 1.7 | 1.2 | 21.1 | 2.3 | 16.0 | 2.1 |

Example 16

Solubility of Selected Prodrugs

General Procedure for Solubility Test of Prodrugs

About 2 mg of each prodrug was dissolved in 1 ml of JP1 or JP2 solution as indicated below. Incubating at a temperature of 37° C., 200 ul of samples were withdrawn at 0 hour, 2 hour and 20 hour. Withdrawn samples were filtered through 0.45 μm syringe filters and analyzed by HPLC system.

Composition of Artificial Gastro-Intestinal Fluids (JP1, JP2)

| JP1 | | JP2 | |
|---|---|---|---|
| PH | 1.2 | pH | 6.8 |
| NaCl | 2.0 g | 0.2 M KH$_2$PO$_4$ | 250 ml |
| 10% HCl | 24.0 ml | 0.2N NaOH | 118 ml |
| Distilled H$_2$O | Adjusted to 1 L | Distilled H$_2$O | Adjusted to 1 L |

Table 11 below shows the results of solubility test of selected prodrugs. The compound numbers on Table 11 are unrelated to those in Table 4, 5 or 10.

TABLE 11

AQUEOUS SOLUBILITY FOR SELECTED PRODRUG COMPOUNDS

| No | Structure | Solubility (37° C., ug/mL) 0 hr, 2 hr, 20 hr | |
|---|---|---|---|
| | | JP1 (pH 1.2) | JP2 (pH 6.8) |
| 1 | 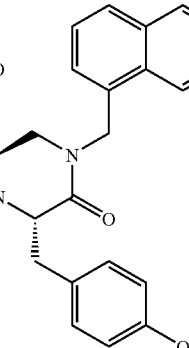 | 60.1<br>87.3<br>92.8 | 1797<br>1867<br>1894 |
| 2 | 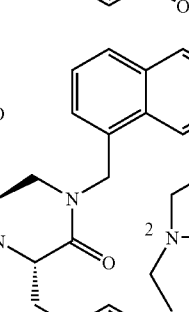 | 122<br>173<br>160 | 1950<br>1939<br>1940 |
| 3 | 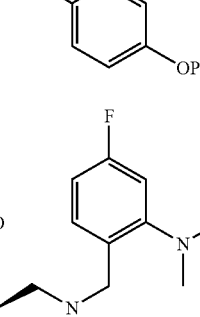 | 1878<br>1971<br>2036 | 1325<br>1902<br>2005 |

TABLE 11-continued

AQUEOUS SOLUBILITY FOR SELECTED PRODRUG COMPOUNDS

| | | Solubility (37° C., ug/mL) 0 hr, 2 hr, 20 hr | |
|---|---|---|---|
| No | Structure | JP1 (pH 1.2) | JP2 (pH 6.8) |
| 4 | [structure with BnHN-C(O)-N, methyl-N, 2,4-difluorobenzyl, and 4-OP(O)(ONa)$_2$ benzyl groups on bicyclic triazine-dione core] | 554<br>646<br>756 | 1982<br>2014<br>2030 |
| 5 | [structure with BnHN-C(O)-N, methyl-N, 1-methylindazol-7-ylmethyl, and 4-OP(O)(OH)$_2$ benzyl groups on bicyclic triazine-dione core] | 406<br>532<br>684 | 1761<br>1778<br>1758 |
| 6 | [structure with BnHN-C(O)-N, allyl-N, quinolin-8-ylmethyl, and 4-OP(O)(ONa)$_2$ benzyl groups on bicyclic triazine-dione core] | 1453<br>1724<br>1787 | 1829<br>1864<br>1867 |

TABLE 11-continued

AQUEOUS SOLUBILITY FOR SELECTED PRODRUG COMPOUNDS

| | | Solubility (37° C., ug/mL) 0 hr, 2 hr, 20 hr | |
|---|---|---|---|
| No | Structure | JP1 (pH 1.2) | JP2 (pH 6.8) |
| 7 | | 309<br>446<br>521 | 2145<br>2221<br>2239 |
| 8 | | 671<br>775<br>921 | 2295<br>2317<br>2272 |
| 9 | | 2251<br>2275<br>2403 | 2322<br>2353<br>2421 |

TABLE 11-continued

AQUEOUS SOLUBILITY FOR SELECTED PRODRUG COMPOUNDS

| No | Structure | Solubility (37° C., ug/mL) 0 hr, 2 hr, 20 hr | |
|---|---|---|---|
| | | JP1 (pH 1.2) | JP2 (pH 6.8) |
| 10 | [Structure: BnHN-C(O)-N(Me)-N-... pyrazino-triazine core with 4,5-difluoro-2-(dimethylamino)benzyl and 4-OP(O)(ONa)₂-benzyl substituents] | 2292<br>2274<br>2327 | 2028<br>2055<br>2027 |
| 11 | [Structure: BnHN-C(O)-N(Me)-N-... pyrazino-triazine core with 4-chloro-3-(dimethylamino)benzyl and 4-OP(O)(ONa)₂-benzyl substituents] | 2006<br>2000<br>1998 | 1636<br>1654<br>1651 |

Example 17

Preparation of Dimethyl-carbamic acid 4-[2-allyl-1benzylcarbamoyl-8-(2,4-difluoro-benzyl)-4,7-dioxo-octahydro-pyrazino[2,1-c][1,2,4]triazin-6-ylmethyl]-phenyl ester

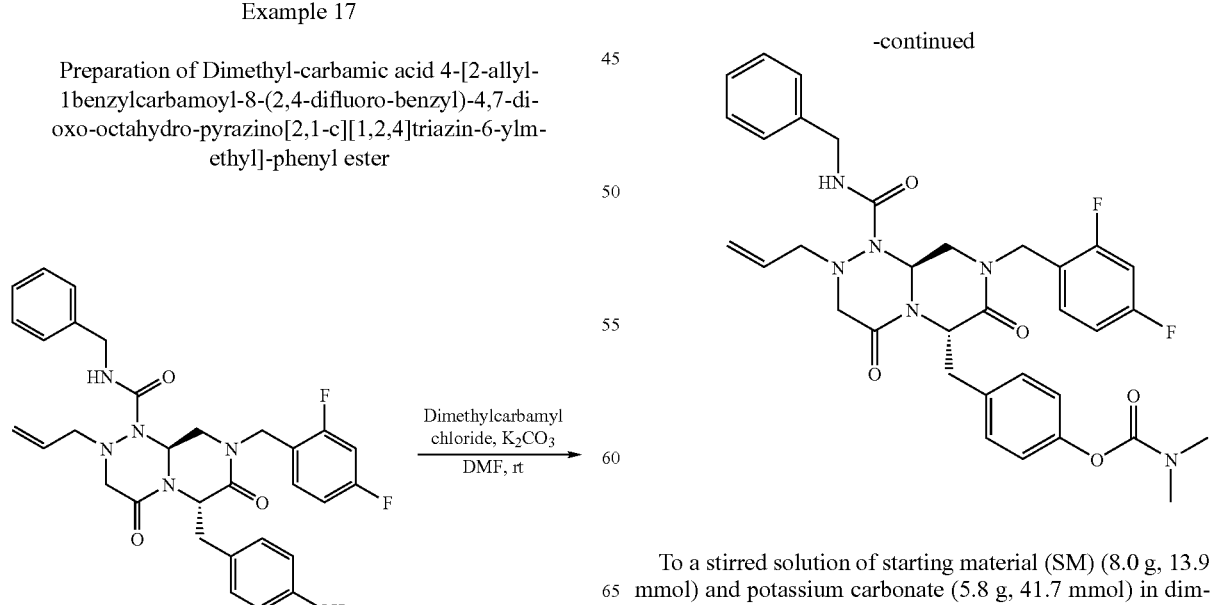

To a stirred solution of starting material (SM) (8.0 g, 13.9 mmol) and potassium carbonate (5.8 g, 41.7 mmol) in dimethylformamide was added dimethylcarbamyl chloride (3.0 g, 27.8 mmol). The reaction mixture was stirred overnight and then dissolved in EtOAc, washed with water five times. The combined organic layer was washed with brine, dried over sodium sulfate, concentrated in vacuo. The residue was chromatographed on silica gel with neat EtOAc to afford product (4.2 g, 32%). The data from analyzing the resulting product by mass spectrometry and NMR are:

MS (ESI): m/e 647 (M+1), 669 (M+Na). $^1$H-NMR (300 MHz, CDCl$_3$) δ 7.27-7.39 (6H, m), 6.78-7.13 (6H, m), 6.68 (1H, t, J=6.0 Hz), 5.61-5.70 (2H, m), 5.34 (1H, t, J=6.0 Hz), 5.06-5.20 (2H, m), 4.31-4.69 (4H, m), 3.24-3.58 (8H, m), 3.07 (3H, s), and 2.99 (3H, s).

Example 18

Preparation of Carbonic acid 4-[2-Allyl-1-Benzyl-carbamoyl-8-(2,4-difluorobenzyl)-4,7-dioxo-octahydro-pyrazino[2,1-c][1,2,4]triazin-6-ylmethyl]-phenyl ester 4-nitro-phenyl ester (2)

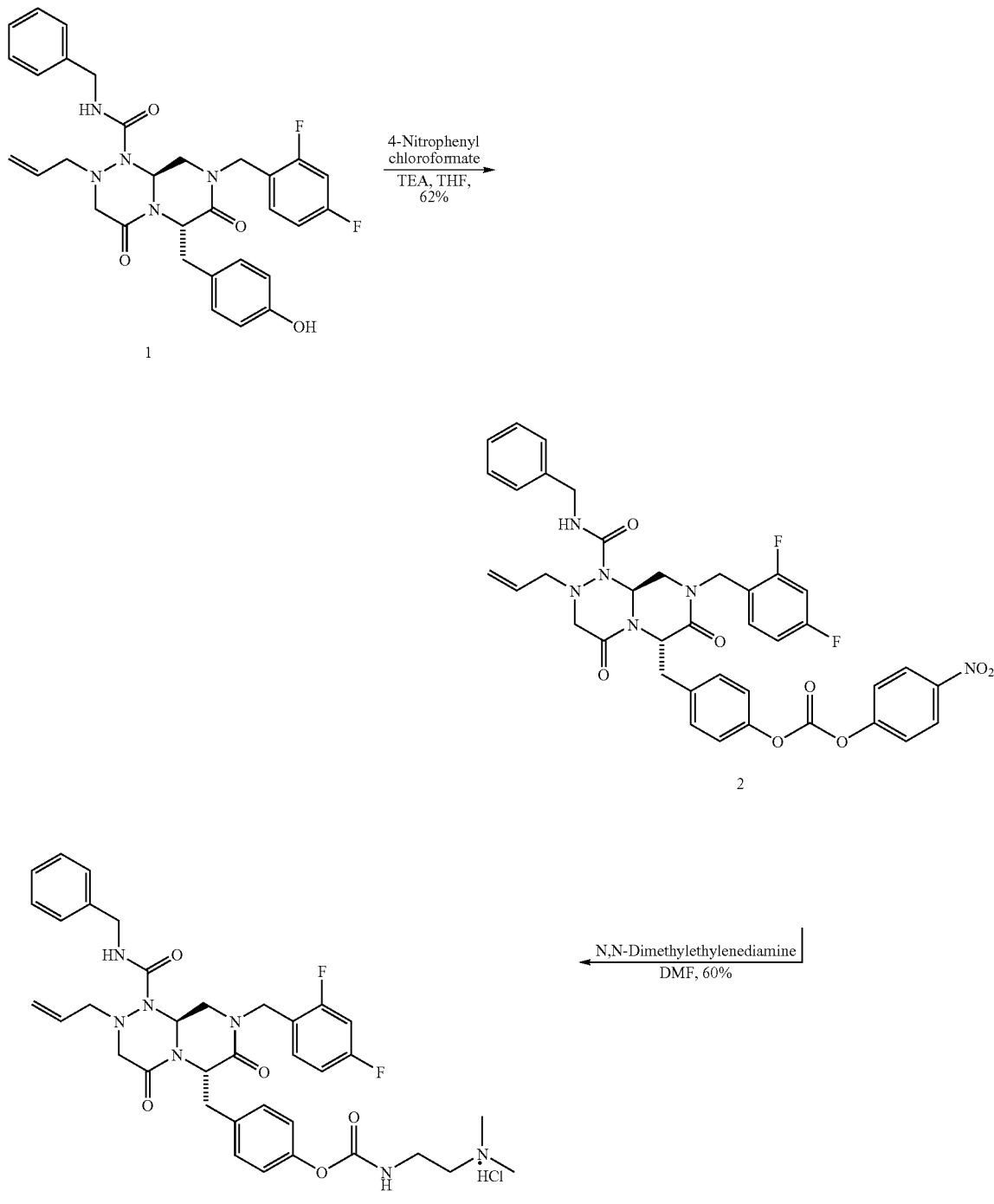

To a stirred solution of 2-Allyl-8-(2,4-difluoro-benzyl)-6-(4-hydroxybenzyl)-4,7-dioxohexahydro-pyrazino[2,1-c][1,2,4]triazine-1-carboxylic acid benzylamine (1) (2 g, 3.47 mmol) in THF (40 ml) was added Triethylamine (0.97 ml, 6.95 mmol) and 4-nitrophenylchloroformate (0.7 g, 3.47 mmol). After stirring at room temperature for overnight, the solvent was removed under reduced pressure. The crude compound was purified by chromatography (Hexane, EtOAc 1:1) to give the compound (1.59 g, 62%). The data from analyzing the purified compound by TLC system and NMR are:

TLC System: $R_f$=0.3 (n-Hexane:EtOAc 1:1) $^1$H NMR (300 MHz, CDCl$_3$): δ 3.25-3.60 (m, 8H), 4.35 (dd, J=14.9 Hz, 5.7 Hz, 1H), 4.43 (dd, J=14.8 Hz, 6.1 Hz, 1H), 4.52 (d, 14.5 Hz, 1H), 4.68 (d, 14.1H), 5.10 (d, 17.1 Hz, 1H), 5.21 (d, 10.3 Hz, 1H), 5.34 (t, J=6.1 Hz, 1H), 5.58 (dd, J=11.1 Hz, 4.1 Hz, 1H), 5.67 (m, 1H), 6.71 (t, J=6.1 Hz, NH), 6.75-6.98 (m, 2H), 7.13 (d, J=8.4 Hz, 2H), 7.21 (d, J=8.7 Hz, 2H), 7.23-7.39 (m, 6H), 7.46 (d, J=9.5 Hz, 2H), and 8.30 (d, J=9.5 Hz, 2H).

Example 19

Preparation of (2-Dimethylamino-ethyl)-Carbamic acid 4-[2-Allyl-1-benzylcarbamoyl-8-(2,4-difluoro-benzyl)-4,7-dioxo-octahydro-pyrazine[2,1-c][1,2,4]triazine-6-ylmethyl]-phenyl ester hydrochloride salt (3)

To a stirred solution of carbonic acid 4-[2-allyl-1-benzyl-carbamoyl-8-(2,4-difluoro-benzyl)-4,7-dioxo-octahydro-pyrazino[2,1-c][1,2,4]triazin-6-ylmethyl]-phenyl ester 4-nitro-phenyl ester (2) (1.2 g, 1.62 mmol) in DMF (25 ml) was added N,N-Dimethylethylenediamine (0.26 ml, 2.43 mmol). After stirring at room temperature for overnight, the solvent was removed under reduced pressure. The residue was diluted with EtOAc and washed with water, brine. The organic layer was dried with Na$_2$SO$_4$ and concentrated in vacuo. The crude compound was purified by chromatography (n-Hexane: EtOAc, 1:1; EtOAc; CH$_2$Cl$_2$:MeOH, 9:1).

The compound was poured with water and was maintained pH 5-6 with 1 N aq. HCl to make HCl salt and then lyophilized to get the compound (0.75 g, 60%). The data from analyzing the resulting compound by TLC system and NMR are:

TLC System: $R_f$=0.35 (CH$_2$Cl$_2$:MeOH, 9:1) ESI-MS: M+H$^+$ 690.39 $^1$H NMR (300 MHz, CDCl$_3$): δ 2.56 (d, J=4.6 Hz, 6H), 3.18 (bm, 4H), 3.41-3.58 (m, 4H), 3.75 (t, J=10.3 Hz, 1H), 4.21 (bt, 2H), 4.35 (d, J=14.9 Hz 1H), 4.70 (d, J=14.9 Hz 1H), 5.05 (m, 1H), 5.12 (m, 1H), 5.42 (m, 6H), 5.80 (m, 1H), 6.91 (d, J=7.6 Hz, 2H), 7.04 (d, J=7.3, 2H), 7.09 (m, 1H), 7.18-7.26 (m, 6H), 7.31 (d, J=6.9 Hz, 2H), 7.33 (m, 1H), 7.84 (bt, NH), 7.98 (bt, NH), 10.7 (bs, 1H)

Example 20

Mouse In Vivo PK Study of Prodrug a after Single I.V. Bolus Injection

Animal Experiment

Drugs were prepared 10 mg/kg/5 ml in 10% Tween 80. Studies were performed in ICR mice. After i.v. bolus injection through the tail vein, blood samples were acquired from inferior vena cava at several time points and separated to plasma by centrifugation. Plasma samples were preserved at −20° C. until they were analyzed. Bleeding time points were 3, 6, 9, 17, 34, 67, 134, 202, 302 min. N=4.

Sample Preparation

For calibration curve, 98 ul aliquots of control mouse plasma were added 2 ul of drug stock solution and added 2 ul internal standard stock solution, 5 ug/ml of internal standard. Final concentrations of calibration samples were 1, 10, 100, 1000 ng/ml and 10 ug/ml. For plasma sample from animal experiment, 100 ul of plasma were added 2 ul of internal standard. Then, all the samples were added 500 ul of acetonitrile, 500 ul of ethylacetate and 100 ul of DW. Samples were mixed for 10 min and centrifuged. The supernatants were transferred another tubes and evaporated. Adding 200 ul of 40% acetonitrile, they were reconstituted and analyzed by LC-MS system.

Results

Figure 18:
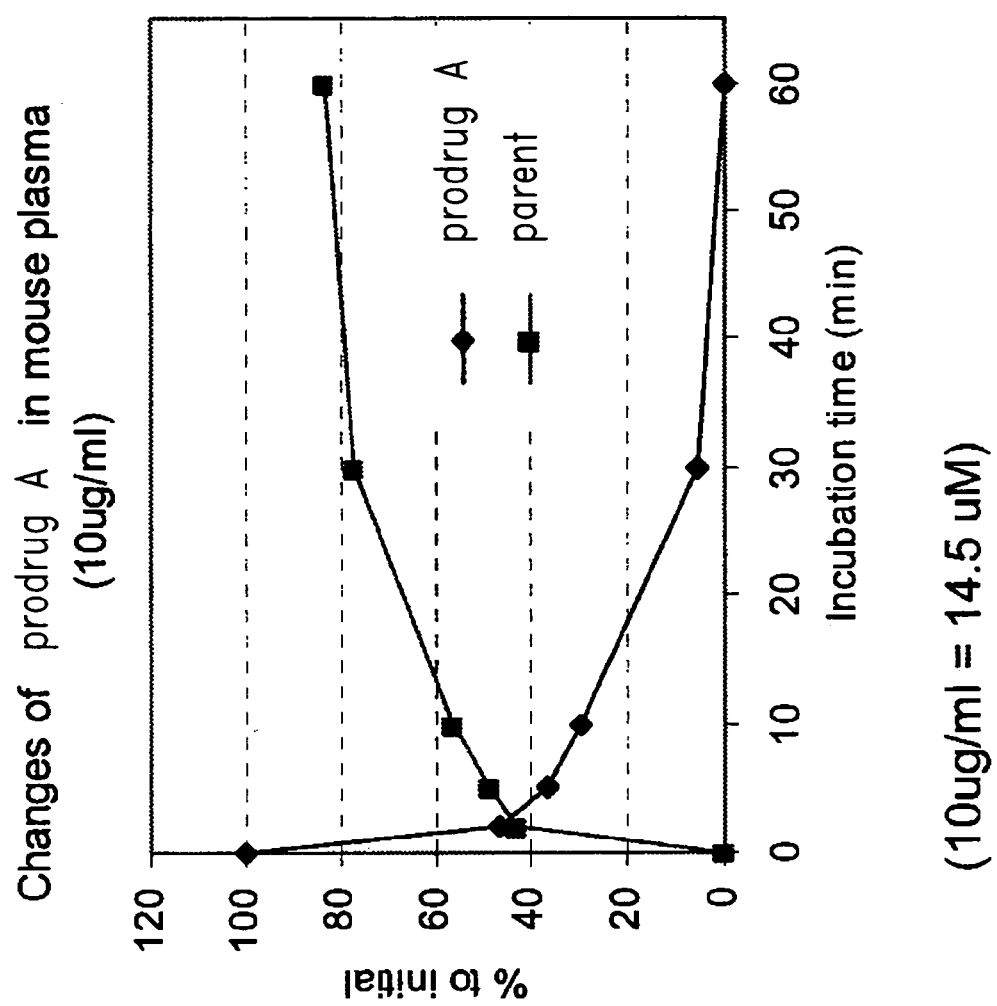
FIG. 18 shows the changes of concentrations of prodrug A and its parent compound in mouse plasma with the increase of time after i.v. bolus injection of prodrug A. Square: parent compound; Diamond: prodrug A.

The changes of concentrations of prodrug A and its parent compound in mouse plasma with the increase of time after i.v. bolus injection of prodrug A are shown in FIG. 18. Square: parent compound; Diamond: prodrug A.

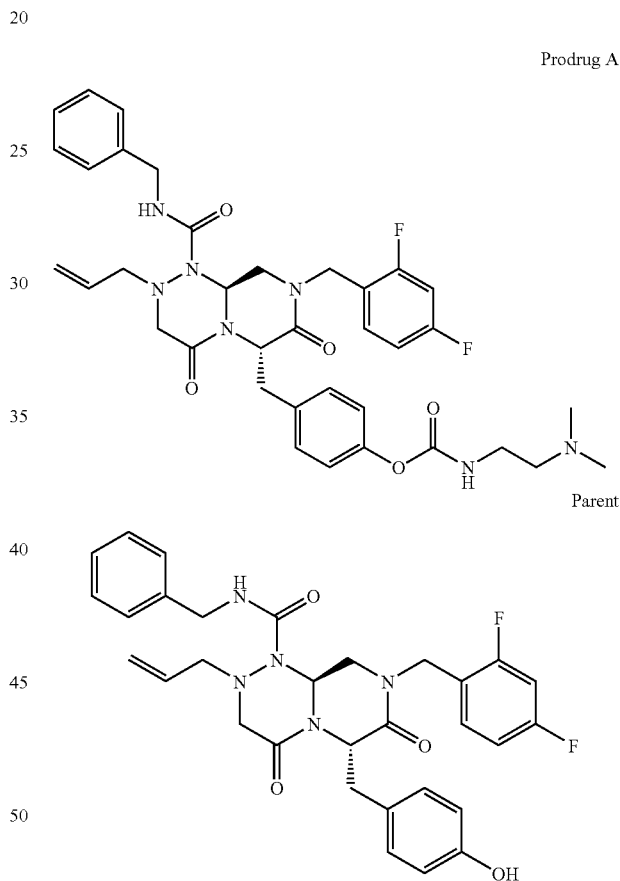

It will be appreciated that, although specific embodiments of the invention have been described herein for the purposes of illustration, various modifications may be made without departing from the spirit and scope of the invention. Accordingly, the invention is not limited except by the appended claims.

All of the above U.S. patents, U.S. patent application publications, U.S. patent applications, foreign patents, foreign patent applications and non-patent publications referred to in this specification and/or listed in the Application Data Sheet, including U.S. patent application Ser. No. 10/087,443 filed on Mar. 1, 2002, and U.S. patent application Ser. No. 09/976,470 filed on Oct. 12, 2001, are incorporated herein by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound having the following general formula (VII)

  (VI)

wherein (VI) is the formula:

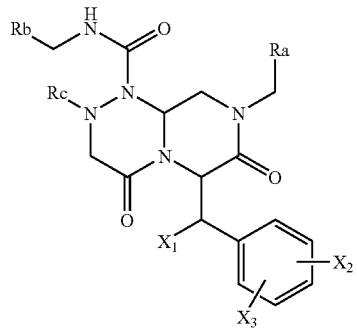

wherein when not linked to $R_{10}$, $R_a$ is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group having 8 to 11 ring members, which may have 1 to 3 heteroatoms selected from nitrogen, oxygen or sulfur;

$R_b$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy groups;

Rc is a saturated or unsaturated $C_{1-6}$alkyl, $C_{1-6}$alkoxy, perfluoro $C_{1-6}$alkyl group; and $X_1$, $X_2$, and $X_3$ may be the same or different and independently selected from hydrogen, hydroxyl, and halide; and Wherein one of $R_a$, $R_b$, $R_c$, $X_1$, $X_2$, and $X_3$ is linked to $R_{10}$ via Y, Y is an oxygen, sulfur, or nitrogen in $R_a$, $R_b$, and $R_c$, or an oxygen in $X_1$, $X_2$ and $X_3$; and Y—$R_{10}$ is hemimalate, dimethylaminoalkylcarbamates, or a salt thereof; or $R_{10}$ is hydroxyalkyl, glycosyl, substituted or unsubstituted piperidine oxycarbonyl, or a salt thereof.

2. A pharmaceutical composition comprising a compound according to claim 1 and pharmaceutically acceptable carrier.

3. The compound of claim 1, wherein when not linked to $R_{10}$, $R_a$ is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; a naphthyl group; a quinolinyl group; an indazolyl group; or a benzpyrazolyl group; an isoquinolinyl group; and $R_b$ is phenyl, pyridyl or piperidyl, all of which may be substituted with one or more substituents selected from a group consisting of halide, hydroxy, cyano, lower alkyl, and lower alkoxy groups.

* * * * *

UNITED STATES PATENT AND TRADEMARK OFFICE
CERTIFICATE OF CORRECTION

PATENT NO. : 7,566,711 B2
APPLICATION NO. : 11/108164
DATED : July 28, 2009
INVENTOR(S) : Sung Hwan Moon et al.

It is certified that error appears in the above-identified patent and that said Letters Patent is hereby corrected as shown below:

Column 2333
Line 9, "-Y-$R_{10}$" should read as -- (VI)-$R_{10}$ --.

Column 2334
Line 16, "dimethylaminoalkylcarbamates" should read as
-- dimethylaminoalkylcarbamate --.

Signed and Sealed this

Twenty-fourth Day of November, 2009

David J. Kappos
*Director of the United States Patent and Trademark Office*